US010576136B2

(12) United States Patent
Honda et al.

(10) Patent No.: US 10,576,136 B2
(45) **Date of Patent: *Mar. 3, 2020**

(54) COMPOSITIONS AND METHODS FOR THE INDUCTION OF CD8+ T-CELLS

(71) Applicants: Keio University, Tokyo (JP); The University of Tokyo, Tokyo (JP)

(72) Inventors: Kenya Honda, Tokyo (JP); Takeshi Tanoue, Tokyo (JP); Masahira Hattori, Tokyo (JP); Yutaka Kawakami, Tokyo (JP)

(73) Assignees: Keio University, Tokyo (JP); The University of Tokyo, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/421,557

(22) Filed: May 24, 2019

(65) Prior Publication Data

US 2019/0343944 A1 Nov. 14, 2019

Related U.S. Application Data

(63) Continuation of application No. PCT/JP2017/046232, filed on Dec. 22, 2017.

(Continued)

(51) Int. Cl.

| | |
|---|---|
| ***A61K 39/02*** | (2006.01) |
| ***A61P 35/00*** | (2006.01) |
| ***A61K 35/74*** | (2015.01) |
| ***A61K 39/114*** | (2006.01) |
| ***A61K 39/395*** | (2006.01) |

(Continued)

(52) U.S. Cl.

CPC .......... *A61K 39/0208* (2013.01); *A61K 35/74* (2013.01); *A61K 39/0216* (2013.01); *A61K 39/114* (2013.01); *A61K 39/39558* (2013.01); *A61P 35/00* (2018.01); *C07K 16/2818* (2013.01); *A61K 2039/505* (2013.01); *A61K 2039/542* (2013.01); *A61K 2039/585* (2013.01)

(58) Field of Classification Search

CPC ........ A61K 35/742; A61K 35/00; A61K 9/48; A61K 45/06; A61K 39/08; A61K 39/0008; A61K 39/39; A61K 2039/57; A61K 2039/52; A61K 45/00; A61K 2039/542; A61K 35/76; A61K 9/0053; A61K 2039/55594; C12Q 2600/158; C12Q 1/689; A01K 67/0275; A01K 2267/0325; G01N 2333/33; G01N 2500/10; G01N 33/505

See application file for complete search history.

(56) References Cited

FOREIGN PATENT DOCUMENTS

WO WO 2013/080561 A1 6/2013
WO WO-2014121298 A2 * 8/2014 .......... A61K 9/0053

(Continued)

OTHER PUBLICATIONS

Pitt et al., (Cancer Research; 76(16); Aug. 2016, 4602-7 Published Online Jul. 29, 2016). (Year: 2016).*

(Continued)

*Primary Examiner* — Jana A Hines
(74) *Attorney, Agent, or Firm* — Wolf, Greenfield & Sacks, P.C.

(57) ABSTRACT

Provided herein are compositions and methods for the induction and/or proliferation of CD8+ T-cells. The disclosure also provides methods of treatment of diseases that can be treated by the induction and/or proliferation of CD8+ T-cells.

29 Claims, 83 Drawing Sheets

Specification includes a Sequence Listing.

Related U.S. Application Data

(60) Provisional application No. 62/574,446, filed on Oct. 19, 2017, provisional application No. 62/491,062, filed on Apr. 27, 2017, provisional application No. 62/484,607, filed on Apr. 12, 2017, provisional application No. 62/438,793, filed on Dec. 23, 2016.

(51) Int. Cl.
*C07K 16/28* (2006.01)
*A61K 39/00* (2006.01)

(56) References Cited

FOREIGN PATENT DOCUMENTS

| | | | |
|---|---|---|---|
| WO | WO 2015/077794 | A1 | 5/2015 |
| WO | WO 2015/156419 | A1 | 10/2015 |
| WO | WO 2016/196605 | A1 | 12/2016 |

OTHER PUBLICATIONS

Genbank accession No. AB247141. Hasegawa et al. Jan. 19, 2006.
Genbank accession No. AB249652. Tamura et al. Oct. 17, 2012.
Genbank accession No. AB261128. Sakamoto et al. Nov. 9, 2012.
Genbank accession No. AB490801. Watanabe et al. Aug. 6, 2010.
Genbank accession No. AB331897. Morotomi et al. Aug. 19, 2009.
Genbank accession No. AB470343. Sakamoto et al. Nov. 9, 2012.
Genbank accession No. AB595134. Sakamoto et al. Nov. 9, 2012.
Genbank accession No. AF139525. Gregg et al. Jun. 2, 1999.
Genbank accession No. AY608696. Song et al. Dec. 2, 2005.
Genbank accession No. CP011531. Russell et al. May 3, 2016.
Genbank accession No. CR626927. Cerdano-Tarraga et al. Feb. 6, 2015.
Genbank accession No. KR822463. Asao et al. Oct. 27, 2016.
Genbank accession No. LN998073. Ndongo et al. Feb. 6, 2016.
Genbank accession No. NR_112933. Sakamoto et al. Feb. 3, 2015.
Genbank accession No. NR_112935. Sakamoto et al. Feb. 3, 2015.
Genbank accession No. NR_112945. Sakamoto et al. Feb. 3, 2015.
Genbank accession No. NR_113076. Sakamoto et al. Feb. 3, 2015.
Genbank accession No. HE974920. Sjoberg et al. Jul. 1, 2013.
Genbank accession No. NZ_CAEG00000000. Apr. 8, 2017.
Genbank accession No. NZ_ACWB00000000. Apr. 17, 2017.
Genbank accession No. NZ_ACWW00000000. Jun. 19, 2017.
U.S. Appl. No. 16/421,578, filed May 24, 2019, Honda et al.
U.S. Appl. No. 16/472,937, filed Jun. 24, 2019, Honda et al.
PCT/JP2017/046232, Apr. 3, 2018, International Search Report and Written Opinion.
PCT/JP2017/046232, Jul. 4, 2019, International Preliminary Report on Patentability.

* cited by examiner

| ID | S_ab score | sequence name | # |
|---|---|---|---|
| 1A1 | 1 | Clostridium innocuum | 26 |
| 1F3 | 0.99 | Ruminococcus sp. | 25 |
| 1E6 | 0.99 | Clostridium lavalense | 24 |
| 1G1 | 0.99 | Hungatella hathewayi | 23 |
| 3F2 | 0.79 | Lachnospiraceae bacterium HGA0140 | 22 |
| 1H8 | 0.99 | Bacteriodes sp. | 21 |
| 2E8 | 0.99 | Parabacteroides goldsteinii | 20 |
| 2D2 | 0.98 | Clostridium sp. | 19 |
| 2B11 | 0.99 | Bacteroides eggerthii | 18 |
| 1A2 | 0.99 | Bacteroides uniformis | 17 |
| 2A12 | 0.99 | Bacteroides fragilis | 16 |
| 2A3 | 0.99 | Bacteroides salyersiae | 15 |
| 1B4 | 1 | Anaerostipes caccae | 14 |
| 2C1 | 0.99 | Bacteroides clarus | 13 |
| 2B7 | 0.99 | Bacteroides cellulosilyticus | 12 |
| 2G9 | 0.99 | Parabacteroides distasonis | 11 |
| 1C1 | 0.99 | Eubacterum limosum | 10 |
| 1H9 | 0.97 | Parabacteroides gordonii | 9 |
| 1E7 | 0.97 | Alistipes sp. | 8 |
| 2F11 | 0.99 | Parabacteroides johnsonii | 7 |
| 2A6 | 0.99 | Paraprevotella xylaniphila | 6 |
| 2B1 | 1 | Subdoligranulum sp. | 5 |
| 2G1 | 0.99 | Bacteroides uniformis | 4 |
| 1B11 | 1 | Bacteroides dorei | 3 |
| 1A6 | 0.99 | Fusobacterium ulcerans | 2 |
| 2G5 | 0.99 | Phascolarctobacterium faecium | 1 |

negatively correlated with IFNγ + CD8T
positively correlated with IFNγ + CD8T
detected in Chloro. B#5
corresponding to isolated strains

Fig. 7B

| Group | ID | S_ab score | Closest sequence | # |
|---|---|---|---|---|
| Detected in Chloro.B#5 | 81A1 | 1 | Clostridium innocuum | 26 |
| | 81F3 | 0.99 | Ruminococcus sp. | 25 |
| | 81E6 | 0.99 | Clostridium lavalense | 24 |
| | 81G1 | 0.99 | Hungatella hathewayi | 23 |
| | 83F2 | 0.79 | Lachnospiraceae bacterium HGA0140 | 22 |
| 10-mix | 81H8 | 0.99 | Bacteroides sp. | 21 |
| | 82E8 | 0.99 | Parabacteroides goldsteinii | 20 |
| | 82D2 | 0.98 | Clostridium sp. | 19 |
| | 82E11 | 0.99 | Bacteroides eggerthii | 18 |
| | 81A2 | 0.99 | Bacteroides uniformis | 17 |
| | 82A12 | 0.99 | Bacteroides fragilis | 16 |
| | 82A3 | 0.99 | Bacteroides salyersiae | 15 |
| | 81B4 | 1 | Anaerostipes caccae | 14 |
| | 82C1 | 0.99 | Bacteroides clarus | 13 |
| | 82B7 | 0.99 | Bacteroides cellulosilyticus | 12 |
| 11-mix | 82G9 | 0.99 | Parabacteroides distasonis | 11 |
| | 81C1 | 0.99 | Eubacterum limosum | 10 |
| | 81H9 | 0.97 | Parabacteroides gordonii | 9 |
| | 81E7 | 0.97 | Alistipes sp. | 8 |
| | 82F11 | 0.99 | Parabacteroides johnsonii | 7 |
| | 82A6 | 0.99 | Paraprevotella xylaniphila | 6 |
| | 82B1 | 1 | Subdoligranulum sp. | 5 |
| | 82G1 | 0.99 | Bacteroides uniformis | 4 |
| | 81B11 | 1 | Bacteroides dorei | 3 |
| | 81A8 | 0.99 | Fusobacterium ulcerans | 2 |
| | 82G5 | 0.99 | Phascolarctobacterium faecium | 1 |

negatively correlated with IFNγ + CD8T (10-mix)

positively correlated with IFNγ + CD8T (11-mix)

detected in Chloro.B#5

Fig. 11

Selected 11 strains

| ID | S_ab score | | # |
|---|---|---|---|
| 1A1 | 1 | Erysipelotrichaceae bacterium | 26 |
| 1F3 | 0.978 | bacterium P1A6 | 25 |
| 1E6 | 0.979 | Clostridium lavalense | 24 |
| 1G1 | 1 | Hungatella hathewayi | 23 |
| 3F2 | 0.791 | Lachnospiraceae bacterium | 22 |
| 1H8 | 1 | bacterium NLAE | 21 |
| 2E8 | 1 | Parabacteroides goldsteinii | 20 |
| 2D2 | 0.946 | Firmicutes bacterium | 19 |
| 2B11 | 0.985 | Bacteroides eggerthii | 18 |
| 1A2 | 0.996 | Bacteroides uniformis | 17 |
| 2A12 | 0.993 | Bacteroides sp. 1AL | 16 |
| 2A3 | 0.986 | Bacteroides salyersiae | 15 |
| 1B4 | 1 | Anaerostipes caccae | 14 |
| 2C1 | 0.973 | Bacteroides clarus | 13 |
| 2B7 | 0.995 | Bacteroides sp. | 12 |
| 2G9 | 0.987 | Parabacteroides distasonis | 11 |
| 1C1 | 0.995 | Eubacterium limosum | 10 |
| 1H9 | 0.903 | Parabacteroides gordonii | 9 |
| 1E7 | 0.979 | Bacteroides sp. | 8 |
| 2F11 | 0.989 | Parabacteroides johnsonii | 7 |
| 2A6 | 0.966 | Paraprevotella xylaniphila | 6 |
| 2B1 | 1 | Ruminococcaceae bacterium | 5 |
| 2G1 | 0.995 | bacterium IARFR67 | 4 |
| 1B11 | 1 | Bacteroides dorei | 3 |
| 1A6 | 1 | Fusobacterium sp. | 2 |
| 2G5 | 0.985 | Phascolarctobacterium faecium | 1 |

Fig. 20

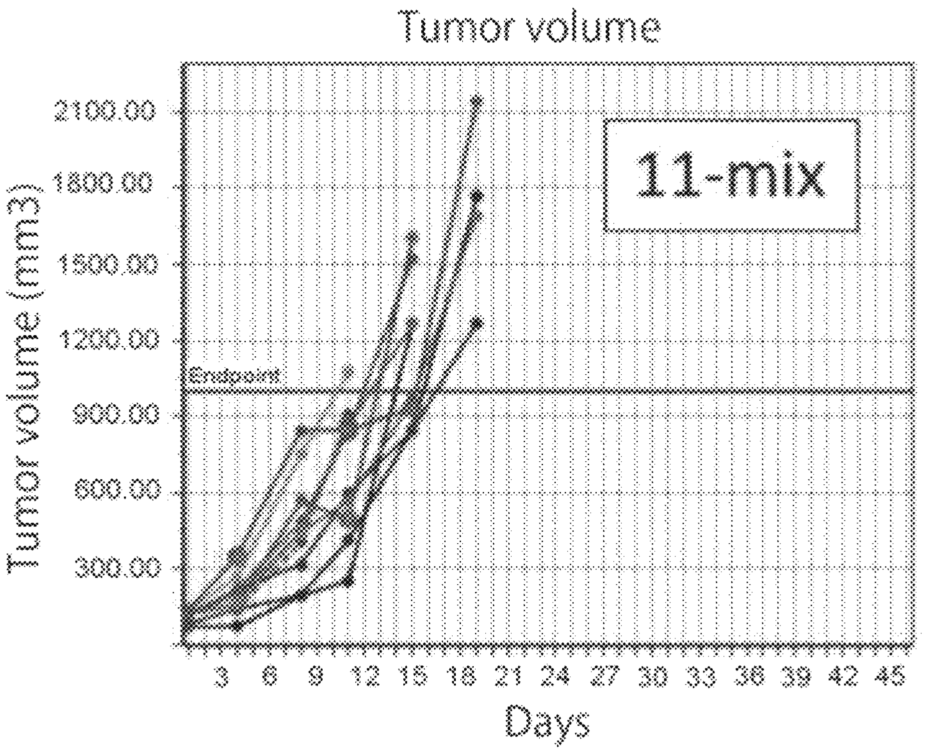
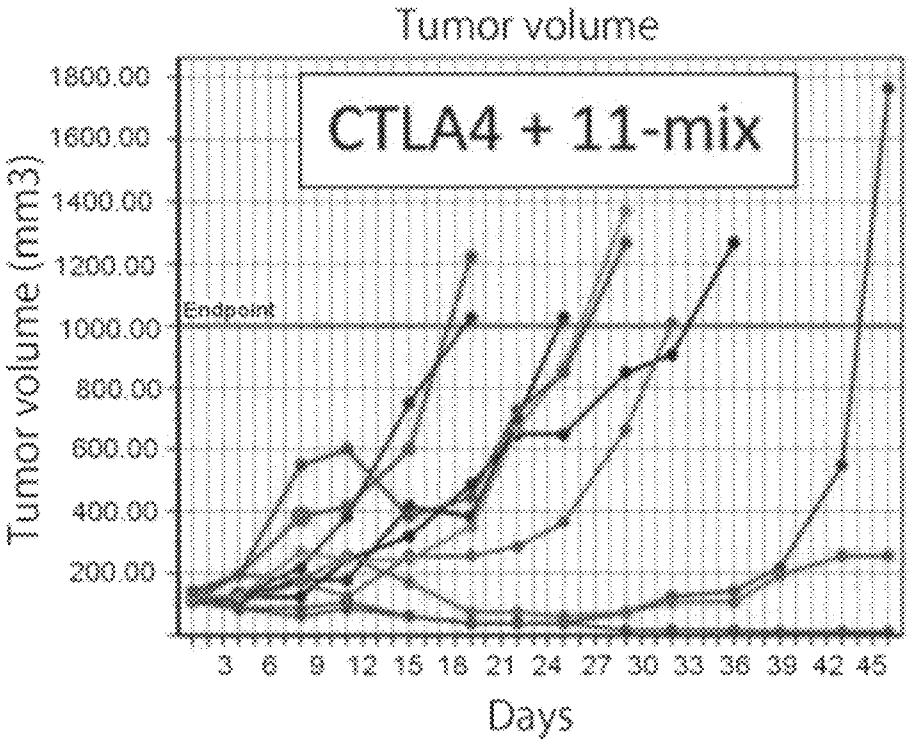
Fig. 27 (Continued)

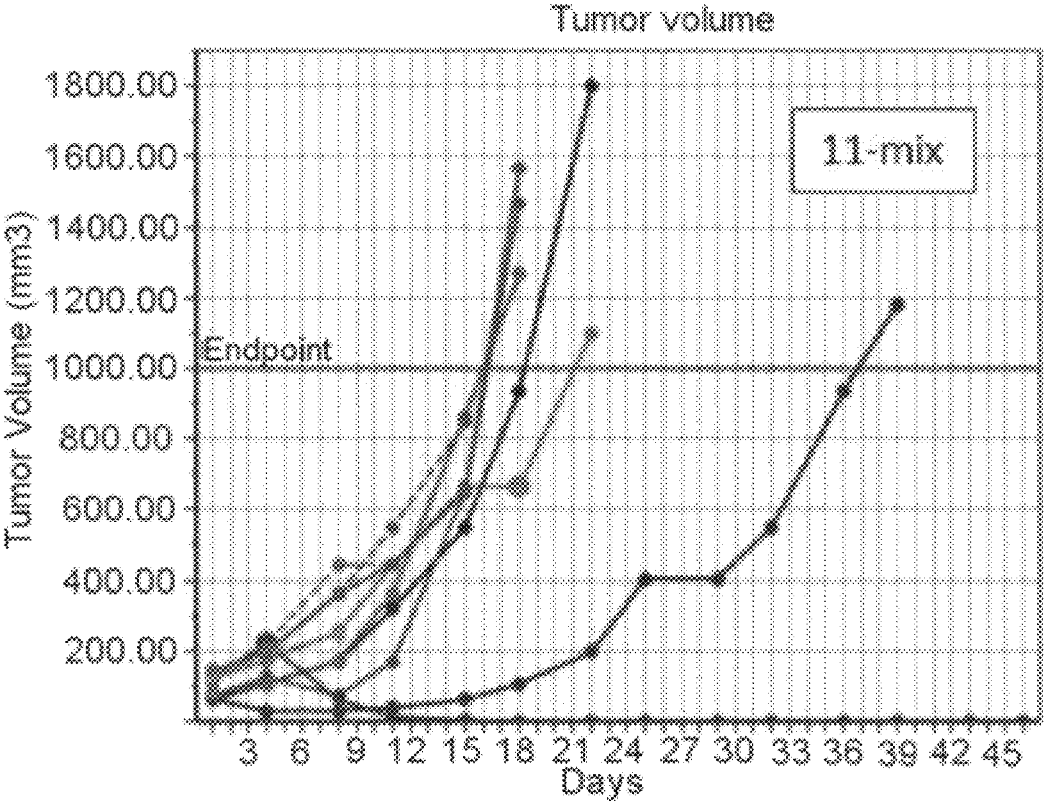
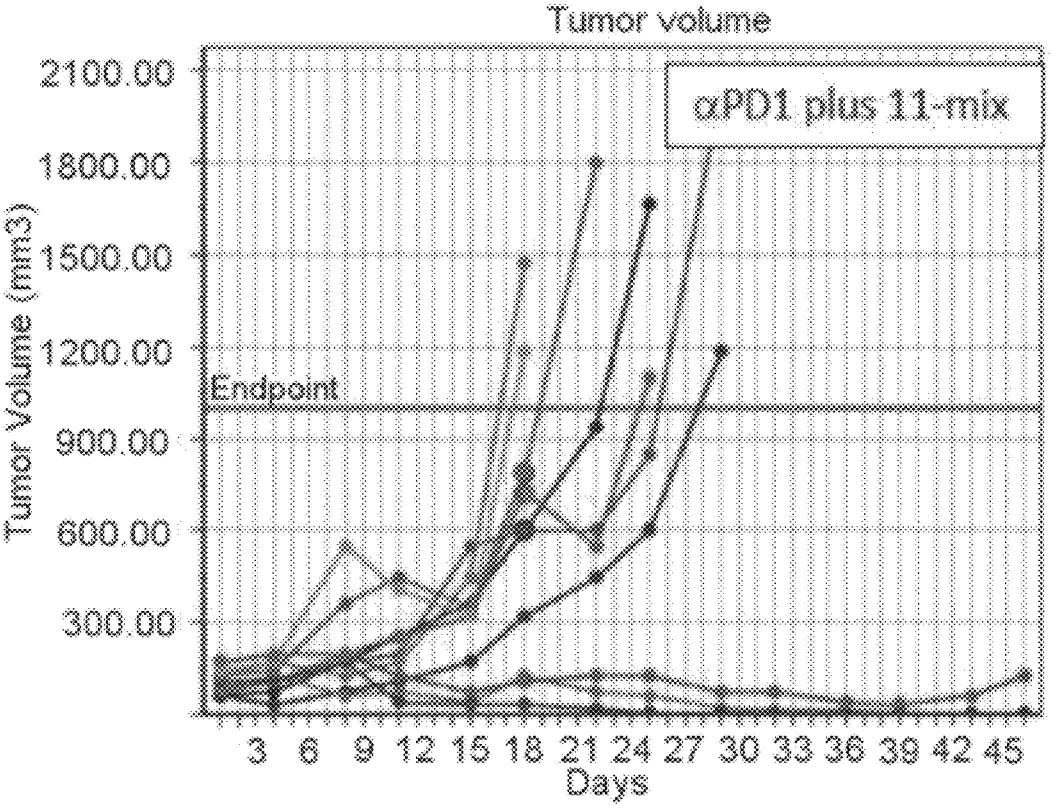
Fig. 30 (Continued)

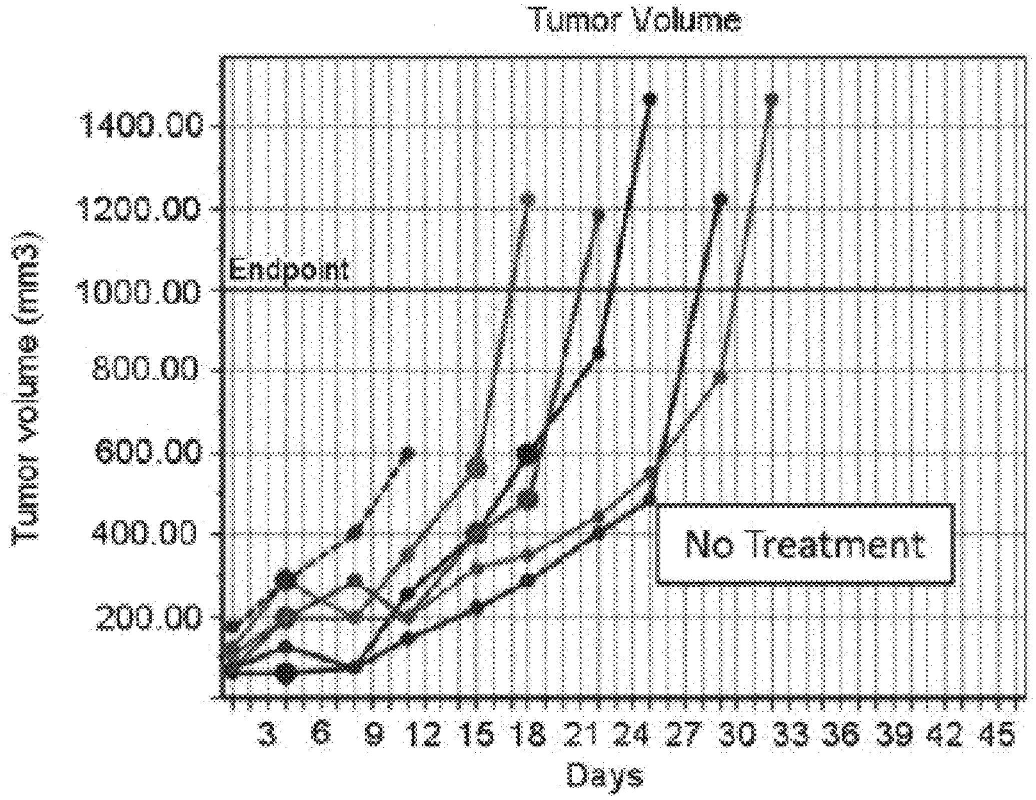
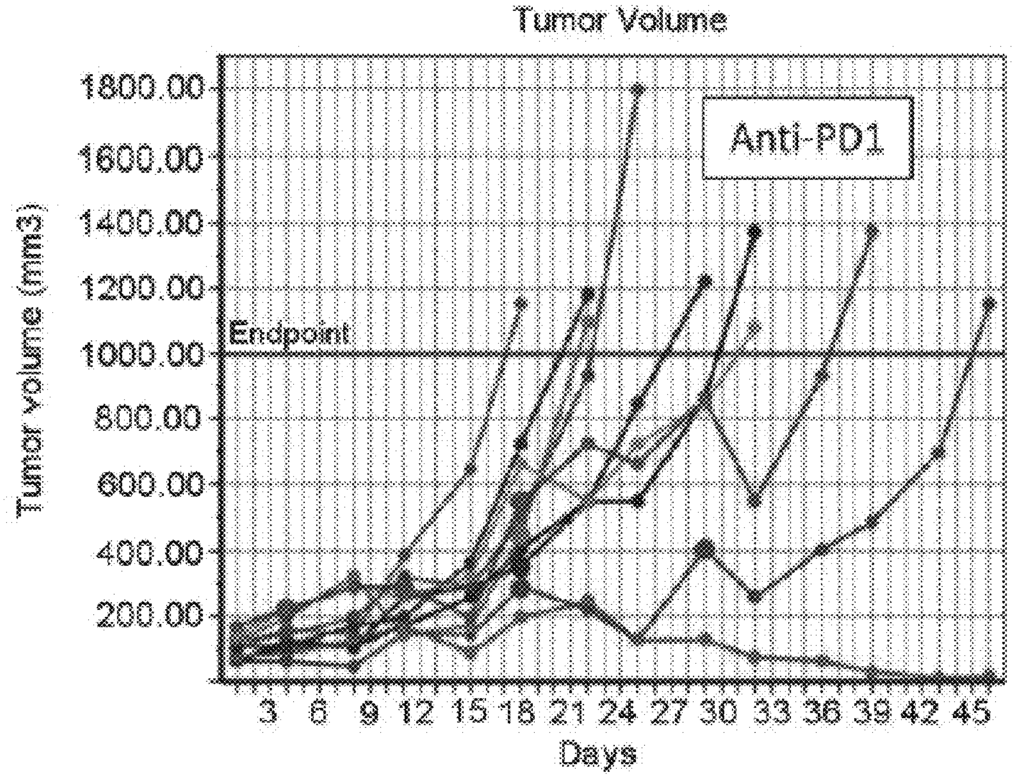
Fig. 32

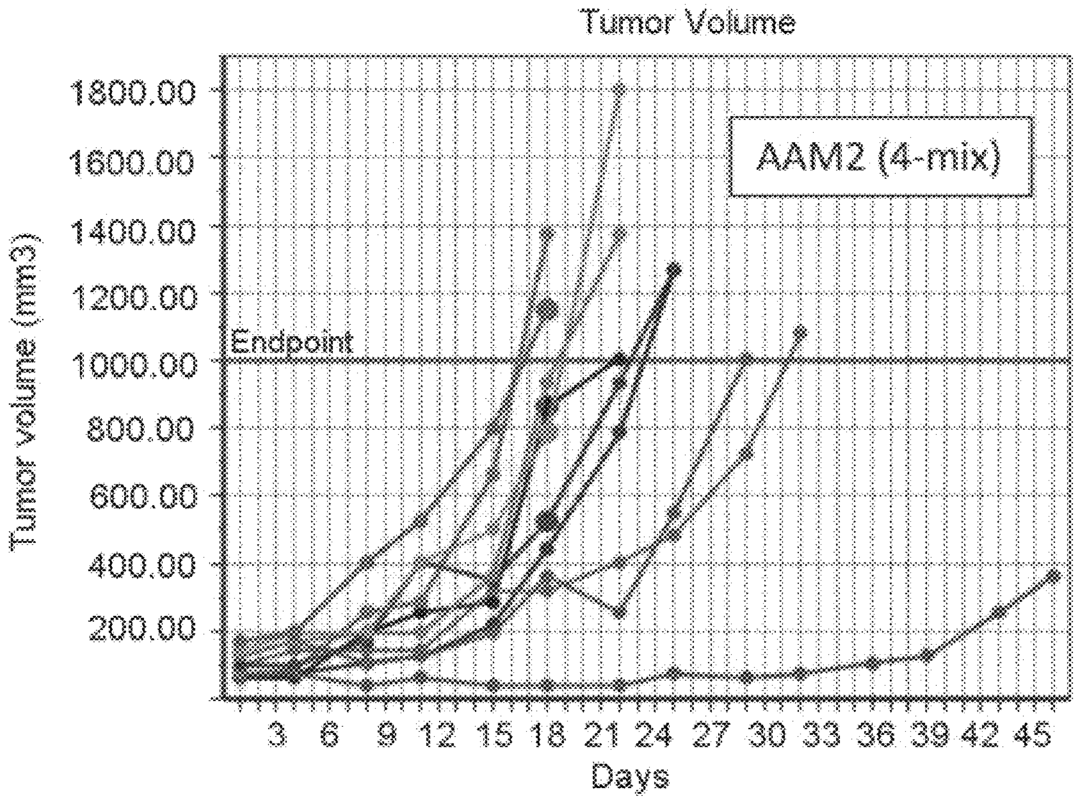
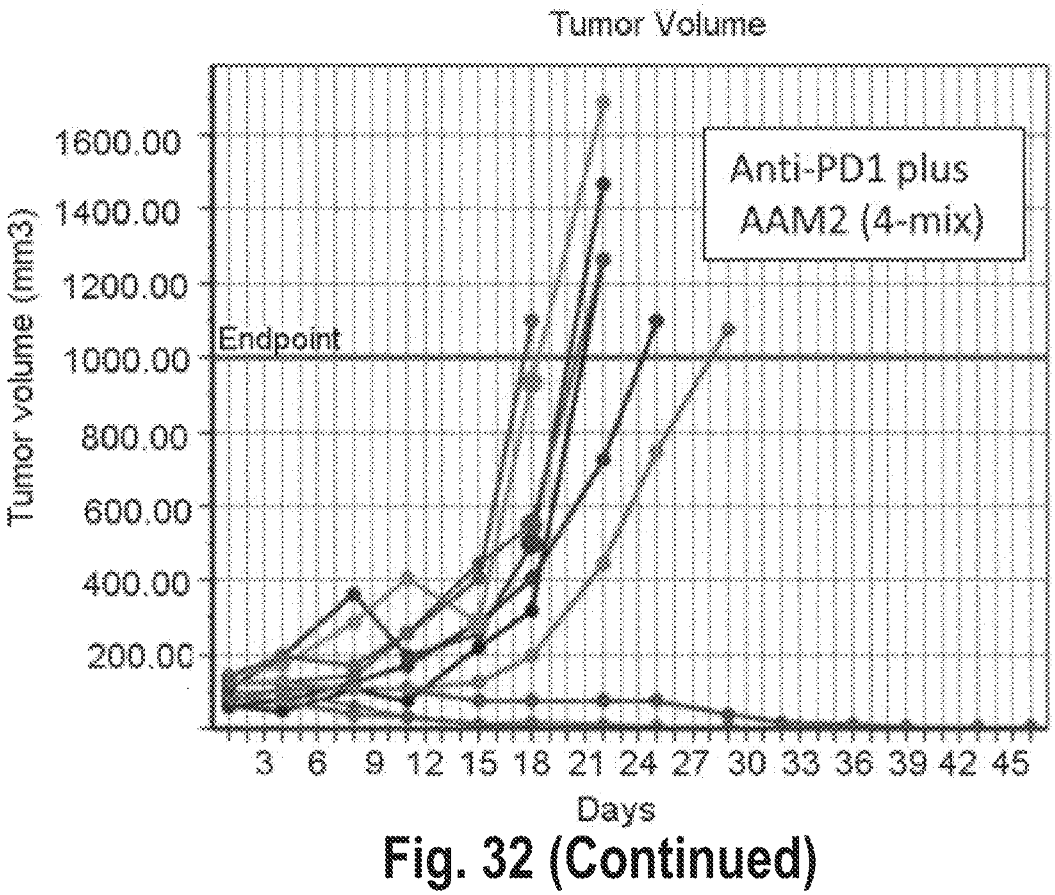
Fig. 32 (Continued)

Day-3~2 : AVMN
Day0 : Braf Pten 7x10[5] cells
Day2~ : water
Day3,6,9 : +/- anti-PD1 200µg + SLC SPF feces +/- 11-mix
2 or 3 times/ week : +11mix

* P <0.05
** P <0.01
*** P <0.001
**** P <0.0001
One-way ANOVA

One mouse in SPF feces group (among 8 mice) died at day 6.
% BW of 11mix group is significantly (P<0.05) higher than the other 2 groups at day3-5.

COMPOSITIONS AND METHODS FOR THE INDUCTION OF CD8+ T-CELLS

RELATED APPLICATIONS

This application is a continuation of international application number PCT/JP2017/046232, filed Dec. 22, 2017 which claims the benefit under 35 U.S.C. § 119(e) of U.S. provisional application No. 62/438,793, filed Dec. 23, 2016; U.S. provisional application No. 62/484,607, filed Apr. 12, 2017; U.S. provisional application No. 62/491,062, filed Apr. 27, 2017; and U.S. provisional application No. 62/574,446, filed Oct. 19, 2017. The entire contents of each of these referenced applications are incorporated by reference herein.

TECHNICAL FIELD

The disclosure relates to compositions and methods for the induction and/or proliferation of CD8+ T-cells. The disclosure also provides methods of treatment of diseases that can be treated by the induction and/or proliferation of CD8+ T-cells.

BACKGROUND ART

Animals, including humans, harbor a multitude of microbes (collectively referred to as the microbiota) in anatomical locations including the mouth, esophagus, stomach, small intestine, large intestine, caecum, vagina, skin, nasal cavities, ear, and lungs. The human microbiota is responsible for a multitude of critical processes, including the development of the immune system, metabolism of carbohydrates, proteins and xenobiotics, formation and regeneration of the epithelium, fat storage, production of hormones, production of vitamins, and protection from pathogen infections, among others (See e.g., LeBlanc et al. Curr. Opin. Biotechnol. (2013) 24(2)460-168; Hooper et al. Science (2012) 336(6086)4268-1273; Hughes et al. Am. J. Gastroenterol. (2013) 108(7)1066-1074). Modification of the human microbiota, which can be caused by a number of factors such as antibiotic use, excessive hygiene, diet, genetic background or combinations of the above, has been associated with a number of unwanted effects including the occurrence of infectious diseases (e.g., *C. difficile* infections), inflammatory, autoimmune and allergic diseases (e.g., ulcerative colitis, Crohn's disease, Type I diabetes, food allergies, asthma, rheumatoid arthritis) and metabolic diseases (e.g., Type II diabetes, metabolic syndrome, obesity, malnutrition), and cancer, among others. For instance, modifications of the microbiota can lead to a loss of tolerance against harmless food antigens or commensal bacterial antigens, subsequent excessive inflammatory responses, metabolic dysregulation, and damage to the intestinal tissue, which compromises its ability to serve as a barrier between the gut lumen and the systemic circulation.

Manipulation of the immune response is of great importance in the treatment of cancer and in vaccination. Cancer therapies that target the immune system have attained improvements in survival rates. However, a large percentage of patients do not respond to cancer immunotherapies. Similarly, large population subsets (e.g., the elderly) cannot mount strong immune responses to vaccines.

Approaches for countering the harmful effects of microbiota modifications on health are limited, despite the role that such modifications play in promoting human pathology. Interventions known to modulate the microbiota include antibiotics, prebiotics, probiotics and fecal transplants, each of which has limitations and potential adverse effects. Additional approaches to counter the detrimental effects of microbiome modification on human health are clearly needed. Furthermore, approaches for promoting stronger immune responses to cancer and to vaccines are also needed.

SUMMARY OF INVENTION

The inventors joined the Innovative Advanced Research and Development Support Project Incubation Type of Japan Agency for Medical Research and Development (AMED) in 2016, whose Research and Development Subject entitled "Creating New Drugs Using Intestinal Bacterial Strain Cocktail" (AMED-LEAP Research Program), and obtained the present invention as the result of the AMED-LEAP Research Program. The disclosure relates to compositions of bacterial strains and methods for the induction and/or proliferation of CD8+ T-cells by administering these compositions. The disclosure also provides compositions and methods for the treatment of diseases that can be treated by the induction and/or proliferation of CD8+ T-cells. Diseases that can be treated by the induction and/or proliferation of CD8+ T-cells include infectious diseases and cancers.

As disclosed herein, for the first-time compositions of human-derived bacterial strains are provided which activate the immune system through the induction of interferon gamma producing CD8+ T cells (also referred to herein as IFNγ+CD8+ T cells, CD8+ IFN γ+ T cells, CD8+ T cells or CD8 positive T-cells). While microbial-based compositions for inducing proliferation or accumulation of regulatory T-cells (WO2011/152566), and composition for inducing Th17 cells (WO2015/156419) were previously reported, this disclosure is the first report on microbial species which induce IFNγ+CD8+ T-cells. IFNγ+CD8+ T-cells play important roles in the immune system, in particular the surveillance of infections (e.g., viral infections) and cancer cell development. The compositions provided herein can therefore be used in, for instance, the treatment of infectious diseases and cancer immunotherapy.

In one aspect, the disclosure provides compositions comprising a purified bacterial mixture comprising one or more bacterial strains of species selected from the group consisting of *Phascolarctobacterium faecium, Fusobacterium ulcerans, Bacteroides dorei, Bacteroides uniformis, Subdoligranulum* sp., *Paraprevotella xylaniphila, Parabacteroides johnsonii, Alistipes* sp., *Parabacteroides gordonii, Eubacterum limosum, Parabacteroides distasonis, Bacteroides cellulosilyticus, Bacteroides clarus, Anaerostipes caccae, Bacteroides salyersiae, Bacteroides fragilis, Bacteroides uniformis, Bacteroides eggerthii, Clostridium* sp., *Parabacteroides goldsteinii, Bacteroides* sp., *Lachnospiraceae bacterium* HGA0140, *Hungatella hathewayi, Clostridium lavalense, Ruminococcus* sp., and *Clostridium innocuum*. In some embodiments of the compositions provided herein, the purified bacterial mixture comprises at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, or at least 26 bacterial strains.

In one aspect, the disclosure provides compositions comprising a purified bacterial mixture comprising two or more bacterial strains of species selected from the group consisting of *Phascolarctobacterium faecium, Fusobacterium ulcerans, Bacteroides dorei, Bacteroides uniformis, Subdoligranulum* sp., *Paraprevotella xylaniphila, Parabacteroides johnsonii, Alistipes* sp., *Parabacteroides gordonii,*

*Eubacterum limosum, Parabacteroides distasonis, Bacteroides cellulosilyticus, Bacteroides clarus, Anaerostipes caccae, Bacteroides salyersiae, Bacteroides fragilis, Bacteroides uniformis, Bacteroides eggerthii, Clostridium* sp., *Parabacteroides goldsteinii, Bacteroides* sp., *Lachnospiraceae bacterium* HGA0140, *Hungatella hathewayi, Clostridium lavalense, Ruminococcus* sp., and *Clostridium innocuum*. In some embodiments of the compositions provided herein, the purified bacterial mixture comprises at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, or at least 26 bacterial strains.

In one aspect, the disclosure provides compositions comprising a purified bacterial mixture comprising one or more bacterial strains of species selected from the group consisting of *Phascolarctobacterium faecium, Fusobacterium ulcerans, Bacteroides dorei, Bacteroides uniformis, Subdoligranulum* sp., *Paraprevotella xylaniphila, Parabacteroides johnsonii, Alistipes* sp., *Parabacteroides gordonii, Eubacterum limosum, Parabacteroides distasonis, Bacteroides cellulosilyticus, Bacteroides clarus, Anaerostipes caccae, Bacteroides salyersiae, Bacteroides fragilis, Bacteroides uniformis, Bacteroides eggerthii, Clostridium* sp., *Parabacteroides goldsteinii*, and *Bacteroides* sp. In some embodiments of the compositions provided herein, the purified bacterial mixture comprises at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, or at least 21 bacterial strains.

In one aspect, the disclosure provides compositions comprising a purified bacterial mixture comprising two or more bacterial strains of species selected from the group consisting of *Phascolarctobacterium faecium, Fusobacterium ulcerans, Bacteroides dorei, Bacteroides uniformis, Subdoligranulum* sp., *Paraprevotella xylaniphila, Parabacteroides johnsonii, Alistipes* sp., *Parabacteroides gordonii, Eubacterum limosum, Parabacteroides distasonis, Bacteroides cellulosilyticus, Bacteroides clarus, Anaerostipes caccae, Bacteroides salyersiae, Bacteroides fragilis, Bacteroides uniformis, Bacteroides eggerthii, Clostridium* sp., *Parabacteroides goldsteinii*, and *Bacteroides* sp.

In some embodiments of the compositions provided herein, the purified bacterial mixture comprises at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, or at least 21 bacterial strains.

In one aspect, the disclosure provides compositions comprising a purified bacterial mixture comprising one or more bacterial strains of species selected from the group consisting of *Phascolarctobacterium faecium, Fusobacterium ulcerans, Bacteroides dorei, Bacteroides uniformis, Subdoligranulum* sp., *Paraprevotella xylaniphila, Parabacteroides johnsonii, Alistipes* sp., *Parabacteroides gordonii, Eubacterum limosum*, and *Parabacteroides distasonis*. In some embodiments of the compositions provided herein, the purified bacterial mixture comprises at least 2, at least 3, at least 4, at least 5, at least 6, at least 7, at least 8, at least 9, at least 10, or at least 11 bacterial strains.

In one aspect, the disclosure provides compositions comprising a purified bacterial mixture comprising *Phascolarctobacterium faecium, Fusobacterium ulcerans, Bacteroides dorei, Bacteroides uniformis, Subdoligranulum* sp., *Paraprevotella xylaniphila, Parabacteroides johnsonii, Alistipes* sp., *Parabacteroides gordonii, Eubacterum limosum*, and *Parabacteroides* distasonis.

In one aspect, the disclosure provides compositions comprising a purified bacterial mixture consisting of *Phascolarctobacterium faecium, Fusobacterium ulcerans, Bacteroides dorei, Bacteroides uniformis, Subdoligranulum* sp., *Paraprevotella xylaniphila, Parabacteroides johnsonii, Alistipes* sp., *Parabacteroides gordonii, Eubacterum limosum*, and *Parabacteroides* distasonis.

In one aspect, the disclosure provides compositions comprising a purified bacterial mixture essentially consisting of *Phascolarctobacterium faecium, Fusobacterium ulcerans, Bacteroides dorei, Bacteroides uniformis, Subdoligranulum* sp., *Paraprevotella xylaniphila, Parabacteroides johnsonii, Alistipes* sp., *Parabacteroides gordonii, Eubacterum limosum*, and *Parabacteroides* distasonis.

In one aspect, the disclosure provides compositions comprising a purified bacterial mixture comprising one or more bacterial strains of species selected from the group consisting of *Phascolarctobacterium faecium, Phascolarctobacterium* sp. CAG:207, *Fusobacterium ulcerans, Fusobacterium varium, Bacteroides dorei, Bacteroides fluxus, Bacteroides uniformis, Bacteroides* sp. D20 *Subdoligranulum* sp., *Ruthenibacterium lactatiformans, Ruminococcaceae bacterium* cv2, *Gemminger formicilis, Paraprevotella xylaniphila, Parabacteroides johnsonii, Alistipes* sp., *Alistipes timonensis, Alistipes senegalesis, Parabacteroides gordonii, Parabacteroides* sp. HGS0025, *Eubacterum limosum, Parabacteroides* sp. CAG2 and *Parabacteroides distasonis*. In some embodiments of the compositions provided herein, the purified bacterial mixture comprises at least 2, at least 3, at least 4, at least 5, at least 6, at least 7, at least 8, at least 9, at least 10, or at least 11 bacterial strains.

In one aspect, the disclosure provides compositions comprising a purified bacterial mixture comprising:

1) *Phascolarctobacterium faecium*, or *Phascolarctobacterium* sp. CAG:207,
2) *Fusobacterium ulcerans*, or *Fusobacterium varium,*
3) *Bacteroides dorei*, or *Bacteroides fluxus,*
4) *Bacteroides uniformis*, or *Bacteroides* sp. D20,
5) *Subdoligranulum* sp., *Ruthenibacterium lactatiformans, Ruminococcaceae bacterium* cv2, or *Gemminger formicilis,*
6) *Paraprevotella xylaniphila,*
7) *Parabacteroides johnsonii,*
8) *Alistipes* sp., *Alistipes timonensis*, or *Alistipes senegalesis,*
9) *Parabacteroides gordonii*, or *Parabacteroides* sp. HGS0025,
10) *Eubacterum limosum*, and
11) *Parabacteroides* sp. CAG:2 or *Parabacteroides distasonis.*

In one aspect, the disclosure provides compositions comprising a purified bacterial mixture consisting of:

1) *Phascolarctobacterium faecium*, or *Phascolarctobacterium* sp. CAG:207,
2) *Fusobacterium ulcerans*, or *Fusobacterium varium,*
3) *Bacteroides dorei*, or *Bacteroides fluxus,*
4) *Bacteroides uniformis*, or *Bacteroides* sp. D20,
5) *Subdoligranulum* sp., *Ruthenibacterium lactatiformans, Ruminococcaceae bacterium* cv2, or *Gemminger formicilis,*
6) *Paraprevotella xylaniphila,*
7) *Parabacteroides johnsonii,*
8) *Alistipes* sp., *Alistipes timonensis*, or *Alistipes senegalesis,*

9) *Parabacteroides gordonii*, or *Parabacteroides* sp. HGS0025, 10) *Eubacterum limosum*, and 11) *Parabacteroides* sp. CAG:2 or *Parabacteroides distasonis.*

In one aspect, the disclosure provides compositions comprising a purified bacterial mixture comprising one or more bacterial strains of species selected from the group consisting of *Phascolarctobacterium faecium, Fusobacterium varium, Bacteroides dorei, Bacteroides uniformis, Ruthenibacterium lactatiformans, Paraprevotella xylaniphila, Parabacteroides johnsonii, Alistipes senegalesis, Parabacteroides gordonii, Eubacterum limosum*, and *Parabacteroides distasonis*. In some embodiments of the compositions provided herein, the purified bacterial mixture comprises at least 2, at least 3, at least 4, at least 5, at least 6, at least 7, at least 8, at least 9, at least 10, or at least 11 bacterial strains.

In one aspect, the disclosure provides compositions comprising a purified bacterial mixture comprising *Phascolarctobacterium faecium, Fusobacterium varium, Bacteroides dorei, Bacteroides uniformis, Ruthenibacterium lactatiformans, Paraprevotella xylaniphila, Parabacteroides johnsonii, Alistipes senegalesis, Parabacteroides gordonii, Eubacterum limosum*, and *Parabacteroides* distasonis.

In one aspect, the disclosure provides compositions comprising a purified bacterial mixture consisting of *Phascolarctobacterium faecium, Fusobacterium varium, Bacteroides dorei, Bacteroides uniformis, Ruthenibacterium lactatiformans, Paraprevotella xylaniphila, Parabacteroides johnsonii, Alistipes senegalesis, Parabacteroides gordonii, Eubacterum limosum*, and *Parabacteroides distasonis.*

In one aspect, the disclosure provides compositions comprising a purified bacterial mixture essentially consisting of *Phascolarctobacterium faecium, Fusobacterium varium, Bacteroides dorei, Bacteroides uniformis, Ruthenibacterium lactatiformans, Paraprevotella xylaniphila, Parabacteroides johnsonii, Alistipes senegalesis, Parabacteroides gordonii, Eubacterum limosum*, and *Parabacteroides* distasonis.

In one aspect, the disclosure provides compositions comprising a purified bacterial mixture comprising one or more bacterial strains of species selected from the group consisting of *Phascolarctobacterium* sp. CAG:207, *Fusobacterium ulcerans, Bacteroides dorei, Bacteroides* sp. D20, *Ruminococcaceae bacterium* cv2, *Paraprevotella xylaniphila, Parabacteroides johnsonii, Alistipes senegalesis, Parabacteroides* sp. HGS0025, *Eubacterum limosum*, and *Parabacteroides* sp. CAG:2. In some embodiments of the compositions provided herein, the purified bacterial mixture comprises at least 2, at least 3, at least 4, at least 5, at least 6, at least 7, at least 8, at least 9, at least 10, or at least 11 bacterial strains.

In one aspect, the disclosure provides compositions comprising a purified bacterial mixture comprising *Phascolarctobacterium* sp. CAG:207, *Fusobacterium ulcerans, Bacteroides dorei, Bacteroides* sp. D20, *Ruminococcaceae bacterium* cv2, *Paraprevotella xylaniphila, Parabacteroides johnsonii, Alistipes senegalesis, Parabacteroides* sp. HGS0025, *Eubacterum limosum*, and *Parabacteroides* sp. CAG:2.

In one aspect, the disclosure provides compositions comprising a purified bacterial mixture consisting of *Phascolarctobacterium* sp. CAG:207, *Fusobacterium ulcerans, Bacteroides dorei, Bacteroides* sp. D20, *Ruminococcaceae bacterium* cv2, *Paraprevotella xylaniphila, Parabacteroides johnsonii, Alistipes senegalesis, Parabacteroides* sp. HGS0025, *Eubacterum limosum*, and *Parabacteroides* sp. CAG:2.

In one aspect, the disclosure provides compositions comprising a purified bacterial mixture essentially consisting of *Phascolarctobacterium* sp. CAG:207, *Fusobacterium ulcerans, Bacteroides dorei, Bacteroides* sp. D20, *Ruminococcaceae bacterium* cv2, *Paraprevotella xylaniphila, Parabacteroides johnsonii, Alistipes senegalesis, Parabacteroides* sp. HGS0025, *Eubacterum limosum*, and *Parabacteroides* sp. CAG:2.

In one aspect, the disclosure provides compositions comprising a purified bacterial mixture comprising two or more bacterial strains of species selected from the group consisting of *Phascolarctobacterium faecium, Fusobacterium ulcerans, Bacteroides dorei, Bacteroides uniformis, Subdoligranulum* sp., *Paraprevotella xylaniphila, Parabacteroides johnsonii, Alistipes* sp., *Parabacteroides gordonii, Eubacterum limosum*, and *Parabacteroides distasonis*. In some embodiments of the compositions provided herein, the purified bacterial mixture comprises at least 3, at least 4, at least 5, at least 6, at least 7, at least 8, at least 9, at least 10, or at least 11 bacterial strains.

In one aspect, the disclosure provides compositions comprising a purified bacterial mixture comprising two or more bacterial strains of species selected from the group consisting of *Phascolarctobacterium faecium, Phascolarctobacterium* sp. CAG:207, *Fusobacterium ulcerans, Fusobacterium varium, Bacteroides dorei, Bacteroides fluxus, Bacteroides uniformis, Bacteroides* sp. D20 *Subdoligranulum* sp., *Ruthenibacterium lactatiformans, Ruminococcaceae bacterium* cv2, *Gemminger formicilis, Paraprevotella xylaniphila, Parabacteroides johnsonii, Alistipes* sp., *Alistipes senegalesis, Parabacteroides gordonii, Parabacteroides* sp. HGS0025, *Eubacterum limosum, Parabacteroides* sp. CAG:2 and *Parabacteroides distasonis*. In some embodiments of the compositions provided herein, the purified bacterial mixture comprises, at least 3, at least 4, at least 5, at least 6, at least 7, at least 8, at least 9, at least 10, or at least 11 bacterial strains.

In one aspect, the disclosure provides compositions comprising a purified bacterial mixture comprising two or more bacterial strains of species selected from the group consisting of *Phascolarctobacterium faecium, Fusobacterium varium, Bacteroides dorei, Bacteroides uniformis, Ruthenibacterium lactatiformans, Paraprevotella xylaniphila, Parabacteroides johnsonii, Alistipes senegalesis, Parabacteroides gordonii, Eubacterum limosum*, and *Parabacteroides distasonis*. In some embodiments of the compositions provided herein, the purified bacterial mixture comprises at least 3, at least 4, at least 5, at least 6, at least 7, at least 8, at least 9, at least 10, or at least 11 bacterial strains.

In one aspect, the disclosure provides compositions comprising a purified bacterial mixture comprising two or more bacterial strains of species selected from the group consisting of *Phascolarctobacterium* sp. CAG:207, *Fusobacterium ulcerans, Bacteroides dorei, Bacteroides* sp. D20, *Ruminococcaceae bacterium* cv2, *Paraprevotella xylaniphila, Parabacteroides johnsonii, Alistipes senegalesis, Parabacteroides* sp. HGS0025, *Eubacterum limosum*, and *Parabacteroides* sp. CAG:2. In some embodiments of the compositions provided herein, the purified bacterial mixture comprises at least 3, at least 4, at least 5, at least 6, at least 7, at least 8, at least 9, at least 10, or at least 11 bacterial strains.

In one aspect, the disclosure provides compositions comprising a purified bacterial mixture comprising one or more bacterial strains of species selected from the group consisting of *Bacteroides* cellulosilyticus, *Bacteroides clarus, Anaerostipes caccae, Bacteroides salyersiae, Bacteroides*

*fragilis, Bacteroides uniformis, Bacteroides eggerthii, Clostridium* sp., *Parabacteroides goldsteinii, Bacteroides* sp., *Lachnospiraceae bacterium* HGA0140, *Hungatella hathewayi, Clostridium lavalense, Ruminococcus* sp., and *Clostridium innocuum*. In some embodiments of the compositions provided herein, the purified bacterial mixture comprises at least 2, at least 3, at least 4, at least 5, at least 6, at least 7, at least 8, at least 9, at least 10, at least 11, at least 12, at least 13, at least 14, or at least 15 bacterial strains.

In one aspect, the disclosure provides compositions comprising a purified bacterial mixture comprising two or more bacterial strains of species selected from the group consisting of *Bacteroides* cellulosilyticus, *Bacteroides clarus, Anaerostipes caccae, Bacteroides salyersiae, Bacteroides fragilis, Bacteroides uniformis, Bacteroides eggerthii, Clostridium* sp., *Parabacteroides goldsteinii, Bacteroides* sp., *Lachnospiraceae bacterium* HGA0140, *Hungatella hathewayi, Clostridium lavalense, Ruminococcus* sp., and *Clostridium innocuum*. In some embodiments of the compositions provided herein, the purified bacterial mixture comprises at least 3, at least 4, at least 5, at least 6, at least 7, at least 8, at least 9, at least 10, at least 11, at least 12, at least 13, at least 14, or at least 15 bacterial strains.

In one aspect, the disclosure provides compositions comprising a purified bacterial mixture comprising one or more bacterial strains of species selected from the group consisting of *Bacteroides* cellulosilyticus, *Bacteroides clarus, Anaerostipes caccae, Bacteroides salyersiae, Bacteroides fragilis, Bacteroides uniformis, Bacteroides eggerthii, Clostridium* sp., *Parabacteroides goldsteinii*, and *Bacteroides* sp. In some embodiments of the compositions provided herein, the purified bacterial mixture comprises at least 2, at least 3, at least 4, at least 5, at least 6, at least 7, at least 8, at least 9, or at least 10 bacterial strains.

In one aspect, the disclosure provides compositions comprising a purified bacterial mixture comprising two or more bacterial strains of species selected from the group consisting of *Bacteroides cellulosilyticus, Bacteroides clarus, Anaerostipes caccae, Bacteroides salyersiae, Bacteroides fragilis, Bacteroides uniformis, Bacteroides eggerthii, Clostridium* sp., *Parabacteroides goldsteinii*, and *Bacteroides* sp. In some embodiments of the compositions provided herein, the purified bacterial mixture comprises at least 3, at least 4, at least 5, at least 6, at least 7, at least 8, at least 9, or at least 10 bacterial strains.

In one aspect, the disclosure provides compositions comprising a purified bacterial mixture comprising one or more bacterial strains of species selected from the group consisting of *Phascolarctobacterium faecium, Fusobacterium ulcerans, Subdoligranulum* sp., and *Eubacterum limosum*. In some embodiments of the compositions provided herein, the purified bacterial mixture comprises at least 2, at least 3, or at least 4 bacterial strains.

In one aspect, the disclosure provides compositions comprising a purified bacterial mixture comprising two or more bacterial strains of species selected from the group consisting of *Phascolarctobacterium faecium, Fusobacterium ulcerans, Subdoligranulum* sp., and *Eubacterum limosum*. In some embodiments of the compositions provided herein, the purified bacterial mixture comprises at least 3, or at least 4 bacterial strains.

In one aspect, the disclosure provides compositions comprising a purified bacterial mixture comprising one or more bacterial strains of species selected from the group consisting of *Bacteroides dorei, Bacteroides uniformis, Paraprevotella xylaniphila, Parabacteroides johnsonii, Alistipes* sp., *Parabacteroides gordonii*, and *Parabacteroides distasonis*. In some embodiments of the compositions provided herein, the purified bacterial mixture comprises at least 2, at least 3, at least 4, at least 5, at least 6, or at least 7 bacterial strains.

In one aspect, the disclosure provides compositions comprising a purified bacterial mixture comprising two or more bacterial strains of species selected from the group consisting of *Bacteroides dorei, Bacteroides uniformis, Paraprevotella xylaniphila, Parabacteroides johnsonii, Alistipes* sp., *Parabacteroides gordonii*, and *Parabacteroides distasonis*. In some embodiments of the compositions provided herein, the purified bacterial mixture comprises at least 3, at least 4, at least 5, at least 6, or at least 7 bacterial strains.

In one aspect, the disclosure provides compositions comprising a purified bacterial mixture comprising one or more bacterial strains comprising 16S rDNA sequences of at least 95% homology to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, or SEQ ID NO:26. In some embodiments of the compositions provided herein, the one or more bacterial strain comprises 16S rDNA sequences of at least 96%, at least 97%, at least 98%, or at least 99% homology to the SEQ ID NOs. In some embodiments of the compositions provided herein, the purified bacterial mixture comprises at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, or at least 26 bacterial strains.

In one aspect, the disclosure provides compositions comprising a purified bacterial mixture comprising one or more bacterial strains comprising 16S rDNA sequences of at least 95% sequence identity with SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, or SEQ ID NO:26. In some embodiments of the compositions provided herein, the one or more bacterial strain comprises 16S rDNA sequences of at least 96%, at least 97%, at least 98%, or at least 99% sequence identity with the SEQ ID NOs. In some embodiments of the compositions provided herein, the purified bacterial mixture comprises at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, or at least 26 bacterial strains.

In one aspect, the disclosure provides compositions comprising a purified bacterial mixture comprising two or more bacterial strains comprising 16S rDNA sequences of at least 95% homology to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, or SEQ ID NO:26. In some embodiments of the compositions provided herein, the bacterial strain comprises 16S rDNA sequences of at least 96%, at least 97%, at least 98%, or at least 99% homology to the SEQ ID NOs. In some embodiments of the compositions provided herein, the purified bacterial mixture comprises at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, or at least 26 bacterial strains.

In one aspect, the disclosure provides compositions comprising a purified bacterial mixture comprising two or more bacterial strains comprising 16S rDNA sequences of at least 95% sequence identity with SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, or SEQ ID NO:26. In some embodiments of the compositions provided herein, the bacterial strain comprises 16S rDNA sequences of at least 96%, at least 97%, at least 98%, or at least 99% sequence identity with the SEQ ID NOs. In some embodiments of the compositions provided herein, the purified bacterial mixture comprises at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, or at least 26 bacterial strains.

In one aspect, the disclosure provides compositions comprising a purified bacterial mixture comprising two or more bacterial strains comprising 16S rDNA sequences of at least 97% homology to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, or SEQ ID NO:26. In some embodiments of the compositions provided herein, the purified bacterial mixture comprises at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, or at least 26 bacterial strains.

In one aspect, the disclosure provides compositions comprising a purified bacterial mixture comprising two or more bacterial strains comprising 16S rDNA sequences of at least 97% sequence identity with SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, or SEQ ID NO:26. In some embodiments of the compositions provided herein, the purified bacterial mixture comprises at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, or at least 26 bacterial strains.

In one aspect, the disclosure provides compositions comprising a purified bacterial mixture comprising one or more bacterial strains comprising 16S rDNA sequences of at least 95% homology to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, or SEQ ID NO:21. In some embodiments of the compositions provided herein, the one or more bacterial strain comprises 16S rDNA sequences of at least 96%, at least 97%, at least 98%, or at least 99% homology to the SEQ ID NOs. In some embodiments of the compositions provided herein, the purified bacterial mixture comprises at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, or at least 21 bacterial strains.

In one aspect, the disclosure provides compositions comprising a purified bacterial mixture comprising one or more bacterial strains comprising 16S rDNA sequences of at least 95% sequence identity with SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, or SEQ ID NO:21. In some embodiments of the compositions provided herein, the one or more bacterial strain comprises 16S rDNA sequences of at least 96%, at least 97%, at least 98%, or at least 99% sequence identity with the SEQ ID NOs. In some embodiments of the compositions provided herein, the purified bacterial mixture comprises at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, or at least 21 bacterial strains.

In one aspect, the disclosure provides compositions comprising a purified bacterial mixture comprising two or more bacterial strains comprising 16S rDNA sequences of at least 95% homology to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, or SEQ ID NO:21. In some embodiments of the compositions provided herein, the bacterial strain comprises 16S rDNA sequences of at least 96%, at least 97%, at least 98%, or at least 99% homology to the SEQ ID NOs. In some embodiments of the compositions provided herein, the purified bacterial mixture comprises at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, or at least 21 bacterial strains.

In one aspect, the disclosure provides compositions comprising a purified bacterial mixture comprising two or more bacterial strains comprising 16S rDNA sequences of at least 95% sequence identity with SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, or SEQ ID NO:21. In some embodiments of the compositions provided herein, the bacterial strain comprises 16S rDNA sequences of at least 96%, at least 97%, at least 98%, or at least 99% sequence identity with the SEQ ID NOs. In some embodiments of the compositions provided herein, the purified bacterial mixture comprises at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, or at least 21 bacterial strains.

In one aspect, the disclosure provides compositions comprising a purified bacterial mixture comprising two or more bacterial strains comprising 16S rDNA sequences of at least 97% homology to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, or SEQ ID NO:21. In some embodiments of the compositions provided herein, the purified bacterial mixture comprises at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, or at least 21 bacterial strains.

In one aspect, the disclosure provides compositions comprising a purified bacterial mixture comprising two or more bacterial strains comprising 16S rDNA sequences of at least 97% sequence identity with SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, or SEQ ID NO:21. In some embodiments of the compositions provided herein, the purified bacterial mixture comprises at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, or at least 21 bacterial strains. In one aspect, the disclosure provides compositions comprising a purified bacterial mixture comprising one or more bacterial strains comprising 16S rDNA sequences of at least 95% homology to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, or SEQ ID NO:11. In some embodiments of the compositions provided herein, the one or more bacterial strain comprises 16S rDNA sequences of at least 96%, at least 97%, at least 98%, or at least 99% homology to the SEQ ID NOs. In some embodiments of the compositions provided herein, the purified bacterial mixture comprises at least 2, at least 3, at least 4, at least 5, at least 6, at least 7, at least 8, at least 9, at least 10, or at least 11 bacterial strains.

In one aspect, the disclosure provides compositions comprising a purified bacterial mixture comprising one or more bacterial strains comprising 16S rDNA sequences of at least 95% sequence identity with SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, or SEQ ID NO:11. In some embodiments of the compositions provided herein, the one or more bacterial strain comprises 16S rDNA sequences of at least 96%, at least 97%, at least 98%, or at least 99% sequence identity with SEQ ID NOs. In some embodiments of the compositions provided herein, the purified bacterial mixture comprises at least 2, at least 3, at least 4, at least 5, at least 6, at least 7, at least 8, at least 9, at least 10, or at least 11 bacterial strains.

In one aspect, the disclosure provides compositions comprising a purified bacterial mixture comprising two or more bacterial strains comprising 16S rDNA sequences of at least 95% homology to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, or SEQ ID NO:11. In some embodiments of the compositions provided herein, the bacterial strain comprises 16S rDNA sequences of at least 96%, at least 97%, at least 98%, or at least 99% homology to the SEQ ID NOs. In some embodiments of the compositions provided herein, the purified bacterial mixture comprises at least 3, at least 4, at least 5, at least 6, at least 7, at least 8, at least 9, at least 10, or at least 11 bacterial strains.

In one aspect, the disclosure provides compositions comprising a purified bacterial mixture comprising two or more bacterial strains comprising 16S rDNA sequences of at least 95% sequence identity with SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, or SEQ ID NO:11. In some embodiments of the compositions provided herein, the bacterial strain comprises 16S rDNA sequences of at least 96%, at least 97%, at least 98%, or at least 99% sequence identity with the SEQ ID NOs. In some embodiments of the compositions provided herein, the purified bacterial mixture comprises at least 3, at least 4, at least 5, at least 6, at least 7, at least 8, at least 9, at least 10, or at least 11 bacterial strains.

In one aspect, the disclosure provides compositions comprising a purified bacterial mixture comprising two or more bacterial strains comprising 16S rDNA sequences of at least 95% sequence identity with SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, or SEQ ID NO:64. In some embodiments of the compositions provided herein, the bacterial strain comprises 16S rDNA sequences of at least 96%, at least 97%, at least 98%, or at least 99% sequence identity with the SEQ ID NOs. In some embodiments of the compositions provided herein, the purified bacterial mixture comprises at least 3, at least 4, at least 5, at least 6, at least 7, at least 8, at least 9, at least 10, or at least 11 bacterial strains.

In one aspect, the disclosure provides compositions comprising a purified bacterial mixture comprising two or more bacterial strains comprising 16S rDNA sequences of at least 97% homology to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, or SEQ ID NO:11. In some embodiments of the compositions provided herein, the purified bacterial mixture comprises at least 3, at least 4, at least 5, at least 6, at least 7, at least 8, at least 9, at least 10, or at least 11 bacterial strains.

In one aspect, the disclosure provides compositions comprising a purified bacterial mixture comprising bacterial strains comprising 16S rDNA sequences of at least 97% homology to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, and SEQ ID NO:11.

In one aspect, the disclosure provides compositions comprising a purified bacterial mixture comprising:

a bacterial strain comprising a 16S rDNA sequence of at least 97% homology to SEQ ID NO:1, a bacterial strain comprising a 16S rDNA sequence of at least 97% homology to SEQ ID NO:2, a bacterial strain comprising a 16S rDNA sequence of at least 97% homology to SEQ ID NO:3, a bacterial strain comprising a 16S rDNA sequence of at least 97% homology to SEQ ID NO:4, a bacterial strain comprising a 16S rDNA sequence of at least 97% homology to SEQ ID NO:5, a bacterial strain comprising a 16S rDNA sequence of at least 97% homology to SEQ ID NO:6, a bacterial strain comprising a 16S rDNA sequence of at least 97% homology to SEQ ID NO:7, a bacterial strain comprising a 16S rDNA sequence of at least 97% homology to SEQ ID NO:8, a bacterial strain comprising a 16S rDNA sequence of at least 97% homology to SEQ ID NO:9, a bacterial strain comprising a 16S rDNA sequence of at least 97% homology to SEQ ID NO:10, and a bacterial strain comprising a 16S rDNA sequence of at least 97% homology to SEQ ID NO:11.

In one aspect, the disclosure provides compositions comprising a purified bacterial mixture consisting of bacterial strains comprising 16S rDNA sequences of at least 97% homology to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, and SEQ ID NO:11.

In one aspect, the disclosure provides compositions comprising a purified bacterial mixture consisting of:

a bacterial strain comprising a 16S rDNA sequence of at least 97% homology to SEQ ID NO:1, a bacterial strain comprising a 16S rDNA sequence of at least 97% homology to SEQ ID NO:2, a bacterial strain comprising a 16S rDNA sequence of at least 97% homology to SEQ ID NO:3, a bacterial strain comprising a 16S rDNA sequence of at least 97% homology to SEQ ID NO:4, a bacterial strain comprising a 16S rDNA sequence of at least 97% homology to SEQ ID NO:5, a bacterial strain comprising a 16S rDNA sequence of at least 97% homology to SEQ ID NO:6, a bacterial strain comprising a 16S rDNA sequence of at least 97% homology to SEQ ID NO:7, a bacterial strain comprising a 16S rDNA sequence of at least 97% homology to SEQ ID NO:8, a bacterial strain comprising a 16S rDNA sequence of at least 97% homology to SEQ ID NO:9, a bacterial strain comprising a 16S rDNA sequence of at least 97% homology to SEQ ID NO:10, and a bacterial strain comprising a 16S rDNA sequence of at least 97% homology to SEQ ID NO:11.

In one aspect, the disclosure provides compositions comprising a purified bacterial mixture comprising two or more bacterial strains comprising 16S rDNA sequences of at least 97% sequence identity with SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, or SEQ ID NO:11. In some embodiments of the compositions provided herein, the purified bacterial mixture comprises at least 3, at least 4, at least 5, at least 6, at least 7, at least 8, at least 9, at least 10, or at least 11 bacterial strains.

In one aspect, the disclosure provides compositions comprising a purified bacterial mixture comprising two or more bacterial strains comprising 16S rDNA sequences of at least 99% sequence identity with SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, or SEQ ID NO:11. In some embodiments of the compositions provided herein, the purified bacterial mixture comprises at least 3, at least 4, at least 5, at least 6, at least 7, at least 8, at least 9, at least 10, or at least 11 bacterial strains.

In one aspect, the disclosure provides compositions comprising a purified bacterial mixture comprising bacterial strains comprising 16S rDNA sequences of at least 97% sequence identity with SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, and SEQ ID NO:11.

In one aspect, the disclosure provides compositions comprising a purified bacterial mixture comprising bacterial strains comprising 16S rDNA sequences of at least 99% sequence identity with SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, and SEQ ID NO:11.

In one aspect, the disclosure provides compositions comprising a purified bacterial mixture comprising:

a bacterial strain comprising a 16S rDNA sequence of at least 97% sequence identity with SEQ ID NO:1, a bacterial strain comprising a 16S rDNA sequence of at least 97% sequence identity with SEQ ID NO:2, a bacterial strain comprising a 16S rDNA sequence of at least 97% sequence identity with SEQ ID NO:3, a bacterial strain comprising a 16S rDNA sequence of at least 97% sequence identity with SEQ ID NO:4, a bacterial strain comprising a 16S rDNA sequence of at least 97% sequence identity with SEQ ID NO:5, a bacterial strain comprising a 16S rDNA sequence of at least 97% sequence identity with SEQ ID NO:6, a bacterial strain comprising a 16S rDNA sequence of at least 97% sequence identity with SEQ ID NO:7, a bacterial strain comprising a 16S rDNA sequence of at least 97% sequence identity with SEQ ID NO:8, a bacterial strain comprising a 16S rDNA sequence of at least 97% sequence identity with SEQ ID NO:9, a bacterial strain comprising a 16S rDNA sequence of at least 97% sequence identity with SEQ ID NO:10, and a bacterial strain comprising a 16S rDNA sequence of at least 97% sequence identity with SEQ ID NO:11.

In one aspect, the disclosure provides compositions comprising a purified bacterial mixture comprising:

a bacterial strain comprising a 16S rDNA sequence of at least 99% sequence identity with SEQ ID NO:1, a bacterial strain comprising a 16S rDNA sequence of at least 99% sequence identity with SEQ ID NO:2, a bacterial strain comprising a 16S rDNA sequence of at least 99% sequence identity with SEQ ID NO:3, a bacterial strain comprising a 16S rDNA sequence of at least 99% sequence identity with SEQ ID NO:4, a bacterial strain comprising a 16S rDNA sequence of at least 99% sequence identity with SEQ ID NO:5, a bacterial strain comprising a 16S rDNA sequence of at least 99% sequence identity with SEQ ID NO:6, a bacterial strain comprising a 16S rDNA sequence of at least 99% sequence identity with SEQ ID NO:7, a bacterial strain comprising a 16S rDNA sequence of at least 99% sequence identity with SEQ ID NO:8, a bacterial strain comprising a 16S rDNA sequence of at least 99% sequence identity with SEQ ID NO:9, a bacterial strain comprising a 16S rDNA sequence of at least 99% sequence identity with SEQ ID NO:10, and a bacterial strain comprising a 16S rDNA sequence of at least 99% sequence identity with SEQ ID NO:11.

In one aspect, the disclosure provides compositions comprising a purified bacterial mixture comprising bacterial strains comprising 16S rDNA sequences with SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, and SEQ ID NO:11.

In one aspect, the disclosure provides compositions comprising a purified bacterial mixture consisting of bacterial strains comprising 16S rDNA sequences of at least 97% sequence identity with SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, and SEQ ID NO:11.

In one aspect, the disclosure provides compositions comprising a purified bacterial mixture consisting of bacterial strains comprising 16S rDNA sequences of at least 99% sequence identity with SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, and SEQ ID NO:11.

In one aspect, the disclosure provides compositions comprising a purified bacterial mixture consisting of:

a bacterial strain comprising a 16S rDNA sequence of at least 97% sequence identity with SEQ ID NO:1, a bacterial strain comprising a 16S rDNA sequence of at least 97% sequence identity with SEQ ID NO:2, a bacterial strain comprising a 16S rDNA sequence of at least 97% sequence identity with SEQ ID NO:3, a bacterial strain comprising a 16S rDNA sequence of at least 97% sequence identity with SEQ ID NO:4, a bacterial strain comprising a 16S rDNA sequence of at least 97% sequence identity with SEQ ID NO:5, a bacterial strain comprising a 16S rDNA sequence of at least 97% sequence identity with SEQ ID NO:6, a bacterial strain comprising a 16S rDNA sequence of at least 97% sequence identity with SEQ ID NO:7, a bacterial strain comprising a 16S rDNA sequence of at least 97% sequence identity with SEQ ID NO:8, a bacterial strain comprising a 16S rDNA sequence of at least 97% sequence identity with SEQ ID NO:9, a bacterial strain comprising a 16S rDNA sequence of at least 97% sequence identity with SEQ ID NO:10, and a bacterial strain comprising a 16S rDNA sequence of at least 97% sequence identity with SEQ ID NO:11.

In one aspect, the disclosure provides compositions comprising a purified bacterial mixture consisting of:

a bacterial strain comprising a 16S rDNA sequence of at least 99% sequence identity with SEQ ID NO:1, a bacterial strain comprising a 16S rDNA sequence of at least 99% sequence identity with SEQ ID NO:2, a bacterial strain comprising a 16S rDNA sequence of at least 99% sequence identity with SEQ ID NO:3, a bacterial strain comprising a 16S rDNA sequence of at least 99% sequence identity with SEQ ID NO:4, a bacterial strain comprising a 16S rDNA sequence of at least 99% sequence identity with SEQ ID NO:5, a bacterial strain comprising a 16S rDNA sequence of at least 99% sequence identity with SEQ ID NO:6, a bacterial strain comprising a 16S rDNA sequence of at least 99% sequence identity with SEQ ID NO:7, a bacterial strain comprising a 16S rDNA sequence of at least 99% sequence identity with SEQ ID NO:8, a bacterial strain comprising a 16S rDNA sequence of at least 97% sequence identity with SEQ ID NO:9, a bacterial strain comprising a 16S rDNA sequence of at least 99% sequence identity with SEQ ID NO:10, and a bacterial strain comprising a 16S rDNA sequence of at least 99% sequence identity with SEQ ID NO:11.

In one aspect, the disclosure provides compositions comprising a purified bacterial mixture consisting of bacterial strains comprising 16S rDNA sequences with SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, and SEQ ID NO:11.

In one aspect, the disclosure provides compositions comprising a purified bacterial mixture comprising two or more bacterial strains comprising 16S rDNA sequences of at least 97% sequence identity with SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, or SEQ ID NO:64. In some embodiments of the compositions provided herein, the purified bacterial mixture comprises at least 3, at least 4, at least 5, at least 6, at least 7, at least 8, at least 9, at least 10, or at least 11 bacterial strains.

In one aspect, the disclosure provides compositions comprising a purified bacterial mixture comprising two or more bacterial strains comprising 16S rDNA sequences of at least 99% sequence identity with SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, or SEQ ID NO:64. In some embodiments of the compositions provided herein, the purified bacterial mixture comprises at least 3, at least 4, at least 5, at least 6, at least 7, at least 8, at least 9, at least 10, or at least 11 bacterial strains.

In one aspect, the disclosure provides compositions comprising a purified bacterial mixture comprising bacterial strains comprising 16S rDNA sequences of at least 97% sequence identity with SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, or SEQ ID NO:64.

In one aspect, the disclosure provides compositions comprising a purified bacterial mixture comprising bacterial strains comprising 16S rDNA sequences of at least 99% sequence identity with SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, or SEQ ID NO:64.

In one aspect, the disclosure provides compositions comprising a purified bacterial mixture comprising:

a bacterial strain comprising a 16S rDNA sequence of at least 97% sequence identity with SEQ ID NO:54, a bacterial strain comprising a 16S rDNA sequence of at least 97% sequence identity with SEQ ID NO:55, a bacterial strain comprising a 16S rDNA sequence of at least 97% sequence identity with SEQ ID NO:56, a bacterial strain comprising a 16S rDNA sequence of at least 97% sequence identity with SEQ ID NO:57, a bacterial strain comprising a 16S rDNA sequence of at least 97% sequence identity with SEQ ID NO:58, a bacterial strain comprising a 16S rDNA sequence of at least 97% sequence identity with SEQ ID NO:59, a bacterial strain comprising a 16S rDNA sequence of at least 97% sequence identity with SEQ ID NO:60, a bacterial strain comprising a 16S rDNA sequence of at least 97% sequence identity with SEQ ID NO:61, a bacterial strain comprising a 16S rDNA sequence of at least 97% sequence identity with SEQ ID NO:62, a bacterial strain comprising a 16S rDNA sequence of at least 97% sequence identity with SEQ ID NO:63, and a bacterial strain comprising a 16S rDNA sequence of at least 97% sequence identity with SEQ ID NO:64.

In one aspect, the disclosure provides compositions comprising a purified bacterial mixture comprising:

a bacterial strain comprising a 16S rDNA sequence of at least 99% sequence identity with SEQ ID NO:54, a bacterial strain comprising a 16S rDNA sequence of at least 99% sequence identity with SEQ ID NO:55, a bacterial strain comprising a 16S rDNA sequence of at least 99% sequence identity with SEQ ID NO:56, a bacterial strain comprising a 16S rDNA sequence of at least 99% sequence identity with SEQ ID NO:57, a bacterial strain comprising a 16S rDNA sequence of at least 99% sequence identity with SEQ ID NO:58, a bacterial strain comprising a 16S rDNA sequence of at least 99% sequence identity with SEQ ID NO:59, a bacterial strain comprising a 16S rDNA sequence of at least 99% sequence identity with SEQ ID NO:60, a bacterial strain comprising a 16S rDNA sequence of at least 99% sequence identity with SEQ ID NO:61, a bacterial strain comprising a 16S rDNA sequence of at least 99% sequence identity with SEQ ID NO:62, a bacterial strain comprising a 16S rDNA sequence of at least 99% sequence identity with SEQ ID NO:63, and a bacterial strain comprising a 16S rDNA sequence of at least 99% sequence identity with SEQ ID NO:64.

In one aspect, the disclosure provides compositions comprising a purified bacterial mixture comprising bacterial strains comprising 16S rDNA sequences with SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, or SEQ ID NO:64.

In one aspect, the disclosure provides compositions comprising a purified bacterial mixture consisting of bacterial strains comprising 16S rDNA sequences of at least 97% sequence identity with SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, or SEQ ID NO:64.

In one aspect, the disclosure provides compositions comprising a purified bacterial mixture consisting of bacterial strains comprising 16S rDNA sequences of at least 99% sequence identity with SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, or SEQ ID NO:64.

In one aspect, the disclosure provides compositions comprising a purified bacterial mixture consisting of:

a bacterial strain comprising a 16S rDNA sequence of at least 97% sequence identity with SEQ ID NO:54, a bacterial strain comprising a 16S rDNA sequence of at least 97% sequence identity with SEQ ID NO:55, a bacterial strain comprising a 16S rDNA sequence of at least 97% sequence identity with SEQ ID NO:56, a bacterial strain comprising a 16S rDNA sequence of at least 97% sequence identity with SEQ ID NO:57, a bacterial strain comprising a 16S rDNA sequence of at least 97% sequence identity with SEQ ID NO:58, a bacterial strain comprising a 16S rDNA sequence of at least 97% sequence identity with SEQ ID NO:59, a bacterial strain comprising a 16S rDNA sequence of at least 97% sequence identity with SEQ ID NO:60, a bacterial strain comprising a 16S rDNA sequence of at least 97% sequence identity with SEQ ID NO:61, a bacterial strain comprising a 16S rDNA sequence of at least 97% sequence identity with SEQ ID NO:62, a bacterial strain comprising a 16S rDNA sequence of at least 97% sequence identity with SEQ ID NO:63, and a bacterial strain comprising a 16S rDNA sequence of at least 97% sequence identity with SEQ ID NO:64.

In one aspect, the disclosure provides compositions comprising a purified bacterial mixture consisting of:

a bacterial strain comprising a 16S rDNA sequence of at least 99% sequence identity with SEQ ID NO:54, a bacterial strain comprising a 16S rDNA sequence of at least 99% sequence identity with SEQ ID NO:55, a bacterial strain comprising a 16S rDNA sequence of at least 99% sequence identity with SEQ ID NO:56, a bacterial strain comprising a 16S rDNA sequence of at least 99% sequence identity with SEQ ID NO:57, a bacterial strain comprising a 16S rDNA sequence of at least 99% sequence identity with SEQ ID NO:58, a bacterial strain comprising a 16S rDNA sequence of at least 99% sequence identity with SEQ ID NO:59, a bacterial strain comprising a 16S rDNA sequence of at least 99% sequence identity with SEQ ID NO:60, a bacterial strain comprising a 16S rDNA sequence of at least 99% sequence identity with SEQ ID NO:61, a bacterial strain comprising a 16S rDNA sequence of at least 99% sequence identity with SEQ ID NO:62, a bacterial strain comprising a 16S rDNA sequence of at least 99% sequence identity with SEQ ID NO:63, and a bacterial strain comprising a 16S rDNA sequence of at least 99% sequence identity with SEQ ID NO:64.

In one aspect, the disclosure provides compositions comprising a purified bacterial mixture consisting of bacterial strains comprising 16S rDNA sequences with SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, or SEQ ID NO:64.

In one aspect, the disclosure provides compositions comprising a purified bacterial mixture comprising one or more bacterial strains comprising 16S rDNA sequences of at least 95% homology to SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, or SEQ ID NO:26. In some embodiments of the compositions provided herein, the one or more bacterial strain comprises 16S rDNA sequences of at least 96%, at least 97%, at least 98%, or at least 99% homology to the SEQ ID NOs. In some embodiments of the compositions provided herein, the purified bacterial mixture comprises at least 2, at least 3, at least 4, at least 5, at least 6, at least 7, at least 8, at least 9, at least 10, at least 11, at least 12, at least 13, at least 14, or at least 15 bacterial strains.

In one aspect, the disclosure provides compositions comprising a purified bacterial mixture comprising one or more bacterial strains comprising 16S rDNA sequences of at least 95% sequence identity with SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, or SEQ ID NO:26. In some embodiments of the compositions provided herein, the one or more bacterial strain comprises 16S rDNA sequences of at least 96%, at least 97%, at least 98%, or at least 99% sequence identity with the SEQ ID NOs. In some embodiments of the compositions provided herein, the purified bacterial mixture comprises at least 2, at least 3, at least 4, at least 5, at least 6, at least 7, at least 8, at least 9, at least 10, at least 11, at least 12, at least 13, at least 14, or at least 15 bacterial strains.

In one aspect, the disclosure provides compositions comprising a purified bacterial mixture comprising two or more bacterial strains comprising 16S rDNA sequences of at least 95% homology to SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, or SEQ ID NO:26. In some embodiments of the compositions provided herein, the bacterial strain comprises 16S rDNA sequences of at least 96%, at least 97%, at least 98%, or at least 99% homology to the SEQ ID NOs. In some embodiments of the compositions provided herein, the purified bacterial mixture comprises at least 3, at least 4, at least 5, at least 6, at least 7, at least 8, at least 9, at least 10, at least 11, at least 12, at least 13, at least 14, or at least 15 bacterial strains.

In one aspect, the disclosure provides compositions comprising a purified bacterial mixture comprising two or more bacterial strains comprising 16S rDNA sequences of at least 95% sequence identity with SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, or SEQ ID NO:26. In some embodiments of the compositions provided herein, the bacterial strain comprises 16S rDNA sequences of at least 96%, at least 97%, at least 98%, or at least 99% sequence identity with the SEQ ID NOs. In some embodiments of the compositions provided herein, the purified bacterial mixture comprises at least 3, at least 4, at least 5, at least 6, at least 7, at least 8, at least 9, at least 10, at least 11, at least 12, at least 13, at least 14, or at least 15 bacterial strains.

In one aspect, the disclosure provides compositions comprising a purified bacterial mixture comprising two or more bacterial strains comprising 16S rDNA sequences of at least 97% homology to SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, or SEQ ID NO:26. In some embodiments of the compositions provided herein, the purified bacterial mixture comprises at least 3, at least 4, at least 5, at least 6, at least 7, at least 8, at least 9, at least 10, at least 11, at least 12, at least 13, at least 14, or at least 15 bacterial strains.

In one aspect, the disclosure provides compositions comprising a purified bacterial mixture comprising two or more bacterial strains comprising 16S rDNA sequences of at least 97% sequence identity with SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, or SEQ ID NO:26. In some embodiments of the compositions provided herein, the purified bacterial mixture comprises at least 3, at least 4, at least 5, at least 6, at least 7, at least 8, at least 9, at least 10, at least 11, at least 12, at least 13, at least 14, or at least 15 bacterial strains.

In one aspect, the disclosure provides compositions comprising one or more bacterial strains comprising 16S rDNA sequences of at least 95% homology to SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, or SEQ ID NO:21. In some embodiments of the compositions provided herein, the one or more bacterial strain comprises 16S rDNA sequences of at least 96%, at least 97%, at least 98%, or at least 99% homology to the SEQ ID NOs. In some embodiments of the compositions provided herein, the purified bacterial mixture comprises at least 2, at least 3, at least 4, at least 5, at least 6, at least 7, at least 8, at least 9, or at least 10 bacterial strains.

In one aspect, the disclosure provides compositions comprising one or more bacterial strains comprising 16S rDNA sequences of at least 95% sequence identity with SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, or SEQ ID NO:21. In some embodiments of the compositions provided herein, the one or more bacterial strain comprises 16S rDNA sequences of at least 96%, at least 97%, at least 98%, or at least 99% sequence identity with the SEQ ID NOs. In some embodiments of the compositions provided herein, the purified bacterial mixture comprises at least 2, at least 3, at least 4, at least 5, at least 6, at least 7, at least 8, at least 9, or at least 10 bacterial strains.

In one aspect, the disclosure provides compositions comprising two or more bacterial strains comprising 16S rDNA sequences of at least 95% homology to SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, or SEQ ID NO:21. In some embodiments of the compositions provided herein, the bacterial strain comprises 16S rDNA sequences of at least 96%, at least 97%, at least 98%, or at least 99% homology to the SEQ ID NOs. In some embodiments of the compositions provided herein, the purified bacterial mixture comprises at least 3, at least 4, at least 5, at least 6, at least 7, at least 8, at least 9, or at least 10 bacterial strains.

In one aspect, the disclosure provides compositions comprising two or more bacterial strains comprising 16S rDNA sequences of at least 95% sequence identity with SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, or SEQ ID NO:21. In some embodiments of the compositions provided herein, the bacterial strain comprises 16S rDNA sequences of at least 96%, at least 97%, at least 98%, or at least 99% sequence identity with the SEQ ID NOs. In some embodiments of the compositions provided herein, the purified bacterial mixture comprises at least 3, at least 4, at least 5, at least 6, at least 7, at least 8, at least 9, or at least 10 bacterial strains.

In one aspect, the disclosure provides compositions comprising two or more bacterial strains comprising 16S rDNA sequences of at least 97% homology to SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, or SEQ ID NO:21. In some embodiments of the compositions provided herein, the purified bacterial mixture comprises at least 3, at least 4, at least 5, at least 6, at least 7, at least 8, at least 9, or at least 10 bacterial strains.

In one aspect, the disclosure provides compositions comprising two or more bacterial strains comprising 16S rDNA sequences of at least 97% sequence identity with SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, or SEQ ID NO:21. In some embodiments of the compositions provided herein, the purified bacterial mixture comprises at least 3, at least 4, at least 5, at least 6, at least 7, at least 8, at least 9, or at least 10 bacterial strains.

In one aspect, the disclosure provides compositions comprising a purified bacterial mixture comprising one or more bacterial strains comprising 16S rDNA sequences of at least 95% homology to SEQ ID NO:1, SEQ ID NO:2, SEQ ID NO:5, or SEQ ID NO:10.

In some embodiments of the compositions provided herein, the one or more bacterial strain comprises 16S rDNA sequences of at least 96%, at least 97%, at least 98%, or at least 99% homology to the SEQ ID NOs. In some embodiments of the compositions provided herein, the purified bacterial mixture comprises at least 2, at least 3, or at least 4 bacterial strains.

In one aspect, the disclosure provides compositions comprising a purified bacterial mixture comprising one or more bacterial strains comprising 16S rDNA sequences of at least 95% sequence identity with SEQ ID NO:1, SEQ ID NO:2, SEQ ID NO:5, or SEQ ID NO:10. In some embodiments of the compositions provided herein, the one or more bacterial strain comprises 16S rDNA sequences of at least 96%, at least 97%, at least 98%, or at least 99% sequence identity with the SEQ ID NOs. In some embodiments of the compositions provided herein, the purified bacterial mixture comprises at least 2, at least 3, or at least 4 bacterial strains.

In one aspect, the disclosure provides compositions comprising a purified bacterial mixture comprising two or more bacterial strains comprising 16S rDNA sequences of at least 95% homology to SEQ ID NO:1, SEQ ID NO:2, SEQ ID NO:5, or SEQ ID NO:10.

In some embodiments of the compositions provided herein, the bacterial strain comprises 16S rDNA sequences of at least 96%, at least 97%, at least 98%, or at least 99% homology to the SEQ ID NOs. In some embodiments of the compositions provided herein, the purified bacterial mixture comprises at least 3, or at least 4 bacterial strains.

In one aspect, the disclosure provides compositions comprising a purified bacterial mixture comprising two or more bacterial strains comprising 16S rDNA sequences of at least 95% sequence identity with SEQ ID NO:1, SEQ ID NO:2, SEQ ID NO:5, or SEQ ID NO:10. In some embodiments of the compositions provided herein, the bacterial strain comprises 16S rDNA sequences of at least 96%, at least 97%, at least 98%, or at least 99% sequence identity with the SEQ ID NOs. In some embodiments of the compositions provided herein, the purified bacterial mixture comprises at least 3, or at least 4 bacterial strains.

In one aspect, the disclosure provides compositions comprising a purified bacterial mixture comprising two or more bacterial strains comprising 16S rDNA sequences of at least 97% homology to SEQ ID NO:1, SEQ ID NO:2, SEQ ID NO:5, or SEQ ID NO:10.

In some embodiments of the compositions provided herein, the purified bacterial mixture comprises at least 3, or at least 4 bacterial strains.

In one aspect, the disclosure provides compositions comprising a purified bacterial mixture comprising two or more bacterial strains comprising 16S rDNA sequences of at least 97% sequence identity with the SEQ ID NO:1, SEQ ID NO:2, SEQ ID NO:5, or SEQ ID NO:10. In some embodiments of the compositions provided herein, the purified bacterial mixture comprises at least 3, or at least 4 bacterial strains.

In one aspect, the disclosure provides compositions comprising a purified bacterial mixture comprising one or more bacterial strains comprising 16S rDNA sequences of at least 95% homology to SEQ ID NO:3, SEQ ID NO:4, SEQ ID NO:6, SEQ ID NO:7, SEQ ID NO:8, SEQ ID NO:9, or SEQ ID NO:11. In some embodiments of the compositions provided herein, the one or more bacterial strain comprises 16S rDNA sequences of at least 96%, at least 97%, at least 98%, or at least 99% homology to the SEQ ID NOs. In some embodiments of the compositions provided herein, the purified bacterial mixture comprises at least 2, at least 3, at least 4, at least 5, at least 6, or at least 7 bacterial strains.

In one aspect, the disclosure provides compositions comprising a purified bacterial mixture comprising one or more bacterial strains comprising 16S rDNA sequences of at least 95% sequence identity with SEQ ID NO:3, SEQ ID NO:4, SEQ ID NO:6, SEQ ID NO:7, SEQ ID NO:8, SEQ ID NO:9, or SEQ ID NO:11. In some embodiments of the compositions provided herein, the one or more bacterial strain comprises 16S rDNA sequences of at least 96%, at least 97%, at least 98%, or at least 99% sequence identity with the SEQ ID NOs. In some embodiments of the compositions provided herein, the purified bacterial mixture comprises at least 2, at least 3, at least 4, at least 5, at least 6, or at least 7 bacterial strains.

In one aspect, the disclosure provides compositions comprising a purified bacterial mixture comprising two or more bacterial strains comprising 16S rDNA sequences of at least 95% homology to SEQ ID NO:3, SEQ ID NO:4, SEQ ID NO:6, SEQ ID NO:7, SEQ ID NO:8, SEQ ID NO:9, or SEQ ID NO:11. In some embodiments of the compositions provided herein, the bacterial strain comprises 16S rDNA sequences of at least 96%, at least 97%, at least 98%, or at least 99% homology to the SEQ ID NOs. In some embodiments of the compositions provided herein, the purified bacterial mixture comprises at least 3, at least 4, at least 5, at least 6, or at least 7 bacterial strains.

In one aspect, the disclosure provides compositions comprising a purified bacterial mixture comprising two or more bacterial strains comprising 16S rDNA sequences of at least 95% sequence identity with SEQ ID NO:3, SEQ ID NO:4, SEQ ID NO:6, SEQ ID NO:7, SEQ ID NO:8, SEQ ID NO:9, or SEQ ID NO:11. In some embodiments of the compositions provided herein, the bacterial strain comprises 16S rDNA sequences of at least 96%, at least 97%, at least 98%, or at least 99% sequence identity with the SEQ ID NOs. In some embodiments of the compositions provided herein, the purified bacterial mixture comprises at least 3, at least 4, at least 5, at least 6, or at least 7 bacterial strains.

In one aspect, the disclosure provides compositions comprising a purified bacterial mixture comprising two or more bacterial strains comprising 16S rDNA sequences of at least 97% homology to SEQ ID NO:3, SEQ ID NO:4, SEQ ID NO:6, SEQ ID NO:7, SEQ ID NO:8, SEQ ID NO:9, or SEQ ID NO:11. In some embodiments of the compositions provided herein, the purified bacterial mixture comprises at least 3, at least 4, at least 5, at least 6, or at least 7 bacterial strains.

In one aspect, the disclosure provides compositions comprising a purified bacterial mixture comprising two or more bacterial strains comprising 16S rDNA sequences of at least 97% sequence identity with SEQ ID NO:3, SEQ ID NO:4, SEQ ID NO:6, SEQ ID NO:7, SEQ ID NO:8, SEQ ID NO:9, or SEQ ID NO:11. In some embodiments of the compositions provided herein, the purified bacterial mixture comprises at least 3, at least 4, at least 5, at least 6, or at least 7 bacterial strains.

In one aspect, the disclosure provides compositions comprising a purified bacterial mixture comprising one or more bacterial strains comprising 16S rDNA sequences of at least 95% homology to SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, or SEQ ID NO:52. In some embodiments of the compositions provided herein, the one or more bacterial strain comprises 16S rDNA sequences of at least 96%, at least 97%, at least 98%, or at least 99% homology to the SEQ ID NOs. In some embodiments of the compositions provided herein, the purified bacterial mixture comprises at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, or at least 26 bacterial strains.

In one aspect, the disclosure provides compositions comprising a purified bacterial mixture comprising one or more bacterial strains comprising 16S rDNA sequences of at least 95% sequence identity with SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, or SEQ ID NO:52. In some embodiments of the compositions provided herein, the one or more bacterial strain comprises 16S rDNA sequences of at least 96%, at least 97%, at least 98%, or at least 99% sequence identity with the SEQ ID NOs. In some embodiments of the compositions provided herein, the purified bacterial mixture comprises at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, or at least 26 bacterial strains.

In one aspect, the disclosure provides compositions comprising a purified bacterial mixture comprising two or more bacterial strains comprising 16S rDNA sequences of at least 95% homology to SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, or SEQ ID NO:52. In some embodiments of the compositions provided herein, the bacterial strain comprises 16S rDNA sequences of at least 96%, at least 97%, at least 98%, or at least 99% homology to the SEQ ID NOs. In some embodiments of the compositions provided herein, the purified bacterial mixture comprises at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, or at least 26 bacterial strains.

In one aspect, the disclosure provides compositions comprising a purified bacterial mixture comprising two or more bacterial strains comprising 16S rDNA sequences of at least 95% sequence identity with SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, or SEQ ID NO:52. In some embodiments of the compositions provided herein, the bacterial strain comprises 16S rDNA sequences of at least 96%, at least 97%, at least 98%, or at least 99% sequence identity with the SEQ ID NOs. In some embodiments of the compositions provided herein, the purified bacterial mixture comprises at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, or at least 26 bacterial strains.

In one aspect, the disclosure provides compositions comprising a purified bacterial mixture comprising two or more bacterial strains comprising 16S rDNA sequences of at least 97% homology to SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, or SEQ ID NO:52. In some embodiments of the compositions provided herein, the purified bacterial mixture comprises at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, or at least 26 bacterial strains.

In one aspect, the disclosure provides compositions comprising a purified bacterial mixture comprising two or more bacterial strains comprising 16S rDNA sequences of at least 97% sequence identity with SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, or SEQ ID NO:52. In some embodiments of the compositions provided herein, the purified bacterial mixture comprises at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, or at least 26 bacterial strains.

In one aspect, the disclosure provides compositions comprising a purified bacterial mixture comprising one or more bacterial strains comprising 16S rDNA sequences of at least 95% homology to SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, and SEQ ID NO:47. In some embodiments of the compositions provided herein, the one or more bacterial strain comprises 16S rDNA sequences of at least 96%, at least 97%, at least 98%, or at least 99% homology to the SEQ ID NOs. In some embodiments of the compositions provided herein, the purified bacterial mixture comprises at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, or at least 21 bacterial strains.

In one aspect, the disclosure provides compositions comprising a purified bacterial mixture comprising one or more bacterial strains comprising 16S rDNA sequences of at least 95% sequence identity with SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, and SEQ ID NO:47. In some embodiments of the compositions provided herein, the one or more bacterial strain comprises 16S rDNA sequences of at least 96%, at least 97%, at least 98%, or at least 99% sequence identity with the SEQ ID NOs. In some embodiments of the compositions provided herein, the purified bacterial mixture comprises at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, or at least 21 bacterial strains.

In one aspect, the disclosure provides compositions comprising a purified bacterial mixture comprising two or more bacterial strains comprising 16S rDNA sequences of at least 95% homology to SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, and SEQ ID NO:47. In some embodiments of the compositions provided herein, the bacterial strain comprises 16S rDNA sequences of at least 96%, at least 97%, at least 98%, or at least 99% homology to the SEQ ID NOs. In some embodiments of the compositions provided herein, the purified bacterial mixture comprises at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, or at least 21 bacterial strains.

In one aspect, the disclosure provides compositions comprising a purified bacterial mixture comprising two or more bacterial strains comprising 16S rDNA sequences of at least 95% sequence identity with SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, and SEQ ID NO:47. In some embodiments of the compositions provided herein, the bacterial strain comprises 16S rDNA sequences of at least 96%, at least 97%, at least 98%, or at least 99% sequence identity with the SEQ ID NOs. In some embodiments of the compositions provided herein, the purified bacterial mixture comprises at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, or at least 21 bacterial strains.

In one aspect, the disclosure provides compositions comprising a purified bacterial mixture comprising two or more bacterial strains comprising 16S rDNA sequences of at least 97% homology to SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, and SEQ ID NO:47. In some embodiments of the compositions provided herein, the purified bacterial mixture comprises at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, or at least 21 bacterial strains.

In one aspect, the disclosure provides compositions comprising a purified bacterial mixture comprising two or more bacterial strains comprising 16S rDNA sequences of at least 97% sequence identity with SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, and SEQ ID NO:47. In some embodiments of the compositions provided herein, the purified bacterial mixture comprises at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, or at least 21 bacterial strains.

In one aspect, the disclosure provides compositions comprising a purified bacterial mixture comprising one or more bacterial strains comprising 16S rDNA sequences of at least 95% homology to SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, or SEQ ID NO:37. In some embodiments of the compositions provided herein, the one or more bacterial strain comprises 16S rDNA sequences of at least 96%, at least 97%, at least 98%, or at least 99% homology to the SEQ ID NOs. In some embodiments of the compositions provided herein, the purified bacterial mixture comprises at least 2, at least 3, at least 4, at least 5, at least 6, at least 7, at least 8, at least 9, at least 10, or at least 11 bacterial strains.

In one aspect, the disclosure provides compositions comprising a purified bacterial mixture comprising one or more bacterial strains comprising 16S rDNA sequences of at least 95% sequence identity with SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, or SEQ ID NO:37. In some embodiments of the compositions provided herein, the one or more bacterial strain comprises 16S rDNA sequences of at least 96%, at least 97%, at least 98%, or at least 99% sequence identify with the SEQ ID NOs. In some embodiments of the compositions provided herein, the purified bacterial mixture comprises at least 2, at least 3, at least 4, at least 5, at least 6, at least 7, at least 8, at least 9, at least 10, or at least 11 bacterial strains.

In one aspect, the disclosure provides compositions comprising a purified bacterial mixture comprising two or more bacterial strains comprising 16S rDNA sequences of at least 95% homology to SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, or SEQ ID NO:37. In some embodiments of the compositions provided herein, the bacterial strain comprises 16S rDNA sequences of at least 96%, at least 97%, at least 98%, or at least 99% homology to the SEQ ID NOs. In some embodiments of the compositions provided herein, the purified bacterial mixture comprises at least 3, at least 4, at least 5, at least 6, at least 7, at least 8, at least 9, at least 10, or at least 11 bacterial strains.

In one aspect, the disclosure provides compositions comprising a purified bacterial mixture comprising two or more bacterial strains comprising 16S rDNA sequences of at least 95% sequence identity with SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, or SEQ ID NO:37. In some embodiments of the compositions provided herein, the bacterial strain comprises 16S rDNA sequences of at least 96%, at least 97%, at least 98%, or at least 99% sequence identity with the SEQ ID NOs. In some embodiments of the compositions provided herein, the purified bacterial mixture comprises at least 3, at least 4, at least 5, at least 6, at least 7, at least 8, at least 9, at least 10, or at least 11 bacterial strains.

In one aspect, the disclosure provides compositions comprising a purified bacterial mixture comprising two or more bacterial strains comprising 16S rDNA sequences of at least 97% homology to SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, or SEQ ID NO:37. In some embodiments of the compositions provided herein, the purified bacterial mixture comprises at least 3, at least 4, at least 5, at least 6, at least 7, at least 8, at least 9, at least 10, or at least 11 bacterial strains.

In one aspect, the disclosure provides compositions comprising a purified bacterial mixture comprising two or more bacterial strains comprising 16S rDNA sequences of at least 97% sequence identity with SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, or SEQ ID NO:37. In some embodiments of the compositions provided herein, the purified bacterial mixture comprises at least 3, at least 4, at least 5, at least 6, at least 7, at least 8, at least 9, at least 10, or at least 11 bacterial strains.

In one aspect, the disclosure provides compositions comprising a purified bacterial mixture comprising one or more bacterial strains comprising 16S rDNA sequences of at least 95% homology to SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, or SEQ ID NO:52. In some embodiments of the compositions provided herein, the one or more bacterial strain comprises 16S rDNA sequences of at least 96%, at least 97%, at least 98%, or at least 99% homology to the SEQ ID NOs. In some embodiments of the compositions provided herein, the purified bacterial mixture comprises at least 2, at least 3, at least 4, at least 5, at least 6, at least 7, at least 8, at least 9, at least 10, at least 11, at least 12, at least 13, at least 14, or at least 15 bacterial strains.

In one aspect, the disclosure provides compositions comprising a purified bacterial mixture comprising one or more bacterial strains comprising 16S rDNA sequences of at least 95% sequence identity with SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, or SEQ ID NO:52. In some embodiments of the compositions provided herein, the one or more bacterial strain comprises 16S rDNA sequences of at least 96%, at least 97%, at least 98%, or at least 99% sequence identity with the SEQ ID NOs. In some embodiments of the compositions provided herein, the purified bacterial mixture comprises at least 2, at least 3, at least 4, at least 5, at least 6, at least 7, at least 8, at least 9, at least 10, at least 11, at least 12, at least 13, at least 14, or at least 15 bacterial strains.

In one aspect, the disclosure provides compositions comprising a purified bacterial mixture comprising two or more bacterial strains comprising 16S rDNA sequences of at least 95% homology to SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, or SEQ ID NO:52. In some embodiments of the compositions provided herein, the bacterial strain comprises 16S rDNA sequences of at least 96%, at least 97%, at least 98%, or at least 99% homology to the SEQ ID NOs. In some embodiments of the compositions provided herein, the purified bacterial mixture comprises at least 3, at least 4, at least 5, at least 6, at least 7, at least 8, at least 9, at least 10, at least 11, at least 12, at least 13, at least 14, or at least 15 bacterial strains.

In one aspect, the disclosure provides compositions comprising a purified bacterial mixture comprising two or more bacterial strains comprising 16S rDNA sequences of at least 95% sequence identity with SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, or SEQ ID NO:52. In some embodiments of the compositions provided herein, the bacterial strain comprises 16S rDNA sequences of at least 96%, at least 97%, at least 98%, or at least 99% sequence identity with the SEQ ID NOs. In some embodiments of the compositions provided herein, the purified bacterial mixture comprises at least 3, at least 4, at least 5, at least 6, at least 7, at least 8, at least 9, at least 10, at least 11, at least 12, at least 13, at least 14, or at least 15 bacterial strains.

In one aspect, the disclosure provides compositions comprising a purified bacterial mixture comprising two or more bacterial strains comprising 16S rDNA sequences of at least 95% homology to SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, or SEQ ID NO:52. In some embodiments of the compositions provided herein, the purified bacterial mixture comprises at least 3, at least 4, at least 5, at least 6, at least 7, at least 8, at least 9, at least 10, at least 11, at least 12, at least 13, at least 14, or at least 15 bacterial strains.

In one aspect, the disclosure provides compositions comprising a purified bacterial mixture comprising two or more bacterial strains comprising 16S rDNA sequences of at least 95% sequence identity with SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, or SEQ ID NO:52. In some embodiments of the compositions provided herein, the purified bacterial mixture comprises at least 3, at least 4, at least 5, at least 6, at least 7, at least 8, at least 9, at least 10, at least 11, at least 12, at least 13, at least 14, or at least 15 bacterial strains.

In one aspect, the disclosure provides compositions comprising a purified bacterial mixture comprising one or more bacterial strains comprising 16S rDNA sequences of at least 97% homology to SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, or SEQ ID NO:47. In some embodiments of the compositions provided herein, the one or more bacterial strain comprises 16S rDNA sequences of at least 96%, at least 97%, at least 98%, or at least 99% homology to the SEQ ID NOs. In some embodiments of the compositions provided herein, the purified bacterial mixture comprises at least 2, at least 3, at least 4, at least 5, at least 6, at least 7, at least 8, at least 9, or at least 10 bacterial strains.

In one aspect, the disclosure provides compositions comprising a purified bacterial mixture comprising one or more bacterial strains comprising 16S rDNA sequences of at least 97% sequence identity with SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, or SEQ ID NO:47. In some embodiments of the compositions provided herein, the one or more bacterial strain comprises 16S rDNA sequences of at least 96%, at least 97%, at least 98%, or at least 99% sequence identity with the SEQ ID NOs. In some embodiments of the compositions provided herein, the purified bacterial mixture comprises at least 2, at least 3, at least 4, at least 5, at least 6, at least 7, at least 8, at least 9, or at least 10 bacterial strains.

In one aspect, the disclosure provides compositions comprising a purified bacterial mixture comprising two or more bacterial strains comprising 16S rDNA sequences of at least 95% homology to SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, or SEQ ID NO:47. In some embodiments of the compositions provided herein, the bacterial strain comprises 16S rDNA sequences of at least 96%, at least 97%, at least 98%, or at least 99% homology to the SEQ ID NOs. In some embodiments of the compositions provided herein, the purified bacterial mixture comprises at least 3, at least 4, at least 5, at least 6, at least 7, at least 8, at least 9, or at least 10 bacterial strains.

In one aspect, the disclosure provides compositions comprising a purified bacterial mixture comprising two or more bacterial strains comprising 16S rDNA sequences of at least 95% sequence identity with SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, or SEQ ID NO:47. In some embodiments of the compositions provided herein, the bacterial strain comprises 16S rDNA sequences of at least 96%, at least 97%, at least 98%, or at least 99% sequence identity with the SEQ ID NOs. In some embodiments of the compositions provided herein, the purified bacterial mixture comprises at least 3, at least 4, at least 5, at least 6, at least 7, at least 8, at least 9, or at least 10 bacterial strains.

In one aspect, the disclosure provides compositions comprising a purified bacterial mixture comprising two or more bacterial strains comprising 16S rDNA sequences of at least 97% homology to SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, or SEQ ID NO:47. In some embodiments of the compositions provided herein, the purified bacterial mixture comprises at least 3, at least 4, at least 5, at least 6, at least 7, at least 8, at least 9, or at least 10 bacterial strains.

In one aspect, the disclosure provides compositions comprising a purified bacterial mixture comprising two or more bacterial strains comprising 16S rDNA sequences of at least 97% sequence identity with SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, or SEQ ID NO:47. In some embodiments of the compositions provided herein, the purified bacterial mixture comprises at least 3, at least 4, at least 5, at least 6, at least 7, at least 8, at least 9, or at least 10 bacterial strains.

In one aspect, the disclosure provides compositions comprising a purified bacterial mixture comprising one or more bacterial strains comprising 16S rDNA sequences of at least 95% homology to SEQ ID NO:27, SEQ ID NO:28, SEQ ID NO:31 or SEQ ID NO:36. In some embodiments of the compositions provided herein, the one or more bacterial strain comprises 16S rDNA sequences of at least 96%, at least 97%, at least 98%, or at least 99% homology to the SEQ ID NOs. In some embodiments of the compositions provided herein, the purified bacterial mixture comprises at least 2, at least 3, or at least 4 bacterial strains.

In one aspect, the disclosure provides compositions comprising a purified bacterial mixture comprising one or more bacterial strains comprising 16S rDNA sequences of at least 95% sequence identity with SEQ ID NO:27, SEQ ID NO:28, SEQ ID NO:31 or SEQ ID NO:36. In some embodiments of the compositions provided herein, the one or more bacterial strain comprises 16S rDNA sequences of at least 96%, at least 97%, at least 98%, or at least 99% sequence identity with the SEQ ID NOs. In some embodiments of the compositions provided herein, the purified bacterial mixture comprises at least 2, at least 3, or at least 4 bacterial strains.

In one aspect, the disclosure provides compositions comprising a purified bacterial mixture comprising two or more bacterial strains comprising 16S rDNA sequences of at least 95% homology to SEQ ID NO:27, SEQ ID NO:28, SEQ ID NO:31 or SEQ ID NO:36.

In some embodiments of the compositions provided herein, the bacterial strain comprises 16S rDNA sequences of at least 96%, at least 97%, at least 98%, or at least 99% homology to the SEQ ID NOs. In some embodiments of the compositions provided herein, the purified bacterial mixture comprises at least 3, or at least 4 bacterial strains.

In one aspect, the disclosure provides compositions comprising a purified bacterial mixture comprising two or more bacterial strains comprising 16S rDNA sequences of at least 95% sequence identity with SEQ ID NO:27, SEQ ID NO:28, SEQ ID NO:31 or SEQ ID NO:36. In some embodiments of the compositions provided herein, the bacterial strain comprises 16S rDNA sequences of at least 96%, at least 97%, at least 98%, or at least 99% sequence identity with the SEQ ID NOs. In some embodiments of the compositions provided herein, the purified bacterial mixture comprises at least 3, or at least 4 bacterial strains.

In one aspect, the disclosure provides compositions comprising a purified bacterial mixture comprising two or more bacterial strains comprising 16S rDNA sequences of at least 97% homology to SEQ ID NO:27, SEQ ID NO:28, SEQ ID NO:31 or SEQ ID NO:36.

In some embodiments of the compositions provided herein, the purified bacterial mixture comprises at least 3, or at least 4 bacterial strains.

In one aspect, the disclosure provides compositions comprising a purified bacterial mixture comprising two or more bacterial strains comprising 16S rDNA sequences of at least 97% sequence identity with SEQ ID NO:27, SEQ ID NO:28, SEQ ID NO:31 or SEQ ID NO:36. In some embodiments of the compositions provided herein, the purified bacterial mixture comprises at least 3, or at least 4 bacterial strains.

In one aspect, the disclosure provides compositions comprising a purified bacterial mixture comprising one or more bacterial strains comprising 16S rDNA sequences of at least 95% homology to SEQ ID NO:29, SEQ ID NO:30, SEQ ID NO:32, SEQ ID NO:33, SEQ ID NO:34, SEQ ID NO:35, or SEQ ID NO:37. In some embodiments of the compositions provided herein, the one or more bacterial strain comprises 16S rDNA sequences of at least 96%, at least 97%, at least 98%, or at least 99% homology to the SEQ ID NOs. In some embodiments of the compositions provided herein, the purified bacterial mixture comprises at least 2, at least 3, at least 4, at least 5, at least 6, or at least 7 bacterial strains.

In one aspect, the disclosure provides compositions comprising a purified bacterial mixture comprising one or more bacterial strains comprising 16S rDNA sequences of at least 95% sequence identity with SEQ ID NO:29, SEQ ID NO:30, SEQ ID NO:32, SEQ ID NO:33, SEQ ID NO:34, SEQ ID NO:35, or SEQ ID NO:37. In some embodiments of the compositions provided herein, the one or more bacterial strain comprises 16S rDNA sequences of at least 96%, at least 97%, at least 98%, or at least 99% sequence identity with the SEQ ID NOs. In some embodiments of the compositions provided herein, the purified bacterial mixture comprises at least 2, at least 3, at least 4, at least 5, at least 6, or at least 7 bacterial strains.

In one aspect, the disclosure provides compositions comprising a purified bacterial mixture comprising two or more bacterial strains comprising 16S rDNA sequences of at least 95% homology to SEQ ID NO:29, SEQ ID NO:30, SEQ ID NO:32, SEQ ID NO:33, SEQ ID NO:34, SEQ ID NO:35, or SEQ ID NO:37. In some embodiments of the compositions provided herein, the bacterial strain comprises 16S rDNA sequences of at least 96%, at least 97%, at least 98%, or at least 99% homology to the SEQ ID NOs. In some embodiments of the compositions provided herein, the purified bacterial mixture comprises at least 3, at least 4, at least 5, at least 6, or at least 7 bacterial strains.

In one aspect, the disclosure provides compositions comprising a purified bacterial mixture comprising two or more bacterial strains comprising 16S rDNA sequences of at least 95% sequence identity with SEQ ID NO:29, SEQ ID NO:30, SEQ ID NO:32, SEQ ID NO:33, SEQ ID NO:34, SEQ ID NO:35, or SEQ ID NO:37. In some embodiments of the compositions provided herein, the bacterial strain comprises 16S rDNA sequences of at least 96%, at least 97%, at least 98%, or at least 99% sequence identity with the SEQ ID NOs. In some embodiments of the compositions provided herein, the purified bacterial mixture comprises at least 3, at least 4, at least 5, at least 6, or at least 7 bacterial strains.

In one aspect, the disclosure provides compositions comprising a purified bacterial mixture comprising two or more bacterial strains comprising 16S rDNA sequences of at least 97% homology to SEQ ID NO:29, SEQ ID NO:30, SEQ ID NO:32, SEQ ID NO:33, SEQ ID NO:34, SEQ ID NO:35, or SEQ ID NO:37. In some embodiments of the compositions provided herein, the purified bacterial mixture comprises at least 3, at least 4, at least 5, at least 6, or at least 7 bacterial strains.

In one aspect, the disclosure provides compositions comprising a purified bacterial mixture comprising two or more bacterial strains comprising 16S rDNA sequences of at least 97% sequence identity with SEQ ID NO:29, SEQ ID NO:30, SEQ ID NO:32, SEQ ID NO:33, SEQ ID NO:34, SEQ ID NO:35, or SEQ ID NO:37. In some embodiments of the compositions provided herein, the purified bacterial mixture comprises at least 3, at least 4, at least 5, at least 6, or at least 7 bacterial strains.

In some embodiments of the compositions provided herein, at least 50% of the bacterial strains belong to the order of Bacteriodales. In some embodiments of the compositions provided herein, one or more of the bacterial strains belong to the order of Bacteriodales and one or more of the bacterial strains belong to the order of Clostridiales. In some embodiments of the compositions provided herein, at least 25% of the bacterial strains belong to the family of Bacteroidaceae. In some embodiments of the compositions provided herein, one or more of the bacterial strains belongs to the genus *Bacteroides.*

In some embodiments of the compositions provided herein, the composition does not include bacterial strains that belong to the order of Bacteriodales.

In some embodiments of the compositions provided herein, one or more of the bacterial strains is a spore-former. In some embodiments of the compositions provided herein, one or more of the bacterial strains is in spore form. In some embodiments of the compositions provided herein, one or more of the bacterial strains is a non-spore former.

In some embodiments of the compositions provided herein, the composition comprises only obligate anaerobic bacterial strains. In some embodiments of the compositions provided herein, one or more of the bacterial strains does not have an antibiotic resistance gene. In some embodiments of the compositions provided herein, the antibiotic resistance gene renders the bacterial strain resistant to vancomycin. In some embodiments of the compositions provided herein, the bacterial strains are human-derived bacteria. In some embodiments of the compositions provided herein, the bacterial strains are derived from more than one human donor. In some embodiments of the compositions provided herein, the composition induces proliferation and/or accumulation of CD8+ T-cells.

In some embodiments of the compositions provided herein, the composition is a pharmaceutical composition. In some embodiments of the pharmaceutical compositions provided herein, the pharmaceutical composition comprises a pharmaceutically acceptable excipient. In some embodiments of the pharmaceutical compositions provided herein, the pharmaceutical composition is formulated for oral administration. In some embodiments of the pharmaceutical compositions provided herein, the pharmaceutical composition is formulated for rectal administration. In some embodiments of the pharmaceutical compositions provided herein, the pharmaceutical composition is formulated for delivery to the intestine. In some embodiments of the pharmaceutical compositions provided herein, the pharmaceutical composition is formulated for delivery to the colon. In some embodiments of the pharmaceutical compositions provided herein, one or more of the bacterial strains is lyophilized. In some embodiments of the pharmaceutical compositions provided herein, the pharmaceutical composition is in the form of a capsule. In some embodiments of the pharmaceutical compositions provided herein, the pharmaceutical composition further comprises a pH sensitive composition comprising one or more enteric polymers.

In one aspect, the disclosure provides a food product comprising any of the compositions provided herein and a nutrient.

In some embodiments of the compositions provided herein, the composition further comprises one or more anticancer agents. In some embodiments of the compositions provided herein, the anticancer agent is a chemotherapy agent. In some embodiments of the compositions provided herein, the anticancer agent is cancer immunotherapy agent. In some embodiments of the compositions provided herein, the cancer immunotherapy agent is an immune checkpoint inhibitor. In some embodiments of the compositions provided herein, the immune checkpoint inhibitor is a PD-1 inhibitor, PD-L-1 inhibitor, or CTLA-4 inhibitor. In some embodiments of the compositions provided herein, the immune checkpoint inhibitor is a PD-1 inhibitor. In some embodiments of the compositions provided herein, the immune checkpoint inhibitor is a CTLA-4 inhibitor. In some embodiments of the compositions provided herein, the composition further comprises one or more cytokines. In some embodiments of the compositions provided herein, the cytokine is IL-2, IL-15, or IL-21. In some embodiments of the compositions provided herein, the composition further comprises one or more costimulatory agents. In some embodiments of the compositions provided herein, the costimulatory agent is a CD-28, OX-40, 4-1BB, or CD40 antibody.

In some embodiments of the compositions provided herein, the composition further comprises one or more vaccines. In some embodiments of the compositions provided herein, the vaccine is a dendritic cell vaccine. In some embodiments of the compositions provided herein, the composition is combined with adoptive cell transfer therapy. In some embodiments of the compositions provided herein, the adoptive cell transfer therapy is the use of engineered T-cell receptors or chimeric antigen receptors.

In one aspect, the disclosure provides a vaccine comprising any of the compositions provided herein and an antigen. In some embodiments of the vaccines provided herein, the antigen is an HIV antigen. In some embodiments of the vaccines provided herein, the antigen is a hepatitis antigen.

In some embodiments of the compositions provided herein, the composition further comprises one or more anti-inflammatory agents. In some embodiments of the compositions provided herein, the anti-inflammatory agent is an NSAID.

In some embodiments of the compositions provided herein, administration of the composition to a subject results in the induction of proliferation and/or accumulation of CD8+ T-cells in the intestine of the subject. In some embodiments of the compositions provided herein, administration of the composition to a subject results in an increase in IFN γ production in the intestine of a subject. In some embodiments of the compositions provided herein, administration of the composition to a subject results in the presence of one or more bacterial strains of the administered composition in the intestine of the subject. In some embodiments of the compositions provided herein, the one or more bacterial strains of the administered composition was not previously present in the intestine of the subject. In some embodiments of the compositions provided herein, administration of the composition to a subject results in the engraftment of one or more bacterial strains of the administered composition in the intestine of the subject. In some embodiments of the compositions provided herein, the one or more bacterial strains of the administered composition was not previously engrafted in the intestine of the subject. In some embodiments of the compositions provided herein, administration of the composition to a subject results in an increase in the number of the bacterial strains of the administered composition in the intestine of the subject. In some embodiments of the compositions provided herein, administration of the composition to a subject results in an increase in the number of the bacterial strains of the administered composition engrafted in the intestine of the subject. In some embodiments of the compositions provided herein, administration of the composition to a subject results in an increase in the amount of bacteria of the bacterial strains of the administered composition in the intestine of the subject. In some embodiments of the compositions provided herein, administration of the composition to a subject results in an increase in the amount of bacteria of the bacterial strains of the administered composition engrafted in the intestine of the subject.

In one aspect, the disclosure provides a method of treating a disease in a subject comprising administering any of the compositions provided herein to the subject in an effective amount to treat the disease. In some embodiments of the methods provided herein, the administration of the composition to the subject results in the induction of proliferation and/or accumulation of CD8+ T-cells in the intestine of the subject. In some embodiments of the methods provided herein, the proliferation and/or accumulation of CD8+ T-cells in the intestine of the subject is increased by at least 10%, at least 20%, at least 30%, at least 40%, at least 50%, at least 100%, or at least 200% when compared to the proliferation and/or accumulation of CD8+ T-cells in the intestine of the subject before the administration of the composition. In some embodiments of the methods provided herein, the administration of the composition to the subject results in an increase of IFN γ production in the intestine of the subject when compared to the IFN γ production in the intestine of the subject before the administration of the composition. In some embodiments of the methods provided herein, the administration of the composition to the subject results in an increase of IFN γ production in the intestine of the subject by at least 10%, at least 20%, at least 30%, at least 40%, at least 50%, at least 100%, or at least 200% when compared to the IFN production in the intestine of the subject before the administration of the composition.

In some embodiments of the methods provided herein, the subject has cancer. In some embodiments of the methods provided herein, the cancer is carcinoma, glioma, mesothelioma, melanoma, lymphoma, leukemia, adenocarcinoma, breast cancer, ovarian cancer, cervical cancer, glioblastoma, multiple myeloma, prostate cancer, Burkitt's lymphoma, head and neck cancer, colon cancer, colorectal cancer, non-small cell lung cancer, small cell lung cancer, cancer of the esophagus, stomach cancer, pancreatic cancer, hepatobiliary cancer, cancer of the gallbladder, cancer of the small intestine, rectal cancer, kidney cancer, bladder cancer, prostate cancer, penile cancer, urethral cancer, testicular cancer, vaginal cancer, uterine cancer, thyroid cancer, parathyroid cancer, adrenal cancer, pancreatic endocrine cancer, carcinoid cancer, bone cancer, skin cancer, retinoblastomas, Hodgkin's lymphoma, non-Hodgkin's lymphoma, Kaposi's sarcoma, multicentric Castleman's disease, AIDS-associated primary effusion lymphoma, neuroectodermal tumors, or rhabdomyosarcoma. In some embodiments of the methods provided herein, the cancer is prostate cancer, bladder cancer, non-small cell lung cancer, urothelial carcinoma, melanoma, or renal cell carcinoma. In some embodiments of the methods provided herein, the subject is undergoing radiation treatment.

In some embodiments of the methods provided herein, the method further includes administering one or more anticancer agents. In some embodiments of the methods provided herein, the anticancer agent is a chemotherapy agent. In some embodiments of the methods provided herein, the anticancer agent is a cancer immunotherapy agent.

In some embodiments of the methods provided herein, the cancer immunotherapy agent is an immune checkpoint inhibitor. In some embodiments of the methods provided herein, the immune checkpoint inhibitor is a PD-1 inhibitor, PD-L-1 inhibitor, or CTLA-4 inhibitor. In some embodiments of the methods provided herein, the immune checkpoint inhibitor is a PD-1 inhibitor. In some embodiments of the methods provided herein, the immune checkpoint inhibitor is a CTLA-4 inhibitor.

In some embodiments of the methods provided herein, the method further includes administering one or more cytokines. In some embodiments of the methods provided herein the cytokine is IL-2, IL-15, or IL-21.

In some embodiments of the methods provided herein, the method further includes administering one or more costimulatory agents. In some embodiments of the methods provided herein the costimulatory agent is a CD-28, OX-40, 4-1BB, or CD40 antibody.

In some embodiments of the methods provided herein, the method further includes administering one or more vaccines. In some embodiments of the methods provided herein, the vaccine is a dendritic cell vaccine.

In some embodiments of the methods provided herein, the method further includes administering adoptive cell transfer therapy. In some embodiments of the methods provided herein, the adoptive cell transfer therapy is the use of engineered T-cell receptors or chimeric antigen receptors.

In some embodiments of the methods provided herein, the subject has an infectious disease. In some embodiments of the methods provided herein, the infectious disease is a bacterial infection, a viral infection, a parasitic infection, or a fungal infection. In some embodiments of the methods provided herein, the infectious disease is a viral infection. In some embodiments of the methods provided herein, the viral infection is HIV. In some embodiments of the methods provided herein, the infection is an infection by a hepatitis virus.

In some embodiments of the methods provided herein, the subject has an autoimmune disease or an allergic disease.

In some embodiments of the methods provided herein, the composition further includes one or more anti-inflammatory agents. In some embodiments of the methods provided herein, the anti-inflammatory is an NSAID. In some embodiments of the methods provided herein, the composition may be administered as one or more dose.

In one aspect, the disclosure provides a method that includes determining if one or more bacterial species of any of the compositions provided herein are present in the intestine of a subject, wherein if less than 100%, less than 90%, less than 80%, less than 70%, less than 60%, less than 50%, less than 40%, less than 30%, less than 20%, less than 10%, or none of the bacterial species are present, the composition is administered to the subject.

In some embodiments of the methods provided herein, the subject is undergoing, or will be undergoing, cancer treatment.

In one aspect, the disclosure provides a method for determining if a subject is expected to respond positively to cancer treatment, wherein the method includes determining if one or more bacterial species of any of the compositions provided herein are present in the intestine of a subject, wherein if less than 100%, less than 90%, less than 80%, less than 70%, less than 60%, less than 50%, less than 40%, less than 30%, less than 20%, less than 10%, or none of the bacterial species are present, the subject is not expected to respond positively to cancer treatment.

In some embodiments of the methods provided herein, the cancer treatment is cancer immunotherapy treatment.

In one aspect, the disclosure provides a method for reducing the risk of a viral infection in a subject, wherein the method includes determining if one or more bacterial species of any of the compositions provided herein are present in the intestine of a subject, wherein if less than 100%, less than 90%, less than 80%, less than 70%, less than 60%, less than 50%, less than 40%, less than 30%, less than 20%, less than 10%, or none of the bacterial species are present, the composition is administered to the subject, thereby reducing the risk of a viral infection in the subject.

In some embodiments of the methods provided herein, determining the presence of one or more of the bacterial species is done by sequencing fecal matter of the subject. In some embodiments of the methods provided herein, determining the presence of one or more of the bacterial species is done by sequencing the 16S rDNA sequences of fecal matter of the subject.

In one aspect, the disclosure provides compositions and methods to induce activation of CD8+ IFN γ-producing T-cells in the intestinal tract.

In one aspect, the disclosure provides a composition comprising a purified bacterial mixture comprising one or more bacterial strains comprising 16S rDNA sequences of at least 95% homology to the sequences of the following NCBI accession numbers: LN998073, KR822463, CP011531, NR_112945, NZ-ACWW00000000, AB331897, AB261128, NZ-CAEG00000000, AB470343, AB595134, HE974920, NR_112933, AB490801, NZ-ACWB00000000, AY608696, CR626927, AB247141, NR_112935, AB249652, NR_113076 and AF139525. In some embodiments of the compositions provided herein, the purified bacterial mixture comprises at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, or at least 21 bacterial strains. In some embodiments of the compositions provided herein, the one or more bacterial strains comprises 16S rDNA sequences with at least 96%, at least 97%, at least 98%, or at least 99% homology with sequences provided herein.

In one aspect, the disclosure provides a composition that induces or activates CD8+ IFN γ-producing T-cells, the composition comprising (i) one or more purified bacterial strains collected from human stool which possesses resistance to ampicillin, or (ii) a culture supernatant of (i). In some embodiments of the compositions provided herein, the composition comprises (a) a purified bacterial mixture comprising one or more bacterial strains of species selected from the group consisting of

*Phascolarctobacterium faecium*; LN998073,
*Fusobacterium ulcerans*; KR822463,
*Bacteroides dorei*; CP011531,
*Bacteroides uniformis*; NR_112945,
*Subdoligranulum* sp. 4_3_54 A2FAA; NZ-ACWW00000000,
*Paraprevotella xylaniphila*; AB331897,
*Parabacteroides johnsonii*; AB261128,
*Alistipes* sp. JC136; NZ-CAEG00000000,
*Parabacteroides gordonii*; AB470343,
*Eubacterium limosum*; AB595134,
*Parabacteroides distasonis*; HE974920,
*Bacteroides cellulosilyticus*; NR_112933,
*Bacteroides clarus*; AB490801,
*Anaerostipes* sp. 3_2_56 FAA; NZ-ACWB00000000,
*Bacteroides salyersiae*; AY608696,
*Bacteroides fragilis*; CR626927,
*Bacteroides uniformis*; AB247141,
*Bacteroides eggerthii*; NR_112935,
*Clostridium* sp. TM-40; AB249652,
*Parabacteroides goldsteinii*; NR_113076, and
*Bacteroides* sp. AR29; AF139525, or (b) one or more bacterial strains comprising a 16S rRNA sequence having at least 97% homology to a 16S rRNA sequence of a species selected from the group consisting of

*Phascolarctobacterium faecium*; LN998073,
*Fusobacterium ulcerans*; KR822463,
*Bacteroides dorei*; CP011531,
*Bacteroides uniformis*; NR_112945,
*Subdoligranulum* sp. 4_3_54 A2FAA; NZ-ACWW00000000,
*Paraprevotella xylaniphila*; AB331897,
*Parabacteroides johnsonii*; AB261128,
*Alistipes* sp. JC136; NZ-CAEG00000000,
*Parabacteroides gordonii*; AB470343,
*Eubacterium limosum*; AB595134,
*Parabacteroides distasonis*; HE974920,
*Bacteroides cellulosilyticus*; NR_112933,
*Bacteroides clarus*; AB490801,
*Anaerostipes* sp. 3_2_56 FAA; NZ-ACWB00000000,
*Bacteroides salyersiae*; AY608696,
*Bacteroides fragilis*; CR626927,

*Bacteroides uniformis*; AB247141,
*Bacteroides eggerthii*; NR_112935,
*Clostridium* sp. TM-40; AB249652,
*Parabacteroides goldsteinii*; NR_113076, and
*Bacteroides* sp. AR29; AF139525

In some embodiments of the compositions provided herein, the composition comprises a purified bacterial mixture comprising (a) one or more bacterial strains of species selected from the group consisting of

*Phascolarctobacterium faecium*; LN998073,
*Fusobacterium ulcerans*; KR822463,
*Bacteroides dorei*; CP011531,
*Bacteroides uniformis*; NR_112945,
*Subdoligranulum* sp. 4_3_54 A2FAA; NZ-ACWW00000000,
*Paraprevotella xylaniphila*; AB331897,
*Parabacteroides johnsonii*; AB261128,
*Alistipes* sp. JC136; NZ-CAEG00000000,
*Parabacteroides gordonii*; AB470343,
*Eubacterium limosum*; AB595134, and
*Parabacteroides distasonis*; HE974920; or (b) one or more bacterial strains comprising a 16S rRNA sequence of a species belonging to the group consisting of

*Phascolarctobacterium faecium*; LN998073,
*Fusobacterium ulcerans*; KR822463,
*Bacteroides dorei*; CP011531,
*Bacteroides uniformis*; NR_112945,
*Subdoligranulum* sp. 4_3_54 A2FAA; NZ-ACWW00000000,
*Paraprevotella xylaniphila*; AB331897,
*Parabacteroides johnsonii*; AB261128,
*Alistipes* sp. JC136; NZ-CAEG00000000,
*Parabacteroides gordonii*; AB470343,
*Eubacterium limosum*; AB595134, and
*Parabacteroides distasonis*; HE974920.

In some embodiments of the compositions provided herein, the CD8+ IFN γ-producing T-cells express CD103 or Granzyme B.

In some embodiments of the compositions provided herein, the composition activates the immune system.

In one aspect, the disclosure provides a method for activating the immune system, the method comprising administration of one or more of the compositions provided herein.

In one aspect, the disclosure provides a method for activating CD8+ IFN γ-producing T-cells, the method comprising administration of one or more of the compositions provided herein to a subject.

In one aspect, the disclosure provides a method for inducing the proliferation and/or accumulation of CD8+ T cells in the intestine, comprising administering to a subject any one or more of the compositions provided herein, wherein the administering results in the induction of proliferation and/or accumulation of CD8+ T cells in the intestine of the subject.

In one aspect, the disclosure provides a method for assisting in treatment, and/or preventing cancer or viral infection, comprising administering to a subject any one or more of the compositions provided herein, wherein the administering prevents, treats, assists in treatment, and/or prevents cancer or viral infection.

In one aspect, the disclosure provides vaccine compositions which induce immune response against bacterial strains of any one of the compositions disclosed herein.

In one aspect, the disclosure provides a vaccine composition containing antigen derived from constituents and/or metabolites of bacterial species of any one of the compositions provided herein.

In one aspect, the disclosure provides a method for inducing an immune response in a subject, comprising administering to the subject any of the vaccines provided herein, wherein the administering results in the induction of immune response of the subject.

In one aspect, the disclosure provides immune suppressive compositions.

In one aspect, the disclosure provides a composition comprising a chemical substance that possesses antibacterial activity towards bacterial species of any one of the compositions provided herein, or a chemical substance which binds a physiologically active substance secreted from bacterial species of any one of the compositions provided herein.

In some embodiments of the compositions provided herein, administration of the composition to a subject results in suppression of activity of CD8+ and IFN γ-producing T-cells in the subject.

In one aspect, the disclosure provides a method for suppressing CD8+ and IFN γ-producing T-cells in the subject, the method comprising administration of one or more of the compositions provided herein to the subject.

In one aspect, the disclosure provides a method for prevention, treatment or improvement in a disease originated by over-activation of CD8+ and IFN γ-producing T-cells of the subject the method comprising administering to the subject any one or more of the compositions provided herein to the subject.

In one aspect, the disclosure provides substances derived from the bacterial strains disclosed herein. In one aspect, the disclosure provides a physiologically active substance derived from a bacterial species of any one of the compositions provided herein. In one aspect, the disclosure provides a bacterial specific antigen of any one of the bacterial species of any one of the compositions provided herein.

In one aspect, the disclosure provides an antibody that specifically binds a bacterial species of any one of the compositions provided herein.

In one aspect, the disclosure provides a bacterial-specific nucleotide sequence contained in any one of the bacterial species of the compositions provided herein.

In one aspect, the disclosure provides animal models and test kits.

In one aspect, the disclosure provides an animal model comprising a non-human mammal, wherein the intestinal tract of the non-human mammal has been inoculated with the bacterial species of any one of the compositions provided herein. In some embodiments of the animal model provided herein, the non-human mammal has a disease originated by irregularity of CD8+ IFN γ-producing T-cells.

In one aspect, the disclosure provides a kit for evaluating the activation of CD8+ IFN γ-producing T cells, the kit comprising: intestinal epithelial cells, peripheral blood mononuclear cells, and a bacterial species of any one of the compositions provided herein.

In one aspect, the disclosure provides methods of detection of CD8+ IFN γ-producing T cells in the human intestinal tract. In one aspect, the disclosure provides kits for evaluating activation of CD8+ IFN γ-producing T cells. In some embodiments, the kits comprise intestinal epithelial cells, peripheral mononuclear cells, and the bacterial species of any of the compositions described herein.

In one aspect, the disclosure provides a method for screening bacteria or a physiologically active substance derived from human intestinal bacteria, wherein the substance induces activation of CD8+ IFN γ-producing T cells in the intestinal tract, comprising (i) allowing a non-human germ-free animal to ingest a physiologically active substance derived from human intestinal bacteria or bacteria, (ii) detecting the number, or activity of, CD8+ IFN γ-producing T cells in the intestinal tract of the non-human aseptic animal, wherein if activation of CD8+ IFN γ-producing T cells is detected, the physiologically active substance is identified as a substance that can activate CD8+ IFN γ-producing T cells.

In one aspect, the disclosure provides a method for screening bacteria or a physiologically active substance derived from human intestinal bacteria a, wherein the substance induces proliferation or activation of CD8+ IFN γ-producing T cells in intestinal tract, comprising (i) adding a physiologically active substance derived from human intestinal bacteria or bacteria to the intestinal epithelial cells in a system comprising intestinal epithelial cells and peripheral blood mononuclear cells; (ii) detecting the number or activity of CD8+ IFN γ-producing T cells in said system, wherein if the activation of CD8+ IFN γ-producing T cells is detected, the physiologically active substance is identified as a substance that can activate CD8+ IFN γ-producing T cells.

In one aspect, the disclosure provides a method for screening for a substance that induces activation of CD8+ IFN γ-producing T cells in intestinal tract, comprising (i) adding a physiologically active substance derived from bacteria or bacteria contained in a composition provided herein to a system containing intestinal epithelial cells and peripheral blood mononuclear cells, (ii) adding a test substance, (iii) detecting the number or activity of CD8+ IFN γ-producing T cells in said system, wherein if the number or activity of CD8+ IFN γ-producing T cells detected in the is increased, the test substance is identified as a substance that induces activation of CD8+ IFN γ-producing T cells.

In one aspect, the disclosure provides a method for screening a substance that induces activation of CD8+ IFN γ-producing T cells in intestinal tract, comprising (i) the method for screening a non-human animal provided herein, (ii) detecting the number or activity of CD8+ IFN γ-producing T cells in the intestinal tract of the non-human animal, wherein if the number or activity of CD8+ IFN γ-producing T cells detected in the above step is increased, the test substance is identified as a substance that induces activation of CD8+ IFN γ-producing T cells.

In one aspect, the disclosure provides a composition for stimulating immunity, the composition comprising, as an active ingredient, a human intestinal bacterium or a physiologically active substance derived from a bacterium obtained by the screening methods provided herein. In some embodiments of the compositions provided herein, the composition induces the activation of CD8+ IFN γ-producing T cells.

In one aspect, the disclosure provides a vaccine composition comprising, as an active ingredient, human intestinal bacteria obtained by any of the screening methods provided herein, or an antigen specific to said bacterium.

In one aspect, the disclosure provides a method for screening a substance having an activity of inducing or exacerbating a disease caused by CD8+ IFN γ-producing T cells, comprising (i) allowing a test substance to be ingested by a non-human animal provided herein, (ii) detecting the degree of a disease-associated damage caused by CD8+ IFN γ-producing T cells in said non-human animal, wherein the test substance is identified as a substance that induces a disease caused by CD8+ IFN γ-producing T cells when the extent of the lesion detected in the above step is increased as compared to when no compound or placebo was added.

In one aspect, the disclosure provides a composition for inducing or exacerbating a disease caused by CD8+ IFN γ-producing T cells, wherein the composition comprises, as an active ingredient, the substance obtained by any one of the screening methods provided herein.

In one aspect, the disclosure provides a composition comprising a processed human fecal sample, wherein the processed human fecal sample is obtained by contacting a human fecal sample with ampicillin, and wherein the processed human fecal sample induces the proliferation and/or accumulation of CD8+ T-cells. In some embodiments, the disclosure provides a method of treatment of a disease in a subject, the method comprising administering to the subject any one of the compositions provided herein in an effective amount to treat the disease in the subject. In some embodiments of the methods provided herein, the disease is cancer or an infection (e.g., a viral infection).

In one aspect, the disclosure provides a method comprising inoculating a human fecal sample in germ free mice, and determining if the human fecal sample induces the proliferation and/or accumulation of CD8+ T-cells.

In one aspect, the disclosure provides a method for determining if a human fecal sample induces proliferation and/or accumulation of CD8+ T cells, comprising inoculating germ-free mice with a human fecal sample, and determining if the human fecal sample induces the proliferation and/or accumulation of CD8+ T-cells. In one aspect, the disclosure provides a method for identifying a human fecal donor, comprising inoculating germ-free mice with a human fecal sample, and determining if the human fecal sample induces the proliferation and/or accumulation of CD8+ T-cells, wherein if the fecal sample induces the proliferation and/or accumulation of CD8+ T-cells, the human subject is identified as a human fecal donor.

In one aspect, the disclosure provides a method for analyzing expression levels of a marker in lymphocytes in a subject, comprising analyzing the expression levels of the marker, wherein the marker is induced by administering to the subject any of the compositions described herein, wherein the marker is CD44, gp70 MC38 peptide (KSPWFTTL; (SEQ ID NO: 53))-specific TCRB, tumor antigen derived ligand-specific TCRB, CD8, IFN γ, and/or GzmB.

In one aspect, the disclosure provides kits for analysis of expression levels of a marker in lymphocytes in a subject after induction, wherein the marker is induced by administering to the subject any of the compositions described herein, wherein the marker is CD44, gp70 MC38 peptide (KSPWFTTL; (SEQ ID NO: 53))-specific TCRB, tumor antigen derived ligand-specific TCRB, CD8, IFN γ, and/or GzmB.

In one aspect, the disclosure provides methods for screening a bacteria or a physiologically active substance derived from human intestinal bacteria, the method comprising, allowing a tumor-bearing non-human animal to ingest a physiologically active substance derived from human intestinal bacteria or bacteria, detecting the expression of a marker, in lymphocytes isolated from the tumor-bearing non-human animal, wherein if an increase in expression levels of the marker is detected, the physiologically active substance is identified as an immunostimulating agent for the tumor; and wherein the marker is CD44, gp70 MC38 peptide (KSPWFTTL; (SEQ ID NO: 53))-specific TCRB, tumor antigen derived ligand-specific TCRB, CD8, IFN γ, and/or GzmB.

In one aspect, the disclosure provides a companion diagnostic method for tumor therapy with an immune checkpoint inhibitor, the method comprising analyzing expression levels of a marker in lymphocytes before and after induction by administering to the subject any of the compositions described herein with or without co-administration of the immune checkpoint inhibitor, wherein if the expression levels of the marker in the lymphocytes of the subject are increased by at least 10%, at least 20%, at least 30%, at least 40%, at least 50%, at least 100%, or at least 200% as compared to the expression levels in the lymphocytes of the subject before the administration of the composition, co-administration of the inhibitor and any of the compositions described herein to the subject, the therapy is continued, wherein if the expression levels in the lymphocytes of the subject are not increased as compared to the expression levels in the lymphocytes of the subject, co-administration of the inhibitor and any of the compositions described herein is discontinued or reanalyzed after repeating the administration of any of the compositions described herein to the subject.

In some embodiments, the methods further comprise analyzing expression levels of tumor antigen derived ligand-specific TCRβs in lymphocytes with specific antibodies that bind to the tumor antigen derived ligand-specific TCRβs or MHC multimers that bind to the tumor antigen derived ligand-specific TCRβs. In some embodiments, the methods are use in a tumor therapy with an immune checkpoint inhibitor, wherein the immune checkpoint inhibitor is a PD-1 inhibitor, PD-L1 inhibitor, or CTLA-4 inhibitor. In some embodiments, the methods further comprise assessing PD-1 expression in T-cells in the subject. In some embodiments, the methods further comprise assessing PD-L1 expression in cancer cells in the subject. In some embodiments, the methods further comprise assessing CTLA-4 expression in T-cells in the subject.

In one aspect, the disclosure provides kits for carrying out companion diagnostic methods, wherein the kit comprises one or more molecules for monitoring of the expression levels of a marker in lymphocytes, wherein the marker is CD44, gp70 MC38 peptide (KSPWFTTL; (SEQ ID NO: 53))-specific TCRB, tumor antigen derived ligand-specific TCRB, CD8, IFN γ, and/or GzmB.

In one aspect, the disclosure provides methods for evaluating the immune activation with the degree of IFN γ production in splenocytes, the method comprising administering to a subject any of the compositions described herein.

In one aspect, the disclosure provides kits for evaluating the immune activation with the degree of IFN γ production in splenocytes, comprising one or more IFN γ marker molecules and one or more bacterial species of any of the compositions described herein.

In one aspect, the disclosure provides methods for identifying an immunostimulating agent for a tumor the method comprising screening a human intestinal bacteria or a physiologically active substance derived from human intestinal bacteria, the method comprising, (i) allowing a tumor-bearing non-human animal to ingest the human intestinal bacteria or the physiologically active substance derived from the human intestinal bacteria, and (ii) detecting IFN γ in splenocytes isolated from the tumor-bearing non-human animal, wherein if induction of IFN γ is detected, the human intestinal bacteria or physiologically active substance is identified as an immunostimulating agent for the tumor.

In one aspect, the disclosure provides a companion diagnostic method for tumor therapy with an immune checkpoint inhibitor, the method comprising evaluating the immune activation with the degree of IFN γ production in splenocytes before and after induction by administering to the subject any of the compositions described herein with or without co-administration of the inhibitor, wherein if the degree of IFN γ production in the splenocytes in the subject is increased by at least 10%, at least 20%, at least 30%, at least 40%, at least 50%, at least 100%, or at least 200% as compared to the degree of IFN γ production in the splenocytes in the subject before the administration of the composition, co-administration of the inhibitor and any of the compositions described herein to the subject is continued, wherein if the degree of IFN γ production in the splenocytes of the subject is not increased, the co-administration of the inhibitor and any of the compositions described herein is discontinued or reanalyzed after repeat administration of any of the compositions described herein to the subject.

In some embodiments, the method further comprises analyzing expression levels of tumor antigens of the therapy target in splenocytes with the specific antibodies or the MHC multimers. In some embodiments, the method is for tumor therapy with an immune checkpoint inhibitor, wherein the tumor inhibitor is a PD-1 inhibitor, PD-L1 inhibitor, or CTLA-4 inhibitor. In some embodiments, the method further comprises assessing PD-1 expression in T-cells in the subject. In some embodiments, the method further comprises assessing PD-L1 expression in cancer cells in the subject. In some embodiments, the method further comprises assessing CTLA-4 expression in T-cells in the subject.

In one aspect, the disclosure provides kits for carrying out the companion diagnostic methods described herein, comprising one or more IFN γ marker molecules.

In one aspect, the disclosure provides compositions comprising a purified bacterial mixture comprising one or more bacterial strains of species selected from the group consisting of *Phascolarctobacterium faecium, Fusobacterium* sp., *Bacteroides dorei*, bacterium IARFR67*, Ruminococcaceae bacterium, Paraprevotella xylaniphila, Parabacteroides johnsonii, Bacteroides* sp., *Parabacteroides gordonii, Eubacterium limosum, Parabacteroides distasonis, Bacteroides cellulosilyticus, Bacteroides clarus, Anaerostipes caccae, Bacteroides salyersiae, Bacteroides fragilis, Bacteroides uniformis, Bacteroides eggerthii, Clostridium* sp., *Parabacteroides goldsteinii, Bacteroides* sp., *Lachnospiraceae bacterium* HGA0140*, Hungatella hathewayi, Clostridium lavalense, Ruminococcus* sp., and *Clostridium innocuum*. In some embodiments of the compositions provided herein, the purified bacterial mixture comprises at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, or at least 26 bacterial strains.

In one aspect, the disclosure provides compositions comprising a purified bacterial mixture comprising one or more bacterial strains of species selected from the group consisting of *Phascolarctobacterium faecium, Fusobacterium* sp., *Bacteroides dorei*, bacterium IARFR67*, Ruminococcaceae bacterium, Paraprevotella xylaniphila, Parabacteroides johnsonii, Bacteroides* sp., *Parabacteroides gordonii, Eubacterum limosum, Parabacteroides distasonis, Bacteroides cellulosilyticus, Bacteroides clarus, Anaerostipes caccae, Bacteroides salyersiae, Bacteroides fragilis, Bacteroides uniformis, Bacteroides eggerthii, Clostridium* sp., *Parabacteroides goldsteinii*, and *Bacteroides* sp.

In some embodiments of the compositions provided herein, the purified bacterial mixture comprises at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, or at least 21 bacterial strains.

In one aspect, the disclosure provides compositions comprising a purified bacterial mixture comprising one or more bacterial strains of species selected from the group consisting of *Phascolarctobacterium faecium, Fusobacterium* sp., *Bacteroides dorei*, bacterium IARFR67, *Ruminococcaceae bacterium, Paraprevotella xylaniphila, Parabacteroides johnsonii, Bacteroides* sp., *Parabacteroides gordonii, Eubacterum limosum*, and *Parabacteroides distasonis*. In some embodiments of the compositions provided herein, the purified bacterial mixture comprises at least 2, at least 3, at least 4, at least 5, at least 6, at least 7, at least 8, at least 9, at least 10, or at least 11 bacterial strains.

In one aspect, the disclosure provides compositions comprising a purified bacterial mixture comprising one or more bacterial strains of species selected from the group consisting of *Phascolarctobacterium faecium, Fusobacterium* sp., *Ruminococcaceae bacterium*, and *Eubacterum limosum*. In some embodiments of the compositions provided herein, the purified bacterial mixture comprises at least 2, at least 3, or at least 4 bacterial strains.

In one aspect, the disclosure provides compositions comprising a purified bacterial mixture comprising one or more bacterial strains of species selected from the group consisting of *Bacteroides dorei*, bacterium IARFR67, *Paraprevotella xylaniphila, Parabacteroides johnsonii, Bacteroides* sp., *Parabacteroides gordonii*, and *Parabacteroides distasonis*. In some embodiments of the compositions provided herein, the purified bacterial mixture comprises at least 2, at least 3, at least 4, at least 5, at least 6, or at least 7 bacterial strains.

Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description or illustrated in the drawings. The invention is capable of other embodiments and of being practiced or of being carried out in various ways.

BRIEF DESCRIPTION OF DRAWINGS

The accompanying drawings are not intended to be drawn to scale. The figures are illustrative only and are not required for enablement of the disclosure. For purposes of clarity, not every component may be labeled in every drawing. In the drawings:

(FIG. 1A) The expression of CD8 and IFN γ by the gated CD3 and TCRβ positive cells of representative mice. (FIG. 1B) Summarized data of the percentages of IFN γ positive cells within CD3, TCR β and CD8+ cells. Each plot represents individual mice. **P<0.01 (Student's t-test).

(FIG. 2A) The expression of IFN γ and CD103 (upper row) or GzmB (lower row) by the gated CD8 T cells of representative mice. (FIG. 2B) Summarized data of the percentages of each IFN positive cell fraction in CD3, TCRβ and CD8+ cells. Each plot represents individual mice. *P<0.05 (Student's t-test).

(FIG. 3A) The expression of CD8 and IFN γ by the gated CD3 and TCR positive cells of representative mice. (FIG. 3B) Summarized data of the percentages of IFN γ positive cells in CD3, TCRβ and CD8+ cells. Each plot represents individual mice. *P<0.05, **P<0.01 (one-way ANOVA).

(FIG. 4A) The expression of CD8 and IFN γ by the gated CD3 and TCRβ positive cells of representative mice. (FIG. 4B) Summarized data of the percentages of IFN γ positive cells in CD3, TCRβ and CD8+ cells. Each plot represents individual mice. *P<0.05, **P<0.01 (one-way ANOVA).

(FIG. 5A) The expression of CD8 and IFN γ by the gated CD3 and TCR β positive cells of representative mice. (FIG. 5B) Summarized data of the percentages of IFN γ positive cells in CD3, TCRβ and CD8+ cells. Each plot represents individual mice. **P<0.01 (one-way ANOVA).

(FIG. 6A) The expression of CD8 and IFN γ by the gated CD3 and TCRβ positive cells of representative mice. (FIG. 6B) Summarized data of the percentages of IFN γ positive cells in CD3, TCRβ and CD8+ cells. Each plot represents individual mice. *P<0.05 (one-way ANOVA).

FIGS. 7A and 7B show 16S rRNA gene sequence data of the cecal microbiota of the mice prepared in FIGS. 6A and 6B, which were comprehensively analyzed using the next generation sequencer. (FIG. 7A) Figure of the proportion of operational taxonomic unit (OTU). On the right end, the OTU corresponding to the isolated strains of the B #5-AMP-2 mouse is shown in green. (FIG. 7B) Identification of isolated strains and the homologous bacterial name (Closest sequence) and similarity (S-ab score) are shown.

(FIG. 8A) The expression of CD8 and IFN γ by the gated CD3 and TCRβ positive cells of representative mice. (FIG. 8B) Summarized data of the percentages of IFN γ positive cells in CD3, TCRβ and CD8+ cells. Each plot represents individual mice. **P<0.01 (Student's t-test).

(FIG. 9A) The expression of IFN γ and CD103 (upper row) or GzmB (lower row) by the gated CD8 T cells of representative mice. (FIG. 9B) Summarized data of the percentages of each IFN γ positive cell fraction in CD3, TCRβ and CD8+ cells. Each plot represents individual mice. *P<0.05, **P<0.01 (Student's t-test).

(FIG. 10A) The expression of CD8 and IFN γ by the gated CD3 and TCRβ positive cells of representative mice. (FIG. 10B) Summarized data of the percentages of IFN γ positive cells in CD3, TCRβ and CD8+ cells. Each plot represents individual mice. *P<0.001, **P<0.0001 (one-way ANOVA).

FIG. 11 shows the compositions of the 10-mix and 11-mix bacterial strains that were inoculated into GF mice (See FIGS. 12A and 12B).

(FIG. 12A) The expression of CD8 and IFN γ by the gated CD3 and TCR β positive cells of representative mice. (FIG. 12B) Summarized data of the percentages of CD8+ IFN γ+ cells in CD3+ TCR β+ cells (left), IFN γ+ cells in CD8T cells (middle) and the numbers of CD8+ IFNγ+ cells (right). Each plot represents individual mice. P<0.01, *P<0.001, ****P<0.0001 (one-way ANOVA).

(FIG. 14A) The expression of CD8 and IFN γ by the gated CD3 and TCR β positive cells of representative mice. (FIG. 14B) Summarized data of the percentages of CD8+ IFN γ+ cells in CD3+ TCR β+ cells (left), IFN γ+ cells in CD8T cells (middle) and the numbers of CD8+ IFN γ+ cells (right). Each plot represents individual mice. *P<0.05, P<0.01, *P<0.001 (one-way ANOVA).

(FIG. 16A) The expression of CD8 and IFN γ by the gated CD3 and TCRB positive cells of representative mice. (FIG. 16B) Summarized data of the percentages of CD8+ IFN γ+ cells in CD3+ TCRB+ cells (left), IFN γ+ cells in CD8T cells (middle) and the numbers of CD8+ IFNγ+ cells (right). Each plot represents individual mice. *P<0.05, P<0.01, *P<0.001 (one-way ANOVA).

(FIG. 17A) The expression of gp70-specific TCR β, CD44, GzmB and IFN γ by the gated CD3, TCR β and CD8+ cells of representative mice. (FIG. 17B). Summarized data of the percentages of each IFN positive cell fraction in CD8T cells. Each plot represents individual mice. P<0.01, *P<0.001, ****P<0.0001 (one-way ANOVA).

FIG. 20 shows data on 26 isolated strains, including 11 selected strains.

FIG. 32 shows tumor volume plots of individual mice treated in experiments of Example 5 (4-mix; αPD-1 Ab; 4-mix+αPD-1 Ab). The tumor volume did not increase in multiple animals in the 4-mix+a PD-1 Ab treatment (bottom right panel).

FIG. 37A shows the percentage of CD8+ IFNγ+ cells in the CD3+ TCRβ+CD8α+ population of cells isolated from the tumors. FIG. 37B shows the number of CD8+ IFN γ+ cells isolated from the tumors. FIG. 37C shows the number of CD8+ IFN γ+ cells per gram of tumors. **P<0.01, *P<0.05 (one-way ANOVA).

FIG. 39A shows the percentage of IFN γ+ GzmB+ cells in the CD3+ TCRβ+ CD8α+ population of cells isolated from the tumors. FIG. 39B shows the percentage of Th1 cells in the CD3+ TCRβ+ CD4+ population of cells isolated from the tumors. FIG. 39C shows the percentage of Th17 cells in the CD3+ TCR β+CD4+ population of cells isolated from the tumors. FIG. 39D shows the percentage of Treg cells in the CD3+ TCR β+CD4+ population of cells isolated from the tumors.

FIG. 41A shows the percentage of CD8+ IFN γ+ cells in the CD3+ TCR β+CD8α+ population of cells isolated from the indicated mice. FIG. 41B shows the number of CD8+ IFN γ+ cells isolated from the indicated mice. FIG. 41C shows the percentage of IFN γ+ cells in the population of CD8T cells isolated from the indicated mice.

FIG. 42A shows the percentage of IFN γ+CD103+ cells in the CD3+ TCR β+CD8α+ population of cells isolated from the indicated mice. FIG. 42B shows the percentage of Th17 cells in the CD3+ TCRβ+ CD4+ population of cells isolated from the indicated mice. FIG. 42C shows the percentage of Th1 cells in the CD3+ TCR β+CD4+ population of cells isolated from the indicated mice.

FIG. 43A shows the percentage of IFN γ+ in the CD3+ TCR β+CD8α+(CD8 T cell) population of cells isolated from the indicated mice. FIG. 43B shows the number of CD8+ IFN γ+ cells. FIG. 43C shows the percentage of Th17 cells in the CD3+ TCRβ+CD4+ population of cells isolated from the indicated mice. **P<0.0001, *P<0.001, **P<0.01, *P<0.05 (one-way ANOVA).

FIG. 44 shows that BATF3 is required for the 11-mix to induce CD8-T cells, as evidenced by the flow cytometry (FIG. 44A), and the percentage of IFN $\gamma$+ in the CD3+ TCR$\beta$+CD8$\alpha$+(CD8 T cells) population of cells isolated from the indicated mice (FIG. 44B).

FIG. 45 shows that feces+11-mix is effective in clearing *Listeria* from infected mice, as evidenced in a decrease in the amount of *Listeria* CFUs in the feces.

FIG. 46 shows that the body weight of *Listeria* infected mice treated with feces and the 11-mix is higher than treatment with feces only.

FIGS. 50-52 show that MHC CLP class cells are activated by the administration of the 11-mix, and that the ac tivation is strongest within the first week of activation. There is no activation of the MHC MLN class cells. The individual measurements are shown in FIGS. 50 and 51, while the accumulated data are depicted in FIG. 52.

DESCRIPTION OF EMBODIMENTS

Detailed Description

Figure 1A:
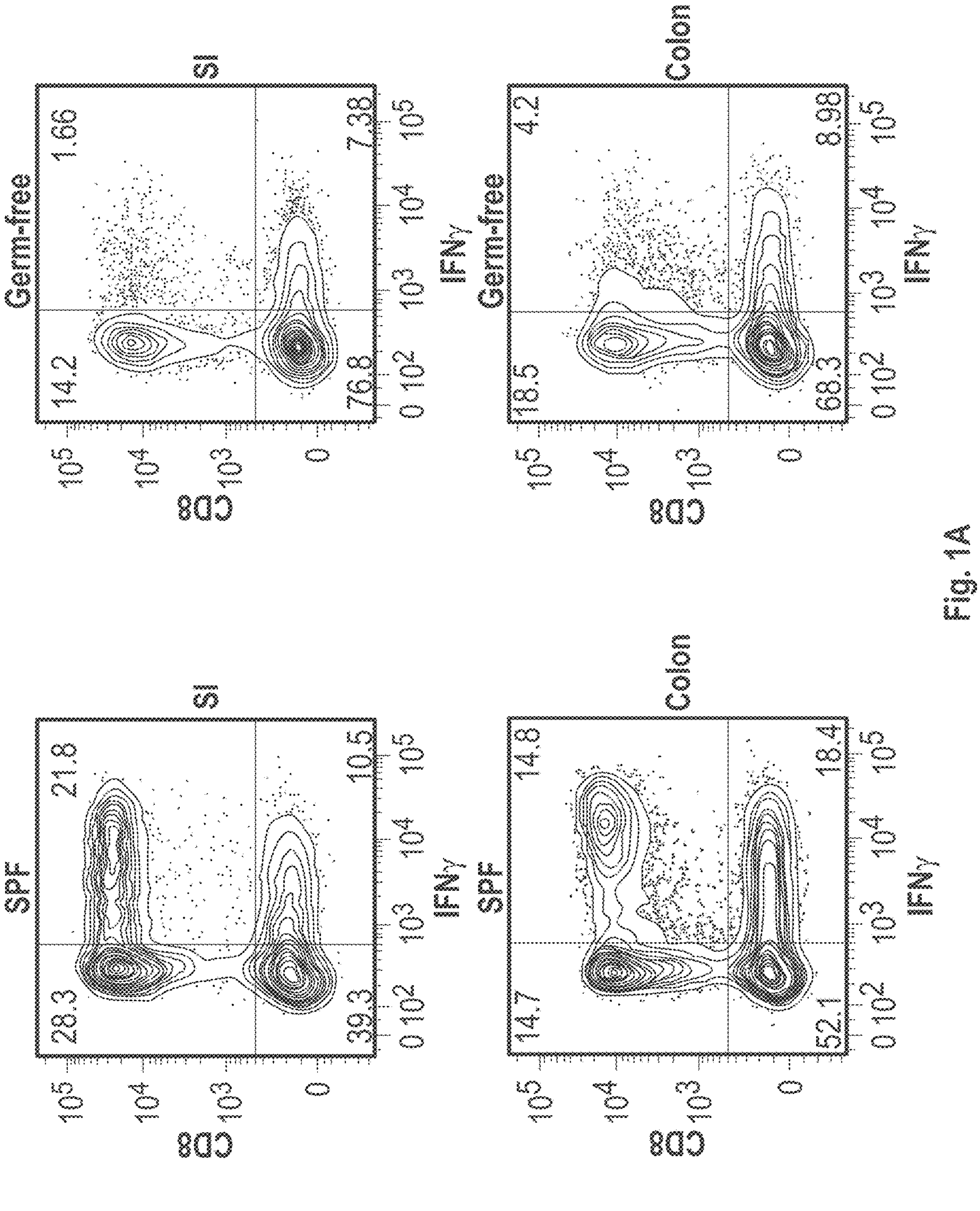
FIGS. 1A and 1B show data of experiments with lymphocytes that were isolated from small intestine (SI) and colon mucosal lamina propria of SPF and germ-free (GF) mice and stimulated with PMA/ionomycin for 3.5 hours. CD3, TCRB, CD8 and IFN γ were stained with antibodies and analyzed by flow cytometry.

Provided herein are compositions and methods for the induction and/or proliferation of CD8+ T-cells, and methods for the treatment of diseases and conditions that can be treated through the induction and/or proliferation of CD8+ T-cells, including infectious diseases and cancers.

In one aspect, the disclosure provides compositions comprising one or more bacterial strains with unique biological properties. In one aspect, the compositions of the bacterial strains disclosed herein, also referred to as bacterial compositions, can induce the proliferation and/or accumulation of CD8+ T-cells. In one aspect, the compositions of the bacterial strains disclosed herein can induce the proliferation and/or accumulation of CD8+ T-cells.

In one aspect, the bacteria of the compositions disclosed herein can be identified by their 16S rRNA (or 16S rDNA) nucleic acid sequence. In general, bacteria are classified as belonging to a specific species and/or genus based on their 16S rRNA nucleic acid sequence. Bacteria, such as bacteria derived from the microbiome, may also be classified into phylogenetic clusters with other closely related strains and species. (See e.g., Rajilic-Stojanovic, M., and de Vos, W. M. (2014). The first 1000 cultured species of the human gastrointestinal microbiota. FEMS Microbiol Rev 38, 996-1047). Methods for determining the identity of specific bacterial species based on their 16S rRNA (or 16S rDNA) nucleic acid sequence are well known in the art (See e.g., Jumpstart Consortium Human Microbiome Project Data Generation Working, G. (2012). Evaluation of 16S rDNA-based community profiling for human microbiome research. PLoS One 7, e39315).

In one aspect, the disclosure provides compositions comprising a purified bacterial mixture comprising one or more bacterial strains comprising 16S rDNA sequences of at least 97% homology to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, or SEQ ID NO:26. In some embodiments of the compositions provided herein, the purified bacterial mixture comprises at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, or at least 26 bacterial strains.

In one aspect, the disclosure provides compositions comprising a purified bacterial mixture comprising one or more bacterial strains comprising 16S rDNA sequences of at least 97% sequence identity with SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, or SEQ ID NO:26. In some embodiments of the compositions provided herein, the purified bacterial mixture comprises at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, or at least 26 bacterial strains.

In one aspect, the disclosure provides compositions comprising a purified bacterial mixture comprising two or more bacterial strains comprising 16S rDNA sequences of at least 97% homology to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, or SEQ ID NO:26. In some embodiments of the compositions provided herein, the purified bacterial mixture comprises at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, or at least 26 bacterial strains.

In one aspect, the disclosure provides compositions comprising a purified bacterial mixture comprising two or more bacterial strains comprising 16S rDNA sequences of at least 97% sequence identity with SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, or SEQ ID NO:26. In some embodiments of the compositions provided herein, the purified bacterial mixture comprises at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, or at least 26 bacterial strains.

In one aspect, the disclosure provides compositions comprising a purified bacterial mixture comprising one or more bacterial strains comprising 16S rDNA sequences of at least 97% homology to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, and SEQ ID NO:21. In some embodiments of the compositions provided herein, the purified bacterial mixture comprises at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, or at least 21 bacterial strains.

In one aspect, the disclosure provides compositions comprising a purified bacterial mixture comprising one or more bacterial strains comprising 16S rDNA sequences of at least 97% sequence identity with SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, and SEQ ID NO:21. In some embodiments of the compositions provided herein, the purified bacterial mixture comprises at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, or at least 21 bacterial strains.

In one aspect, the disclosure provides compositions comprising a purified bacterial mixture comprising two or more bacterial strains comprising 16S rDNA sequences of at least 97% homology to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, and SEQ ID NO:21. In some embodiments of the compositions provided herein, the purified bacterial mixture comprises at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, or at least 21 bacterial strains.

In one aspect, the disclosure provides compositions comprising a purified bacterial mixture comprising two or more bacterial strains comprising 16S rDNA sequences of at least 97% sequence identity with SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, and SEQ ID NO:21. In some embodiments of the compositions provided herein, the purified bacterial mixture comprises at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, or at least 21 bacterial strains.

In one aspect, the disclosure provides compositions comprising a purified bacterial mixture comprising one or more bacterial strains comprising 16S rDNA sequences of at least 97% homology to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, or SEQ ID NO:11. In some embodiments of the compositions provided herein, the purified bacterial mixture comprises at least 2, at least 3, at least 4, at least 5, at least 6, at least 7, at least 8, at least 9, at least 10, or at least 11 bacterial strains.

In one aspect, the disclosure provides compositions comprising a purified bacterial mixture comprising one or more bacterial strains comprising 16S rDNA sequences of at least 97% sequence identity with SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, or SEQ ID NO:11. In some embodiments of the compositions provided herein, the purified bacterial mixture comprises at least 2, at least 3, at least 4, at least 5, at least 6, at least 7, at least 8, at least 9, at least 10, or at least 11 bacterial strains.

In one aspect, the disclosure provides compositions comprising a purified bacterial mixture comprising one or more bacterial strains comprising 16S rDNA sequences of at least 97% sequence identity with SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, or SEQ ID NO:64. In some embodiments of the compositions provided herein, the purified bacterial mixture comprises at least 2, at least 3, at least 4, at least 5, at least 6, at least 7, at least 8, at least 9, at least 10, or at least 11 bacterial strains.

In one aspect, the disclosure provides compositions comprising a purified bacterial mixture comprising two or more bacterial strains comprising 16S rDNA sequences of at least 97% homology to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, or SEQ ID NO:11. In some embodiments of the compositions provided herein, the purified bacterial mixture comprises at least 3, at least 4, at least 5, at least 6, at least 7, at least 8, at least 9, at least 10, or at least 11 bacterial strains.

In one aspect, the disclosure provides compositions comprising a purified bacterial mixture comprising two or more bacterial strains comprising 16S rDNA sequences of at least 97% sequence identity with SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, or SEQ ID NO:11. In some embodiments of the compositions provided herein, the purified bacterial mixture comprises at least 3, at least 4, at least 5, at least 6, at least 7, at least 8, at least 9, at least 10, or at least 11 bacterial strains.

In one aspect, the disclosure provides compositions comprising a purified bacterial mixture comprising two or more bacterial strains comprising 16S rDNA sequences of at least 97% sequence identity with SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, or SEQ ID NO:64. In some embodiments of the compositions provided herein, the purified bacterial mixture comprises at least 3, at least 4, at least 5, at least 6, at least 7, at least 8, at least 9, at least 10, or at least 11 bacterial strains.

In one aspect, the disclosure provides compositions comprising a purified bacterial mixture comprising one or more bacterial strains comprising 16S rDNA sequences of at least 97% homology to SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, or SEQ ID NO:26. In some embodiments of the compositions provided herein, the purified bacterial mixture comprises at least 2, at least 3, at least 4, at least 5, at least 6, at least 7, at least 8, at least 9, at least 10, at least 11, at least 12, at least 13, at least 14, or at least 15 bacterial strains.

In one aspect, the disclosure provides compositions comprising a purified bacterial mixture comprising one or more bacterial strains comprising 16S rDNA sequences of at least 97% sequence identity with SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, or SEQ ID NO:26. In some embodiments of the compositions provided herein, the purified bacterial mixture comprises at least 2, at least 3, at least 4, at least 5, at least 6, at least 7, at least 8, at least 9, at least 10, at least 11, at least 12, at least 13, at least 14, or at least 15 bacterial strains.

In one aspect, the disclosure provides compositions comprising a purified bacterial mixture comprising two or more bacterial strains comprising 16S rDNA sequences of at least 97% homology to SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, or SEQ ID NO:26. In some embodiments of the compositions provided herein, the purified bacterial mixture comprises at least 3, at least 4, at least 5, at least 6, at least 7, at least 8, at least 9, at least 10, at least 11, at least 12, at least 13, at least 14, or at least 15 bacterial strains.

In one aspect, the disclosure provides compositions comprising a purified bacterial mixture comprising two or more bacterial strains comprising 16S rDNA sequences of at least 97% sequence identity with SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, or SEQ ID NO:26. In some embodiments of the compositions provided herein, the purified bacterial mixture comprises at least 3, at least 4, at least 5, at least 6, at least 7, at least 8, at least 9, at least 10, at least 11, at least 12, at least 13, at least 14, or at least 15 bacterial strains.

In one aspect, the disclosure provides compositions comprising one or more bacterial strains comprising 16S rDNA sequences of at least 97% homology to SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, or SEQ ID NO:21. In some embodiments of the compositions provided herein, the purified bacterial mixture comprises at least 2, at least 3, at least 4, at least 5, at least 6, at least 7, at least 8, at least 9, or at least 10 bacterial strains.

In one aspect, the disclosure provides compositions comprising one or more bacterial strains comprising 16S rDNA sequences of at least 97% sequence identity with SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, or SEQ ID NO:21. In some embodiments of the compositions provided herein, the purified bacterial mixture comprises at least 2, at least 3, at least 4, at least 5, at least 6, at least 7, at least 8, at least 9, or at least 10 bacterial strains.

In one aspect, the disclosure provides compositions comprising two or more bacterial strains comprising 16S rDNA sequences of at least 97% homology to SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, or SEQ ID NO:21. In some embodiments of the compositions provided herein, the purified bacterial mixture comprises at least 3, at least 4, at least 5, at least 6, at least 7, at least 8, at least 9, or at least 10 bacterial strains.

In one aspect, the disclosure provides compositions comprising two or more bacterial strains comprising 16S rDNA sequences of at least 97% sequence identity with SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, or SEQ ID NO:21. In some embodiments of the compositions provided herein, the purified bacterial mixture comprises at least 3, at least 4, at least 5, at least 6, at least 7, at least 8, at least 9, or at least 10 bacterial strains.

In one aspect, the disclosure provides compositions comprising a purified bacterial mixture comprising one or more bacterial strains comprising 16S rDNA sequences of at least 97% homology to SEQ ID NO:1, SEQ ID NO:2, SEQ ID NO:5, or SEQ ID NO:10. In some embodiments of the compositions provided herein, the purified bacterial mixture comprises at least 2, at least 3, or at least 4 bacterial strains.

In one aspect, the disclosure provides compositions comprising a purified bacterial mixture comprising one or more bacterial strains comprising 16S rDNA sequences of at least 97% sequence identity with SEQ ID NO:1, SEQ ID NO:2, SEQ ID NO:5, or SEQ ID NO:10. In some embodiments of the compositions provided herein, the purified bacterial mixture comprises at least 2, at least 3, or at least 4 bacterial strains.

In one aspect, the disclosure provides compositions comprising a purified bacterial mixture comprising two or more bacterial strains comprising 16S rDNA sequences of at least 97% homology to SEQ ID NO:1, SEQ ID NO:2, SEQ ID NO:5, or SEQ ID NO:10. In some embodiments of the compositions provided herein, the purified bacterial mixture comprises at least 3, or at least 4 bacterial strains.

In one aspect, the disclosure provides compositions comprising a purified bacterial mixture comprising two or more bacterial strains comprising 16S rDNA sequences of at least 97% sequence identity with SEQ ID NO:1, SEQ ID NO:2, SEQ ID NO:5, or SEQ ID NO:10. In some embodiments of the compositions provided herein, the purified bacterial mixture comprises at least 3, or at least 4 bacterial strains.

In one aspect, the disclosure provides compositions comprising a purified bacterial mixture comprising one or more bacterial strains comprising 16S rDNA sequences of at least 97% homology to SEQ ID NO:3, SEQ ID NO:4, SEQ ID NO:6, SEQ ID NO:7, SEQ ID NO:8, SEQ ID NO:9, or SEQ ID NO:11. In some embodiments of the compositions provided herein, the purified bacterial mixture comprises at least 2, at least 3, at least 4, at least 5, at least 6, or at least 7 bacterial strains.

In one aspect, the disclosure provides compositions comprising a purified bacterial mixture comprising one or more bacterial strains comprising 16S rDNA sequences of at least 97% sequence identity with SEQ ID NO:3, SEQ ID NO:4, SEQ ID NO:6, SEQ ID NO:7, SEQ ID NO:8, SEQ ID NO:9, or SEQ ID NO:11. In some embodiments of the compositions provided herein, the purified bacterial mixture comprises at least 2, at least 3, at least 4, at least 5, at least 6, or at least 7 bacterial strains.

In one aspect, the disclosure provides compositions comprising a purified bacterial mixture comprising two or more bacterial strains comprising 16S rDNA sequences of at least 97% homology to SEQ ID NO:3, SEQ ID NO:4, SEQ ID NO:6, SEQ ID NO:7, SEQ ID NO:8, SEQ ID NO:9, or SEQ ID NO:11. In some embodiments of the compositions provided herein, the purified bacterial mixture comprises at least 3, at least 4, at least 5, at least 6, or at least 7 bacterial strains.

In one aspect, the disclosure provides compositions comprising a purified bacterial mixture comprising two or more bacterial strains comprising 16S rDNA sequences of at least 97% sequence identity with SEQ ID NO:3, SEQ ID NO:4, SEQ ID NO:6, SEQ ID NO:7, SEQ ID NO:8, SEQ ID NO:9, or SEQ ID NO:11. In some embodiments of the compositions provided herein, the purified bacterial mixture comprises at least 3, at least 4, at least 5, at least 6, or at least 7 bacterial strains.

In one aspect, the disclosure provides compositions comprising a purified bacterial mixture comprising one or more bacterial strains comprising 16S rDNA sequences of at least 97% homology to SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, or SEQ ID NO:52. In some embodiments of the compositions provided herein, the purified bacterial mixture comprises at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, or at least 26 bacterial strains.

In one aspect, the disclosure provides compositions comprising a purified bacterial mixture comprising one or more bacterial strains comprising 16S rDNA sequences of at least 97% sequence identity with SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, or SEQ ID NO:52. In some embodiments of the compositions provided herein, the purified bacterial mixture comprises at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, or at least 26 bacterial strains.

In one aspect, the disclosure provides compositions comprising a purified bacterial mixture comprising two or more bacterial strains comprising 16S rDNA sequences of at least 97% homology to SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, or SEQ ID NO:52. In some embodiments of the compositions provided herein, the purified bacterial mixture comprises at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, or at least 26 bacterial strains.

In one aspect, the disclosure provides compositions comprising a purified bacterial mixture comprising two or more bacterial strains comprising 16S rDNA sequences of at least 97% sequence identity with SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, or SEQ ID NO:52. In some embodiments of the compositions provided herein, the purified bacterial mixture comprises at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, or at least 26 bacterial strains.

In one aspect, the disclosure provides compositions comprising a purified bacterial mixture comprising one or more bacterial strains comprising 16S rDNA sequences of at least 97% homology to SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, or SEQ ID NO:47. In some embodiments of the compositions provided herein, the purified bacterial mixture comprises at least 2, least 3, at least 4, at least 5, at least 6, at least 7, at least 8, at least 9, at least 10, at least 11, at least 12, at least 13, at least 14, at least 15, at least 16, at least 17, at least 18, at least 19, at least 20, or at least 21 bacterial strains.

In one aspect, the disclosure provides compositions comprising a purified bacterial mixture comprising one or more bacterial strains comprising 16S rDNA sequences of at least 97% sequence identity with SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, or SEQ ID NO:47. In some embodiments of the compositions provided herein, the purified bacterial mixture comprises at least 2, least 3, at least 4, at least 5, at least 6, at least 7, at least 8, at least 9, at least 10, at least 11, at least 12, at least 13, at least 14, at least 15, at least 16, at least 17, at least 18, at least 19, at least 20, or at least 21 bacterial strains.

In one aspect, the disclosure provides compositions comprising a purified bacterial mixture comprising two or more bacterial strains comprising 16S rDNA sequences of at least 97% homology to SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, or SEQ ID NO:47. In some embodiments of the compositions provided herein, the purified bacterial mixture comprises at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, or at least 21 bacterial strains.

In one aspect, the disclosure provides compositions comprising a purified bacterial mixture comprising two or more bacterial strains comprising 16S rDNA sequences of at least 97% sequence identity with SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, or SEQ ID NO:47. In some embodiments of the compositions provided herein, the purified bacterial mixture comprises at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, or at least 21 bacterial strains.

In one aspect, the disclosure provides compositions comprising a purified bacterial mixture comprising one or more bacterial strains comprising 16S rDNA sequences of at least 97% homology to SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, or SEQ ID NO:37. In some embodiments of the compositions provided herein, the purified bacterial mixture comprises at least 2, at least 3, at least 4, at least 5, at least 6, at least 7, at least 8, at least 9, at least 10, or at least 11 bacterial strains.

In one aspect, the disclosure provides compositions comprising a purified bacterial mixture comprising one or more bacterial strains comprising 16S rDNA sequences of at least 97% sequence identity with SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, or SEQ ID NO:37. In some embodiments of the compositions provided herein, the purified bacterial mixture comprises at least 2, at least 3, at least 4, at least 5, at least 6, at least 7, at least 8, at least 9, at least 10, or at least 11 bacterial strains.

In one aspect, the disclosure provides compositions comprising a purified bacterial mixture comprising two or more bacterial strains comprising 16S rDNA sequences of at least 97% homology to SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, or SEQ ID NO:37. In some embodiments of the compositions provided herein, the purified bacterial mixture comprises at least 3, at least 4, at least 5, at least 6, at least 7, at least 8, at least 9, at least 10, or at least 11 bacterial strains.

In one aspect, the disclosure provides compositions comprising a purified bacterial mixture comprising two or more bacterial strains comprising 16S rDNA sequences of at least 97% sequence identity with SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, or SEQ ID NO:37. In some embodiments of the compositions provided herein, the purified bacterial mixture comprises at least 3, at least 4, at least 5, at least 6, at least 7, at least 8, at least 9, at least 10, or at least 11 bacterial strains.

In one aspect, the disclosure provides compositions comprising a purified bacterial mixture comprising one or more bacterial strains comprising 16S rDNA sequences of at least 97% homology to SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, or SEQ ID NO:52. In some embodiments of the compositions provided herein, the purified bacterial mixture comprises at least 2, at least 3, at least 4, at least 5, at least 6, at least 7, at least 8, at least 9, at least 10, at least 11, at least 12, at least 13, at least 14, or at least 15 bacterial strains.

In one aspect, the disclosure provides compositions comprising a purified bacterial mixture comprising one or more bacterial strains comprising 16S rDNA sequences of at least 97% sequence identity with SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, or SEQ ID NO:52. In some embodiments of the compositions provided herein, the purified bacterial mixture comprises at least 2, at least 3, at least 4, at least 5, at least 6, at least 7, at least 8, at least 9, at least 10, at least 11, at least 12, at least 13, at least 14, or at least 15 bacterial strains.

In one aspect, the disclosure provides compositions comprising a purified bacterial mixture comprising two or more bacterial strains comprising 16S rDNA sequences of at least 97% homology to SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, or SEQ ID NO:52. In some embodiments of the compositions provided herein, the purified bacterial mixture comprises at least 3, at least 4, at least 5, at least 6, at least 7, at least 8, at least 9, at least 10, at least 11, at least 12, at least 13, at least 14, or at least 15 bacterial strains.

In one aspect, the disclosure provides compositions comprising a purified bacterial mixture comprising two or more bacterial strains comprising 16S rDNA sequences of at least 97% sequence identity with SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, or SEQ ID NO:52. In some embodiments of the compositions provided herein, the purified bacterial mixture comprises at least 3, at least 4, at least 5, at least 6, at least 7, at least 8, at least 9, at least 10, at least 11, at least 12, at least 13, at least 14, or at least 15 bacterial strains.

In one aspect, the disclosure provides compositions comprising a purified bacterial mixture comprising one or more bacterial strains comprising 16S rDNA sequences of at least 97% homology to SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, or SEQ ID NO:47. In some embodiments of the compositions provided herein, the purified bacterial mixture comprises at least 2, at least 3, at least 4, at least 5, at least 6, at least 7, at least 8, at least 9, or at least 10 bacterial strains.

In one aspect, the disclosure provides compositions comprising a purified bacterial mixture comprising one or more bacterial strains comprising 16S rDNA sequences of at least 97% sequence identity with SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, or SEQ ID NO:47. In some embodiments of the compositions provided herein, the purified bacterial mixture comprises at least 2, at least 3, at least 4, at least 5, at least 6, at least 7, at least 8, at least 9, or at least 10 bacterial strains.

In one aspect, the disclosure provides compositions comprising a purified bacterial mixture comprising two or more bacterial strains comprising 16S rDNA sequences of at least 97% homology to SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, or SEQ ID NO:47. In some embodiments of the compositions provided herein, the purified bacterial mixture comprises at least 3, at least 4, at least 5, at least 6, at least 7, at least 8, at least 9, or at least 10 bacterial strains.

In one aspect, the disclosure provides compositions comprising a purified bacterial mixture comprising two or more bacterial strains comprising 16S rDNA sequences of at least 97% sequence identity with SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, or SEQ ID NO:47. In some embodiments of the compositions provided herein, the purified bacterial mixture comprises at least 3, at least 4, at least 5, at least 6, at least 7, at least 8, at least 9, or at least 10 bacterial strains.

In one aspect, the disclosure provides compositions comprising a purified bacterial mixture comprising one or more bacterial strains comprising 16S rDNA sequences of at least 97% homology to SEQ ID NO:27, SEQ ID NO:28, SEQ ID NO:31 or SEQ ID NO:36. In some embodiments of the compositions provided herein, the purified bacterial mixture comprises at least 2, at least 3, or at least 4 bacterial strains.

In one aspect, the disclosure provides compositions comprising a purified bacterial mixture comprising one or more bacterial strains comprising 16S rDNA sequences of at least 97% sequence identity with SEQ ID NO:27, SEQ ID NO:28, SEQ ID NO:31 or SEQ ID NO:36. In some embodiments of the compositions provided herein, the purified bacterial mixture comprises at least 2, at least 3, or at least 4 bacterial strains.

In one aspect, the disclosure provides compositions comprising a purified bacterial mixture comprising two or more bacterial strains comprising 16S rDNA sequences of at least 97% homology to SEQ ID NO:27, SEQ ID NO:28, SEQ ID NO:31 or SEQ ID NO:36. In some embodiments of the compositions provided herein, the purified bacterial mixture comprises at least 3, or at least 4 bacterial strains.

In one aspect, the disclosure provides compositions comprising a purified bacterial mixture comprising two or more bacterial strains comprising 16S rDNA sequences of at least 97% sequence identity with SEQ ID NO:27, SEQ ID NO:28, SEQ ID NO:31 or SEQ ID NO:36. In some embodiments of the compositions provided herein, the purified bacterial mixture comprises at least 3, or at least 4 bacterial strains.

In one aspect, the disclosure provides compositions comprising a purified bacterial mixture comprising one or more bacterial strains comprising 16S rDNA sequences of at least 97% homology to SEQ ID NO:29, SEQ ID NO:30, SEQ ID NO:32, SEQ ID NO:33, SEQ ID NO:34, SEQ ID NO:35, or SEQ ID NO:37. In some embodiments of the compositions provided herein, the purified bacterial mixture comprises at least 2, at least 3, at least 4, at least 5, at least 6, or at least 7 bacterial strains.

In one aspect, the disclosure provides compositions comprising a purified bacterial mixture comprising one or more bacterial strains comprising 16S rDNA sequences of at least 97% sequence identity with SEQ ID NO:29, SEQ ID NO:30, SEQ ID NO:32, SEQ ID NO:33, SEQ ID NO:34, SEQ ID NO:35, or SEQ ID NO:37. In some embodiments of the compositions provided herein, the purified bacterial mixture comprises at least 2, at least 3, at least 4, at least 5, at least 6, or at least 7 bacterial strains.

In one aspect, the disclosure provides compositions comprising a purified bacterial mixture comprising two or more bacterial strains comprising 16S rDNA sequences of at least 97% homology to SEQ ID NO:29, SEQ ID NO:30, SEQ ID NO:32, SEQ ID NO:33, SEQ ID NO:34, SEQ ID NO:35, or SEQ ID NO:37. In some embodiments of the compositions provided herein, the purified bacterial mixture comprises at least 3, at least 4, at least 5, at least 6, or at least 7 bacterial strains.

In one aspect, the disclosure provides compositions comprising a purified bacterial mixture comprising two or more bacterial strains comprising 16S rDNA sequences of at least 97% sequence identity with SEQ ID NO:29, SEQ ID NO:30, SEQ ID NO:32, SEQ ID NO:33, SEQ ID NO:34, SEQ ID NO:35, or SEQ ID NO:37. In some embodiments of the compositions provided herein, the purified bacterial mixture comprises at least 3, at least 4, at least 5, at least 6, or at least 7 bacterial strains.

In one aspect, the disclosure provides compositions comprising a bacterial strain comprising a 16S rDNA sequence with a nucleic acid sequence selected from the group consisting of SEQ ID NOs:1-26. In one aspect, the disclosure provides compositions comprising as an active ingredient a bacterial strain comprising a 16S rDNA sequence with a nucleic acid sequence selected from the group consisting of SEQ ID NOs:1-26. It should be appreciated that for all compositions provided herein, in some embodiments, the bacterial strain or the bacterial strains are the active ingredient of the composition.

In one aspect, the disclosure provides compositions comprising a bacterial strain comprising a 16S rDNA sequence with a nucleic acid sequence selected from the group consisting of SEQ ID NOs:1-21. In one aspect, the disclosure provides compositions comprising as an active ingredient a bacterial strain comprising a 16S rDNA sequence with a nucleic acid sequence selected from the group consisting of SEQ ID NOs:1-21.

In one aspect, the disclosure provides compositions comprising a bacterial strain comprising a 16S rDNA sequence with a nucleic acid sequence selected from the group consisting of SEQ ID NOs:1-11. In one aspect, the disclosure provides compositions comprising as an active ingredient a bacterial strain comprising a 16S rDNA sequence with a nucleic acid sequence selected from the group consisting of SEQ ID NOs:1-11.

In one aspect, the disclosure provides compositions comprising a bacterial strain comprising a 16S rDNA sequence with a nucleic acid sequence selected from the group consisting of SEQ ID NOs:54-64. In one aspect, the disclosure provides compositions comprising as an active ingredient a bacterial strain comprising a 16S rDNA sequence with a nucleic acid sequence selected from the group consisting of SEQ ID NOs:54-64. It should be appreciated that for all compositions provided herein, in some embodiments, the bacterial strains are purified. Thus, for example the disclosure provides purified bacterial strains comprising a 16S rDNA sequence with a nucleic acid sequence selected from the group consisting of SEQ ID NOs:1-26. In addition, for example, the disclosure provides compositions comprising purified bacterial strains comprising a 16S rDNA sequence with a nucleic acid sequence selected from the group consisting of SEQ ID NOs:1-26. The bacterial strains disclosed herein originally may have been obtained and purified from the microbiota of one or more human individuals or obtained from sources other than the human microbiota, including soil and non-human microbiota. As provided herein, in some embodiments, bacteria isolated from the human microbiota, non-human microbiota, soil, or any alternative source are purified prior to use in the compositions and methods provided herein.

In one aspect, the disclosure provides compositions comprising one or more bacterial strains, wherein the one or more bacterial strains comprise a 16S rDNA sequence with a nucleic acid sequence selected from the group consisting of SEQ ID NOs:1-26. In one aspect, the disclosure provides compositions comprising one or more bacterial strains wherein the one or more bacterial strains comprise 16S rDNA sequences having at least 97% homology with nucleic acid sequences selected from the group consisting of SEQ ID NOs:1-26. As discussed previously, in some embodiments, the bacterial strains are purified. Thus, in one aspect, the disclosure provides compositions comprising one or more purified bacterial strains wherein the one or more purified bacterial strains comprise 16S rDNA sequences having at least 97% homology with nucleic acid sequences selected from the group consisting of SEQ ID NOs:1-26. In one aspect, the disclosure provides compositions comprising one or more bacterial strains wherein the one or more bacterial strains comprise 16S rDNA sequences having at least 97% sequence identity with nucleic acid sequences selected from the group consisting of SEQ ID NOs:1-26. As discussed previously, in some embodiments, the bacterial strains are purified. Thus, in one aspect, the disclosure provides compositions comprising one or more purified bacterial strains wherein the one or more purified bacterial strains comprise 16S rDNA sequences having at least 97% sequence identity with nucleic acid sequences selected from the group consisting of SEQ ID NOs:1-26.

In one aspect, the disclosure provides compositions comprising two or more purified bacterial strains wherein the two or more purified bacterial strains comprise 16S rDNA sequences having at least 97% homology with nucleic acid sequences selected from the group consisting of SEQ ID NOs:1-26. As discussed above, in some embodiments, the bacterial strains are the active ingredient of the composition. Thus, in some embodiments, the disclosure provides compositions comprising as an active ingredient two or more purified bacterial strains wherein the two or more purified bacterial strains comprise 16S rDNA sequences having at least 97% homology with nucleic acid sequences selected from the group consisting of SEQ ID NOs:1-26.

In one aspect, the disclosure provides compositions comprising two or more purified bacterial strains wherein the two or more purified bacterial strains comprise 16S rDNA sequences having at least 97% sequence identity with nucleic acid sequences selected from the group consisting of SEQ ID NOs:1-26. As discussed above, in some embodiments, the bacterial strains are the active ingredient of the composition. Thus, in some embodiments, the disclosure provides compositions comprising as an active ingredient two or more purified bacterial strains wherein the two or more purified bacterial strains comprise 16S rDNA sequences having at least 97% sequence identity with nucleic acid sequences selected from the group consisting of SEQ ID NOs:1-26.

In one aspect, the disclosure provides bacterial strains and combinations of bacterial strains that are homologous or have a high percent of homology with bacterial strains comprising 16S rDNA sequences selected from the group consisting of SEQ ID NOs:1-26. As discussed previously, in some embodiments, the bacterial strains are purified. The bacterial strains disclosed herein that have a 16S rDNA sequence with a nucleic acid sequence selected from the group consisting of SEQ ID NOs:1-26 have a high percent of homology (e.g., greater than 90%) or sequence identity, with 16S rDNA sequences of bacterial strains that have been described in various databases (See e.g., the National Center for Biotechnology Information). Table 1 provides the closest known species by homology when the 16S rDNA sequences comprising SEQ ID NOs: 1-26 are compared to 16S rDNA sequences of bacterial species available in public databases.

By way of example, the bacterial strain comprising a 16S rDNA sequence with SEQ ID NO:1 disclosed herein has the highest homology with a bacterial strain of the species *Phascolarctobacterium faecium* as defined by NCBI Accession # LN998073 (having 16S rDNA sequence SEQ ID NO:27). While the bacterial strain with SEQ ID NO:1 has homology with other published bacterial strains as well, the highest homology is with a bacterial strain of the species

*Phascolarctobacterium faecium* as defined by NCBI Accession # LN998073. It should be appreciated that multiple bacterial strains disclosed herein may have the highest homology with the same species.

It should further be appreciated that the bacterial strains disclosed herein that have a 16S rDNA sequence with a nucleic acid sequence selected from the group consisting of SEQ ID NOs:1-26, are also homologous to other strains based on their whole genome sequence, or subset of their whole genome sequence.

Thus, it should be appreciated that, in one aspect, the disclosure also provides compositions and methods comprising bacterial species with close homology to the bacterial strains that have a 16S rDNA sequence with a nucleic acid sequence selected from the group consisting of SEQ ID NOs:1-26.

In one aspect, the disclosure provides compositions comprising one or more bacterial strains wherein the one or more bacterial strains are of species selected from the group consisting of *Phascolarctobacterium faecium, Fusobacterium ulcerans, Bacteroides dorei, Bacteroides uniformis, Subdoligranulum* sp., *Paraprevotella xylaniphila, Parabacteroides johnsonii, Alistipes* sp., *Parabacteroides gordonii, Eubacterum limosum, Parabacteroides distasonis, Bacteroides cellulosilyticus, Bacteroides clarus, Anaerostipes caccae, Bacteroides salyersiae, Bacteroides fragilis, Bacteroides uniformis, Bacteroides eggerthii, Clostridium* sp., *Parabacteroides goldsteinii, Bacteroides* sp., *Lachnospiraceae bacterium* HGA0140, *Hungatella hathewayi, Clostridium lavalense, Ruminococcus* sp., and *Clostridium innocuum*

In one aspect, the disclosure provides compositions comprising one or more bacterial strains wherein the one or more bacterial strains are of species selected from the group consisting of *Phascolarctobacterium faecium, Fusobacterium ulcerans, Bacteroides dorei, Bacteroides uniformis, Subdoligranulum* sp., *Paraprevotella xylaniphila, Parabacteroides johnsonii, Alistipes* sp., *Parabacteroides gordonii, Eubacterum limosum, Parabacteroides distasonis, Bacteroides cellulosilyticus, Bacteroides clarus, Anaerostipes caccae, Bacteroides salyersiae, Bacteroides fragilis; Bacteroides uniformis, Bacteroides eggerthii, Clostridium* sp., *Parabacteroides goldsteinii*, and *Bacteroides* sp.

In one aspect, the disclosure provides compositions comprising one or more bacterial strains wherein the one or more bacterial strains are of species selected from the group consisting of *Phascolarctobacterium faecium, Fusobacterium ulcerans, Bacteroides dorei, Bacteroides uniformis, Subdoligranulum* sp., *Paraprevotella xylaniphila, Parabacteroides johnsonii, Alistipes* sp., *Parabacteroides gordonii, Eubacterum limosum*, and *Parabacteroides distasonis*.

In one aspect, the disclosure provides compositions comprising one or more bacterial strains wherein the one or more bacterial strains are of species selected from the group consisting of *Bacteroides cellulosilyticus, Bacteroides clarus, Anaerostipes caccae, Bacteroides salyersiae, Bacteroides fragilis, Bacteroides uniformis, Bacteroides eggerthii, Clostridium* sp., *Parabacteroides goldsteinii, Bacteroides* sp., *Lachnospiraceae bacterium* HGA0140, *Hungatella hathewayi, Clostridium lavalense, Ruminococcus* sp., and *Clostridium innocuum.*

In one aspect, the disclosure provides compositions comprising one or more bacterial strains wherein the one or more bacterial strains are of species selected from the group consisting of *Bacteroides cellulosilyticus, Bacteroides clarus, Anaerostipes caccae, Bacteroides salyersiae, Bacteroides fragilis, Bacteroides uniformis, Bacteroides eggerthii, Clostridium* sp., *Parabacteroides goldsteinii*, and *Bacteroides* sp.

In one aspect, the disclosure provides compositions comprising a purified bacterial mixture comprising two or more bacterial strains of species selected from the group consisting of *Phascolarctobacterium faecium, Fusobacterium ulcerans, Bacteroides dorei, Bacteroides uniformis, Subdoligranulum* sp., *Paraprevotella xylaniphila, Parabacteroides johnsonii, Alistipes* sp., *Parabacteroides gordonii, Eubacterum limosum, Parabacteroides distasonis, Bacteroides cellulosilyticus, Bacteroides clarus, Anaerostipes caccae, Bacteroides salyersiae, Bacteroides fragilis, Bacteroides uniformis, Bacteroides eggerthii, Clostridium* sp., *Parabacteroides goldsteinii, Bacteroides* sp., *Lachnospiraceae bacterium* HGA0140, *Hungatella hathewayi, Clostridium lavalense, Ruminococcus* sp., and *Clostridium innocuum*. In some embodiments of the compositions provided herein, the purified bacterial mixture comprises at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, or at least 26 bacterial strains.

In one aspect, the disclosure provides compositions comprising a purified bacterial mixture comprising two or more bacterial strains of species selected from the group consisting of *Phascolarctobacterium faecium, Fusobacterium ulcerans, Bacteroides dorei, Bacteroides uniformis, Subdoligranulum* sp., *Paraprevotella xylaniphila, Parabacteroides johnsonii, Alistipes* sp., *Parabacteroides gordonii, Eubacterum limosum, Parabacteroides distasonis, Bacteroides cellulosilyticus, Bacteroides clarus, Anaerostipes caccae, Bacteroides salyersiae, Bacteroides fragilis, Bacteroides uniformis, Bacteroides eggerthii, Clostridium* sp., *Parabacteroides goldsteinii*, and *Bacteroides* sp.

In some embodiments of the compositions provided herein, the purified bacterial mixture comprises at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, or at least 21 bacterial strains.

In one aspect, the disclosure provides compositions comprising a purified bacterial mixture comprising two or more bacterial strains of species selected from the group consisting of *Phascolarctobacterium faecium, Fusobacterium ulcerans, Bacteroides dorei, Bacteroides uniformis, Subdoligranulum* sp., *Paraprevotella xylaniphila, Parabacteroides johnsonii, Alistipes* sp., *Parabacteroides gordonii, Eubacterum limosum*, and *Parabacteroides distasonis*. In some embodiments of the compositions provided herein, the purified bacterial mixture comprises at least 3, at least 4, at least 5, at least 6, at least 7, at least 8, at least 9, at least 10, or at least 11 bacterial strains.

In one aspect, the disclosure provides compositions comprising a purified bacterial mixture comprising *Phascolarctobacterium faecium, Fusobacterium ulcerans, Bacteroides dorei, Bacteroides uniformis, Subdoligranulum* sp., *Paraprevotella xylaniphila, Parabacteroides johnsonii, Alistipes* sp., *Parabacteroides gordonii, Eubacterum limosum*, and *Parabacteroides distasonis.*

In one aspect, the disclosure provides compositions comprising a purified bacterial mixture consisting of *Phascolarctobacterium faecium, Fusobacterium ulcerans, Bacteroides dorei, Bacteroides uniformis, Subdoligranulum* sp., *Paraprevotella xylaniphila, Parabacteroides johnsonii,*

*Alistipes* sp., *Parabacteroides gordonii, Eubacterum limosum*, and *Parabacteroides distasonis.*

In one aspect, the disclosure provides compositions comprising a purified bacterial mixture comprising one or more bacterial strains of species selected from the group consisting of *Phascolarctobacterium faecium, Phascolarctobacterium* sp. CAG:207, *Fusobacterium ulcerans, Fusobacterium varium, Bacteroides dorei, Bacteroides fluxus, Bacteroides uniformis, Bacteroides* sp. D20 *Subdoligranulum* sp., *Ruthenibacterium lactatiformans, Ruminococcaceae bacterium* cv2, *Gemminger formicilis, Paraprevotella xylaniphila, Parabacteroides johnsonii, Alistipes* sp., *Alistipes senegalesis, Parabacteroides gordonii, Parabacteroides* sp. HGS0025, *Eubacterum limosum, Parabacteroides* sp. CAG:2 and *Parabacteroides distasonis*. In some embodiments of the compositions provided herein, the purified bacterial mixture comprises at least 2, at least 3, at least 4, at least 5, at least 6, at least 7, at least 8, at least 9, at least 10, or at least 11 bacterial strains.

In one aspect, the disclosure provides compositions comprising a purified bacterial mixture comprising:

1) *Phascolarctobacterium faecium*, or *Phascolarctobacterium* sp. CAG:207;

2) *Fusobacterium ulcerans*, or *Fusobacterium varium;*

3) *Bacteroides dorei*, or *Bacteroides fluxus,*

4) *Bacteroides uniformis*, or *Bacteroides* sp. D20,

5) *Subdoligranulum* sp., *Ruthenibacterium lactatiformans, Ruminococcaceae bacterium* cv2, or *Gemminger formicilis,*

6) *Paraprevotella xylaniphila,*

7) *Parabacteroides johnsonii,*

8) *Alistipes* sp., *Alistipes timonensis*, or *Alistipes senegalesis,*

9) *Parabacteroides gordonii*, or *Parabacteroides* sp. HGS0025,

10) *Eubacterum limosum*, and

11) *Parabacteroides* sp. CAG:2 or *Parabacteroides distasonis.*

In one aspect, the disclosure provides compositions comprising a purified bacterial mixture consisting of:

1) *Phascolarctobacterium faecium*, or *Phascolarctobacterium* sp. CAG:207;

2) *Fusobacterium ulcerans*, or *Fusobacterium varium;*

3) *Bacteroides dorei*, or *Bacteroides fluxus,*

4) *Bacteroides uniformis*, or *Bacteroides* sp. D20,

5) *Subdoligranulum* sp., *Ruthenibacterium lactatiformans, Ruminococcaceae bacterium* cv2, or *Gemminger formicilis,*

6) *Paraprevotella xylaniphila,*

7) *Parabacteroides johnsonii,*

8) *Alistipes* sp., *Alistipes timonensis*, or *Alistipes senegalesis,*

9) *Parabacteroides gordonii*, or *Parabacteroides* sp. HGS0025,

10) *Eubacterum limosum*, and

11) *Parabacteroides* sp. CAG:2 or *Parabacteroides distasonis.*

In one aspect, the disclosure provides compositions comprising a purified bacterial mixture comprising one or more bacterial strains of species selected from the group consisting of *Phascolarctobacterium faecium, Fusobacterium varium, Bacteroides dorei, Bacteroides uniformis, Ruthenibacterium lactatiformans, Paraprevotella xylaniphila, Parabacteroides johnsonii, Alistipes senegalesis, Parabacteroides gordonii, Eubacterum limosum*, and *Parabacteroides distasonis*. In some embodiments of the compositions provided herein, the purified bacterial mixture comprises at least 2, at least 3, at least 4, at least 5, at least 6, at least 7, at least 8, at least 9, at least 10, or at least 11 bacterial strains.

In one aspect, the disclosure provides compositions comprising a purified bacterial mixture comprising *Phascolarctobacterium faecium, Fusobacterium varium, Bacteroides dorei, Bacteroides uniformis, Ruthenibacterium lactatiformans, Paraprevotella xylaniphila, Parabacteroides johnsonii, Alistipes senegalesis, Parabacteroides gordonii, Eubacterum limosum*, and *Parabacteroides distasonis.*

In one aspect, the disclosure provides compositions comprising a purified bacterial mixture consisting of *Phascolarctobacterium faecium, Fusobacterium varium, Bacteroides dorei, Bacteroides uniformis, Ruthenibacterium lactatiformans, Paraprevotella xylaniphila, Parabacteroides johnsonii, Alistipes senegalesis, Parabacteroides gordonii, Eubacterum limosum*, and *Parabacteroides distasonis.*

In one aspect, the disclosure provides compositions comprising a purified bacterial mixture comprising one or more bacterial strains of species selected from the group consisting of *Phascolarctobacterium* sp. CAG:207, *Fusobacterium ulcerans, Bacteroides dorei, Bacteroides* sp. D20, *Ruminococcaceae bacterium* cv2, *Paraprevotella xylaniphila, Parabacteroides johnsonii, Alistipes senegalesis, Parabacteroides* sp. HGS0025, *Eubacterum limosum*, and *Parabacteroides* sp. CAG:2. In some embodiments of the compositions provided herein, the purified bacterial mixture comprises at least 2, at least 3, at least 4, at least 5, at least 6, at least 7, at least 8, at least 9, at least 10, or at least 11 bacterial strains.

In one aspect, the disclosure provides compositions comprising a purified bacterial mixture comprising *Phascolarctobacterium* sp. CAG:207, *Fusobacterium ulcerans, Bacteroides dorei, Bacteroides* sp. D20, *Ruminococcaceae bacterium* cv2, *Paraprevotella xylaniphila, Parabacteroides johnsonii, Alistipes senegalesis, Parabacteroides* sp. HGS0025, *Eubacterum limosum*, and *Parabacteroides* sp. CAG:2.

In one aspect, the disclosure provides compositions comprising a purified bacterial mixture consisting of *Phascolarctobacterium* sp. CAG:207, *Fusobacterium ulcerans, Bacteroides dorei, Bacteroides* sp. D20, *Ruminococcaceae bacterium* cv2, *Paraprevotella xylaniphila, Parabacteroides johnsonii, Alistipes senegalesis, Parabacteroides* sp. HGS0025, *Eubacterum limosum*, and *Parabacteroides* sp. CAG:2.

In one aspect, the disclosure provides compositions comprising a purified bacterial mixture comprising two or more bacterial strains of species selected from the group consisting of *Phascolarctobacterium faecium, Phascolarctobacterium* sp. CAG:207, *Fusobacterium ulcerans, Fusobacterium varium, Bacteroides dorei, Bacteroides fluxus, Bacteroides uniformis, Bacteroides* sp. D20 *Subdoligranulum* sp., *Ruthenibacterium lactatiformans, Ruminococcaceae bacterium* cv2, *Gemminger formicilis, Paraprevotella xylaniphila, Parabacteroides johnsonii, Alistipes* sp., *Alistipes timonensis, Alistipes senegalesis, Parabacteroides gordonii, Parabacteroides* sp. HGS0025, *Eubacterum limosum, Parabacteroides* sp. CAG:2 and *Parabacteroides distasonis*. In some embodiments of the compositions provided herein, the purified bacterial mixture comprises, at least 3, at least 4, at least 5, at least 6, at least 7, at least 8, at least 9, at least 10, or at least 11 bacterial strains.

In one aspect, the disclosure provides compositions comprising a purified bacterial mixture comprising two or more bacterial strains of species selected from the group consisting of *Phascolarctobacterium faecium, Fusobacterium*

*varium, Bacteroides dorei, Bacteroides uniformis, Ruthenibacterium lactatiformans, Paraprevotella xylaniphila, Parabacteroides johnsonii, Alistipes senegalesis, Parabacteroides gordonii, Eubacterum limosum*, and *Parabacteroides distasonis*. In some embodiments of the compositions provided herein, the purified bacterial mixture comprises at least 2, at least 3, at least 4, at least 5, at least 6, at least 7, at least 8, at least 9, at least 10, or at least 11 bacterial strains.

In one aspect, the disclosure provides compositions comprising a purified bacterial mixture comprising two or more bacterial strains of species selected from the group consisting of *Phascolarctobacterium* sp. CAG:207, *Fusobacterium ulcerans, Bacteroides dorei, Bacteroides* sp. D20, *Ruminococcaceae bacterium* cv2, *Paraprevotella xylaniphila, Parabacteroides johnsonii, Alistipes senegalesis, Parabacteroides* sp. HGS0025, *Eubacterum limosum*, and *Parabacteroides* sp. CAG:2. In some embodiments of the compositions provided herein, the purified bacterial mixture comprises at least 2, at least 3, at least 4, at least 5, at least 6, at least 7, at least 8, at least 9, at least 10, or at least 11 bacterial strains.

In one aspect, the disclosure provides compositions comprising a purified bacterial mixture comprising two or more bacterial strains of species selected from the group consisting of *Bacteroides cellulosilyticus, Bacteroides clarus, Anaerostipes caccae, Bacteroides salyersiae, Bacteroides fragilis, Bacteroides uniformis, Bacteroides eggerthii, Clostridium* sp., *Parabacteroides goldsteinii, Bacteroides* sp., *Lachnospiraceae bacterium* HGA0140, *Hungatella hathewayi, Clostridium lavalense, Ruminococcus* sp., and *Clostridium innocuum*. In some embodiments of the compositions provided herein, the purified bacterial mixture comprises at least 3, at least 4, at least 5, at least 6, at least 7, at least 8, at least 9, at least 10, at least 11, at least 12, at least 13, at least 14, or at least 15 bacterial strains.

In one aspect, the disclosure provides compositions comprising a purified bacterial mixture comprising two or more bacterial strains of species selected from the group consisting of *Bacteroides cellulosilyticus, Bacteroides clarus, Anaerostipes caccae, Bacteroides salyersiae, Bacteroides fragilis, Bacteroides uniformis, Bacteroides eggerthii, Clostridium* sp., *Parabacteroides goldsteinii*, and *Bacteroides* sp. In some embodiments of the compositions provided herein, the purified bacterial mixture comprises at least 3, at least 4, at least 5, at least 6, at least 7, at least 8, at least 9, or at least 10 bacterial strains.

In one aspect, the disclosure provides compositions comprising a purified bacterial mixture comprising two or more bacterial strains of species selected from the group consisting of *Phascolarctobacterium faecium, Fusobacterium ulcerans, Subdoligranulum* sp., and *Eubacterum limosum*. In some embodiments of the compositions provided herein, the purified bacterial mixture comprises at least 3, or at least 4 bacterial strains.

In one aspect, the disclosure provides compositions comprising a purified bacterial mixture comprising two or more bacterial strains of species selected from the group consisting of *Bacteroides dorei, Bacteroides uniformis, Paraprevotella xylaniphila, Parabacteroides johnsonii, Alistipes* sp., *Parabacteroides gordonii*, and *Parabacteroides distasonis*. In some embodiments of the compositions provided herein, the purified bacterial mixture comprises, at least 3, at least 4, at least 5, at least 6, or at least 7 bacterial strains.

It should be appreciated that the compositions may include multiple strains of a particular species. Thus, for illustration, a non-limiting example of the compositions disclosed herein, comprises one strain of *Bacteroides salyersiae* and two strains of *Bacteroides uniformis*.

The disclosure provides also encompasses compositions comprising bacterial strains that are close in homology to and/or fall within the species *Phascolarctobacterium faecium, Fusobacterium ulcerans, Bacteroides dorei, Bacteroides uniformis, Subdoligranulum* sp., *Paraprevotella xylaniphila, Parabacteroides johnsonii, Alistipes* sp., *Parabacteroides gordonii, Eubacterum limosum, Parabacteroides distasonis, Bacteroides cellulosilyticus, Bacteroides clarus, Anaerostipes caccae, Bacteroides salyersiae, Bacteroides fragilis, Bacteroides uniformis, Bacteroides eggerthii, Clostridium* sp., *Parabacteroides goldsteinii, Bacteroides* sp., *Lachnospiraceae bacterium* HGA0140, *Hungatella hathewayi, Clostridium lavalense, Ruminococcus* sp., and *Clostridium innocuum*.

Thus, in one embodiment, the compositions of the disclosure include one or more bacterial strains comprising 16S rDNA sequences having at least 97% homology with nucleic acid sequences selected from the group consisting of SEQ ID NOs:27-52. In some embodiments, the compositions of the disclosure include two or more bacterial strains comprising 16S rDNA sequences having at least 97% homology with nucleic acid sequences selected from the group consisting of SEQ ID NOs:27-52.

Thus, in one embodiment, the compositions of the disclosure include one or more bacterial strains comprising 16S rDNA sequences having at least 97% sequence identity with nucleic acid sequences selected from the group consisting of SEQ ID NOs:27-52. In some embodiments, the compositions of the disclosure include two or more bacterial strains comprising 16S rDNA sequences having at least 97% sequence identity with nucleic acid sequences selected from the group consisting of SEQ ID NOs:27-52.

In one aspect, the compositions of the disclosure include two or more purified bacterial strains comprising 16S rDNA sequences having at least 97% homology with nucleic acid sequences selected from the group consisting of SEQ ID NOs:1-26. In some embodiments, the compositions of the disclosure include two or more purified bacterial strains comprising 16S rDNA sequences having at least 97% sequence identity with nucleic acid sequences selected from the group consisting of SEQ ID NOs:1-26. In some embodiments, the compositions of the disclosure include two or more bacterial strains of species selected from the group consisting of *Phascolarctobacterium faecium, Fusobacterium ulcerans, Bacteroides dorei, Bacteroides uniformis, Subdoligranulum* sp., *Paraprevotella xylaniphila, Parabacteroides johnsonii, Alistipes* sp., *Parabacteroides gordonii, Eubacterum limosum, Parabacteroides distasonis, Bacteroides cellulosilyticus, Bacteroides clarus, Anaerostipes caccae, Bacteroides salyersiae, Bacteroides fragilis, Bacteroides uniformis, Bacteroides eggerthii, Clostridium* sp., *Parabacteroides goldsteinii, Bacteroides* sp., *Lachnospiraceae bacterium* HGA0140, *Hungatella hathewayi, Clostridium lavalense, Ruminococcus* sp., and *Clostridium innocuum*. In some embodiments, the compositions of the disclosure include two or more purified bacterial strains comprising 16S rDNA sequences having at least 97% homology with nucleic acid sequences selected from the group consisting of SEQ ID NO:27-52. In some embodiments, the compositions of the disclosure include two or more purified bacterial strains comprising 16S rDNA sequences having at least 97% sequence identity with nucleic acid sequences selected from the group consisting of SEQ ID NO:27-52.

In some embodiments, the disclosure provides compositions with two or more purified bacterial strains that comprise 16S rDNA sequences with nucleic acid sequences selected from the group consisting of SEQ ID NOs:1-26. In some embodiments, the disclosure provides compositions with five or more purified bacterial strains that comprise 16S rDNA sequences with nucleic acid sequences selected from the group consisting of SEQ ID NOs:1-26. In some embodiments, the disclosure provides compositions with at least ten purified bacterial strains, wherein the bacterial strains comprise 16S rDNA sequences with nucleic acid sequences SEQ ID NOs:1-26, respectively. In some embodiments, the disclosure provides a composition consisting of ten purified bacterial strains, wherein the bacterial strains comprise 16S rDNA sequences with nucleic acid sequences SEQ ID NOs:1-26, respectively. In some embodiments, the disclosure provides a composition essentially consisting of eleven purified bacterial strains, wherein the bacterial strains comprise 16S rDNA sequences with nucleic acid sequences SEQ ID NOs:1-26, respectively. As used herein, essentially consisting of refers to a composition that includes no additional bacterial strains.

In some embodiments, the disclosure provides compositions with bacterial strains that comprise 16S rDNA sequences having at least 97% homology with nucleic acid sequences selected from the group consisting of: SEQ ID NOs:1-26. In some embodiments, the disclosure provides compositions with two or more purified bacterial strains that comprise 16S rDNA sequences having at least 97% homology with nucleic acid sequences selected from the group consisting of SEQ ID NOs:1-26. In some embodiments, the disclosure provides compositions with five or more purified bacterial strains that comprise 16S rDNA having at least 97% homology with nucleic acid sequences selected from the group consisting of SEQ ID NOs:1-26. In some embodiments, the disclosure provides compositions with at least ten purified bacterial strains, wherein the bacterial strains comprise 16S rDNA sequences having at least 97% homology with nucleic acid sequences SEQ ID NOs:1-26, respectively. In some embodiments, the disclosure provides a composition consisting of ten purified bacterial strains, wherein the bacterial strains comprise 16S rDNA sequences having at least 97% homology with nucleic acid sequences SEQ ID NOs:1-26, respectively. In some embodiments, the disclosure provides a composition essentially consisting of ten purified bacterial strains, wherein the bacterial strains comprise 16S rDNA sequences having at least 97% homology with nucleic acid sequences SEQ ID NOs:1-26, respectively.

In some embodiments, the disclosure provides compositions with bacterial strains that comprise 16S rDNA sequences having at least 97% sequence identity with nucleic acid sequences selected from the group consisting of: SEQ ID NOs:1-26. In some embodiments, the disclosure provides compositions with two or more purified bacterial strains that comprise 16S rDNA sequences having at least 97% sequence identity with nucleic acid sequences selected from the group consisting of SEQ ID NOs:1-26. In some embodiments, the disclosure provides compositions with five or more purified bacterial strains that comprise 16S rDNA having at least 97% sequence identity with nucleic acid sequences selected from the group consisting of SEQ ID NOs:1-26. In some embodiments, the disclosure provides compositions with at least ten purified bacterial strains, wherein the bacterial strains comprise 16S rDNA sequences having at least 97% sequence identity with nucleic acid sequences SEQ ID NOs:1-26, respectively.

In some embodiments, the disclosure provides a composition consisting of ten purified bacterial strains, wherein the bacterial strains comprise 16S rDNA sequences having at least 97% sequence identity with nucleic acid sequences SEQ ID NOs:1-26, respectively.

In some embodiments, the disclosure provides a composition essentially consisting of ten purified bacterial strains, wherein the bacterial strains comprise 16S rDNA sequences having at least 97% sequence identity with nucleic acid sequences SEQ ID NOs:1-26, respectively.

In one aspect, the disclosure provides a composition comprising bacterial strains that are related to the following bacterial species: *Phascolarctobacterium faecium, Fusobacterium ulcerans, Bacteroides dorei, Bacteroides uniformis, Subdoligranulum* sp., *Paraprevotella xylaniphila, Parabacteroides johnsonii, Alistipes* sp., *Parabacteroides gordonii, Eubacterum limosum, Parabacteroides distasonis, Bacteroides cellulosilyticus, Bacteroides clarus, Anaerostipes caccae, Bacteroides salyersiae, Bacteroides fragilis, Bacteroides uniformis, Bacteroides eggerthii, Clostridium* sp., *Parabacteroides goldsteinii, Bacteroides* sp., *Lachnospiraceae bacterium* HGA0140*, Hungatella hathewayi, Clostridium lavalense, Ruminococcus* sp., and *Clostridium innocuum* (See e.g., Table 1). It should be appreciated that multiple bacterial strains of the compositions disclosed herein can have the same related bacterial species. In some embodiments, the disclosure provides compositions with two or more purified bacterial strains comprising 16S rDNA sequences having at least 97% homology with nucleic acid sequences selected from the group consisting of SEQ ID NO:27-52. In some embodiments, the disclosure provides compositions with two or more purified bacterial strains comprising 16S rDNA sequences having at least 97% sequence identity with nucleic acid sequences selected from the group consisting of SEQ ID NO:27-52.

In one aspect, the disclosure provides bacterial strains with 16S rDNA sequences that have homology to a nucleic acid sequence of any one of the sequences of the bacterial strains or species described herein. In some embodiments, the bacterial strain has at least 60%, at least 70%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or up to 100% homology relative to any of the strains or bacterial species described herein over a specified region or over the entire sequence. It would be appreciated by one of skill in the art that the term "homology" or "percent homology," in the context of two or more nucleic acid sequences or amino acid sequences, refers to a measure of similarity between two or more sequences or portion(s) thereof. The homology may exist over a region of a sequence that is at least about 50 nucleotides in length, or more preferably over a region that is 100 to 500 or 1000 or more nucleotides in length. In some embodiments, the homology exists over the length the 16S rRNA or 16S rDNA sequence, or a portion thereof.

Additionally, or alternatively, two or more sequences may be assessed for the identity between the sequences. The terms "identical" or percent "identity" in the context of two or more nucleic acids or amino acid sequences, refer to two or more sequences or subsequences that are the same. Two sequences are "substantially identical" if two sequences have a specified percentage of amino acid residues or nucleotides that are the same (e.g., at least 80%, 85%, 90%, 95%, 96%, 97%, 98%, 99%, 99.5%, 99.6%, 99.7%, 99.8% or 99.9% identical) over a specified region or over the entire sequence, when compared and aligned for maximum correspondence over a comparison window, or designated region as measured using one of the following sequence comparison algorithms or by manual alignment and visual inspection. Optionally, the identity exists over a region that is at least about 50 nucleotides in length, or more preferably over a region that is 100 to 500 or 1000 or more nucleotides in length. In some embodiments, the identity exists over the length the 16S rRNA or 16S rDNA sequence.

Additionally, or alternatively, two or more sequences may be assessed for the alignment between the sequences. The terms "alignment" or percent "alignment" in the context of two or more nucleic acids or amino acid sequences, refer to two or more sequences or subsequences that are the same. Two sequences are "substantially aligned" if two sequences have a specified percentage of amino acid residues or nucleotides that are the same (e.g., at least 80%, 85%, 90%, 95%, 96%, 97%, 98%, 99%, 99.5%, 99.6%, 99.7%, 99.8% or 99.9% identical) over a specified region or over the entire sequence, when compared and aligned for maximum correspondence over a comparison window, or designated region as measured using one of the following sequence comparison algorithms or by manual alignment and visual inspection. Optionally, the alignment exists over a region that is at least about 50 nucleotides in length, or more preferably over a region that is 100 to 500 or 1000 or more nucleotides in length. In some embodiments, the identity exists over the length the 16S rRNA or 16S rDNA sequence.

For sequence comparison, typically one sequence acts as a reference sequence, to which test sequences are compared. Methods of alignment of sequences for comparison are well known in the art. See, e.g., by the local homology algorithm of Smith and Waterman (1970) Adv. Appl. Math. 2:482c, by the homology alignment algorithm of Needleman and Wunsch, J. Mol. Biol. 48:443, 1970, by the search for similarity method of Pearson and Lipman. Proc. Natl. Acad. Sci. USA 85:2444, 1988, by computerized implementations of these algorithms (GAP, BESTFIT, FASTA, and TFASTA in the Wisconsin Genetics Software Package, Genetics Computer Group. Madison. Wis.), or by manual alignment and visual inspection (see. e.g., Brent et al., Current Protocols in Molecular Biology, John Wiley & Sons, Inc. (Ringbou ed., 2003)). Two examples of algorithms that are suitable for determining percent sequence identity and sequence similarity are the BLAST and BLAST 2.0 algorithms, which are described in Altschul et al., Nuc. Acids Res. 25:3389-3402, 1977; and Altschul et al., J. Mol. Biol. 215:403-410, 1990, respectively.

In one aspect, the disclosure provides compositions comprising multiple purified bacterial strains. In one aspect, the 16S rDNA sequences of purified bacterial strains of the compositions were compared to 16S rDNA sequences of known bacterial species/strains in a bacterial genome database to identify the closest known related bacterial species to the bacterial strains disclosed herein (See e.g., Table 1 and Table 3). It should be appreciated that multiple bacterial strains of the compositions disclosed herein may have the same closest related bacterial species. In one aspect, the disclosure provides compositions comprising one or more bacterial strains or species with 16S rDNA sequences that have homology to a nucleic acid sequence of any one of the sequences provided by SEQ ID NOs:1-26. In some embodiments, the species with 16S rDNA sequences with homology to a nucleic acid sequence of any one of the closest related species to any of the strains described herein, correspond to bacterial strains with 16S rDNA sequences provided by SEQ ID NOs:27-52. In one aspect, the disclosure provides compositions comprising one or more bacterial strains or species with 16S rDNA sequences that have homology to a nucleic acid sequence of any one of the sequences provided by SEQ ID NOs:1-21. In some embodiments, the species with 16S rDNA sequences with homology to a nucleic acid sequence of any one of the closest related species to any of the strains described herein, correspond to bacterial strains with 16S rDNA sequences provided by SEQ ID NOs:27-47. In one aspect, the disclosure provides compositions comprising one or more bacterial strains or species with 16S rDNA sequences that have homology to a nucleic acid sequence of any one of the sequences provided by SEQ ID NOs:1-11. In some embodiments, the species with 16S rDNA sequences with homology to a nucleic acid sequence of any one of the closest related species to any of the strains described herein, correspond to bacterial strains with 16S rDNA sequences provided by SEQ ID NOs:27-37. In one aspect, the disclosure provides compositions comprising one or more bacterial strains or species with 16S rDNA sequences that have homology to a nucleic acid sequence of any one of the sequences provided by SEQ ID NOs:12-26. In some embodiments, the species with 16S rDNA sequences with homology to a nucleic acid sequence of any one of the closest related species to any of the strains described herein, correspond to bacterial strains with 16S rDNA sequences provided by SEQ ID NOs:38-52. In one aspect, the disclosure provides compositions comprising one or more bacterial strains or species with 16S rDNA sequences that have homology to a nucleic acid sequence of any one of the sequences provided by SEQ ID NOs:12-21. In some embodiments, the species with 16S rDNA sequences with homology to a nucleic acid sequence of any one of the closest related species to any of the strains described herein, correspond to bacterial strains with 16S rDNA sequences provided by SEQ ID NOs:38-47.

In some embodiments, the compositions disclosed herein provide at least one of the bacterial strains (e.g., purified bacterial strains) described herein. In some embodiments, the compositions that comprise at least one bacterial strain, comprise at least one bacterial strain with a 16S rDNA sequence selected from any one of SEQ ID NOs:1-26. In some embodiments, the compositions that comprise at least one bacterial strain, comprise at least one bacterial strain with a 97% homology to 16S rDNA sequence selected from any one of SEQ ID NOs:1-26. In some embodiments, the compositions that comprise at least one bacterial strain, comprise at least one bacterial strain with a 97% sequence identity with a 16S rDNA sequence selected from any one of SEQ ID NOs:1-26.

In some embodiments, the compositions disclosed herein comprise two or more bacterial strains. In some embodiments, the compositions described herein comprise at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, or at least 20 or more bacterial strains (e.g., purified bacterial strains).

In some embodiments of the compositions provided herein, at least 50% of the bacterial strains belong to the order of Bacteriodales. In some embodiments of the compositions provided herein, at least 50% of the bacterial strains belong to the genus *Bacteroides* or *Parabacteroides*. In some embodiments of the compositions provided herein, one or more strains belongs to the genus *Bacteroides* and one or more strains belongs to the genus *Parabacteroides*. In some embodiments of the compositions provided herein, at least 25% of the bacterial strains belong to the family of Bacteroidaceae. In some embodiments of the compositions provided herein, one or more of the bacterial strains belongs to the genus *Bacteroides*. In some embodiments of the compositions provided herein, one or more of the bacterial strains belongs to the genus *Parabacteroides*.

In some embodiments of the compositions provided herein, the composition does not include bacterial strains that belong to the order of Bacteriodales.

In some embodiments of the compositions provided herein, one or more of the bacterial strains belong to the order of Bacteriodales and one or more of the bacterial strains belong to the order of Clostridiales. In some embodiments of the compositions provided herein, at least 50% of the bacterial strains belong to the order of Bacteriodales and one or more of the bacterial strains belong to the order of Clostridiales. In some embodiments of the compositions provided herein, at least 75% of the bacterial strains belong to the order of Bacteriodales and one or more of the bacterial strains belong to the order of Clostridiales. In some embodiments of the compositions provided herein, at least 90% of the bacterial strains belong to the order of Bacteriodales and one or more of the bacterial strains belong to the order of Clostridiales.

In some embodiments, the compositions provided herein do not include *E. coli*. In some embodiments, the compositions provided herein do not include *Bifidobacterium*. In some embodiments, the compositions provided herein do not include *Bacillus*. In some embodiments, the compositions provided herein do not include *Enterococcus*. In some embodiments, the compositions provided herein do not include *Barnesiella*. In some embodiments, the compositions provided herein do not include *B. fragilis*. In some embodiments, the compositions provided herein do not include *B. thetaiotaomicron*. In some embodiments, the compositions provided herein do not include *Akkermansia*. In some embodiments, the compositions provided herein do not include *Proteobacteria*.

In some embodiments, the compositions provided herein do not include *Burkholderia*.

In some embodiments, the compositions provided herein do not include *clostridium* species belonging to Cluster IV. In some embodiments, the compositions provided herein do not include *Faecalibacterium*. In some embodiments, the compositions provided herein do not include *clostridium* species belonging to Cluster XIVa. In some embodiments, the compositions do not comprise fungi, such as *Monilla* species.

In one aspect, the disclosure provides purified fractions of human stool sample that can induce CD8 T cells.

In some embodiments of the compositions provided herein, one or more of the bacterial strains are human-derived bacteria. In some embodiments of the compositions provided herein, all of the bacterial strains are human-derived bacteria. In some embodiments of the compositions provided herein, the bacterial strains are derived from more than one human donor.

The bacterial strains used in the compositions provided herein generally are isolated from the microbiome of healthy individuals. In some embodiments, the compositions include strains originating from a single individual. In some embodiments, the compositions include strains originating from multiple individuals. In some embodiments, the bacterial strains are obtained from multiple individuals, isolated and grown up individually. The bacterial compositions that are grown up individually may subsequently be combined to provide the compositions of the disclosure. It should be appreciated that the origin of the bacterial strains of the compositions provided herein is not limited to the human microbiome from a healthy individual. In some embodiments, the bacterial strains originate from a human with a microbiome in dysbiosis. In some embodiments, the bacterial strains originate from non-human animals or the environment (e.g., soil or surface water). In some embodiments, the combinations of bacterial strains provided herein originate from multiple sources (e.g., human and non-human animals).

In some embodiments of the compositions provided herein, the composition includes one or more anaerobic bacteria. In some embodiments of the compositions provided herein, the composition includes only anaerobic bacteria. In some embodiments of the compositions provided herein, the composition includes one or more facultative anaerobic bacteria. In some embodiments of the compositions provided herein, the composition includes only facultative anaerobic bacteria. In some embodiments of the compositions provided herein, the composition includes one or more obligate anaerobic bacteria. In some embodiments of the compositions provided herein, the composition includes only obligate anaerobic bacteria.

In some embodiments of the compositions provided herein, one or more of the bacterial strains does not have an antibiotic resistance gene. In some embodiments of the compositions provided herein, the bacterial strains do not have an antibiotic resistance gene that renders the bacterial strain resistant to vancomycin.

In some embodiments of the compositions provided herein, the compositions do not include bacterial strains that are resistant to one or more antibiotics. It should be appreciated that it may be desirable to have a mechanism to remove the bacterial compositions provided herein from the body after administration. One such mechanism is to remove the bacterial compositions by antibiotic treatment. Thus, in some embodiments, the compositions do not include bacterial strains that are resistant to one or more antibiotics. In some embodiments, the compositions do not include bacterial strains that are resistant to one or more antibiotics selected from the group consisting of penicillin, benzylpenicillin, ampicillin, sulbactam, amoxicillin, clavulanate, tazobactam, piperacillin, cefmetazole, vancomycin, imipenem, meropenem, metronidazole and clindamycin. In some embodiments, the compositions do not include bacterial strains that are resistant to vancomycin.

In some embodiments, the compositions include bacterial strains that are susceptible to at least four antibiotics that are efficacious in humans. In some embodiments, the compositions include bacterial strains that are susceptible to at least three antibiotics that are efficacious in humans. In some embodiments, the compositions include bacterial strains that are susceptible to at least two antibiotics that are efficacious in humans. In some embodiments, the compositions include bacterial strains that are susceptible to at least one antibiotic that is efficacious in humans. In some embodiments, the compositions include only bacterial strains that are susceptible to at least four antibiotics that are efficacious in humans. In some embodiments, the compositions include only bacterial strains that are susceptible to at least three antibiotics that are efficacious in humans. In some embodiments, the compositions include only bacterial strains that are susceptible to at least two antibiotics that are efficacious in humans. In some embodiments, the compositions include bacterial strains that are susceptible to at least one antibiotic that is efficacious in humans. (An "antibiotic that is efficacious in a human" as used herein is an antibiotic that has been used to successfully treat bacterial infections in a human).

In some embodiments of the compositions provided herein, one or more of the bacterial strains is a spore-former. In some embodiments of the compositions provided herein, one or more of the bacterial strains is in spore form. In some embodiments of the compositions provided herein, one or more of the bacterial strains is a non-spore former.

In some embodiments, the compositions described herein comprise spore forming and non-spore forming bacterial strains. In some embodiments, the compositions described herein comprise spore-forming bacterial strains. In some embodiments, the compositions described herein comprise only spore-forming bacterial strains. In some embodiments, the compositions described herein comprise only non-spore forming bacterial strains. The spore-forming bacteria can be in spore form (i.e., as spores) or in vegetative form (i.e., as vegetative cells). In spore form, bacteria are generally more resistant to environmental conditions, such as heat, acid, radiation, oxygen, chemicals, and antibiotics. In contrast, in the vegetative state or actively growing state, bacteria are more susceptible to such environmental conditions, compared to in the spore form. In general, bacterial spores are able to germinate from the spore form into a vegetative/actively growing state, under appropriate conditions. For instance, bacteria in spore format may germinate when they are introduced in the intestine.

In some embodiments, at least one (e.g., 1, 2, 3, 4, 5, or more) of the bacterial strains in the composition is a spore former. In some embodiments, at least one (e.g., 1, 2, 3, 4, 5, or more) of the bacterial strains in the composition is in spore form. In some embodiments, at least one (e.g., 1, 2, 3, 4, 5, or more) of the bacterial strains in the composition is a non-spore former. In some embodiments, at least one (e.g., 1, 2, 3, 4, 5, or more) of the bacterial strains in the composition is in vegetative form (as discussed above, spore forming bacteria can also be in vegetative form). In some embodiments, at least one (e.g., 1, 2, 3, 4, 5, or more) of the bacterial strains in the composition is in spore form and at least one (e.g., 1, 2, 3, 4, 5, or more) of the bacterial strains in the composition is in vegetative form. In some embodiments, at least one bacterial strain that is considered able to form spores (i.e., a spore-former) but is present in the composition in vegetative form. In some embodiments, at least one bacterial strain that is considered able to form spores is present in the composition both in spore form and in vegetative form.

It is envisioned that the bacterial strains of the compositions provided herein are alive and will be alive when they reach the target area (e.g., the intestines). Bacterial spores are considered to be alive in this regards. In some embodiments, bacteria that are administered as spores may germinate in the target area (e.g., the intestines). It should further be appreciated that not all of the bacteria are alive and the compositions can include a percentage (e.g., by weight) that is not alive. In addition, in some embodiments, the compositions include bacterial strains that are not alive when administered or at the time when the composition reaches the target area (e.g., the intestines). It is envisioned that non-living bacteria may still be useful by providing some nutrients and metabolites for the other bacterial strains in the composition.

In any of the compositions provided herein, in some embodiments, the bacterial strains are purified. In any of the compositions provided herein, in some embodiments, the bacterial strains are isolated. Any of the bacterial strains described herein may be isolated and/or purified, for example, from a source such as a culture or a microbiota sample (e.g., fecal matter). The bacterial strains used in the compositions provided herein generally are isolated from the microbiome of healthy individuals. However, bacterial strains can also be isolated from individuals that are considered not to be healthy. In some embodiments, the compositions include strains originating from multiple individuals. As used herein, the term "isolated" bacteria that have been separated from one or more undesired component, such as another bacterium or bacterial strain, one or more component of a growth medium, and/or one or more component of a sample, such as a fecal sample. In some embodiments, the bacteria are substantially isolated from a source such that other components of the source are not detected. As also used herein, the term "purified" refers to a bacterial strain or composition comprising such that has been separated from one or more components, such as contaminants. In some embodiments, the bacterial strain is substantially free of contaminants. In some embodiments, one or more bacterial strains of a composition may be independently purified from one or more other bacteria produced and/or present in a culture or a sample containing the bacterial strain. In some embodiments, a bacterial strain is isolated or purified from a sample and then cultured under the appropriate conditions for bacterial replication, e.g., under anaerobic culture conditions. The bacteria that is grown under appropriate conditions for bacterial replication can subsequently be isolated/purified from the culture in which it is grown.

In one aspect, the disclosure provides bacterial strains and mixtures of bacterial strains with unique biological properties. In some embodiments of the compositions provided herein, the composition induces proliferation and/or accumulation of CD8+ T-cells. In some embodiments, the bacterial strains of the compositions provided herein can induce proliferation and/or accumulation of CD8+ T-cells, because of the synergy between the bacterial strains. Thus, without being limiting to a specific mechanism, in some embodiments, the combination of the bacterial strains of the compositions provided herein act synergistically in the induction of proliferation and/or accumulation of CD8+ T-cells because the combination of the strains is particularly well-suited to generate metabolites and/or cellular signals that stimulate the induction of proliferation and/or accumulation of CD8+ T-cells. The bacterial compositions may do so, for instance through the use of nutrients in the intestinal tract (e.g., the colon or the cecum), and/or metabolic interactions that result in metabolites and/or cellular signals that stimulate the induction of proliferation and/or accumulation of CD8+ T-cells. In addition, without being limiting to a specific mechanism, in some embodiments, the combination of the bacterial strains of the compositions provided herein act synergistically in the induction of proliferation and/or accumulation of CD8+ T-cells because the combination of the strains is superior in engrafting specific niches in the intestinal tract (e.g., the colon or the cecum) that will result in the induction of proliferation and/or accumulation of CD8+ T-cells (e.g., by providing a favorable microenvironment). In some embodiments, the combination of the bacterial strains of the compositions provided herein act synergistically in the induction of proliferation and/or accumulation of CD8+ T-cells because the combination of the strains is particularly well-suited to generate metabolites and/or cellular signals that stimulate the induction of proliferation and/or accumulation of CD8+ T-cells, and the combination is well suited to engraft in specific niches, that result in localization of the metabolites and/or cellular signals to a target for the induction of proliferation and/or accumulation of CD8+ T-cells Treatment of Diseases Cancer In one aspect, the disclosure includes compositions and methods for the treatment of diseases in a subject. In some embodiments of the methods provided herein, the subject has cancer. In one aspect, the cancers that can be treated according to the compositions and methods provided herein, include without limitation, carcinoma, glioma, mesothelioma, melanoma, lymphoma, leukemia, adenocarcinoma, breast cancer, ovarian cancer, cervical cancer, glioblastoma, multiple myeloma, prostate cancer, Burkitt's lymphoma, head and neck cancer, colon cancer, colorectal cancer, non-small cell lung cancer, small cell lung cancer, cancer of the esophagus, stomach cancer, pancreatic cancer, hepatobiliary cancer, cancer of the gallbladder, cancer of the small intestine, rectal cancer, kidney cancer, bladder cancer, prostate cancer, penile cancer, urethral cancer, testicular cancer, vaginal cancer, uterine cancer, thyroid cancer, parathyroid cancer, adrenal cancer, pancreatic endocrine cancer, carcinoid cancer, bone cancer, skin cancer, retinoblastomas, Hodgkin's lymphoma, non-Hodgkin's lymphoma, Kaposi's sarcoma, multicentric Castleman's disease, AIDS-associated primary effusion lymphoma, neuroectodermal tumors, or rhabdomyosarcoma. In some embodiments of the methods provided herein, the cancer is prostate cancer, bladder cancer, non-small cell lung cancer, urothelial carcinoma, melanoma, or renal cell carcinoma. In some embodiments of the methods provided herein, the subject is undergoing radiation treatment.

In some embodiments of the methods provided herein, the method further includes administering one or more anticancer agents. In some embodiments of the methods provided herein, the anticancer agent is a chemotherapy agent. In some embodiments of the methods provided herein, the anticancer agent is a cancer immunotherapy agent.

In some embodiments of the methods provided herein, the cancer immunotherapy agent is an immune checkpoint inhibitor. In some embodiments of the methods provided herein, the immune checkpoint inhibitor is a PD-1 inhibitor, PD-L-1 inhibitor, or CTLA-4 inhibitor. In some embodiments of the methods provided herein, the immune checkpoint inhibitor is a PD-1 inhibitor. In some embodiments of the methods provided herein, the immune checkpoint inhibitor is a CTLA-4 inhibitor.

In some embodiments of the methods provided herein, the cancer immunotherapy agent is a cancer vaccine that acts to increase the response of a subject's immune system to cancer cells. For example, cancer vaccines include cancer antigen(s) that act to induce or stimulate an immune response against cells bearing the cancer antigen(s). The immune response induced or stimulated can include an antibody (humoral) immune response and/or a T-cell (cell-mediated) immune response. CD8+ T-cells can differentiate into cytotoxic T-cells that kill target cells bearing the antigen recognized by CD8+ T-cells. Induction of CD8+ T-cells can, therefore, enhance the immune response to cancer antigens provided in a cancer vaccine.

In some embodiments of the methods provided herein, the cancer immunotherapy agent is a CAR-T therapeutic. CAR-T cells include T-cells taken from a patient that are genetically engineered to produce chimeric antigen receptors (CARs) on their surface. The CARs are engineered to recognize a specific antigen on cancer cells. After the CAR-T cells are infused into the patient, they recognize and kill cancer cells that express the specific antigen on their surfaces. Induction of CD8+ T-cells is useful to provide cells for conversion into CAR-T cells.

In some embodiments of the methods provided herein, the method further includes administering one or more cytokines. In some embodiments of the methods provided herein the cytokine is IL-2, IL-15, or IL-21.

In some embodiments of the methods provided herein, the method further includes administering one or more costimulatory agents. In some embodiments of the methods provided herein the costimulatory agent is a CD-28, OX-40, 4-1BB, or CD40 antibody.

In some embodiments of the methods provided herein, the method further includes administering one or more vaccines. In some embodiments of the methods provided herein, the vaccine is a dendritic cell vaccine.

In some embodiments of the methods provided herein, the method further includes administering adoptive cell transfer therapy. In some embodiments of the methods provided herein, the adoptive cell transfer therapy is the use of engineered T-cell receptors or chimeric antigen receptors.

In some embodiments of the compositions provided herein, the composition further comprises one or more anticancer agents. In some embodiments of the compositions provided herein, the anticancer agent is a chemotherapy agent. In some embodiments of the compositions provided herein, the anticancer agent is cancer immunotherapy agent. In some embodiments of the compositions provided herein, the cancer immunotherapy agent is an immune checkpoint inhibitor. In some embodiments of the compositions provided herein, the immune checkpoint inhibitor is a PD-1 inhibitor, PD-L-1 inhibitor, or CTLA-4 inhibitor. In some embodiments of the compositions provided herein, the immune checkpoint inhibitor is a PD-1 inhibitor, PD-L-1 inhibitor, CTLA-4 inhibitor, IDO1 inhibitor, LAG3 inhibitor or TIM3 inhibitor. In some embodiments of the compositions provided herein, the immune checkpoint inhibitor is a PD-1 inhibitor. In some embodiments, the PD-1 inhibitor is nivolumab. In some embodiments, the PD-1 inhibitor is pembrolizumab. In some embodiments, the PD-1 inhibitor is pidiluzimab. In some embodiments of the compositions provided herein, the immune checkpoint inhibitor is a PD-L-1 inhibitor. In some embodiments, the PD-L-1 inhibitor is atezolizumab. In some embodiments, the PD-L-1 inhibitor is avelumab. In some embodiments, the PD-L-1 inhibitor is durvalumab. In some embodiments of the methods provided herein, the immune checkpoint inhibitor is a CTLA-4 inhibitor. In some embodiments, the CTLA-4 inhibitor is an anti-CTLA-4 antibody. Examples of anti-CTLA-4 antibodies include, without limitation, ipilimumab, tremelimumab (CP-675,206), 9H10, 4F10, and 9D9. In some embodiments, the CTLA-4 inhibitor is ipilimumab. In some embodiments, the CTLA-4 inhibitor is tremelimumab. It should further be appreciated that multiple anticancer agents (e.g., immune checkpoint inhibitors) may be included in the compositions and methods disclosed herein. For instance, in a non-limiting example, the compositions and methods disclosed include both a PD-1 inhibitor and a CTLA-4 inhibitor.

In one aspect, the disclosure provides a composition comprising a purified bacterial mixture comprising *Phascolarctobacterium faecium, Fusobacterium ulcerans, Bacteroides dorei, Bacteroides uniformis, Subdoligranulum* sp., *Paraprevotella xylaniphila, Parabacteroides johnsonii, Alistipes* sp., *Parabacteroides gordonii, Eubacterum limosum*, and *Parabacteroides distasonis*, and a PD-1 inhibitor.

In one aspect, the disclosure provides a composition comprising a purified bacterial mixture comprising *Phas-*

*colarctobacterium faecium, Fusobacterium ulcerans, Bacteroides dorei, Bacteroides uniformis, Subdoligranulum* sp., *Paraprevotella xylaniphila, Parabacteroides johnsonii, Alistipes* sp., *Parabacteroides gordonii, Eubacterum limosum*, and *Parabacteroides distasonis*, and a PD-L-1 inhibitor.

In one aspect, the disclosure provides a composition comprising a purified bacterial mixture comprising *Phascolarctobacterium faecium, Fusobacterium ulcerans, Bacteroides dorei, Bacteroides uniformis, Subdoligranulum* sp., *Paraprevotella xylaniphila, Parabacteroides johnsonii, Alistipes* sp., *Parabacteroides gordonii, Eubacterum limosum*, and *Parabacteroides distasonis*, and a CTLA-4 inhibitor.

In one aspect, the disclosure provides compositions comprising a purified bacterial mixture comprising bacterial strains comprising 16S rDNA sequences of at least 97% homology to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, and SEQ ID NO:11, and a PD-1 inhibitor.

In one aspect, the disclosure provides compositions comprising a purified bacterial mixture comprising bacterial strains comprising 16S rDNA sequences of at least 97% homology to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, and SEQ ID NO:11, and a PD-L-1 inhibitor.

In one aspect, the disclosure provides compositions comprising a purified bacterial mixture comprising bacterial strains comprising 16S rDNA sequences of at least 97% homology to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, and SEQ ID NO:11, and a CTLA-4 inhibitor.

In one aspect, the disclosure provides compositions comprising a purified bacterial mixture comprising bacterial strains comprising 16S rDNA sequences of at least 97% sequence identity with SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, and SEQ ID NO:11, and a PD-1 inhibitor.

In one aspect, the disclosure provides compositions comprising a purified bacterial mixture comprising bacterial strains comprising 16S rDNA sequences of at least 97% sequence identity with SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, and SEQ ID NO:11, and a PD-L-1 inhibitor.

In one aspect, the disclosure provides compositions comprising a purified bacterial mixture comprising bacterial strains comprising 16S rDNA sequences of at least 97% sequence identity with SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, and SEQ ID NO:11, and a CTLA-4 inhibitor.

In one aspect, the disclosure provides compositions comprising a purified bacterial mixture comprising bacterial strains comprising 16S rDNA sequences of at least 97% sequence identity with SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, and SEQ ID NO:64, and a PD-1 inhibitor.

In one aspect, the disclosure provides compositions comprising a purified bacterial mixture comprising bacterial strains comprising 16S rDNA sequences of at least 97% sequence identity with SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, and SEQ ID NO:64, and a PD-L-1 inhibitor.

In one aspect, the disclosure provides compositions comprising a purified bacterial mixture comprising bacterial strains comprising 16S rDNA sequences of at least 97% sequence identity with SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, and SEQ ID NO:64, and a CTLA-4 inhibitor.

In some embodiments of the compositions provided herein, the composition further includes one or more cytokines. In some embodiments of the compositions provided herein, the cytokine is IL-2, IL-15, or IL-21. In some embodiments of the compositions provided herein, the composition further comprises one or more costimulatory agents.

In some embodiments of the compositions provided herein, the costimulatory agent is a CD-28, OX-40, 4-1BB, or CD40 antibody.

In some embodiments of the compositions provided herein, the composition further comprises one or more vaccines. In some embodiments of the compositions provided herein, the vaccine is a dendritic cell vaccine. In some embodiments of the compositions provided herein, the composition is combined with adoptive cell transfer therapy. In some embodiments of the compositions provided herein, the adoptive cell transfer therapy is the use of engineered T-cell receptors or chimeric antigen receptors.

Infectious Disease

In one aspect, the disclosure includes compositions and methods for the treatment of diseases in a subject. In some embodiments of the methods provided herein, the subject has an infectious disease. In some embodiments of the methods provided herein, the infectious disease is a bacterial infection, a viral infection, a parasitic infection, or a fungal infection. In some embodiments of the methods provided herein, the infectious disease is a viral infection. In some embodiments of the methods provided herein, the viral infection is HIV. In some embodiments of the methods provided herein, the infection is an infection by a hepatitis virus.

In some embodiments, the compositions provided herein can be used as a pharmaceutical composition for preventing or treating (reducing, partially or completely the adverse effects of) an infectious disease, such as a bacterial infection, a viral infection, a parasitic infection, and a fungal infection.

Bacterial infections that can be treated according to the methods provided herein include, but are not limited to *P. aeruginosa, E. coli, C. tetani, N. gonorrhoeae, C. botulinum, Klebsiella* sp., *Serratia* sp., *Pseudomanas* sp., *P. cepacia, Acinetobacter* sp., *S. epidermis, E. faecalis, S. pneumonias, S. aureus, S. mutans, Haemophilus* sp., *Neisseria* Sp., *N. meningitides, Bacteroides* sp., *Citrobacter* sp., *Branhamella* sp., *Salmonella* sp., *Shigella* sp., *S. pyogenes, Proteus* sp., *Clostridium* sp., *Erysipelothrix* sp., *Listeria* sp., *Pasteurella multocida, Streptobacillus* sp., *Spirillum* sp., *Fusospirocheta* sp., *Treponema pallidum, Borrelia* sp., *Actinomycetes, Mycoplasma* sp., *Chlamydia* sp., *Rickettsia* sp., *Spirochaeta, Borellia burgdorferi, Legionella* sp., *Mycobacteria* sp, *Ureaplasma* sp, *Streptomyces* sp., *Trichomoras* sp., *P. mirabilis; Vibrio cholera, enterotoxigenic Escherichia coli, Clostridium difficile, Salmonella typhi, C. diphtheria, Mycobacterium leprae, Mycobacterium lepromatosi*. Bacterial infections caused by drug resistant bacteria that can be treated according to the methods provided herein include, but are not limited to *Clostridium perfringens; Clostridium botulinum; Clostridium tributrycum; Clostridium sporogenes; Escherichia coli; Pseudomonas aeruginosa*, such as Multidrug Resistant *Pseudomonas aeruginosa*; Vancomycin Resistant *Enterococci* (VRE); Carbapenem Resistant *Enterobacteriaceae* (CRE); *Neisseria gonorrheae; Acinetobacter*, Multidrug Resistant *Acinetobacter; Campylobacter*; Multidrug-resistant *Campylobacter; Candida*, Fluconazole-Resistant *Candida*, Extended spectrum beta-lactamase (ESBL) producing *Enterobacteriaceae; Salmonella, Salmonella Typhimurium*, Drug resistant non-typhoid *Salmonella* spp.; Drug resistant *Salmonella Typhi*; Drug resistant *Shigella; Staphylococcus aureus*, such as Methicillin Resistant *S. aureus* or vancomycin resistant *S. aureus*; Drug resistant *Streptococcus pneumoniae*; Drug resistant Tuberculosis; Erythromycin Resistant Group A *Streptococcus*; Clindamycin resistant Group B *Streptococcus*, and any combinations thereof.

Viral infections that can be treated according to the methods provided herein include, but are not limited to, picornaviridae, caliciviridae, togaviridae, flaviviridae, coronaviridae, rhabdoviridae, filoviridae, paramyxoviridae, orthomyxoviridae, bunyaviridae, arenaviridae, reoviridae, retroviridae, hepadnaviridae, parvoviridae, papovaviridae, adenoviridae, herpesviridae, poxviridae, rotavirus, parainfluenza virus, influenza virus A and B, hepatitis virus, syphilis, HIV, rabies virus, Epstein-Barr virus, and herpes simplex virus.

Viral infections that can be treated according to the methods provided herein include, but are not limited to *Plasmodium falciparum, P. vivax, P. ovale, P. malaria, Toxoplasma gondii, Leishmania mexicana, L. tropica, L. major, L. aethiopica, L. donovani, Trypanosoma cruzi, T. brucei, Schistosoma mansoni, S. haematobium, S. japonium, Trichinella spiralis, Wuchereria bancrofti, Brugia malayli, Entamoeba histolytica, Enterobius vermiculoarus, Taenia solium, T. saginata, Trichomonas vaginatis, T. hominis, T. tenax; Giardia lamblia, Cryptosporidium parvum, Pneumocytis carinii, Babesia bovis, B. divergens, B. microti, Isospore belli, L hominis, Dientamoeba jragiles, Onchocerca volvulus, Ascaris lumbricoides, Necator americanis, Ancylostoma duodenale, Strongyloides stercoralis, Capillaria philippinensis, Angiostrongylus cantonensis, Hymenolepis nana, Diphyllobothrium latum, Echinococcus granulosus, E. multilocularis, Paragonimus westermani, P. caliensis, Chlonorchis sinensis, Opisthorchis felineas, G. Viverini, Fasciola hepatica, Sarcoptes scabiei, Pediculus humanus, Phthirius pubis*, and *Dermatobia hominis*.

Fungal infections that can be treated according to the methods provided herein include, but are not limited to *Cryptococcus neoformans, Blastomyces dermatitidis, Aiellomyces dermatitidis, Histoplasfria capsulatum, Coccidioides immitis, Candida* species, including *C. albicans, C. tropicalis, C. parapsilosis, C. guilliermondii* and *C. krusei, Aspergillus* species, including *A. fumigatus, Aflavus, A. niger, Rhizopusspecies, Rhizomucor* species, *Cunninghammella* species, *Apophysomyces* species, including *A. saksenaea, A. mucor* and *A. absidia, Sporothrix schenckii, Paracoccidioides brasiliensis, Pseudallescheria boydii, Torulopsis glabrata*; and *Dermatophyres* species.

In one aspect, the disclosure provides a vaccine comprising any of the compositions provided herein and an antigen. In some embodiments of the vaccines provided herein, the antigen is an HIV antigen. In some embodiments of the vaccines provided herein, the antigen is a hepatitis antigen. In some embodiments, the bacterial compositions are administered as an adjuvant in combination with antigenic material. The antigenic material can include one or more portions of the protein coat, protein core, or functional proteins and peptides of a pathogen, or a full pathogen (live, killed, inactivated, or attenuated), or may comprise one or a plurality of cancer epitopes or cancer antigens. The antigenic material can be co-administered, administered before, or after the bacterial composition. The bacterial composition may also be administered with existing mucosal vaccines such as influenza vaccines, (e.g. FluMist from MedImmune or NASOVAC from Serum Institute of India), rotavirus vaccines (e.g. RotaTeq from Merck or Rotarix from GlaxoSmithKline), typhoid vaccines (e.g. Vivotif from Crucell, Ty21A), cholera vaccines (e.g. Orochol from Crucell, Shanchol from Shantha Biotechnics), traveller's diarrhea vaccines (e.g. Dukoral from Crucell), and with antigens of live attenuated Influenza A virus HI strain, live attenuated Influenza A virus H3 strain, Influenza B virus, live attenuated H1N1 influenza virus (swine flu), live attenuated rotavirus, mono- and multi-valent poliovirus, live attenuated *Salmonella Typhi*, live recombinant *Vibrio cholerae* lacking cholera toxin subunit A, whole killed *Vibrio cholerae* 01 classical and El Tor biotypes with or without cholera toxin subunit B, cancer antigens, cancer epitopes, and combinations thereof.

Autoimmune Disease or Allergic Disease

In one aspect, the disclosure includes compositions and methods for the treatment of diseases in a subject. In some embodiments of the methods provided herein, the subject has an autoimmune disease or an allergic disease.

The compositions and methods of the current disclosure can be used for preventing or treating autoimmune disease and allergic disease. Autoimmune disease that can be treated include, but are not limited to, inflammatory bowel disease, systemic lupus erythematosus, rheumatoid arthritis, multiple sclerosis, or Hashimoto's disease. Allergic diseases that can be treated include, but are not limited to, food allergy, pollenosis, or asthma.

Additional examples of autoimmune and allergic disease that can be treated according to the methods and compositions provided herein include, without limitation, rejection in organ transplantations, such as inflammatory bowel disease (IBD), ulcerative colitis, Crohn's disease, sprue, autoimmune arthritis, rheumatoid arthritis, Type I diabetes, multiple sclerosis, graft vs. host disease following bone marrow transplantation, osteoarthritis, juvenile chronic arthritis, Lyme arthritis, psoriatic arthritis, reactive arthritis, spondy loarthropathy, systemic lupus erythematosus, insulin dependent diabetes mellitus, thyroiditis, asthma, psoriasis, dermatitis scleroderma, atopic dermatitis, graft versus host disease, acute or chronic immune disease associated with organ transplantation, sarcoidosis, atherosclerosis, disseminated intravascular coagulation, Kawasaki's disease, Grave's disease, nephrotic syndrome, chronic fatigue syndrome, Wegener's granulomatosis, Henoch-Schoenlejn purpurea, microscopic vasculitis of the kidneys, chronic active hepatitis, uveitis, septic shock, toxic shock syndrome, sepsis syndrome, cachexia, acquired immunodeficiency syndrome, acute transverse myelitis, Huntington's chorea, Parkinson's disease, Alzheimer's disease, stroke, primary biliary cirrhosis, hemolytic anemia, polyglandular deficiency type I syndrome and polyglandular deficiency type II syndrome, Schmidt's syndrome, adult (acute) respiratory distress syndrome, alopecia, alopecia areata, seronegative arthopathy, arthropathy, Reiter's disease, psoriatic arthropathy, chlamydia, yersinia and *salmonella* associated arthropathy, spondyloarhopathy, atheromatous disease/arteriosclerosis, allergic colitis, atopic allergy, food allergies such as peanut allergy, tree nut allergy, egg allergy, milk allergy, soy allergy, wheat allergy, seafood allergy, shellfish allergy, or sesame seed allergy, autoimmune bullous disease, pemphigus vulgaris, pemphigus foliaceus, pemphigoid, linear IgA disease, autoimmune haemolytic anaemia, Coombs positive haemolytic anaemia, acquired pernicious anaemia, juvenile pernicious anaemia, myalgic encephalitis/Royal Free Disease, chronic mucocutaneous candidiasis, giant cell arteritis, primary sclerosing hepatitis, cryptogenic autoimmune hepatitis, Acquired Immunodeficiency Disease Syndrome, Acquired Immunodeficiency Related Diseases, Hepatitis C, common varied immunodeficiency (common variable hypogammaglobulinaemia), dilated cardiomyopathy, fibrotic lung disease, cryptogenic fibrosing alveolitis, postinflammatory interstitial lung disease, interstitial pneumonitis, connective tissue disease associated interstitial lung disease, mixed connective tissue disease associated lung disease, systemic sclerosis associated interstitial lung disease, rheumatoid arthritis associated interstitial lung disease, systemic lupus erythematosus associated lung disease, dermatomyositis/polymyositis associated lung disease, Sjogren's disease associated lung disease, ankylosing spondylitis associated lung disease, vasculitic diffuse lung disease, haemosiderosis associated lung disease, drug-induced interstitial lung disease, radiation fibrosis, bronchiolitis obliterans, chronic eosinophilic pneumonia, lymphocytic infiltrative lung disease, postinfectious interstitial lung disease, gouty arthritis, autoimmune hepatitis, type-1 autoimmune hepatitis (classical autoimmune or lupoid hepatitis), type-2 autoimmune hepatitis (anti-LKM antibody hepatitis), autoimmune mediated hypoglycemia, type B insulin resistance with acanthosis nigricans, hypoparathyroidism, acute immune disease associated with organ transplantation, chronic immune disease associated with organ transplantation, osteoarthrosis, primary sclerosing cholangitis, idiopathic leucopenia, autoimmune neutropenia, renal disease NOS, glomerulonephritides, microscopic vasulitis of the kidneys, discoid lupus, erythematosus, male infertility idiopathic or NOS, sperm autoimmunity, multiple sclerosis (all subtypes), insulin dependent diabetes mellitus, sympathetic ophthalmia, pulmonary hypertension secondary to connective tissue disease, Goodpasture's syndrome, pulmonary manifestation of polyarteritis nodosa, acute rheumatoid fever, rheumatoid spondylitis, Still's disease, systemic sclerosis, Takayasu's disease/arteritis, autoimmune thrombocytopenia, idiopathic thrombocytopenia, autoimmune thyroid disease, hyperthyroidism, goitrous autoimmune hypothyroidism (Hashimoto's disease), atrophic autoimmune hypothyroidism, primary myxoedema, phacogenic uveitis, primary vasculitis, vitiligo, allergic rhinitis (pollen allergies), anaphylaxis, pet allergies, latex allergies, drug allergies, allergic rhinoconjuctivitis, eosinophilic esophagitis, hypereosinophilic syndrome, eosinophilic gastroenteritis cutaneous lupus erythematosus, eosinophilic esophagitis, hypereosinophilic syndrome, eosinophilic gastroenteritis, and diarrhea.

In some embodiments of the methods and compositions provided herein, the composition further comprises one or more anti-inflammatory agents. In some embodiments of the methods and compositions provided herein, the anti-inflammatory agent is a non-steroidal anti-inflammatory drug (NSAID). Exemplary NSAIDs include, but are not limited to, aspirin, ibuprofen, naproxen, celecoxib, rofecoxib, diclofenac, diflunisal, etodolac, fenoprofen, flurbiprofen, ketoprofen, ketorolac, mefenamic acid, meloxicam, nabumetone, oxaprozin, piroxicam, sulindac, tolmetin and combinations thereof. In some embodiments, the NSAID is an immune selective anti-inflammatory derivative (ImSAID).

Treatment of Disease

In one aspect, the disclosure provides compositions and methods of treatment for disease in a subject. In one aspect, and without being limiting, the compositions disclosed herein can treat disease because their administration results in the induction of proliferation and/or accumulation of CD8+ T-cells. In some embodiments, the disclosure provides compositions and methods of treatment for disease in a subject for diseases that can be treated by the induction of proliferation and/or accumulation of CD8+ T-cells. In some embodiments, the diseases that can be treated by the induction of proliferation and/or accumulation of CD8+ T-cell is cancer, an infectious disease, an autoimmune disease or allergic disease.

In one aspect, the disclosure provides a method of treating a disease in a subject comprising administering any of the compositions provided herein to the subject in an effective amount to treat the disease. In some embodiments of the methods provided herein, the administration of the composition to the subject results in the induction of proliferation and/or accumulation of CD8+ T-cells in the intestine of the subject. In some embodiments of the methods provided herein, the proliferation and/or accumulation of CD8+ T-cells in the intestine of the subject is increased by at least 10%, at least 20%, at least 30%, at least 40%, at least 50%, at least 100%, or at least 200% when compared to the proliferation and/or accumulation of CD8+ T-cells in the intestine of the subject before the administration of the composition In some embodiments of the methods provided herein, the administration of the composition to the subject results in an increase of IFN γ production in the intestine of the subject when compared to the IFN γ production in the intestine of the subject before the administration of the composition. In some embodiments of the methods provided herein, the administration of the composition to the subject results in an increase of IFN γ production in the intestine of the subject by at least 10%, at least 20%, at least 30%, at least 40%, at least 50%, at least 100%, or at least 200% when compared to the IFN γ production in the intestine of the subject before the administration of the composition.

Any of the compositions described herein may be administered to a subject in a therapeutically effective amount or a dose of a therapeutically effective amount to treat or prevent a disease (e.g., cancer or infectious disease). The terms "treat" or "treatment" refer to reducing or alleviating one or more of the symptoms associated with a disease (e.g., cancer or infectious disease). The terms "prevent" or "prevention" encompass prophylactic administration and may reduce the incidence or likelihood of the occurrence of the disease (e.g., cancer or infectious disease). For instance, in some embodiments, administration of the compositions provided herein result in a healthy microbiome that induces proliferation and/or accumulation of CD8+ T-cells thereby protecting a subject against cancer and/or infectious disease.

As used herein, a "therapeutically effective amount" of composition, such as a pharmaceutical composition, is any amount that results in a desired response or outcome in a subject, such as those described herein, including but not limited to prevention of infection, an immune response or an enhanced immune response and/or augmentation of cancer treatment. It should be appreciated that the term effective amount may be expressed in number of bacteria or CFUs to be administered. It should further be appreciated that the bacteria can multiply once administered. Thus, administration of even a relatively small amount of bacteria may have therapeutic effects.

In some embodiments, the therapeutically effective amount of any of the compositions described herein is an amount sufficient to treat the disease, e.g., enhance survival of the subject, suppress an infection and/or treat the cancer.

Any of the methods described herein may be for the treatment of cancer in a subject. As used herein, methods of treating cancer involve relieving or alleviating at least one symptom associated with the cancer, or slowing or reversing the cancer progression. A method of treating cancer may, for example, eliminate or reduce a subject's tumor burden, reduce the number or replication of cancer cells, and/or prevent, delay or inhibit metastasis.

Also provided herein are methods for the treatment or prevention of an infectious disease in a subject. As used herein, methods of treating an infectious disease may involve relieving or alleviating at least one symptom associated with infection, or slowing or reversing the progression of the infection. A method of treating an infectious disease may, for example, eliminate or reduce the load of an infectious organism (e.g., bacteria, virus, fungus, or parasite), or inhibit or reduce one or more symptoms of the infection. As also used herein, the terms "prevent," "prevention," and "preventing," include the administration of a composition to a subject to reduce, or delay the onset of the manifestation of clinical or subclinical symptoms, complications, pathologies or biochemical indicia of the infection, or to reduce or inhibit the spread/transmission of the infectious organism (e.g., bacteria, virus, fungus, or parasite).

Aspects of the present disclosure are related to methods for treating a disease or condition in a subject by administering a therapeutically effective amount of any of the compositions described herein. In some embodiments, the subject is a mammalian subject, such as a human, non-human primate, rodent, rabbit, sheep, pig, dog, cat, horse, or cow. In some embodiments, the subject is a human subject.

The compositions and methods described herein may be utilized in conjunction with other types of therapy (i.e., combination treatment), such as additional therapeutic agents. Examples of additional combination therapies include, without limitation, surgery, radiation, gene therapy, and administration of additional therapeutic agents, such as chemotherapeutics, antibiotics, antivirals, anti-fungals, anti-parasitics, immunomodulatory agents, anti-inflammatory agents. In general, combination therapies can be administered simultaneously or sequentially (in any order) with the compositions and methods described herein. In some embodiments, any of the compositions described herein is administered simultaneously with one or more additional therapeutic agents, for example in a single dose or in multiple doses that are administered at substantially the same time.

In some embodiments, the compositions described herein are administered to a subject concomitantly with one or more additional therapeutic agents. In some embodiments, the compositions described herein are administered to a subject followed by administration of one or more additional therapeutic agent. In some embodiments, any of the compositions described herein is administered at least about 1 day, 2 days, 3 days, 4 days, 5 days, 6 days, 1 week, 2 weeks, 3 weeks, 4 weeks, 5 weeks, 6 weeks, 7 weeks, 8 weeks, 9 weeks, 10 weeks, 11 weeks, 12 weeks, 3 months, 4 months, 5 months, 6 months or more prior to administration of the one or more additional therapeutic agent. Alternatively, in some embodiments, one or more therapeutic agent administered to a subject followed by administration of any of the compositions described herein. In some embodiments, one or more therapeutic agent is administered at least about 1 day, 2 days, 3 days, 4 days, 5 days, 6 days, 1 week, 2 weeks, 3 weeks, 4 weeks, 5 weeks, 6 weeks, 7 weeks, 8 weeks, 9 weeks, 10 weeks, 11 weeks, 12 weeks, 3 months, 4 months, 5 months, 6 months or more prior to administration of any the compositions described herein.

Additional Methods

Also within the scope of the present disclosure are methods of assessing whether one or more bacterial strains of any of the compositions described herein are present in the intestine of a subject. In some embodiments, if fewer than a threshold number of bacterial strains are detected in the intestine of the subject, any of the compositions described herein are administered to the subject to increase the number of the bacterial strains in the intestine of the subject. In some embodiments, the method further comprises identifying the subject as a candidate for a treatment of the disease based on the number of bacterial strains detected in the intestine.

Measuring the levels of the biomarker sets may also be useful in the evaluation and treatment of a disease.

In general, the bacterial population of the intestine (e.g., presence or absence of one or more bacterial strains) may be determined by assessing a sample obtained from the subject, such as a fecal sample.

In some embodiments of the compositions provided herein, administration of the composition to a subject results in the induction of proliferation and/or accumulation of CD8+ T-cells in the intestine of the subject. In some embodiments of the compositions provided herein, administration of the composition to a subject results in an increase in IFN $\gamma$ production in the intestine of a subject. In some embodiments of the compositions provided herein, administration of the composition to a subject results in the presence of one or more bacterial strains of the administered composition in the intestine of the subject. In some embodiments of the compositions provided herein, the one or more bacterial strains of the administered composition was not previously present in the intestine of the subject. In some embodiments of the compositions provided herein, administration of the composition to a subject results in the engraftment of one or more bacterial strains of the administered composition in the intestine of the subject. In some embodiments of the compositions provided herein, the one or more bacterial strains of the administered composition was not previously engrafted in the intestine of the subject. In some embodiments of the compositions provided herein, administration of the composition to a subject results in an increase in the number of the bacterial strains of the administered composition in the intestine of the subject. In some embodiments of the compositions provided herein, administration of the composition to a subject results in an increase in the engrafted number of the bacterial strains of the administered composition in the intestine of the subject. In some embodiments of the compositions provided herein, administration of the composition to a subject results in an increase in the abundance of total bacteria of the bacterial strains of the administered composition in the intestine of the subject. In some embodiments of the compositions provided herein, administration of the composition to a subject results in an increase in the engrafted total bacterial strains of the administered composition in the intestine of the subject.

In one aspect, the disclosure provides a method that includes determining if one or more bacterial species of any of the compositions provided herein are present in the intestine of a subject, wherein if less than 100%, less than 90%, less than 80%, less than 70%, less than 60%, less than 50%, less than 40%, less than 30%, less than 20%, less than 10%, or none of the bacterial species are present, the composition is administered to the subject.

In some embodiments of the methods provided herein, the subject is undergoing, or will be undergoing, cancer treatment.

In one aspect, the disclosure provides a method for determining if a subject is expected to respond positively to cancer treatment, wherein the method includes determining if one or more bacterial species of any of the compositions provided herein are present in the intestine of a subject, wherein if less than 100%, less than 90%, less than 80%, less than 70%, less than 60%, less than 50%, less than 40%, less than 30%, less than 20%, less than 10%, or none of the bacterial species are present, the subject is not expected to respond positively to cancer treatment.

In some embodiments of the methods provided herein, the cancer treatment is cancer immunotherapy treatment.

In one aspect, the disclosure provides a method for reducing the risk of a viral infection in a subject, wherein the method includes determining if one or more bacterial species of any of the compositions provided herein are present in the intestine of a subject, wherein if less than 100%, less than 90%, less than 80%, less than 70%, less than 60%, less than 50%, less than 40%, less than 30%, less than 20%, less than 10%, or none of the bacterial species are present, the composition is administered to the subject, thereby reducing the risk of a viral infection in the subject.

In some embodiments of the methods provided herein, determining the presence of one or more of the bacterial species is done by sequencing fecal matter of the subject.

Pharmaceutical Compositions

In one aspect, the disclosure provides pharmaceutical compositions comprising the bacterial strains and combinations of bacterial strains provided herein. In some embodiments of the compositions provided herein, the composition is a pharmaceutical composition. In some embodiments of the pharmaceutical compositions provided herein, the pharmaceutical composition comprises a pharmaceutically acceptable excipient. In some embodiments of the pharmaceutical compositions provided herein, the pharmaceutical composition is formulated for oral administration. In some embodiments of the pharmaceutical compositions provided herein, the pharmaceutical composition is formulated for rectal administration. In some embodiments of the pharmaceutical compositions provided herein, the pharmaceutical composition is formulated for delivery to the intestine. In some embodiments of the pharmaceutical compositions provided herein, the pharmaceutical composition is formulated for delivery to the colon. In some embodiments of the pharmaceutical compositions provided herein, one or more of the bacterial strains is lyophilized. In some embodiments of the pharmaceutical compositions provided herein, the pharmaceutical composition is in the form of a capsule. In some embodiments of the pharmaceutical compositions provided herein, the pharmaceutical composition further comprises a pH sensitive composition comprising one or more enteric polymers.

Any of the compositions described herein, including the pharmaceutical compositions and food products comprising the compositions, may contain bacterial strains in any form, for example in an aqueous form, such as a solution or a suspension, embedded in a semi-solid form, in a powdered form or freeze dried form. In some embodiments, the composition or the bacterial strains of the composition are lyophilized. In some embodiments, a subset of the bacterial strains in a composition is lyophilized. Methods of lyophilizing compositions, specifically compositions comprising bacteria, are well known in the art. See, e.g., U.S. Pat. Nos. 3,261,761; 4,205,132; PCT Publications WO 2014/029578 and WO 2012/098358, herein incorporated by reference in their entirety. The bacteria may be lyophilized as a combination and/or the bacteria may be lyophilized separately and combined prior to administration. A bacterial strain may be combined with a pharmaceutical excipient prior to combining it with the other bacterial strain or multiple lyophilized bacteria may be combined while in lyophilized form and the mixture of bacteria, once combined may be subsequently be combined with a pharmaceutical excipient. In some embodiments, the bacterial strain is a lyophilized cake. In some embodiments, the compositions comprising the one or more bacterial strains are a lyophilized cake.

The bacterial strains of the composition can be manufactured using fermentation techniques well known in the art. In some embodiments, the active ingredients are manufactured using anaerobic fermenters, which can support the rapid growth of anaerobic bacterial species. The anaerobic fermenters may be, for example, stirred tank reactors or disposable wave bioreactors. Culture media such as BL media and EG media, or similar versions of these media devoid of animal components, can be used to support the growth of the bacterial species. The bacterial product can be purified and concentrated from the fermentation broth by traditional techniques, such as centrifugation and filtration, and can optionally be dried and lyophilized by techniques well known in the art.

In some embodiments, the composition of bacterial strains may be formulated for administration as a pharmaceutical composition. The term "pharmaceutical composition" as used herein means a product that results from the mixing or combining of at least one active ingredient, such as any two or more purified bacterial strains described herein, and one or more inactive ingredients, which may include one or more pharmaceutically acceptable excipient.

An "acceptable" excipient refers to an excipient that must be compatible with the active ingredient and not deleterious to the subject to which it is administered. In some embodiments, the pharmaceutically acceptable excipient is selected based on the intended route of administration of the composition, for example a composition for oral or nasal administration may comprise a different pharmaceutically acceptable excipient than a composition for rectal administration. Examples of excipients include sterile water, physiological saline, solvent, a base material, an emulsifier, a suspending agent, a surfactant, a stabilizer, a flavoring agent, an aromatic, an excipient, a vehicle, a preservative, a binder, a diluent, a tonicity adjusting agent, a soothing agent, a bulking agent, a disintegrating agent, a buffer agent, a coating agent, a lubricant, a colorant, a sweetener, a thickening agent, and a solubilizer.

Pharmaceutical compositions can be prepared in accordance with methods well known and routinely practiced in the art (see e.g., Remington: The Science and Practice of Pharmacy, Mack Publishing Co. 20th ed. 2000). The pharmaceutical compositions described herein may further comprise any carriers or stabilizers in the form of a lyophilized formulation or an aqueous solution. Acceptable excipients, carriers, or stabilizers may include, for example, buffers, antioxidants, preservatives, polymers, chelating reagents, and/or surfactants. Pharmaceutical compositions are preferably manufactured under GMP conditions. The pharmaceutical compositions can be used orally, nasally or parenterally, for instance, in the form of capsules, tablets, pills, sachets, liquids, powders, granules, fine granules, film-coated preparations, pellets, troches, sublingual preparations, chewables, buccal preparations, pastes, syrups, suspensions, elixirs, emulsions, liniments, ointments, plasters, cataplasms, transdermal absorption systems, lotions, inhalations, aerosols, injections, suppositories, and the like.

In some embodiments, the bacteria are formulated for delivery to the intestines (e.g., the small intestine and/or the colon). In some embodiments, the bacteria are formulated with an enteric coating that increases the survival of the bacteria through the harsh environment in the stomach. The enteric coating is one which resists the action of gastric juices in the stomach so that the bacteria which are incorporated therein will pass through the stomach and into the intestines. The enteric coating may readily dissolve when in contact with intestinal fluids, so that the bacteria enclosed in the coating will be released in the intestinal tract. Enteric coatings may consist of polymer and copolymers well known in the art, such as commercially available EUDRAGIT (Evonik Industries). (See e.g., Zhang, AAPS PharmSciTech, 2016, 17 (1), 56-67).

The bacteria may also be formulated for rectal delivery to the intestine (e.g., the colon). Thus, in some embodiments, the bacterial compositions may be formulated for delivery by suppository, colonoscopy, endoscopy, sigmoidoscopy or enema. A pharmaceutical preparation or formulation and particularly a pharmaceutical preparation for oral administration, may include an additional component that enables efficient delivery of the compositions of the disclosure to the intestine (e.g., the colon). A variety of pharmaceutical preparations that allow for the delivery of the compositions to the intestine (e.g., the colon) can be used. Examples thereof include pH sensitive compositions, more specifically, buffered sachet formulations or enteric polymers that release their contents when the pH becomes alkaline after the enteric polymers pass through the stomach. When a pH sensitive composition is used for formulating the pharmaceutical preparation, the pH sensitive composition is preferably a polymer whose pH threshold of the decomposition of the composition is between about 6.8 and about 7.5. Such a numeric value range is a range in which the pH shifts toward the alkaline side at a distal portion of the stomach, and hence is a suitable range for use in the delivery to the colon. It should further be appreciated that each part of the intestine (e.g., the duodenum, jejunum, ileum, cecum, colon and rectum), has different biochemical and chemical environment. For instance, parts of the intestines have different pHs, allowing for targeted delivery by compositions that have a specific pH sensitivity. Thus, the compositions provided herein may be formulated for delivery to the intestine or specific parts of the intestine (e.g., the duodenum, jejunum, ileum, cecum, colon and rectum) by providing formulations with the appropriate pH sensitivity. (See e.g., Villena et al., Int J Pharm 2015, 487 (1-2): 314-9).

Another embodiment of a pharmaceutical preparation useful for delivery of the compositions to the intestine (e.g., the colon) is one that ensures the delivery to the colon by delaying the release of the contents (e.g., the bacterial strains) by approximately 3 to 5 hours, which corresponds to the small intestinal transit time. In one embodiment of a pharmaceutical preparation for delayed release, a hydrogel is used as a shell. The hydrogel is hydrated and swells upon contact with gastrointestinal fluid, with the result that the contents are effectively released (released predominantly in the colon). Delayed release dosage units include drug-containing compositions having a material which coats or selectively coats a drug or active ingredient to be administered. Examples of such a selective coating material include in vivo degradable polymers, gradually hydrolyzable polymers, gradually water-soluble polymers, and/or enzyme degradable polymers. A wide variety of coating materials for efficiently delaying the release is available and includes, for example, cellulose-based polymers such as hydroxypropyl cellulose, acrylic acid polymers and copolymers such as methacrylic acid polymers and copolymers, and vinyl polymers and copolymers such as polyvinylpyrrolidone.

Additional examples of pharmaceutical compositions that allow for the delivery to the intestine (e.g., the colon) include bioadhesive compositions which specifically adhere to the colonic mucosal membrane (for example, a polymer described in the specification of U.S. Pat. No. 6,368,586) and compositions into which a protease inhibitor is incorporated for protecting particularly a biopharmaceutical preparation in the gastrointestinal tracts from decomposition due to an activity of a protease.

Another example of a system enabling the delivery to the intestine (e.g., the colon) is a system of delivering a composition to the colon by pressure change in such a way that the contents are released by utilizing pressure change caused by generation of gas in bacterial fermentation at a distal portion of the stomach. Such a system is not particularly limited, and a more specific example thereof is a capsule which has contents dispersed in a suppository base and which is coated with a hydrophobic polymer (for example, ethyl cellulose).

A further example of a system enabling the delivery of a composition to the intestine (e.g., the colon), is a composition that includes a coating that can be removed by an enzyme present in the gut (e.g., the colon), such as, for example, a carbohydrate hydrolase or a carbohydrate reductase. Such a system is not particularly limited, and more specific examples thereof include systems which use food components such as non-starch polysaccharides, amylose, xanthan gum, and azopolymers.

The compositions provided herein can also be delivered to specific target areas, such as the intestine, by delivery through an orifice (e.g., a nasal tube) or through surgery. In addition, the compositions provided herein that are formulated for delivery to a specific area (e.g., the cecum or the colon), may be administered by a tube (e.g., directly into the small intestine). Combining mechanical delivery methods such as tubes with chemical delivery methods such as pH specific coatings, allow for the delivery of the compositions provided herein to a desired target area (e.g., the cecum or the colon).

The compositions comprising bacterial strains are formulated into pharmaceutically acceptable dosage forms by conventional methods known to those of skill in the art. Dosage regimens are adjusted to provide the optimum desired response (e.g., the prophylactic or therapeutic effect) . In some embodiments, the dosage form of the composition is a tablet, pill, capsule, powder, granules, solution, or suppository. In some embodiments, the pharmaceutical composition is formulated for oral administration. In some embodiments, the pharmaceutical composition is formulated such that the bacteria of the composition, or a portion thereof, remain viable after passage through the stomach of the subject. In some embodiments, the pharmaceutical composition is formulated for rectal administration, e.g. as a suppository. In some embodiments, the pharmaceutical composition is formulated for delivery to the intestine or a specific area of the intestine (e.g., the colon) by providing an appropriate coating (e.g., a pH specific coating, a coating that can be degraded by target area specific enzymes, or a coating that can bind to receptors that are present in a target area).

Dosages of the active ingredients in the pharmaceutical compositions can be varied so as to obtain an amount of the active ingredient which is effective to achieve the desired pharmaceutical response for a particular subject, composition, and mode of administration, without being toxic or having an adverse effect on the subject. The selected dosage level depends upon a variety of factors including the activity of the particular compositions employed, the route of administration, the time of administration, the duration of the treatment, other drugs, compounds and/or materials used in combination with the particular compositions employed, the age, sex, weight, condition, general health and prior medical history of the subject being treated, and like factors.

A physician, veterinarian or other trained practitioner, can start doses of the pharmaceutical composition at levels lower than that required to achieve the desired therapeutic effect and gradually increase the dosage until the desired effect (e.g., treatment of a pathogenic infection, reduction of bacterial burden of pathogenic infection, reduction or inhibition of toxin production) is achieved. In general, effective doses of the compositions disclosed herein, for the prophylactic treatment of groups of people as described herein vary depending upon many different factors, including routes of administration, physiological state of the subject, whether the subject is human or an animal, other medications administered, and the therapeutic effect desired. Dosages need to be titrated to optimize safety and efficacy. In some embodiments, the dosing regimen entails oral administration of a dose of any of the compositions described herein. In some embodiments, the dosing regimen entails oral administration of multiple doses of any of the compositions described herein. In some embodiments, the composition is administered orally the subject once, twice, 3 times, 4 times, 5 times, 6 times, 7 times, 8 times, 9 times, or at least 10 times.

The compositions, including the pharmaceutical compositions disclosed herein, include compositions with a range of active ingredients (e.g., live bacteria, bacteria in spore format). The amount of bacteria in the compositions may be expressed in weight, number of bacteria and/or CFUs (colony forming units). In some embodiments, the pharmaceutical compositions disclosed herein contain about 10, about $10^2$, about $10^3$, about $10^4$, about $10^5$, about $10^6$, about $10^7$, about $10^8$, about $10^9$, about $10^{10}$, about $10^{11}$, about $10^{12}$, about $10^{13}$ or more of each of the bacteria of the composition per dosage amount. In some embodiments, the pharmaceutical compositions disclosed herein contain about 10, about $10^2$, about $10^3$, about $10^4$, about $10^5$, about $10^6$, about $10^7$, about $10^8$, about $10^9$, about $10^{10}$, about $10^{11}$, about $10^{12}$, about $10^{13}$ or more total bacteria per dosage amount. It should further be appreciated that the bacteria of the compositions may be present in different amounts. Thus, for instance, as a non-limiting example, a composition may include $10^3$ of bacteria A, $10^4$ of bacteria B and $10^6$ of bacteria C. In some embodiments, the pharmaceutical compositions disclosed herein contain about 10, about $10^2$, about $10^3$, about $10^4$, about $10^5$, about $10^6$, about $10^7$, about $10^8$, about $10^9$, about $10^{10}$, about $10^{11}$, about $10^{12}$, about $10^{13}$ or more CFUs of each of the bacteria in the composition per dosage amount. In some embodiments, the pharmaceutical compositions disclosed herein contain about $10^1$, about $10^2$, about $10^3$, about $10^4$, about $10^5$, about $10^6$, about $10^7$, about $10^8$, about $10^9$, about $10^{10}$, about $10^{11}$, about $10^{12}$, about $10^{13}$ or more CFUs in total for all of the bacteria combined per dosage amount. As discussed above, bacteria of the compositions may be present in different amounts. In some embodiments, the pharmaceutical compositions disclosed herein contain about $10^{-7}$, about $10^{-6}$, about $10^{-5}$, about $10^{-4}$, about $10^{-3}$, about $10^{-2}$, about $10^{-1}$ or more grams of each of the bacteria in the composition per dosage amount. In some embodiments, the pharmaceutical compositions disclosed herein contain about $10^{-7}$, about $10^{-6}$, about $10^{-5}$, about $10^{-4}$, about $10^{-3}$, about $10^{-2}$, about $10^{-1}$ or more grams in total for all of the bacteria combined per dosage amount. In some embodiment, the dosage amount is one administration device (e.g., one table, pill or capsule). In some embodiment, the dosage amount is the amount that is administered in a particular period (e.g., one day or one week).

In some embodiments, the pharmaceutical compositions disclosed herein contain between 10 and $10^{13}$, between $10^2$ and $10^{13}$, between $10^3$ and $10^{13}$, between $10^4$ and $10^{13}$, between $10^5$ and $10^{13}$, between $10^6$ and $10^{13}$, between $10^7$ and $10^{13}$, between $10^8$ and $10^{13}$, between $10^9$ and $10^{13}$, between $10^{10}$ and $10^{13}$, between $10^{11}$ and $10^{13}$, between $10^{12}$ and $10^{13}$, between 10 and $10^{12}$, between $10^2$ and $10^{12}$, between $10^3$ and $10^{12}$, between $10^4$ and $10^{12}$, between $10^5$ and $10^{12}$, between $10^6$ and $10^{12}$, between $10^7$ and $10^{12}$, between $10^8$ and $10^{12}$, between $10^9$ and $10^{12}$, between $10^{10}$ and $10^{12}$, between $10^{11}$ and $10^{12}$, between 10 and $10^{11}$, between $10^2$ and $10^{11}$, between $10^3$ and $10^{13}$, between $10^4$ and $10^{13}$, between $10^5$ and $10^{13}$, between $10^6$ and $10^{13}$, between $10^7$ and $10^{11}$, between $10^8$ and $10^{11}$, between $10^9$ and $10^{11}$, between $10^{10}$ and $10^{11}$, between 10 and $10^{10}$, between $10^2$ and $10^{10}$, between $10^3$ and $10^{10}$, between $10^4$ and $10^{10}$, between $10^5$ and $10^{10}$, between $10^6$ and $10^{10}$, between $10^7$ and $10^{10}$, between $10^8$ and $10^{10}$, between $10^9$ and $10^{10}$, between $10^{10}$ and $10^9$, between $10^2$ and $10^9$, between $10^3$ and $10^9$, between $10^4$ and $10^9$, between $10^5$ and $10^9$, between $10^6$ and $10^9$, between $10^7$ and $10^9$, between $10^8$ and $10^9$, between 10 and $10^8$, between $10^2$ and $10^8$, between $10^3$ and $10^8$, between $10^4$ and $10^8$, between $10^5$ and $10^8$, between $10^6$ and $10^8$, between $10^7$ and $10^8$, between 10 and $10^7$, between $10^2$ and $10^7$, between $10^3$ and $10^7$, between $10^4$ and $10^7$, between $10^5$ and $10^7$, between $10^6$ and $10^7$, between 10 and $10^6$, between $10^2$ and $10^6$, between $10^3$ and $10^6$, between $10^4$ and $10^6$, between $10^5$ and $10^6$, between 10 and $10^5$, between $10^2$ and $10^5$, between $10^3$ and $10^5$, between $10^4$ and $10^5$, between 10 and $10^4$, between $10^2$ and $10^4$, between $10^3$ and $10^4$, between 10 and $10^3$, between $10^2$ and $10^3$, or between 10 and $10^2$ of each of the bacteria of the composition per dosage amount. In some embodiments, the pharmaceutical compositions disclosed herein contain between 10 and $10^{13}$, between $10^2$ and $10^{13}$, between $10^3$ and $10^{13}$, between $10^4$ and $10^{13}$, between $10^5$ and $10^{13}$, between $10^6$ and $10^{13}$, between $10^7$ and $10^{13}$, between $10^8$ and $10^{13}$, between $10^9$ and $10^{13}$, between $10^{10}$ and $10^{13}$, between $10^{11}$ and $10^{13}$, between $10^{12}$ and $10^{13}$, between 10 and $10^{12}$, between $10^2$ and $10^{12}$, between $10^3$ and $10^{12}$, between $10^4$ and $10^{12}$, between $10^5$ and $10^{12}$, between $10^6$ and $10^{12}$, between $10^7$ and $10^{12}$, between $10^8$ and $10^{12}$, between $10^9$ and $10^{12}$, between $10^{10}$ and $10^{12}$, between $10^{11}$ and $10^{12}$, between 10 and $10^{11}$, between $10^2$ and $10^{11}$, between $10^3$ and $10^{13}$, between $10^4$ and $10^{13}$, between $10^5$ and $10^{13}$, between $10^6$ and $10^{13}$, between $10^7$ and $10^{11}$, between $10^8$ and $10^{11}$, between $10^9$ and $10^{11}$, between $10^{10}$ and $10^{11}$, between 10 and $10^{10}$, between $10^2$ and $10^{10}$, between $10^3$ and $10^{10}$, between $10^4$ and $10^{10}$, between $10^5$ and $10^{10}$, between $10^6$ and $10^{10}$, between $10^7$ and $10^{10}$, between $10^8$ and $10^{10}$, between $10^9$ and $10^{10}$, between 10 and $10^9$, between $10^2$ and $10^9$, between $10^3$ and $10^9$, between $10^4$ and $10^9$, between $10^5$ and $10^9$, between $10^6$ and $10^9$, between $10^7$ and $10^9$, between $10^8$ and $10^9$, between 10 and $10^8$, between $10^2$ and $10^8$, between $10^3$ and $10^8$, between $10^4$ and $10^8$, between $10^5$ and $10^8$, between $10^6$ and $10^8$, between $10^7$ and $10^8$, between 10 and $10^7$, between $10^2$ and $10^7$, between $10^3$ and $10^7$, between $10^4$ and $10^7$, between $10^5$ and $10^7$, between $10^6$ and $10^7$, between 10 and $10^6$, between $10^2$ and $10^6$, between $10^3$ and $10^6$, between $10^4$ and $10^6$, between $10^5$ and $10^6$, between 10 and $10^5$, between $10^2$ and $10^5$, between $10^3$ and $10^5$, between $10^4$ and $10^5$, between 10 and $10^4$, between $10^2$ and $10^4$, between $10^3$ and $10^4$, between 10 and $10^3$, between $10^2$ and $10^3$, or between 10 and $10^2$ total bacteria per dosage amount.

In some embodiments, the pharmaceutical compositions disclosed herein contain between 10 and $10^{13}$, between $10^2$ and $10^{13}$, between $10^3$ and $10^{13}$, between $10^4$ and $10^{13}$, between $10^5$ and $10^{13}$, between $10^6$ and $10^{13}$, between $10^7$ and $10^{13}$, between $10^8$ and $10^{13}$, between $10^9$ and $10^{13}$, between $10^{10}$ and $10^{13}$, between $10^{11}$ and $10^{13}$, between $10^{12}$ and $10^{13}$, between 10 and $10^{12}$, between $10^2$ and $10^{12}$, between $10^3$ and $10^{12}$, between $10^4$ and $10^{12}$, between $10^5$ and $10^{12}$, between $10^6$ and $10^{12}$, between $10^7$ and $10^{12}$, between $10^8$ and $10^{12}$, between $10^9$ and $10^{12}$, between $10^{10}$ and $10^{12}$, between $10^{11}$ and $10^{12}$, between 10 and $10^{11}$, between $10^2$ and $10^{11}$, between $10^3$ and $10^{13}$, between $10^4$ and $10^{13}$, between $10^5$ and $10^{13}$, between $10^6$ and $10^{13}$, between $10^7$ and $10^{11}$, between $10^8$ and $10^{11}$, between $10^9$ and $10^{11}$, between $10^{10}$ and $10^{11}$, between 10 and $10^{10}$, between $10^2$ and $10^{10}$, between $10^3$ and $10^{10}$, between $10^4$ and $10^{10}$, between $10^5$ and $10^{10}$, between $10^6$ and $10^{10}$, between $10^7$ and $10^{10}$, between $10^8$ and $10^{10}$, between $10^9$ and $10^{10}$, between 10 and $10^9$, between $10^2$ and $10^9$, between $10^3$ and $10^9$, between $10^4$ and $10^9$, between $10^5$ and $10^9$, between $10^6$ and $10^9$, between $10^7$ and $10^9$, between $10^8$ and $10^9$, between 10 and $10^8$, between $10^2$ and $10^8$, between $10^3$ and $10^8$, between $10^4$ and $10^8$, between $10^5$ and $10^8$, between $10^6$ and $10^8$, between $10^7$ and $10^8$, between 10 and $10^7$, between $10^2$ and $10^7$, between $10^3$ and $10^7$, between $10^4$ and $10^7$, between $10^5$ and $10^7$, between $10^6$ and $10^7$, between 10 and $10^6$, between $10^2$ and $10^6$, between $10^3$ and $10^6$, between $10^4$ and $10^6$, between $10^5$ and $10^6$, between 10 and $10^5$, between $10^2$ and $10^5$, between $10^3$ and $10^5$, between $10^4$ and $10^5$, between 10 and $10^4$, between $10^2$ and $10^4$, between $10^3$ and $10^4$, between 10 and $10^3$, between $10^2$ and $10^3$, or between 10 and $10^2$ CFUs of each of the bacteria of the composition per dosage amount. In some embodiments, the pharmaceutical compositions disclosed herein contain between 10 and $10^{13}$, between $10^2$ and $10^{13}$, between $10^3$ and $10^{13}$, between $10^4$ and $10^{13}$, between $10^5$ and $10^{13}$, between $10^6$ and $10^{13}$, between $10^7$ and $10^{13}$, between $10^8$ and $10^{13}$, between $10^9$ and $10^{13}$, between $10^{10}$ and $10^{13}$, between $10^{11}$ and $10^{13}$, between $10^{12}$ and $10^{13}$, between 10 and $10^{12}$, between $10^2$ and $10^{12}$, between $10^3$ and $10^{12}$, between $10^4$ and $10^{12}$, between $10^5$ and $10^{12}$, between $10^6$ and $10^{12}$, between $10^7$ and $10^{12}$, between $10^8$ and $10^{12}$, between $10^9$ and $10^{12}$, between $10^{10}$ and $10^{12}$, between $10^{11}$ and $10^{12}$, between 10 and $10^{11}$, between $10^2$ and $10^{11}$, between $10^3$ and $10^{13}$, between $10^4$ and $10^{13}$, between $10^5$ and $10^{13}$, between $10^6$ and $10^{13}$, between $10^7$ and $10^{11}$, between $10^8$ and $10^{11}$, between $10^9$ and $10^{11}$, between $10^{10}$ and $10^{11}$, between 10 and $10^{10}$, between $10^2$ and $10^{10}$, between $10^3$ and $10^{10}$, between $10^4$ and $10^{10}$, between $10^5$ and $10^{10}$, between $10^6$ and $10^{10}$, between $10^7$ and $10^{10}$, between $10^8$ and $10^{10}$, between $10^9$ and $10^{10}$, between 10 and $10^9$, between $10^2$ and $10^9$, between $10^3$ and $10^9$, between $10^4$ and $10^9$, between $10^5$ and $10^9$, between $10^6$ and $10^9$, between $10^7$ and $10^9$, between $10^8$ and $10^9$, between 10 and $10^8$, between $10^2$ and $10^8$, between $10^3$ and $10^8$, between $10^4$ and $10^8$, between $10^5$ and $10^8$, between $10^6$ and $10^8$, between $10^7$ and $10^8$, between 10 and $10^7$, between $10^2$ and $10^7$, between $10^3$ and $10^7$, between $10^4$ and $10^7$, between $10^5$ and $10^7$, between $10^6$ and $10^7$, between 10 and $10^6$, between $10^2$ and $10^6$, between $10^3$ and $10^6$, between $10^4$ and $10^6$, between $10^5$ and $10^6$, between 10 and $10^5$, between $10^2$ and $10^5$, between $10^3$ and $10^5$, between $10^4$ and $10^5$, between 10 and $10^4$, between $10^2$ and $10^4$, between $10^3$ and $10^4$, between 10 and $10^3$, between $10^2$ and $10^3$, or between 10 and $10^2$ total CFUs per dosage amount.

In some embodiments, the pharmaceutical compositions disclosed herein contain between $10^{-7}$ and $10^{-1}$, between $10^{-6}$ and $10^{-1}$, between $10^{-5}$ and $10^{-1}$, between $10^{-4}$ and $10^{-1}$, between $10^{-3}$ and $10^{-1}$, between $10^{-2}$ and $10^{-1}$, between $10^{-7}$ and $10^{-2}$, between $10^{-6}$ and $10^{-2}$, between $10^{-5}$ and $10^{-2}$, between $10^{-4}$ and $10^{-2}$, between $10^{-3}$ and $10^{-2}$, between $10^{-7}$ and $10^{-3}$, between $10^{-6}$ and $10^{-3}$, between $10^{-5}$ and $10^{-3}$, between $10^{-4}$ and $10^{-3}$, between $10^{-7}$ and $10^{-4}$, between $10^{-6}$ and $10^{-4}$, between $10^{-5}$ and $10^{-4}$, between $10^{-7}$ and $10^{-5}$, between $10^{-6}$ and $10^{-5}$, or between $10^{-7}$ and $10^{-6}$ grams of each of the bacteria in the composition per dosage amount. In some embodiments, the pharmaceutical compositions disclosed herein contain between $10^{-7}$ and $10^{-1}$, between $10^{-6}$ and $10^{-1}$, between $10^{-5}$ and $10^{-1}$, between $10^{-4}$ and $10^{-1}$, between $10^{-3}$ and $10^{-1}$, between $10^{-2}$ and $10^{-1}$, between $10^{-7}$ and $10^{-2}$, between $10^{-6}$ and $10^{-2}$, between $10^{-5}$ and $10^{-2}$, between $10^{-4}$ and $10^{-2}$, between $10^{-3}$ and $10^{-2}$, between $10^{-7}$ and $10^{-3}$, between $10^{-6}$ and $10^{-3}$, between $10^{-5}$ and $10^{-3}$, between $10^{-4}$ and $10^{-3}$, between $10^{-7}$ and $10^{-4}$, between $10^{-6}$ and $10^{-4}$, between $10^{-5}$ and $10^{-4}$, between $10^{-7}$ and $10^{-5}$, between $10^{-6}$ and $10^{-5}$, or between $10^{-7}$ and $10^{-6}$ grams of all of the bacteria combined per dosage amount.

In one aspect, the disclosure provides a food product comprising any of the compositions provided herein and a nutrient. Also with the scope of the present disclosure are food products comprising any of the bacterial strains described herein and a nutrient. Food products are, in general, intended for the consumption of a human or an animal. Any of the bacterial strains described herein may be formulated as a food product. In some embodiments, the bacterial strains are formulated as a food product in spore form. In some embodiments, the bacterial strains are formulated as a food product in vegetative form. In some embodiments, the food product comprises both vegetative bacteria and bacteria in spore form. The compositions disclosed herein can be used in a food or beverage, such as a health food or beverage, a food or beverage for infants, a food or beverage for pregnant women, athletes, senior citizens or other specified group, a functional food, a beverage, a food or beverage for specified health use, a dietary supplement, a food or beverage for patients, or an animal feed. Non-limiting examples of the foods and beverages include various beverages such as juices, refreshing beverages, tea beverages, drink preparations, jelly beverages, and functional beverages; alcoholic beverages such as beers; carbohydrate-containing foods such as rice food products, noodles, breads, and pastas; paste products such as fish hams, sausages, paste products of seafood; retort pouch products such as curries, food dressed with a thick starchy sauces, soups; dairy products such as milk, dairy beverages, ice creams, cheeses, and yogurts; fermented products such as fermented soybean pastes, yogurts, fermented beverages, and pickles; bean products; various confectionery products such as Western confectionery products including biscuits, cookies, and the like, Japanese confectionery products including steamed bean-jam buns, soft adzuki-bean jellies, and the like, candies, chewing gums, gummies, cold desserts including jellies, cream caramels, and frozen desserts; instant foods such as instant soups and instant soy-bean soups; microwavable foods; and the like. Further, the examples also include health foods and beverages prepared in the forms of powders, granules, tablets, capsules, liquids, pastes, and jellies.

Food products containing bacterial strains described herein may be produced using methods known in the art and may contain the same amount of bacteria (e.g., by weight, amount or CFU) as the pharmaceutical compositions provided herein. Selection of an appropriate amount of bacteria in the food product may depend on various factors, including for example, the serving size of the food product, the frequency of consumption of the food product, the specific bacterial strains contained in the food product, the amount of water in the food product, and/or additional conditions for survival of the bacteria in the food product.

Examples of food products which may be formulated to contain any of the bacterial strains described herein include, without limitation, a beverage, a drink, a bar, a snack, a dairy product, a confectionery product, a cereal product, a ready-to-eat product, a nutritional formula, such as a nutritional supplementary formulation, a food or beverage additive.

In some embodiments, the subject has not received a dose of an antibiotic prior to administration of the bacterial composition. In some embodiments, the subject has not been administered an antibiotic at least 1, at least 2, at least 3, at least 5, at least 10, at least 15, at least 20, at least 25, at least 30, at least 60, at least 90, at least 120, at least 180 or at least 360 days prior to administration of the compositions provided herein.

In some embodiments, the subject may be administered one or more doses of an antibiotic prior to or concurrently with a bacterial composition. Antibiotics may be administered for a variety of reasons. For instance, antibiotics may be administered to remove bacterial species from the colon and/or intestine prior to administration of the bacterial compositions provided herein. Antibiotics may also be administered to suppress unwanted infections in the case of cancer treatment. In some instances, antibiotics may be administered as a treatment method for an infectious disease.

In some embodiments, the subject is administered a single dose of an antibiotic prior to the bacterial composition. In some embodiments, the subject is administered multiple doses of an antibiotic prior to the bacterial composition. In some embodiments, the subject is administered at least 2, 3, 4, 5 or more doses of an antibiotic prior to the bacterial composition. In some embodiments, the subject is administered a dose of an antibiotic at substantially the same time as the bacterial composition. Examples of antibiotics that can be administered include, without limitation, kanamycin, gentamicin, colistin, metronidazole, vancomycin, clindamycin, fidaxomicin, and cefoperazone.

Diagnostics and Prognostic Methods

Also described herein are diagnostic methods (e.g., companion diagnostics) for use in determining whether a subject should receive a treatment, such as a composition as described herein and/or any of the immune checkpoint inhibitors described herein. Such methods can be used for diagnosing a disease, monitoring the progress of a disease, assessing the efficacy of a treatment for the disease, and/or identifying patients suitable for a particular treatment.

Accordingly, the methods described herein are based on the level of a marker in a sample (e.g., a biological sample containing lymphocytes) obtained from a subject. In some embodiments, the methods involve analyzing the presence and/or level of a marker in one or more samples from a subject.

In some embodiments, the level of the marker in a sample obtained from a subject can then be compared with a reference sample or a control sample to determine a value indicating the amount of the marker in the sample. In some embodiments, a value for a marker is obtained by comparing the level of a marker in a sample to the level of another marker (e.g., an internal control or internal standard) in the sample. The value of the marker can be compared to a reference value to determine whether the subject has or is at risk for the disease. In some embodiments, the level of the marker is compared to a predetermined threshold for the marker, a deviation from which may indicate the subject has a disease. In some embodiments, if the level or value of the marker is higher than a reference level or value, the subject can be identified as having or at risk for a disease, as described herein. In some embodiments, if the level or value of the marker is lower than a reference level or value, the subject can be identified as having or at risk for a disease, as described herein.

In some embodiments, the level of the marker in a sample from a subject is compared to the level of the marker in another sample obtained from the same subject, for example, a sample obtained from the subject at a different time. In some embodiments, the level of the marker in a sample from a subject is compared to the level of the marker in a sample obtained from the subject at an earlier time, such as prior to administration of any of the compositions described herein. In some embodiments, the level of the marker in a sample from a subject is compared to the level of the marker in a sample obtained from the subject at a later time, such as after administration of any of the compositions described herein.

In some embodiments, if the level or value of the marker is higher in a sample as compared to the level or value of the marker in a sample from the subject obtained prior to administration of a composition described herein, the subject is administered an immune checkpoint inhibitor and a composition described herein. In some embodiments, if the level or value of the marker is higher in a sample as compared to the level or value of the marker in a sample from the subject obtained prior to administration of a composition described herein, the subject continues a therapy involving administration of an immune checkpoint inhibitor and a composition described herein. In some embodiments, the level or value of the marker in a sample is enhanced at least 10%, 15%, 20%, 25%, 30%, 35%, 40%, 45%, 50%, 55%, 60%, 65%, 70%, 75%, 80%, 85%, 90%, 95%, 100%, 110%, 120%, 130%, 140%, 150%, 160%, 170%, 180%, 190%, or at least 200% as compared the level of value of the marker in a sample prior to administration of a composition as described herein.

In some embodiments, if the level or value of the marker is not increased (e.g., equal to or lower) in a sample as compared to the level or value of the marker in a sample from the subject obtained prior to administration of a composition described herein, administration of an immune checkpoint inhibitor and a composition described herein is discontinued. In some embodiments, if the level or value of the marker is not increased (e.g., equal to or lower) in a sample as compared to the level or value of the marker in a sample from the subject obtained prior to administration of a composition described herein, the administration of an immune checkpoint inhibitor and a composition described herein is reanalyzed after administration of a composition as described herein.

In some embodiments, the level or value of the marker in a sample is reduced at least 10%, 15%, 20%, 25%, 30%, 35%, 40%, 45%, 50%, 55%, 60%, 65%, 70%, 75%, 80%, 85%, 90%, 95%, 100%, 110%, 120%, 130%, 140%, 150%, 160%, 170%, 180%, 190%, or at least 200% as compared the level of value of the marker in a sample prior to administration of a composition as described herein.

In some embodiments, the level of the marker is determined by analyzing the expression of the marker (e.g., protein or nucleic acid level) and/or the cell type in which the marker is expressed. Any method known the art may be used to analyze the expression of the marker and/or cell type in which the marker is expressed.

Also provided herein are methods based on the level or degree of IFN γ production in a sample (e.g., a biological sample containing splenocytes) obtained from a subject. In some embodiments, the methods involve analyzing the presence and/or level of IFN γ production in one or more samples from a subject.

In some embodiments, the level of IFN γ production in a sample obtained from a subject can then be compared with a reference sample or a control sample to determine a value indicating the amount of the IFN γ production in the sample. In some embodiments, a value for IFN γ production is obtained by comparing the level of IFN γ production in a sample to the level of another molecule (e.g., an internal control or internal standard) in the sample. The value of IFN γ production can be compared to a reference value to determine whether the subject has or is at risk for the disease. In some embodiments, the level of IFN γ production is compared to a predetermined threshold for IFN γ production, a deviation from which may indicate the subject has a disease. In some embodiments, if the level or value of IFN γ production is higher than a reference level or value, the subject can be identified as having or at risk for a disease, as described herein. In some embodiments, if the level or value of IFN γ production is lower than a reference level or value, the subject can be identified as having or at risk for a disease, as described herein.

In some embodiments, the level of IFN γ production in a sample from a subject is compared to the level of IFN γ production in another sample obtained from the same subject, for example, a sample obtained from the subject at a different time. In some embodiments, the level of IFN γ production in a sample from a subject is compared to the level of IFN γ production in a sample obtained from the subject at an earlier time, such as prior to administration of any of the compositions described herein. In some embodiments, the level of IFN γ production in a sample from a subject is compared to the level of IFN γ production in a sample obtained from the subject at a later time, such as after administration of any of the compositions described herein.

In some embodiments, if the level or value of IFN γ production is higher in a sample as compared to the level or value of IFN γ production in a sample from the subject obtained prior to administration of a composition described herein, the subject is administered an immune checkpoint inhibitor and a composition described herein. In some embodiments, if the level or value of IFN γ production is higher in a sample as compared to the level or value of IFN γ production in a sample from the subject obtained prior to administration of a composition described herein, the subject continues a therapy involving administration of an immune checkpoint inhibitor and a composition described herein. In some embodiments, the level or value of IFN γ production in a sample is enhanced at least 10%, 15%, 20%, 25%, 30%, 35%, 40%, 45%, 50%, 55%, 60%, 65%, 70%, 75%, 80%, 85%, 90%, 95%, 100%, 110%, 120%, 130%, 140%, 150%, 160%, 170%, 180%, 190%, or at least 200% as compared the level of value of IFN γ production in a sample prior to administration of a composition as described herein.

In some embodiments, if the level or value of IFN γ production is not increased (e.g., equal to or lower) in a sample as compared to the level or value of IFN γ production in a sample from the subject obtained prior to administration of a composition described herein, administration of an immune checkpoint inhibitor and a composition described herein is discontinued. In some embodiments, if the level or value of IFN γ production is not increased (e.g., equal to or lower) in a sample as compared to the level or value of IFN γ production in a sample from the subject obtained prior to administration of a composition described herein, the administration of an immune checkpoint inhibitor and a composition described herein is reanalyzed after administration of a composition as described herein. In some embodiments, the level or value of IFN γ production in a sample is reduced at least 10%, 15%, 20%, 25%, 30%, 35%, 40%, 45%, 50%, 55%, 60%, 65%, 70%, 75%, 80%, 85%, 90%, 95%, 100%, 110%, 120%, 130%, 140%, 150%, 160%, 170%, 180%, 190%, or at least 200% as compared the level of value of IFN γ production in a sample prior to administration of a composition as described herein.

In some embodiments, the level of IFN γ production is determined by analyzing the expression of IFN γ(e.g., protein or nucleic acid level) and/or the cell type by which IFN γ is produced. Any method known the art may be used to analyze the expression of IFN γ and/or identify the cell type that produces IFN γ.

The control level can also be a predetermined level or threshold. Such a predetermined level can represent the level of the marker or IFN γ production in a population of subjects that do not have or are not at risk for the target disease. It can also represent the level of the marker or IFN γ production in a population of subjects that have the target disease.

The predetermined level can take a variety of forms. For example, it can be single cut-off value, such as a median or mean. In some embodiments, such a predetermined level can be established based upon comparative groups, such as where one defined group is known to have a target disease and another defined group is known to not have the target disease. Alternatively, the predetermined level can be a range, for example, a range representing the levels of the metabolite in a control population.

As used herein, "an elevated level" or "an increased level" means that the level of the marker or IFN γ production is higher than a reference value or the level in another sample, such as a sample obtained from the subject prior to administration of any of the compositions described herein. An elevated level of a marker or IFN production includes a level of the marker or IFN γ production that is, for example, 1%, 5%, 10%, 20%, 30%, 40%, 50%, 60%, 70%, 80%, 90%, 100%, 150%, 200%, 300%, 400%, 500% or more above a reference value or above the level in another sample from the subject. In some embodiments, the level of the marker or IFN γ production in the test sample is at least 1.1, 1.2, 1.3, 1.4, 15, 1.6, 1.7, 1.8, 1.9, 2, 2.5, 3, 3.5, 4, 4.5, 5, 5.5, 6, 7, 8, 9, 10, 50, 100, 150, 200, 300, 400, 500, 1000, 10000-fold or more, higher than the level in a reference sample or the level in another sample from the subject.

As used herein, "a decreased level" means that the level of the marker or IFN γ production is lower than a reference value or the level in another sample, such as a sample obtained from the subject prior to administration of any of the compositions described herein. A decreased level of the marker or IFN γ production includes a level of the marker or IFN 7 production that is, for example, 1%, 5%, 10%, 20%, 30%, 40%, 50%, 60%, 70%, 80%, 90%, 100%, 150%, 200%, 300%, 400%, 500% or more lower than a reference value or the level in another sample from the subject. In some embodiments, the level of the marker or IFN 7 production in the test sample is at least 1.1, 1.2, 1.3, 1.4, 15, 1.6, 1.7, 1.8, 1.9, 2, 2.5, 3, 3.5, 4, 4.5, 5, 5.5, 6, 7, 8, 9, 10, 50, 100, 150, 200, 300, 400, 500, 1000, 10000-fold or more lower than the level of the marker or IFN γproduction in a reference sample or the level in another sample from the subject.

A subject identified in the methods described herein may be subject to a suitable treatment, such as treatment with a combination of an immune checkpoint inhibitor and any of the composition, as described herein.

The assay methods and kits described herein also can be applied for evaluation of the efficacy of a treatment for a disease, such as those described herein, given the correlation between the level of the marker or IFN γ production and such diseases. For examples, multiple biological samples can be collected from a subject to whom a treatment is performed either before and after the treatment or during the course of the treatment. The levels of a marker or IFN γ production may be indicative as to whether the treatment is effective.

If the subject is identified as not responsive to the treatment, a higher dose and/or frequency of dosage of the composition and/or immune checkpoint inhibitors are administered to the subject identified. In some embodiments, the dosage or frequency of dosage of the therapeutic agent is maintained, lowered, or ceased in a subject identified as responsive to the treatment or not in need of further treatment. Alternatively, a different treatment can be applied to the subject who is found as not responsive to the first treatment.

In other embodiments, the values of a marker or IFN γ production can also be relied on to identify a disease may be treatable, for example by administering the compositions described herein.

Screening Methods

Provided herein are methods for screening bacteria or physiologically active substances derived from bacteria to identify bacteria or physiologically active substances thereof that produce a desired response. For example, in some embodiments, the screening methods are used to identify bacteria or physiologically active substances derived from bacteria that induce activation of CD8+ IFN γ-producing T cells. In some embodiments, the screening methods are used to identify bacteria or physiologically active substances derived from bacteria that induce activation of CD8+ IFN γ-producing T cells. In some embodiments, the screening methods are used to identify bacteria or physiologically active substances derived from bacteria as an immunostimulatory agent.

Also provided herein are methods for screening test substances to identify substances that induce activation induce or exacerbate a disease caused by CD8+ IFN γ-producing T cells.

In general, the screening methods may be performed in vitro (e.g., using cells) or in vivo (e.g., using non-human animal models). In some embodiments, the methods involve contacting a population of cells (e.g., intestinal epithelial cells, peripheral blood mononuclear cells) with a test substance (e.g., bacteria or physiologically active substances thereof) and assessing a response. In some embodiments, the response is the number and/or activity of a desired cell population (e.g., CD8+ IFN γ T cells).

In some embodiments, the methods involve inoculating a non-human animal model with a test substance (e.g., bacteria or physiologically active substances thereof) and assessing a response. In some embodiments, the non-human animal model ingests the test substance. In some embodiments, the response is the number and/or activity of a desired cell population (e.g., CD8+ IFN γ T cells). In some embodiments, the response is an improvement of a disease or symptom thereof, or induction/exacerbation of a disease or symptom thereof.

In some embodiments, the bacteria and/or the physiologically active substances derived from bacteria identified in any of the screening methods described herein may be administered to a subject, for example for the treatment of a disease.

Kits

The present disclosure also provides kits for use in evaluating the immune system activation, for example based on the degree or level of IFN γ production in splenocytes, involving administering to a subject any of the compositions as described herein. In some embodiments, a sample may be obtained from the subject prior to, during, and/or after administration of any of the compositions described herein.

In some embodiments, the kit contains one or more molecules for detecting and/or measuring the amount of IFN γ production in a sample. In some embodiments, the molecule that detects or measures the amount of IFN γ production can comprise one or more binding agents that specifically bind to IFN γ. In some embodiments, the binding agent is an antibody that specifically binds to IFN γ. In some embodiments, the binding agent is part of a reporter system, such as a receptor on a cell that binds to the IFN γ and induces expression of a gene encoding a reporter molecule. In some embodiments, the kit also contains a standard or control sample to which the amount of IFN γ in the sample(s) obtained from the subject may be compared.

In some embodiments, the kit may be for carrying out any of the companion diagnostic methods described herein.

In some embodiments, the kit contains one or more molecules for detecting and/or measuring the amount or presence of any one of the bacterial species described herein, or component thereof. In some embodiments, the molecule that detects or measures the amount of a bacterial strain can comprise one or more binding agents that specifically bind to the bacterial strain. In some embodiments, the binding agent specifically binds to a feature of one or more bacterial species that identifies the bacterial species. In some embodiments, the binding agent is a nucleic acid that specifically binds to a nucleic acid sequence of one or more of the bacterial species described herein, such as a specific 16S rRNA sequence. In some embodiments, the kit also contains a standard or control sample to which the sample(s) obtained from the subject may be compared.

The present disclosure also provides kits for use in determining a treatment method, for example, a tumor therapy, involving analyzing the expression of a marker (e.g., CD44, CD8, IFN γ, GzmB, gp70 MC38 peptide (KSPWFTTL; (SEQ ID NO: 53))-specific TCRB, or an antigen-derived ligand-specific TCR β), prior to, during, and/or after administration of any of the compositions described herein. Also provided herein are kits comprising companion diagnostics for tumor therapy with an immune checkpoint inhibitor (e.g., a PD-1 inhibitor).

In some embodiments, the kit includes one or more components for analyzing or monitoring expression levels of a marker, such as CD44, CD8, IFN γ, GzmB, or a tumor antigen-derived ligand-specific TCR β. In some embodiments, the marker is analyzed by detecting the presence of the marker, by measuring the level (amount) of the marker, and/or a specific cell type on which the marker is presented. In some embodiments, the molecule that detects or measures the amount of the marker can comprise one or more binding agents that specifically bind to the marker. In some embodiments, the binding agent is an antibody that specifically binds to the marker. In some embodiments, the binding agent is an MHC multimer that specifically binds to the marker.

In some embodiments, the marker is analyzed by detecting the presence of a nucleic acid encoding the marker, by measuring the level (amount) of a nucleic acid encoding the marker, and/or a specific cell type in which the nucleic acid encoding the marker is expressed. In some embodiments, the kit includes one or more reagents for the isolation of nucleic acids (e.g., RNA) from a sample obtained from subject.

In some embodiments, the kits further comprise a detection agent (e.g., an antibody binding to the binding agent) for detecting binding of the agent to the target (e.g., IFN γ, bacterial species) in the sample. The detection agent can be conjugated to a label. In some embodiments, the detection agent is an antibody that specifically binds to at least one of the binding agents. In some embodiments, the binding agent comprises a tag that can be identified and, directly or indirectly, bound by a detection agent.

In some embodiments, the kit may further include one or more therapeutics and/or compositions for administering to the subject. For example, in some embodiments, the kit may include one or more immune checkpoint inhibitor (e.g., PD-1 inhibitor, PD-L inhibitor, CTLA-4 inhibitor). In some embodiments, the kit may include a composition comprising one or more of the bacterial strains described herein.

In some embodiments, the kits may be for screening bacteria or substances derived from bacteria, for example of activation of CD8+ IFN γ-producing T cells. In some embodiments, the kits include cells, such as cells of a cell line. In some embodiments, the cells are intestinal epithelial cells, peripheral blood mononuclear cells.

In some embodiments, the kit or device further includes a support member. In some embodiments, the support member is a membrane, such as a nitrocellulose membrane, a polyvinylidene fluoride (PVDF) membrane, or a cellulose acetate membrane. In some examples, the immunoassay may be in a Western blot assay format or a lateral flow assay format.

In some embodiments, the support member is a multi-well plate, such as an ELISA plate. In some embodiments, the immunoassays described herein can be carried out on high throughput platforms. In some embodiments, multi-well plates, e.g., 24-, 48-, 96-, 384- or greater well plates, may be used for high throughput detection assays.

In the kit or detecting device, one or more of the binding agents may be immobilized on a support member, which can be a membrane, a bead, a slide, or a multi-well plate. Selection of an appropriate support member for the immunoassay will depend on various factor such as the number of samples and method of detecting the signal released from label conjugated to the second agent.

The kit can also comprise one or more buffers as described herein but not limited to a coating buffer, a blocking buffer, a wash buffer, and/or a stopping buffer.

In some embodiments, the kit can comprise instructions for use in accordance with any of the methods described herein. The instructions relating to the use of the kit generally include information as to the amount of each component and suitable conditions for performing the assay methods described herein. The components in the kits may be in unit doses, bulk packages (e.g., multi-dose packages), or sub-unit doses. Instructions supplied in the kits of the present disclosure are typically written instructions on a label or package insert (e.g., a paper sheet included in the kit), but machine-readable instructions (e.g., instructions carried on a magnetic or optical storage disk) are also acceptable.

The label or package insert indicates that the kit is used for evaluating the level of immune system activation, selecting a treatment, and/or diagnostic purposes. Instructions may be provided for practicing any of the methods described herein.

The kits of this present disclosure are in suitable packaging. Suitable packaging includes, but is not limited to, vials, bottles, jars, flexible packaging (e.g., sealed Mylar or plastic bags), and the like.

Kits may optionally provide additional components such as interpretive information, such as a control and/or standard or reference sample. Normally, the kit comprises a container and a label or package insert(s) on or associated with the container. In some embodiments, the present disclosure provides articles of manufacture comprising contents of the kits described above.

Table 1 below provides sequence identifier numbers (SEQ ID NOs) used in the compositions of the experiments disclosed herein. The closest bacterial species to the indicated strain is presented by genus-species. The 16S rDNA sequence associated with each genus species identified as the closest related genus species is also provided. The percent alignment presents the percent identity between the sequence of the indicated strain with the sequence from the closest genus species and the length of the alignment. The GenBank Accession Number of the closest related species is provided in the last column.

TABLE 1

[Strains and species with highest homology]

| Strain # | SEQ ID NO | Strain ID | Species with highest homology | NCBI accession # of 16S locus | SEQ ID of NCBI 16S locus |
|---|---|---|---|---|---|
| 1 | 1 | 2G5 | *Phascolarctobacterium faecium* | LN998073 | 27 |
| 2 | 2 | 1A6 | *Fusobacterium ulcerans* | KR822463 | 28 |
| 3 | 3 | 1B11 | *Bacteroides dorei* | CP011531 | 29 |
| 4 | 4 | 2G1 | *Bacteroides uniformis* | NR112945 | 30 |
| 5 | 5 | 2B1 | *Subdoligranulum* sp. | KM098109 | 31 |
| 6 | 6 | 2A6 | *Paraprevotella xylaniphila* | NR113078 | 32 |
| 7 | 7 | 2F11 | *Parabacteroides johnsonii* | NR041464 | 33 |
| 8 | 8 | 1E7 | *Alistipes* sp. | LT223566 | 34 |
| 9 | 9 | 1H9 | *Parabacteroides gordonii* | NR112835 | 35 |

TABLE 1-continued

[Strains and species with highest homology]

| Strain # | SEQ ID NO | Strain ID | Species with highest homology | NCBI accession # of 16S locus | SEQ ID of NCBI 16S locus |
|---|---|---|---|---|---|
| 10 | 10 | 1C1 | *Eubacterum limosum* | NR113248 | 36 |
| 11 | 11 | 2G9 | *Parabacteroides distasonis* | NR041342 | 37 |
| 12 | 12 | 2B7 | *Bacteroides cellulosilyticus* | NR112933 | 38 |
| 13 | 13 | 2C1 | *Bacteroides clarus* | NR112893 | 39 |
| 14 | 14 | 1B4 | *Anaerostipes caccae* | HE974918 | 40 |
| 15 | 15 | 2A3 | *Bacteroides salyersiae* | NR043016 | 41 |
| 16 | 16 | 2A12 | *Bacteroides fragilis* | AB618791 | 42 |
| 17 | 17 | 1A2 | *Bacteroides uniformis* | AB215083 | 43 |
| 18 | 18 | 2B11 | *Bacteroides eggerthii* | NR112935 | 44 |
| 19 | 19 | 2D2 | *Clostridium* sp. | AB249652 | 45 |
| 20 | 20 | 2E8 | *Parabacteroides goldsteinii* | NR113076 | 46 |
| 21 | 21 | 1H8 | *Bacteroides* sp. | NR112944 | 47 |
| 22 | 22 | 3F2 | Lachnospiraceae bacterium HGA0140 | JX519760 | 48 |
| 23 | 23 | 1G1 | *Hungatella hathewayi* | AJ311620 | 49 |
| 24 | 24 | 1E6 | *Clostridium lavalense* | EF564278 | 50 |
| 25 | 25 | 1F3 | *Ruminococcus* sp. | KT156811 | 51 |
| 26 | 26 | 1A1 | *Clostridium innocuum* | HM008265 | 52 |

The nucleic acid sequences of the 16S rDNA, or portion thereof, for the bacterial strains described herein are provided below:

SEQ ID NO: 1 strain 1 2G5_*Phascolarctobacterium faecium*_LN998073

GACGAACGCTGGCGGCGTGCCTAACACATGCAAGTCGAACGGAGAATTTTATTTCG

GTAGAATTCTTAGTGGCGAACGGGTGAGTAACGCGTAGGCAACCTACCCTTTAGAC

GGGGACAACATTCCGAAAGGAGTGCTAATACCGGATGTGATCATCTTGCCGCATGG

CAGGATGAAGAAAGATGGCCTCTACAAGTAAGCTATCGCTAAAGGATGGGCCTGCG

TCTGATTAGCTAGTTGGTAGTGTAACGGACTACCAAGGCGATGATCAGTAGCCGGT

CTGAGAGGATGAACGGCCACATTGGGACTGAGACACGGCCCAAACTCCTACGGGA

GGCAGCAGTGGGGAATCTTCCGCAATGGACGAAAGTCTGACGGAGCAACGCCGCG

TGAGTGATGAAGGATTTCGGTCTGTAAAGCTCTGTTGTTTATGACGAACGTGCAGT

GTGTGAACAATGCATTGCAATGACGGTAGTAAACGAGGAAGCCACGGCTAACTACG

TGCCAGCAGCCGCGGTAATACGTAGGTGGCGAGCGTTGTCCGGAATTATTGGGCGT

AAAGAGCATGTAGGCGGCTTAATAAGTCGAGCGTGAAAATGCGGGGCTCAACCCC

GTATGGCGCTGGAAACTGTTAGGCTTGAGTGCAGGAGAGGAAAGGGGAATTCCCA

GTGTAGCGGTGAAATGCGTAGATATTGGGAGGAACACCAGTGGCGAAGGCGCCTT

TCTGGACTGTGTCTGACGCTGAGATGCGAAAGCCAGGGTAGCGAACGGGATTAGA

TACCCCGGTAGTCCTGGCCGTAAACGATGGGTACTAGGTGTAGGAGGTATCGACCC

CTTCTGTGCCGGAGTTAACGCAATAAGTACCCCGCCTGGGGAGTACGGCCGCAAG

GTTGAAACTCAAAGGAATTGACGGGGGCCCGCACAAGCGGTGGAGTATGTGGTTT

AATTCGACGCAACGCGAAGAACCTTACCAAGGCTTGACATTGATTGAACGCTCTAG

AGATAGAGATTTCCCTTCGGGGACAAGAAAACAGGTGGTGCATGGCTGTCGTCAG

CTCGTGTCGTGAGATGTTGGGTTAAGTCCCGCAACGAGCGCAACCCCTATCCTATG

TTACCAGCAAGTAAAGTTGGGGACTCATGGGAGACTGCCAGGGACAACCTGGAGG

AAGGCGGGGATGACGTCAAGTCATCATGCCCCTTATGTCTTGGGCTACACACGTAC

TACAATGGTCGGAAACAGAGGGAAGCGAAGCCGCGAGGCAGAGCAAACCCCAGAA

-continued

ACCCGATCTCAGTTCGGATCGCAGGCTGCAACCCGCCTGCGTGAAGTCGGAATCG

CTAGTAATCGCAGGTCAGCATACTGCGGTGAATACGTTCCCGGGCCTTGTACACAC

CGCCCGTCACACCACGAAAGTTGGTAACACCCGAAGCCGGTGAGGTAACCTA

SEQ ID NO: 2 strain 2 1A6_*Fusobacterium ulcerans*_KR822463

GATGAACGCTGACAGAATGCTTAACACATGCAAGTCTACTTGATCCTTCGGGTGAA

GGTGGCGGACGGGTGAGTAACGCGTAAAGAACTTGCCTTACAGACTGGGACAACA

TTTGGAAACGAATGCTAATACCGGATATTATGATTGGGTCGCATGATCTGATTATGA

AAGCTATATGCGCTGTGAGAGAGCTTTGCGTCCCATTAGTTAGTTGGTGAGGTAAC

GGCTCACCAAGACGATGATGGGTAGCCGGCCTGAGAGGGTGAACGGCCACAAGGG

GACTGAGACACGGCCCTTACTCCTACGGGAGGCAGCAGTGGGGAATATTGGACAA

TGGACCAAAAGTCTGATCCAGCAATTCTGTGTGCACGAAGAAGTTTTTCGGAATGT

AAAGTGCTTTCAGTTGGGAAGAAGTCAGTGACGGTACCAACAGAAGAAGCGACGG

CTAAATACGTGCCAGCAGCCGCGGTAATACGTATGTCGCAAGCGTTATCCGGATTTA

TTGGGCGTAAAGCGCGTCTAGGCGGCTTAGTAAGTCTGATGTGAAAATGCGGGGCT

CAACCCCGTATTGCGTTGGAAACTGCTAAACTAGAGTACTGGAGAGGTAGGCGGAA

CTACAAGTGTAGAGGTGAAATTCGTAGATATTTGTAGGAATGCCGATGGGGAAGCC

AGCCTACTGGACAGATACTGACGCTAAAGCGCGAAAGCGTGGGTAGCAAACAGGA

TTAGATACCCTGGTAGTCCACGCCGTAAACGATGATTACTAGGTGTTGGGGGTCGA

ACCTCAGCGCCCAAGCTAACGCGATAAGTAATCCGCCTGGGGAGTACGTACGCAAG

TATGAAACTCAAAGGAATTGACGGGGACCCGCACAAGCGGTGGAGCATGTGGTTT

AATTCGACGCAACGCGAGGAACCTTACCAGCGTTTGACATCCCAAGAAGTTAACAG

AGATGTTTTCGTGCCTCTTCGGAGGAACTTGGTGACAGGTGGTGCATGGCTGTCGT

CAGCTCGTGTCGTGAGATGTTGGGTTAAGTCCCGCAACGAGCGCAACCCCTTTCGT

ATGTTACCATCATTAAGTTGGGGACTCATGCGAGACTGCCTGCGATGAGCAGGAGG

AAGGTGGGGATGACGTCAAGTCATCATGCCCCTTATACGCTGGGCTACACACGTGC

TACAATGGGTAGTACAGAGAGCTGCAAACCTGCGAGGGTAAGCTAATCTCATAAAA

CTATTCTTAGTTCGGATTGTACTCTGCAACTCGAGTACATGAAGTTGGAATCGCTAG

TAATCGCAAATCAGCTATGTTGCGGTGAATACGTTCTCGGGTCTTGTACACACCGC

CCGTCACACCACGAGAGTTGGTTGCACCTGAAGTAACAGGCCTAACCGTAA

SEQ ID NO: 3 strain 3 1B11_*Bacteroides dorei*_CP011531

AGTTTGNNNTATGGCTCAGGATGAACGCTAGCTACAGGCTTAACACATGCAAGTCG

AGGGGCAGCATGGTCTTAGCTTGCTAAGGCTGATGGCGACCGGCGCACGGGTGAG

TAACACGTATCCAACCTGCCGTCTACTCTTGGCCAGCCTTCTGAAAGGAAGATTAAT

CCAGGATGGGATCATGAGTTCACATGTCCGCATGATTAAAGGTATTTTCCGGTAGA

CGATGGGGATGCGTTCCATTAGATAGTAGGCGGGGTAACGGCCCACCTAGTCAACG

ATGGATAGGGGTTCTGAGAGGAAGGTCCCCCACATTGGAACTGAGACACGGTCCA

AACTCCTACGGGAGGCAGCAGTGAGGAATATTGGTCAATGGGCGATGGCCTGAAC

CAGCCAAGTAGCGTGAAGGATGACTGCCCTATGGGTTGTAAACTTCTTTTATAAAG

GAATAAAGTCGGGTATGCATACCCGTTTGCATGTACTTTATGAATAAGGATCGGCTA

ACTCCGTGCCAGCAGCCGCGGTAATACGGAGGATCCGAGCGTTATCCGGATTTATT

GGGTTTAAAGGGAGCGTAGATGGATGTTTAAGTCAGTTGTGAAAGTTTGCGGCTCA

-continued

ACCGTAAAATTGCAGTTGATACTGGATGTCTTGAGTGCAGTTGAGGCAGGCGGAAT

TCGTGGTGTAGCGGTGAAATGCTTAGATATCACGAAGAACTCCGATTGCGAAGGCA

GCCTGCTAAGCTGCAACTGACATTGAGGCTCGAAAGTGTGGGTATCAAACAGGATT

AGATACCCTGGTAGTCCACACGGTAAACGATGAATACTCGCTGTTTGCGATATACG

GCAAGCGGCCAAGCGAAAGCGTTAAGTATTCCACCTGGGGAGTACGCCGGCAACG

GTGAAACTCAAAGGAATTGACGGGGGCCCGCACAAGCGGAGGAACATGTGGTTTA

ATTCGATGATACGCGAGGAACCTTACCCGGGCTTAAATTGCACTCGAATGATCCGG

AAACGGTTCAGCTAGCAATAGCGAGTGTGAAGGTGCTGCATGGTTGTCGTCAGCTC

GTGCCGTGAGGTGTCGGCTTAAGTGCCATAACGAGCGCAACCCTTGTTGTCAGTTA

CTAACAGGTGATGCTGAGGACTCTGACAAGACTGCCATCGTAAGATGTGAGGAAG

GTGGGGATGACGTCAAATCAGCACGGCCCTTACGTCCGGGGCTACACACGTGTTAC

AATGGGGGGTACAGAGGGCCGCTACCACGCGAGTGGATGCCAATCCCTAAAACCC

CTCTCAGTTCGGACTGGAGTCTGCAACCCGACTCCACGAAGCTGGATTCGCTAGTA

ATCGCGCATCAGCCACGGCGCGGTGAATACGTTCCCGGGCCTTGTACACACCGCCC

GTCAAGCCATGGGAGCCGGGGGTACCTGAAGTGCGTAACCGCGAGGAT

SEQ ID NO: 4 strain 4 2G1_*Bacteroides uniformis*_NR_112945

GATGAACGCTAGCTACAGGCTTAACACATGCAAGTCGAGGGGCAGCATGAACTTAG

CTTGCTAAGTTTGATGGCGACCGGCGCACGGGTGAGTAACACGTATCCAACCTGCC

GATGACTCGGGGATAGCCTTTCGAAAGAAAGATTAATACCCGATGGCATAGTTCTT

CCGCATGGTAGAACTATTAAAGAATTTCGGTCATCGATGGGGATGCGTTCCATTAG

GTTGTTGGCGGGGTAACGGCCCACCAAGCCTTCGATGGATAGGGGTTCTGAGAGG

AAGGTCCCCCACATTGGAACTGAGACACGGTCCAAACTCCTACGGGAGGCAGCAG

TGAGGAATATTGGTCAATGGACGAGAGTCTGAACCAGCCAAGTAGCGTGAAGGAT

GACTGCCCTATGGGTTGTAAACTTCTTTTATACGGGAATAAAGTGAGGCACGTGTG

CCTTTTTGTATGTACCGTATGAATAAGGATCGGCTAACTCCGTGCCAGCAGCCGCG

GTAATACGGAGGATCCGAGCGTTATCCGGATTTATTGGGTTTAAAGGGAGCGTAGG

CGGACGCTTAAGTCAGTTGTGAAAGTTTGCGGCTCAACCGTAAAATTGCAGTTGAT

ACTGGGTGTCTTGAGTACAGTAGAGGCAGGCGGAATTCGTGGTGTAGCGGTGAAA

TGCTTAGATATCACGAAGAACTCCGATTGCGAAGGCAGCCTGCTGGACTGTAACTG

ACGCTGATGCTCGAAAGTGTGGGTATCAAACAGGATTAGATACCCTGGTAGTCCAC

ACCAGTAAACGATGAATACTCGCTGTTTGCGATATACAGTAAGCGGCCAAGCGAAA

GCGTTAAGTATTCCACCTGGGGAGTACGCCGGCAACGGTGAAACTCAAAGGAATTG

ACGGGGGCCCGCACAAGCGGAGGAACATGTGGTTTAATTCGATGATACGCGAGGA

ACCTTACCCGGGCTTGAATTGCAACTGAATGATGTGGAGACATGTCAGCCGCAAGG

CAGTTGTGAAGGTGCTGCATGGTTGTCGTCAGCTCGTGCCGTGAGGTGTCGGCTT

AAGTGCCATAACGAGCGCAACCCTTATCGATAGTTACCATCAGGTGATGCTGGGGA

CTCTGTCGAGACTGCCGTCGTAAGATGTGAGGAAGGTGGGGATGACGTCAAATCA

GCACGGCCCTTACGTCCGGGGCTACACACGTGTTACAATGGGGGGTACAGAAGGC

AGCTACACGGCGACGTGATGCTAATCCCGAAAGCCTCTCTCAGTTCGGATTGGAGT

CTGCAACCCGACTCCATGAAGCTGGATTCGCTAGTAATCGCGCATCAGCCACGGCG

-continued

CGGTGAATACGTTCCCGGGCCTTGTACACACCGCCCGTCAAGCCATGAAAGCCGG

GGGTACCTGAAGTGCGTAACCGCAAGGAG

SEQ ID NO: 5
strain 5 2B1_*Subdoligranulum* sp. 4_3_54A2FAA_NZ-ACWW00000000
GACGAACGCTGGCGGCGCGCCTAACACATGCAAGTCGAACGGAGCTGTTTTCTCT

GAAGTTTTCGGATGGAAGAGAGTTCAGCTTAGTGGCGAACGGGTGAGTAACACGT

GAGCAACCTGCCTTTCAGTGGGGGACAACATTTGGAAACGAATGCTAATACCGCAT

AAGACCACAGTGTCGCATGGCACAGGGGTCAAAGGATTTATCCGCTGAAAGATGG

GCTCGCGTCCGATTAGCTAGATGGTGAGGTAACGGCCCACCATGGCGACGATCGGT

AGCCGGACTGAGAGGTTGAACGGCCACATTGGGACTGAGACACGGCCCAGACTCC

TACGGGAGGCAGCAGTGGGGAATATTGCACAATGGGGGAAACCCTGATGCAGCGA

CGCCGCGTGGAGGAAGAAGGTCTTCGGATTGTAAACTCCTGTCCCAGGGGACGAT

AATGACGGTACCCTGGGAGGAAGCACCGGCTAACTACGTGCCAGCAGCCGCGGTA

AAACGTAGGGTGCAAGCGTTGTCCGGAATTACTGGGTGTAAAGGGAGCGCAGGCG

GATTGGCAAGTTGGGAGTGAAATCTATGGGCTCAACCCATAAATTGCTTTCAAAAC

TGTCAGTCTTGAGTGGTGTAGAGGTAGGCGGAATTCCCGGTGTAGCGGTGGAATG

CGTAGATATCGGGAGGAACACCAGTGGCGAAGGCGGCCTACTGGGCACTAACTGA

CGCTGAGGCTCGAAAGCATGGGTAGCAAACAGGATTAGATACCCTGGTAGTCCATG

CCGTAAACGATGATTACTAGGTGTGGGAGGATTGACCCCTTCCGTGCCGCAGTTAA

CACAATAAGTAATCCACCTGGGGAGTACGACCGCAAGGTTGAAACTCAAAGGAATT

GACGGGGGCCCGCACAAGCAGTGGAGTATGTGGTTTAATTCGAAGCAACGCGAAG

AACCTTACCAGGTCTTGACATCGGATGCATACCTAAGAGATTAGGGAAGTCCTTCG

GGACATCCAGACAGGTGGTGCATGGTTGTCGTCAGCTCGTGTCGTGAGATGTTGG

GTTAAGTCCCGCAACGAGCGCAACCCTTATCGTTAGTTACTACGCAAGAGGACTCT

AGCGAGACTGCCGTTGACAAAACGGAGGAAGGTGGGGATGACGTCAAATCATCAT

GCCCTTTATGACCTGGGCTACACACGTACTACAATGGCTATTAACAGAGAGAAGCG

ATACCGCGAGGTGGAGCAAACCTCACAAAAATAGTCTCAGTTCGGATCGCAGGCTG

CAACCCGCCTGCGTGAAGCCGGAATTGCTAGTAATCGCGGATCAGCATGCCGCGGT

GAATACGTTCCCGGGCCTTGTACACACCGCCCGTCACACCATGAGAGCCGGGGGG

ACCCGAAGTCGGTAGTCTAACCGC

SEQ ID NO: 6
strain 6 2A6_*Paraprevotella xylaniphila*_AB331897
GATGAACGCTAGCTACAGGCTTAACACATGCAAGTCGAGGGGCAGCATGAACTTAG

CTTGCTAAGTTTGATGGCGACCGGCGCACGGGTGAGTAACGCGTATCCAACCTGCC

CTTTACCCGGGGATAGCCTTCTGAAAAGGAAGTTTAATACCCGATGAATTCGTTTAG

TCGCATGGCTNGATGAATAAAGATTAATTGGTAAAGGATGGGGATGCGTCCCATTA

GCTTGTTGGCGGGGTAACGGCCCACCAAGGCGACGATGGGTAGGGGTTCTGAGAG

GAAGGTCCCCCACATTGGAACTGAGACACGGTCCAAACTCCTACGGGAGGCAGCA

GTGAGGAATATTGGTCAATGGGCGCGAGCCTGAACCAGCCAAGTAGCGTGGAGGA

CGACGGCCCTACGGGTTGTAAACTCCTTTTATAAGGGGATAAAGTTGGCCATGTAT

GGCCATTTGCAGGTACCTTATGAATAAGCATCGGCTAATTCCGTGCCAGCAGCCGC

GGTAATACGGAAGATGCGAGCGTTATCCGGATTTATTGGGTTTAAAGGGAGCGTAG

GCGGGCTGTCAAGTCAGCGGTCAAATGGCGCGGCTCAACCGCGTTCCGCCGTTGA

-continued

AACTGGCAGCCTTGAGTATGCACAGGGTACATGGAATTCGTGGTGTAGCGGTGAAA

TGCTTAGATATCACGAGGAACTCCGATCGCGCAGGCATTGTACCGGGGCATTACTG

ACGCTGAGGCTCGAAGGTGCGGGTATCAAACAGGATTAGATACCCTGGTAGTCCGC

ACAGTAAACGATGAATGCCCGCTGTCGGCGACATAGTGTCGGCGGCCAAGCGAAA

GCGTTAAGCATTCCACCTGGGGAGTACGCCGGCAACGGTGAAACTCAAAGGAATT

GACGGGGGCCCGCACAAGCGGAGGAACATGTGGTTTAATTCGATGATACGCGAGG

AACCTTACCCGGGCTTGAATCGCAGGTGCATGGGCCGGAGACGGCCCTTTCCTTC

GGGACTCCTGCGAAGGTGCTGCATGGTTGTCGTCAGCTCGTGCCGTGAGGTGTCG

GCTTAAGTGCCATAACGAGCGCAACCCCCCTCCCCAGTTGCCACCGGGTAATGCCG

GGCACTTTGGGGACACTGCCACCGCAAGGTGCGAGGAAGGTGGGGATGACGTCAA

ATCAGCACGGCCCTTACGTCCGGGGCGACACACGTGTTACAATGGGGGGTACAGA

GGGCCGCTGCCCGGTGACGGTTGGCCAATCCCTAAAACCCCTCTCAGTTCGGACT

GGAGTCTGCAACCCGACTCCACGAAGCTGGATTCGCTAGTAATCGCGCATCAGCCA

TGGCGCGGTGAATACGTTCCCGGGCCTTGTACACACCGCCCGTCAAGCCATGAAA

GCCGGGGGTGCCTGAAGTCCGTNNCCGCGA

SEQ ID NO: 7 strain 7 2F11_*Parabacteroides johnsonii*_AB261128

GATGAACGCTAGCGACAGGCTTAACACATGCAAGTCGAGGGGCAGCATGGTAAGT

AGCAATACTTATTGATGGCGACCGGCGCACGGGTGAGTAACGCGTATGCAACTTAC

CTATCAGAGGGGGATAGCCCGGCGAAAGTCGGATTAATACTCCATAAAACAGGGGT

TCCGCATGGGACTATTTGTTAAAGATTCATCGCTGATAGATAGGCATGCGTTCCATT

AGGCAGTTGGCGGGGTAACGGCCCACCAAACCGACGATGGATAGGGGTTCTGAGA

GGAAGGTCCCCCACATTGGTACTGAGACACGGACCAAACTCCTACGGGAGGCAGC

AGTGAGGAATATTGGTCAATGGCCGAGAGGCTGAACCAGCCAAGTCGCGTGAAGG

ATGAAGGATCTATGGTTTGTAAACTTCTTTTATAGGGGAATAAAGTGTGGGACGTGT

TCCATTTTGTATGTACCCTATGAATAAGCATCGGCTAACTCCGTGCCAGCAGCCGCG

GTAATACGGAGGATGCGAGCGTTATCCGGATTTATTGGGTTTAAAGGGTGCGTAGG

TGGTAATTTAAGTCAGCGGTGAAAGTTTGTGGCTCAACCATAAAATTGCCGTTGAA

ACTGGGTTACTTGAGTGTGTTTGAGGTAGGCGGAATGCGTGGTGTAGCGGTGAAAT

GCATAGATATCACGCAGAACTCCAATTGCGAAGGCAGCTTACTAAACCATAACTGA

CACTGAAGCACGAAAGCGTGGGTATCAAACAGGATTAGATACCCTGGTAGTCCACG

CAGTAAACGATGATTACTAGGAGTTTGCGATACACAGTAAGCTCTACAGCGAAAGC

GTTAAGTAATCCACCTGGGGAGTACGCCGGCAACGGTGAAACTCAAAGGAATTGAC

GGGGGCCCGCACAAGCGGAGGAACATGTGGTTTAATTCGATGATACGCGAGGAAC

CTTACCCGGGTTTGAACGTAGTCAGACCGACCTTGAAAGAGGTTTTCTAGCAATAG

CTGATTACGAGGTGCTGCATGGTTGTCGTCAGCTCGTGCCGTGAGGTGTCGGCTTA

AGTGCCATAACGAGCGCAACCCTTATCACTAGTTACTAACAGGTTAAGCTGAGGAC

TCTGGTGAGACTGCCAGCGTAAGCTGTGAGGAAGGTGGGGATGACGTCAAATCAG

CACGGCCCTTACATCCGGGGCGACACACGTGTTACAATGGCATGGACAAAGGGCA

GCTACCTGGCGACAGGATGCTAATCTCTAAACCATGTCTCAGTTCGGATCGGAGTC

TGCAACTCGACTCCGTGAAGCTGGATTCGCTAGTAATCGCGCATCAGCCATGGCGC

-continued

GGTGAATACGTTCCCGGGCCTTGTACACACCGCCCGTCAAGCCATGGGAGCCGGG

GGTACCTGAAGTCCGTAACCGCAA

SEQ ID NO: 8
strain 8 1E7_*Alistipes* sp.JC136_NZ -CAEG00000000
GATGAACGCTAGCGGCAGGCCTAACACATGCAAGTCGAGGGGCAGCGGGATTGAA

GCTTGCTTCAGTTGCCGGCGACCGGCGCACGGGTGCGTAACGCGTATGCAACCTA

CCCATAACAGGGGGATAACACTGAGAAATCGGTACTAATATCCCATAACATCAAGAG

GGGCATCCCTTTTGGTTGAAAACTCCGGTGGTTATGGATGGGCATGCGTTGTATTA

GCTAGTTGGTGAGGTAACGGCTCACCAAGGCGACGATACATAGGGGGACTGAGAG

GTTAACCCCCCACATTGGTACTGAGACACGGACCAAACTCCTACGGGAGGCAGCA

GTGAGGAATATTGGTCAATGGACGCAAGTCTGAACCAGCCATGCCGCGTGCAGGAT

GACGGCTCTATGAGTTGTAAACTGCTTTTGTACGAGGGTAAACCCGGATACGTGTA

TCCGGCTGAAAGTATCGTACGAATAAGGATCGGCTAACTCCGTGCCAGCAGCCGCG

GTAATACGGAGGATTCAAGCGTTATCCGGATTTATTGGGTTTAAAGGGTGCGTAGG

CGGTTTGATAAGTTAGAGGTGAAATACCGGTGCTTAACACCGGAACTGCCTCTAAT

ACTGTTGAGCTAGAGAGTAGTTGCGGTAGGCGGAATGTATGGTGTAGCGGTGAAAT

GCTTAGAGATCATACAGAACACCGATTGCNGAAGGCAGCTTACCAAACTATATCTG

ACGTTNGAGGCACGAAAGCGTGGGGGAGCAAACAGGATTAGATACCCTGGTAGTC

CACGCAGTAAACGATGATAACTCGCTGTCGGCGATACACAGTCGGTGGCTAAGCGA

AAGCGATAAGTTATCCACCTGGGGAGTACGTTCGCAAGAATGAAACTCAAAGGAAT

TGACGGGGGCCCGCACAAGCGGAGGAACATGTGGTTTAATTCGATGATACGCGAG

GAACCTTACCCGGGCTTGAAAGTTACTGACGATTCTGGAAACAGGATTTCCCTTCG

GGGCAGGAAACTAGGTGCTGCATGGTTGTCGTCAGCTCGTGCCGTGAGGTGTCGG

GTTAAGTCCCATAACGAGCGCAACCCCTACCGTTAGTTGCCATCAGGTCAAGCTGG

GCACTCTGGCGGGACTGCCGGTGTAAGCCGAGAGGAAGGTGGGGATGACGTCAAA

TCAGCACGGCCCTTACGTCCGGGGCTACACACGTGTTACAATGGTAGGTACAGAGG

GCAGCTACCCAGTGATGGGATGCGAATCTCGAAAGCCTATCTCAGTTCGGATTGGA

GGCTGAAACCCGCCTCCATGAAGTTGGATTCGCTAGTAATCGCGCATCAGCCATGG

CGCGGTGAATACGTTCCCGGGCCTTGTACACACCGCCCGTCAAGCCATGGAAGCT

GGGGGTGCCTGAAGTTCGTGAC

SEQ ID NO: 9
strain 9 1H9_*Parabacteroides gordonii*_AB470343
GATGAACGCTAGCGACAGGCTTAACACATGCAAGTCGAGGGGCAGCAGGAAGTAG

CAATACTTTGCTGGCGACCGGCGCACGGGTGAGTAACGCGTATGCAACCTACCTAT

CAGAGGGGGATAACCCGGCGAAAGTCGGACTAATACCGCATAAAACAGGGGTCCC

GCATGGGAATATTTGTTAAAGATTTATTGCTGATAGATGGGCATGCGTTCCATTAGA

TAGTTGGTGAGGTAACGGCTCACCAAGTCTTCGATGGATAGGGGTTCTGAGAGGAA

GGTCCCCCACACTGGTACTGAGACACGGACCAGACTCCTACGGGAGGCAGCAGTG

AGGAATATTGGTCAATGGGCGAGAGCCTGAACCAGCCAAGTCGCGTGAAGGATGA

AGGATCTATGGTTCGTAAACTTCTTTTATAGGGGAATAAAGTGCAGGACGTGTCCT

GTTTTGTATGTACCCTATGAATAAGGATCGGCTAACTCCGTGCCAGCAGCCGCGGT

AATACGGAGGATCCGAGCGTTATCCGGATTTATTGGGTTTAAAGGGTGCGTAGGTG

GCTTTTTAAGTCAGCGGTGAAAGTTTGTGGCTCAACCATAAAATTGCCGTTGAAAC

-continued

TGGAGGGCTTGAGTATATTTGAGGTAGGCGGAATGCGTGGTGTAGCGGTGAAATGC

ATAGATATCACGCAGAACTCCAATTGCGAAGGCAGCTTACTAAACTATAACTGACAC

TGAAGCACGAAAGCGTGGGGATCAAACAGGATTAGATACCCTGGTAGTCCACGCA

GTAAACGATGATTACTAGGAGTTTGCGATACACAGTAAGCTCTACAGCGAAAGCGT

TAAGTAATCCACCTGGGGAGTACGCCGGCAACGGTGAAACTCAAAGGAATTGACG

GGGGCCCGCACAAGCGGAGGAACATGTGGTTTAATTCGATGATACGCGAGGAACC

TTACCCGGGTTTGAACGTAAGTTGACCGGAGTGGAAACACTCTTTCTAGCAATAGC

AATTTACGAGGTGCTGCATGGTTGTCGTCAGCTCGTGCCGTGAGGTGTCGGCTTAA

GTGCCATAACGAGCGCAACCCTTATCTTTAGTTACTAACAGGTCGAGCTGAGGACT

CTAAAGAGACTGCCAGCGTAAGCTGTGAGGAAGGTGGGGATGACGTCAAATCAGC

ACGGCCCTTACATCCGGGGCGACACACGTGTTACAATGGTGGGGACAAAGGGCAG

CTACCTGGCGACAGGATGCTAATCTCCAAACCCCATCTCAGTTCGGATCGAAGTCT

GCAACCCGACTTCGTGAAGCTGGATTCGCTAGTAATCGCGCATCAGCCATGGCGCG

GTGAATACGTTCCCGGGCCTTGTACACACCGCCCGTCAAGCCATGGGAGTTGGGG

GTACCTAAAGTCCGTNACCGCAAG

SEQ ID NO: 10 strain 10 1C1_*Eubacterium limosum*_AB595134

GACGAACGCTGGCGGTATGCTTAACACATGCAAGTCGAACGAGAAGGTTTTGATGG

ATCCTTCGGGTGACATTAGAACTGGAAAGTGGCGAACGGGTGAGTAACGCGTGGG

TAACCTGCCCTATGGAAAGGAATAGCCTCGGGAAACTGGGAGTAAAGCCTTATATT

ATGGTTTTGTCGCATGGCAAGATCATGAAAACTCCGGTGCCATAGGATGGACCCGC

GTCCCATTAGCTAGTTGGTGAGATAACAGCCCACCAAGGCGACGATGGGTAACCGG

TCTGAGAGGGCGAACGGTCACACTGGAACTGAGACACGGTCCAGACTCCTACGGG

AGGCAGCAGTGGGGAATATTGCGCAATGGGGGCAACCCTGACGCAGCAATACCGC

GTGAGTGAAGAAGGTTTTCGGATCGTAAAGCTCTGTTATTGGGGAAGAAGAATGAC

GGTACCCAATGAGGAAGTCCCGGCTAACTACGTGCCAGCAGCCGCGGTAATACGTA

GGGGACAAGCGTTGTCCGGAATGACTGGGCGTAAAGGGCGCGTAGGCGGTCTATT

AAGTCTGATGTGAAAGGTACCGGCTCAACCGGTGAAGTGCATTGGAAACTGGTAG

ACTTGAGTATTGGAGAGGCAAGTGGAATTCCTAGTGTAGCGGTGAAATGCGTAGAT

ATTAGGAGGAACACCAGTGGCGAAGGCGGCTTGCTGGACAAATACTGACGCTGAG

GTGCGAAAGCGTGGGGAGCGAACAGGATTAGATACCCTGGTAGTCCACGCCGTAA

ACGATGAATGCTAGGTGTTGGGGAAACTCAGTGCCGCAGTTAACACAATAAGCATT

CCGCCTGGGGAGTACGACCGCAAGGTTGAAACTCAAAGGAATTGACGGGGACCCG

CACAAGCAGCGGAGCATGTGGTTTAATTCGAAGCAACGCGAAGAACCTTACCAGGT

CTTGACATCCTCTGACGAGCCTAGAGATAGGAAGTTTCCTTCGGGAACAGAGAGAC

AGGTGGTGCATGGTTGTCGTCAGCTCGTGTCGTGAGATGTTGGGTTAAGTCCCGCA

ACGAGCGCAACCCCTGCCTTTAGTTGCCAGCATTAAGTTGGGCACTCTAGAGGGAC

TGCCGTAGACAATACGGAGGAAGGTGGGGACGACGTCAAATCATCATGCCCCTTAT

GACCTGGGCTACACACGTGCTACAATGGTCTGAACAGAGGGCCGCGAAGCCGCGA

GGTGAAGCAAATCCCTTAAAACAGATCCCAGTTCGGATTGCAGGCTGCAACTCGCC

TGCATGAAGTTGGAGTTGCTAGTAATCGCGGATCAGAATGCCGCGGTGAATGCGTT

-continued

CCCGGGTCTTGTACACACCGCCCGTCACACCACGAGAGTTGGCAACACCCGAAGC

CTGTGAGAGAACCGTAAGGACTCAGCAGT

SEQ ID NO: 11 strain 11 2G9_*Parabacteroides distasonis*_HE974920

GATGAACGCTAGCGACAGGCTTAACACATGCAAGTCGAGGGGCAGCACAGGTAGC

AATACCGGGTGGCGACCGGCGCACGGGTGAGTAACGCGTATGCAACTTGCCTATCA

GAGGGGGATAACCCGGCGAAAGTCGGACTAATACCGCATGAAGCAGGGGCCCCGC

ATGGGGATATTTGCTAAAGATTCATCGCTGATAGATAGGCATGCGTTCCATTAGGCA

GTTGGCGGGGTAACGGCCCACCAAACCGACGATGGATAGGGGTTCTGAGAGGAAG

GTCCCCCACATTGGTACTGAGACACGGACCAAACTCCTACGGGAGGCAGCAGTGA

GGAATATTGGTCAATGGCCGAGAGGCTGAACCAGCCAAGTCGCGTGAGGGATGAA

GGTTCTATGGATCGTAAACCTCTTTTATAAGGGAATAAAGTGCGGGACGTGTCCCG

TTTTGTATGTACCTTATGAATAAGGATCGGCTAACTCCGTGCCAGCAGCCGCGGTAA

TACGGAGGATCCGAGCGTTATCCGGATTTATTGGGTTTAAAGGGTGCGTAGGCGGC

CTTTTAAGTCAGCGGTGAAAGTCTGTGGCTCAACCATAGAATTGCCGTTGAAACTG

GGGGGCTTGAGTATGTTTGAGGCAGGCGGAATGCGTGGTGTAGCGGTGAAATGCA

TAGATATCACGCAGAACCCCGATTGCGAAGGCAGCCTGCCAAGCCATTACTGACGC

TGATGCACGAAAGCGTGGGGATCAAACAGGATTAGATACCCTGGTAGTCCACGCAG

TAAACGATGATCACTAGCTGTTTGCGATACACTGTAAGCGGCACAGCGAAAGCGTT

AAGTGATCCACCTGGGGAGTACGCCGGCAACGGTGAAACTCAAAGGAATTGACGG

GGGCCCGCACAAGCGGAGGAACATGTGGTTTAATTCGATGATACGCGAGGAACCTT

ACCCGGGTTTGAACGCATTCGGACCGAGGTGGAAACACCTTTTCTAGCAATAGCCG

TTTGCGAGGTGCTGCATGGTTGTCGTCAGCTCGTGCCGTGAGGTGTCGGCTTAAGT

GCCATAACGAGCGCAACCCTTGCCACTAGTTACTAACAGGTAAAGCTGAGGACTCT

GGTGGGACTGCCAGCGTAAGCTGCGAGGAAGGCGGGGATGACGTCAAATCAGCAC

GGCCCTTACATCCGGGGCGACACACGTGTTACAATGGCGTGGACAAAGGGAAGCC

ACCTGGCGACAGGGAGCGAATCCCCAAACCACGTCTCAGTTCGGATCGGAGTCTG

CAACCCGACTCCGTGAAGCTGGATTCGCTAGTAATCGCGCATCAGCCATGGCGCGG

TGAATACGTTCCCGGGCCTTGTACACACCGCCCGTCAAGCCATGGGAGCCNGGGG

TACCTGAAGTCCGTAACCGCGA

SEQ ID NO: 12 strain 12 2B7_*Bacteroides cellulosilyticus*_NR_112933

GATGAACGCTAGCTACAGGCTTAACACATGCAAGTCGAGGGGCAGCATGACCTAGC

AATAGGTTGATGGCGACCGGCGCACGGGTGAGTAACACGTATCCAACCTACCGGTT

ATTCCGGGATAGCCTTTCGAAAGAAAGATTAATACCGGATAGTATAACGAGAAGGC

ATCTTTTTGTTATTAAAGAATTTCGATAACCGATGGGGATGCGTTCCATTAGTTTGT

TGGCGGGGTAACGGCCCACCAAGACATCGATGGATAGGGGTTCTGAGAGGAAGGT

CCCCCACATTGGAACTGAGACACGGTCCAAACTCCTACGGGAGGCAGCAGTGAGG

AATATTGGTCAATGGACGAGAGTCTGAACCAGCCAAGTAGCGTGAAGGATGACTGC

CCTATGGGTTGTAAACTTCTTTTATATGGGAATAAAGTGAGCCACGTGTGGCTTTTT

GTATGTACCATACGAATAAGGATCGGCTAACTCCGTGCCAGCAGCCGCGGTAATAC

GGAGGATCCGAGCGTTATCCGGATTTATTGGGTTTAAAGGGAGCGTAGGCGGACTA

TTAAGTCAGCTGTGAAAGTTTGCGGCTCAACCGTAAAATTGCAGTTGATACTGGTC

-continued

GTCTTGAGTGCAGTAGAGGTAGGCGGAATTCGTGGTGTAGCGGTGAAATGCTTAGA

TATCACGAAGAACTCCGATTGCGAAGGCAGCTTACTGGACTGTAACTGACGCTGAT

GCTCGAAAGTGTGGGTATCAAACAGGATTAGATACCCTGGTAGTCCACACAGTAAA

CGATGAATACTCGCTGTTTGCGATATACAGCAAGCGGCCAAGCGAAAGCATTAAGT

ATTCCACCTGGGGAGTACGCCGGCAACGGTGAAACTCAAAGGAATTGACGGGGGC

CCGCACAAGCGGAGGAACATGTGGTTTAATTCGATGATACGCGAGGAACCTTACCC

GGGCTTAAATTGCATCTGAATAATTTGGAAACAGATTAGCCGTAAGGCAGATGTGA

AGGTGCTGCATGGTTGTCGTCAGCTCGTGCCGTGAGGTGTCGGCTTAAGTGCCATA

ACGAGCGCAACCCTTATCTTTAGTTACTAACAGGTCATGCTGAGGACTCTAGAGAG

ACTGCCGTCGTAAGATGTGAGGAAGGTGGGGATGACGTCAAATCAGCACGGCCCT

TACGTCCGGGGCTACACACGTGTTACAATGGGGGGTACAGAAGGCAGCTACACAG

CGATGTGATGCTAATCCCAAAAGCCTCTCTCAGTTCGGATTGGAGTCTGCAACCCG

ACTCCATGAAGCTGGATTCGCTAGTAATCGCGCATCAGCCACGGCGCGGTGAATAC

GTTCCCGGGCCTTGTACACACCGCCCGTCAAGCCATGAAAGCCGGGGGTACCTGA

AGTCCGTAAC

SEQ ID NO: 13 strain 13 2C1_*Bacteroides clarus*_AB490801

GATGAACGCTAGCTACAGGCTTAACACATGCAAGTCGAGGGGCAGCGGGGTTGAA

GCTTGCTTCAACCGCCGGCGACCGGCGCACGGGTGAGTAACACGTATCCAACCTG

CCGATAACTCCGGGATAGCCTTTCGAAAGAAAGATTAATACCGGATGGCATAGTTTT

CCCGCATGGAATAACTATTAAAGAATTTCGGTTATCGATGGGGATGCGTTCCATTAG

GCAGTTGGCGGGGTAACGGCCCACCAAACCGACGATGGATAGGGGTTCTGAGAGG

AAGGTCCCCCACATTGGAACTGAGACACGGTCCAAACTCCTACGGGAGGCAGCAG

TGAGGAATATTGGTCAATGGACGAGAGTCTGAACCAGCCAAGTAGCGTGAAGGAT

GACTGCCCTATGGGTTGTAAACTTCTTTTATACGGGAATAAAGTTGGCCACGTGTG

GTTTTTTGCATGTACCGTATGAATAAGGATCGGCTAACTCCGTGCCAGCAGCCGCG

GTAATACGGAGGATCCGAGCGTTATCCGGATTTATTGGGTTTAAAGGGAGCGTAGG

CGGGGTATTAAGTCAGTTGTGAAAGTTTGCGGCTCAACCGTAAAATTGCAGTTGAT

ACTGGTATCCTTGAGTGCAGCAGAGGTGGGCGGAATTCGTGGTGTAGCGGTGAAA

TGCTTAGATATCACGAAGAACTCCGATTGCGAAGGCAGCTCACTGGAGTGTAACTG

ACGCTGATGCTCGAAAGTGTGGGTATCAAACAGGATTAGATACCCTGGTAGTCCAC

ACAGTAAACGATGAATACTCGCTGTTGGCGATACAATGTCAGCGGCCAAGCGAAAG

CATTAAGTATTCCACCTGGGGAGTACGCCGGCAACGGTGAAACTCAAAGGAATTGA

CGGGGGCCCGCACAAGCGGAGGAACATGTGGTTTAATTCGATGATACGCGAGGAA

CCTTACCCGGGCTTGAATTGCAACTGACTGAGCTGGAAACAGTTCTTTCTTCGGAC

AGTTGTGAAGGTGCTGCATGGTTGTCGTCAGCTCGTGCCGTGAGGTGTCGGCTTA

AGTGCCATAACGAGCGCAACCCTTATCTATAGTTACCATCAGGTCATGCTGGGGAC

TCTATGGAGACTGCCGTCGTAAGATGTGAGGAAGGTGGGGATGACGTCAAATCAG

CACGGCCCTTACGTCCGGGGCTACACACGTGTTACAATGGGGGGTACAGAAGGCA

GCTACACGGCGACGTGATGCTAATCCCAAAAACCTCTCTCAGTTCGGATTGGAGTC

TGCAACCCGACTCCATGAAGCTGGATTCGCTAGTAATCGCGCATCAGCCACGGCGC

-continued

GGTGAATACGTTCCCGGGCCTTGTACACACCGCCCGTCAAGCCATGAAAGCCGGG

GGTACCTGAAGTACGTAACCGCAA

SEQ ID NO: 14
strain 14 1B4_*Anaerostipes* sp. 3_2_56FAA_NZ-ACWB00000000
GATGAACGCTGGCGGCGTGCTTAACACATGCAAGTCGAACGAAGCATTTAGGATTG

AAGTTTTCGGATGGATTTCCTATATGACTGAGTGGCGGACGGGTGAGTAACGCGTG

GGGAACCTGCCCTATACAGGGGGATAACAGCTGGAAACGGCTGCTAATACCGCATA

AGCGCACAGAATCGCATGATTCAGTGTGAAAAGCCCTGGCAGTATAGGATGGTCCC

GCGTCTGATTAGCTGGTTGGTGAGGTAACGGCTCACCAAGGCGACGATCAGTAGC

CGGCTTGAGAGAGTGAACGGCCACATTGGGACTGAGACACGGCCCAAACTCCTAC

GGGAGGCAGCAGTGGGGAATATTGCACAATGGGGGAAACCCTGATGCAGCGACGC

CGCGTGAGTGAAGAAGTATTTCGGTATGTAAAGCTCTATCAGCAGGGAAGAAAACA

GACGGTACCTGACTAAGAAGCCCCGGCTAACTACGTGCCAGCAGCCGCGGTAATAC

GTAGGGGGCAAGCGTTATCCGGAATTACTGGGTGTAAAGGGTGCGTAGGTGGCAT

GGTAAGTCAGAAGTGAAAGCCCGGGGCTTAACCCCGGGACTGCTTTTGAAACTGT

CATGCTGGAGTGCAGGAGAGGTAAGCGGAATTCCTAGTGTAGCGGTGAAATGCGT

AGATATTAGGAGGAACACCAGTGGCGAAGGCGGCTTACTGGACTGTCACTGACACT

GATGCACGAAAGCGTGGGGAGCAAACAGGATTAGATACCCTGGTAGTCCACGCCG

TAAACGATGAATACTAGGTGTCGGGGCCGTAGAGGCTTCGGTGCCGCAGCAAACG

CAGTAAGTATTCCACCTGGGGAGTACGTTCGCAAGAATGAAACTCAAAGGANTTGA

CGGGGACCGCNNNAGCGGTGGAGCATGTGGTTAATTCGAAGCACGCGAAG

SEQ ID NO: 15
strain 15 2A3_*Bacteroides salyersiae*_AY608696
GATGAACGCTAGCTACAGGCTTAACACATGCAAGTCGAGGGGCATCAGGGTGTAGC

AATACACCGCTGGCGACCGGCGCACGGGTGAGTAACACGTATCCAACCTGCCCTTT

ACTCGGGGATAGCCTTTCGAAAGAAAGATTAATACCCGATGGTATAACATGACCTCC

TGGTTTTGTTATTAAAGAATTTCGGTAGAGGATGGGGATGCGTTCCATTAGGCAGTT

GGCGGGGTAACGGCCCACCAAACCTTCGATGGATAGGGGTTCTGAGAGGAAGGTC

CCCCACATTGGAACTGAGACACGGTCCAAACTCCTACGGGAGGCAGCAGTGAGGA

ATATTGGTCAATGGGCGAGAGCCTGAACCAGCCAAGTAGCGTGAAGGATGACCGC

CCTATGGGTTGTAAACTTCTTTTATATGGGAATAAAGTCTGCCACGTGTGGCATTTT

GTATGTACCATATGAATAAGGATCGGCTAACTCCGTGCCAGCAGCCGCGGTAATAC

GGAGGATCCGAGCGTTATCCGGATTTATTGGGTTTAAAGGGAGCGTAGGTGGACAT

GTAAGTCAGTTGTGAAAGTTTGCGGCTCAACCGTAAAATTGCAGTTGAAACTGCGT

GTCTTGAGTACAGTAGAGGTGGGCGGAATTCGTGGTGTAGCGGTGAAATGCTTAGA

TATCACGAAGAACTCCGATTGCGAAGGCAGCTCACTGGACTGCAACTGACACTGAT

GCTCGAAAGTGTGGGTATCAAACAGGATTAGATACCCTGGTAGTCCACACAGTAAA

CGATGAATACTCGCTGTTTGCGATATACAGTAAGCGGCCAAGCGAAAGCATTAAGT

ATTCCACCTGGGGAGTACGCCGGCAACGGTGAAACTCAAAGGAATTGACGGGGGC

CCGCACAAGCGGAGGAACATGTGGTTTAATTCGATGATACGCGAGGAACCTTACCC

GGGCTTAAATTGCAAATGAATATGCCGGAAACGGCATAGCCGCAAGGCATTTGTGA

AGGTGCTGCATGGTTGTCGTCAGCTCGTGCCGTGAGGTGTCGGCTTAAGTGCCATA

ACGAGCGCAACCCTTATCTTCAGTTACTAACAGGTCATGCTGAGGACTCTGGAGAG

-continued

ACTGCCGTCGTAAGATGTGAGGAAGGTGGGGATGACGTCAAATCAGCACGGCCCT

TACGTCCGGGGCTACACACGTGTTACAATGGGGGGTACAGAAGGCCGCTACACAG

CGATGTGATGCCAATCCCTAAAGCCCCTCTCAGTTCGGATCGAAGTCTGCAACCCG

ACTTCGTGAAGCTGGATTCGCTAGTAATCGCGCATCAGCCACGGCGCGGTGAATAC

GTTCCCGGGCCTTGTACACACCGCCCGTCAAGCCATGGGAGCCGGGGGTACCTGA

AGTACGTAAC

SEQ ID NO: 16 strain 16 2A12_*Bacteroides fragilis*_CR626927

GATGAACGCTAGCTACAGGCTTAACACATGCAAGTCGAGGGGCATCAGGAAGAAA

GCTTGCTTTCTTTGCTGGCGACCGGCGCACGGGTGAGTAACACGTATCCAACCTGC

CCTTTACTCGGGGATAGCCTTTCGAAAGAAAGATTAATACCCGATAGCATAATGATT

CCGCATGGTTTCATTATTAAAGGATTCCGGTAAAGGATGGGGATGCGTTCCATTAG

GTTGTTGGTGAGGTAACGGCTCACCAAGCCTTCGATGGATAGGGGTTCTGAGAGG

AAGGTCCCCCACATTGGAACTGAGACACGGTCCAAACTCCTACGGGAGGCAGCAG

TGAGGAATATTGGTCAATGGGCGCTAGCCTGAACCAGCCAAGTAGCGTGAAGGATG

AAGGCTCTATGGGTCGTAAACTTCTTTTATATAAGAATAAAGTGCAGTATGTATACT

GTTTTGTATGTATTATATGAATAAGGATCGGCTAACTCCGTGCCAGCAGCCGCGGTA

ATACGGAGGATCCGAGCGTTATCCGGATTTATTGGGTTTAAAGGGAGCGTAGGTGG

ACTGGTAAGTCAGTTGTGAAAGTTTGCGGCTCAACCGTAAAATTGCAGTTGATACT

GTCAGTCTTGAGTACAGTAGAGGTGGGCGGAATTCGTGGTGTAGCGGTGAAATGC

TTAGATATCACGAAGAACTCCGATTGCGAAGGCAGCTCACTGGACTGCAACTGACA

CTGATGCTCGAAAGTGTGGGTATCAAACAGGATTAGATACCCTGGTAGTCCACACA

GTAAACGATGAATACTCGCTGTTTGCGATATACAGTAAGCGGCCAAGCGAAAGCAT

TAAGTATTCCACCTGGGGAGTACGCCGGCAACGGTGAAACTCAAAGGAATTGACG

GGGGCCCGCACAAGCGGAGGAACATGTGGTTTAATTCGATGATACGCGAGGAACC

TTACCCGGGCTTAAATTGCAGTGGAATGATGTGGAAACATGTCAGTGAGCAATCAC

CGCTGTGAAGGTGCTGCATGGTTGTCGTCAGCTCGTGCCGTGAGGTGTCGGCTTA

AGTGCCATAACGAGCGCAACCCTTATCTTTAGTTACTAACAGGTTATGCTGAGGACT

CTAGAGAGACTGCCGTCGTAAGATGTGAGGAAGGTGGGGATGACGTCAAATCAGC

ACGGCCCTTACGTCCGGGGCTACACACGTGTTACAATGGGGGGTACAGAAGGCAG

CTAACGGGTGACCGTATGCTAATCCCAAAAGCCTCTCTCAGTTCGGATCGAAGTCT

GCAACCCGACTTCGTGAAGCTGGATTCGCTAGTAATCGCGCATCAGCCACGGCGCG

GTGAATACGTTCCCGGGCCTTGTACACACCGCCCGTCAAGCCATGGGAGCCGGGG

GTACCTGAAGTACGTAACCGCAA

SEQ ID NO: 17 strain 17 1A2_*Bacteroides uniformis*_AB247141

GATGAACGCTAGCTACAGGCTTAACACATGCAAGTCGAGGGGCATCAGGAAGAAA

GCTTGCTTTCTTTGCTGGCGACCGGCGCACGGGTGAGTAACACGTATCCAACCTGC

CGATGACTCGGGGATAGCCTTTCGAAAGAAAGATTAATACCCGATGGTATATCTGAA

AGGCATCTTTCAGCTATTAAAGAATTTCGGTCATTGATGGGGATGCGTTCCATTAGG

TTGTTGGCGGGGTAACGGCCCACCAAGCCATCGATGGATAGGGGTTCTGAGAGGA

AGGTCCCCCACATTGGAACTGAGACACGGTCCAAACTCCTACGGGAGGCAGCAGT

-continued

GAGGAATATTGGTCAATGGACGAGAGTCTGAACCAGCCAAGTAGCGTGAAGGATG

ACTGCCCTATGGGTTGTAAACTTCTTTTATACGGGAATAAAGTTAGGCACGTGTGCC

TTTTTGTATGTACCGTATGAATAAGGATCGGCTAACTCCGTGCCAGCAGCCGCGGT

AATACGGAGGATCCGAGCGTTATCCGGATTTATTGGGTTTAAAGGGAGCGTAGGCG

GATGCTTAAGTCAGTTGTGAAAGTTTGCGGCTCAACCGTAAAATTGCAGTTGATAC

TGGGTGTCTTGAGTACAGTAGAGGCAGGCGGAATTCGTGGTGTAGCGGTGAAATG

CTTAGATATCACGAAGAACTCCGATTGCGAAGGCAGCTTGCTGGACTGTAACTGAC

GCTGATGCTCGAAAGTGTGGGTATCAAACAGGATTAGATACCCTGGTAGTCCACAC

AGTAAACGATGAATACTCGCTGTTTGCGATATACAGTAAGCGGCCAAGCGAAAGCG

TTAAGTATTCCACCTGGGGAGTACGCCGGCAACGGTGAAACTCAAAGGAATTGACG

GGGGCCCGCACAAGCGGAGGAACATGTGGTTTAATTCGATGATACGCGAGGAACC

TTACCCGGGCTTAAATTGCAAATGAATGTTCTGGAAACAGATCAGCCGCAAGGCAT

TTGTGAAGGTGCTGCATGGTTGTCGTCAGCTCGTGCCGTGAGGTGTCGGCTTAAGT

GCCATAACGAGCGCAACCCTTATCGATAGTTACCATCAGGTTATGCTGGGGACTCT

GTCGAGACTGCCGTCGTAAGATGTGAGGAAGGTGGGGATGACGTCAAATCAGCAC

GGCCCTTACGTCCGGGGCTACACACGTGTTACAATGGGGGGTACAGAAGGCAGCT

ACACGGCGACGTGATGCTAATCCCTAAAACCTCTCTCAGTTCGGATTGGAGTCTGC

AACCCGACTCCATGAAGCTGGATTCGCTAGTAATCGCGCATCAGCCACGGCGCGGT

GAATACGTTCCCGGGCCTTGTACACACCGCCCGTCAAGCCATGAAAGCCGGGGGT

ACCTGAAGTGCGT

SEQ ID NO: 18 strain 18 2B11_*Bacteroides eggerthii*_NR_112935

GATGAACGCTAGCTACAGGCTTAACACATGCAAGTCGAGGGGCAGCATGATTGAAG

CTTGCTTCAATCGATGGCGACCGGCGCACGGGTGAGTAACACGTATCCAACCTGCC

GATAACTCGGGGATAGCCTTTCGAAAGAAAGATTAATACCCGATAGCATAGTATTTC

CGCATGGTTTCACTATTAAAGAATTTCGGTTATCGATGGGGATGCGTTCCNTTAGAT

AGTTGGCGGGGTAACGGCCCACCAAGTCAACGATGGATAGGGGTTCTGAGAGGAA

GGTCCCCCACATTGGAACTGAGACACGGTCCAAACTCCTACGGGAGGCAGCAGTG

AGGAATATTGGTCAATGGACGAGAGTCTGAACCAGCCAAGTAGCGTGAAGGATGA

CTGCCCTATGGGTTGTAAACTTCTTTTATACGGGAATAAAGTGGAGTATGCATACTC

CTTTGTATGTACCGTATGAATAAGGATCGGCTAACTCCGTGCCAGCAGCCGCGGTA

ATACGGAGGATCCGAGCGTTATCCGGATTTATTGGGTTTAAAGGGAGCGTAGGCGG

GTGCTTAAGTCAGTTGTGAAAGTTTGCGGCTCAACCGTAAAATTGCAGTTGATACT

GGGCGCCTTGAGTGCAGCATAGGTAGGCGGAATTCGTGGTGTAGCGGTGAAATGC

TTAGATATCACGAAGAACTCCGATTGCGAAGGCAGCTTACTGGACTGTAACTGACG

CTGATGCTCGAAAGTGTGGGTATCAAACAGGATTAGATACCCTGGTAGTCCACACA

GTAAACGATGAATACTCGCTGTTGGCGATACACAGTCAGCGGCCAAGCGAAAGCAT

TAAGTATTCCACCTGGGGAGTACGCCGGCAACGGTGAAACTCAAAGGAATTGACG

GGGGCCCGCACAAGCGGAGGAACATGTGGTTTAATTCGATGATACGCGAGGAACC

TTACCCGGGCTTAAATTGCAGCGGAATGTAGTGGAAACATTACAGCCTTCGGGCCG

CTGTGAAGGTGCTGCATGGTTGTCGTCAGCTCGTGCCGTGAGGTGTCGGCTTAAG

TGCCATAACGAGCGCAACCCTTATCTATAGTTACTATCAGGTCATGCTGAGGACTCT

-continued

ATGGAGACTGCCGTCGTAAGATGTGAGGAAGGTGGGGATGACGTCAAATCAGCAC

GGCCCTTACGTCCGGGGCTACACACGTGTTACAATGGGGGGTACAGAAGGCAGCT

ACCTGGCGACAGGATGCTAATCCCTAAAACCTCTCTCAGTTCGGATTGGAGTCTGC

AACCCGACTCCATGAAGCTGGATTCGCTAGTAATCGCGCATCAGCCACGGCGCGGT

GAATACGTTCCCGGGCCTTGTACACACCGCCCGTCAAGCCATGAAAGCCGGGGGT

ACCTGAAGTACGTAACCGCAAGGAGC

SEQ ID NO: 19 strain 19 2D2_*Clostridium* sp. TM-40_AB249652
GATGAACGCTGGCGGCGTGCCTAATACATGCAAGTCGGACGCAATGCTTCGGCATT

GAGTGGCGAACGGGTGAGTAATACATAAGCAACCTGCCCCTGTGAGGGGGATAAC

TGCTGGAAACGGCAGCTAAGACCGCATATGCATACATGACGCATGTCGAGTATGTT

AAATATCCCACGGGATAGCACAGGGATGGGCTTATGACGCATTAGCTAGCTGGTGA

GGTAGAGGCTCACCAGGGCGACGATGCGTAGCCGGCCTGAGAGGGTGGACGGCC

ACACTGGGACTGAGACACGGCCCAGACTCCTACGGGAGGCAGCAGTAGGGAATTT

TCGGCAATGGGCGAAAGCCTGACCGAGCAACGCCGCGTGAAGGAAGAAGTCATTC

GTGATGTAAACTTCTGTTATAAAGGAAGAACGGCGCCTGTAGGGAATGACAGGCGA

GTGACGGTACTTTATGAGGAAGCCACGGCTAACTACGTGCCAGCAGCCGCGGTAAT

ACGTAGGTGGCGAGCGTTATCCGGAATCATTGGGCGTAAAGAGGGAGCAGGCGGC

AGTGCAGGTCTGCGGTGAAAGCCCGAAGCTAAACTTCGGTAAGCCGTGGAAACCG

CACAGCTAGAGAGCATCAGAGGATCGCGGAATTCCATGTGTAGCGGTGAAATGCGT

AGATATATGGAGGAACACCAGTGGCGAAGGCGGCGGTCTGGGGTGCAGCTGACGC

TCAGTCCCGAAAGCGTGGGGAGCAAATAGGATTAGATACCCTAGTAGTCCACGCCG

TAAACGATGAGTGCTAAGTGTTGGGGGTCAGACCTCAGTGCTGCAGTTAACGCAAT

AAGCACTCCGCCTGAGTAGTACGTTCGCAAGAATGAAACTCAAAGGAATTGACGGG

GGCCCGCACAAGCGGTGGAGCATGTGGTTTAATTCGAAGCAACGCGAAGAACCTT

ACCAGGTCTTGACATGGAGATAAAGGCTCTGGAGACAGAGAGATAGGTATATCTCA

CACAGGTGGTGCATGGTTGTCGTCAGCTCGTGTCGTGAGATGTTGGGTTAAGTCCC

GCAACGAGCGCAACCCCTGTTGCCAGTTGCCAGCATTAGGTTGGGGACTCTGGCG

AGACTGCCTCTGCAAGGAGGAGGAAGGCGGGGATGACGTCAAATCATCATGCCCC

TTATGACCTGGGCTACACACGTGCTACAATGGACGGATCAGAGGGAGGCGAAGCC

GCGAGGTGGAGCGAAACCCAGAAACCCGTTCACAGTTCGGACTGCAGTCTGCAAC

TCGACTGCACGAAGCTGGAATCGCTAGTAATCGCGAATCAGCATGTCGCGGTGAAT

ACGTTCTCGGGCCTTGTACACACCGCCCGTCACACCATGAGAGTTGGTAACACCCG

AAGCCGGTGGCCCAACCGCAA

SEQ ID NO: 20 strain 20 2E8_*Parabacteroides goldsteinii*_NR_113076
GATGAACGCTAGCGACAGGCTTAACACATGCAAGTCGAGGGGCAGCACGATGTAG

CAATACATTGGTGGCGACCGGCGCACGGGTGAGTAACGCGTATGCAACCTACCTAT

CAGAGGGGAATAACCCGGCGAAAGTCGGACTAATACCGCATAAAACAGGGGTTCC

ACATGGAAATATTTGTTAAAGAATTATCGCTGATAGATGGGCATGCGTTCCATTAGA

TAGTTGGTGAGGTAACGGCTCACCAAGTCCACGATGGATAGGGGTTCTGAGAGGA

AGGTCCCCCACACTGGTACTGAGACACGGACCAGACTCCTACGGGAGGCAGCAGT

-continued

GAGGAATATTGGTCAATGGGCGAGAGCCTGAACCAGCCAAGTCGCGTGAAGGATG

AAGGATCTATGGTTTGTAAACTTCTTTTATATGGGAATAAAGTGAGGAACGTGTTCC

TTTTTGTATGTACCATATGAATAAGCATCGGCTAACTCCGTGCCAGCAGCCGCGGTA

ATACGGAGGATGCGAGCGTTATCCGGATTTATTGGGTTTAAAGGGTGCGTAGGTGG

TTAATTAAGTCAGCGGTGAAAGTTTGTGGCTCAACCATAAAATTGCCGTTGAAACT

GGTTGACTTGAGTATATTTGAGGTAGGCGGAATGCGTGGTGTAGCGGTGAAATGCA

TAGATATCACGCAGAACTCCGATTGCGAAGGCAGCTTACTAAACTATAACTGACACT

GAAGCACGAAAGCGTGGGGATCAAACAGGATTAGATACCCTGGTAGTCCACGCAGT

AAACGATGATTACTAGCTGTTTGCGATACACAGTAAGCGGCACAGCGAAAGCGTTA

AGTAATCCACCTGGGGAGTACGCCGGCAACGGTGAAACTCAAAGGAATTGACGGG

GGCCCGCACAAGCGGAGGAACATGTGGTTTAATTCGATGATACGCGAGGAACCTTA

CCCGGGTTTGAACGCATATTGACAGCTCTGGAAACAGAGTCTCTAGTAATAGCAAT

TTGCGAGGTGCTGCATGGTTGTCGTCAGCTCGTGCCGTGAGGTGTCGGCTTAAGT

GCCATAACGAGCGCAACCCTTATCACTAGTTACTAACAGGTCATGCTGAGGACTCT

AGTGAGACTGCCAGCGTAAGCTGTGAGGAAGGTGGGGATGACGTCAAATCAGCAC

GGCCCTTACATCCGGGGCGACACACGTGTTACAATGGTGGGGACAAAGGGCAGCT

ACCGTGTGAGCGGATGCAAATCTCCAAACCCCATCTCAGTTCGGATCGAAGTCTGC

AACCCGACTTCGTGAAGCTGGATTCGCTAGTAATCGCGCATCAGCCATGGCGCGGT

GAATACGTTCCCGGGCCTTGTACACACCGCCCGTCAAGCCATGGGAGTTGGGGGT

ACCTAAAGTCCGTAACCGC

SEQ ID NO: 21 strain 21 1H8_*Bacteroides* sp. AR29_AF139525

GATGAACGCTAGCTACAGGCTTAACACATGCAAGTCGAGGGGCAGCATTTCAGTTT

GCTTGCAAACTGGAGATGGCGACCGGCGCACGGGTGAGTAACACGTATCCAACCT

GCCGATAACTCGGGGATAGCCTTTCGAAAGAAAGATTAATACCCGATGGTATAATN

AGACCGCATGGTCTTGTTATTAAAGAATTTCGGTTATCGATGGGGATGCGTTCCATT

AGGCAGTTGGTGAGGTAACGGCTCACCAAACCTTCGATGGATAGGGGTTCTGAGA

GGAAGGTCCCCCACATTGGAACTGAGACACGGTCCAAACTCCTACGGGAGGCAGC

AGTGAGGAATATTGGTCAATGGGCGCAGGCCTGAACCAGCCAAGTAGCGTGAAGG

ATGACTGCCCTATGGGTTGTAAACTTCTTTTATATGGGAATAAAGTTTTCCACGTGT

GGAATTTTGTATGTACCATATGAATAAGGATCGGCTAACTCCGTGCCAGCAGCCGC

GGTAATACGGAGGATCCGAGCGTTATCCGGATTTATTGGGTTTAAAGGGAGCGTAG

GTGGACAGTTAAGTCAGTTGTGAAAGTTTGCGGCTCAACCGTAAAATTGCAGTTGA

TACTGGCTGTCTTGAGTACAGTAGAGGTGGGCGGAATTCGTGGTGTAGCGGTGAAA

TGCTTAGATATCACGAAGAACTCCGATTGCGAAGGCAGCTCACTGGACTGCAACTG

ACACTGATGCTCGAAAGTGTGGGTATCAAACAGGATTAGATACCCTGGTAGTCCAC

ACAGTAAACGATGAATACTCGCTGTTTGCGATATACAGTAAGCGGCCAAGCGAAAG

CATTAAGTATTCCACCTGGGGAGTACGCCGGCAACGGTGAAACTCAAAGGAATTGA

CGGGGGCCCGCACAAGCGGAGGAACATGTGGTTTAATTCGATGATACGCGAGGAA

CCTTACCCGGGCTTAAATTGCATTTGAATATATTGGAAACAGTATAGCCGTAAGGCA

AATGTGAAGGTGCTGCATGGTTGTCGTCAGCTCGTGCCGTGAGGTGTCGGCTTAA

-continued

GTGCCATAACGAGCGCAACCCTTATCTTTAGTTACTAACAGGTCATGCTGAGGACT

CTAGAGAGACTGCCGTCGTAAGATGTGA

SEQ ID NO: 22 strain 22 > 3F2-PREMIX.fasta
NNNNNNNNNTGCAGTCGAACGAAGCGATTTGAATGAAGTTTTCGGATGGATTTCA

ANTTGACTGAGTGGCGGACGGGTGAGTAACGCGTGGGTAACCTGCCCCATACAGG

GGGATAACAGTTAGAAATGACTGCTAATACCGCATAAGACCACAGNNCCGCATGGT

GCAGGGGTAAAAACTCCGGTGGTATGGGATGGACCCGCGTCTGATTAGCTTGTTGG

CGGGGTAACGGCCCACCAAGGCGACGATCAGTAGCCGACCTGAGAGGGTGACCGG

CCACATTGGGACTGAGACACGGCCCAAACTCCTACGGGAGGCAGCAGTGGGGAAT

ATTGCACAATGGGGGAAACCCTGATGCAGCGACGCCGCGTGAGTGATGAAGTATTT

CGGTATGTAAAGCTCTATCAGCAGGGAAGAAAATGACGGTACCTGACTAAGAAGCC

CCGGCTAACTACGTGCCAGCAGCCGCGGTAATACGTAGGGGGCAAGCGTTATCCG

GATTTACTGGGTGTAAAGGGAGCGTAGACGGCTGTGCAAGTCTGGAGTGAAAGCC

CGGGGCTCAACCCCGGGACTGCTTTGGAAACTGTACGGCTGGAGTGCTGGAGAGG

CAAGCGGAATTCCTAGTGTAGCGGTGAAATGCGTAGATATTAGGAGGAACACCAGT

GGCGAAGGCGGCTTGCTGGACAGTAACTGACGTTGAGGCTCGAAAGCGTGGGGAG

CAAACAGGATTAGATACCCTGGTAGTCCACGCCGTAAACGATGAATGCTAGGTGTC

GGGGAGCAAAGCTCTTCGGTGCCGCCGCAAACGCAATAAGCATTCCACCTGGGGA

GTACGTTCGCAAGAATGAAACTCAAAGGANTTGACGGGGACCGCACANNGGTGGA

GCATGTGGTTATTCGAGCACGCGAAANCTTACCAGTCTTGNNNCCCCTGANGNNN

NGTATGTCGCTNCTNNGNNNNGGN

SEQ ID NO: 23 strain 23 > 1G1_3-PREMIX.fasta
AGTTTGATTATGGCTCAGGATGAACGCTGGCGGCGTGCTTAACACATGCAAGTCGA

GCGAAGCGGTTTCAATGAAGTTTTCGGATGGATTTGAAATTGACTTAGCGGCGGAC

GGGTGAGTAACGCGTGGGTAACCTGCCTTACACTGGGGGATAACAGTTAGAAATGA

CTGCTAATACCGCATAAGCGCACAGGGCCGCATGGTCCGGTGTGAAAAACTCCGGT

GGTGTAAGATGGACCCGCGTCTGATTAGGTAGTTGGCGGGGTAACGGCCCACCAA

GCCGACGATCAGTAGCCGACCTGAGAGGGTGACCGGCCACATTGGGACTGAGACA

CGGCCCAAACTCCTACGGGAGGCAGCAGTGGGGAATATTGGACAATGGGCGAAAG

CCTGATCCAGCGACGCCGCGTGAGTGAAGAAGTATTTCGGTATGTAAAGCTCTATC

AGCAGGGAAGAAAATGACGGTACCTGACTAAGAAGCCCCGGCTAACTACGTGCCA

GCAGCCGCGGTAATACGTAGGGGGCAAGCGTTATCCGGATTTACTGGGTGTAAAGG

GAGCGTAGACGGTTTAGCAAGTCTGAAGTGAAAGCCCGGGGCTCAACCCCGGTAC

TGCTTTGGAAACTGTTAGACTTGAGTGCAGGAGAGGTAAGTGGAATTCCTAGTGTA

GCGGTGAAATGCGTAGATATTAGGAGGAACACCAGTGGCGAAGGCGGCTTACTGG

ACTGTAACTGACGTTGAGGCTCGAAAGCGTGGGGAGCAAACAGGATTAGATACCCT

GGTAGTCCACGCCGTAAACGATGAATACTAGGTGTCGGGGGGCAAAGCCCTTCGG

TGCCGCCGCAAACGCAATAAGTATTCCACCTGGGGAGTACGTTCGCAAGAATGAAA

CTCAAAGGAATTGACGGGGACCCGCACAAGCGGTGGAGCATGTGGTTTAATTCGA

AGCAACGCGAAGAACCTTACCAAGTCTTGACATCCCACTGAAAACACTTTAACCGG

-continued

TGTCCCTCTTCGGAGCAGTGGAGACAGGTGGTGCATGGTTGTCGTCAGCTCGTGT

CGTGAGATGTTGGGTTAAGTCCCGCAACGAGCGCAACCCTTATCCTTAGTAGCCAG

CGAGTAGAGTCGGGCACTCTGGGGAGACTGCCAGGGATAACCTGGAGGAAGGTGG

GGATGACGTCAAATCATCATGCCCCTTATGATTTGGGCTACACACGTGCTACAATGG

CGTAAACAAAGGGAGGCAAAGGAGCGATCTGGAGCAAACCCCAAAAATAACGTCT

CAGTTCGGATTGCAGGCTGCAACTCGCCTGCATGAAGCTGGAATCGCTAGTAATCG

CGAATCAGAATGTCGCGGTGAATACGTTCCCGGGTCTTGTACACACCGCCCGTCAC

ACCATGGGAGTTGGTAACGCCCGAAGTCAGTGACCCAACCGCAAGGAGGNAGCTG

CCGAANNNNNNN

SEQ ID NO: 24 strain 24 > 1E6_27Fmod-PREMIX_Length_957

AGTTTGNNNNNGCTCAGGATGAACGCTGGCGGCGTGCCTAACACATGCAAGTCGA

ACGAAGCATTTCAGATGAAGTTTTCGGATGGATTCTGAGATGACTGAGTGGCGGAC

GGGTGAGTAACACGTGGATAACCTGCCTCACACTGGGGGACAACAGTTAGAAATG

ACTGCTAATACCGCATAAGCGCACAGTACCGCATGGTACAGTGTGAAAAACTCCGG

TGGTGTGAGATGGATCCGCGTCTGATTAGCCAGTTGGCGGGGTAACGGCCCACCA

AAGCGACGATCAGTAGCCGACCTGAGAGGGTGACCGGCCACATTGGGACTGAGAC

ACGGCCCAAACTCCTACGGGAGGCAGCAGTGGGGAATATTGCACAATGGGCGAAA

GCCTGATGCAGCGACGCCGCGTGAGTGAAGAAGTATTTCGGTATGTAAAGCTCTAT

CAGCAGGGAAGATAATGACGGTACCTGACTAAGAAGCCCCGGCTAACTACGTGCCA

GCAGCCGCGGTAATACGTAGGGGGCAAGCGTTATCCGGATTTACTGGGTGTAAAGG

GAGCGTAGACGGCATGGCAAGTCTGAAGTGAAAACCCAGGGCTCAACCCTGGGAC

TGCTTTGGAAACTGTCAAGCTAGAGTGCAGGAGAGGTAAGTGGAATTCCTAGTGTA

GCGGTGAAATGCGTAGATATTAGGAGGAACACCAGTGGCGAAGGCGGCTTACTGG

ACTGTAACTGACGTTGAGGCTCGAAAGCGTGGGGAGCAAACAGGATTAGATACCCT

GGTAGTCCACGCCGTAAACGATGAGTGCTAGGTGTTGGGGGGCAAAGCCCTTCGG

TGCCGTCGCAAACGCAATAAGCACTCCACCTGGGGAGTACGTTCGCAAGAATGAAA

CTCAAAGGAATTGACGGGGACCCGCACAAGCGGTGGAGCATGTGGTTTAATTCGA

AGCAACGCGAAGAACCTTACCAAGTCTTGACATCCTCTTGACCGGCGTGTAACGGC

GCCTTTCCTTCGGGACAAGAGAGACAGGTGGTGCATGGTTGTCGTCAGCTCGTGT

CGTGAGATGTTGGGTTAAGTCCCGCAACGAGCGCAACCCTTATCCTTAGTAGCCAG

CATTAAGATGGGCACTCTAGGGAGACTGCCAGGGACAACCTGGAGGAAGGTGGGG

ATGACGTCAAATCATCATGCCCCTTATGATTTGGGCTACACACGTGCTACAATGGCG

TAAACAAAGGGAAGCGACCCTGCGAAGGTGAGCAAATCTCAAAAATAACGTCCCA

GTTCGGACTGTAGTCTGCAACCCGACTACACGAAGCNNGAATCGCTAGTAATCGCG

AATCAGAATGTCGCGGTGAATACGNTCCCGGGTCTTGTACACACCGCCCGTCACAC

CATGGGAGTCAGCAACGNCCGAAGTCAGTGACCCAACCGAAAGGAGGGAGNTGC

NGAAGNNGNNNNN

SEQ ID NO: 25 strain 25 > 1F3_27Fmod-PREMIX.fasta

AGTTTGANNTTGGCTCAGGATGAACGCTGGCGGCGTGCCTAACACATGCAAGTCG

AGCGAAGCGCTGTTTTCAGAATCTTCGGAGGAAGAGGACAGTGACTGAGCGGCGG

ACGGGTGAGTAACGCGTGGGCAACCTGCCTCATACAGGGGGATAACAGTTAGAAAT

-continued

GACTGCTAATACCGCATAAGCGCACAGGACCGCATGGTGTAGTGTGAAAAACTCCG
GTGGTATGAGATGGACCCGCGTCTGATTAGGTAGTTGGTGGGGTAAAGGCCTACCA
AGCCGACGATCAGTAGCCGACCTGAGAGGGTGACCGGCCACATTGGGACTGAGAC
ACGGCCCAAACTCCTACGGGAGGCAGCAGTGGGGAATATTGCACAATGGGGGAAA
CCCTGATGCAGCGACGCCGCGTGAAGGAAGAAGTATTTCGGTATGTAAACTTCTAT
CAGCAGGGAAGAAGATGACGGTACCTGAGTAAGAAGCACCGGCTAAATACGTGCC
AGCAGCCGCGGTAATACGTATGGTGCAAGCGTTATCCGGATTTACTGGGTGTAAAG
GGAGCGTAGACGGATAGGCAAGTCTGGAGTGAAAACCCAGGGCTCAACTCTGGGA
CTGCTTTGGAAACTGCAGATCTGGAGTGCCGGAGAGGTAAGCGGAATTCCTAGTGT
AGCGGTGAAATGCGTAGATATTAGGAGGAACACCAGTGGCGAAGGCGGCTTACTG
GACGGTGACTGACGTTGAGGCTCGAAAGCGTGGGGAGCAAACAGGATTAGATACC
CTGGTAGTCCACGCCGTAAACGATGACTACTAGGTGTCGGTGTGCAAAGCACATCG
GTGCCGCAGCAAACGCAATAAGTAGTCCACCTGGGGAGTACGTTCGCAAGAATGA
AACTCAAAGGAATTGACGGGGACCCGCACAAGCGGTGGAGCATGTGGTTTAATTC
GAAGCAACGCGAAGAACCTTACCTGGTCTTGACATCCGGATGACGGGCGAGTAAT
GTCGCCGTCCCTTCGGGGCATCCGAGACAGGTGGTGCATGGTTGTCGTCAGCTCG
TGTCGTGAGATGTTGGGTTAAGTCCCGCAACGAGCGCAACCCTTATCTTCAGTAGC
CAGCATATAAGGTGGGCACTCTGGAGAGACTGCCAGGGAGAACCTGGAGGAAGGT
GGGGATGACGTCAAATCATCATGCCCCTTATGGCCAGGGCTACACACGTGCTACAA
TGGCGTAAACAAAGGGAAGCGAGAGGGTGACCTGAAGCGAATCCCAAAAATAACG
TCTCAGTTCGGATTGTAGTCTGCAACTCGACTACATGAAGCTGGAATCGCTAGTAAT
CGCGGATCAGCATGCCGCGGTGAATACGTTCCCGGGTCTTGTACACACCGCCCGTC
ACACCATGGGAGTCAGTAACGCCCGAAGCCANTGACCCAACCTTAGAGGAGGGAG
NNNNNNNNNNNNN

SEQ ID NO: 26 strain 26 1A1_27Fmod-PREMIX_Length_998
AGTTTGATTATGGCTCAGGATGAACGCTGGCGGCATGCCTAATACATGCAAGTCGA
ACGAAGTTTCGAGGAAGCTTGCTTCCAAAGAGACTTAGTGGCGAACGGGTGAGTA
ACACGTAGGTAACCTGCCCATGTGTCCGGGATAACTGCTGGAAACGGTAGCTAAAA
CCGGATAGGTATACAGAGCGCATGCTCAGTATATTAAAGCGCCCATCAAGGCGTGA
ACATGGATGGACCTGCGGCGCATTAGCTAGTTGGTGAGGTAACGGCCCACCAAGG
CGATGATGCGTAGCCGGCCTGAGAGGGTAAACGGCCACATTGGGACTGAGACACG
GCCCAAACTCCTACGGGAGGCAGCAGTAGGGAATTTTCGTCAATGGGGGAAACCC
TGAACGAGCAATGCCGCGTGAGTGAAGAAGGTCTTCGGATCGTAAAGCTCTGTTGT
AAGTGAAGAACGGCTCATAGAGGAAATGCTATGGGAGTGACGGTAGCTTACCAGAA
AGCCACGGCTAACTACGTGCCAGCAGCCGCGGTAATACGTAGGTGGCAAGCGTTAT
CCGGAATCATTGGGCGTAAAGGGTGCGTAGGTGGCGTACTAAGTCTGTAGTAAAAG
GCAATGGCTCAACCATTGTAAGCTATGGAAACTGGTATGCTGGAGTGCAGAAGAGG
GCGATGGAATTCCATGTGTAGCGGTAAAATGCGTAGATATATGGAGGAACACCAGT
GGCGAAGGCGGTCGCCTGGTCTGTAACTGACACTGAGGCACGAAAGCGTGGGGAG
CAAATAGGATTAGATACCCTAGTAGTCCACGCCGTAAACGATGAGAACTAAGTGTT -continued

GGAGGAATTCAGTGCTGCAGTTAACGCAATAAGTTCTCCGCCTGGGGAGTATGCAC

GCAAGTGTGAAACTCAAAGGAATTGACGGGGGCCCGCACAAGCGGTGGAGTATGT

GGTTTAATTCGAAGCAACGCGAAGAACCTTACCAGGCCTTGACATGGAAACAAATA

CCCTAGAGATAGGGGGATAATTATGGATCACACAGGTGGTGCATGGTTGTCGTCAG

CTCGTGTCGTGAGATGTTGGGTTAAGTCCCGCAACGAGCGCAACCCTTGTCGCATG

TTACCAGCATCAAGTTGGGGACTCATGCGAGACTGCCGGTGACAAACCGGAGGAA

GGTGGGGATGACGTCAAATCATCATGCCCCTTATGGCCTGGGCTACACACGTACTA

CAATGGCGACCACAAAGAGCAGCGACACAGTGATGTGAAGCGAATCTCATAAAGG

TCGTCTCAGTTCGGATTGAAGTCTGCAACTCGACTTCATGAAGTCGGAATCGCTAG

TAATCGCAGATCAGCATGCTGCGGTGAATACGTTCTCGGGCCTTGTACACACCGCC

CGTCAAACCATGGGAGTCAGTAATACCCGAAGCCGGTGGCATAACCNTAAGGNNN

NNCCNNNNNNA

SEQ ID NO: 27
16S RNA sequence corresponding to LN998073

SEQ ID NO: 28
16S RNA sequence corresponding to KR822463

SEQ ID NO: 29
16S RNA sequence corresponding to CP011531

SEQ ID NO: 30
16S RNA sequence corresponding to NR112945

SEQ ID NO: 31
16S RNA sequence corresponding to KM098109

SEQ ID NO: 32
16S RNA sequence corresponding to NR113078

SEQ ID NO: 33
16S RNA sequence corresponding to NR041464

SEQ ID NO: 34
16S RNA sequence corresponding to LT223566

SEQ ID NO: 35
16S RNA sequence corresponding to NR112835

SEQ ID NO: 36
16S RNA sequence corresponding to NR113248

SEQ ID NO: 37
16S RNA sequence corresponding to NR041342

SEQ ID NO: 38
16S RNA sequence corresponding to NR112933

SEQ ID NO: 39
16S RNA sequence corresponding to NR112893

SEQ ID NO: 40
16S RNA sequence corresponding to HE974918

SEQ ID NO: 41
16S RNA sequence corresponding to NR043016

SEQ ID NO: 42
16S RNA sequence corresponding to AB618791

SEQ ID NO: 43
16S RNA sequence corresponding to AB215083

SEQ ID NO: 44
16S RNA sequence corresponding to NR112935

SEQ ID NO: 45
16S RNA sequence corresponding to AB249652

-continued

SEQ ID NO: 46
16S RNA sequence corresponding to NR113076

SEQ ID NO: 47
16S RNA sequence corresponding to NR112944

SEQ ID NO: 48
16S RNA sequence corresponding to JX519760

SEQ ID NO: 49
16S RNA sequence corresponding to AJ311620

SEQ ID NO: 50
16S RNA sequence corresponding to EF564278

SEQ ID NO: 51
16S RNA sequence corresponding to KT156811

SEQ ID NO: 52
16S RNA sequence corresponding to HM008265

Additional sequences of interest are provided below:

SEQ ID NO: 54
H81A6_16S_ribosomal_RNA
CGAAGAGTTTGATCCTGGCTCAGGATGAACGCTGACAGAATGCTTAACACATGCAA

GTCTACTTGATCCTTCGGGTGAAGGTGGCGGACGGGTGAGTAACGCGTAAAGAAC

TTGCCTTACAGACTGGGACAACATTTGGAAACGAATGCTAATACCGGATATTATGAT

TGGGTCGCATGATCTGATTATGAAAGCTATATGCGCTGTGAGAGAGCTTTGCGTCC

CATTAGTTAGTTGGTGAGGTAACGGCTCACCAAGACGATGATGGGTAGCCGGCCTG

AGAGGGTGAACGGCCACAAGGGGACTGAGACACGGCCCTTACTCCTACGGGAGGC

AGCAGTGGGGAATATTGGACAATGGACCAAAAGTCTGATCCAGCAATTCTGTGTGC

ACGAAGAAGTTTTTCGGAATGTAAAGTGCTTTCAGTTGGGAAGAAGTCAGTGACGG

TACCAACAGAAGAAGCGACGGCTAAATACGTGCCAGCAGCCGCGGTAATACGTATG

TCGCAAGCGTTATCCGGATTTATTGGGCGTAAAGCGCGTCTAGGCGGCTTAGTAAG

TCTGATGTGAAAATGCGGGGCTCAACCCCGTATTGCGTTGGAAACTGCTAAACTAG

AGTACTGGAGAGGTAGGCGGAACTACAAGTGTAGAGGTGAAATTCGTAGATATTTG

TAGGAATGCCGATGGGGAAGCCAGCCTACTGGACAGATACTGACGCTAAAGCGCG

AAAGCGTGGGTAGCAAACAGGATTAGATACCCTGGTAGTCCACGCCGTAAACGATG

ATTACTAGGTGTTGGGGGTCGAACCTCAGCGCCCAAGCTAACGCGATAAGTAATCC

GCCTGGGGAGTACGTACGCAAGTATGAAACTCAAAGGAATTGACGGGGACCCGCA

CAAGCGGTGGAGCATGTGGTTTAATTCGACGCAACGCGAGGAACCTTACCAGCGTT

TGACATCCCAAGAAGTTAACAGAGATGTTTTCGTGCCTCTTCGGAGGAACTTGGTG

ACAGGTGGTGCATGGCTGTCGTCAGCTCGTGTCGTGAGATGTTGGGTTAAGTCCC

GCAACGAGCGCAACCCCTTTCGTATGTTACCATCATTAAGTTGGGGACTCATGCGA

GACTGCCTGCGATGAGCAGGAGGAAGGTGGGGATGACGTCAAGTCATCATGCCCC

TTATACGCTGGGCTACACACGTGCTACAATGGGTAGTACAGAGAGCTGCAAACCTG

CGAGGGTAAGCTAATCTCATAAAACTATTCTTAGTTCGGATTGTACTCTGCAACTCG

AGTACATGAAGTTGGAATCGCTAGTAATCGCAAATCAGCTATGTTGCGGTGAATAC

GTTCTCGGGTCTTGTACACACCGCCCGTCACACCACGAGAGTTGGTTGCACCTGAA

GTAACAGGCCTAACCGTAAGGAGGGATGTTCCGAGGGTGTGATTAGCGATTGGGG

TGAAGTCGTAACAAGGTATCCGTACGGGAACGTGCGGATGGATCACCTCCTT

-continued

SEQ ID NO: 55
H82F11_16S_ribosomal_RNA
CGAAGAGTTTGATCCTGGCTCAGGATGAACGCTAGCGACAGGCTTAACACATGCAA

GTCGAGGGGCATCATGGTAAGTAGCAATACTTATTGATGGCGACCGGCGCACGGGT

GAGTAACGCGTATGCAACTTACCTATCAGAGGGGGATAGCCCGGCGAAAGTCGGAT

TAATACTCCATAAAACAGGGGTTCCGCATGGGACTATTTGTTAAAGATTCATCGCTG

ATAGATAGGCATGCGTTCCATTAGGCAGTTGGCGGGGTAACGGCCCACCAAACCGA

CGATGGATAGGGGTTCTGAGAGGAAGGTCCCCCACATTGGTACTGAGACACGGAC

CAAACTCCTACGGGAGGCAGCAGTGAGGAATATTGGTCAATGGCCGAGAGGCTGA

ACCAGCCAAGTCGCGTGAAGGATGAAGGATCTATGGTTTGTAAACTTCTTTTATAG

GGGAATAAAGTGTGGGACGTGTTCCATTTTGTATGTACCCTATGAATAAGCATCGGC

TAACTCCGTGCCAGCAGCCGCGGTAATACGGAGGATGCGAGCGTTATCCGGATTTA

TTGGGTTTAAAGGGTGCGTAGGTGGTAATTTAAGTCAGCGGTGAAAGTTTGTGGCT

CAACCATAAAATTGCCGTTGAAACTGGGTTACTTGAGTGTGTTTGAGGTAGGCGGA

ATGCGTGGTGTAGCGGTGAAATGCATAGATATCACGCAGAACTCCAATTGCGAAGG

CAGCTTACTAAACCATAACTGACACTGAAGCACGAAAGCGTGGGTATCAAACAGGA

TTAGATACCCTGGTAGTCCACGCAGTAAACGATGATTACTAGGAGTTTGCGATACAC

AGTAAGCTCTACAGCGAAAGCGTTAAGTAATCCACCTGGGGAGTACGCCGGCAACG

GTGAAACTCAAAGGAATTGACGGGGGCCCGCACAAGCGGAGGAACATGTGGTTTA

ATTCGATGATACGCGAGGAACCTTACCCGGGTTTGAACGTAGTCAGACCGACCTTG

AAAGAGGTTTTCTAGCAATAGCTGATTACGAGGTGCTGCATGGTTGTCGTCAGCTC

GTGCCGTGAGGTGTCGGCTTAAGTGCCATAACGAGCGCAACCCTTATCACTAGTTA

CTAACAGGTTAAGCTGAGGACTCTGGTGAGACTGCCAGCGTAAGCTGTGAGGAAG

GTGGGGATGACGTCAAATCAGCACGGCCCTTACATCCGGGGCGACACACGTGTTA

CAATGGCATGGACAAAGGGCAGCTACCTGGCGACAGGATGCTAATCTCTAAACCAT

GTCTCAGTTCGGATCGGAGTCTGCAACTCGACTCCGTGAAGCTGGATTCGCTAGTA

ATCGCGCATCAGCCATGGCGCGGTGAATACGTTCCCGGGCCTTGTACACACCGCCC

GTCAAGCCATGGGAGCCGGGGGTACCTGAAGTCCGTAACCGCAAGGATCGGCCTA

GGGTAAAACTGGTGACTGGGGCTAAGTCGTAACAAGGTAGCCGTACCGGAAGGTG

CGGCTGGAACACCTCCTT

SEQ ID NO: 56
H82A6_16S_ribosomal_RNA
AATAAAGATTAATTGGTAAAGGATGGGGATGCGTCCCATTAGCTTGTTGGCGGGGT

AACGGCCCACCAAGGCGACGATGGGTAGGGGTTCTGAGAGGAAGGTCCCCCACAT

TGGAACTGAGACACGGTCCAAACTCCTACGGGAGGCAGCAGTGAGGAATATTGGT

CAATGGGCGCGAGCCTGAACCAGCCAAGTAGCGTGGAGGACGACGGCCCTACGGG

TTGTAAACTCCTTTTATAAGGGGATAAAGTTGGCCATGTATGGCCATTTGCAGGTAC

CTTATGAATAAGCATCGGCTAATTCCGTGCCAGCAGCCGCGGTAATACGGAAGATG

CGAGCGTTATCCGGATTTATTGGGTTTAAAGGGAGCGTAGGCGGGCAGTCAAGTCA

GCGGTCAAATGGCGCGGCTCAACCGCGTTCCGCCGTTGAAACTGGCAGCCTTGAG

TATGCACAGGGTACATGGAATTCGTGGTGTAGCGGTGAAATGCTTAGATATCACGA

GGAACTCCGATCGCGCAGGCATTGTACCGGGGCATTACTGACGCTGAGGCTCGAA

GGTGCGGGTATCAAACAGGATTAGATACCCTGGTAGTCCGCACAGTAAACGATGAA

-continued

TGCCCGCTGTCGGCGACATAGTGTCGGCGGCCAAGCGAAAGCGTTAAGCATTCCA

CCTGGGGAGTACGCCGGCAACGGTGAAACTCAAAGGAATTGACGGGGGCCCGCAC

AAGCGGAGGAACATGTGGTTTAATTCGATGATACGCGAGGAACCTTACCCGGGCTT

GAATCGCAGGTGCATGGGCCGGAGACGGCCCTTTCCTTCGGGACTCCTGCGAAGG

TGCTGCATGGTTGTCGTCAGCTCGTGCCGTGAGGTGTCGGCTTAAGTGCCATAACG

AGCGCAACCCCCCTCCCCAGTTGCCACCGGGTAATGCCGGGCACTTTGGGGACAC

TGCCACCGCAAGGTGCGAGGAAGGTGGGGATGACGTCAAATCAGCACGGCCCTTA

CGTCCGGGGCGACACACGTGTTACAATGGGGGGTACAGAGGGCCGCTGCCCGGTG

ACGGTTGGCCAATCCCTAAAACCCCTCTCAGTTCGGACTGGAGTCTGCAACCCGAC

TCCACGAAGCTGGATTCGCTAGTAATCGCGCATCAGCCATGGCGCGGTGAATACGT

TCCCGGGCCTTGTACACACCGCCCGTCAAGCCATGAAAGCCGGGGGTGCCTGAAG

TCCGTGACCGCGAGGGTCGGCCTAGGGTAAAACCGGTGATTGGGGCTAAGTCGTA

ACAAGGTAGCCGTACCGGAAGGTGCGGCTGGAACACCTCCTTT

SEQ ID NO: 57

H82G9_16S_ribosomal_RNA

CGAAGAGTTTGATCCTGGCTCAGGATGAACGCTAGCGACAGGCTTAACACATGCAA

GTCGAGGGGCAGCACAGGTAGCAATACCGGGTGGCGACCGGCGCACGGGTGAGTA

ACGCGTATGCAACTTGCCTATCAGAGGGGGATAACCCGGCGAAAGTCGGACTAATA

CCGCATGAAGCAGGGGCCCCGCATGGGGATATTTGCTAAAGATTCATCGCTGATAG

ATAGGCATGCGTTCCATTAGGCAGTTGGCGGGGTAACGGCCCACCAAACCGACGAT

GGATAGGGGTTCTGAGAGGAAGGTCCCCCACATTGGTACTGAGACACGGACCAAA

CTCCTACGGGAGGCAGCAGTGAGGAATATTGGTCAATGGCCGAGAGGCTGAACCA

GCCAAGTCGCGTGAGGGATGAAGGTTCTATGGATCGTAAACCTCTTTTATAAGGGA

ATAAAGTGCGGGACGTGTCCCGTTTTGTATGTACCTTATGAATAAGGATCGGCTAAC

TCCGTGCCAGCAGCCGCGGTAATACGGAGGATCCGAGCGTTATCCGGATTTATTGG

GTTTAAAGGGTGCGTAGGCGGCCTTTTAAGTCAGCGGTGAAAGTCTGTGGCTCAAC

CATAGAATTGCCGTTGAAACTGGGGGGCTTGAGTATGTTTGAGGCAGGCGGAATGC

GTGGTGTAGCGGTGAAATGCATAGATATCACGCAGAACCCCGATTGCGAAGGCAGC

CTGCCAAGCCATTACTGACGCTGATGCACGAAAGCGTGGGGATCAAACAGGATTAG

ATACCCTGGTAGTCCACGCAGTAAACGATGATCACTAGCTGTTTGCGATACACTGTA

AGCGGCACAGCGAAAGCGTTAAGTGATCCACCTGGGGAGTACGCCGGCAACGGTG

AAACTCAAAGGAATTGACGGGGGCCCGCACAAGCGGAGGAACATGTGGTTTAATT

CGATGATACGCGAGGAACCTTACCCGGGTTTGAACGCATTCGGACCGAGGTGGAA

ACACCTTTTCTAGCAATAGCCGTTTGCGAGGTGCTGCATGGTTGTCGTCAGCTCGT

GCCGTGAGGTGTCGGCTTAAGTGCCATAACGAGCGCAACCCTTGCCACTAGTTACT

AACAGGTAAAGCTGAGGACTCTGGTGGGACTGCCAGCGTAAGCTGCGAGGAAGGC

GGGGATGACGTCAAATCAGCACGGCCCTTACATCCGGGGCGACACACGTGTTACAA

TGGCGTGGACAAAGGGAAGCCACCTGGCGACAGGGAGCGAATCCCCAAACCACGT

CTCAGTTCGGATCGGAGTCTGCAACCCGACTCCGTGAAGCTGGATTCGCTAGTAAT

CGCGCATCAGCCATGGCGCGGTGAATACGTTCCCGGGCCTTGTACACACCGCCCGT

CAAGCCATGGGAGCCGGGGGTACCTGAAGTCCGTAACCGCGAGGATCGGCCTAGG

-continued

GTAAAACTGGTGACTGGGGCTAAGTCGTAACAAGGTAGCCGTACCGGAAGGTGCG

GCTGGAACACCTCCTTT

SEQ ID NO: 58
H81E7_16S_ribosomal_RNA
ATGGAGAGTTTGATCCTGGCTCAGGATGAACGCTAGCGGCAGGCCTAACACATGCA

AGTCGAGGGGCAGCGGGATTGAAGCTTGCTTCAGTTGCCGGCGACCGGCGCACGG

GTGCGTAACGCGTATGCAACCTACCCATAACAGGGGGATAACACTGAGAAATCGGT

ACTAATATCCCATAACATCAAGAGGGGCATCCCTTTTGGTTGAAAACTCCGGTGGTT

ATGGATGGGCATGCGTTGTATTAGCTAGTTGGTGAGGTAACGGCTCACCAAGGCGA

CGATACATAGGGGGACTGAGAGGTTAACCCCCCACATTGGTACTGAGACACGGACC

AAACTCCTACGGGAGGCAGCAGTGAGGAATATTGGTCAATGGACGCAAGTCTGAA

CCAGCCATGCCGCGTGCAGGATGACGGCTCTATGAGTTGTAAACTGCTTTTGTACG

AGGGTAAACCCGGATACGTGTATCCGGCTGAAAGTATCGTACGAATAAGGATCGGC

TAACTCCGTGCCAGCAGCCGCGGTAATACGGAGGATTCAAGCGTTATCCGGATTTA

TTGGGTTTAAAGGGTGCGTAGGCGGTTTGATAAGTTAGAGGTGAAATACCGGTGCT

TAACACCGGAACTGCCTCTAATACTGTTGAGCTAGAGAGTAGTTGCGGTAGGCGGA

ATGTATGGTGTAGCGGTGAAATGCTTAGAGATCATACAGAACACCGATTGCGAAGG

CAGCTTACCAAACTATATCTGACGTTGAGGCACGAAAGCGTGGGGAGCAAACAGGA

TTAGATACCCTGGTAGTCCACGCAGTAAACGATGATAACTCGCTGTCGGCGATACA

CAGTCGGTGGCTAAGCGAAAGCGATAAGTTATCCACCTGGGGAGTACGTTCGCAAG

AATGAAACTCAAAGGAATTGACGGGGGCCCGCACAAGCGGAGGAACATGTGGTTT

AATTCGATGATACGCGAGGAACCTTACCCGGGCTTGAAAGTTACTGACGATTCTGG

AAACAGGATTTCCCTTCGGGGCAGGAAACTAGGTGCTGCATGGTTGTCGTCAGCTC

GTGCCGTGAGGTGTCGGGTTAAGTCCCATAACGAGCGCAACCCCTACCGTTAGTTG

CCATCAGGTCAAGCTGGGCACTCTGGCGGGACTGCCGGTGTAAGCCGAGAGGAAG

GTGGGGATGACGTCAAATCAGCACGGCCCTTACGTCCGGGGCTACACACGTGTTAC

AATGGTAGGTACAGAGGGCAGCTACCCAGTGATGGGATGCGAATCTCGAAAGCCTA

TCTCAGTTCGGATTGGAGGCTGAAACCCGCCTCCATGAAGTTGGATTCGCTAGTAA

TCGCGCATCAGCCATGGCGCGGTGAATACGTTCCCGGGCCTTGTACACACCGCCCG

TCAAGCCATGGAAGCTGGGGGTGCCTGAAGTTCGTGACCGCAAGGAGCGACCTAG

GGCAAAACCGGTGACTGGGGCTAAGTCGTAACAAGGTAGCCGTACCGGAAGGTGC

GGCTGGAACACCTCCTTT

SEQ ID NO: 59
H81C1_16S_ribosomal_RNA
TATTGAGAGTTTGATCCTGGCTCAGGACGAACGCTGGCGGTATGCTTAACACATGC

AAGTCGAACGAGAAGGTTTTGATGGATCCTTCGGGTGATATCAGAACTGGAAAGTG

GCGAACGGGTGAGTAACGCGTGGGTAACCTGCCCTATGGAAAGGAATAGCCTCGG

GAAACTGGGAGTAAAGCCTTATATTATGGTTTTGTCGCATGGCAAGATCATGAAAAC

TCCGGTGCCATAGGATGGACCCGCGTCCCATTAGCTAGTTGGTGAGATAACAGCCC

ACCAAGGCGACGATGGGTAACCGGTCTGAGAGGGCGAACGGTCACACTGGAACTG

AGACACGGTCCAGACTCCTACGGGAGGCAGCAGTGGGGAATATTGCGCAATGGGG

GCAACCCTGACGCAGCAATACCGCGTGAGTGAAGAAGGTTTTCGGATCGTAAAGCT

CTGTTATTGGGGAAGAAGAATGACGGTACCCAATGAGGAAGTCCCGGCTAACTACG

-continued

TGCCAGCAGCCGCGGTAATACGTAGGGGACAAGCGTTGTCCGGAATGACTGGGCG

TAAAGGGCGCGTAGGCGGTCTATTAAGTCTGATGTGAAAGGTACCGGCTCAACCGG

TGAAGTGCATTGGAAACTGGTAGACTTGAGTATTGGAGAGGCAAGTGGAATTCCTA

GTGTAGCGGTGAAATGCGTAGATATTAGGAGGAACACCAGTGGCGAAGGCGGCTT

GCTGGACAAATACTGACGCTGAGGTGCGAAAGCGTGGGGAGCGAACAGGATTAGA

TACCCTGGTAGTCCACGCCGTAAACGATGAATGCTAGGTGTTGGGGAAACTCAGTG

CCGCAGTTAACACAATAAGCATTCCGCCTGGGGAGTACGACCGCAAGGTTGAAACT

CAAAGGAATTGACGGGGACCCGCACAAGCAGCGGAGCATGTGGTTTAATTCGAAG

CAACGCGAAGAACCTTACCAGGTCTTGACATCCTCTGACGAGCCTAGAGATAGGAA

GTTTCCTTCGGGAACAGAGAGACAGGTGGTGCATGGTTGTCGTCAGCTCGTGTCG

TGAGATGTTGGGTTAAGTCCCGCAACGAGCGCAACCCCTGCCTTTAGTTGCCAGCA

TTAAGTTGGGCACTCTAGAGGGACTGCCGTAGACAATACGGAGGAAGGTGGGGAC

GACGTCAAATCATCATGCCCCTTATGACCTGGGCTACACACGTGCTACAATGGTCT

GAACAGAGGGCCGCGAAGCCGCGAGGTGAAGCAAATCCCTTAAAACAGATCCCAG

TTCGGATTGCAGGCTGCAACTCGCCTGCATGAAGTTGGAGTTGCTAGTAATCGCGG

ATCAGAATGCCGCGGTGAATGCGTTCCCGGGTCTTGTACACACCGCCCGTCACACC

ACGAGAGTTGGCAACACCCGAAGCCTGTGAGAGAACCGTAAGGACTCAGCAGTCG

AAGGTGGGGCTAGTAATTGGGGTGAAGTCGTAACAAGGTAGCCGTATCGGAAGGT

GCGGCTGGATCACCTCCTTT

SEQ ID NO: 60

H81B11_16S_ribosomal_RNA

ATGAAGAGTTTGATCCTGGCTCAGGATGAACGCTAGCTACAGGCTTAACACATGCA

AGTCGAGGGGCAGCATGGTCTTAGCTTGCTAAGGCTGATGGCGACCGGCGCACGG

GTGAGTAACACGTATCCAACCTGCCGTCTACTCTTGGCCAGCCTTCTGAAAGGAAG

ATTAATCCAGGATGGGATCATGAGTTCACATGTCCGCATGATTAAAGGTATTTTCCG

GTAGACGATGGGGATGCGTTCCATTAGATAGTAGGCGGGGTAACGGCCCACCTAGT

CAACGATGGATAGGGGTTCTGAGAGGAAGGTCCCCCACATTGGAACTGAGACACG

GTCCAAACTCCTACGGGAGGCAGCAGTGAGGAATATTGGTCAATGGGCGATGGCC

TGAACCAGCCAAGTAGCGTGAAGGATGACTGCCCTATGGGTTGTAAACTTCTTTTA

TAAAGGAATAAAGTCGGGTATGCATACCCGTTTGCATGTACTTTATGAATAAGGATC

GGCTAACTCCGTGCCAGCAGCCGCGGTAATACGGAGGATCCGAGCGTTATCCGGAT

TTATTGGGTTTAAAGGGAGCGTAGATGGATGTTTAAGTCAGTTGTGAAAGTTTGCG

GCTCAACCGTAAAATTGCAGTTGATACTGGATGTCTTGAGTGCAGTTGAGGCAGGC

GGAATTCGTGGTGTAGCGGTGAAATGCTTAGATATCACGAAGAACTCCGATTGCGA

AGGCAGCCTGCTAAGCTGCAACTGACATTGAGGCTCGAAAGTGTGGGTATCAAACA

GGATTAGATACCCTGGTAGTCCACACGGTAAACGATGAATACTCGCTGTTTGCGATA

TACGGCAAGCGGCCAAGCGAAAGCGTTAAGTATTCCACCTGGGGAGTACGCCGGC

AACGGTGAAACTCAAAGGAATTGACGGGGGCCCGCACAAGCGGAGGAACATGTGG

TTTAATTCGATGATACGCGAGGAACCTTACCCGGGCTTAAATTGCACTCGAATGATC

CGGAAACGGTTCAGCTAGCAATAGCGAGTGTGAAGGTGCTGCATGGTTGTCGTCA

GCTCGTGCCGTGAGGTGTCGGCTTAAGTGCCATAACGAGCGCAACCCTTGTTGTCA

-continued

GTTACTAACAGGTGATGCTGAGGACTCTGACAAGACTGCCATCGTAAGATGTGAGG

AAGGTGGGGATGACGTCAAATCAGCACGGCCCTTACGTCCGGGGCTACACACGTG

TTACAATGGGGGGTACAGAGGGCCGCTACCACGCGAGTGGATGCCAATCCCTAAAA

CCCCTCTCAGTTCGGACTGGAGTCTGCAACCCGACTCCACGAAGCTGGATTCGCTA

GTAATCGCGCATCAGCCACGGCGCGGTGAATACGTTCCCGGGCCTTGTACACACCG

CCCGTCAAGCCATGGGAGCCGGGGGTACCTGAAGTGCGTAACCGCGAGGATCGCC

CTAGGGTAAAACTGGTGACTGGGGCTAAGTCGTAACAAGGTAGCCGTACCGGAAG

GTGCGGCTGGAACACCTCCTT

SEQ ID NO: 61

H81H9_16S_ribosomal_RNA

CGAAGAGTTTGATCCTGGCTCAGGATGAACGCTAGCGACAGGCTTAACACATGCAA

GTCGAGGGGCAGCAGGAAGTAGCAATACTTTGCTGGCGACCGGCGCACGGGTGAG

TAACGCGTATGCAACCTACCTATCAGAGGGGGATAACCCGGCGAAAGTCGGACTAA

TACCGCATAAAACAGGGGTCCCGCATGGGAATATTTGTTAAAGATTTATTGCTGATA

GATGGGCATGCGTTCCATTAGATAGTTGGTGAGGTAACGGCTCACCAAGTCTTCGA

TGGATAGGGGTTCTGAGAGGAAGGTCCCCCACACTGGTACTGAGACACGGACCAG

ACTCCTACGGGAGGCAGCAGTGAGGAATATTGGTCAATGGGCGAGAGCCTGAACC

AGCCAAGTCGCGTGAAGGATGAAGGATCTATGGTTCGTAAACTTCTTTTATAGGGG

AATAAAGTGCAGGACGTGTCCTGTTTTGTATGTACCCTATGAATAAGGATCGGCTAA

CTCCGTGCCAGCAGCCGCGGTAATACGGAGGATCCGAGCGTTATCCGGATTTATTG

GGTTTAAAGGGTGCGTAGGTGGCTTTTTAAGTCAGCGGTGAAAGTTTGTGGCTCAA

CCATAAAATTGCCGTTGAAACTGGAGGGCTTGAGTATATTTGAGGTAGGCGGAATG

CGTGGTGTAGCGGTGAAATGCATAGATATCACGCAGAACTCCAATTGCGAAGGCAG

CTTACTAAACTATAACTGACACTGAAGCACGAAAGCGTGGGGATCAAACAGGATTA

GATACCCTGGTAGTCCACGCAGTAAACGATGATTACTAGGAGTTTGCGATACACAG

TAAGCTCTACAGCGAAAGCGTTAAGTAATCCACCTGGGGAGTACGCCGGCAACGGT

GAAACTCAAAGGAATTGACGGGGGCCCGCACAAGCGGAGGAACATGTGGTTTAAT

TCGATGATACGCGAGGAACCTTACCCGGGTTTGAACGTAAGTTGACCGGAGTGGAA

ACACTCTTTCTAGCAATAGCAATTTACGAGGTGCTGCATGGTTGTCGTCAGCTCGT

GCCGTGAGGTGTCGGCTTAAGTGCCATAACGAGCGCAACCCTTATCTTTAGTTACT

AACAGGTCGAGCTGAGGACTCTAAAGAGACTGCCAGCGTAAGCTGTGAGGAAGGT

GGGGATGACGTCAAATCAGCACGGCCCTTACATCCGGGGCGACACACGTGTTACAA

TGGTGGGGACAAAGGGCAGCTACCTGGCGACAGGATGCTAATCTCCAAACCCCAT

CTCAGTTCGGATCGAAGTCTGCAACCCGACTTCGTGAAGCTGGATTCGCTAGTAAT

CGCGCATCAGCCATGGCGCGGTGAATACGTTCCCGGGCCTTGTACACACCGCCCGT

CAAGCCATGGGAGTTGGGGGTACCTAAAGTCCGTAACCGCAAGGATCGGCCTAGG

GTAAAACCGATGACTGGGGCTAAGTCGTAACAAGGTAGCCGTACCGGAAGGTGCG

GCTGGAACACCTCCTTT

SEQ ID NO: 62

H82B1_16S_ribosomal_RNA

AATGAAGAGTTTGATCCTGGCTCAGGACGAACGCTGGCGGCGCGCCTAACACATG

CAAGTCGAACGGAGCTGTTTTCTCTGAAGTTTTCGGATGGAAGAGAGTTCAGCTTA

GTGGCGAACGGGTGAGTAACACGTGAGCAACCTGCCTTTCAGTGGGGGACAACAT

-continued

TTGGAAACGAATGCTAATACCGCATAAGACCACAGTGTCGCATGGCACAGGGGTCA

AAGGATTTATCCGCTGAAAGATGGGCTCGCGTCCGATTAGCTAGATGGTGAGGTAA

CGGCCCACCATGGCGACGATCGGTAGCCGGACTGAGAGGTTGAACGGCCACATTG

GGACTGAGACACGGCCCAGACTCCTACGGGAGGCAGCAGTGGGGAATATTGCACA

ATGGGGGAAACCCTGATGCAGCGACGCCGCGTGGAGGAAGAAGGTCTTCGGATTG

TAAACTCCTGTCCCAGGGGACGATAATGACGGTACCCTGGGAGGAAGCACCGGCT

AACTACGTGCCAGCAGCCGCGGTAAAACGTAGGGTGCAAGCGTTGTCCGGAATTA

CTGGGTGTAAAGGGAGCGCAGGCGGATTGGCAAGTTGGGAGTGAAATCTATGGGC

TCAACCCATAAATTGCTTTCAAAACTGTCAGTCTTGAGTGGTGTAGAGGTAGGCGG

AATTCCCGGTGTAGCGGTGGAATGCGTAGATATCGGGAGGAACACCAGTGGCGAA

GGCGGCCTACTGGGCACTAACTGACGCTGAGGCTCGAAAGCATGGGTAGCAAACA

GGATTAGATACCCTGGTAGTCCATGCCGTAAACGATGATTACTAGGTGTGGGAGGA

TTGACCCCTTCCGTGCCGCAGTTAACACAATAAGTAATCCACCTGGGGAGTACGAC

CGCAAGGTTGAAACTCAAAGGAATTGACGGGGGCCCGCACAAGCAGTGGAGTATG

TGGTTTAATTCGAAGCAACGCGAAGAACCTTACCAGGTCTTGACATCGGATGCATA

CCTAAGAGATTAGGGAAGTCCTTCGGGACATCCAGACAGGTGGTGCATGGTTGTCG

TCAGCTCGTGTCGTGAGATGTTGGGTTAAGTCCCGCAACGAGCGCAACCCTTATCG

TTAGTTACTACGCAAGAGGACTCTAGCGAGACTGCCGTTGACAAAACGGAGGAAG

GTGGGGATGACGTCAAATCATCATGCCCTTTATGACCTGGGCTACACACGTACTAC

AATGGCTATTAACAGAGAGAAGCGATACCGCGAGGTGGAGCAAACCTCACAAAAAT

AGTCTCAGTTCGGATCGCAGGCTGCAACCCGCCTGCGTGAAGCCGGAATTGCTAGT

AATCGCGGATCAGCATGCCGCGGTGAATACGTTCCCGGGCCTTGTACACACCGCCC

GTCACACCATGAGAGCCGGGGGGACCCGAAGTCGGTAGTCTAACCGCAAGGAGGA

CGCCGCCGAAGGTAAAACTGGTGATTGGGGTGAAGTCGTAACAAGGTAGCCGTAT

CGGAAGGTGCGGCTGGATCACCTCCTTT

SEQ ID NO: 63

H82G1_16S_ribosomal_RNA

ATGAAGAGTTTGATCCTGGCTCAGGATGAACGCTAGCTACAGGCTTAACACATGCA

AGTCGAGGGGCAGCATGAACTTAGCTTGCTAAGTTTGATGGCGACCGGCGCACGG

GTGAGTAACACGTATCCAACCTGCCGATGACTCGGGGATAGCCTTTCGAAAGAAAG

ATTAATACCCGATGGCATAGTTCTTCCGCATGGTGGAACTATTAAAGAATTTCGGTC

ATCGATGGGGATGCGTTCCATTAGGTTGTTGGCGGGGTAACGGCCCACCAAGCCTT

CGATGGATAGGGGTTCTGAGAGGAAGGTCCCCCACATTGGAACTGAGACACGGTC

CAAACTCCTACGGGAGGCAGCAGTGAGGAATATTGGTCAATGGACGAGAGTCTGA

ACCAGCCAAGTAGCGTGAAGGATGACTGCCCTATGGGTTGTAAACTTCTTTTATAC

GGGAATAAAGTGAGGCACGTGTGCCTTTTTGTATGTACCGTATGAATAAGGATCGG

CTAACTCCGTGCCAGCAGCCGCGGTAATACGGAGGATCCGAGCGTTATCCGGATTT

ATTGGGTTTAAAGGGAGCGTAGGCGGACGCTTAAGTCAGTTGTGAAAGTTTGCGG

CTCAACCGTAAAATTGCAGTTGATACTGGGTGTCTTGAGTACAGTAGAGGCAGGCG

GAATTCGTGGTGTAGCGGTGAAATGCTTAGATATCACGAAGAACTCCGATTGCGAA

GGCAGCCTGCTGGACTGTAACTGACGCTGATGCTCGAAAGTGTGGGTATCAAACA

-continued

GGATTAGATACCCTGGTAGTCCACACAGTAAACGATGAATACTCGCTGTTTGCGATA

TACAGTAAGCGGCCAAGCGAAAGCGTTAAGTATTCCACCTGGGGAGTACGCCGGC

AACGGTGAAACTCAAAGGAATTGACGGGGGCCCGCACAAGCGGAGGAACATGTGG

TTTAATTCGATGATACGCGAGGAACCTTACCCGGGCTTGAATTGCAACTGAATGAT

GTGGAGACATGTCAGCCGCAAGGCAGTTGTGAAGGTGCTGCATGGTTGTCGTCAG

CTCGTGCCGTGAGGTGTCGGCTTAAGTGCCATAACGAGCGCAACCCTTATCGATAG

TTACCATCAGGTGATGCTGGGGACTCTGTCGAGACTGCCGTCGTAAGATGTGAGGA

AGGTGGGGATGACGTCAAATCAGCACGGCCCTTACGTCCGGGGCTACACACGTGT

TACAATGGGGGGTACAGAAGGCAGCTACACGGCGACGTGATGCTAATCCCGAAAG

CCTCTCTCAGTTCGGATTGGAGTCTGCAACCCGACTCCATGAAGCTGGATTCGCTA

GTAATCGCGCATCAGCCACGGCGCGGTGAATACGTTCCCGGGCCTTGTACACACCG

CCCGTCAAGCCATGAAAGCCGGGGGTACCTGAAGTGCGTAACCGCAAGGAGCGCC

CTAGGGTAAAACTGGTGATTGGGGCTAAGTCGTAACAAGGTAGCCGTACCGGAAG

GTGCGGCTGGAACACCTCCTT

SEQ ID NO: 64

H82G5_16S_ribosomal_RNA

ATTGGAGAGTTTGATCCTGGCTCAGGACGAACGCTGGCGGCGTGCCTAACACATG

CAAGTCGAACGGAGAATTTTATTTCGGTAGAATTCTTAGTGGCGAACGGGTGAGTA

ACGCGTAGGCAACCTACCCTTTAGACGGGGACAACATTCCGAAAGGAGTGCTAATA

CCGGATGTGATCATCTTGCCGCATGGCAGGATGAAGAAAGATGGCCTCTACAAGTA

AGCTATCGCTAAAGGATGGGCCTGCGTCTGATTAGCTAGTTGGTAGTGTAACGGAC

TACCAAGGCGATGATCAGTAGCCGGTCTGAGAGGATGAACGGCCACATTGGGACT

GAGACACGGCCCAAACTCCTACGGGAGGCAGCAGTGGGGAATCTTCCGCAATGGA

CGAAAGTCTGACGGAGCAACGCCGCGTGAGTGATGAAGGATTTCGGTCTGTAAAG

CTCTGTTGTTTATGACGAACGTGCAGTGTGTGAACAATGCATTGCAATGACGGTAG

TAAACGAGGAAGCCACGGCTAACTACGTGCCAGCAGCCGCGGTAATACGTAGGTG

GCGAGCGTTGTCCGGAATTATTGGGCGTAAAGAGCATGTAGGCGGCTTAATAAGTC

GAGCGTGAAAATGCGGGGCTCAACCCCGTATGGCGCTGGAAACTGTTAGGCTTGA

GTGCAGGAGAGGAAAGGGGAATTCCCAGTGTAGCGGTGAAATGCGTAGATATTGG

GAGGAACACCAGTGGCGAAGGCGCCTTTCTGGACTGTGTCTGACGCTGAGATGCG

AAAGCCAGGGTAGCGAACGGGATTAGATACCCCGGTAGTCCTGGCCGTAAACGATG

GGTACTAGGTGTAGGAGGTATCGACCCCTTCTGTGCCGGAGTTAACGCAATAAGTA

CCCCGCCTGGGGAGTACGGCCGCAAGGTTGAAACTCAAAGGAATTGACGGGGGCC

CGCACAAGCGGTGGAGTATGTGGTTTAATTCGACGCAACGCGAAGAACCTTACCAA

GGCTTGACATTGATTGAACGCTCTAGAGATAGAGATTTCCCTTCGGGGACAAGAAA

ACAGGTGGTGCATGGCTGTCGTCAGCTCGTGTCGTGAGATGTTGGGTTAAGTCCC

GCAACGAGCGCAACCCCTATCCTATGTTACCAGCAAGTAAAGTTGGGGACTCATGG

GAGACTGCCAGGGACAACCTGGAGGAAGGCGGGGATGACGTCAAGTCATCATGCC

CCTTATGTCTTGGGCTACACACGTACTACAATGGTCGGAAACAGAGGGAAGCGAAG

CCGCGAGGCAGAGCAAACCCCAGAAACCCGATCTCAGTTCGGATCGCAGGCTGCA

ACCCGCCTGCGTGAAGTCGGAATCGCTAGTAATCGCAGGTCAGCATACTGCGGTGA

ATACGTTCCCGGGCCTTGTACACACCGCCCGTCACACCACGAAAGTTGGTAACACC

-continued

CGAAGCCGGTGAGGTAACCTATTAGGAGCCAGCCGTCTAAGGTGGGGCCGATGAT

TGGGGTGAAGTCGTAACAAGGTAGCCGTATCGGAAGGTGCGGCTGGATCACCTCC

TTT

The invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Unless otherwise defined herein, scientific and technical terms used in connection with the present disclosure shall have the meanings that are commonly understood by those of ordinary skill in the art. Further, unless otherwise required by context, singular terms shall include pluralities and plural terms hall include the singular. The methods and techniques of the present disclosure are generally performed according to conventional methods well-known in the art. Generally, nomenclatures used in connection with, and techniques of biochemistry, enzymology, molecular and cellular biology, microbiology, virology, cell or tissue culture, genetics and protein and nucleic chemistry described herein are those well-known and commonly used in the art. The methods and techniques of the present disclosure are generally performed according to conventional methods well known in the art and as described in various general and more specific references that are cited and discussed throughout the present specification unless otherwise indicated.

The present invention is further illustrated by the following Examples, which in no way should be construed as further limiting. The entire contents of all of the references (including literature references, issued patents, published patent applications, and co-pending patent applications) cited throughout this application are hereby expressly incorporated by reference, in particular for the teaching that is referenced hereinabove. However, the citation of any reference is not intended to be an admission that the reference is prior art.

EXAMPLES

Example 1: Identification of a CD8+ T-Cell Inducing Bacterial Cocktail

Figure 1B:
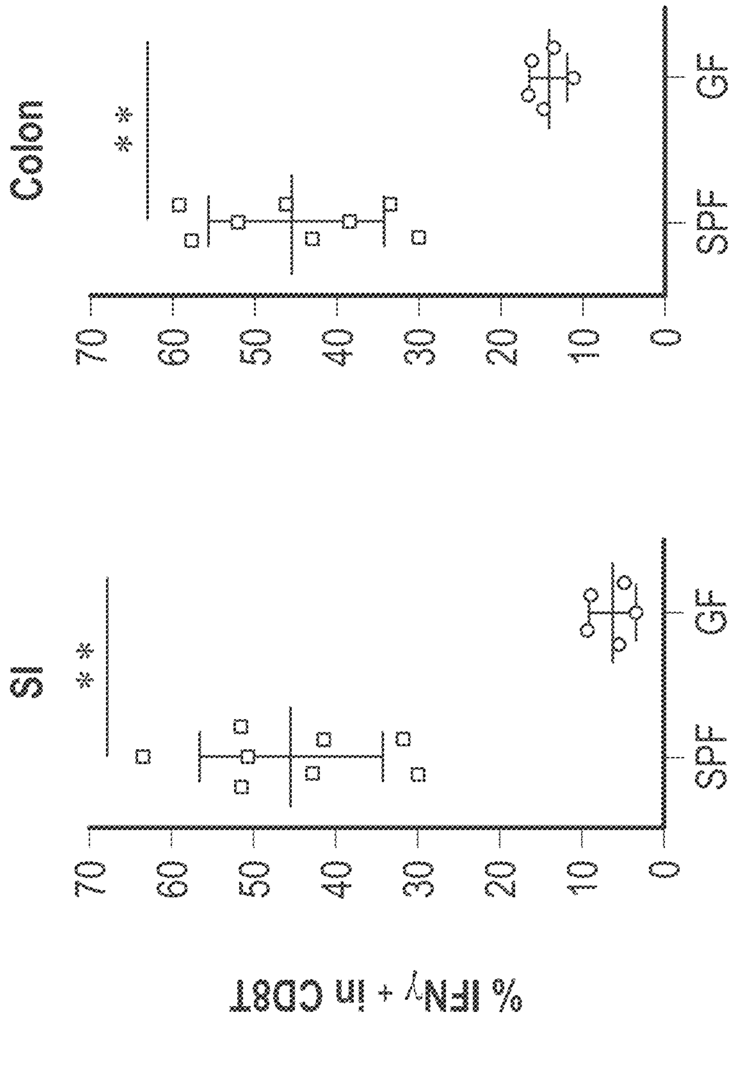
Figures 2A, 2B:
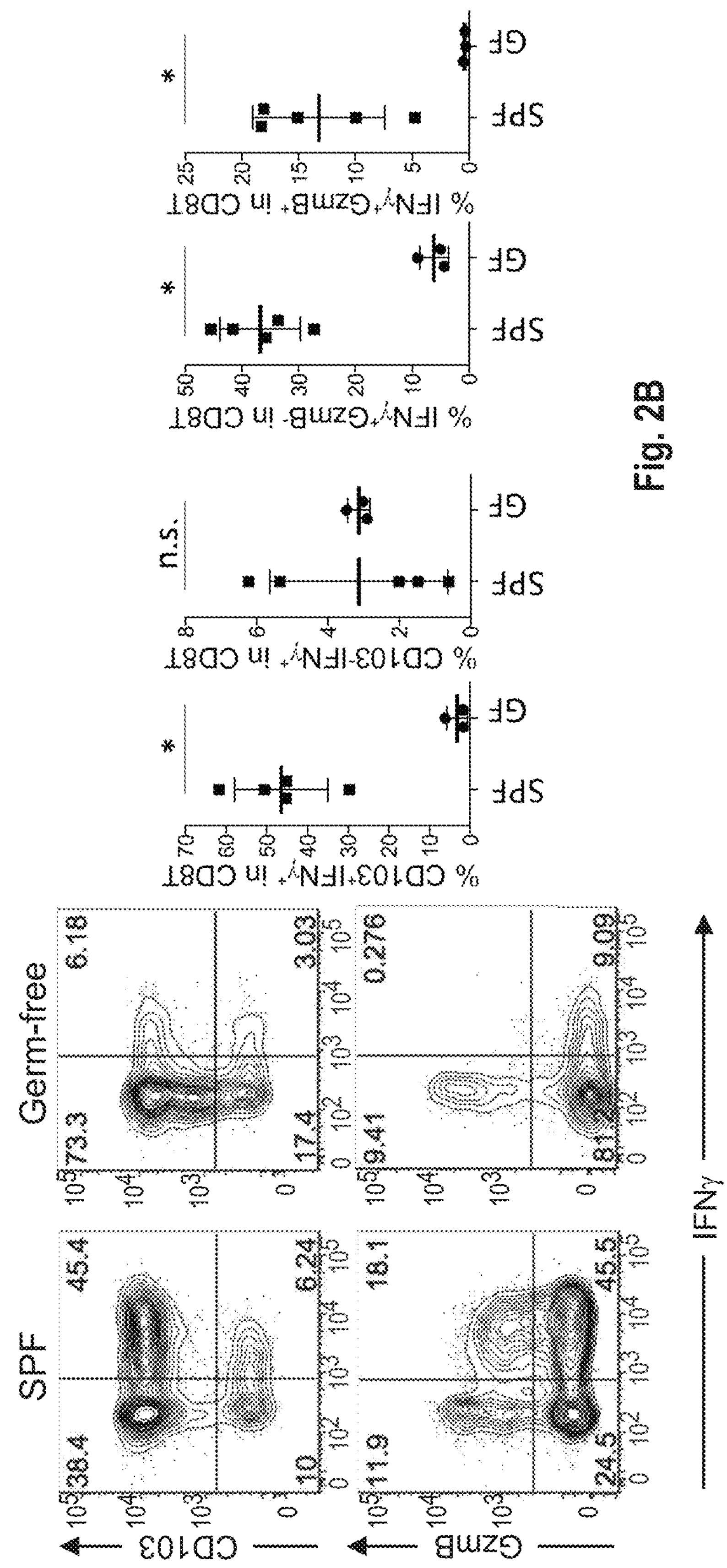
FIGS. 2A and 2B show data of experiments with lymphocytes that were isolated from the small intestinal mucosal lamina propria of SPF and germ-free mice and stimulated with PMA/ionomycin for 3.5 hours. CD3, TCRβ, CD8, CD103, IFN γ and GzmB were stained with antibodies and analyzed by flow cytometry.
Figures 3A, 3B:
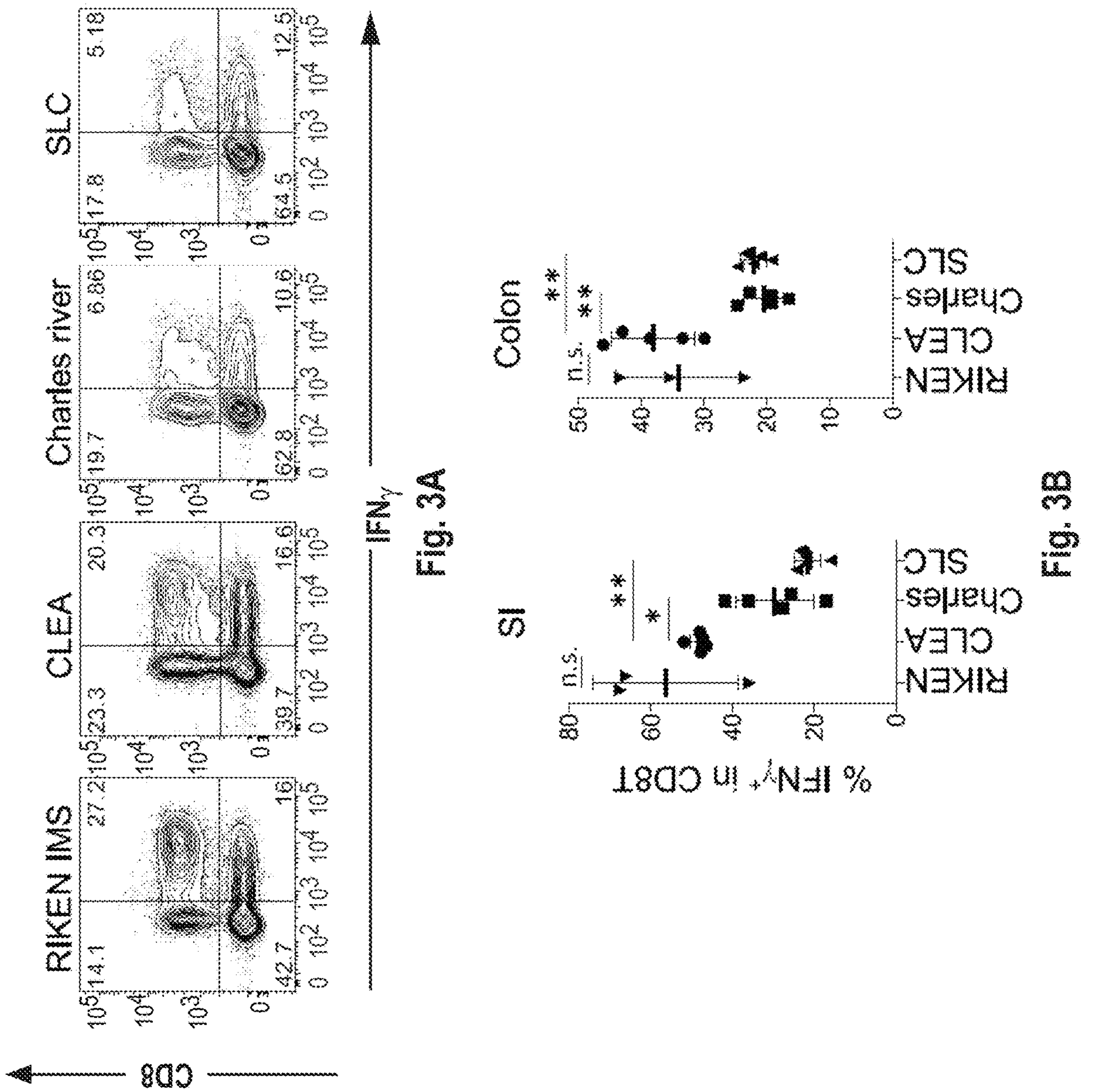
FIGS. 3A and 3B show data of experiments with lymphocytes that were isolated from small intestine (SI) and large intestine (Colon) mucosal lamina propria of SPF mice delivered from different laboratory animal facilities and stimulated with PMA/ionomycin for 3.5 hours. CD3, TCRβ, CD8 and IFN γ were stained with antibodies and analyzed by flow cytometry.
Figure 4A:
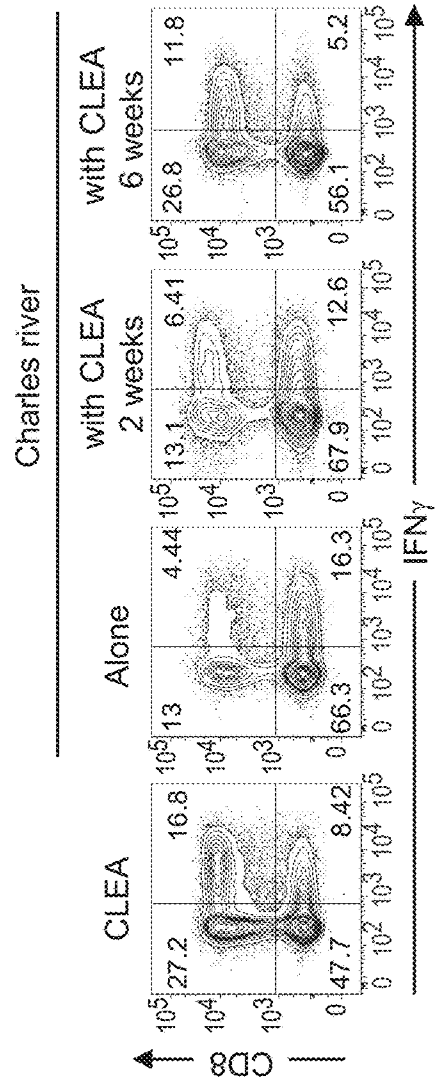
FIGS. 4A and 4B show data of experiments in which after co-housing of SPF mice from Charles River Laboratories with CLEA Japan for 2 or 6 weeks, lymphocytes were isolated from intestinal (SI) and colon mucosal lamina propria and stimulated with PMA/ionomycin for 3.5 h. CD3, TCRβ, CD8 and IFN γ were stained with antibodies and analyzed by flow cytometry.
Figure 4B:
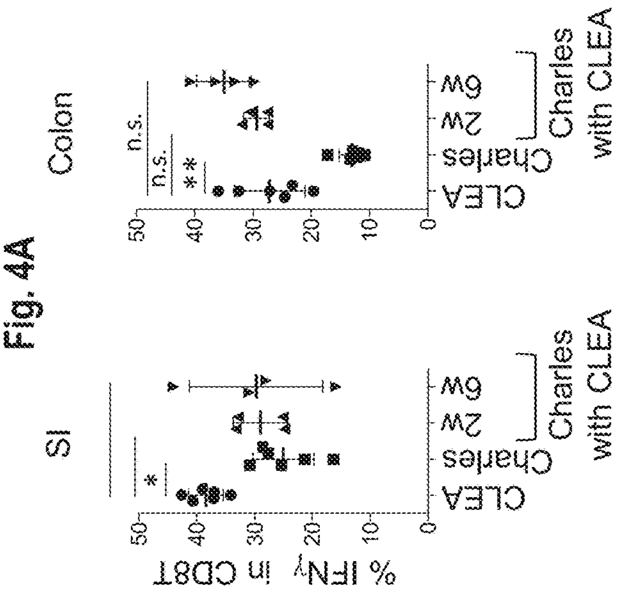

C57BL/6 mice kept under specific-pathogen free (SPF) conditions which possess resident microbiota have abundant IFN γ+CD8+ T-cells, whereas markedly few IFN γ+CD8+ T-cells were found in intestinal lamina propria of germ free mice (See FIG. 1). This indicates that gut microbiota induces the accumulation of IFN γ+CD8+ T-cells. A subset of IFN γ+CD8+ T cells also expressed CD103 as well as GranzymeB (see FIG. 2A), suggesting that the subset was tissue-resident memory T cells. FIG. 3A shows that remarkably small numbers of IFN γ+CD8+ T-cells were found in SPF C57BL/6 mice purchased from Charles River Laboratories Inc. and Japan SLC Inc. as compared to SPF C57BL/6 mice purchased from CLEA Japan Inc. and mice bred in RIKEN. When SPF C57BL/6 mice from Charles River Laboratories Inc. were co-housed together with CLEA mice in the same cage, an increase of IFN γ+CD8+ T-cells was observed in mice delivered from Charles River Laboratories Inc. (FIGS. 4A and 4B). This finding strongly supports a hypothesis that there are specific microbial species in the mouse microbiota which induce and accumulate IFN γ+CD8+ T cells in the intestine.

Next, it was investigated whether the human gut microbiota contained microbes which were able to induce IFN γ+CD8+ T cells. Stool samples were collected from six healthy human volunteers (A-F). The samples were individually administered orally into germ free C57BL/6 mice kept in sterile isolators (five or six mice per group). Four weeks after oral inoculation of stool samples, mice were sacrificed, and small intestine and colons were harvested and investigated for IFN γ+CD8+ T-cells by FACS.

Figures 5A, 5B:
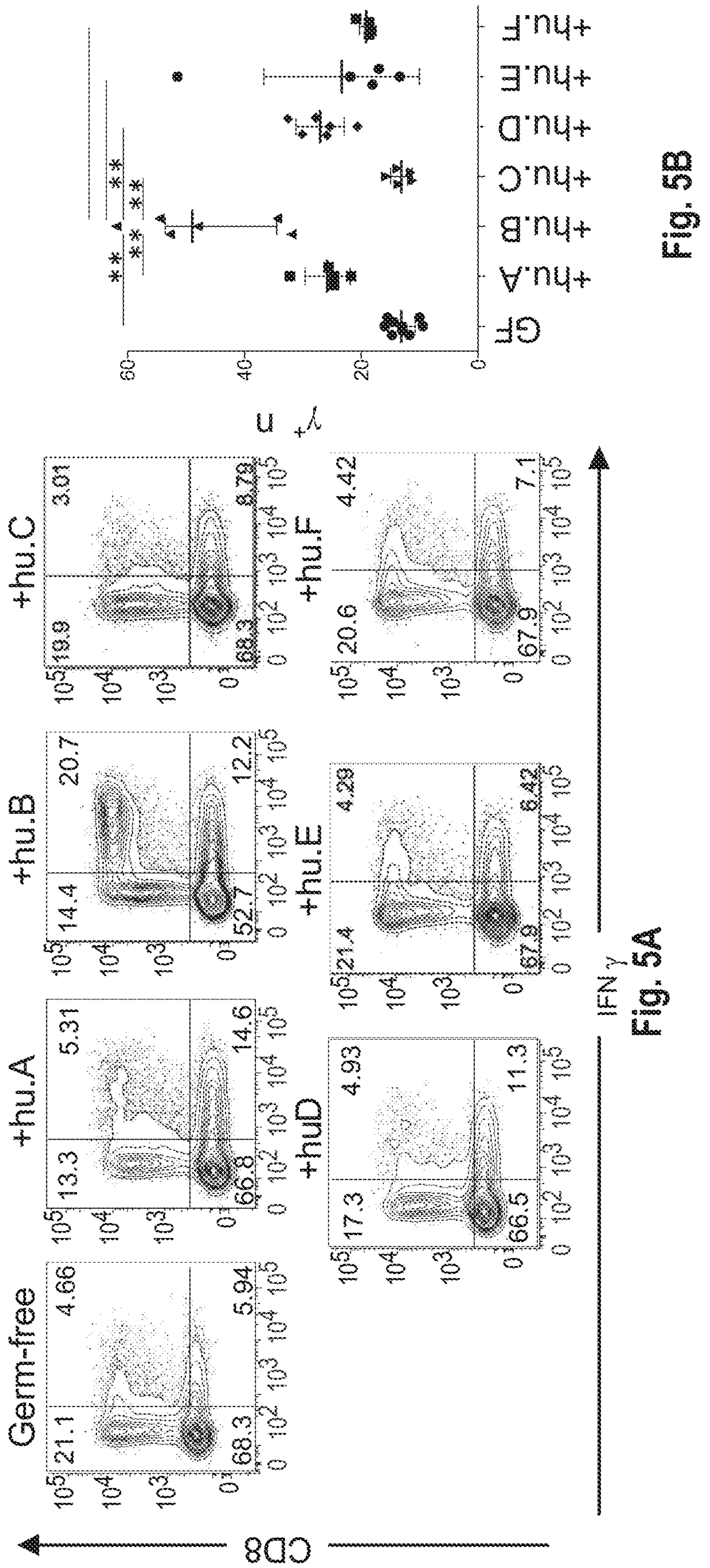
FIGS. 5A and 5B show data of experiments with stools from healthy volunteers (A~F) which were orally administered into germ free mice individually in sterile vinyl isolators. Four weeks later, lymphocytes were isolated from the lamina propria of the large intestine and stimulated with PMA/ionomycin for 3.5 hours. CD3, TCRβ, CD8 and IFN γ were stained with antibodies and analyzed by flow cytometry.
Figure 6A:
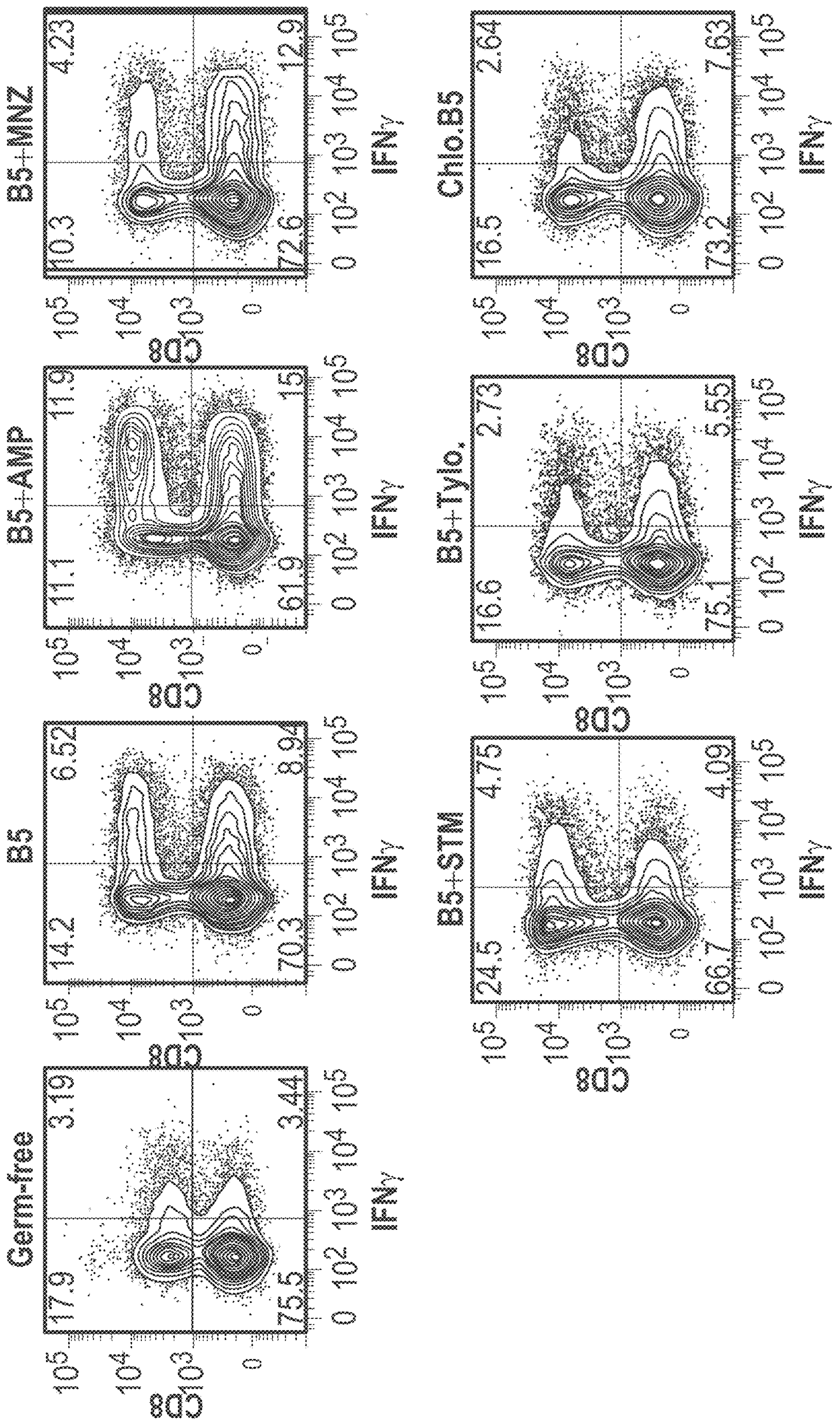
FIGS. 6A and 6B show data of experiments with the cecal contents of B #5 mouse, which was orally administered to germ free mice. One day later, their drinking waters were switched to ampicillin (AMP), metronidazole (MNZ), streptomycin (STM) or tylosin (Tylo.) until the end of experiment. The contents of the cecum of B #5 treated with 3% of chloroform were administered to germ free mice. Four weeks later, lymphocytes were isolated from the lamina propria of the large intestine and stimulated with PMA/ionomycin for 3.5 hours. CD3, TCRβ, CD8, IFN γ were stained with antibodies and analyzed by flow cytometry.
Figure 6B:
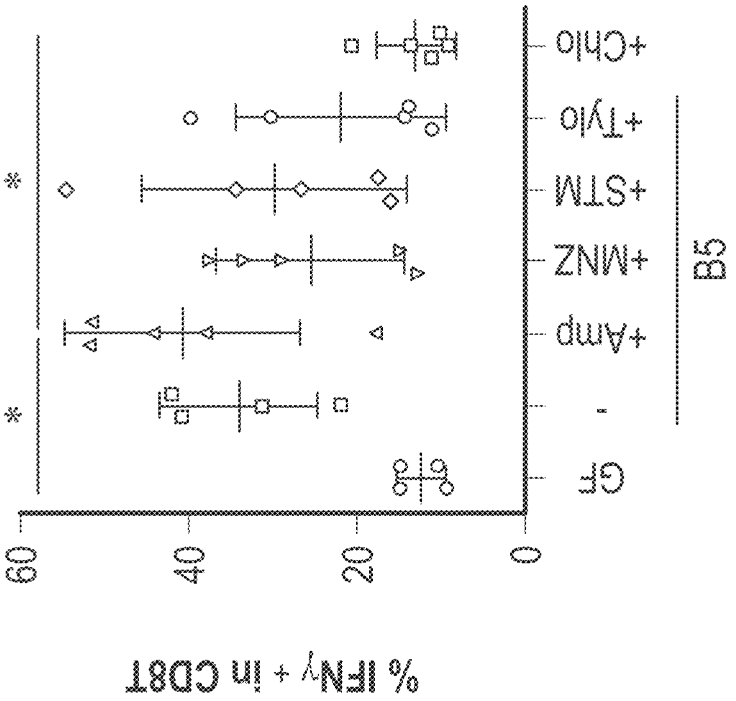

As shown in FIGS. 5A and 5B, colonic IFN γ+CD8+ T-cells were most remarkably induced in mice inoculated with a stool sample collected from donor B. Among mice inoculated with the donor B stool sample, we selected a mouse that exhibited the highest frequency of IFN γ+CD8+ T cells (called 'mouse B #5' hereafter). In order to concentrate microbes responsible for IFN γ+CD8+ T cell induction, cecal contents were collected from the mouse B #5 and inoculated into another germ-free mouse. The mice were then orally administrated drinking water with or without Ampicillin, Metronidazole, Streptomycin or Tylosin (five mice per group). Alternatively, cecal contents of mouse B #5 were treated with 3% chloroform and orally inoculated into another five germ-free mice ('B #5+Chrolo'). FIGS. 6A and 6B show that Ampicillin treatment enhanced induction of colonic lamina propria IFN γ+CD8+ T-cells by the mouse B #5 microbiota, whereas other antibiotics treatment or chloroform treatment reduced the induction capability of IFN γ+CD8+ T-Cells by the mouse B #5 microbiota.

Figure 7A:
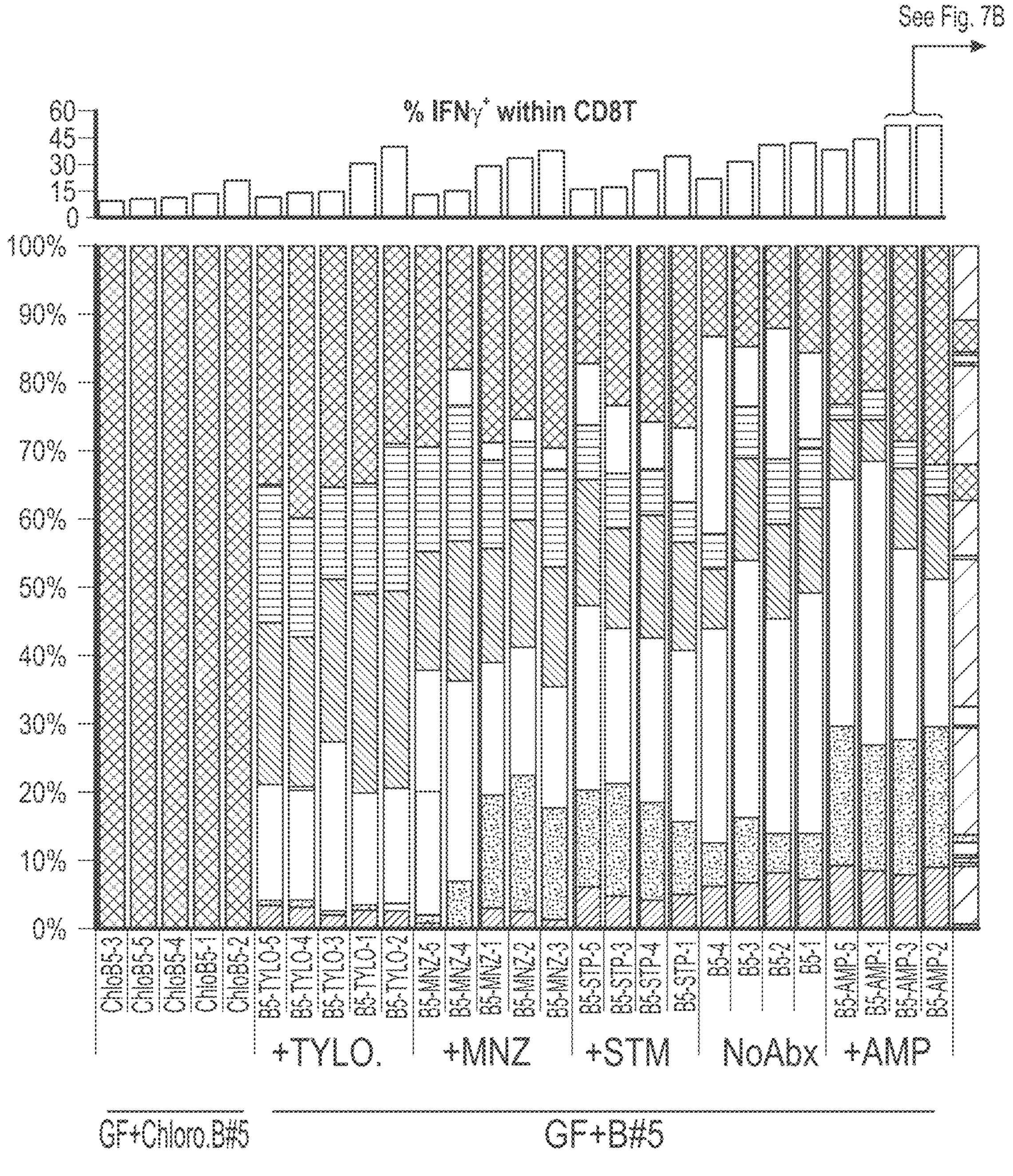
Figure 8B:
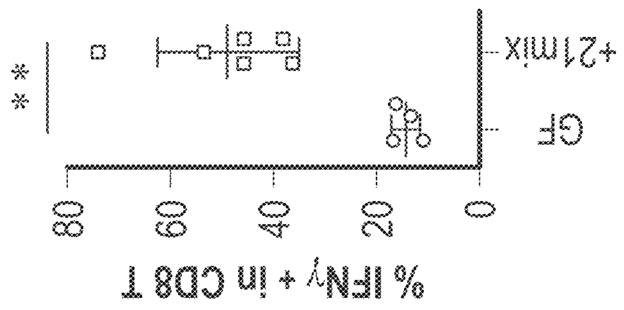
FIGS. 8A and 8B show data on the mixture of 21 isolated strains which was orally administered to germ free mice. Four weeks later, lymphocytes were isolated from the lamina propria of the large intestine and stimulated with PMA/ionomycin for 3.5 hours. CD3, TCRβ, CD8 and IFN γ were stained with antibodies and analyzed by flow cytometry.
Figure 8A:
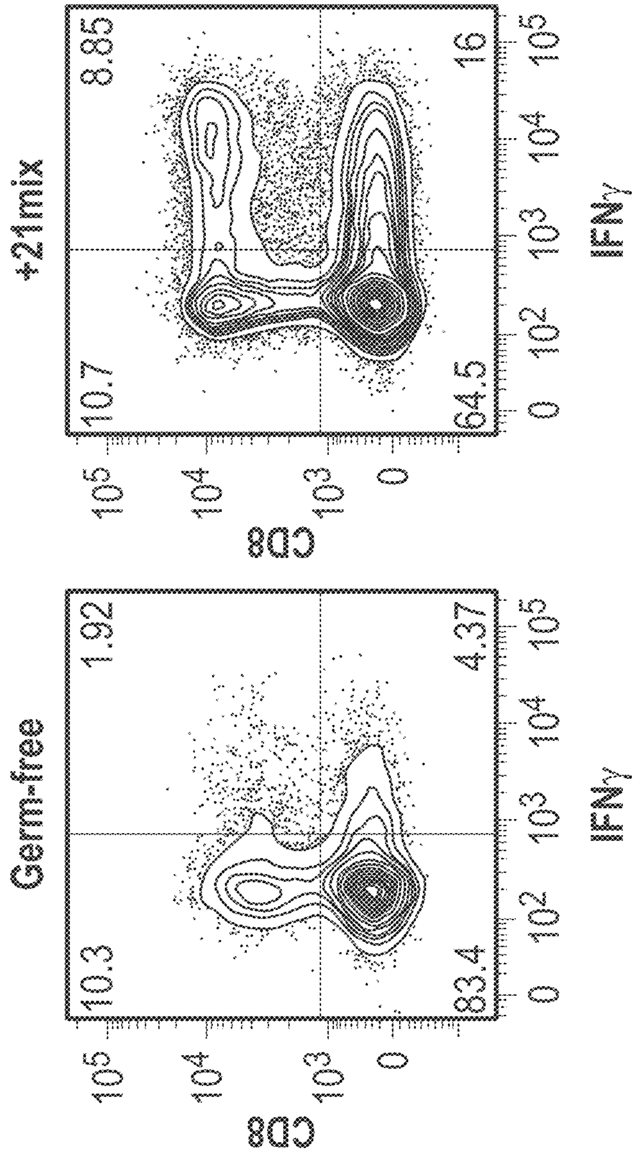
Figure 9B:
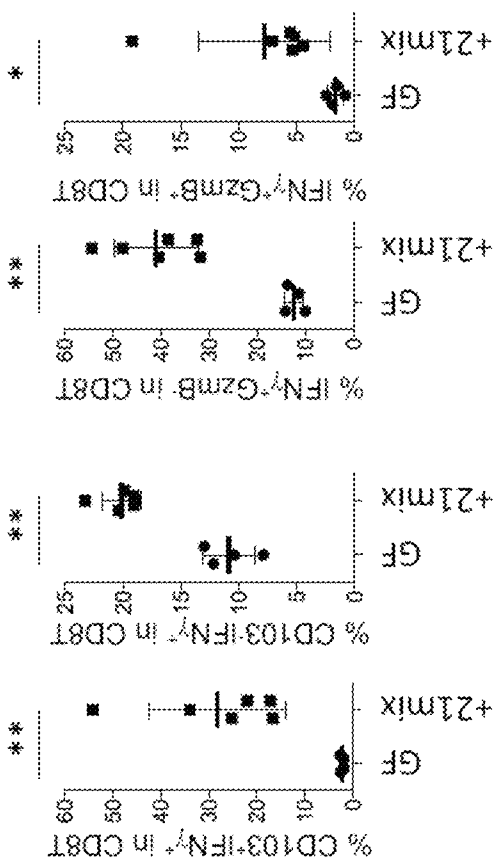
FIGS. 9A and 9B show data on the mixture of 21 isolated strains which was orally administered to germ free mice. Four weeks later, lymphocytes were isolated from the lamina propria of the large intestine and stimulated with PMA/ionomycin for 3.5 hours. CD3, TCR β, CD8, CD103, IFN γ and GzmB were stained with antibodies and analyzed by flow cytometry.
Figure 9A:
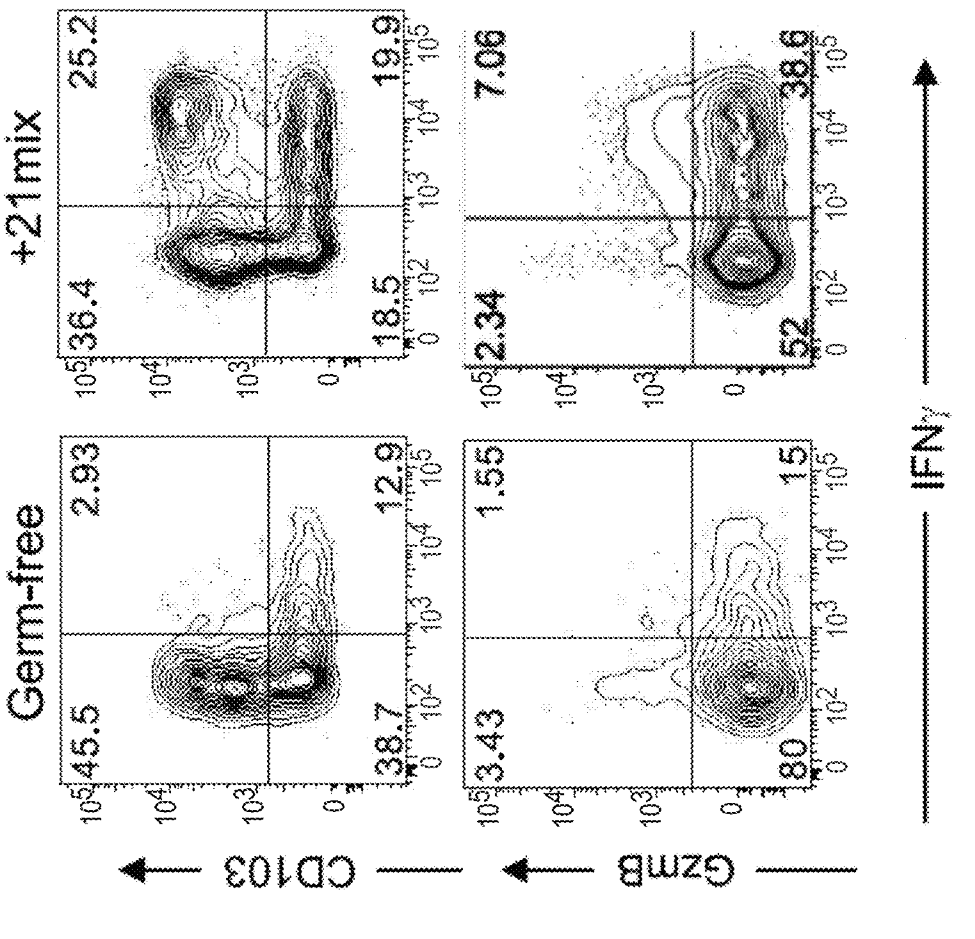
Figures 10A, 10B:
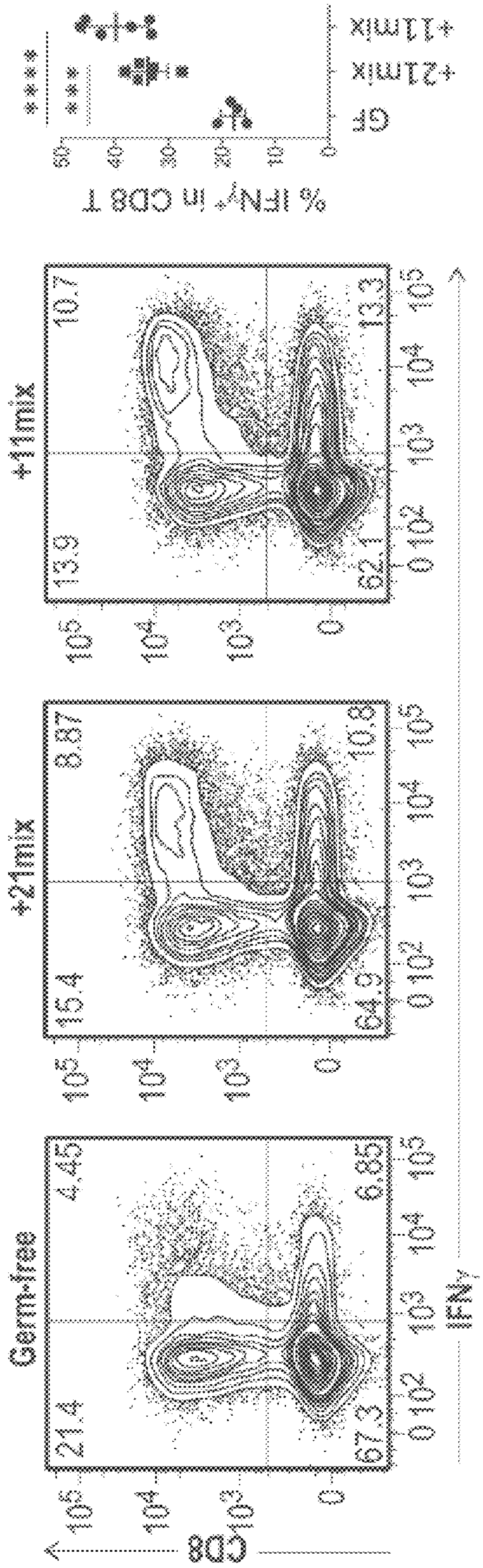
FIGS. 10A and 10B show data on the mixture of the 21 strains or 11 strains (11 strain mixture corresponds to strains #1-11; See Table 1), which were orally administered to germ free mice. Four weeks later, lymphocytes were isolated from the lamina propria of the large intestine and stimulated with PMA/ionomycin for 3.5 hours. CD3, TCRβ, CD8 and IFN γ were stained with antibodies and analyzed by flow cytometry.

FIGS. 7A and 7B show the operational taxonomic unit (OTU) analysis of intestinal contents of mice inoculated with mouse B #5 microbiota and treated with/without antibiotics or chloroform. Cecal contents were collected from two B #5+AMP mice that exhibited the highest frequency of IFN γ+CD8+ T cells (mouse B #5+AMP-2 and mouse B #5+AMP-3) and cultured in an anaerobic chamber. 304 colonies were picked and sequencing of the 16S rRNA gene revealed that 26 strains were isolated. Twenty-one strains were selected from the 26 strains, excluding 5 strains which were included in the microbiota of B #5+Chrolo mice (therefore predicted to be unnecessary for induction of IFN γ+CD8+ T-cells). The mixture of 21 strains was orally inoculated into germ free mice and strong induction of IFN γ+CD8+ T-cells was observed (FIGS. 8A and 8B). IFN γ+CD8+ T cells induced by the 21 strains also expressed CD103 and a part of the IFN γ+CD8+ T-cells expressed Granzyme B as well (FIGS. 9A and 9B). A mixture of 11 strains with the highest correlation with IFN γ+CD8+ T-cells was inoculated into GF mice as well. The mixture of 11 strains (11 mix) was orally a strong induction of IFN γ+CD8+ T-cells, even when compared to the 21 strains mixture (21 mix) (FIGS. 10A and 10B). Identification of the bacterial species with the highest homology to each of the strains in the 11 mix is provided in Table 2, below.

TABLE 2

[Mixture of 11 strains]

| Strain # | SEQ ID NO | Strain ID | Species with highest homology | NCBI accession # of 16S locus | SEQ ID of NCBI 16S locus |
|---|---|---|---|---|---|
| 1 | 1 | 2G5 | *Phascolarctobacterium faecium* | LN998073 | 27 |
| 2 | 2 | 1A6 | *Fusobacterium ulcerans* | KR822463 | 28 |
| 3 | 3 | 1B11 | *Bacteroides dorei* | CP011531 | 29 |
| 4 | 4 | 2G1 | *Bacteroides uniformis* | NR112945 | 30 |
| 5 | 5 | 2B1 | *Subdoligranulum* sp. | KM098109 | 31 |
| 6 | 6 | 2A6 | *Paraprevotella xylaniphila* | NR113078 | 32 |
| 7 | 7 | 2F11 | *Parabacteroides johnsonii* | NR041464 | 33 |
| 8 | 8 | 1E7 | *Alistipes* sp. | LT223566 | 34 |
| 9 | 9 | 1H9 | *Parabacteroides gordonii* | NR112835 | 35 |
| 10 | 10 | 1C1 | *Eubacterum limosum* | NR113248 | 36 |
| 11 | 11 | 2G9 | *Parabacteroides distasonis* | NR041342 | 37 |

Example 1A: Further Characterization of the Mixture of 11 Strains (Composition A)

The strains of Table 2 were characterized further by resequencing of the 16S sequences and by whole genome sequencing. The results of the further characterization are found in Table 3.

TABLE 3

[Further characterization of the 11-mix (the mixture of 11 strains)]

| Strain # | SEQ ID NO | Strain ID | species with highest homology based on original 16S analysis | NCBI accession ID | species with highest homology based on 16S resequencing | 16S Identity (%) of resequencing | species with highest homology based on whole genome sequencing (WGS) | WGS Identity (%) | WGS Coverage (%) | Alternative species with high(est) homology |
|---|---|---|---|---|---|---|---|---|---|---|
| 2 | 2 | 1A6 | *Fusobacterium ulcerans* | K0052822463 | *Fusobacterium varium* | 99 | *Fusobacterium ulcerans* | 93.2 | 78.6 | |
| 7 | 7 | 2F11 | *Parabacteroides johnsonii* | NR041464 | *Parabacteroides johnsonii* | 99 | *Parabacteroides johnsonii* | 99.9 | 90.5 | |
| 6 | 6 | 2A6 | *Paraprevotella xylaniphila* | NR113078 | *Paraprevotella xylaniphila* | 99 | *Paraprevotella xylaniphila* | 98.9 | 92.1 | |
| 11 | 11 | 2G9 | *Parabacteroides distasonis* | NR041342 | *Parabacteroides distasonis* | 99 | *Parabacteroides* sp. CAG: 2 | 99.4 | 95.4 | |
| 8 | 8 | 1E7 | *Alistipes* sp. | LT223566 | *Alistipes senegalensis* | 99 | *Alistipes senegalensis* | 98.7 | 72.2 | *Alistipes timonensis* |
| 10 | 10 | 1C1 | *Eubacterium limosum* | NR113248 | *Eubacterium limosum* | 99 | *Eubacterium limosum* | 95 | 81 | |
| 3 | 3 | 1B11 | *Bacteroides dorei* | CP011531 | *Bacteroides dorei* | 99 | *Bacteroides dorei* | 99.3 | 79.5 | *Bacteroides fluxus* |
| 9 | 9 | 1H9 | *Parabacteroides gordonii* | NR112835 | *Parabacteroides gordonii* | 97 | *Parabacteroides* sp. HGS0025 | 90 | 50 | |
| 5 | 5 | 2B1 | *Subdolino-granulum* sp. | KM098109 | *Gemminger formicilis* | 99 | *Ruminococcaceae bacterium* cv2 | 99.2 | 73.9 | *Rutheni-bacterium lactatiformans* |
| 4 | 4 | 2G1 | *Bacteroides uniformis* | NR112945 | *Bacteroides uniformis* | 99 | *Bacteroides* sp. D20 | 98.5 | 81 | |
| 1 | 1 | 2G5 | *Phascolarcto-bacterium faecium* | LN998073 | *Phascolarcto-bacterium faecium* | 99 | *Phascolarcto-bacterium* sp. CAG: 207 | 99.2 | 87 | |

Figure 12A:
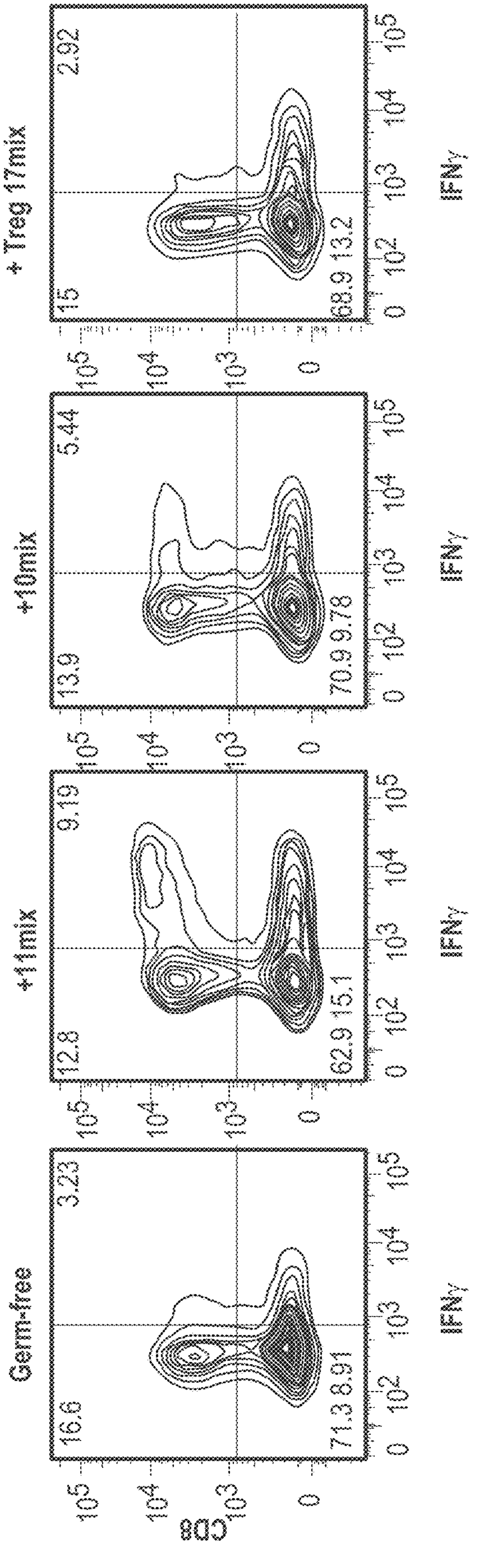
FIGS. 12A and 12B show data obtained from mixtures of 11 or 10 strains (see FIG. 11), or a mixture of 17 strains that are known Treg-inducers, which were orally administered to germ free mice. Four weeks later, lymphocytes were isolated from the lamina propria of the large intestine and stimulated with PMA/ionomycin for 3.5 hours. CD3, TCR β, CD8 and IFN γ were stained with antibodies and analyzed by flow cytometry.
Figure 12B:
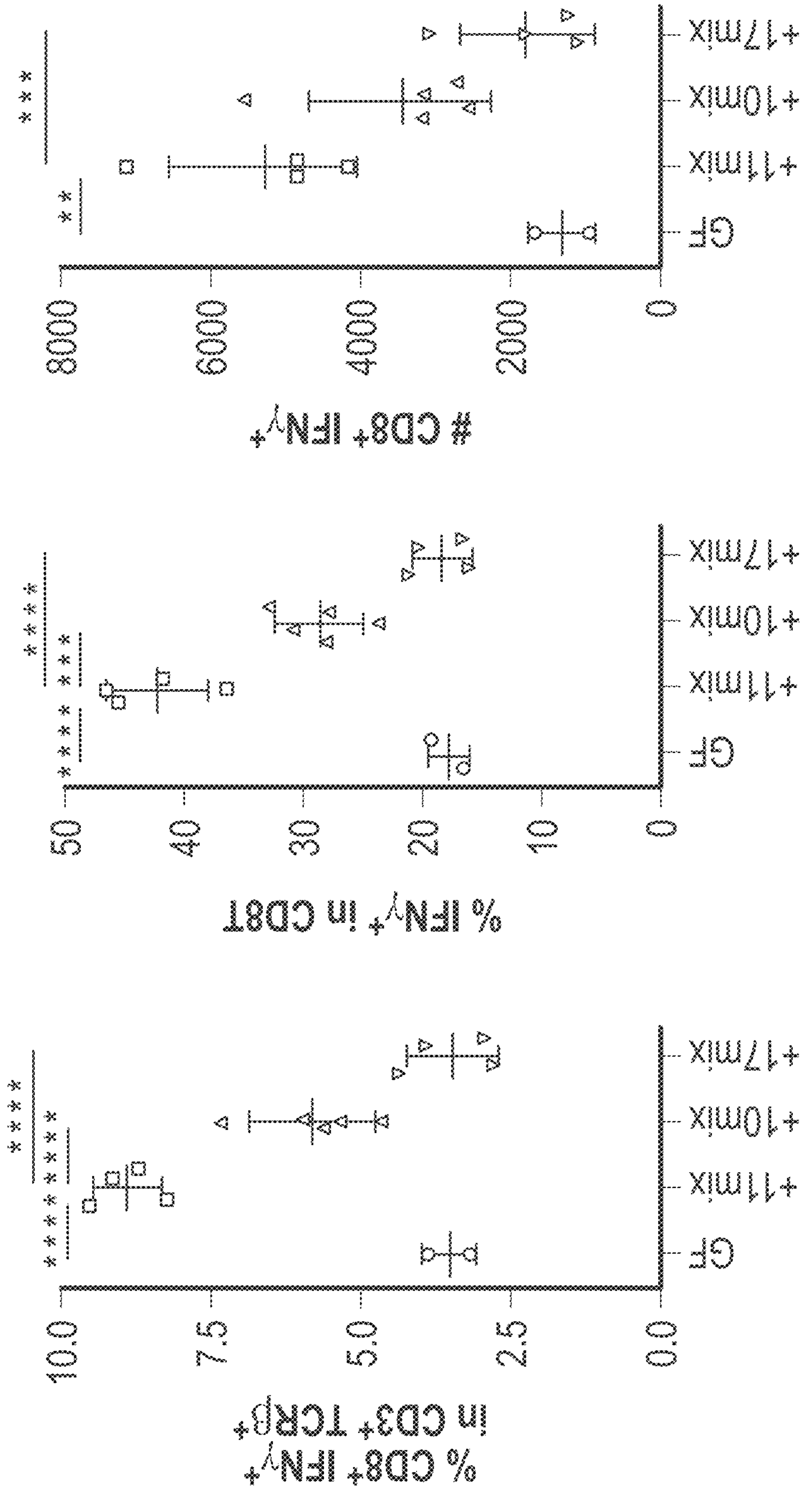

Example 2: Further Characterization of a CD8+ T-Cell Inducing Bacterial Cocktail Twenty six strains isolated from cecal contents of B #5+AMP mice that exhibited high frequencies of IFN γ+CD8+ T cells are shown in FIG. 11. Among the 26 strains, 11 strains ("11 mix") were positively correlated with the frequency of IFN γ+CD8+ T cells. Therefore, these 11 strains were selected for further experiments, and the mixture of 11 strains ("11-mix") was inoculated into germ-free mice (see also Table 2). Colonization with the 11-mix resulted in a strong induction of colonic IFN γ+CD8+ T cells (FIGS. 10A, 10B, 12A, and 12B), whereas the other 10 strains ("10-mix") weakly induced IFN γ+CD8+ T cells compared to the levels induced by the 11-mix (FIGS. 12A and 12B). Mice inoculated with a mixture of 17 Treg-inducing bacterial strains (See e.g., WO2013/080561; Atarashi et al., Nature (2013) 500 (7461): 232-236; Narushima et al. Gut Microbes (2014)5(3): 333-339) did not accumulate IFN 7+CD8+ T cells (FIGS. 12A and 12B).

Figure 13:
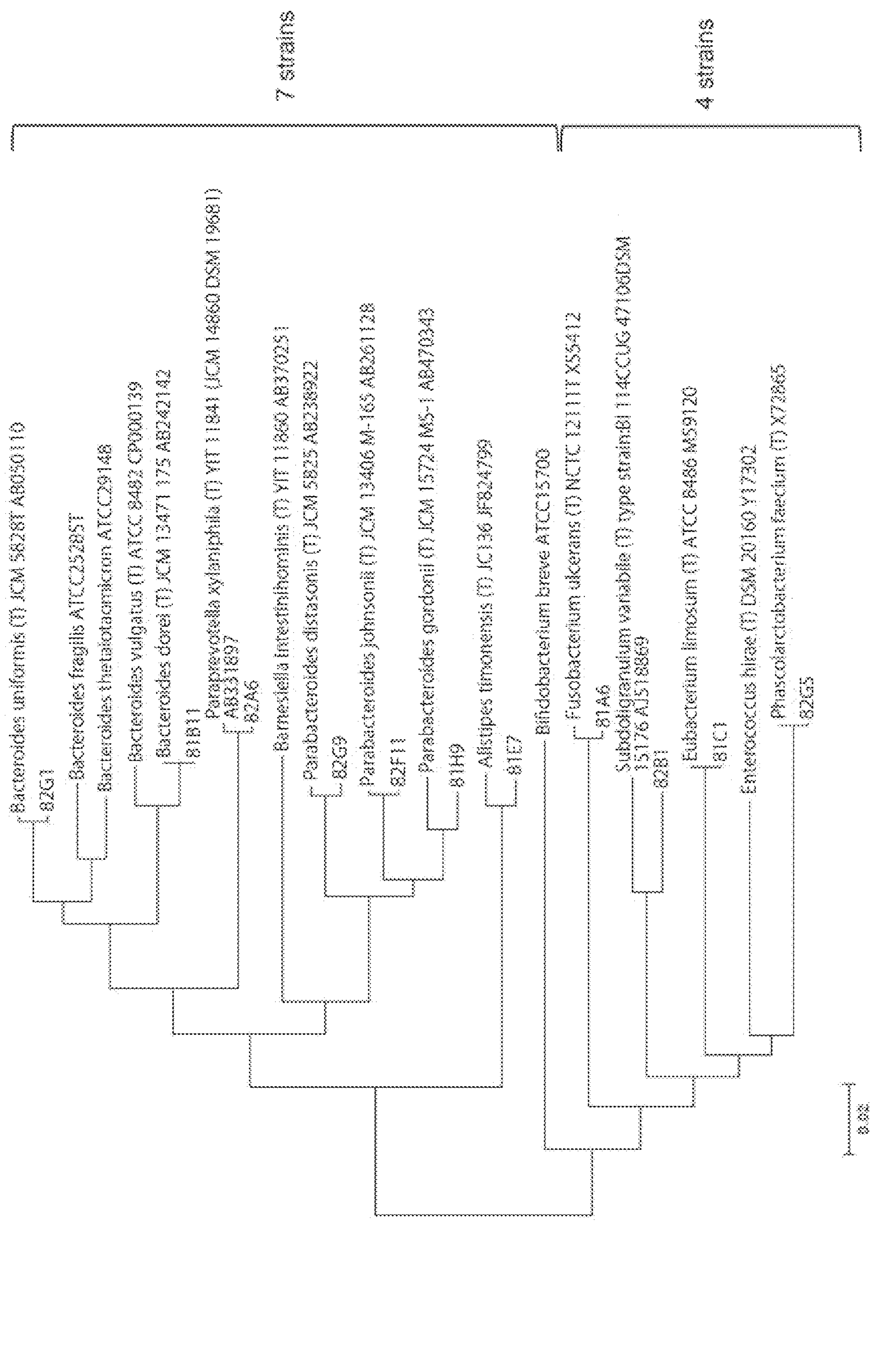
FIG. 13 shows a phylogenetic tree which was constructed from the 16S rRNA gene sequences of the 11 strains (See FIG. 11), their closest sequences and some type strains using the MEGA v5.0 package and the neighbor-joining method. The strains which were inoculated into GF mice as a 7 mix or 4 mix are shown as well (The results of the inoculation experiments are shown in FIGS. 14A and 14B).

A phylogenetic comparison using 16S rRNA gene sequences showed that the 11 strain mixture (also referred to as "the 11 mix") consists of 7 strains falling within Bacteroidales ("7 strains") and 4 strains of non-Bacteroidales: 2 Clostridiales, 1 Fusobacteriales and 1 Selenomonadales ("4 strains") (See FIG. 13 and Table 4).

Figure 14A:
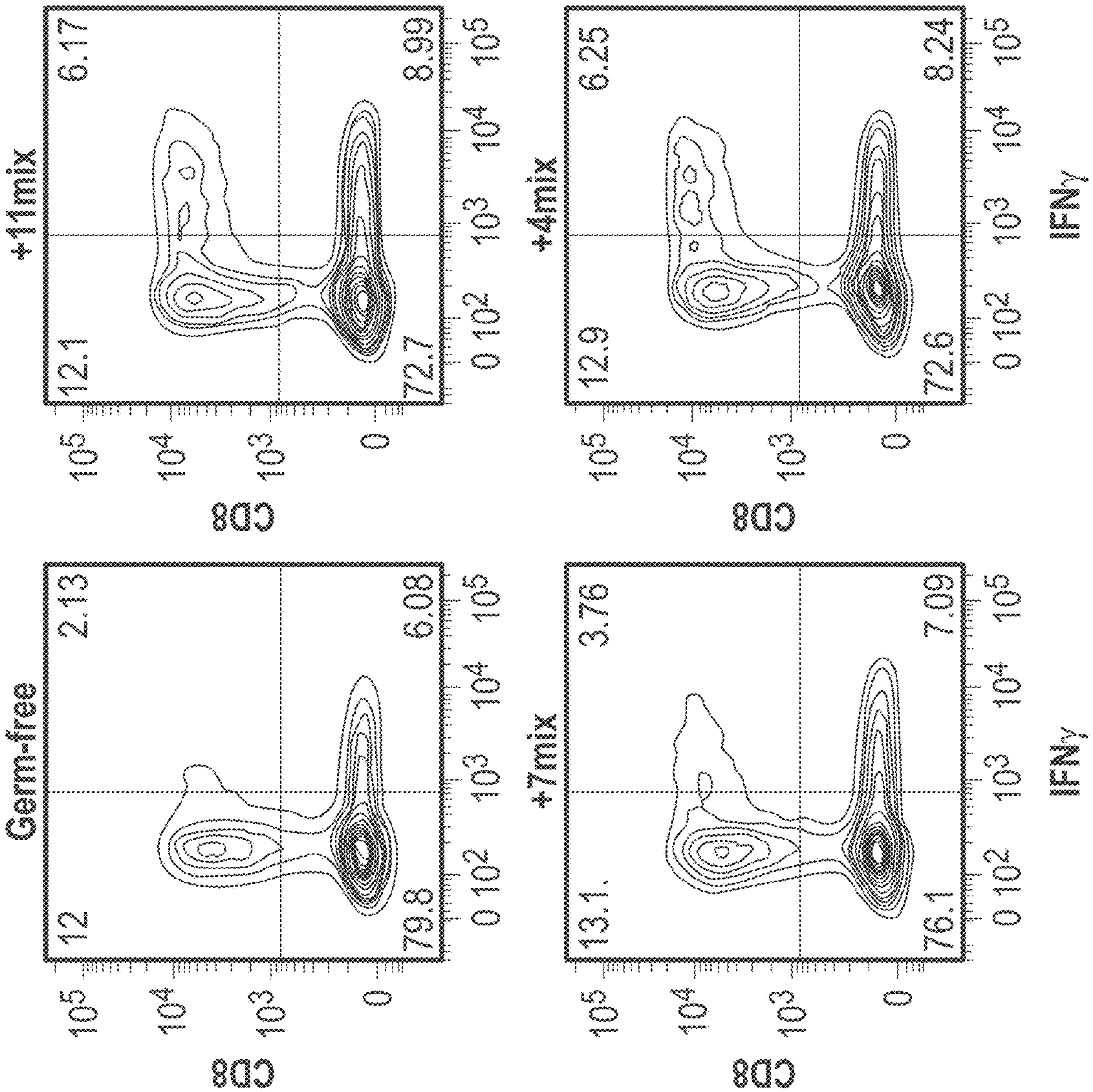
FIGS. 14A and 14B show data of the mixtures of the 11 strains, 7 or 4 strains mixtures listed in FIG. 13, which were orally administered to germ free mice. Four weeks later, lymphocytes were isolated from the lamina propria of the large intestine and stimulated with PMA/ionomycin for 3.5 hours. CD3, TCR β, CD8 and IFN γ were stained with antibodies and analyzed by flow cytometry.
Figure 14B:
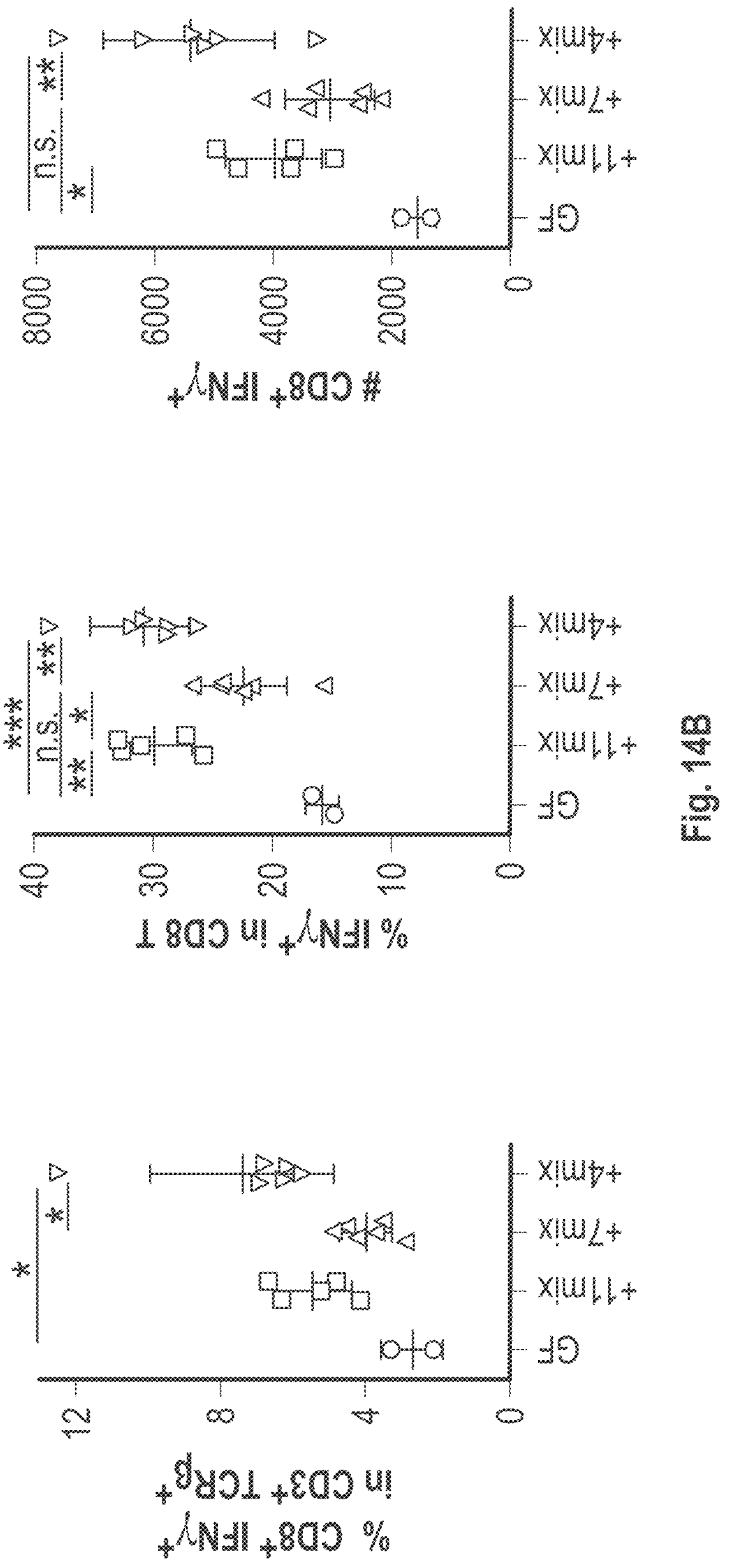

Inoculation with the mixture of 4 non-Bacteroidales strains ("4-mix") resulted in a strong accumulation of colonic IFN γ+CD8+ T cells, comparable to the level of colonic IFN γ+CD8+ T cells observed in mice colonized with the 11 mix. In contrast, colonization with 7 Bacteroidales strains ("7-mix") weakly induced IFN γ+CD8+ T cells (FIGS. 14A and 14B).

Figure 47A:
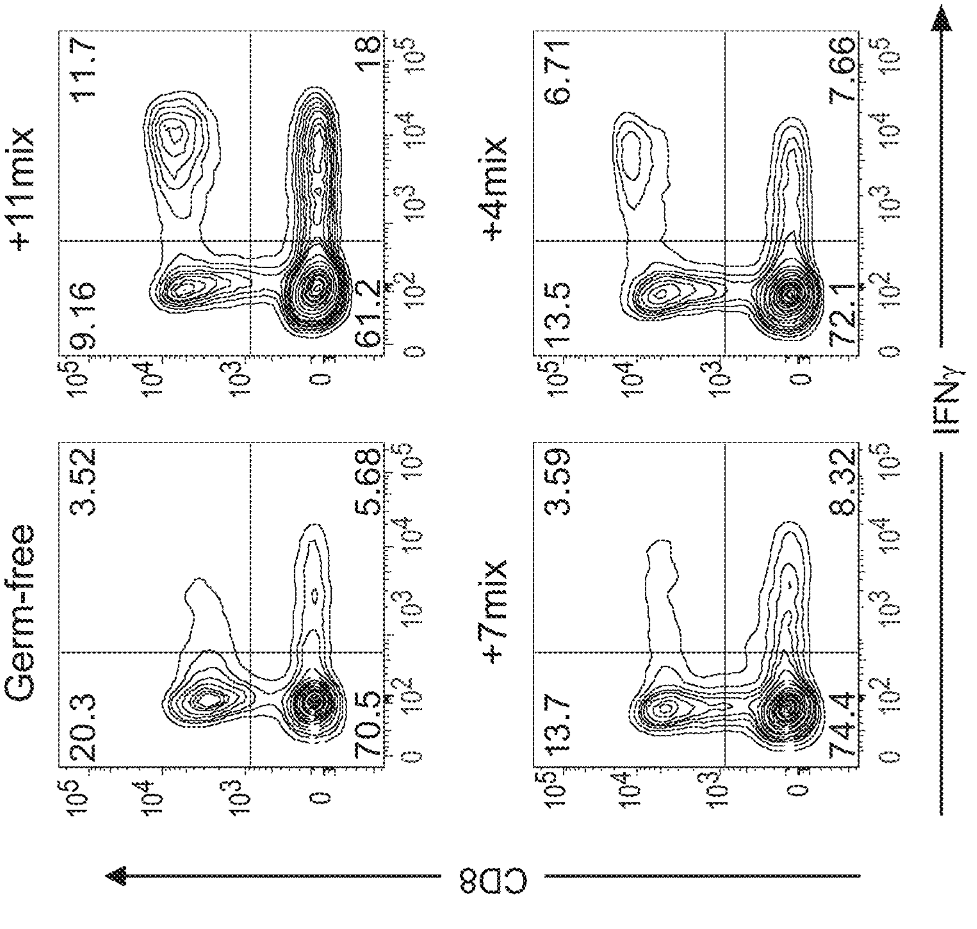
FIGS. 47A and 47B shows data relating to Example 2. The mixtures of the 11 strains, 7 or 4 strains mixtures listed in FIG. 13, were orally administered to germ free mice. Four weeks later, lymphocytes were isolated from the lamina propria of the large intestine and stimulated with PMA/ionomycin for 3.5 hours. CD3, TCR $\beta$, CD8 and IFN $\gamma$ were stained with antibodies and analyzed by flow cytometry (FIG. 47A). The expression of CD8 and IFN $\gamma$ by the gated CD3 and TCR $\beta$ positive cells of representative mice is show in FIG. 47B, as indicated by the percentage of IFN $\gamma$+ cells in CD8T cells. Each plot represents individual mice. *$P<0.05$, $P<0.01$, *$P<0.001$ (one-way ANOVA).
Figure 47B:
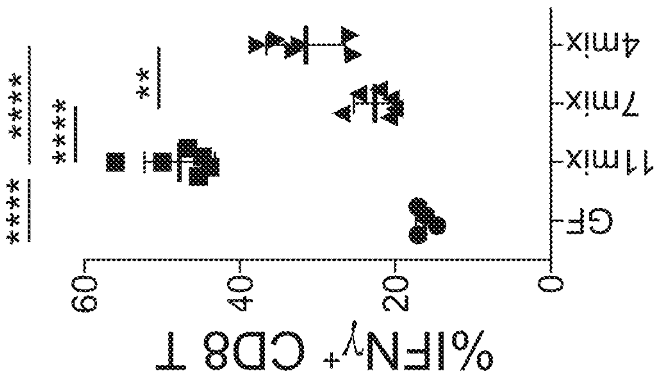

A repeat of the experiment is shown in FIG. 47, which shows that the 11-mix is more effective than either the 7-mix or the 4-mix. The data of the experiment shown in FIG. 47 have strong statistical support.

Identification of the bacterial species with the highest homology to each of the strains in the 4 mix is provided in Table 4, below.

TABLE 4

[Mixture of 4 strains]

| Strain # | SEQ ID NO | Strain ID | Species with highest homology | NCBI accession # of 16S locus | SEQ ID of NCBI 16S locus |
|---|---|---|---|---|---|
| 1 | 1 | 2G5 | *Phascolarctobacterium faecium* | LN998073 | 27 |
| 2 | 2 | 1A6 | *Fusobacterium ulcerans* | KR822463 | 28 |
| 5 | 5 | 2B1 | *Subdoligranulum sp.* | KM098109 | 31 |
| 10 | 10 | 1C1 | *Eubacterum limosum* | NR113248 | 36 |

Example 3: Anti-Cancer Characteristics of CD8+ T-Cell Inducing Bacterial Cocktail To investigate whether colonization with the 11 mix could enhance anticancer immune responses, a subcutaneous tumor model was used. SPF mice were treated with mixture of antibiotics (1 g/L ampicillin, 0.5 g/L vancomycin, 1 g/L metronidazole, and 1 g/L neomycin) via the drinking water from day −7 to day 2. A MC38 colon cancer cell line (3×105 cells per mouse) was subcutaneously injected into the right flank of mice at day 0. Antibiotics treatment was stopped at day 2, and mice were gavaged with fecal microbiota from SPF mice mixed with or without 11-mix on day 3. For the 11-mix treatment groups, mice were gavaged with the 11 mix two or three times per week until the end of the experiment. For the anti-PD-1 antibody (Ab) treatment groups, mice were intraperitoneally injected with 200 μg of anti-PD1 monoclonal Ab (clone J43) at days 3, 5 and 9. Tumor size was measured using a caliper and tumor volume was determined as length×width 2×0.5.

Figure 15:
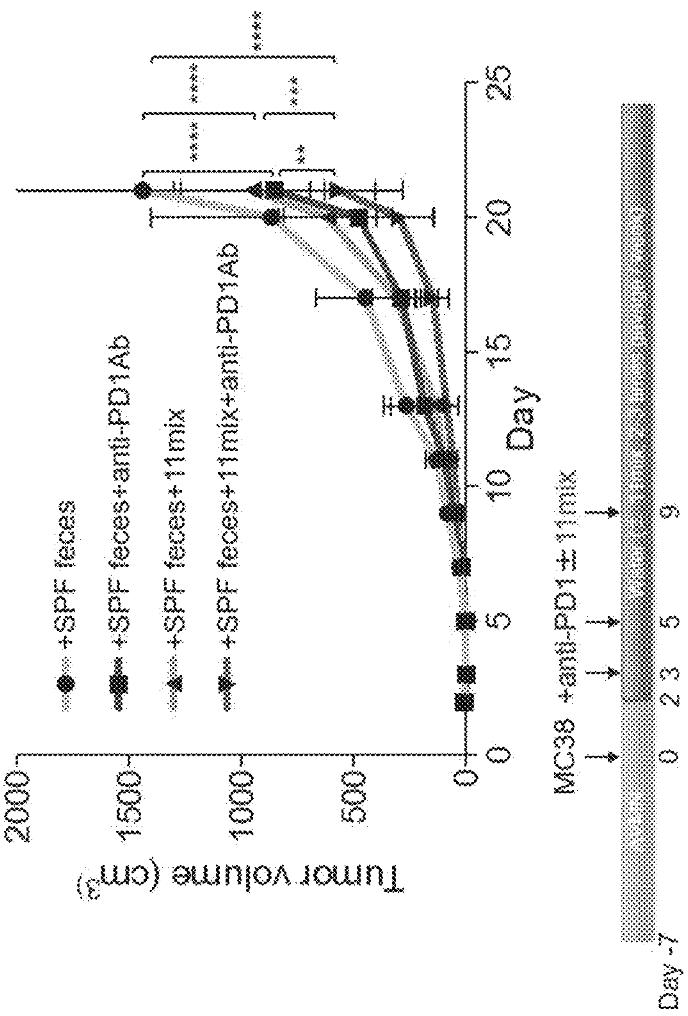
FIG. 15 shows data on experiments with six weeks-old SPF C57BL/6 mice, which were purchased from Japan SLC and treated with antibiotics (1 g/L Ampicillin, 0.5 g/L Vancomycin, 1 g/L Metronidazole and 1 g/L Neomycin; "AVMN") in their drinking water. Then, mice were subcutaneously injected into the right flank with 3×105 MC38 tumor cells line at day 0. When tumors appeared and were palpable, antibiotics treatment was stopped (day 2). Mice were injected intraperitoneally with 200 μg of anti-PD1 antibody (clone J43) at day 3, 5 and 9 ("+anti-PD1Ab"). Mice were gavaged with the 11 mix 2 or 3 times a week including day 3, 5 and 9 ("+11 mix"). Tumor size was measured using a caliper and tumor volume was determined as length×width2×0.5. P<0.01, *P<0.001, ****P<0.0001 (two-way ANOVA).
Figure 16A:
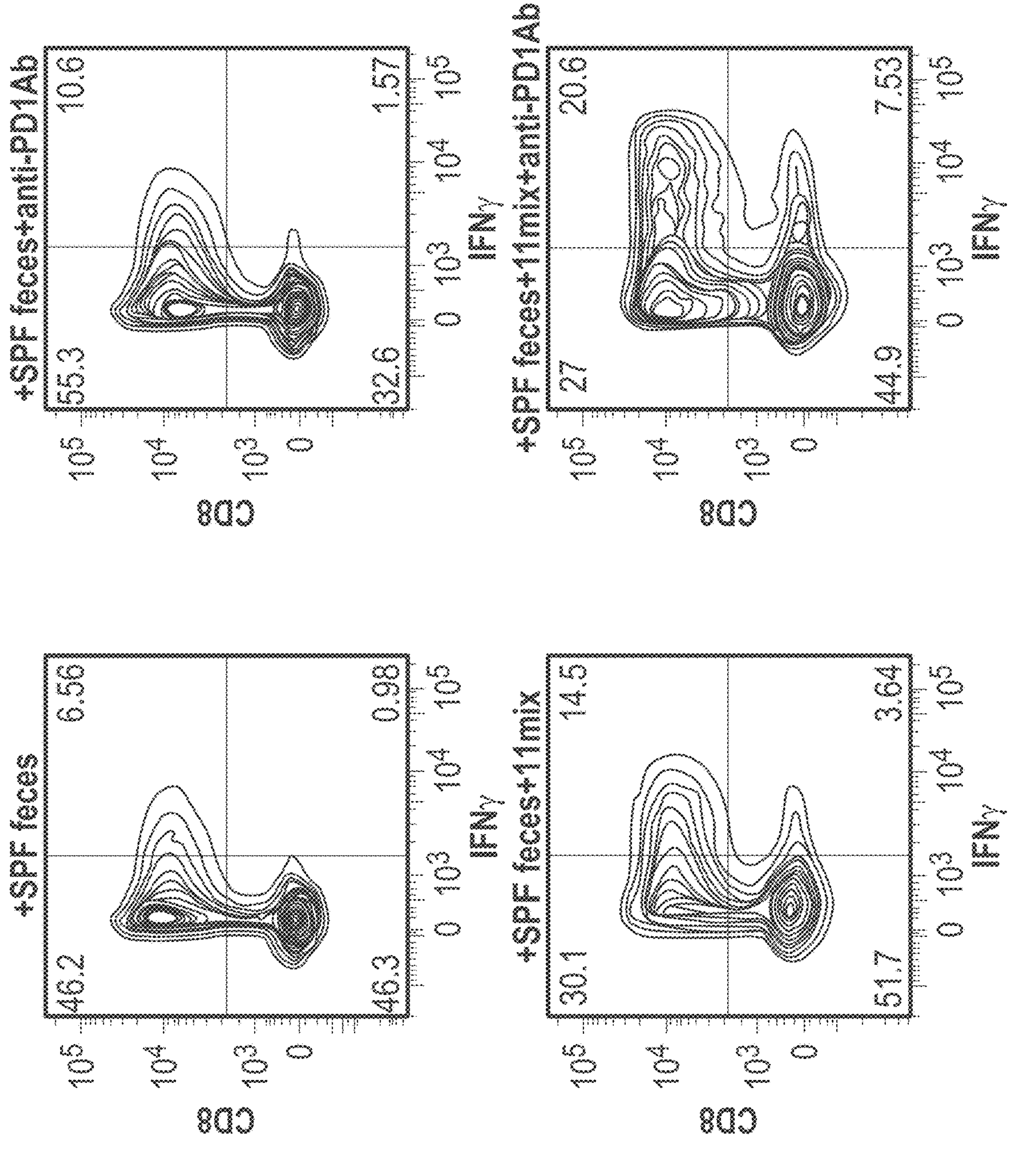
FIGS. 16A and 16B show data on lymphocytes isolated from tumor cells. At day 23 or 27, lymphocytes were isolated from tumors and stimulated with PMA/ionomycin for 4 hours. CD3, TCRβ, CD8 and IFN γ were stained with antibodies and analyzed by flow cytometry.
Figure 16B:
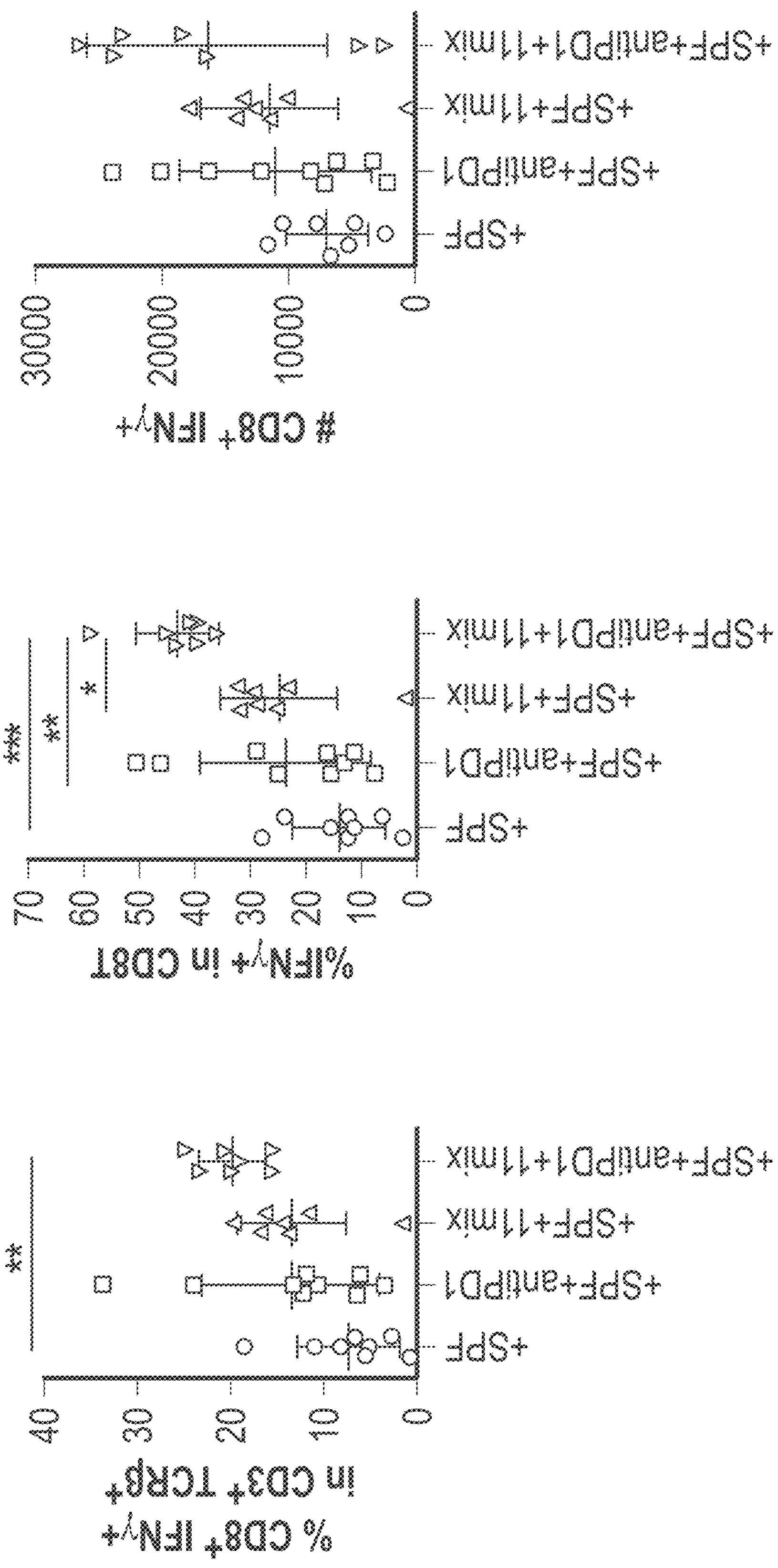
Figure 17A:
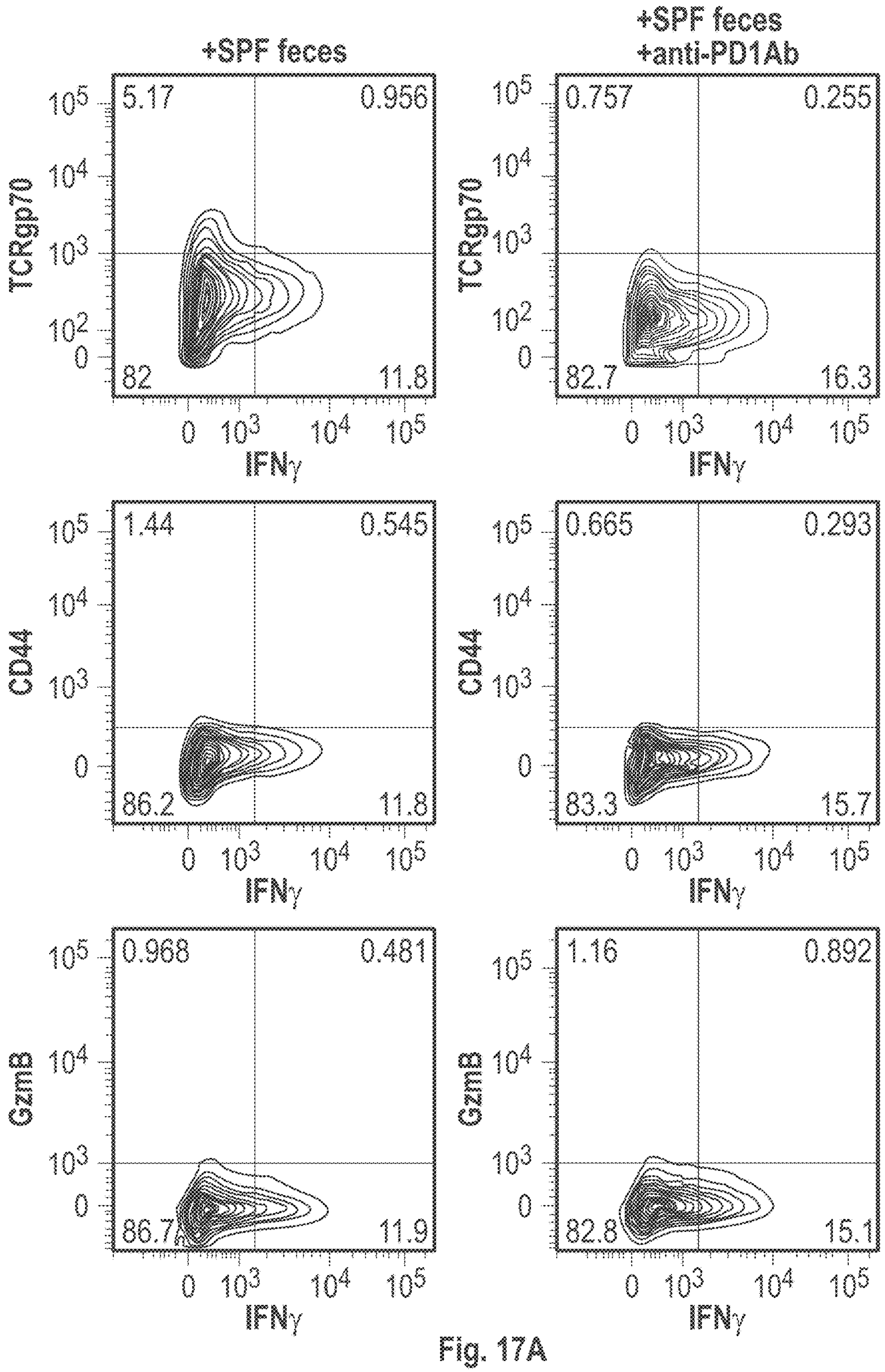
FIGS. 17A, 17B show data on lymphocytes isolated from tumor cells. At day 23 or 27, lymphocytes were isolated from tumors and stimulated with PMA/ionomycin for 4 hours. CD3, TCRβ, CD8, gp70 MC38 peptide (KSPWFTTL (SEQ ID NO: 53))-specific TCR β, CD44, GzmB and IFN γ were stained with antibodies and peptide-H2 Kb tetramer, and analyzed by flow cytometry.
Figure 17A:
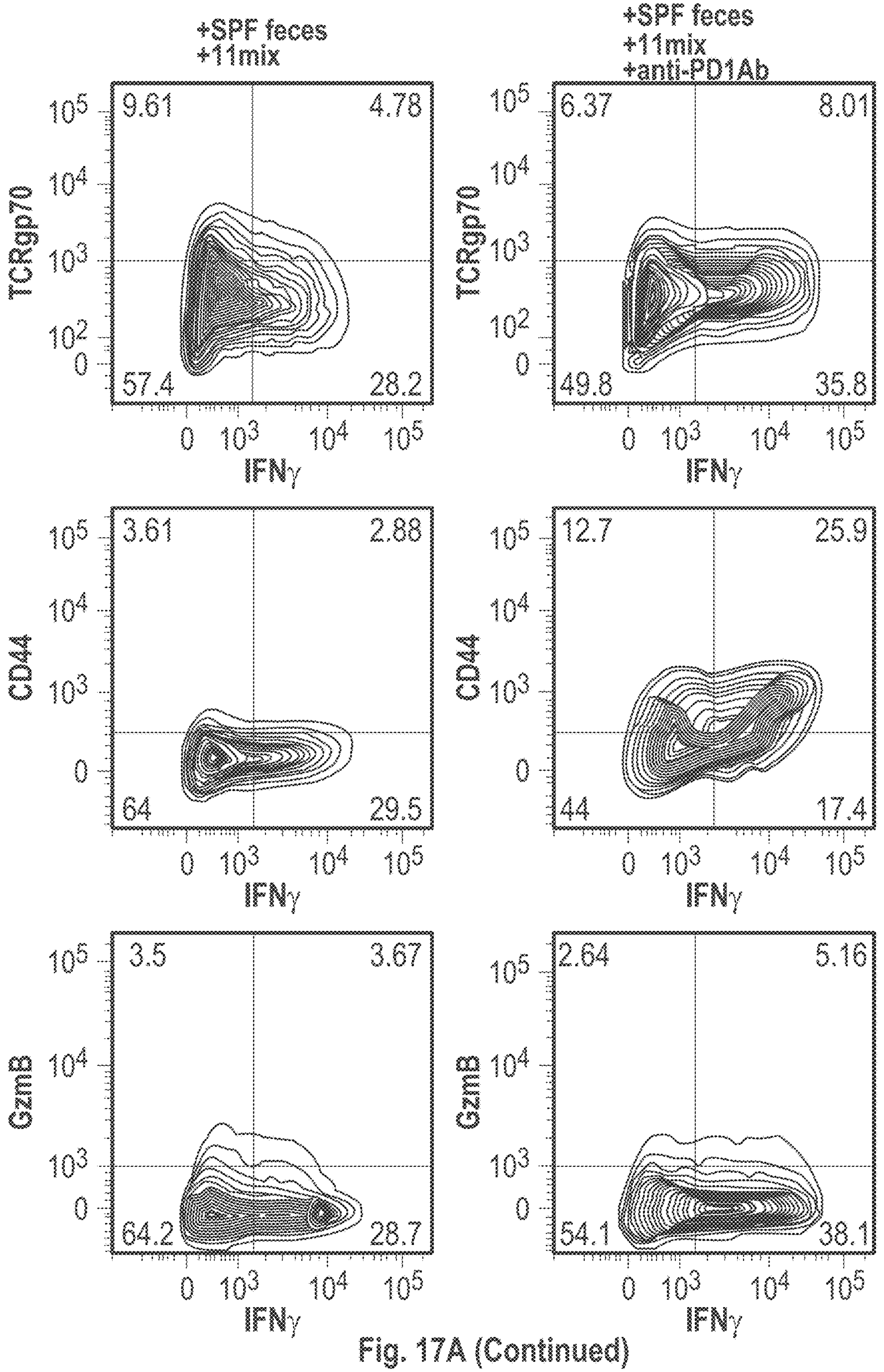
Figure 17B:
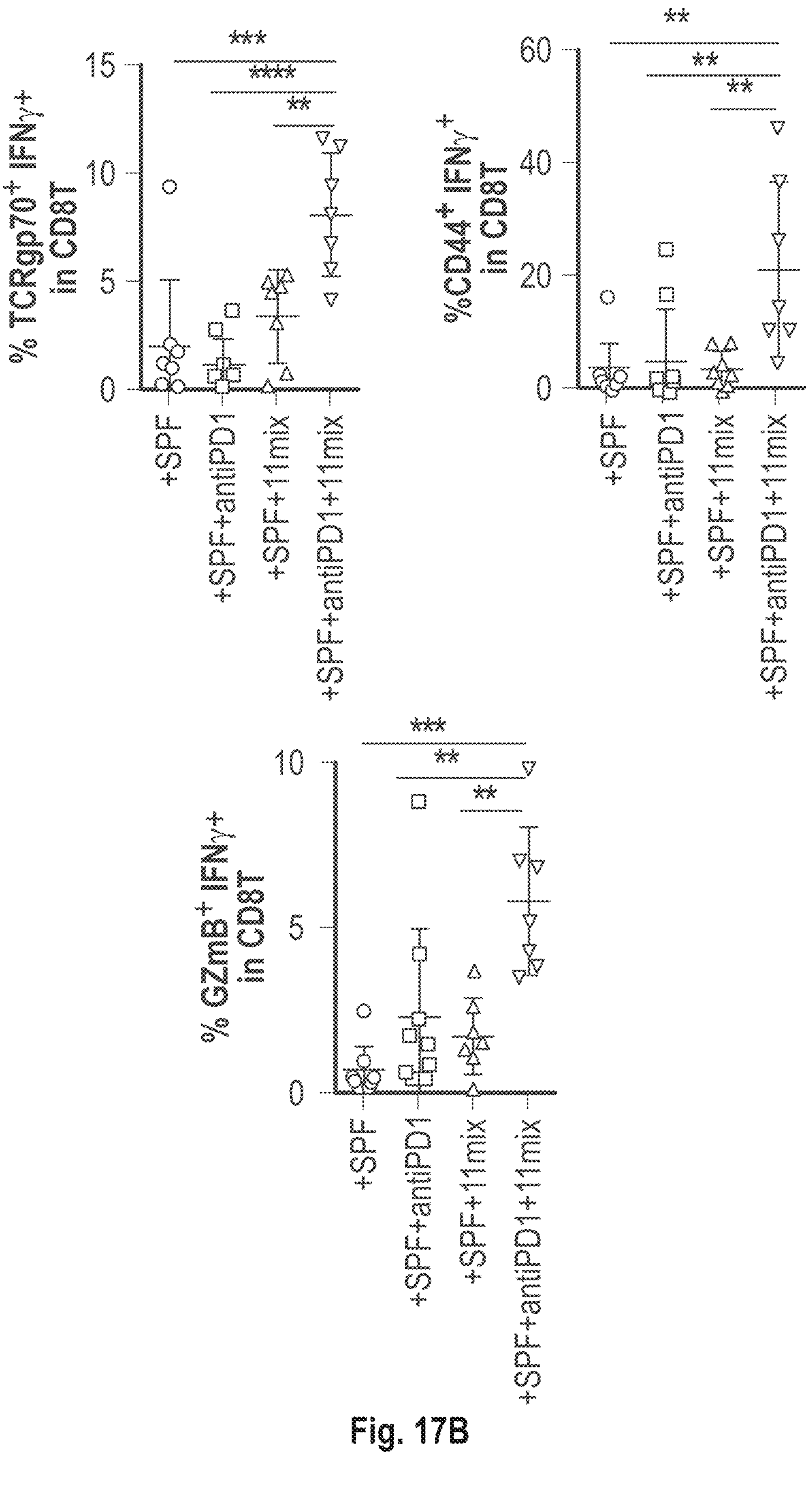
Figure 18:
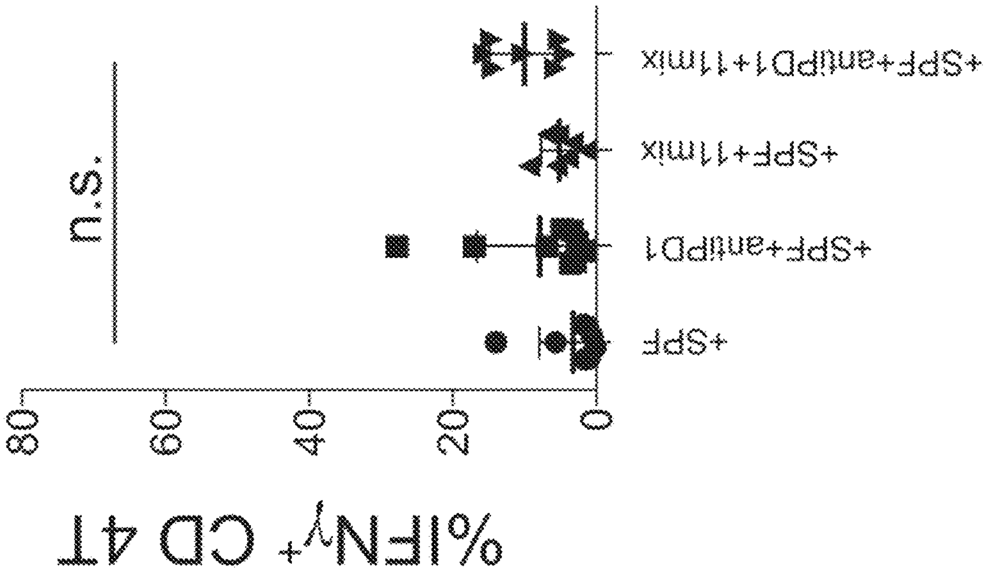
FIG. 18 shows data on lymphocytes isolated from tumor cells. The effect on IFN γ+CD4 T cells is shown in FIG. 18.

Treatment with the 11 mix alone (i.e., without anti-PD1 Ab) significantly suppressed MC38 tumor growth (see FIG. 15). The combination of the 11 mix and anti-PD1 Ab exhibited the strongest suppressive effect on the growth of tumor cells (see FIG. 15). Treatment with the 11 mix and anti-PD1 Ab resulted in elevated accumulation of IFN γ+CD8+ T cells in the MC38 tumor mass (see FIGS. 16A and 16B). A subset of the IFN γ+CD8+ T cells in tumors expressed T-cell receptors specific for gp70p15E604-611 (KSPWFTTL; SEQ ID NO: 53), which is an immunodominant epitope of MC38 (FIG. 17A). Furthermore, a subset of IFN γ+CD8+ T cells expressed CD44 and Granzyme B, suggesting that the IFN γ+CD8+ T cells accumulated in the tumor included tumor-specific and memory-type cytotoxic CD8+ T cells (see FIGS. 17A and 17B). The effect on IFN γ+CD4 T cells is shown in FIG. 18.

Figure 19:
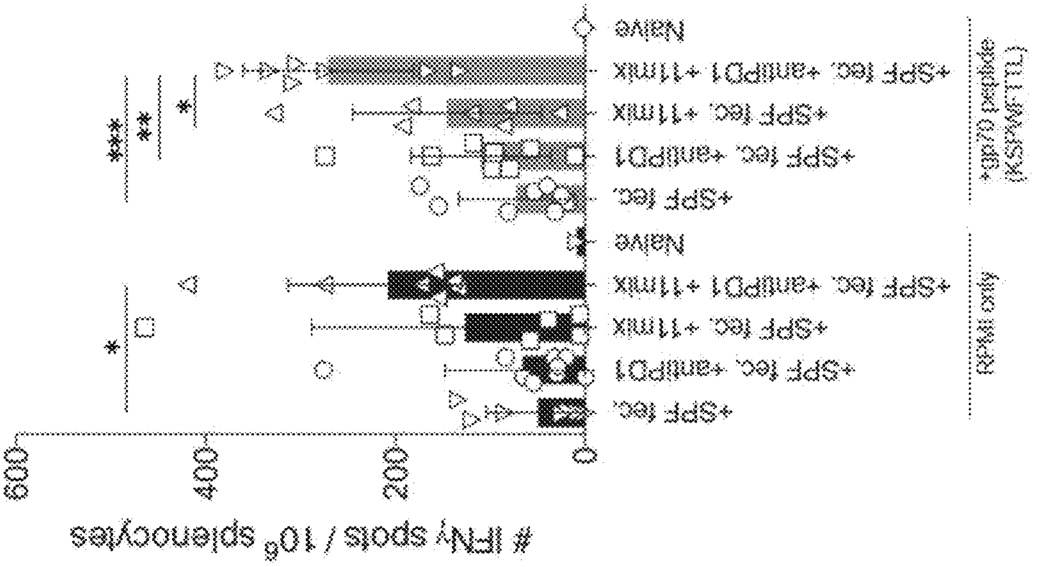
FIG. 19 shows data on lymphocytes isolated from tumor cells. At day 23 or 27, whole splenocytes were isolated and plated at 106 cells per well and stimulated with 0.5 μg/mL gp70 MC38 peptide (KSPWFTTL (SEQ ID NO: 53)) for 36 hours at 37° C. Spots were developed using the Mouse IFN γ ELISPOT Ready-SET Go!R kit (eBioscience), and the number of spots was measured using an Immunospot Series 4 Analyzer and analyzed using ImmunoSpot software (Cellular Technology). Each plot represents individual mice. "Naive" is a mouse which was not treated with antibiotics, not injected with MC38 cells and not treated with 11mix and anti-PD1 antibody. *P<0.05, P<0.01, *P<0.001 (one-way ANOVA).
Figure 21:
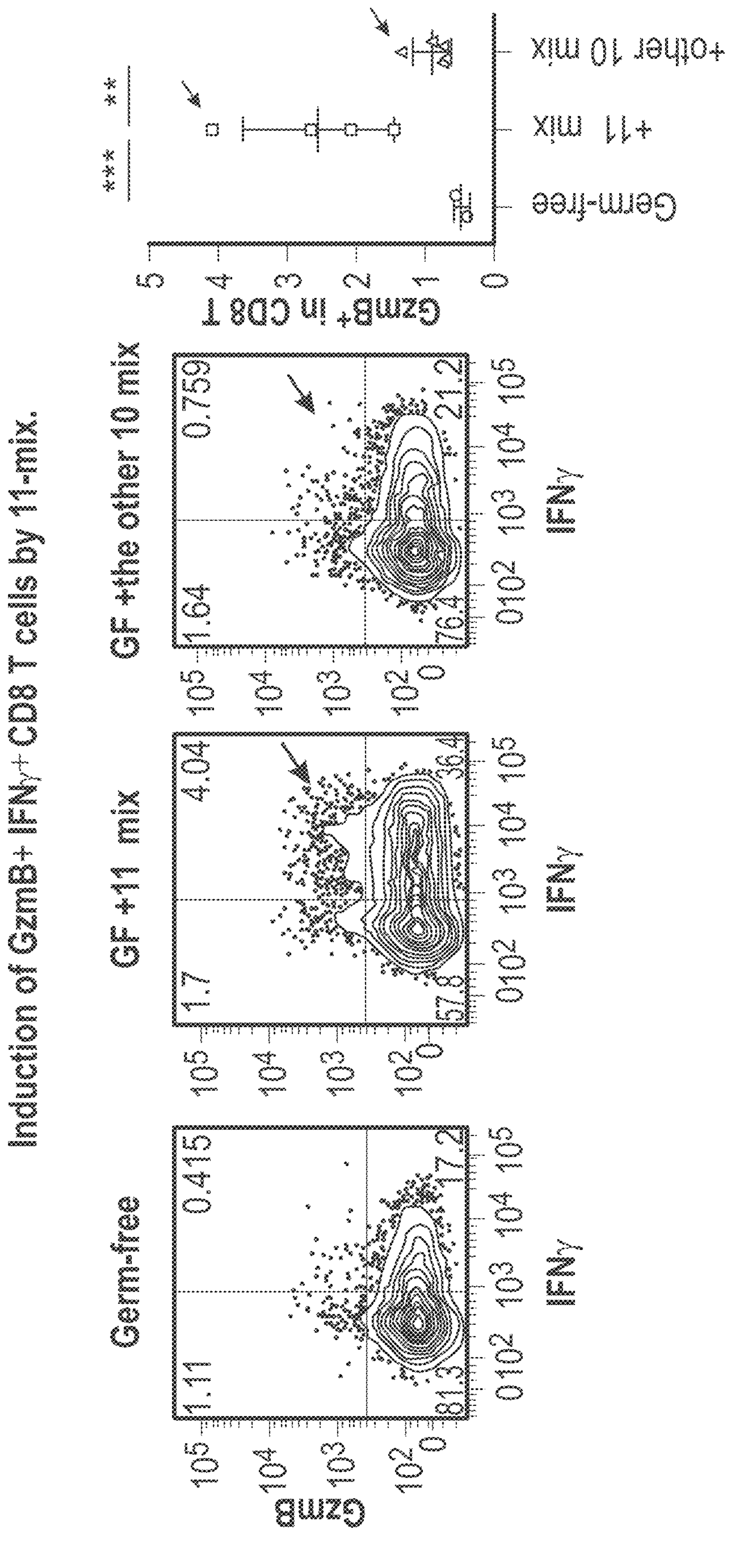
FIG. 21 shows data on induction of GzmB+ IFNγ+CD8 T cells by 11-mix bacterial strains.
Figure 22:
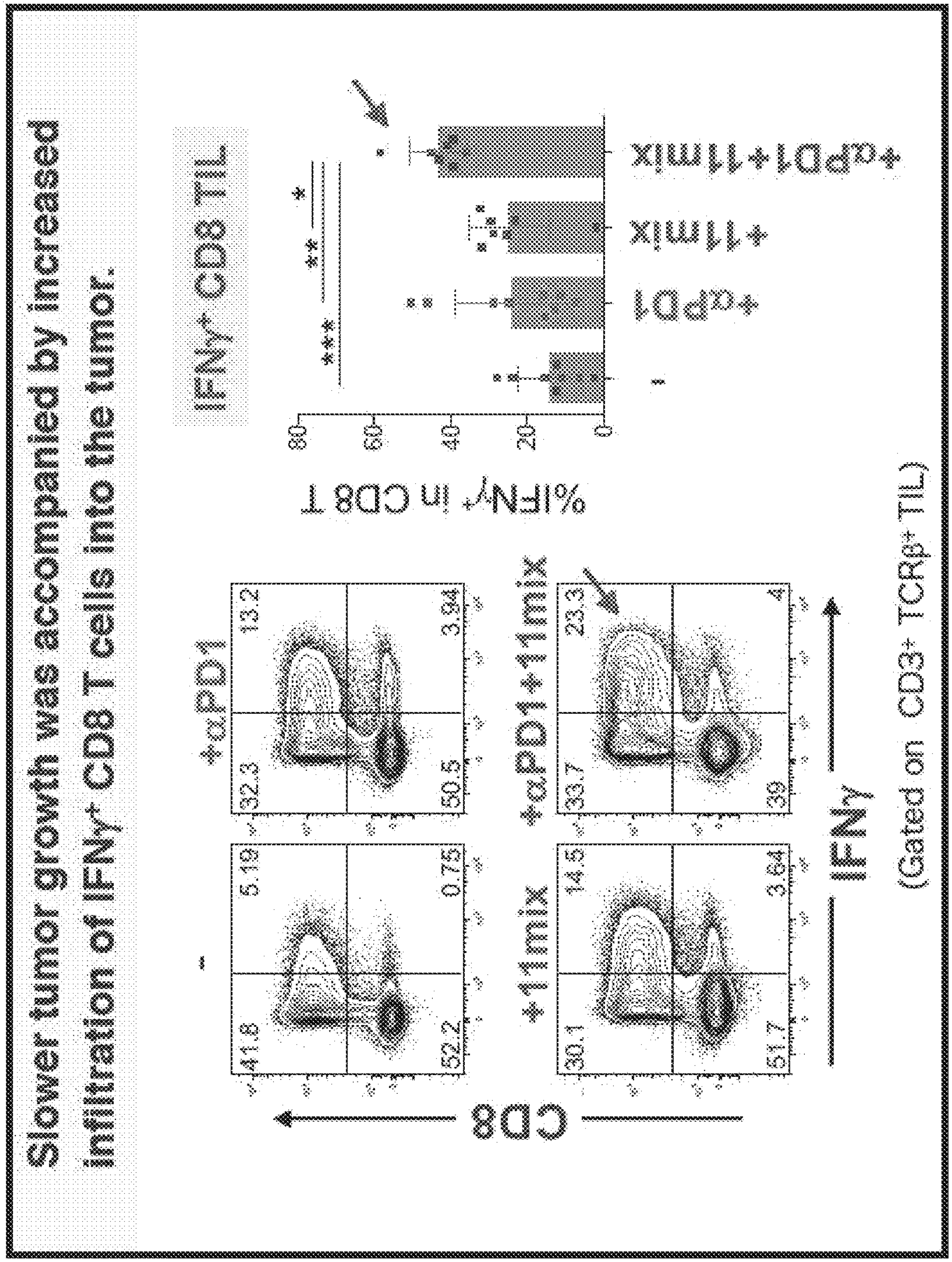
FIG. 22 shows that slower tumor growth was accompanied by increased infiltration of IFN γ+CD8 T cells into the tumor.
Figure 23:
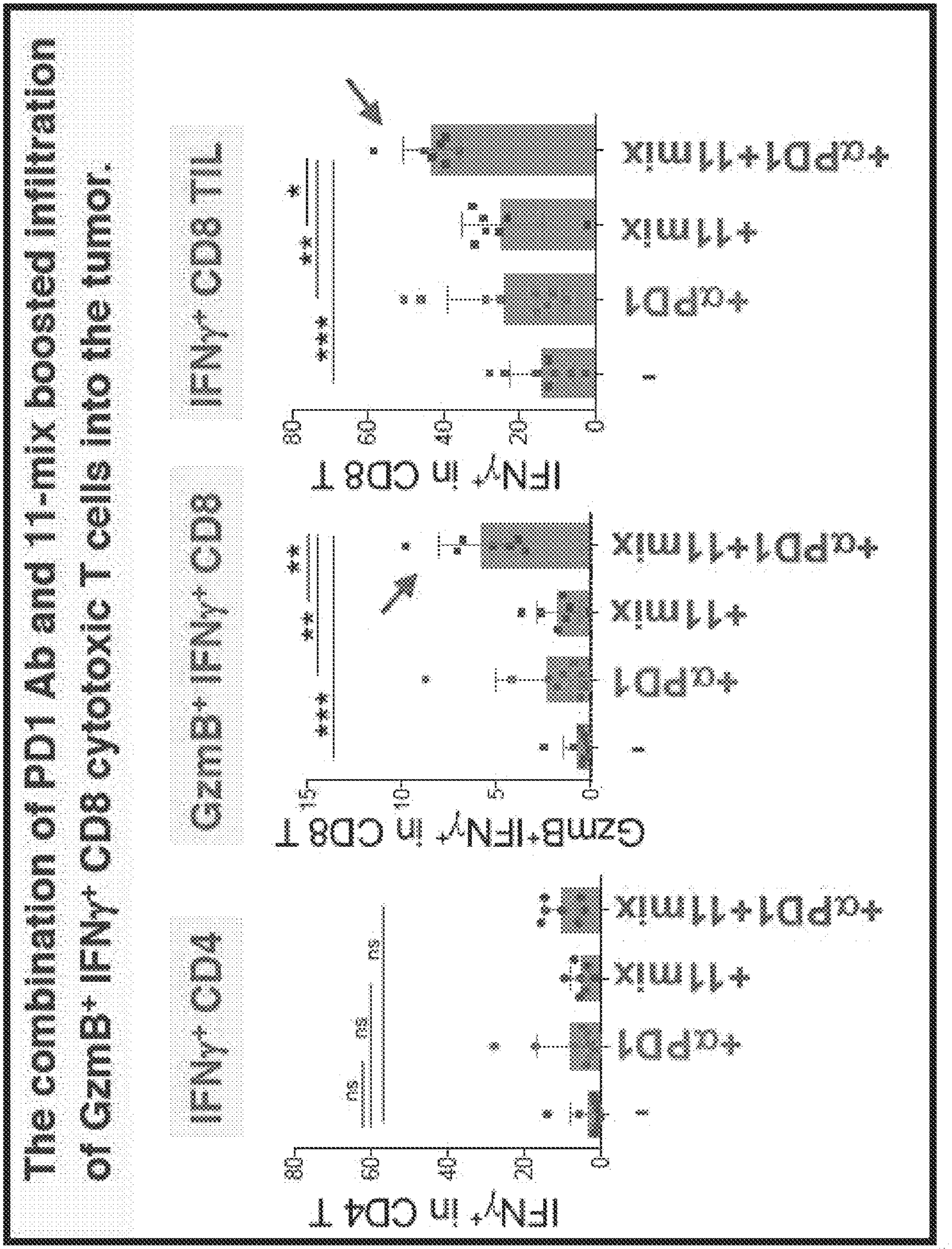
FIG. 23 shows that the combination of αPD1 Ab and 11-mix bacterial strains boosted infiltration of GzmB+ IFN γ+CD8 cytotoxic T cells into the tumor.

Oral inoculation with the 11 mix resulted in the increased numbers of IFN γ-producing splenocytes, even in the absence of tumor antigen stimulation (see FIG. 19).

These results show that treatment with 11 mix in combination with, or without, anti-PD1 Ab systemically activate CD8 T cells that respond to tumor cells.

Figure 24:
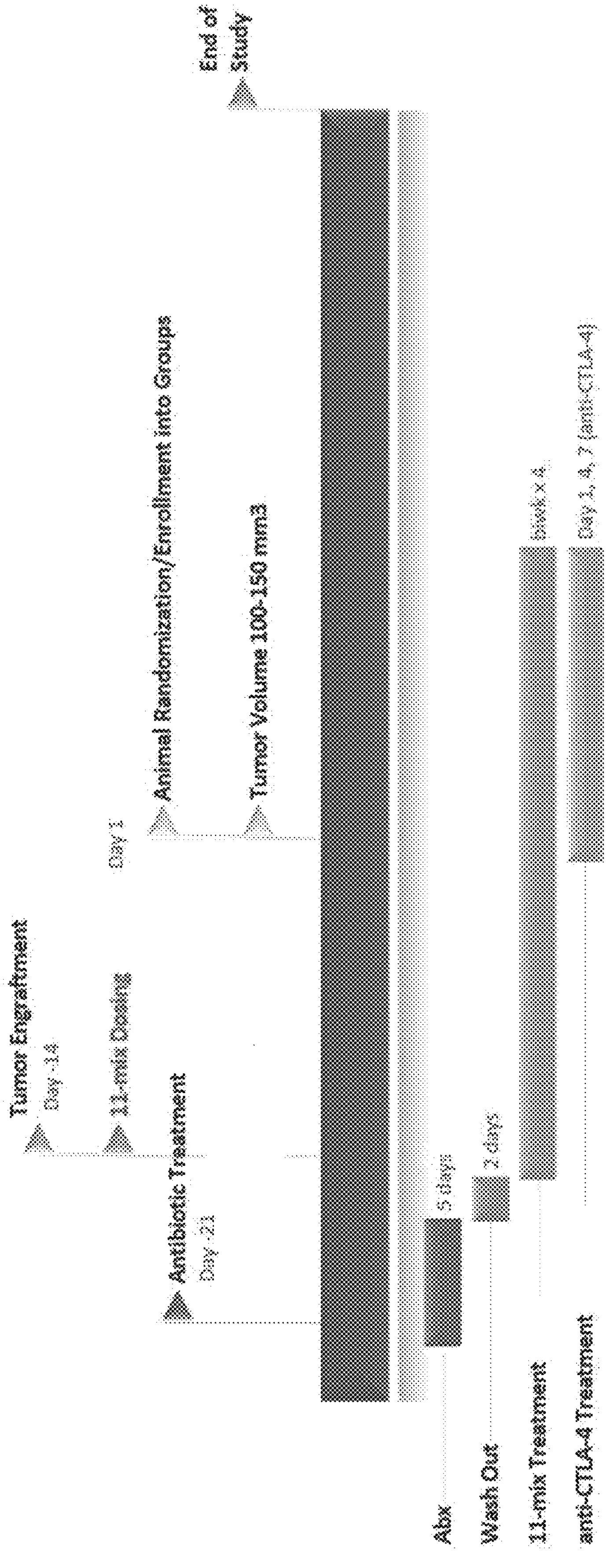
FIG. 24 shows a schematic of the experimental plan described in Example 4 relating to treatment with the 11-mix and/or an anti-CTLA-4 antibody.
Figure 25:
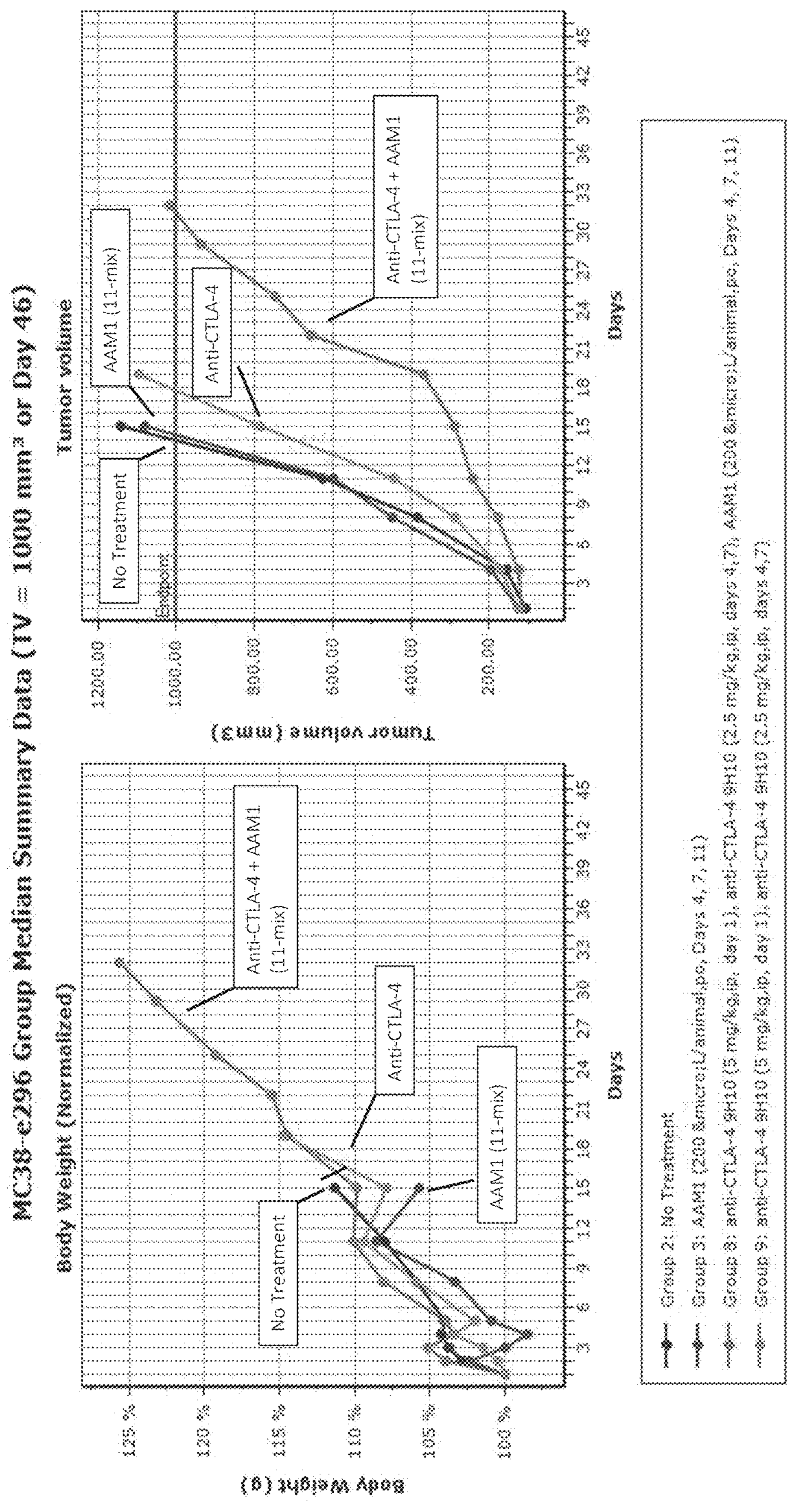
FIG. 25 shows body weight of mice that received the combination of a CTLA-4 Ab and the 11-mix of bacterial strains (left panel). Mice that received the combination of a CTLA-4 Ab and the 11-mix of bacterial strains had a significant reduction in tumor growth (right panel) in the experiment presented in FIG. 24 (Example 4).
Figure 26:
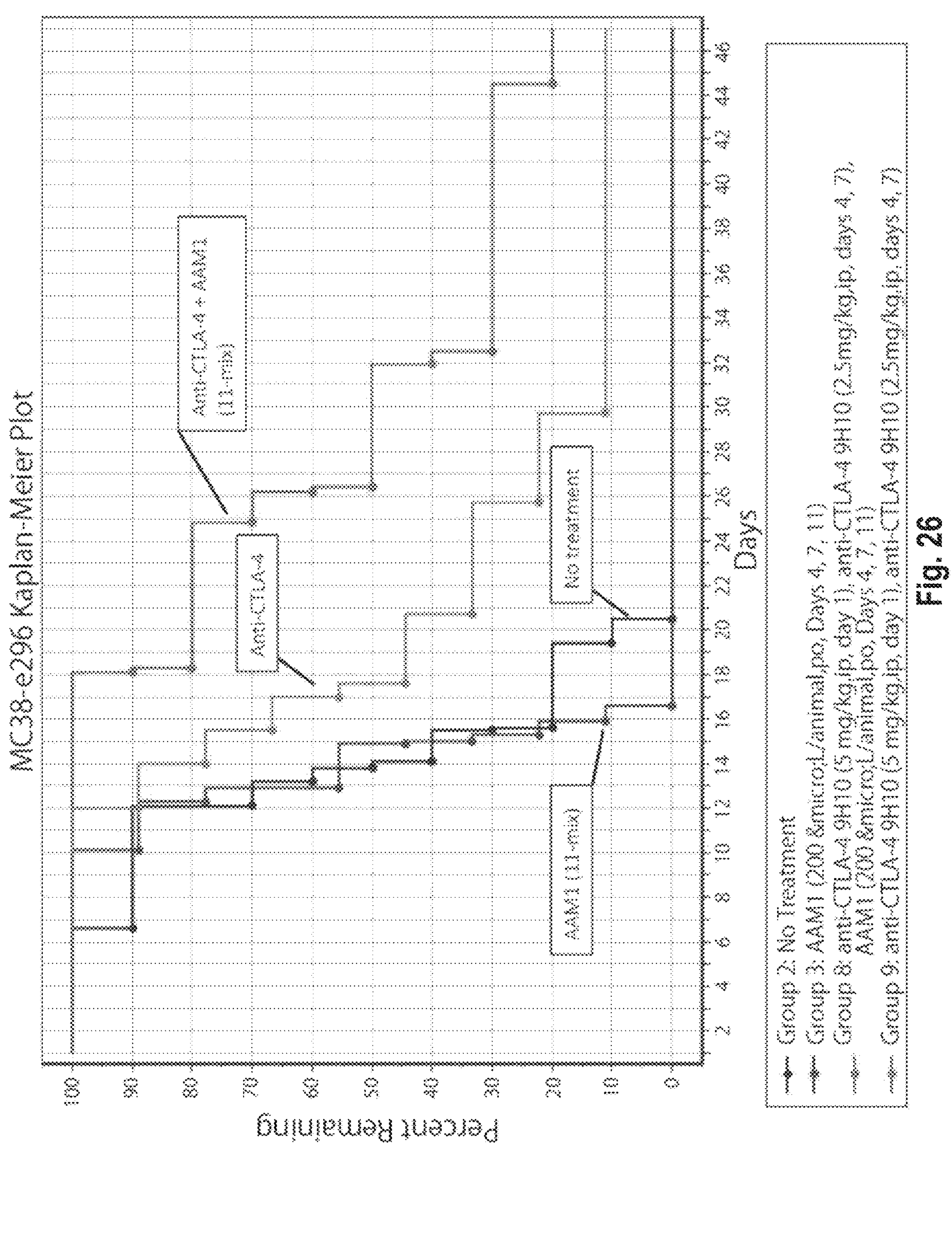
FIG. 26 shows that the combination of αCTLA-4 Ab and the 11-mix of bacterial strains had a significant effect on the survival of the mice in the experiment presented in FIG. 24 (Example 4).

Example 4: Anti-Cancer Characteristics of CD8+ T-Cell Inducing Bacterial Cocktail in Combination with CTLA-4 Immune Checkpoint Inhibitor To investigate whether colonization with the 11-mix in combination with immune checkpoint inhibitor CTLA4 could enhance anticancer immune response, a subcutaneous tumor model was used (FIG. 24). Mice were treated with mixture of antibiotics for 5 days (from day −21 to day −16), followed by a two-day period to wash out the antibiotics. A MC38 colon cancer cell line (3×105 cells per mouse) was subcutaneously injected into the right flank of mice at day −14. The animals were randomized into the following treatment groups:

Group 1: No antibiotics, no treatments (provides a reference for standard progression of MC38 tumor model);

Group 2: Antibiotic pre-treatment, no treatment (provides a reference for the progression of the MC38 tumor model with antibiotic pre-treatment);

Group 3: 11-mix monotherapy (referred to as AAM1 in FIGS. 25 and 26);

Group 8: anti-CTLA-4 antibody (9H10) and 11-mix (referred to as AAM1 in FIGS. 25 and 26) combination;

Group 9: anti-CTLA-4 antibody (9H10) monotherapy.

Bacterial cocktail treatments were also begun on day −14 and administered biweekly 4 times. For groups receiving the CTLA-4 immune checkpoint inhibitor, the treatment was begun once the tumor volume reached approximately 100 mm3 (100-150 mm3). The anti-CTLA-4 antibody was administered on days 1, 4, and 7. The mice were assessed for weight and survival through the course of the experiment. Tumor size and volume were measured.

Tumor Measurements

Figure 27:
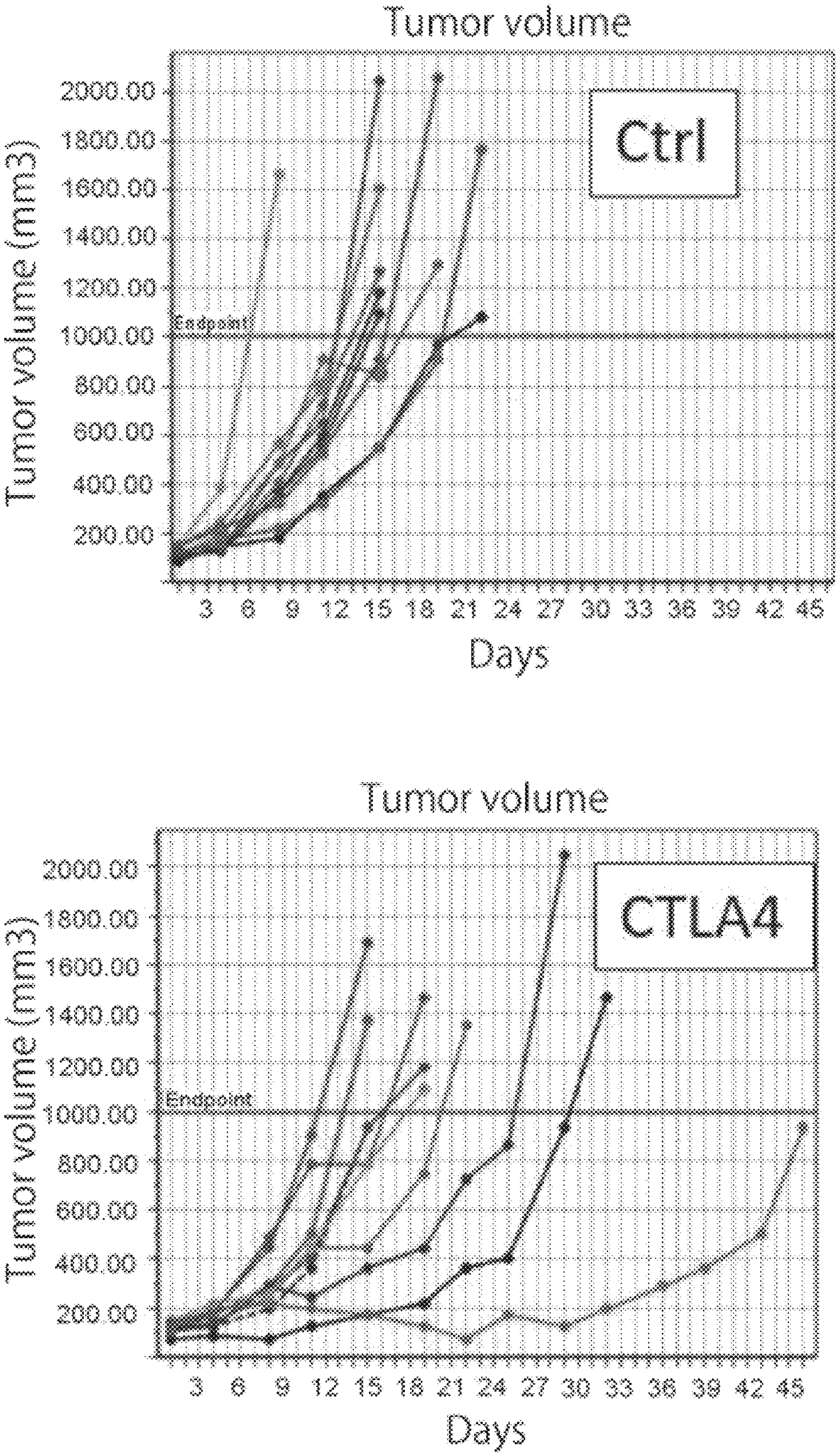
FIG. 27 shows tumor volume plots of individual mice treated in the experiments described in Example 4 (control, 11-mix; αCTLA-4 Ab; 11-mix+αCTLA-4 Ab).

The group of mice that received the anti-CTLA-4 antibody alone (Group 9) had slightly reduced tumor growth compared to control mice. The combination of the 11-mix (referred to as "AAM1" in FIG. 25) and the anti-CTLA-4 antibody (Group 8) significantly reduced the tumor growth as compared to the 11-mix on its own and as compared to the anti-CTLA-4 antibody on its own. See FIG. 25. Tumor volume plots of individual mice are shown in FIG. 27.

Survival

The group of mice that received the anti-CTLA-4 antibody alone had slightly increased survival compared to control mice. The 11-mix by itself had no impact on survival. The combination of the 11-mix (referred to as "AAM1" in FIG. 26) and the anti-CTLA-4 antibody significantly enhanced survival of the treated mice (Group 8). See FIG. 26.

Figure 28:
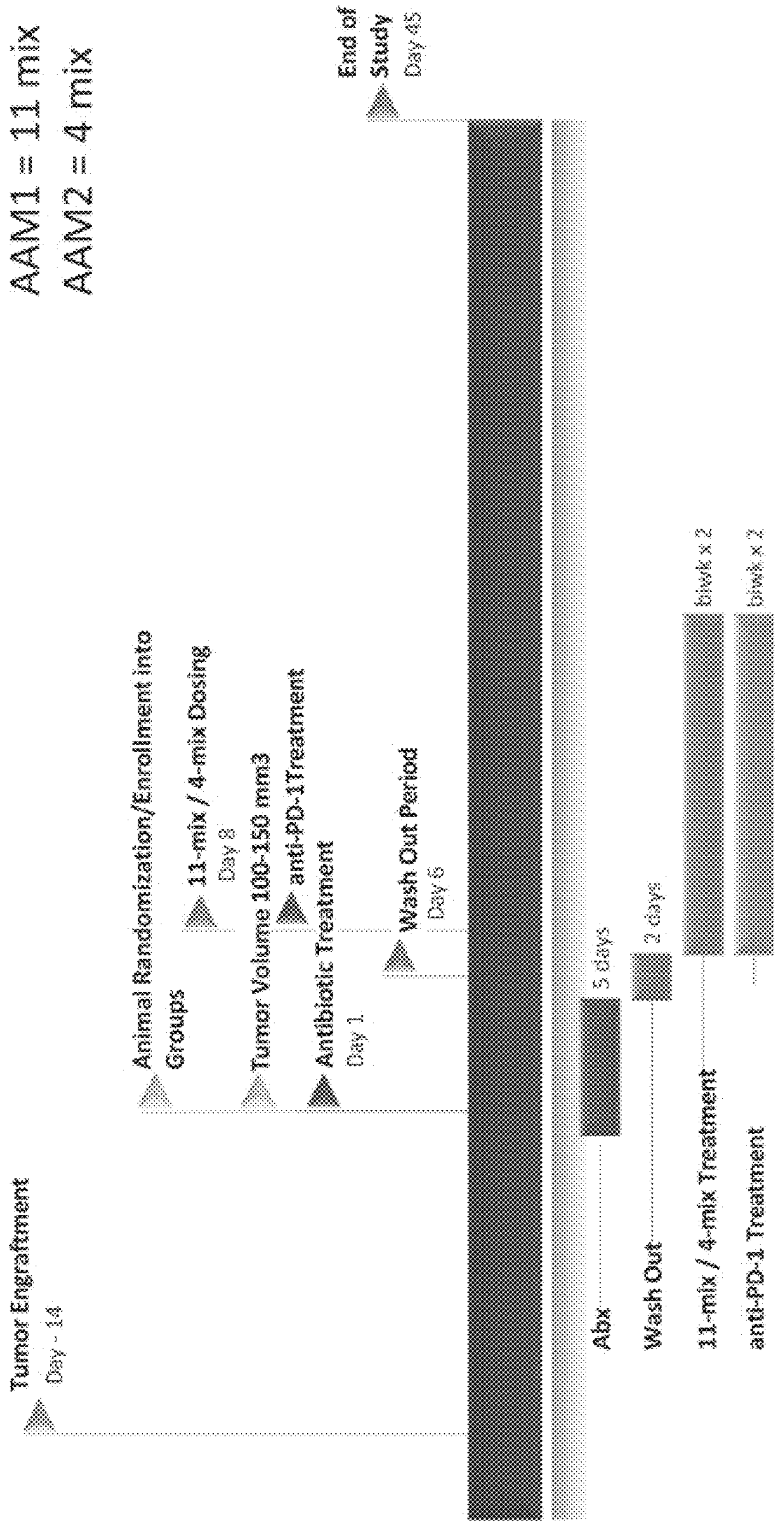
FIG. 28 shows a schematic of the experimental plan described in Example 5 relating to treatment with the 11-mix or 4-mix and/or an anti-PD-1 antibody.
Figure 29:
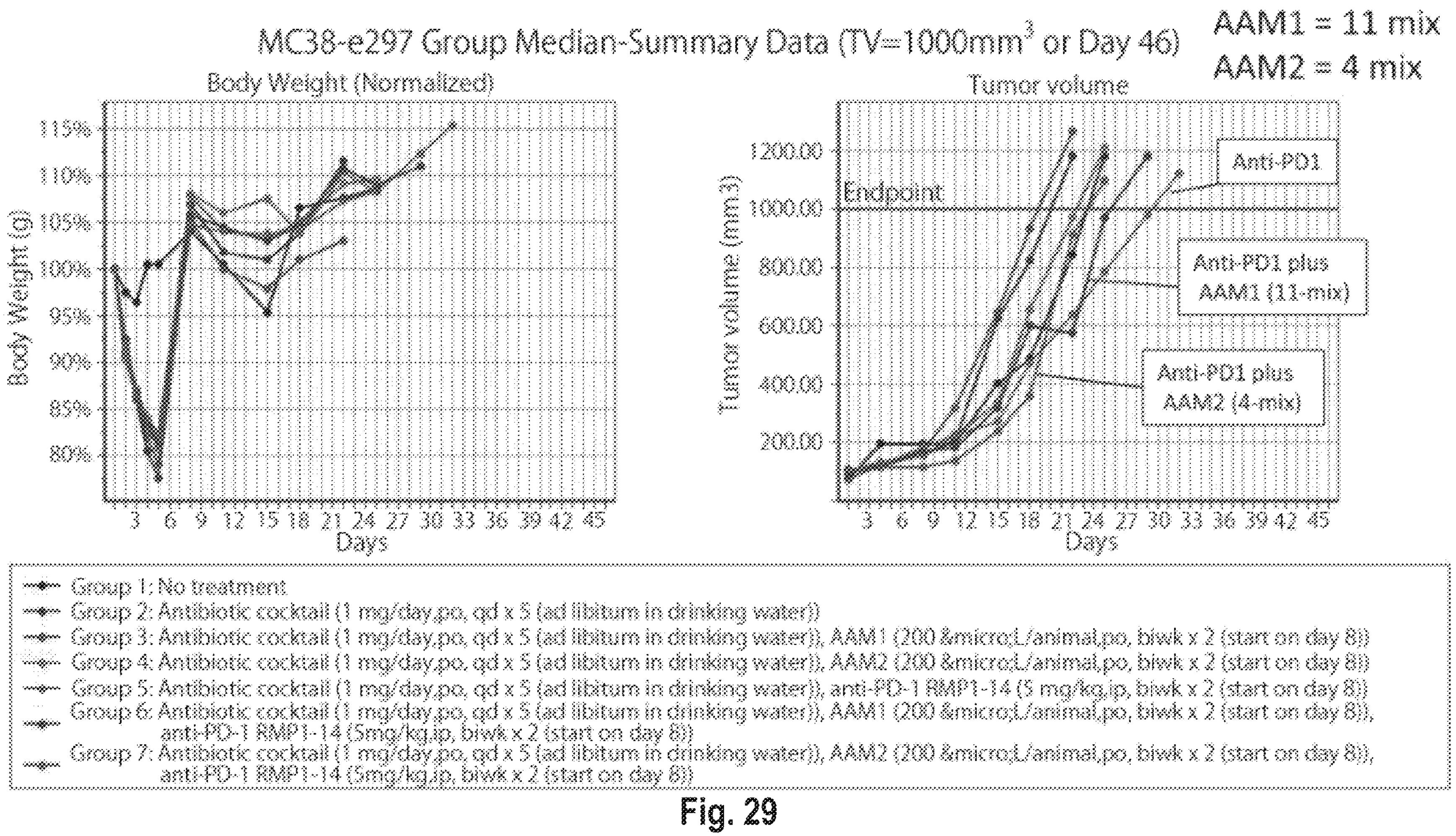
FIG. 29 shows body weight (left panel) and tumor volume (right panel) of mice that received the combination of α PD1 Ab and the 4-mix of bacterial strains or αPD1 Ab and the 11-mix of bacterial strains, and the various control groups.

Example 5: Anti-Cancer Characteristics of CD8+ T-Cell Inducing Bacterial Cocktails in Combination with an Anti-PD1 Antibody To investigate whether colonization with the 4-mix or 11-mix in combination with immune checkpoint inhibitor anti-PD1 could enhance anticancer immune responses in the absence of antibiotic pretreatment and prior engraftment, a MC38 colon cancer cell line (3×105 cells per mouse) was subcutaneously injected into the right flank of mice at day −14 (See FIG. 28). The animals were randomized into the following treatment groups:

Group 1: No treatment;

Group 3: 11-mix monotherapy (referred to as "AAM1" in FIGS. 28 and 29);

Group 4: 4-mix monotherapy (referred to as "AAM2" in FIGS. 28 and 29);

Group 5: anti-PD1 antibody (RMP1-14) monotherapy;

Group 6: anti-PD1 antibody (RMP1-14) and 11-mix (referred to as "AAM1" in FIGS. 28 and 29) combination; and Group 7: anti-PD1 antibody (RMP1-14) and 4-mix (referred to as "AAM2" in FIGS. 28 and 29) combination.

The treatments were begun at day 1 (tumor volume approximately 100-150 mm3). Bacterial cocktail treatment and the anti-PD1 antibody were administered biweekly twice. The mice were assessed for weight and survival through the course of the experiment. Tumor size and volume were measured.

Tumor Measurement

Figure 30:
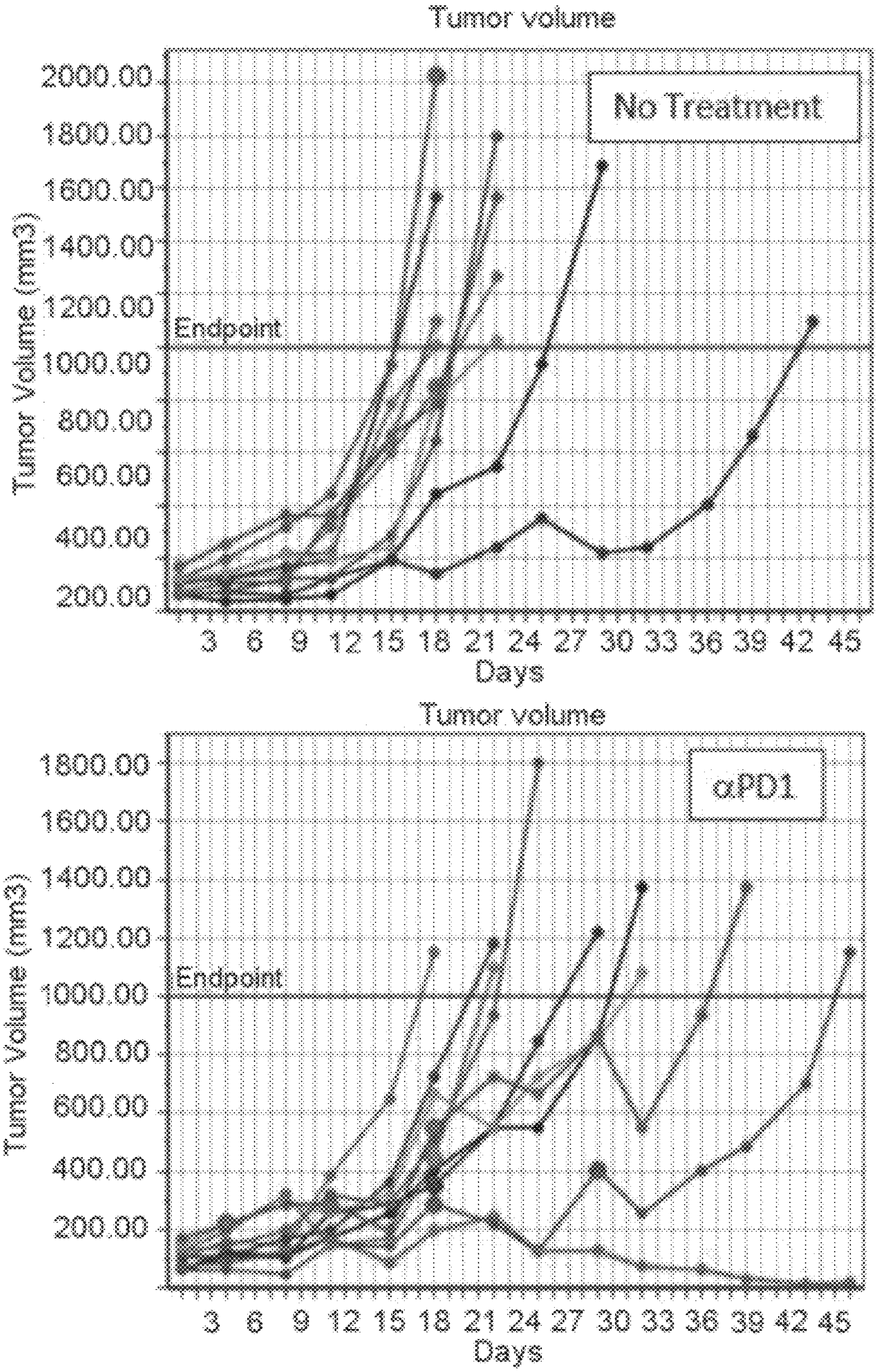
FIG. 30 shows tumor volume plots of individual mice treated in experiments of Example 5 (11-mix; αPD-1 Ab; 11-mix+αPD-1 Ab). The tumor volume did not increase in multiple animals in the 11-mix+αPD-1 Ab treatment group (bottom right panel).

Treatment with the anti-PD1 antibody alone or in combination with either the 4-mix or the 11-mix resulted in a reduction in tumor growth as compared to no treatment. FIG. 30 shows tumor volume plots of the individual mice treated in experiments of Example 5 (control, 11-mix; αPD-1 Ab; 11-mix+αPD-1 Ab). The tumor volume did not increase in multiple animals in the 11-mix+αPD-1 Ab treatment group (bottom right panel). FIG. 32 shows tumor volume plots of individual mice treated in experiments of Example 5 (control, 4-mix; a PD-1 Ab; 4-mix+a PD-1 Ab). The tumor volume did not increase in multiple animals in the 4-mix+a PD-1 Ab treatment group (bottom right panel).

Survival

Figure 31:
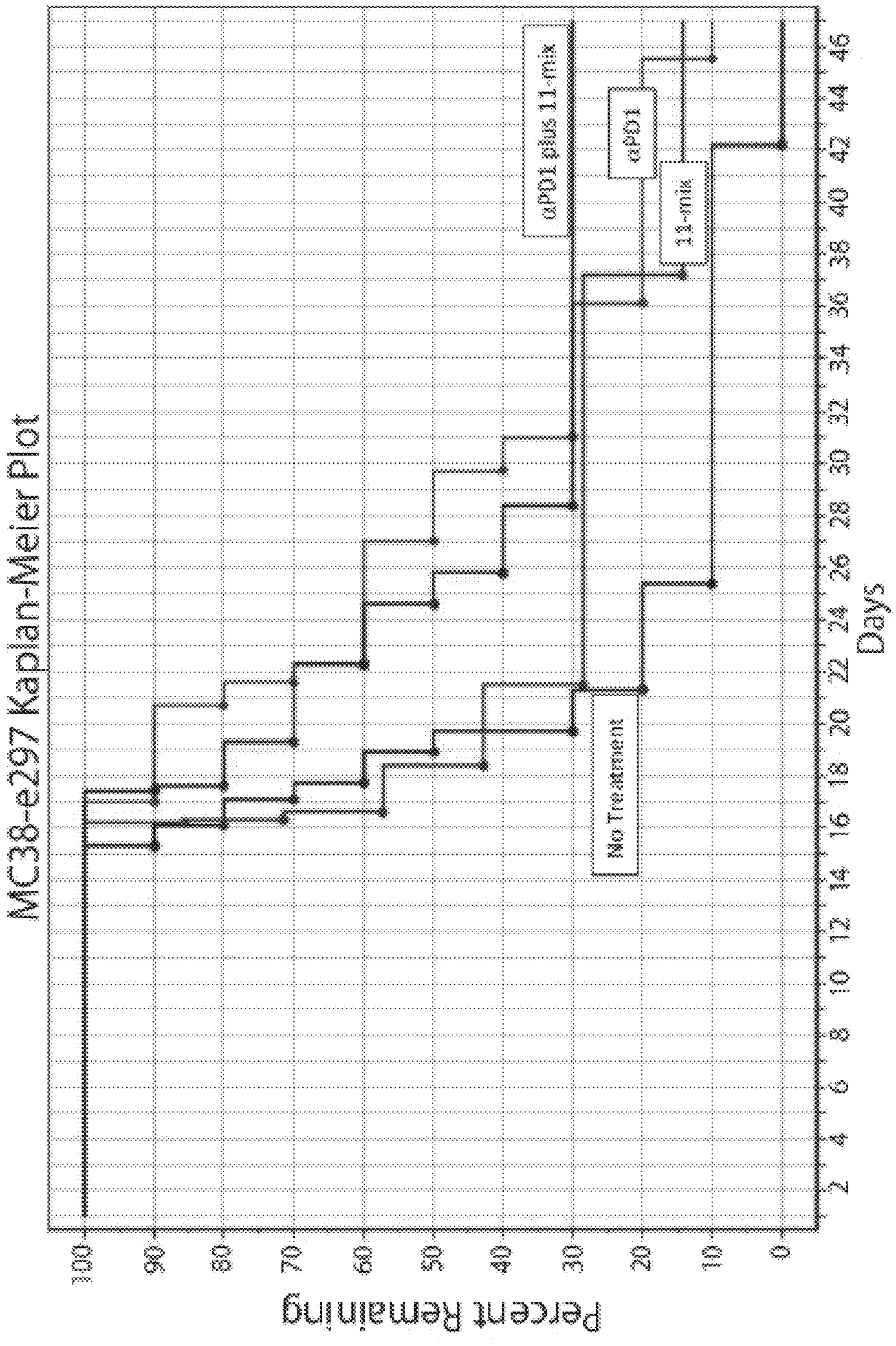
FIG. 31 shows survival plots of mice treated in experiments of Example 5 (11-mix; αPD-1 Ab; 11-mix+αPD-1 Ab).

Survival data are shown in FIG. 31 for the control, 11-mix; PD-1 Ab; and 11-mix+PD-1 Ab groups. The combination of the 11-mix and the αPD-1 Ab showed increased survival when compared to either the 11-mix or the αPD-1 Ab on its own.

Figure 33:
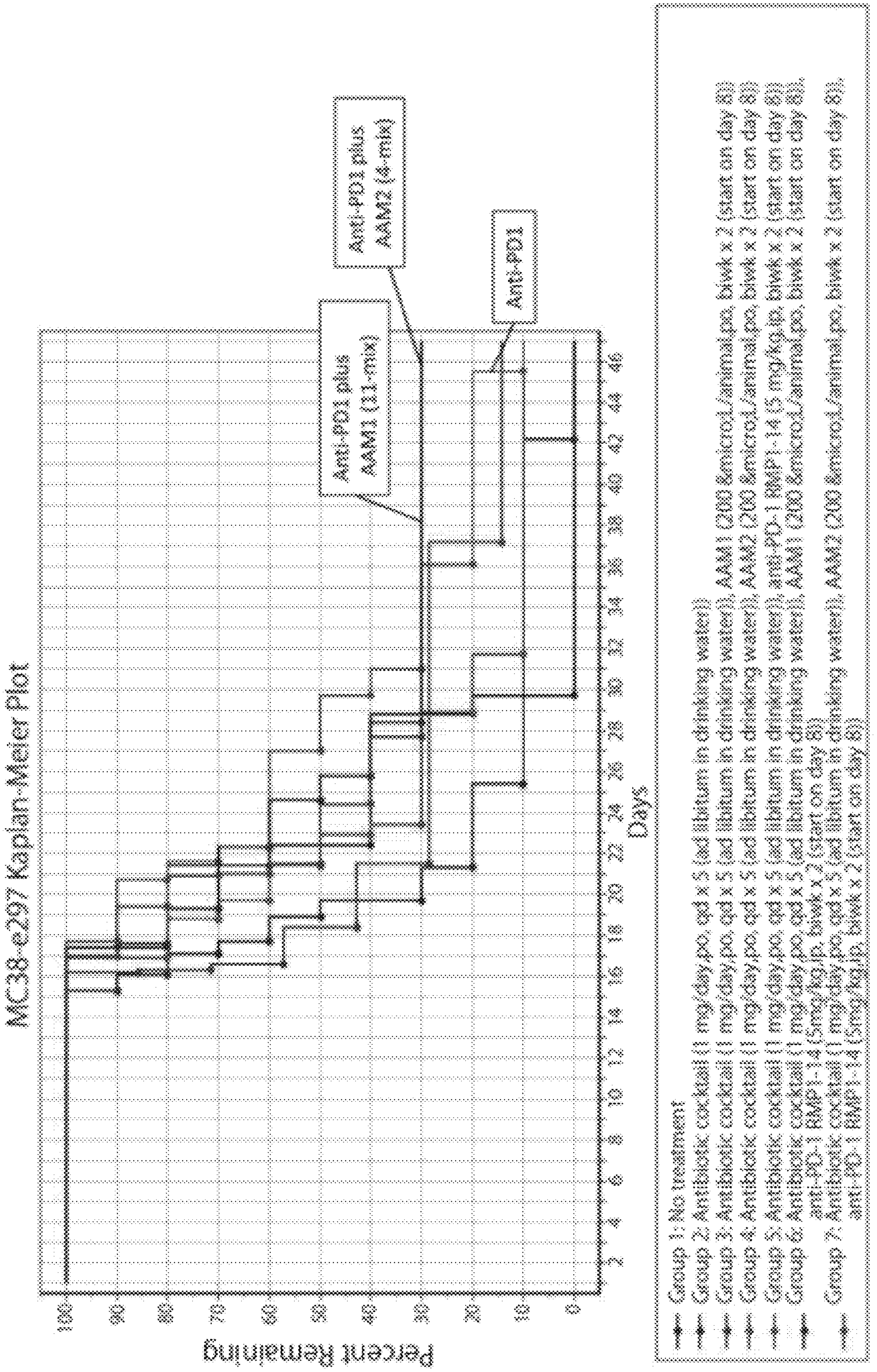
FIG. 33 shows plots of mice treated in experiments of Example 5. Highlighted are treatment with αPD-1 Ab, 11-mix+αPD-1 Ab, and 4-mix+αPD-1 Ab.

The combined survival data of mice in the control, 4-mix; αPD-1 Ab; 4-mix+αPD-1 Ab, 11-mix, and 11-mix+α PD-1 Ab groups are shown in FIG. 33. Both the combination of the 4-mix and the αPD-1 Ab and the combination of the 11-mix and the αPD-1 antibody showed increased survival when compared to the αPD-1 Ab on its own.

Example 6: Anti-Cancer Characteristics of CD8+ T-Cell Inducing Bacterial Cocktail Combination with an Anti-PD1 Antibody in a Melanoma Model A melanoma engraftment mouse model was used to evaluate the efficacy of the 11-mix in combination with α PD-1 antibody in the treatment of melanoma. As shown in the timelines in FIGS. 34 and 35, mice received antibiotics (Ampicillin, Vancomycin, Metronidazole, and Neomycin: "AVMN") from day −3 to day 2. On day 0, the mice were engrafted with 7×105 Braf Pten melanoma cells. The mice were grouped in the following treatment groups:

Specific Pathogen Free (SPF) feces;

SPF feces+anti-PD1 antibody;

SPF feces+11-mix; and

SPF feces+11-mix+anti-PD1 antibody.

Figure 34:
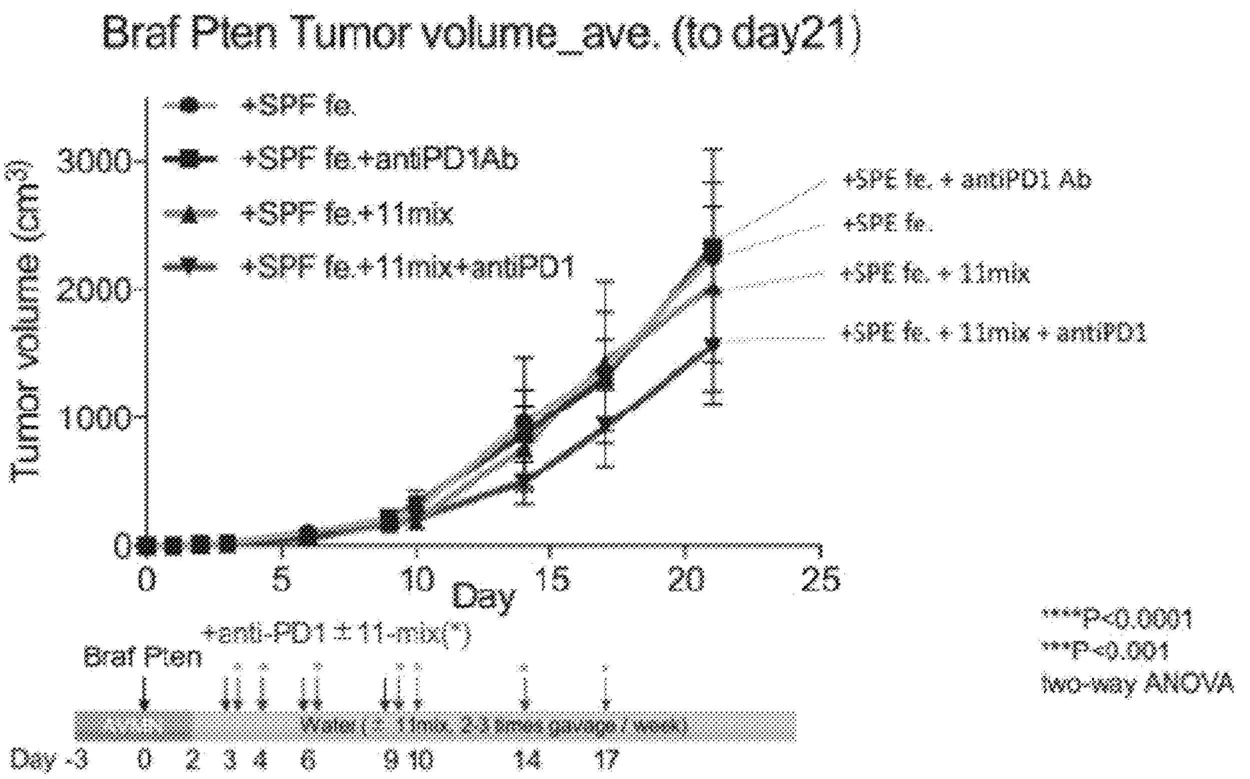
FIG. 34 shows data of experiments with the Braf Pten melanoma model (Example 6). Briefly, mice were administered antibiotics ("AVMN") from day −3 to day 2 and engrafted with 7×105 Braf Pten cells on day 0. On days 3, 6, and 9 the indicated groups of mice were administered an anti-PD1 antibody (arrows on the timeline) and SLC SPF feces from specific-pathogen free (SPF) mice obtained from Japan SLC (SLC SPF feces), with or without the 11-mix (arrows with asterisk on the timeline). The groups of mice indicated as having received the 11-mix were administered the 11-mix 2 or 3 times per week. The plot shows the average tumor volume at each of the timepoints for the groups of mice**P<0.0001, *P<0.001 (two-way ANOVA).
Figure 35:
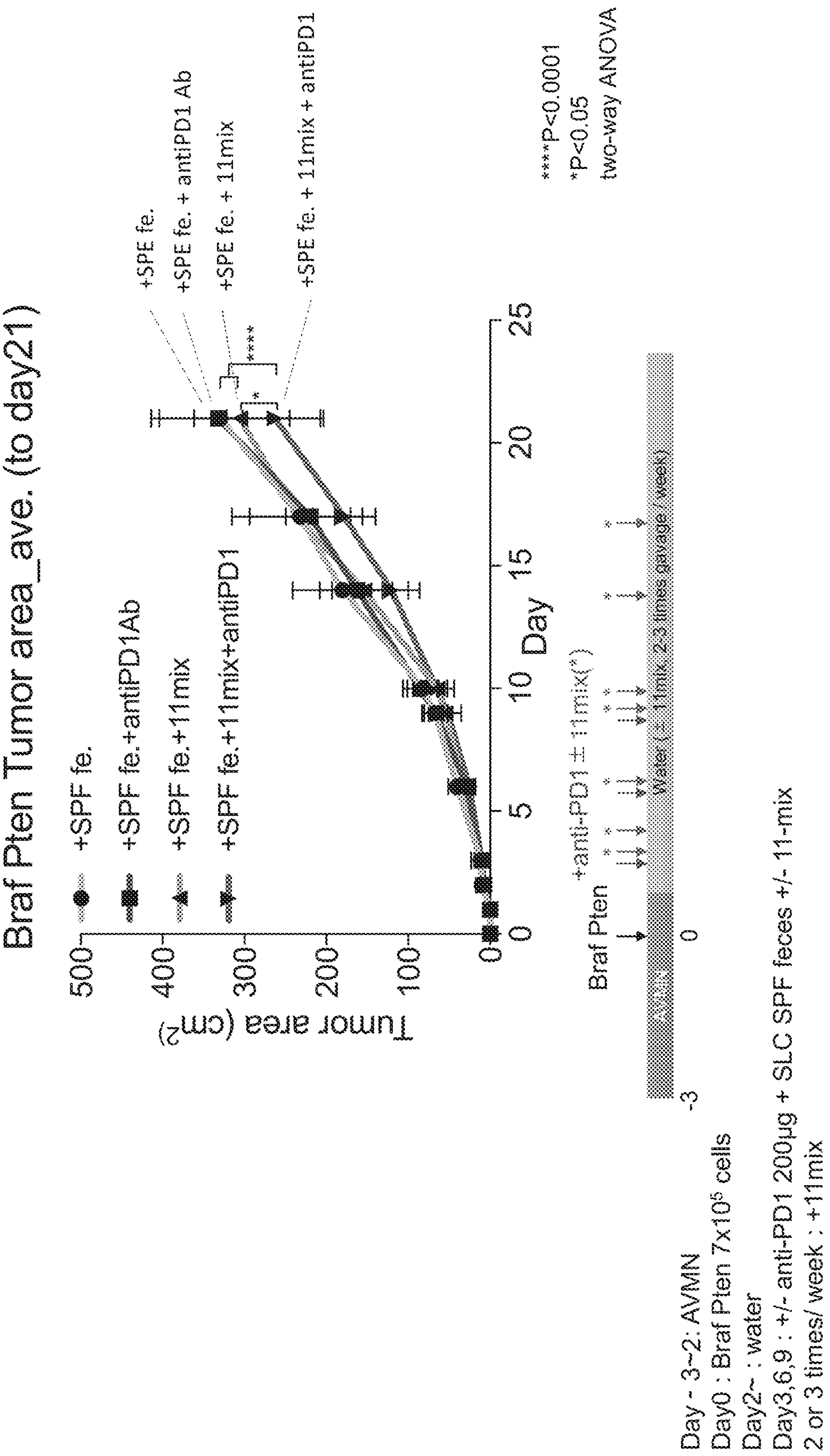
FIG. 35 shows data of experiments with the Braf Pten melanoma model (Example 6). Briefly, mice were administered antibiotics ("AVMN") from day −3 to day 2 and engrafted with 7×105 Braf Pten cells on day 0. On days 3, 6, and 9 the indicated groups of mice were administered an anti-PD1 antibody (arrows on the timeline) and SLC SPF feces from specific-pathogen free (SPF) mice obtained from Japan SLC (SLC SPF feces), with or without the 11-mix (arrows with asterisk on the timeline). The groups of mice indicated as having received the 11-mix were administered the 11-mix 2 or 3 times per week. The plot shows the average tumor area at each of the timepoints for the groups of mice. **P<0.0001, *P<0.001 (two-way ANOVA).
Figure 36:
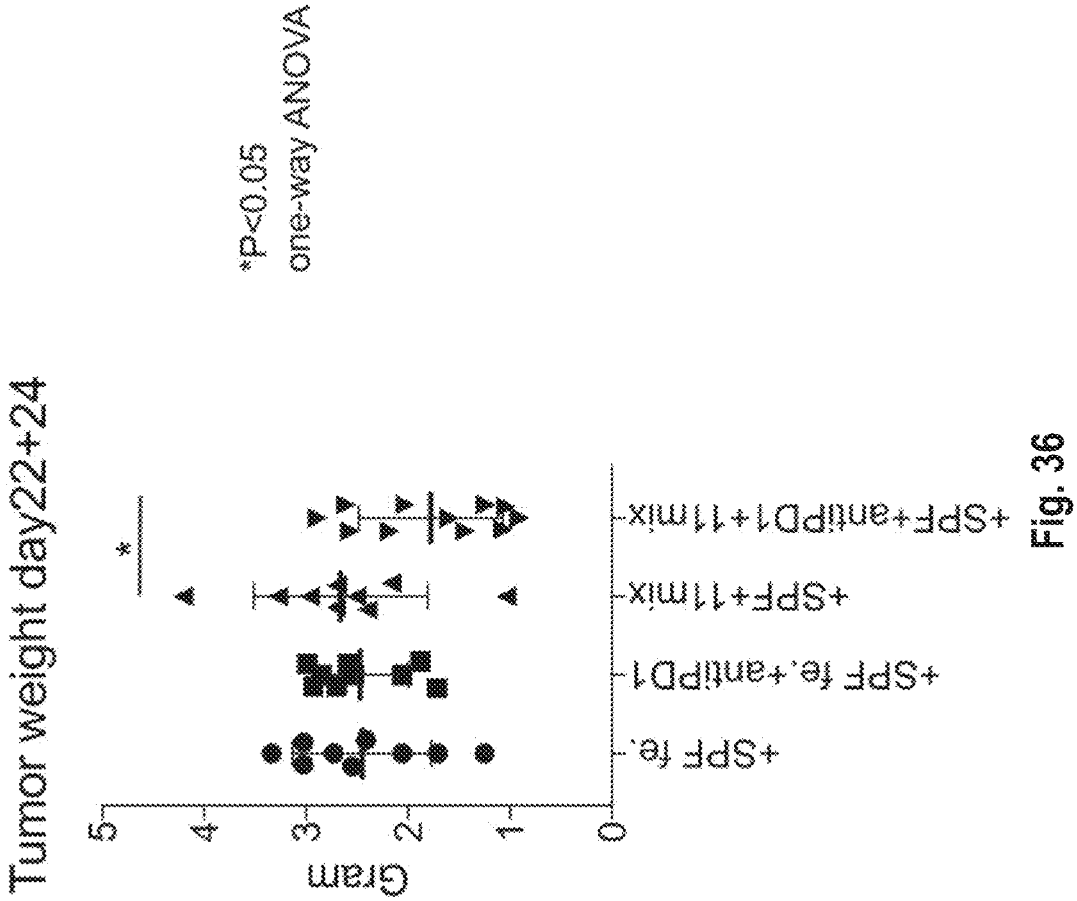
FIG. 36 shows data on the weight of tumors obtained on days 22 and 24 from the indicated groups of mice. *P<0.05 (one-way ANOVA).
Figure 37A:
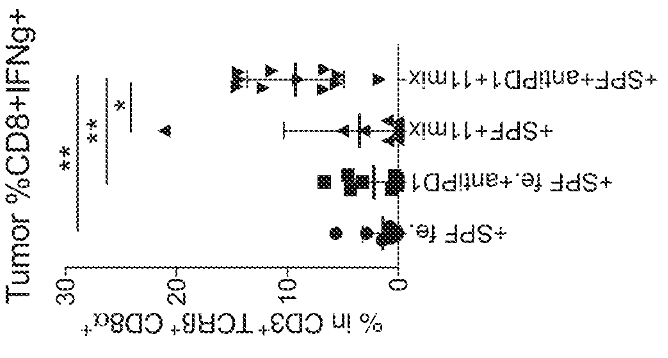
FIGS. 37A-37C show data on lymphocytes isolated from tumor cells. On days 22 and 24, lymphocytes were isolated from tumors. CD3, TCRβ, CD8, and IFN γ were stained with antibodies.
Figure 37B:
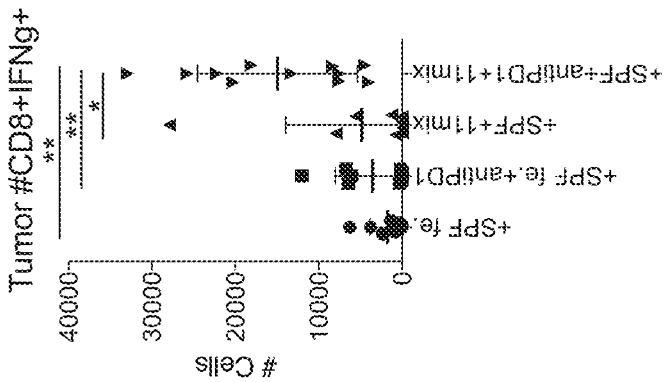
Figure 37C:
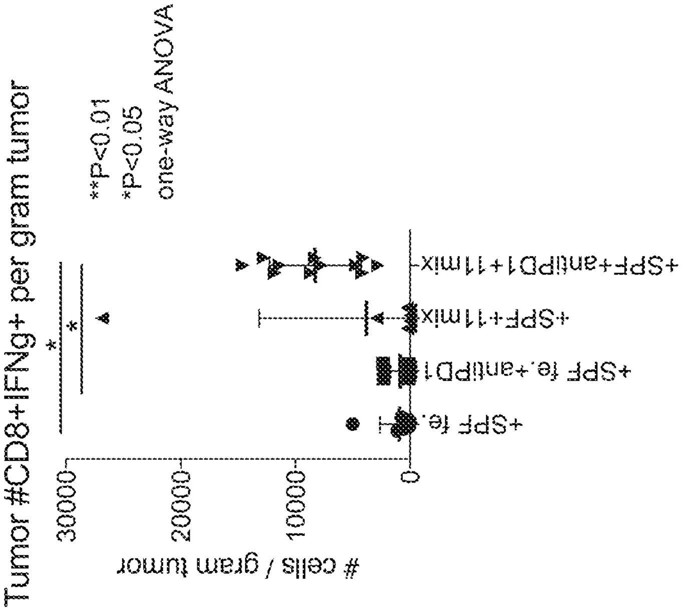
Figure 38:
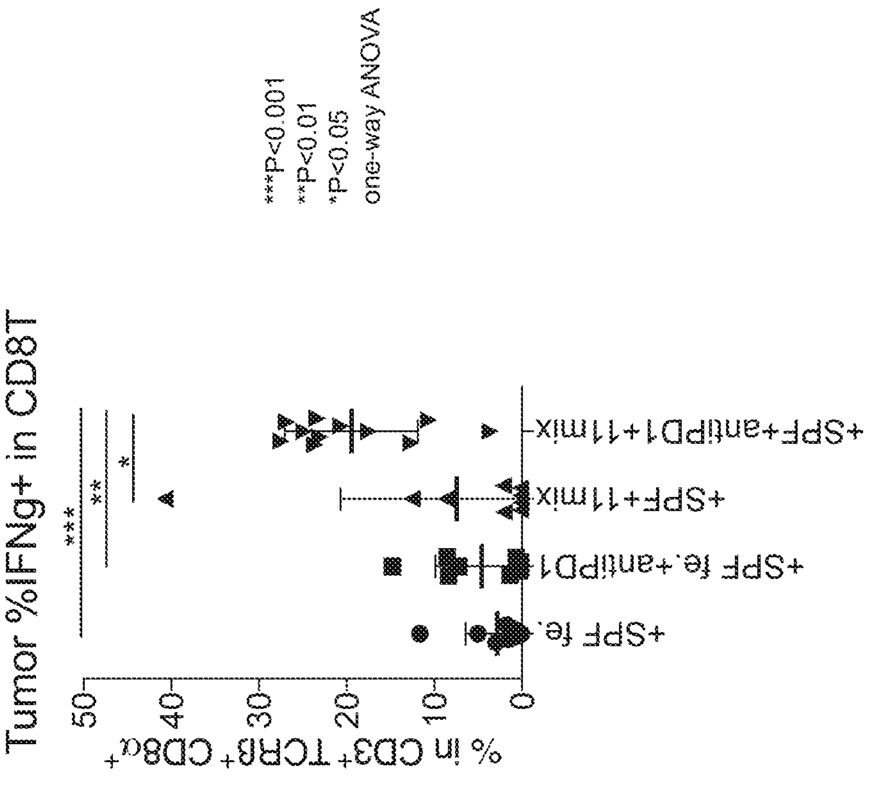
FIG. 38 shows the percentage of IFN γ+ cells in the population of CD8T cells isolated from the tumors. *P<0.001, P<0.01, *P<0.05 (one-way ANOVA).
Figure 39A:
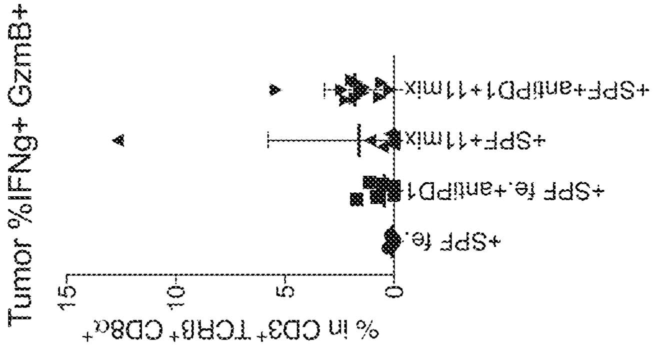
FIGS. 39A-39D show data on lymphocytes isolated from tumor cells. On days 22 and 24, lymphocytes were isolated from tumors. CD3, TCR β, CD8, IFN γ, GzmB, IL-17, and CD4 were stained with antibodies.
Figure 39B:
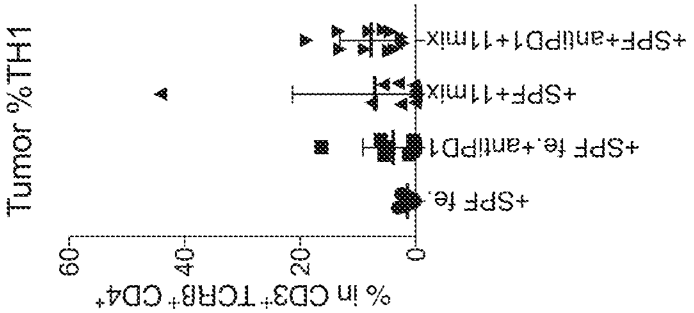
Figure 39C:
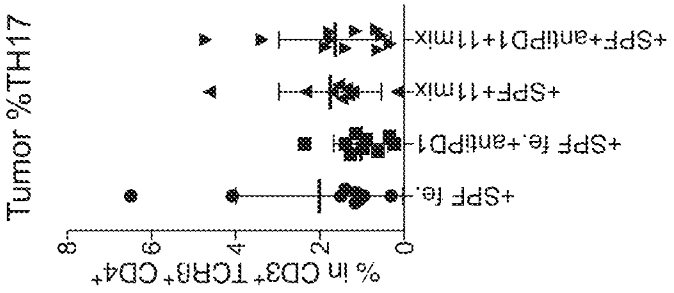
Figure 39D:
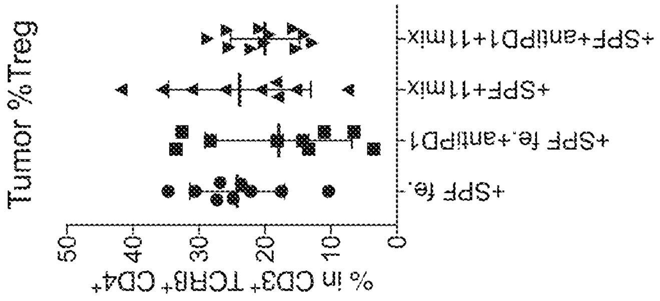

On days 3, 6, and 9, the mice were administered SLC SPF feces from specific-pathogen free (SPF) mice obtained from Japan SLC (SLC SPF feces), an anti-PD1 antibody (arrows on the timelines in FIGS. 34 and 35) and/or the 11-mix (arrows with asterisk on the timelines in FIGS. 34 and 35). The 11-mix was administered to the indicated groups of mice 2 or 3 times per week by gavage. Mice that received the combination of the anti-PD1 antibody and the 11-mix had reduced tumor volume (FIG. 34), tumor area (FIG. 35), and tumor weight (FIG. 36) as compared to the other groups of mice.

Lymphocytes were isolated from tumors obtained from the mice on days 22 and 24 and stained using antibodies to cell markers, including CD3, TCRβ, CD8, CD4, IFN γ, Granzyme, and IL-17. Treatment with the 11-mix and anti-PD1 antibody combination resulted in elevated accumulation of IFN γ+CD8+ T cells in the melanoma tumor. FIGS. 37A-37C and 38. In this experiment, there was no significant difference in the number of IFN γ+ GzmB+ cells, Th1 cells, Th17 cells, or Treg cells between the groups of mice. FIGS. 39A-39D.

These results show that treatment with 11-mix in combination with the anti-PD1 antibody systemically activates CD8 T cells in the melanoma.

Example 7: CD8 T-Cell Induction in Specific-Pathogen Free (SPF) Mice

Experimental parameters were evaluated for the induction of CD8 T cells by the 11-mix bacterial cocktail. The animals used in this study were specific pathogen free mice (SPF mice) as compared to germ-free mice.

Figure 40:
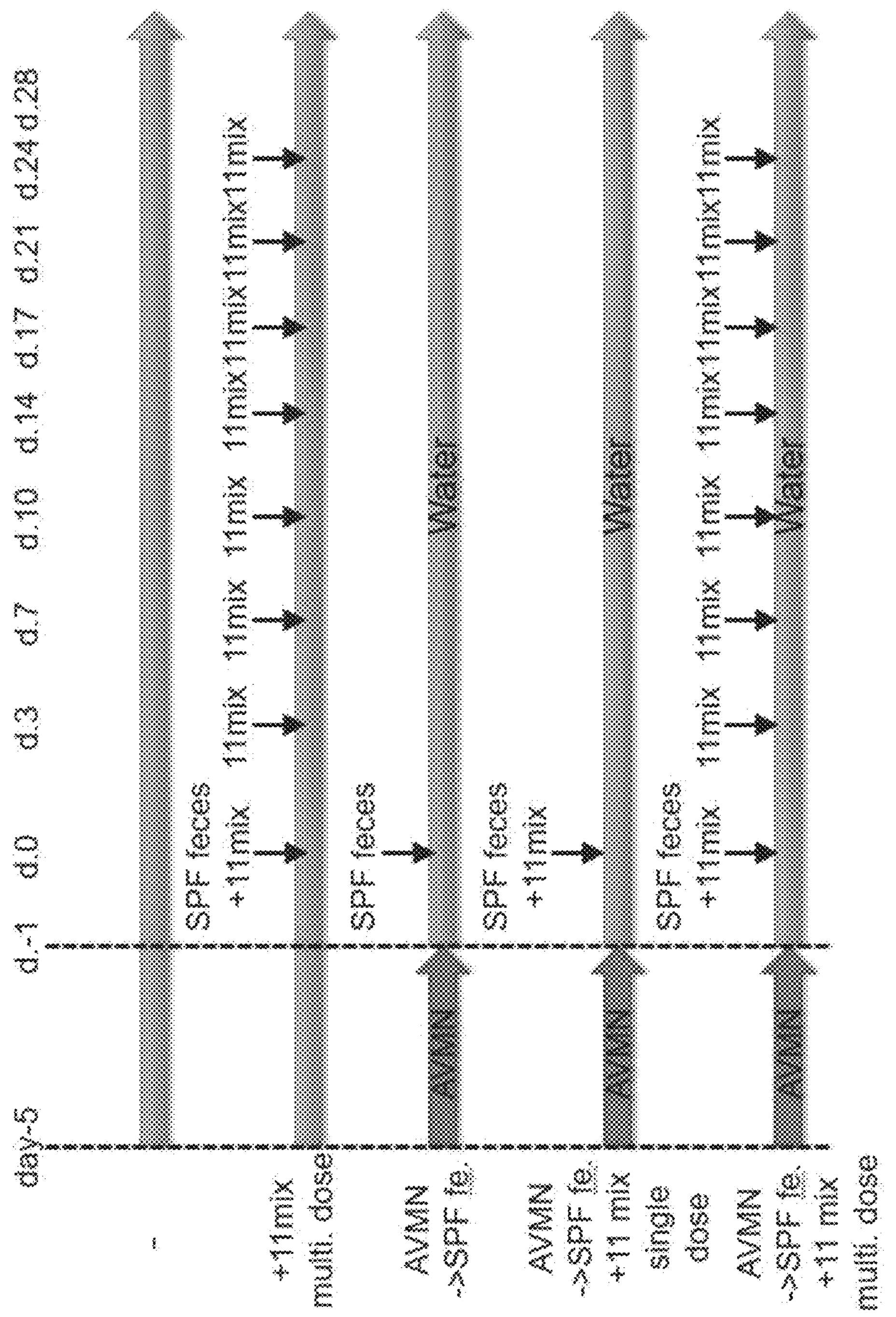
FIG. 40 shows a schematic of the experimental plan described in Example 7 (the dosing study).

As shown in FIG. 40, the mice were grouped in the following treatment groups:

11-mix multi-dose;

AVMN+SPF feces;

AVMN+SPF feces+11-mix single dose; and

AVMN+SPF feces+11-mix multi-dose.

The indicated groups of mice received antibiotics (Ampicillin, Vancomycin, Metronidazole, and Neomycin: "AVMN") in their drinking water from day −5 to day −1. Mice were inoculated with SPF feces with or without the 11-mix on day 0. For groups that received multiple doses of the 11-mix, the bacterial cocktail was also administered in the water on days 3, 7, 10, 14, 17, 21, 24, and 28.

Figure 41C:
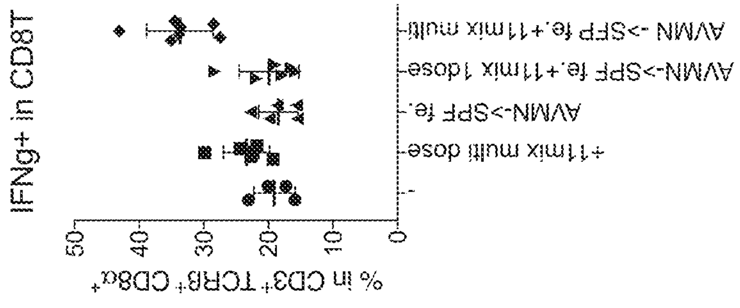
FIGS. 41A-41C show data on lymphocytes isolated from mice in the experiment shown in FIG. 40 (Example 7). CD3, TCRβ, CD8, and IFN γ were stained with antibodies.
Figure 41B:
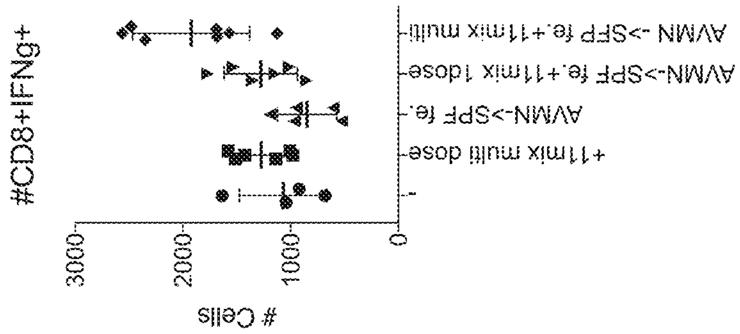
Figure 41A:
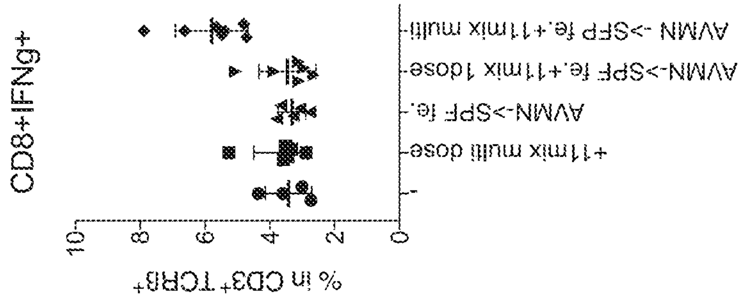
Figure 42C:
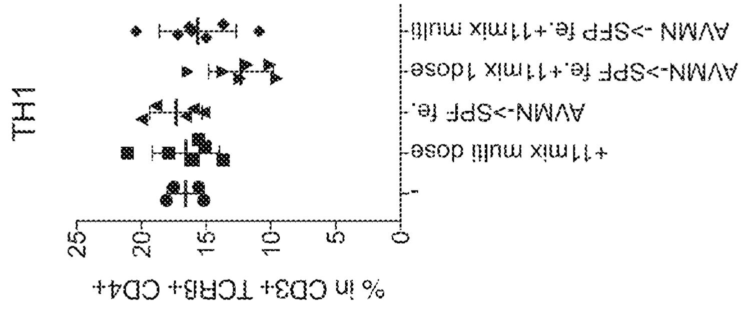
FIGS. 42A-42C show data on lymphocytes isolated from mice from the experiment shown in FIG. 40 (Example 7). CD3, TCRβ, CD8, IFNγ, CD103, IL-17, and CD4 were stained with antibodies.
Figure 42B:
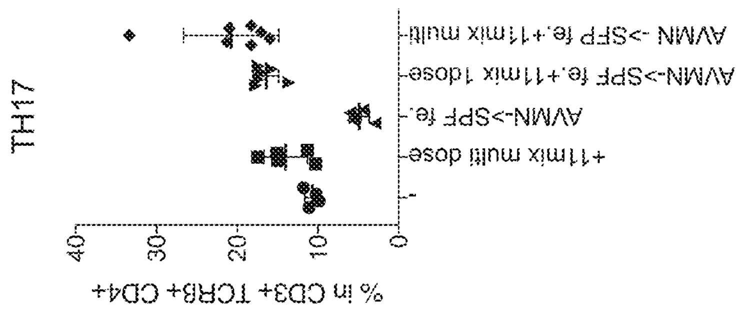
Figure 42A:
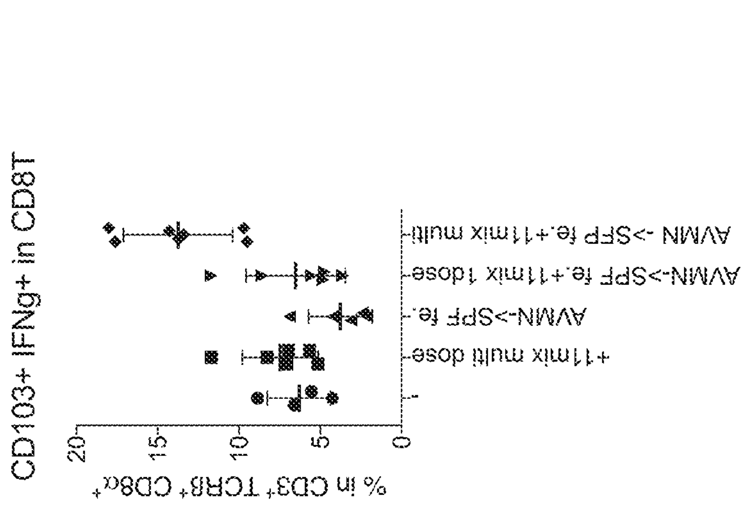

Lymphocytes were isolated from the mice on days 22 and 24 and stained using antibodies to cell markers, including CD3, TCRβ, CD8, CD4, IFN γ, Granzyme, and IL-17. Mice that received the antibiotic pretreatment and multiple doses of the 11-mixed showed enhanced levels of IFN γ+CD8+ T cells. FIGS. 41A-41C. The mice that received the antibiotic pretreatment and multiple doses of the 11-mixes also had enhanced levels of CD103+ IFN γ+ cells in the CD8T cell population of cells (FIG. 42A) and slightly enhanced levels of Th17 cells (FIG. 42B). There was no significant difference in the number of Th1 cells between the groups of mice. (FIG. 42C). These data show that the 11-mix can induce CD8+ T cells in a complex background: a specific pathogen free mouse (as compared to a germ free mouse).

Example 8: The Role of Transcription Factor BATF3

Figure 43A:
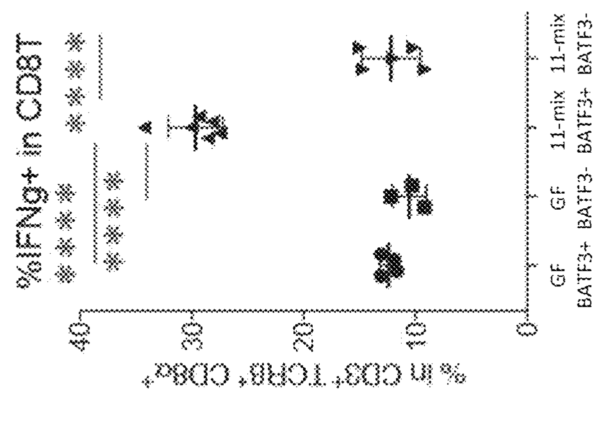
FIGS. 43A-43C and 44 show the results from the experiments of Example 8. The experiments show that BATF3 is required for the 11-mix to induce CD8-T cells. BATF3 is not required to induce Th17.
Figure 43B:
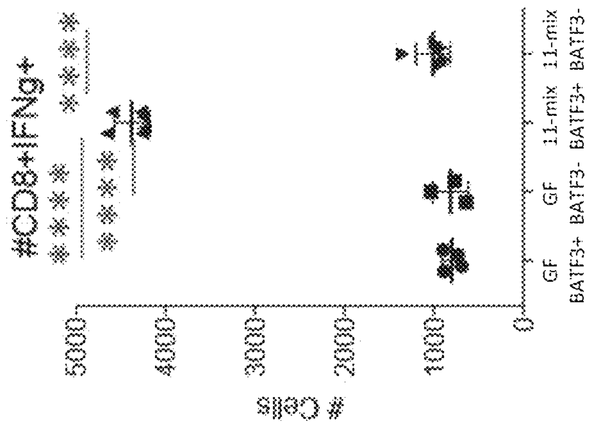
Figure 43C:
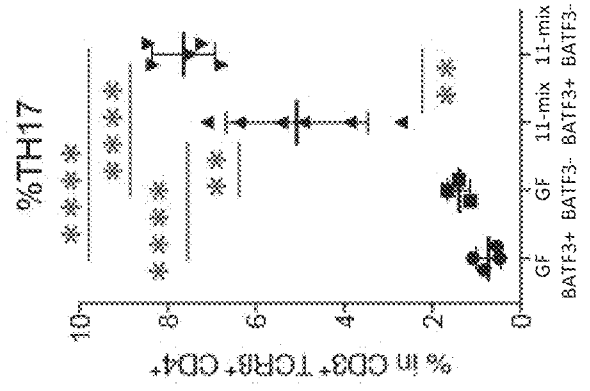
Figures 44A, 44B:
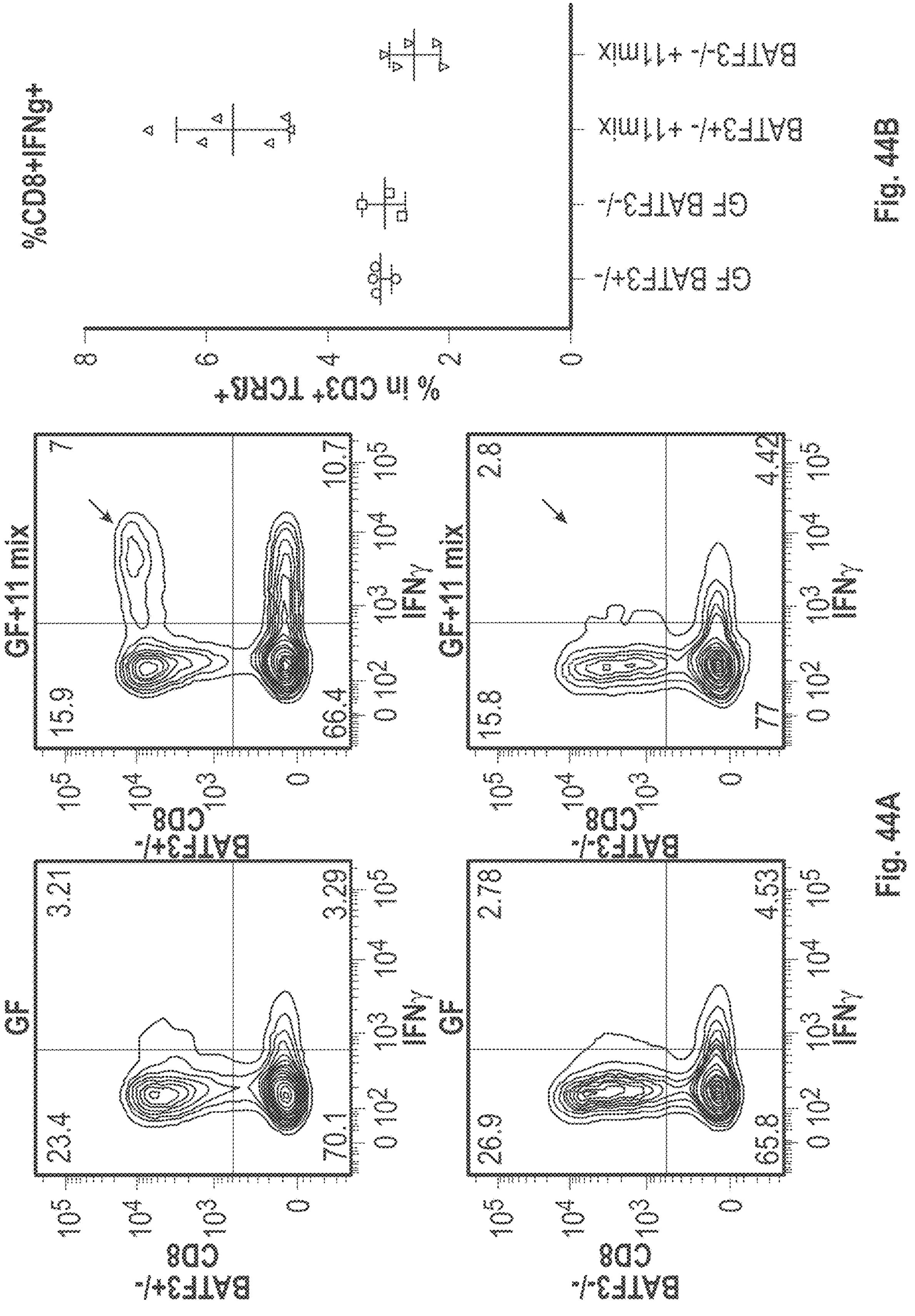

The 11-mix was administered to mice that have the BATF3 transcription factor and mice that do not have the BATF3 transcription factor. Mice that do not have the transcription factor BATF3 are not susceptible to CD8 T cell induction by the 11-mix. (FIGS. 43A and 43B). It is likely that CD103-CD11b dendritic cells are required for stimulation of IFN γ producing CD8 and Th1 cells. The induction of Th17 cells by the 11-mix cocktail is independent of BAFT3 status. (FIG. 43C). FIGS. 43 and 44 show the results from the experiments of Example 8. The experiments show that BATF3 is required for the 11-mix to induce CD8-T cells. BATF3 is not required to induce Th17.

Example 9: Treatment of *Listeria* Infected Mice

Figure 45:
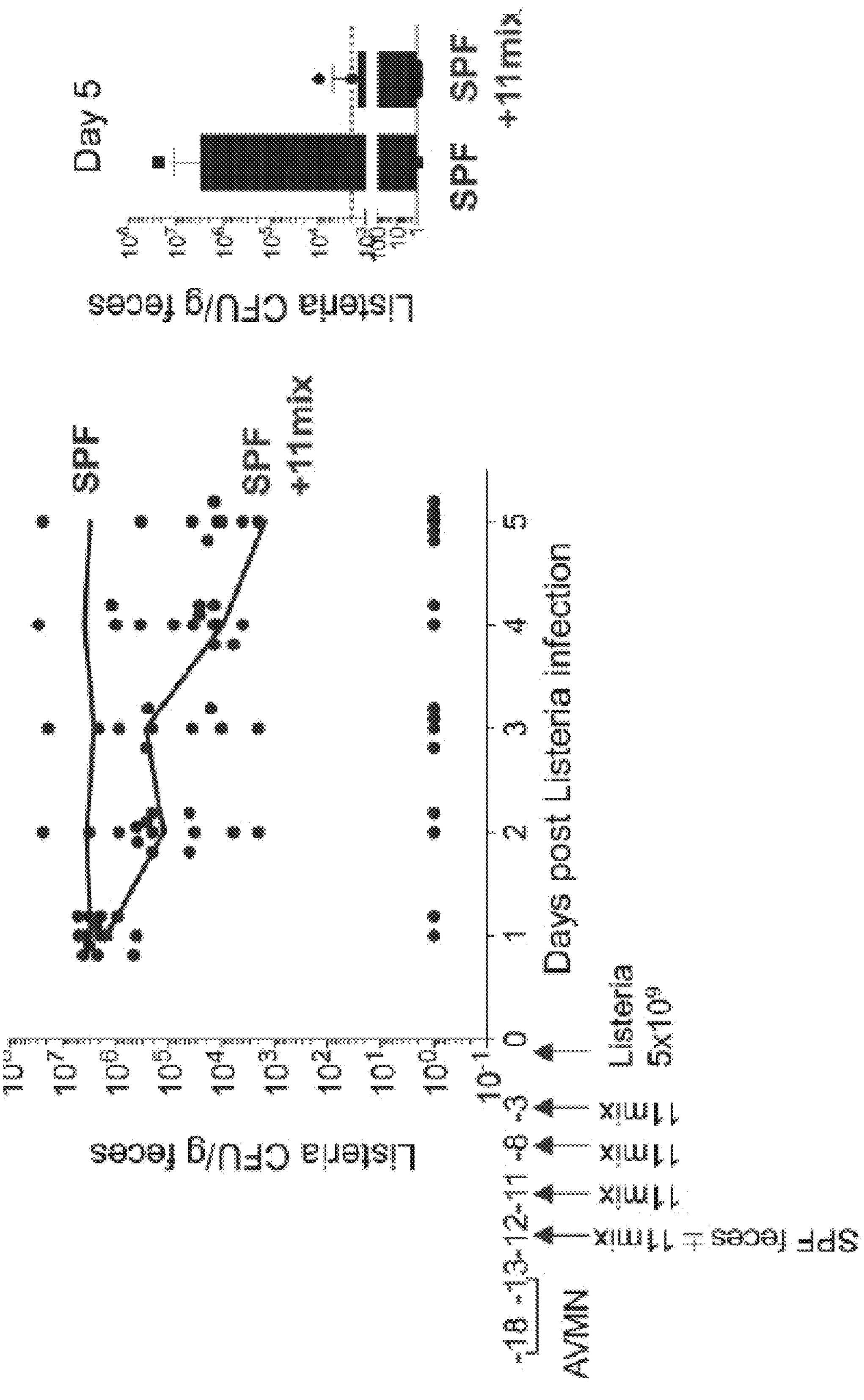
FIGS. 45-46 show the results from the experiments of Example 9. The experiments show that the 11-mix is effective in treating *Listeria* infections.
Figure 46:
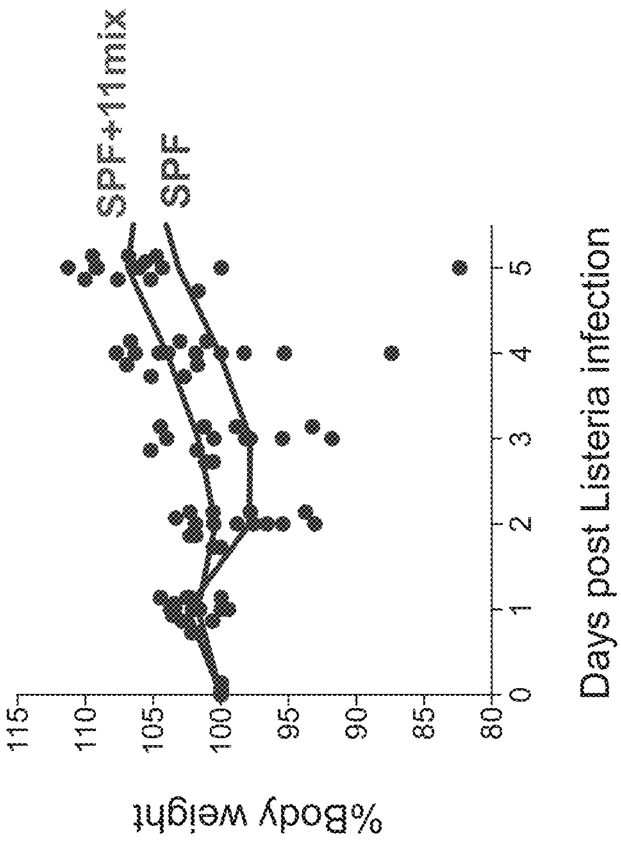

Since IFN γ+CD8+ T cells have been reported to play critical roles in controlling intracellular pathogens, it was evaluated whether oral supplementation with the 11 strain mixture in a multiple dosing regimen could augment host protective immunity against *Listeria monocytogenes* infection. SPF mice were treated with AVMN (ampicillin, vancomycin, metronidazole, neomycin) for 5 days via the drinking water. After one day washout of antibiotics, multiple oral administrations of the 11-mix (4 times) were performed. To reconstitute complex microbiota, fecal microbiota from SPF mice were introduced together with the first administration of 11-mix. The mice were then orally infected with *Listeria monocytogenes* on day 0. Fecal *Listeria* CFU and body weight of mice were determined. Treatment with 11-mix significantly reduced *Listeria monocytogenes* colonization of the gut lumen (FIG. 45) and maintained the body weight of the mice (FIG. 46). Thus, administration of the 11 strain-mixture can provide protective immunity against an intracellar, infectious pathogen.

Example 10: Localization of the CD8 T-Cells Induced by the 11-Mix

Figure 48:
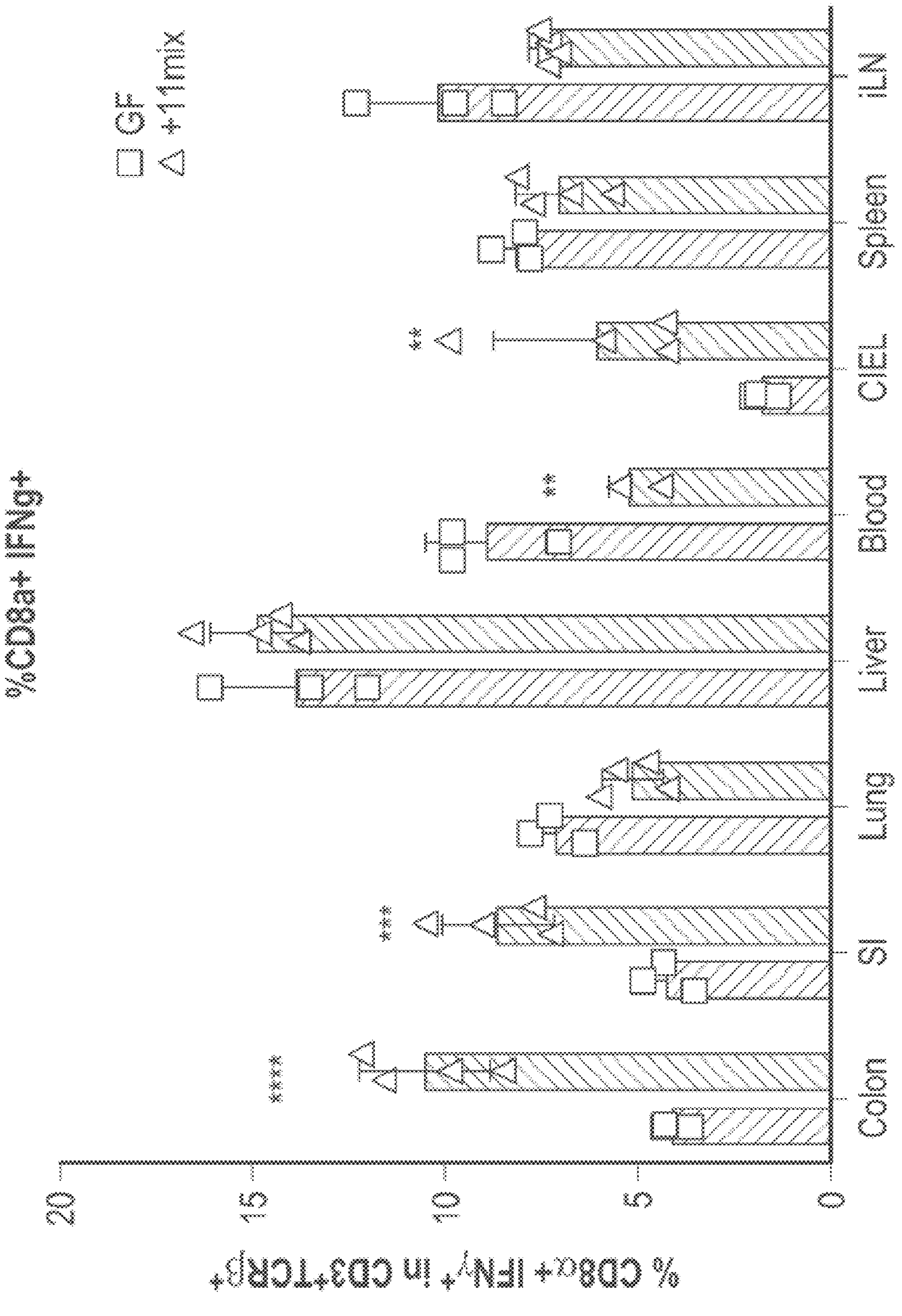
FIG. 48 relates to Example 10 and shows that the CD8 induction effect of the 11-mix in mice that are not otherwise challenged is limited to the intestine/gut compartment. (SI=short intestine, CIEL=colonic intraepithelial lymphocytes, LN=lymph nodes)

The 11-mix was administered to normal healthy mice (i.e., mice that were not otherwise stressed). Various organs and compartments in the mice were investigated for the presence of CD8 positive $T^-$ cells. As shown in FIG. 48, the CD8 positive $T^-$ cell induction effect of the 11-mix is limited to the intestine/gut (SI=small intestine, CIEL=colonic intraepithelial lymphocytes, LN=lymph nodes).

Figure 49:
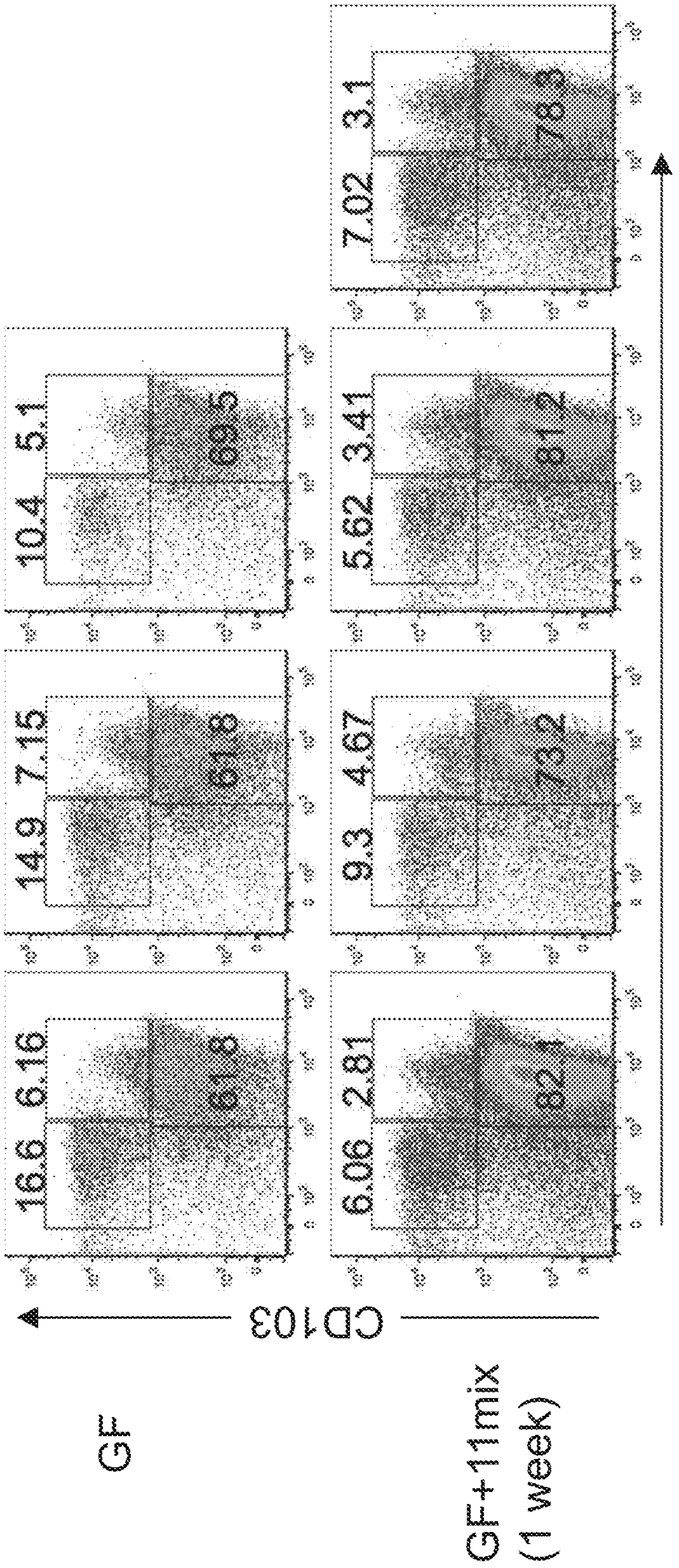
FIG. 49 shows that the frequencies of DC subsets in colonic LP were only slightly changed by the colonization with 11-mix.
Figure 50:
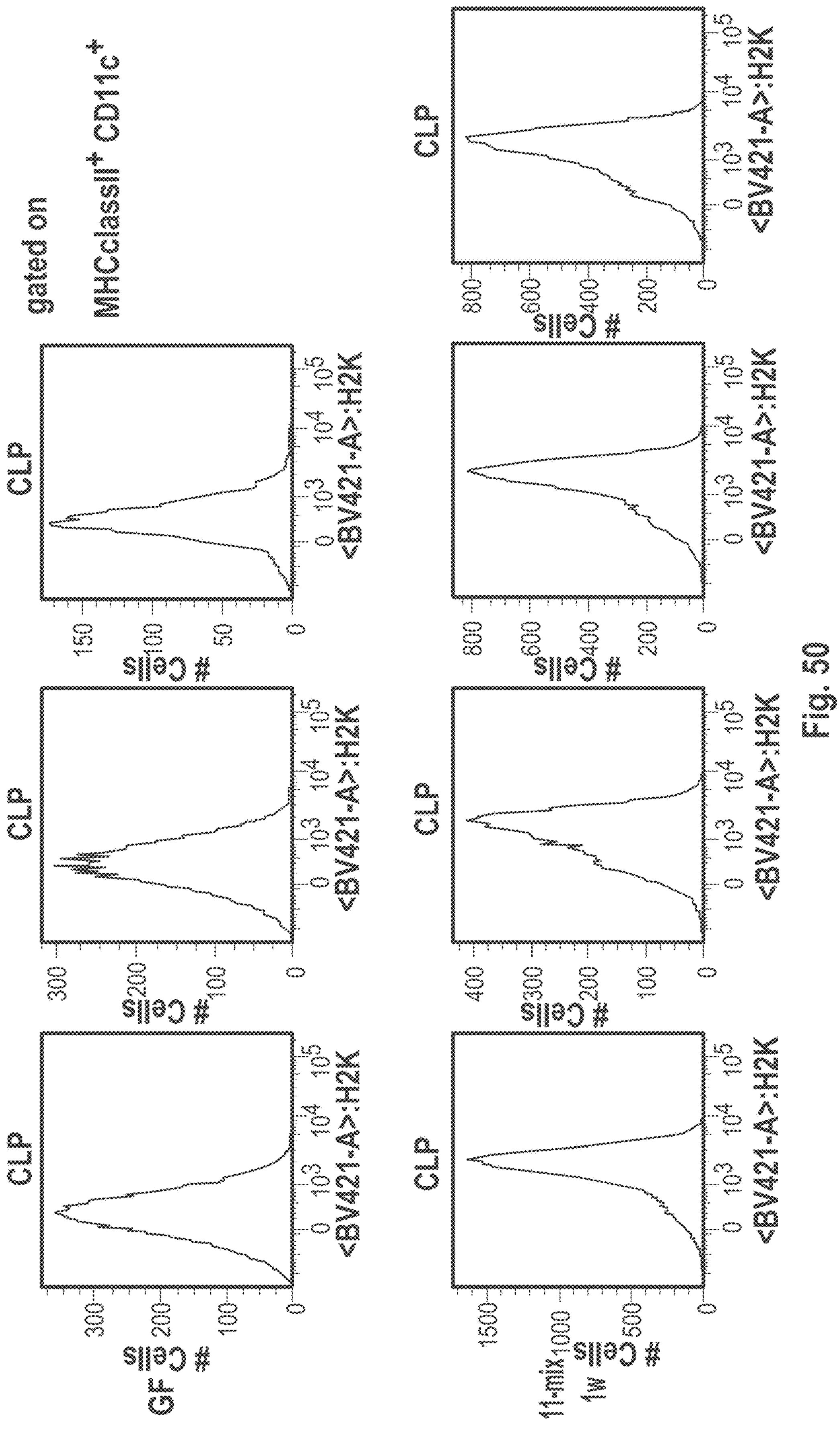
FIGS. 50-52 show that MHC CLP class cells are activated by the administration of the 11-mix, and that the activation is strongest within the first week of activation. There is no activation of the MHC MLN class cells. The individual measurements are shown in FIGS. 50 and 51, while the accumulated data are depicted in FIG. 52.
Figure 50:
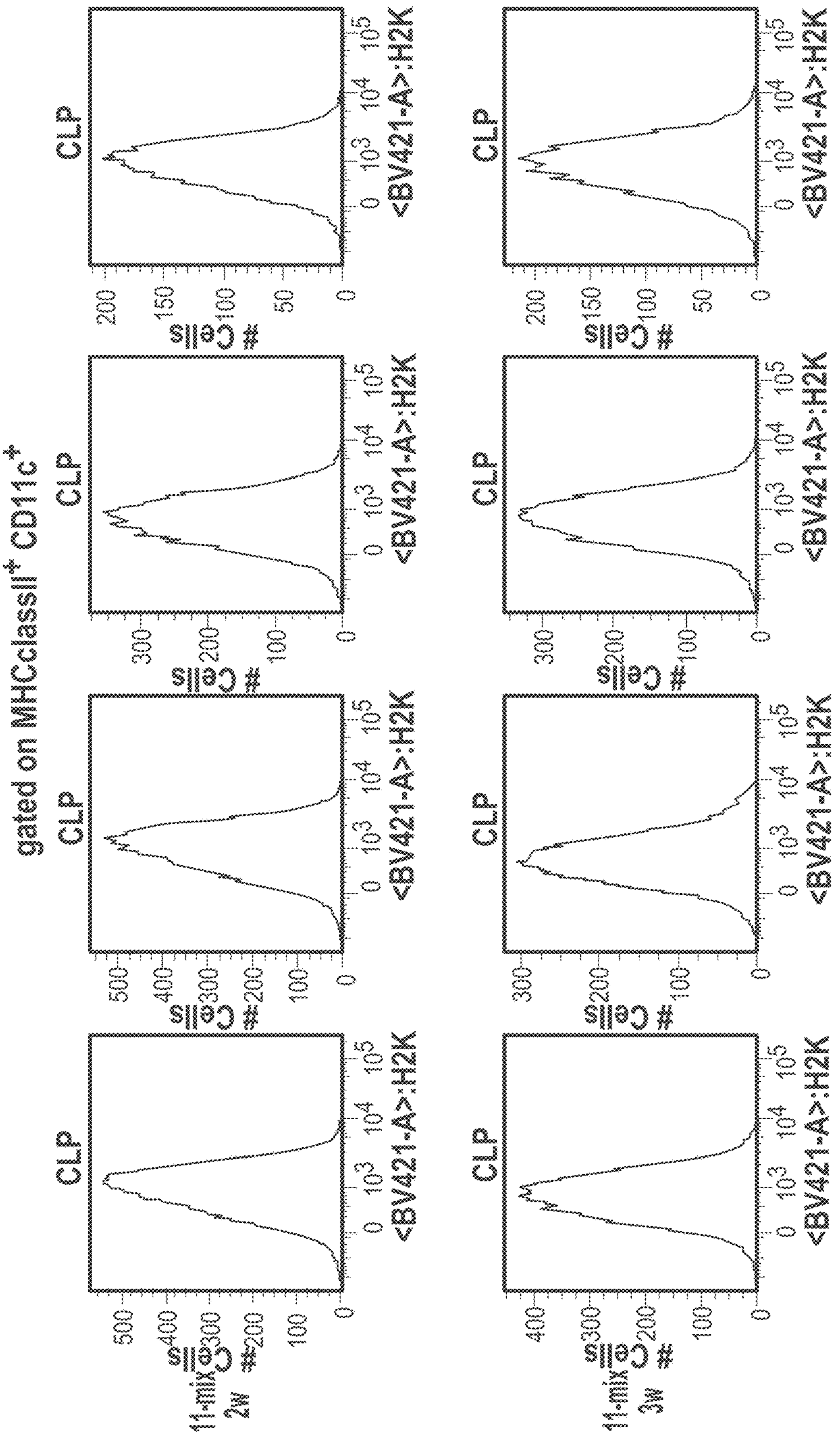
Figure 50:
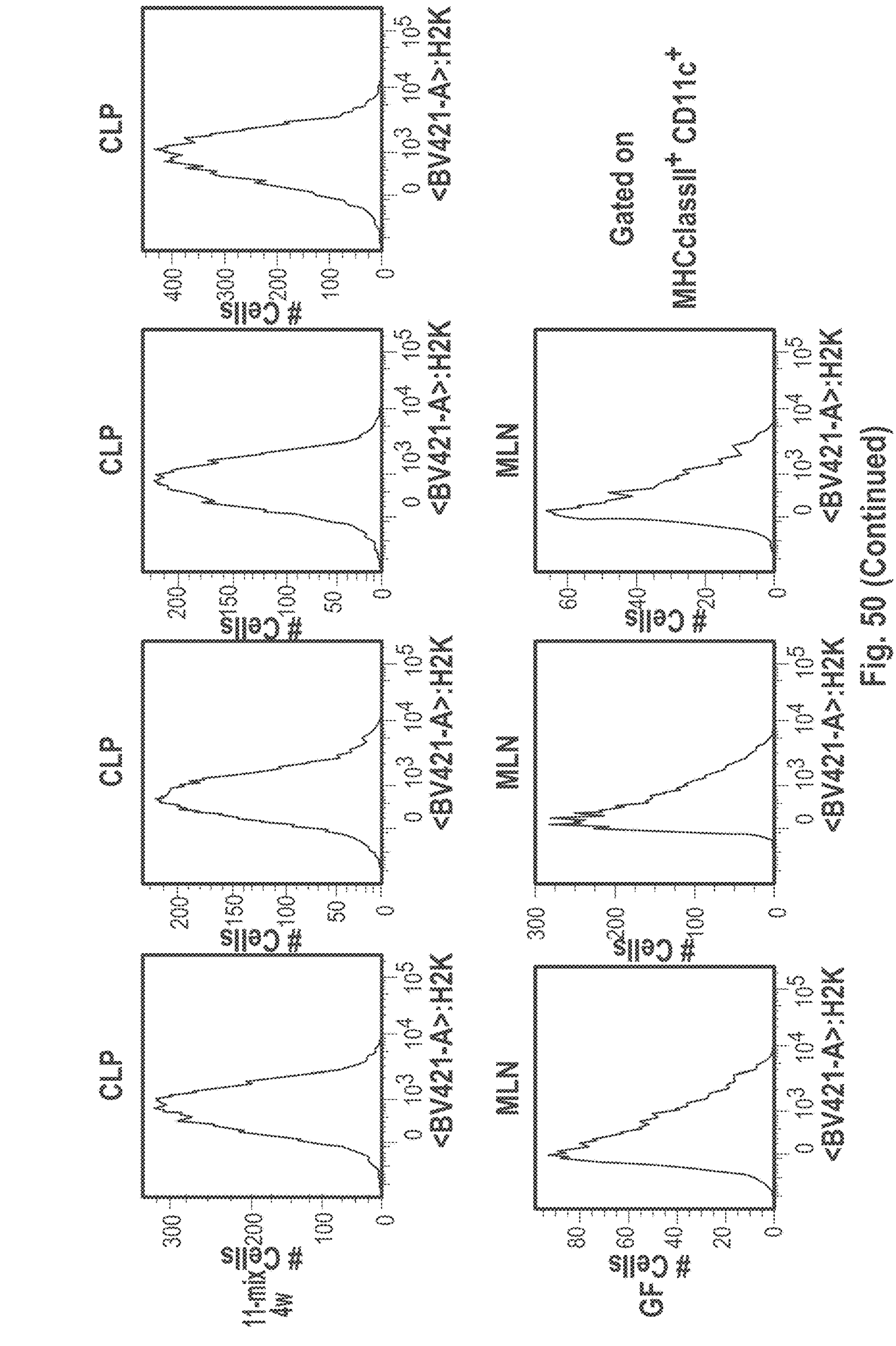
Figure 50:
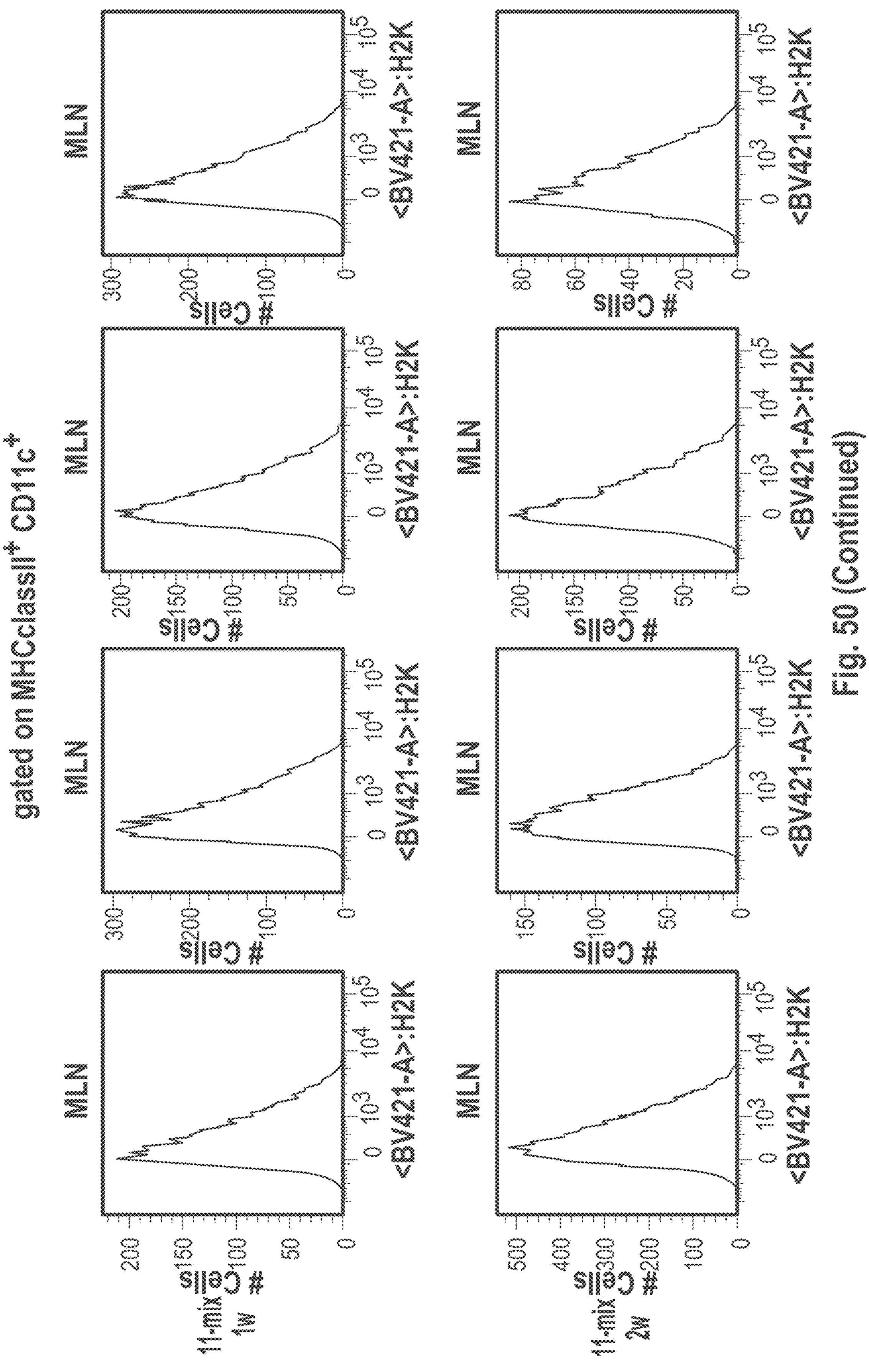
Figure 50:
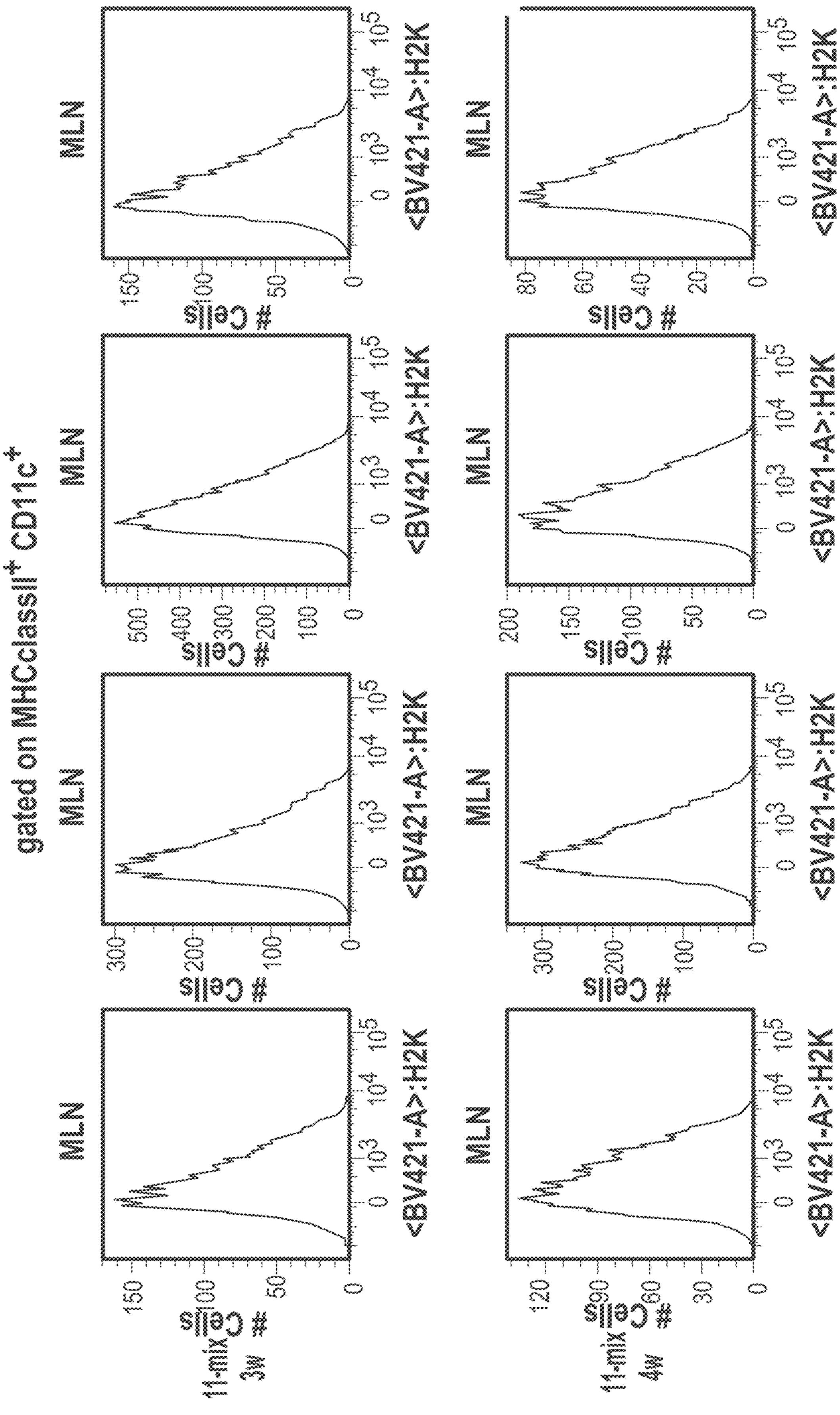
Figure 51:
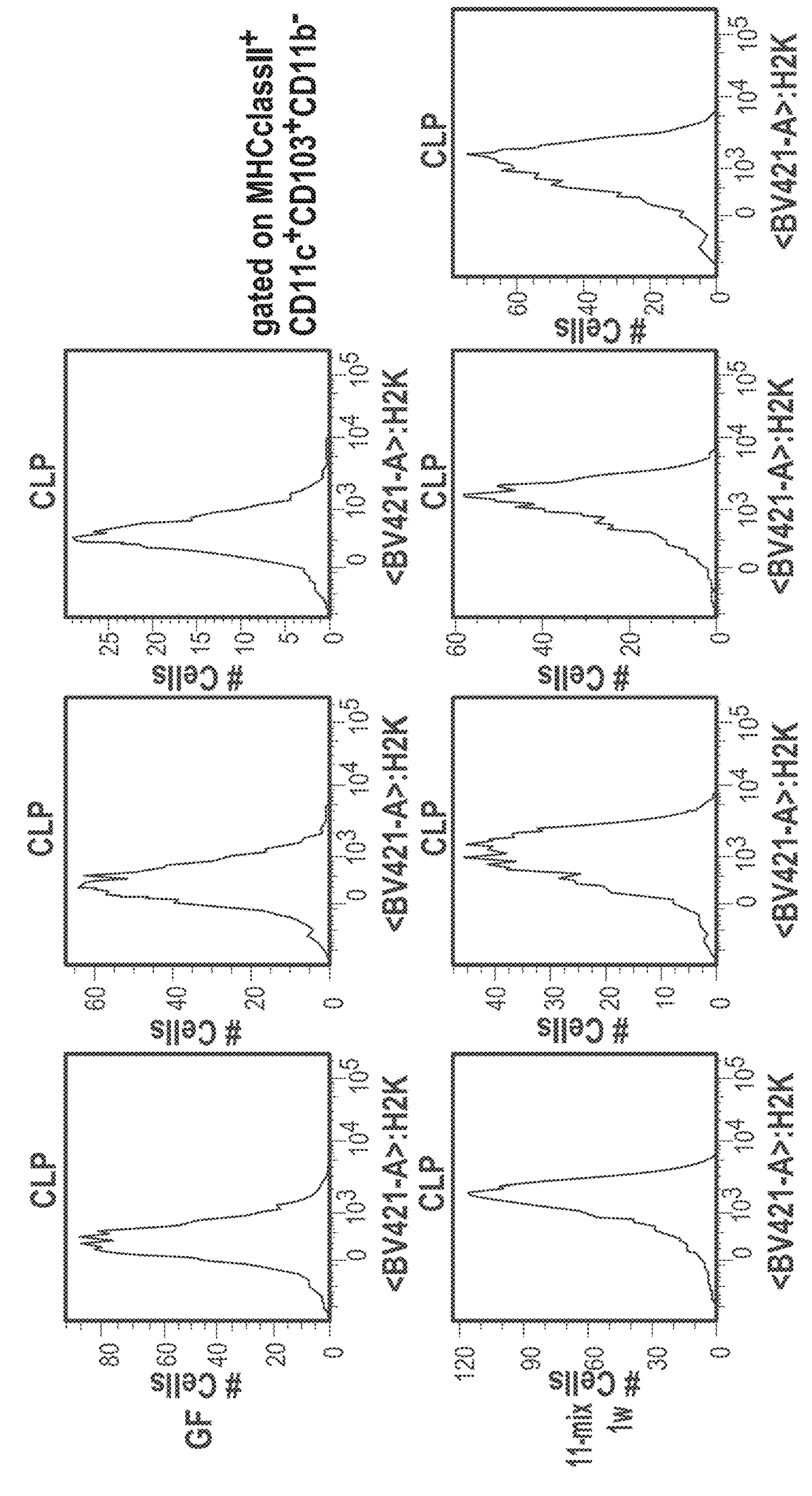
Figure 51:
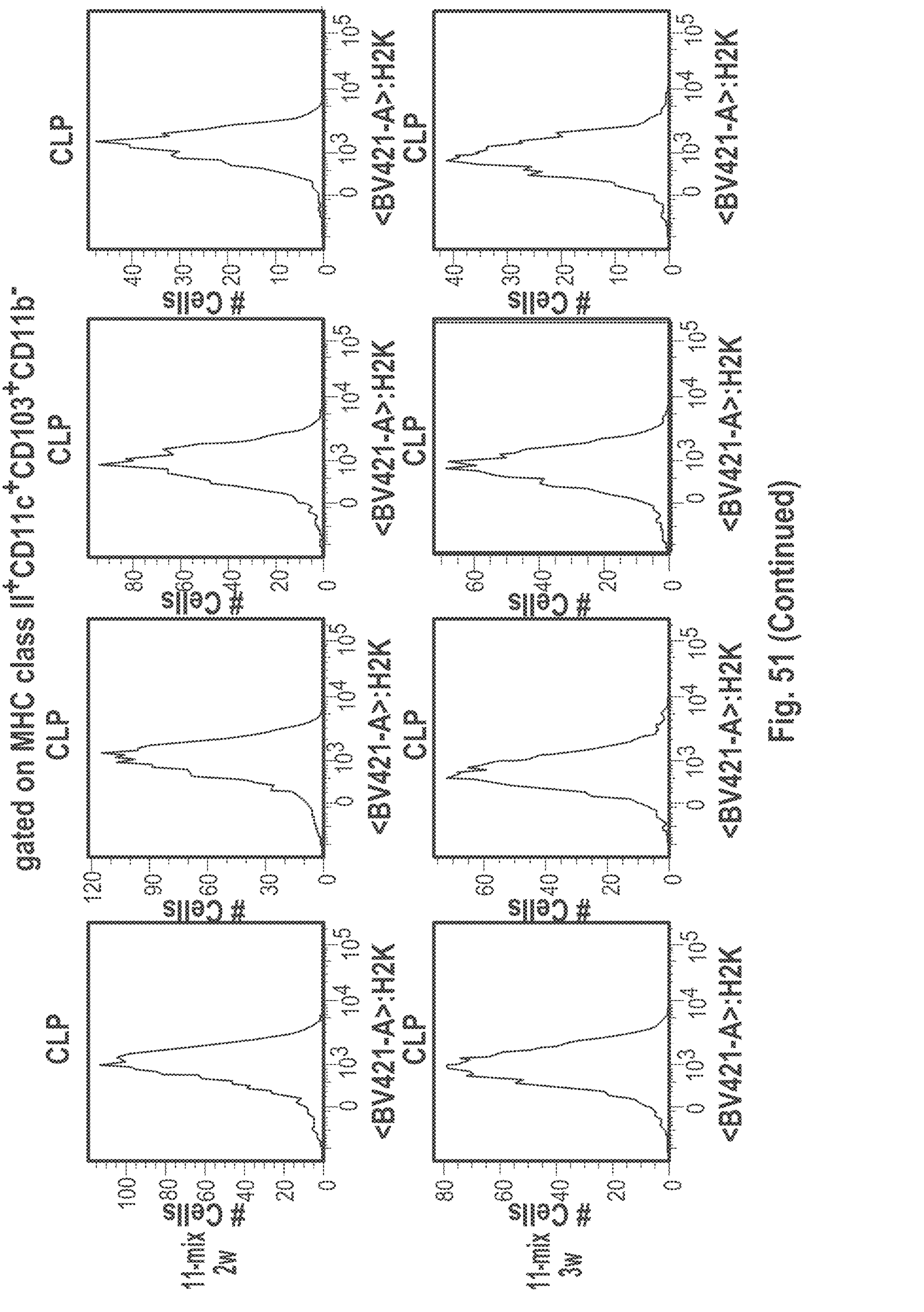
Figure 51:
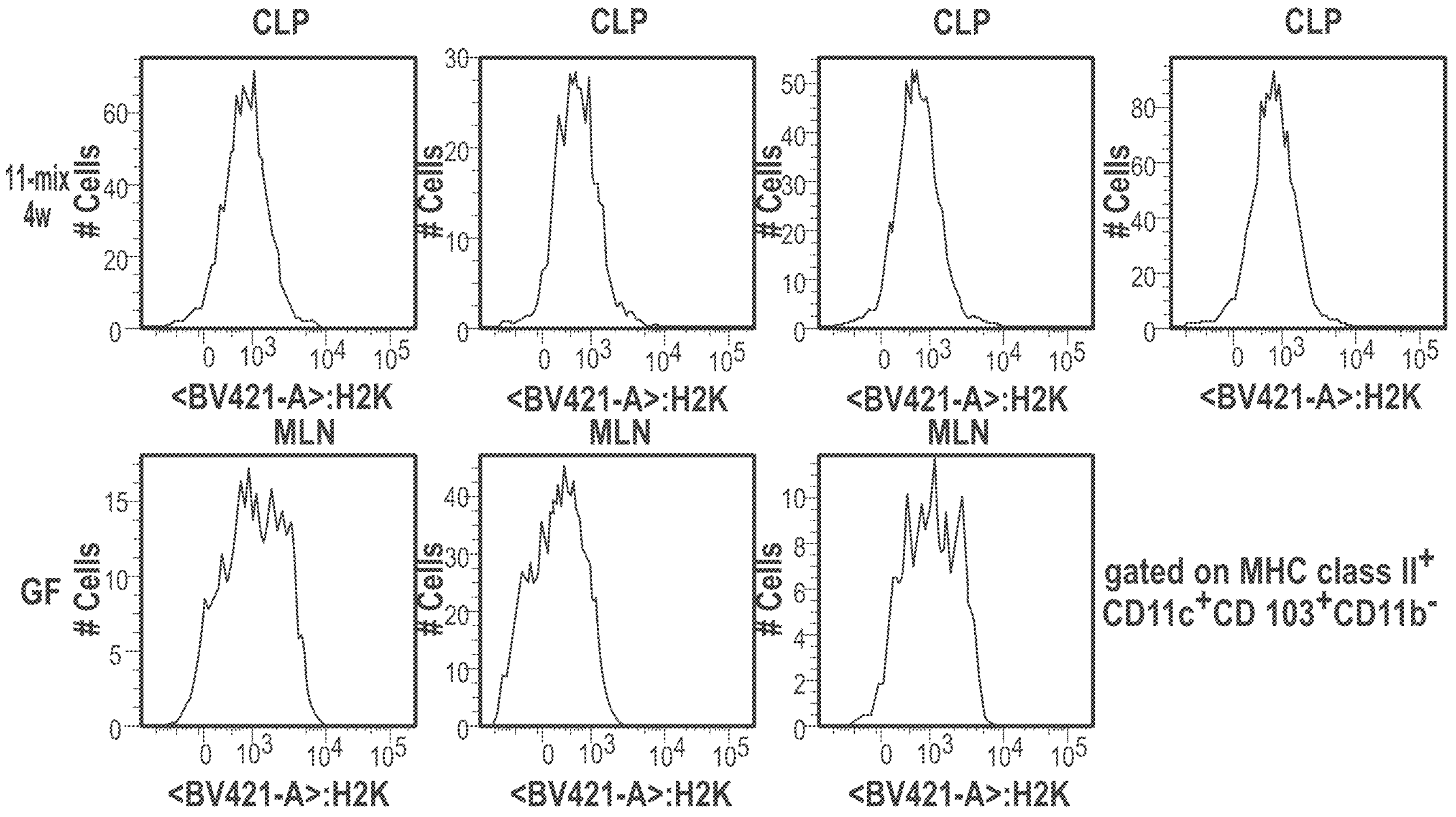
Figure 51:
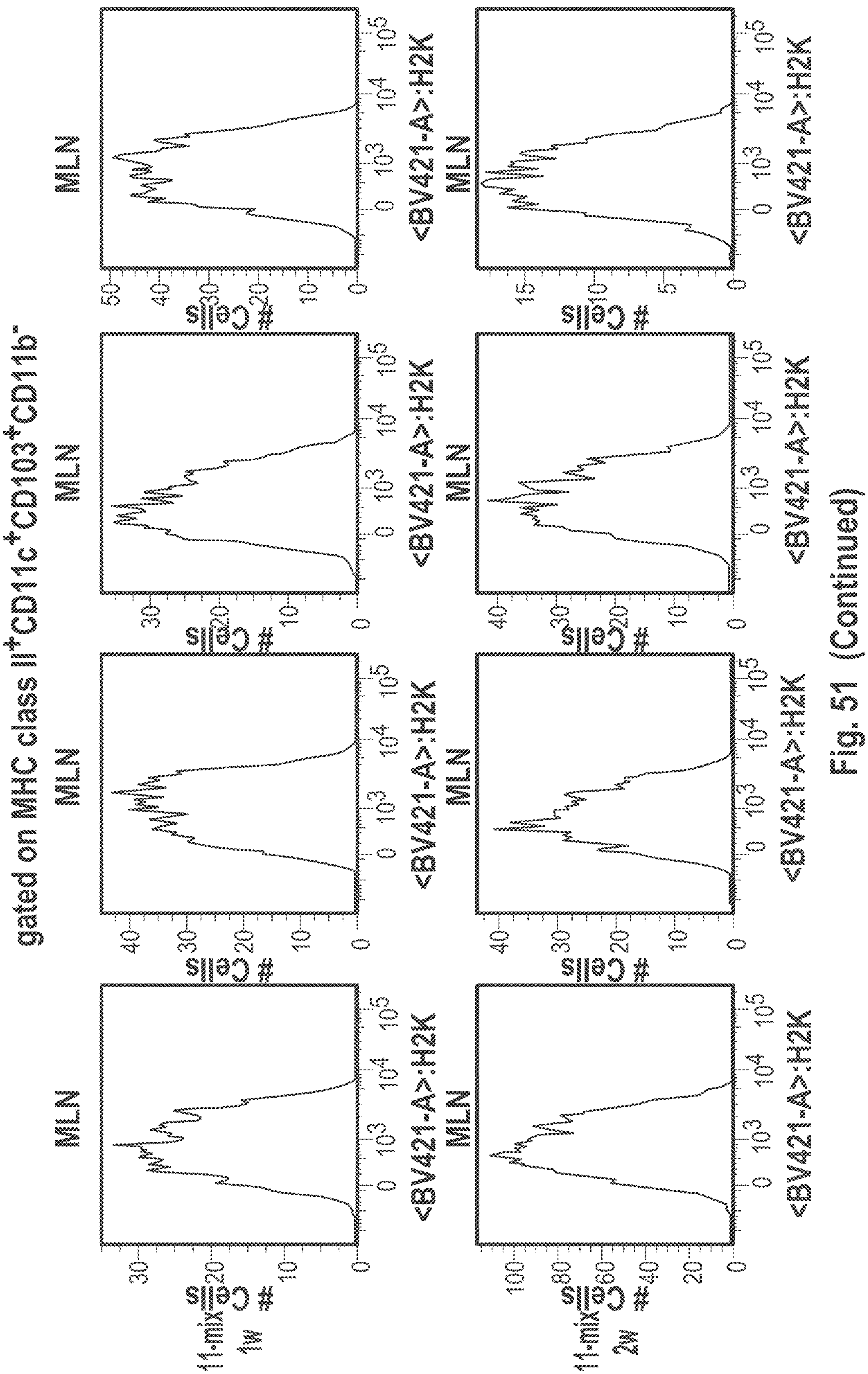
Figure 51:
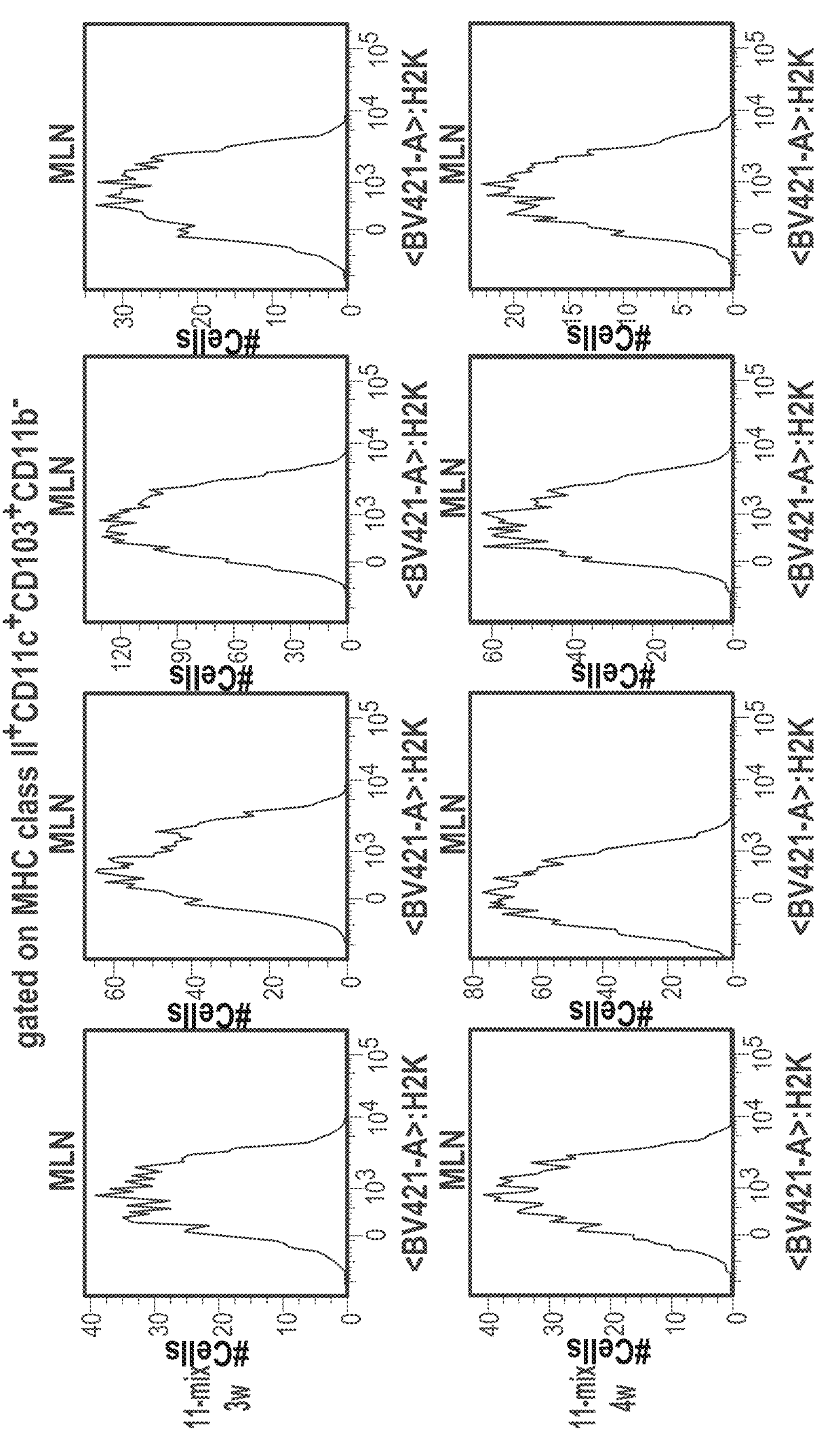
Figure 52:
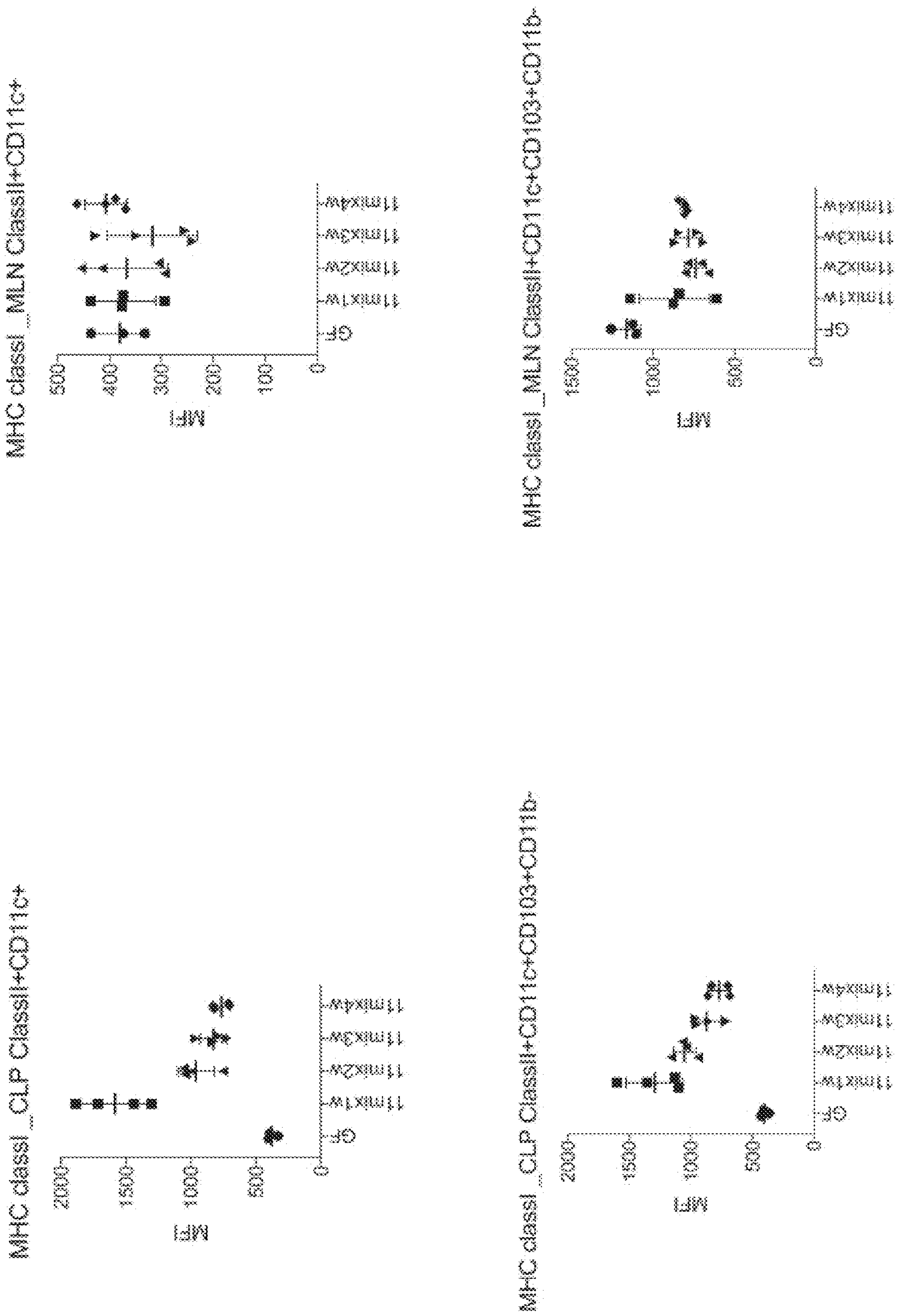
Figure 53:
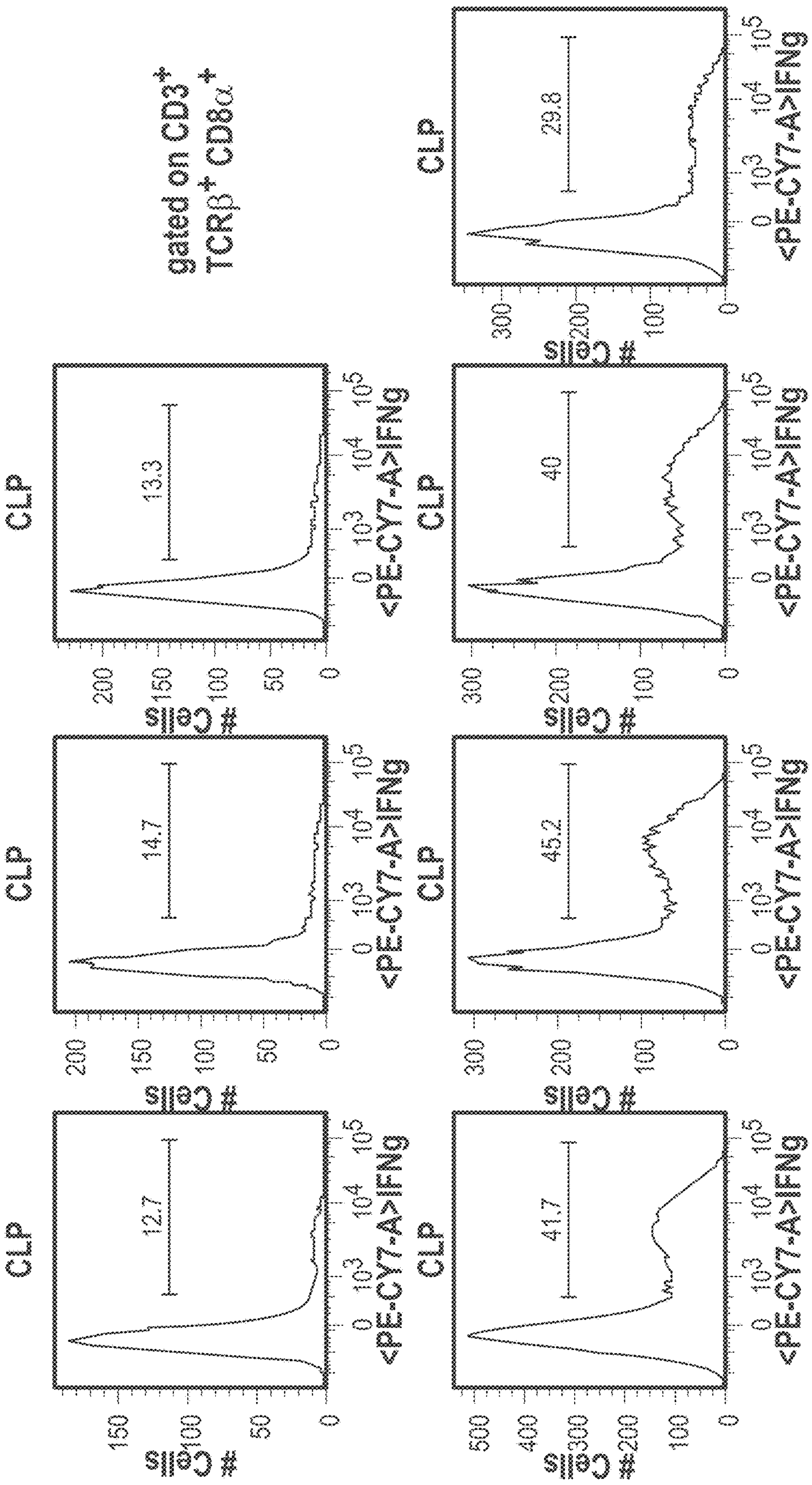
FIGS. 53 and 54 show that MHC CLP class cells are activated by the administration of the 11-mix, while there is no activation of the MHC MLN class cells. The individual measurements are shown in FIG. 53, while the accumulated data are depicted in FIG. 54 expressed as percentage of CD3+ TCDRbeta+CD8alpha+ cells.
Figure 53:
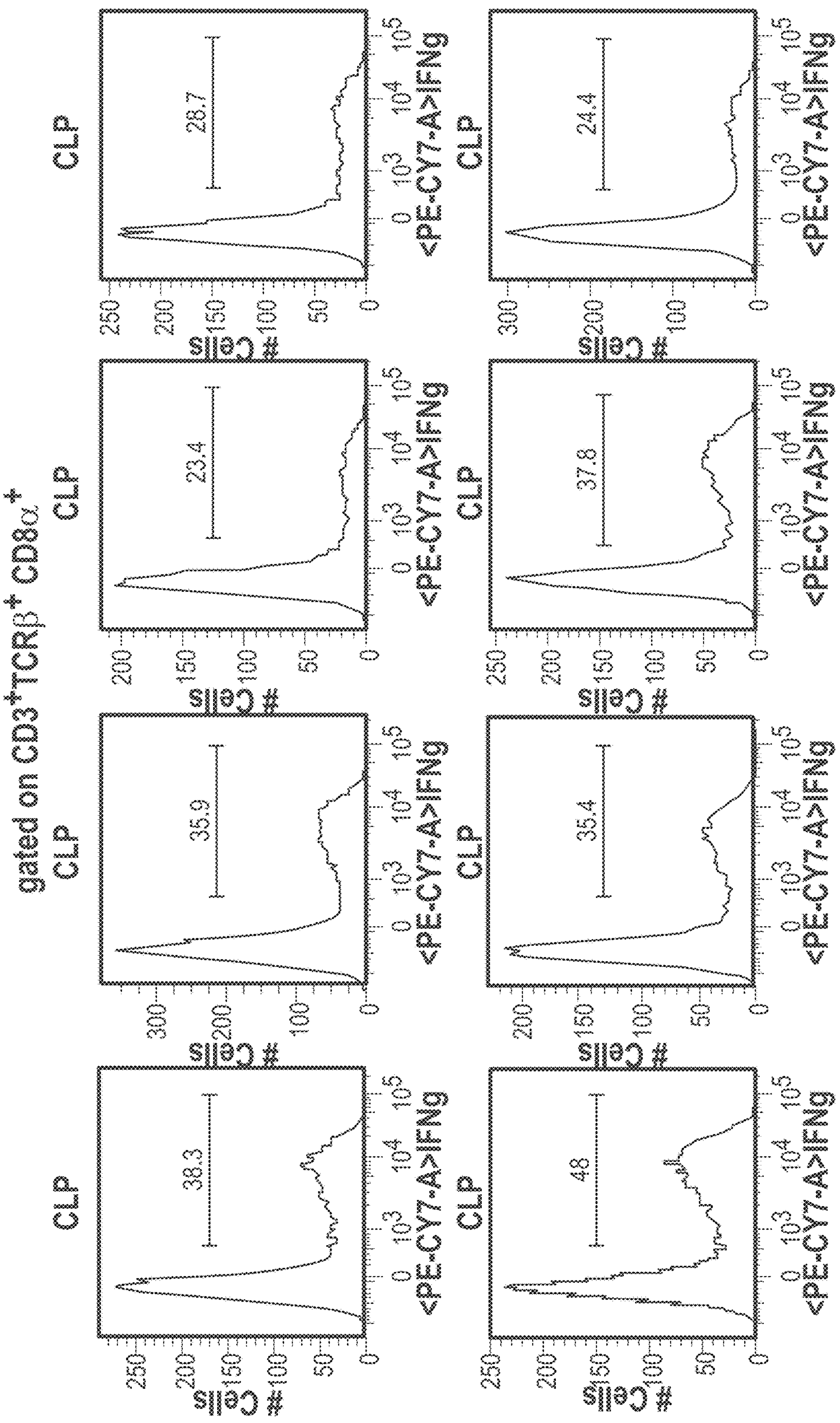
Figure 53:
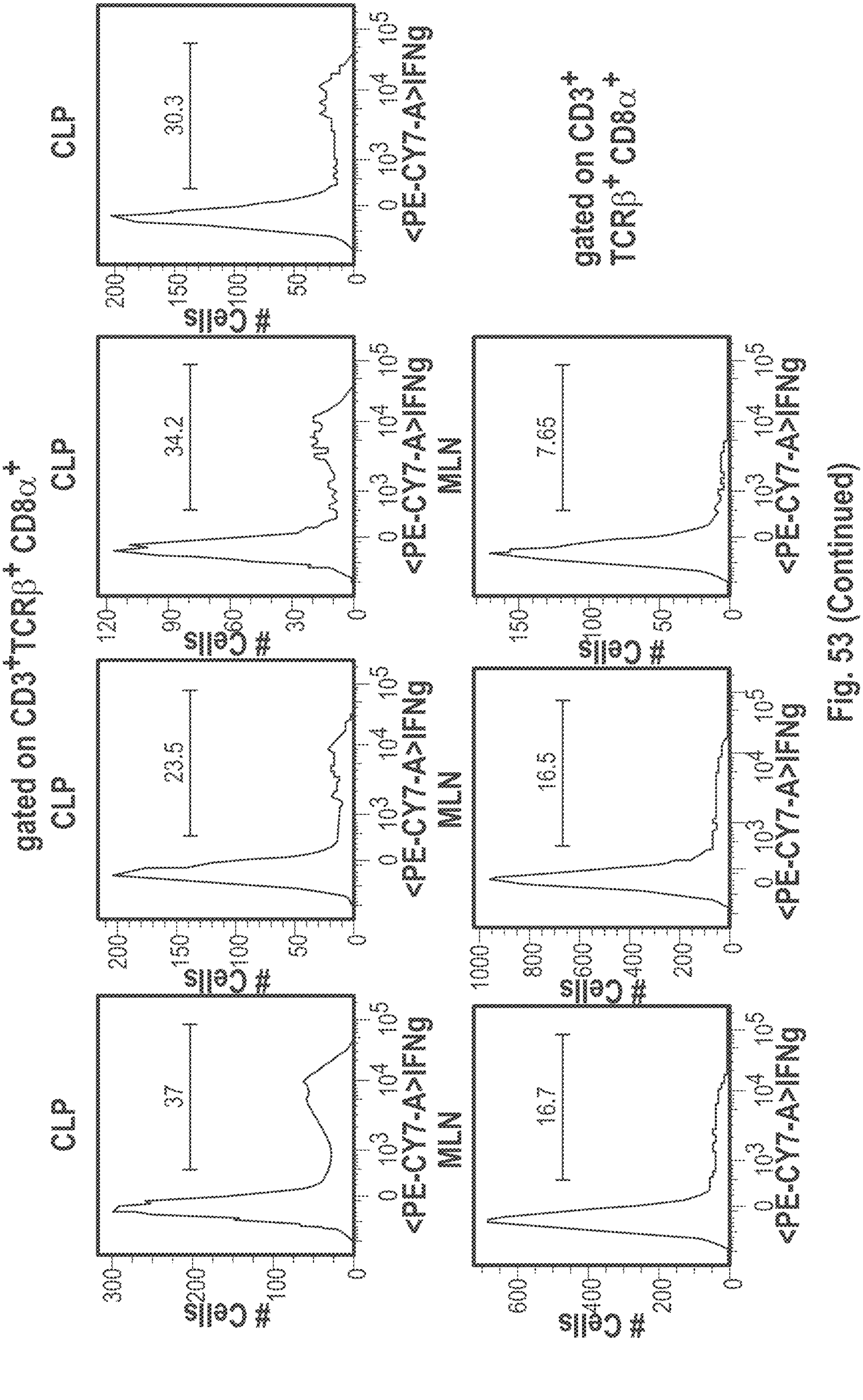
Figure 53:
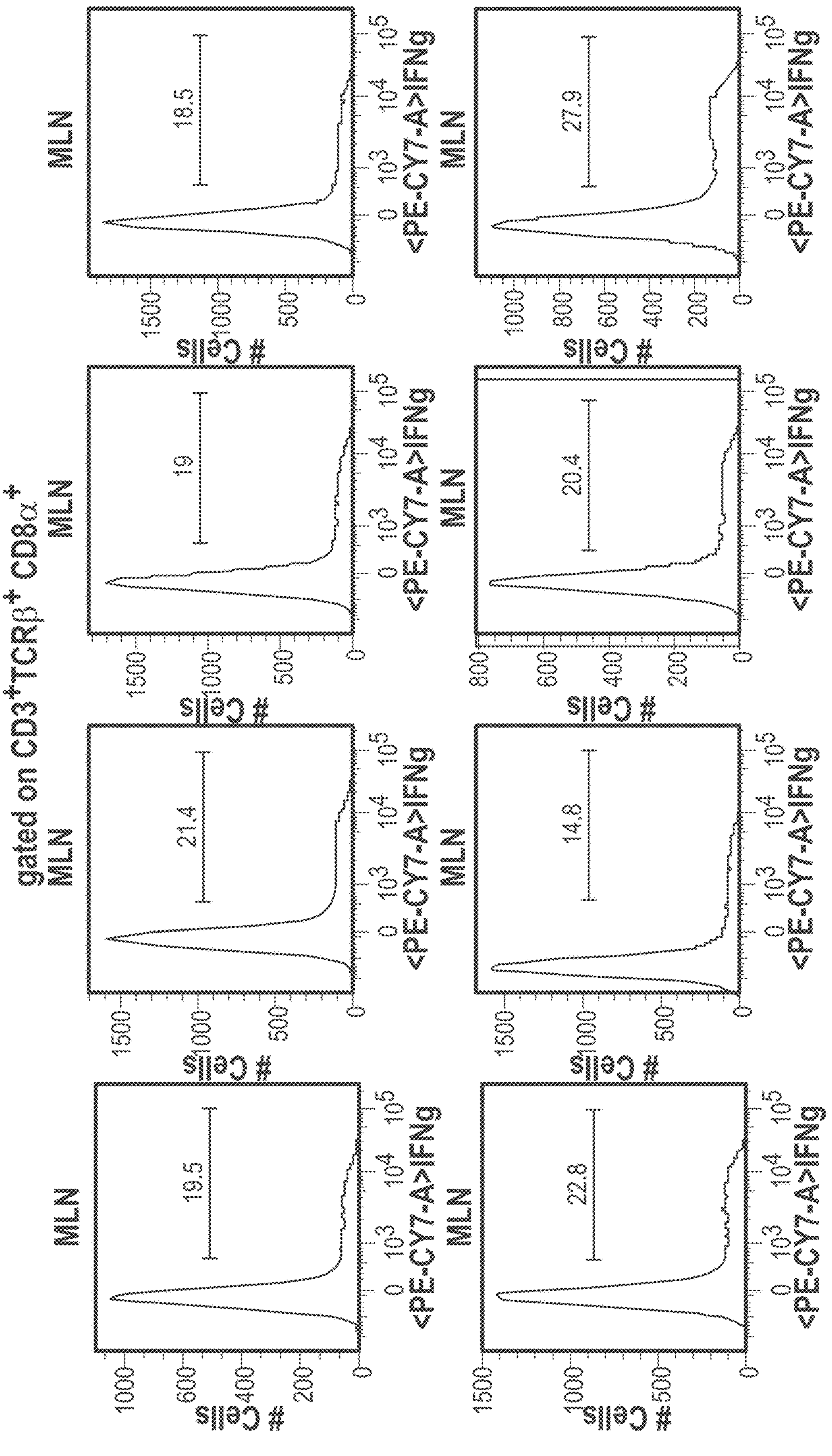
Figure 53:
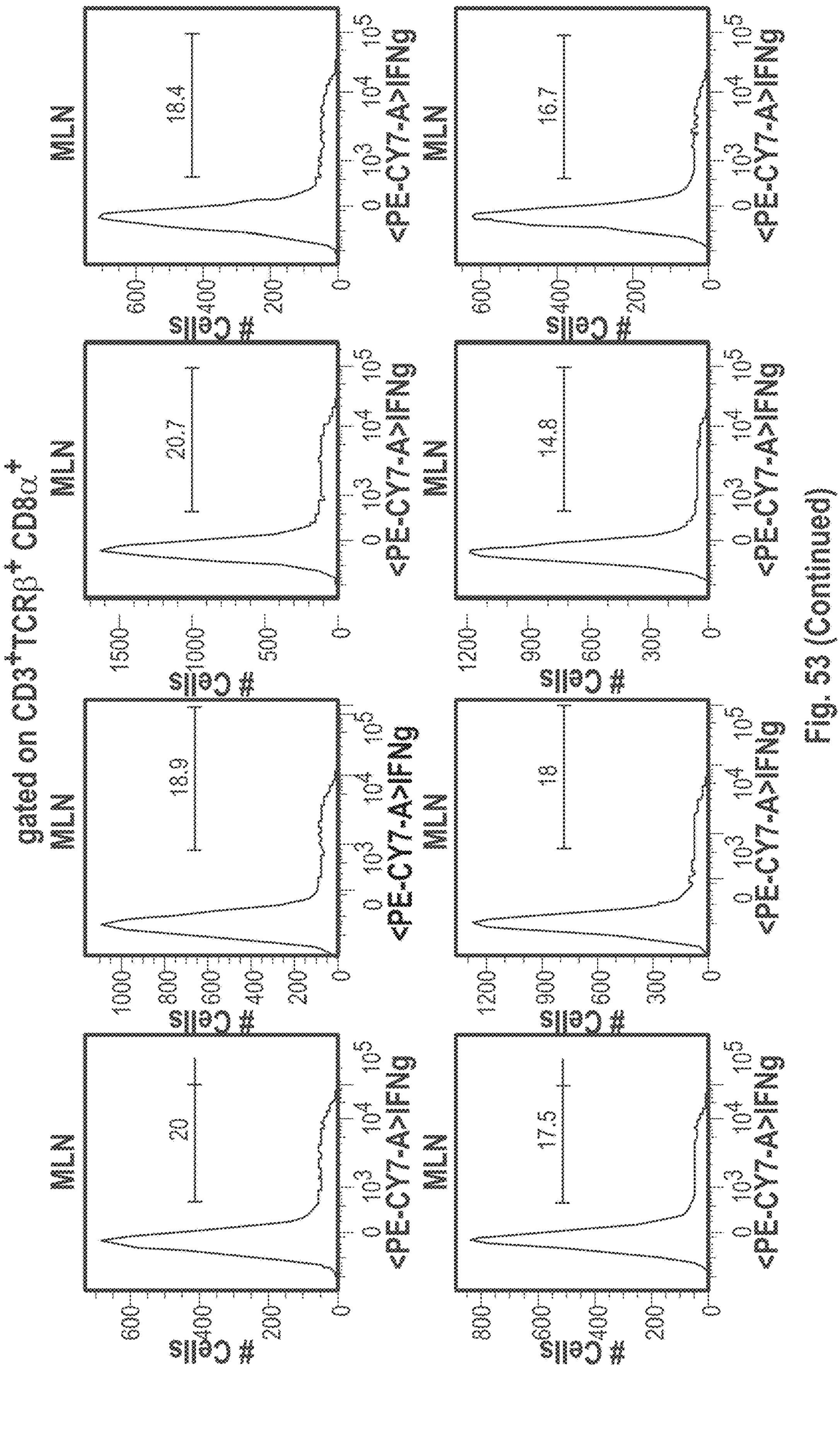
Figure 54:
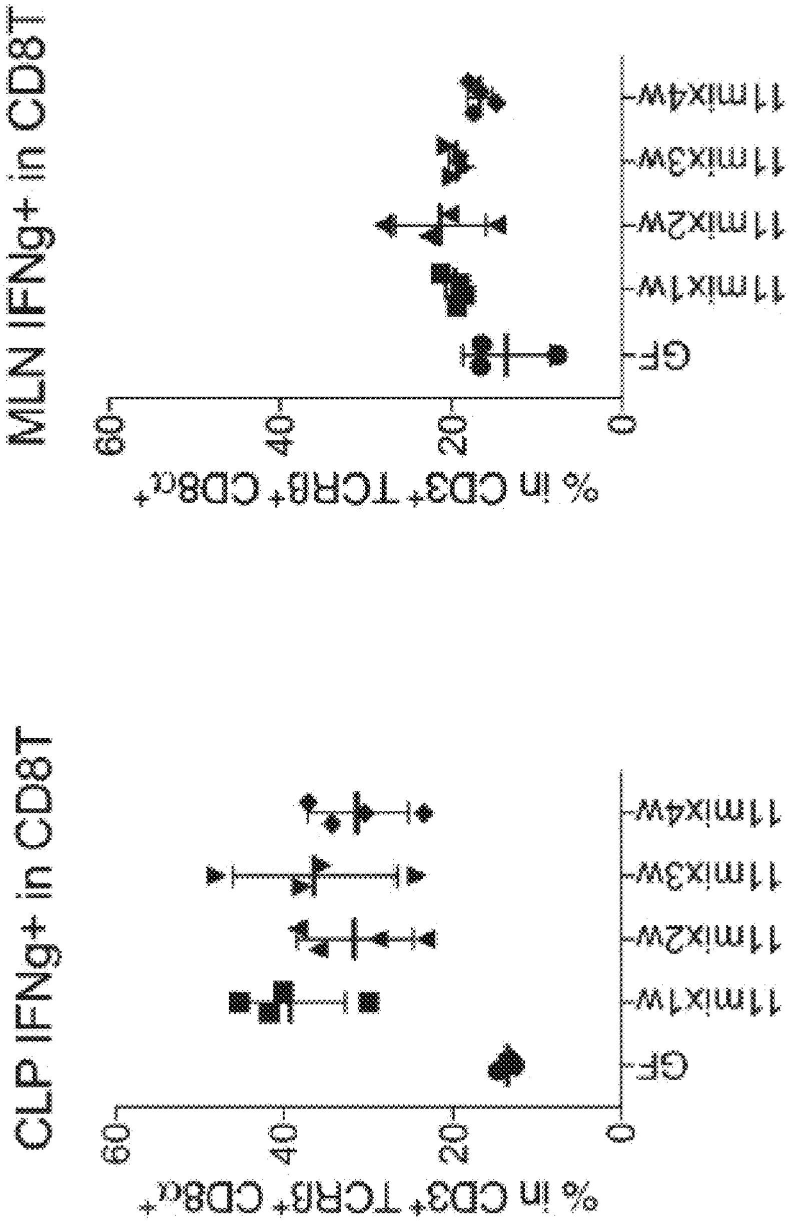

Example 11: Selective and Temporal Activation of Subsets of Lamina Propria Dendritic Cells As CD8 cells can be activated through certain subclasses of dendritic cells, the number and activation state of lamina propria CD11b− CD103+ dendritic cells was investigated following administration of the 11-mix. As shown in FIG. 49, the administration of the 11-mix did not change the proportion of the lamina propria CD11b− CD103+ dendritic cell subset.

The temporality/kinetics of activation was also investigated. GF mice were colonized with the 11-mix for 1, 2, 3, and 4 weeks. The frequency of colonic LP and MLN dendritic cells (DCs)/macrophage subsets were not affected by the colonization with 11 mix. However, expression of MHC class I on colonic LP DCs (but not MLN DCs), particularly on colonic LP CD103+DC subset (namely, Batf3-dependent DC subset), was significantly enhanced by the colonization with 11-mix. Upregulation of MHC class I expression most strongly occurred at 1 week after colonization. (See FIGS. 50-54) Without being limited to a particular mechanism it is likely that induction of the CD8 positive T cells is mostly due to proliferation rather than antigen-specific de novo differentiation.

Figure 55:
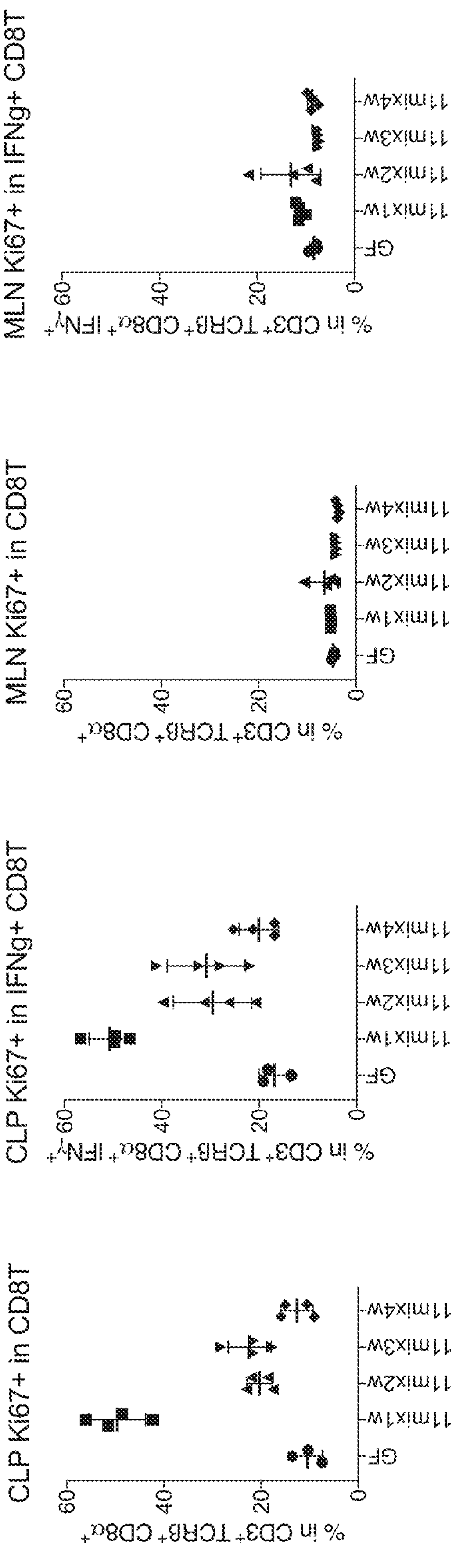
FIG. 55 shows that MHC CLP class cells are activated by the administration of the 11-mix, as evidenced by Ki67 status, while there is no activation of the MHC MLN class cells.
Figure 56:
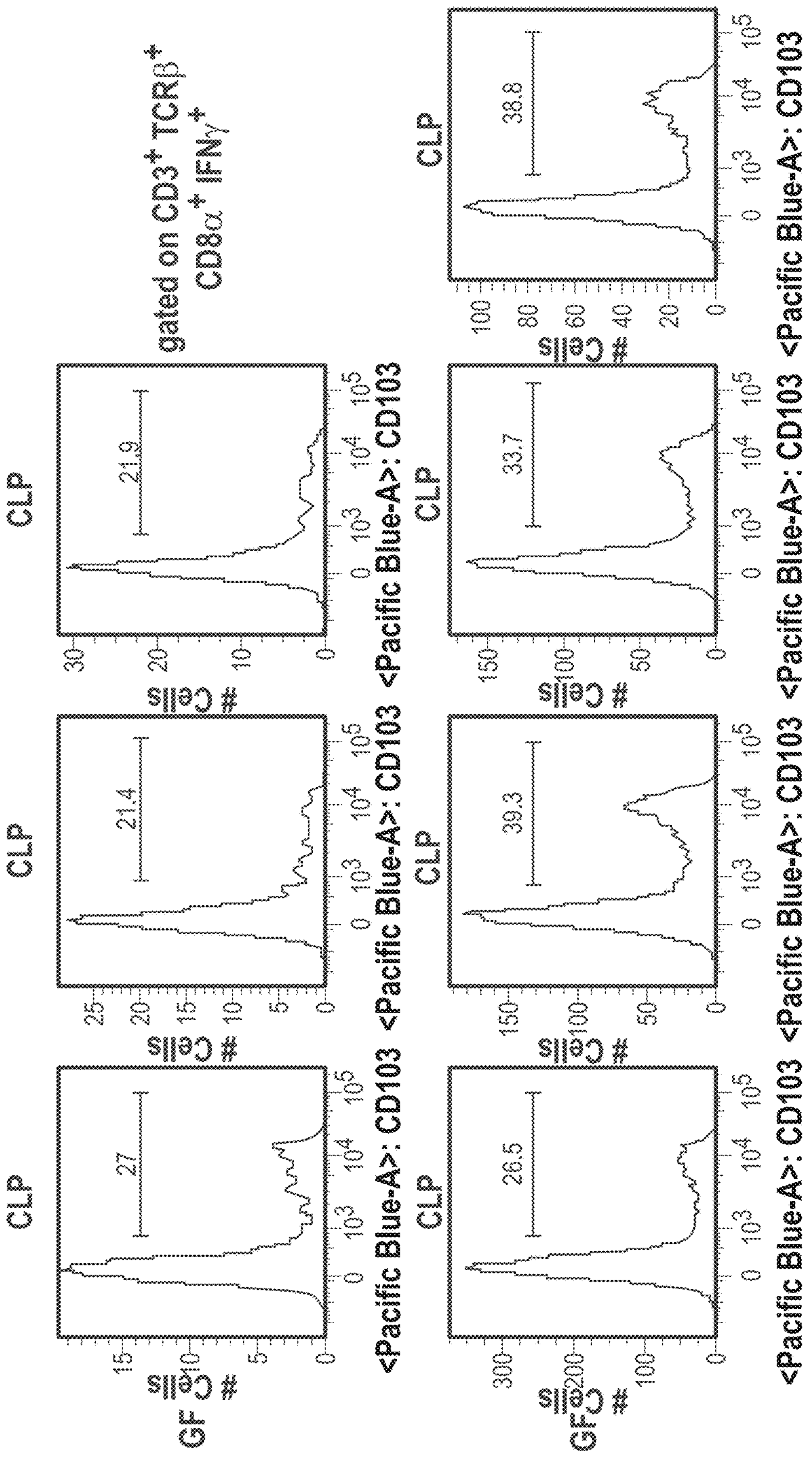
FIGS. 56 and 57 show that MHC CLP class cells are activated by the administration of the 11-mix, as evidenced by CD103+ status, while there is no activation of the MHC MLN class cells. The individual measurements are shown in FIG. 56, while the accumulated data are depicted in FIG. 57 expressed as percentage of CD3+ TCRBeta+CD8alpha+ IFN $\gamma$+ cells.
Figure 56:
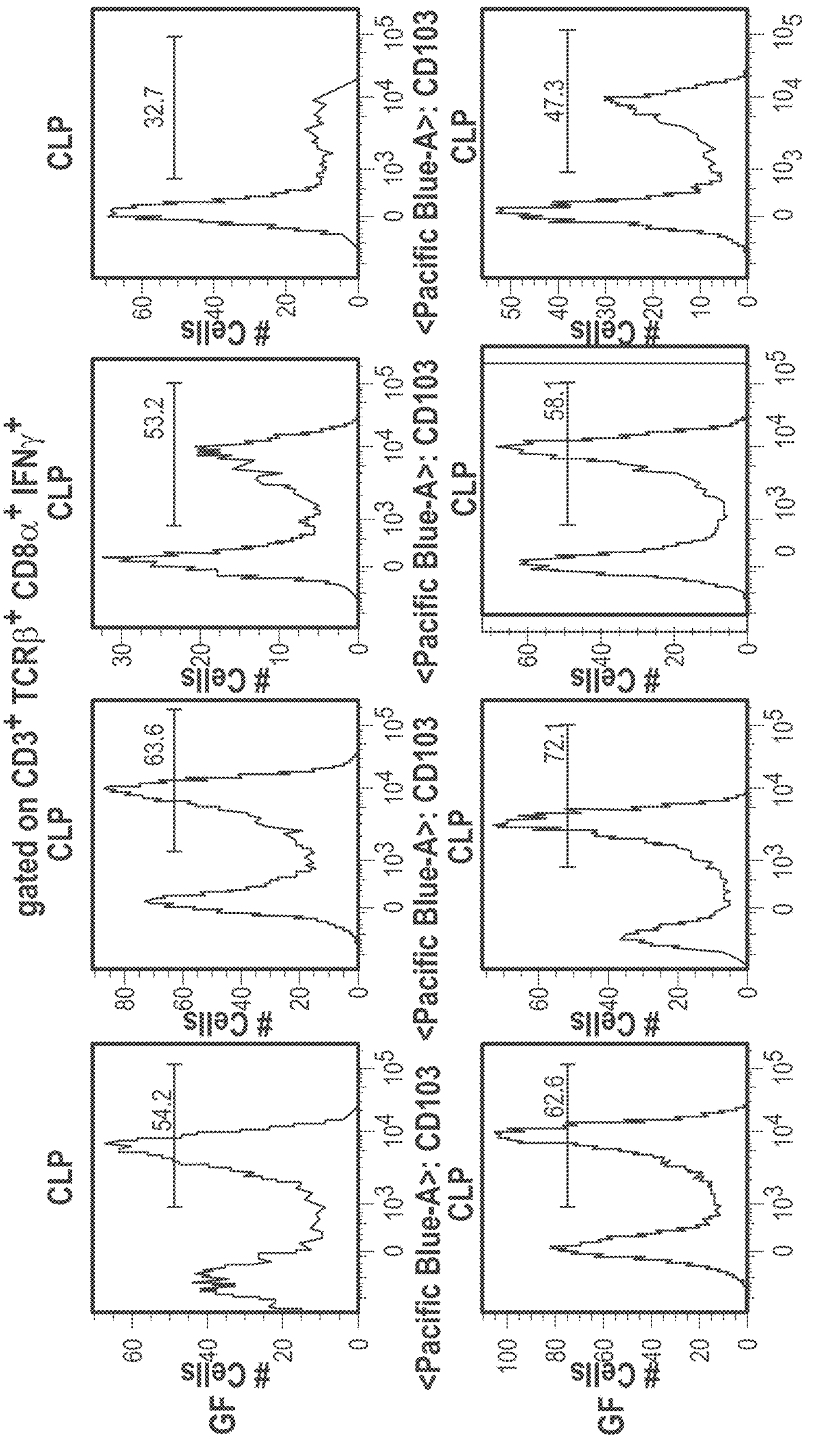
Figure 56:
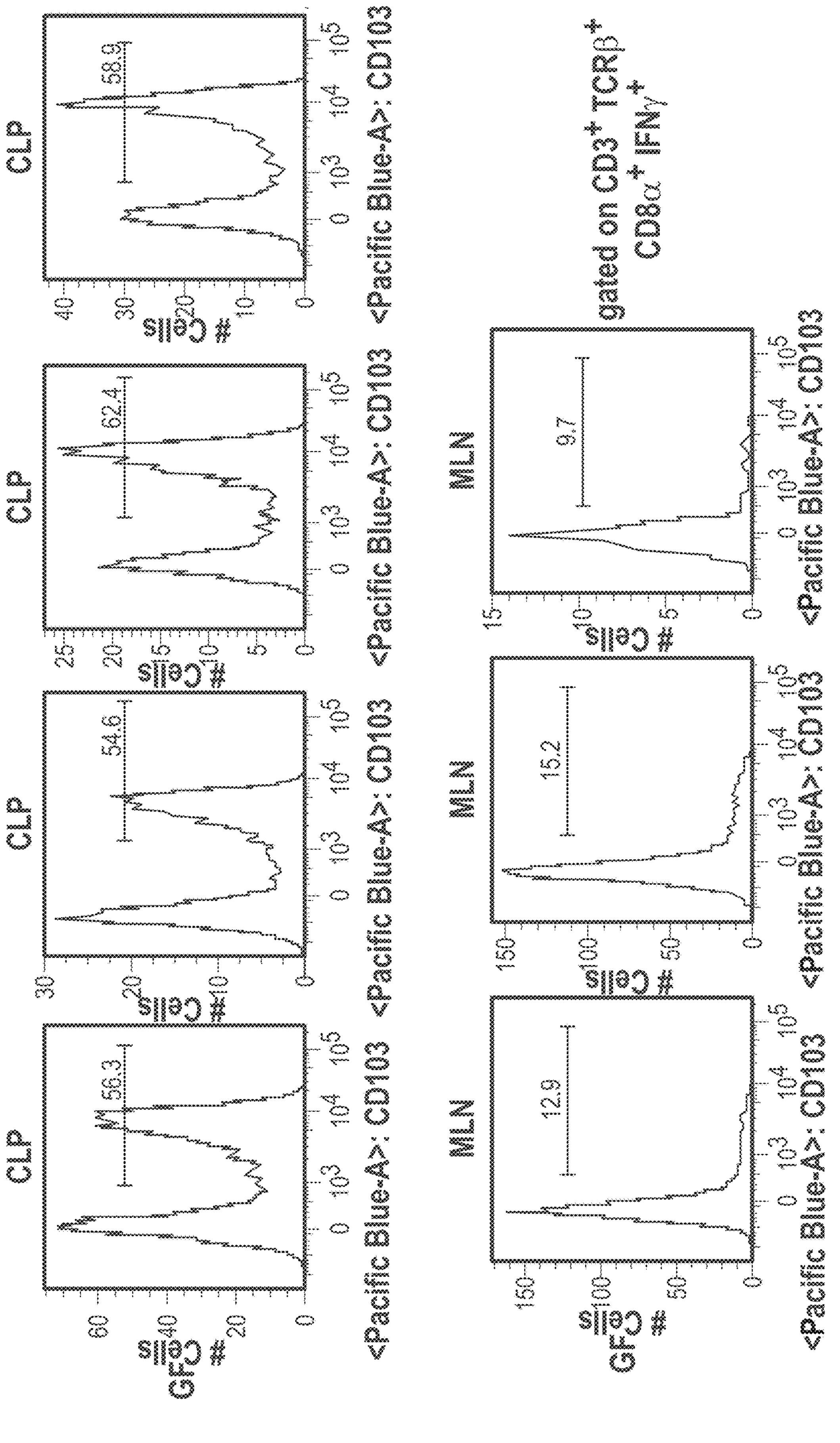
Figure 56:
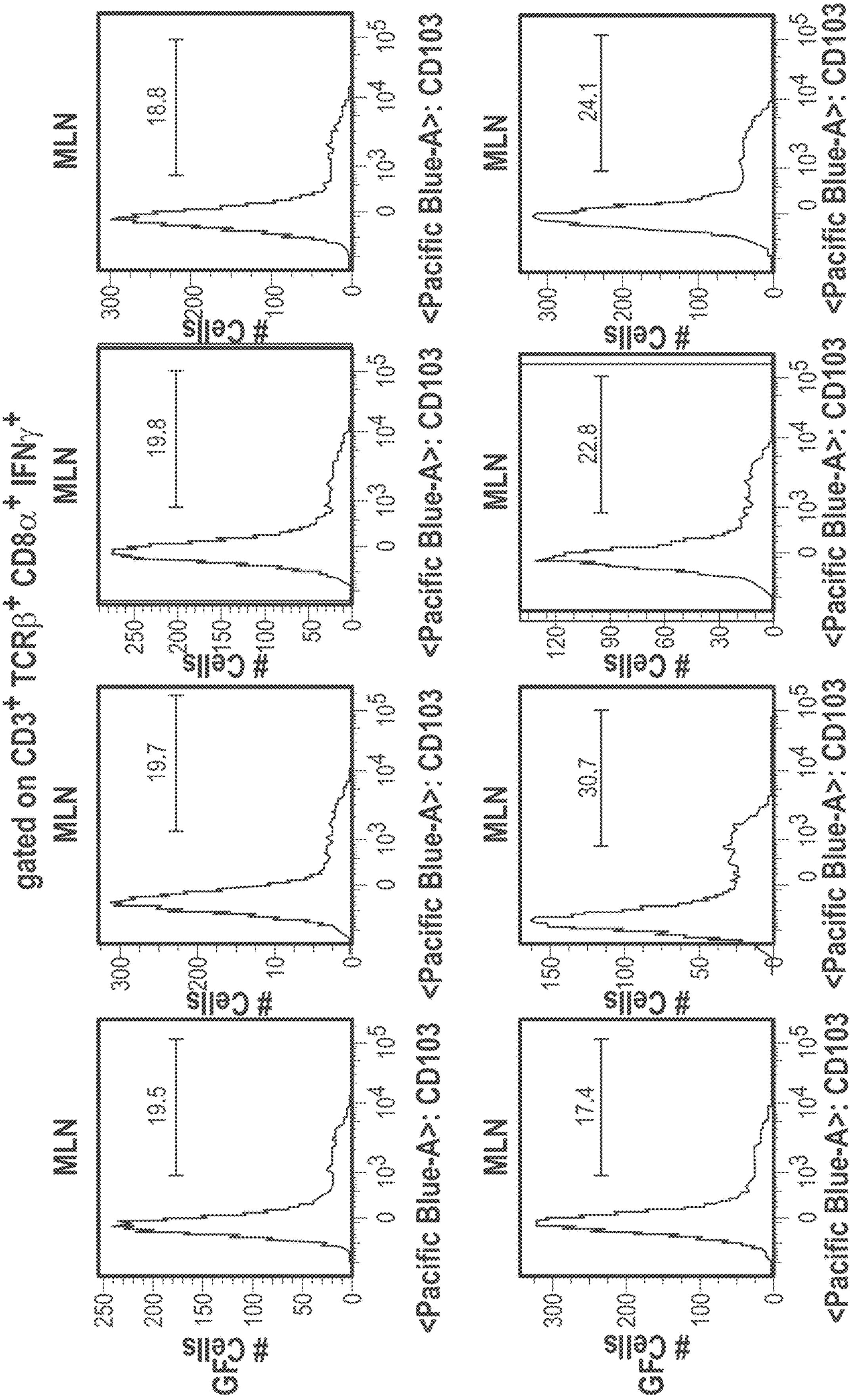
Figure 56:
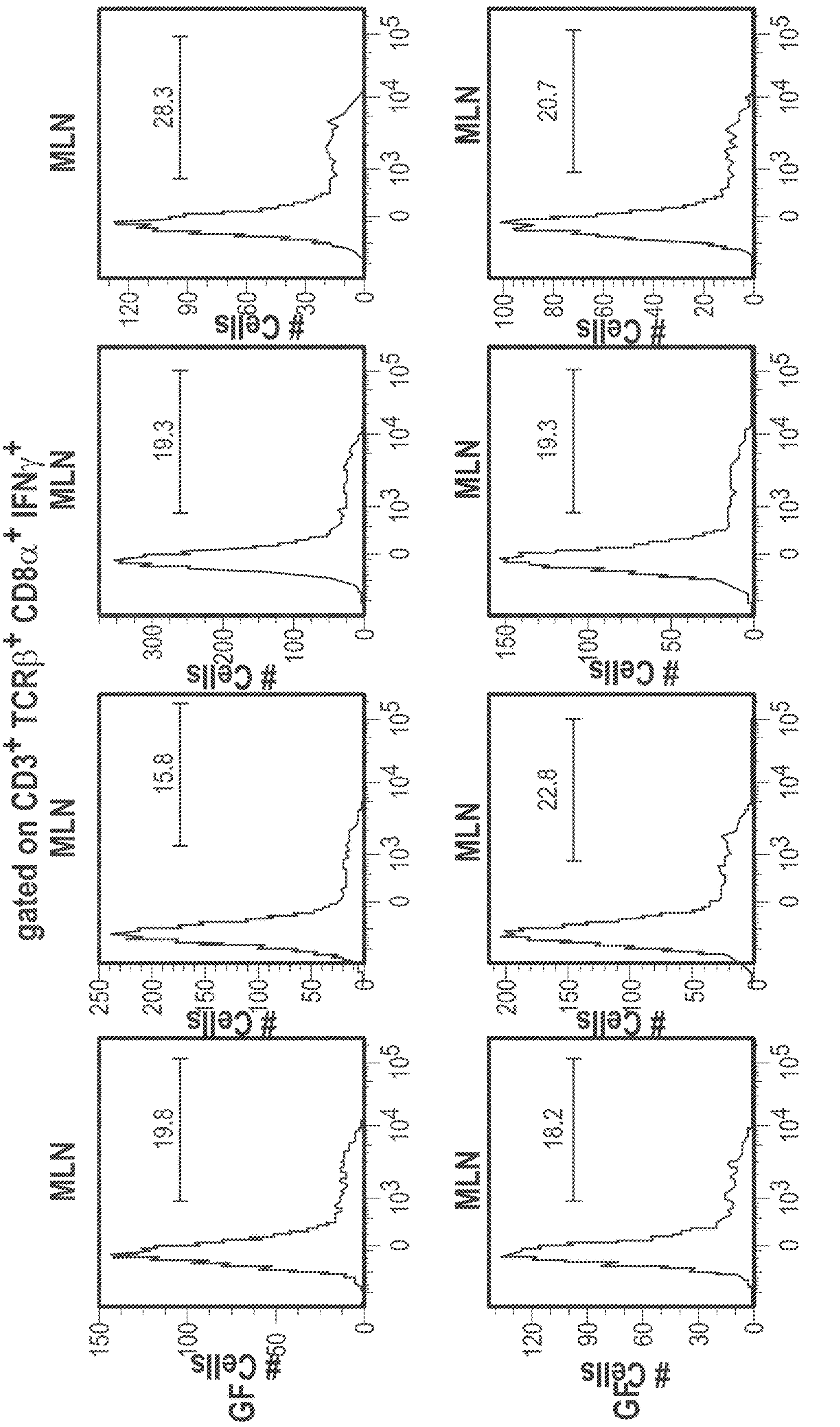
Figure 57:
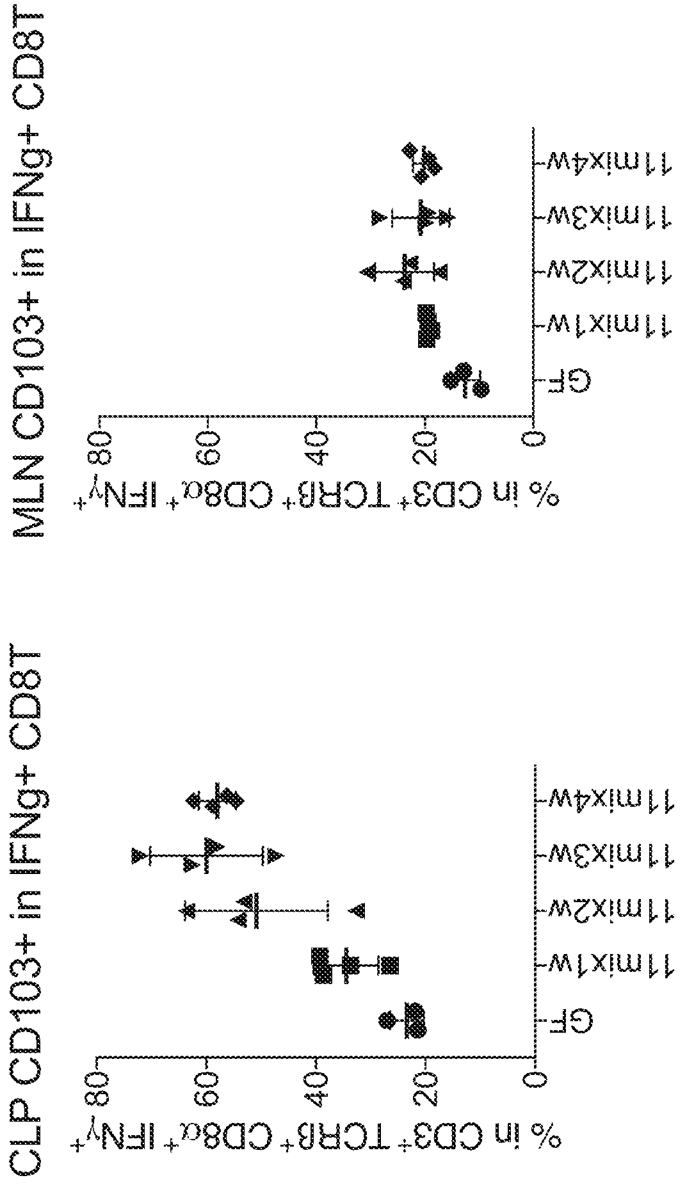

Ki67 staining revealed that expansion of CD8 positive T cells occurred at 1 week, accompanied by increase with IFN γ+CD8+ T in the colonic LP (See FIG. 55). CD103 staining revealed that induced IFN γ+CD8+ T at 1 week post colonization were mostly CD103 negative, and that CD103+ IFNγ+CD8 T (tissue resident memory phenotype CD8+ T) were gradually increased (See FIGS. 56 and 57).

Sequence Listing

Sequence_List.TXT

The invention claimed is:

1. A pharmaceutical composition comprising a purified bacterial mixture consisting of bacterial strains comprising 16S rDNA sequences of at least 99% sequence identity with SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, and SEQ ID NO:lh wherein the bacterial strains are lyophilized.

2. The pharmaceutical composition of claim 1, wherein the composition further comprises an anti-cancer agent.

3. The pharmaceutical composition of claim 2, wherein the anti-cancer agent is an immune checkpoint inhibitor.

4. The pharmaceutical composition of claim 3, wherein the immune checkpoint inhibitor is a PD-1 inhibitor.

5. The pharmaceutical composition of claim 3, wherein the immune checkpoint inhibitor is nivolumab.

6. The pharmaceutical composition of claim 3, wherein the immune checkpoint inhibitor is pembrolizumab.

7. The pharmaceutical composition of claim 3, wherein the immune checkpoint inhibitor is a CTLA-4 inhibitor.

8. The pharmaceutical composition of claim 1, further comprising a pharmaceutically acceptable excipient.

9. The pharmaceutical composition of claim 1, wherein the pharmaceutical composition is formulated for oral administration.

10. The pharmaceutical composition of claim 1, wherein the pharmaceutical composition is formulated for delivery to the intestine.

11. The pharmaceutical composition of claim 1, wherein the pharmaceutical composition is formulated for delivery to the colon.

12. The pharmaceutical composition of claim 1, wherein the pharmaceutical composition is in the form of a capsule.

13. The pharmaceutical composition of claim 1, wherein the pharmaceutical composition further comprises a pH sensitive composition comprising one or more enteric polymers.

14. The pharmaceutical composition of claim 1, wherein the pharmaceutical composition induces proliferation and/or accumulation of CD8+ T cells.

15. A pharmaceutical composition comprising a purified bacterial mixture consisting of bacterial strains comprising 16S rDNA sequences of at least 99% sequence identity with SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, and SEQ ID NO:11, wherein the pharmaceutical composition further comprises a pH sensitive composition comprising one or more enteric polymers.

16. The pharmaceutical composition of claim 15, wherein the composition further comprises an anti-cancer agent.

17. The pharmaceutical composition of claim 16, wherein the anti-cancer agent is an immune checkpoint inhibitor.

18. The pharmaceutical composition of claim 17, wherein the immune checkpoint inhibitor is a PD-1 inhibitor.

19. The pharmaceutical composition of claim 17, wherein the immune checkpoint inhibitor is nivolumab.

20. The pharmaceutical composition of claim 17, wherein the immune checkpoint inhibitor is pembrolizumab.

21. The pharmaceutical composition of claim 15, wherein the immune checkpoint inhibitor is a CTLA-4 inhibitor.

22. The pharmaceutical composition of claim 15, further comprising a pharmaceutically acceptable excipient.

23. The pharmaceutical composition of claim 15, wherein the pharmaceutical composition is formulated for oral administration.

24. The pharmaceutical composition of claim 15, wherein the pharmaceutical composition is formulated for delivery to the intestine.

25. The pharmaceutical composition of claim 15, wherein the pharmaceutical composition is formulated for delivery to the colon.

26. The pharmaceutical composition of claim 15, wherein the bacterial strains are lyophilized.

27. The pharmaceutical composition of claim 15, wherein the bacterial strains are in powdered form.

28. The pharmaceutical composition of claim 15, wherein the pharmaceutical composition is in the form of a capsule.

29. The pharmaceutical composition of claim 15, wherein the pharmaceutical composition induces proliferation and/or accumulation of CD8+ T cells.

* * * * *

UNITED STATES PATENT AND TRADEMARK OFFICE

CERTIFICATE OF CORRECTION

PATENT NO. : 10,576,136 B2
APPLICATION NO. : 16/421557
DATED : March 3, 2020
INVENTOR(S) : Kenya Honda et al.

It is certified that error appears in the above-identified patent and that said Letters Patent is hereby corrected as shown below:

In the Claims

At Column 249, Lines 38-44, (approx.) Claim 1 should read:
1. A pharmaceutical composition comprising a purified bacterial mixture consisting of bacterial strains comprising 16S rDNA sequences of at least 99% sequence identity with SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, and SEQ ID NO:11, wherein the bacterial strains are lyophilized.

Signed and Sealed this
Fifth Day of May, 2020

Andrei Iancu
*Director of the United States Patent and Trademark Office*

```
                         SEQUENCE LISTING

<160> NUMBER OF SEQ ID NOS: 64

<210> SEQ ID NO 1
<211> LENGTH: 1440
<212> TYPE: DNA
<213> ORGANISM: Phascolarctobacterium faecium

<400> SEQUENCE: 1

gacgaacgct ggcggcgtgc ctaacacatg caagtcgaac ggagaatttt atttcggtag      60

aattcttagt ggcgaacggg tgagtaacgc gtaggcaacc taccctttag acggggacaa     120

cattccgaaa ggagtgctaa taccggatgt gatcatcttg ccgcatggca ggatgaagaa     180

agatggcctc tacaagtaag ctatcgctaa aggatgggcc tgcgtctgat tagctagttg     240

gtagtgtaac ggactaccaa ggcgatgatc agtagccggt ctgagaggat gaacggccac     300

attgggactg agacacggcc caaactccta cgggaggcag cagtggggaa tcttccgcaa     360

tggacgaaag tctgacggag caacgccgcg tgagtgatga aggatttcgg tctgtaaagc     420

tctgttgttt atgacgaacg tgcagtgtgt gaacaatgca ttgcaatgac ggtagtaaac     480

gaggaagcca cggctaacta cgtgccagca gccgcggtaa tacgtaggtg gcgagcgttg     540

tccggaatta ttgggcgtaa agagcatgta ggcggcttaa taagtcgagc gtgaaaatgc     600

ggggctcaac cccgtatggc gctggaaact gttaggcttg agtgcaggag aggaaagggg     660

aattcccagt gtagcggtga aatgcgtaga tattgggagg aacaccagtg gcgaaggcgc     720

ctttctggac tgtgtctgac gctgagatgc gaaagccagg gtagcgaacg ggattagata     780
```

```
ccccggtagt cctggccgta aacgatgggt actaggtgta ggaggtatcg accccttctg    840

tgccggagtt aacgcaataa gtaccccgcc tggggagtac ggccgcaagg ttgaaactca    900

aaggaattga cgggggcccg cacaagcggt ggagtatgtg gtttaattcg acgcaacgcg    960

aagaacctta ccaaggcttg acattgattg aacgctctag agatagagat ttcccttcgg   1020

ggacaagaaa acaggtggtg catggctgtc gtcagctcgt gtcgtgagat gttgggttaa   1080

gtcccgcaac gagcgcaacc cctatcctat gttaccagca agtaaagttg gggactcatg   1140

ggagactgcc agggacaacc tggaggaagg cggggatgac gtcaagtcat catgcccctt   1200

atgtcttggg ctacacacgt actacaatgg tcggaaacag agggaagcga agccgcgagg   1260

cagagcaaac cccagaaacc cgatctcagt tcggatcgca ggctgcaacc cgcctgcgtg   1320

aagtcggaat cgctagtaat cgcaggtcag catactgcgg tgaatacgtt cccgggcctt   1380

gtacacaccg cccgtcacac cacgaaagtt ggtaacaccc gaagccggtg aggtaaccta   1440
```

<210> SEQ ID NO 2
<211> LENGTH: 1392
<212> TYPE: DNA
<213> ORGANISM: Fusobacterium ulcerans

<400> SEQUENCE: 2

```
gatgaacgct gacagaatgc ttaacacatg caagtctact tgatccttcg ggtgaaggtg     60

gcggacgggt gagtaacgcg taaagaactt gccttacaga ctgggacaac atttggaaac    120

gaatgctaat accggatatt atgattgggt cgcatgatct gattatgaaa gctatatgcg    180

ctgtgagaga gctttgcgtc ccattagtta gttggtgagg taacggctca ccaagacgat    240

gatgggtagc cggcctgaga gggtgaacgg ccacaagggg actgagacac ggcccttact    300

cctacgggag gcagcagtgg ggaatattgg acaatggacc aaaagtctga tccagcaatt    360

ctgtgtgcac gaagaagttt ttcggaatgt aaagtgcttt cagttgggaa gaagtcagtg    420

acggtaccaa cagaagaagc gacggctaaa tacgtgccag cagccgcggt aatacgtatg    480

tcgcaagcgt tatccggatt tattgggcgt aaagcgcgtc taggcggctt agtaagtctg    540

atgtgaaaat gcggggctca accccgtatt gcgttggaaa ctgctaaact agagtactgg    600

agaggtaggc ggaactacaa gtgtagaggt gaaattcgta gatatttgta ggaatgccga    660

tggggaagcc agcctactgg acagatactg acgctaaagc gcgaaagcgt gggtagcaaa    720

caggattaga taccctggta gtccacgccg taaacgatga ttactaggtg ttgggggtcg    780

aacctcagcg cccaagctaa cgcgataagt aatccgcctg gggagtacgt acgcaagtat    840

gaaactcaaa ggaattgacg gggacccgca caagcggtgg agcatgtggt ttaattcgac    900

gcaacgcgag gaaccttacc agcgtttgac atcccaagaa gttaacagag atgttttcgt    960

gcctcttcgg aggaacttgg tgacaggtgg tgcatggctg tcgtcagctc gtgtcgtgag   1020

atgttgggtt aagtcccgca acgagcgcaa ccccttttcgt atgttaccat cattaagttg   1080

gggactcatg cgagactgcc tgcgatgagc aggaggaagg tggggatgac gtcaagtcat   1140

catgcccctt atacgctggg ctacacacgt gctacaatgg gtagtacaga gagctgcaaa   1200

cctgcgaggg taagctaatc tcataaaact attcttagtt cggattgtac tctgcaactc   1260

gagtacatga agttggaatc gctagtaatc gcaaatcagc tatgttgcgg tgaatacgtt   1320

ctcgggtctt gtacacaccg cccgtcacac cacgagagtt ggttgcacct gaagtaacag   1380

gcctaaccgt aa                                                       1392
```

<210> SEQ ID NO 3
<211> LENGTH: 1443
<212> TYPE: DNA
<213> ORGANISM: Bacteroides dorei
<220> FEATURE:
<221> NAME/KEY: misc_feature
<222> LOCATION: (7)..(9)
<223> OTHER INFORMATION: n is a, c, g, or t

<400> SEQUENCE: 3

```
agtttgnnnt atggctcagg atgaacgcta gctacaggct taacacatgc aagtcgaggg     60

gcagcatggt cttagcttgc taaggctgat ggcgaccggc gcacgggtga gtaacacgta    120

tccaacctgc cgtctactct tggccagcct tctgaaagga agattaatcc aggatgggat    180

catgagttca catgtccgca tgattaaagg tattttccgg tagacgatgg ggatgcgttc    240

cattagatag taggcggggt aacggcccac ctagtcaacg atggataggg gttctgagag    300

gaaggtcccc cacattggaa ctgagacacg gtccaaactc ctacgggagg cagcagtgag    360

gaatattggt caatgggcga tggcctgaac cagccaagta gcgtgaagga tgactgccct    420

atgggttgta aacttctttt ataaaggaat aaagtcgggt atgcataccc gtttgcatgt    480

actttatgaa taaggatcgg ctaactccgt gccagcagcc gcggtaatac ggaggatccg    540

agcgttatcc ggatttattg ggtttaaagg gagcgtagat ggatgtttaa gtcagttgtg    600

aaagtttgcg gctcaaccgt aaaattgcag ttgatactgg atgtcttgag tgcagttgag    660

gcaggcggaa ttcgtggtgt agcggtgaaa tgcttagata tcacgaagaa ctccgattgc    720

gaaggcagcc tgctaagctg caactgacat tgaggctcga aagtgtgggt atcaaacagg    780

attagatacc ctggtagtcc acacggtaaa cgatgaatac tcgctgtttg cgatatacgg    840

caagcggcca agcgaaagcg ttaagtattc cacctgggga gtacgccggc aacggtgaaa    900

ctcaaaggaa ttgacggggg cccgcacaag cggaggaaca tgtggtttaa ttcgatgata    960

cgcgaggaac cttacccggg cttaaattgc actcgaatga tccggaaacg gttcagctag   1020

caatagcgag tgtgaaggtg ctgcatggtt gtcgtcagct cgtgccgtga ggtgtcggct   1080

taagtgccat aacgagcgca acccttgttg tcagttacta acaggtgatg ctgaggactc   1140

tgacaagact gccatcgtaa gatgtgagga aggtggggat gacgtcaaat cagcacggcc   1200

cttacgtccg gggctacaca cgtgttacaa tgggggggtac agagggccgc taccacgcga   1260

gtggatgcca atccctaaaa cccctctcag ttcggactgg agtctgcaac ccgactccac   1320

gaagctggat tcgctagtaa tcgcgcatca gccacggcgc ggtgaatacg ttcccgggcc   1380

ttgtacacac cgcccgtcaa gccatgggag ccgggggtac ctgaagtgcg taaccgcgag   1440

gat                                                                 1443
```

<210> SEQ ID NO 4
<211> LENGTH: 1420
<212> TYPE: DNA
<213> ORGANISM: Bacteroides uniformis

<400> SEQUENCE: 4

```
gatgaacgct agctacaggc ttaacacatg caagtcgagg ggcagcatga acttagcttg     60

ctaagtttga tggcgaccgg cgcacgggtg agtaacacgt atccaacctg ccgatgactc    120

ggggatagcc tttcgaaaga aagattaata cccgatggca tagttcttcc gcatggtaga    180

actattaaag aatttcggtc atcgatgggg atgcgttcca ttaggttgtt ggcggggtaa    240

cggcccacca agccttcgat ggataggggt tctgagagga aggtccccca cattggaact    300
```

gagacacggt ccaaactcct acgggaggca gcagtgagga atattggtca atggacgaga 360
gtctgaacca gccaagtagc gtgaaggatg actgccctat gggttgtaaa cttcttttat 420
acgggaataa agtgaggcac gtgtgccttt ttgtatgtac cgtatgaata aggatcggct 480
aactccgtgc cagcagccgc ggtaatacgg aggatccgag cgttatccgg atttattggg 540
tttaaaggga gcgtaggcgg acgcttaagt cagttgtgaa agtttgcggc tcaaccgtaa 600
aattgcagtt gatactgggt gtcttgagta cagtagaggc aggcggaatt cgtggtgtag 660
cggtgaaatg cttagatatc acgaagaact ccgattgcga aggcagcctg ctggactgta 720
actgacgctg atgctcgaaa gtgtgggtat caaacaggat tagataccct ggtagtccac 780
accagtaaac gatgaatact cgctgtttgc gatatacagt aagcggccaa gcgaaagcgt 840
taagtattcc acctggggag tacgccggca acggtgaaac tcaaaggaat tgacgggggc 900
ccgcacaagc ggaggaacat gtggtttaat tcgatgatac gcgaggaacc ttacccgggc 960
ttgaattgca actgaatgat gtggagacat gtcagccgca aggcagttgt gaaggtgctg 1020
catggttgtc gtcagctcgt gccgtgaggt gtcggcttaa gtgccataac gagcgcaacc 1080
cttatcgata gttaccatca ggtgatgctg ggactctgt cgagactgcc gtcgtaagat 1140
gtgaggaagg tggggatgac gtcaaatcag cacggccctt acgtccgggg ctacacacgt 1200
gttacaatgg ggggtacaga aggcagctac acggcgacgt gatgctaatc ccgaaagcct 1260
ctctcagttc ggattggagt ctgcaacccg actccatgaa gctggattcg ctagtaatcg 1320
cgcatcagcc acggcgcggt gaatacgttc ccgggccttg tacacaccgc ccgtcaagcc 1380
atgaaagccg gggtacctg aagtgcgtaa ccgcaaggag 1420

<210> SEQ ID NO 5
<211> LENGTH: 1410
<212> TYPE: DNA
<213> ORGANISM: Subdoligranulum sp.

<400> SEQUENCE: 5
gacgaacgct ggcggcgcgc ctaacacatg caagtcgaac ggagctgttt tctctgaagt 60
tttcggatgg aagagagttc agcttagtgg cgaacgggtg agtaacacgt gagcaacctg 120
cctttcagtg gggggacaaca tttggaaacg aatgctaata ccgcataaga ccacagtgtc 180
gcatggcaca ggggtcaaag gatttatccg ctgaaagatg ggctcgcgtc cgattagcta 240
gatggtgagg taacggccca ccatggcgac gatcggtagc cggactgaga ggttgaacgg 300
ccacattggg actgagacac ggcccagact cctacgggag gcagcagtgg ggaatattgc 360
acaatggggg aaaccctgat gcagcgacgc cgcgtggagg aagaaggtct tcggattgta 420
aactcctgtc ccaggggacg ataatgacgg taccctggga ggaagcaccg gctaactacg 480
tgccagcagc cgcggtaaaa cgtagggtgc aagcgttgtc cggaattact gggtgtaaag 540
ggagcgcagg cggattggca agttgggagt gaaatctatg ggctcaaccc ataaattgct 600
ttcaaaactg tcagtcttga gtggtgtaga ggtaggcgga attcccggtg tagcggtgga 660
atgcgtagat atcgggagga acaccagtgg cgaaggcggc ctactgggca ctaactgacg 720
ctgaggctcg aaagcatggg tagcaaacag gattagatac cctggtagtc catgccgtaa 780
acgatgatta ctaggtgtgg gaggattgac cccttccgtg ccgcagttaa cacaataagt 840
aatccacctg ggagtacga ccgcaaggtt gaaactcaaa ggaattgacg ggggcccgca 900
caagcagtgg agtatgtggt ttaattcgaa gcaacgcgaa gaaccttacc aggtcttgac 960

```
atcggatgca tacctaagag attagggaag tccttcggga catccagaca ggtggtgcat   1020

ggttgtcgtc agctcgtgtc gtgagatgtt gggttaagtc ccgcaacgag cgcaacccct   1080

atcgttagtt actacgcaag aggactctag cgagactgcc gttgacaaaa cggaggaagg   1140

tggggatgac gtcaaatcat catgcccttt atgacctggg ctacacacgt actacaatgg   1200

ctattaacag agagaagcga taccgcgagg tggagcaaac ctcacaaaaa tagtctcagt   1260

tcggatcgca ggctgcaacc cgcctgcgtg aagccggaat tgctagtaat cgcggatcag   1320

catgccgcgg tgaatacgtt cccgggcctt gtacacaccg cccgtcacac catgagagcc   1380

ggggggaccc gaagtcggta gtctaaccgc                                    1410


<210> SEQ ID NO 6
<211> LENGTH: 1418
<212> TYPE: DNA
<213> ORGANISM: Paraprevotella xylaniphila
<220> FEATURE:
<221> NAME/KEY: misc_feature
<222> LOCATION: (180)..(180)
<223> OTHER INFORMATION: n is a, c, g, or t
<220> FEATURE:
<221> NAME/KEY: misc_feature
<222> LOCATION: (1411)..(1412)
<223> OTHER INFORMATION: n is a, c, g, or t

<400> SEQUENCE: 6

gatgaacgct agctacaggc ttaacacatg caagtcgagg ggcagcatga acttagcttg     60

ctaagtttga tggcgaccgg cgcacgggtg agtaacgcgt atccaacctg ccctttaccc    120

ggggatagcc ttctgaaaag gaagtttaat acccgatgaa ttcgtttagt cgcatggctn    180

gatgaataaa gattaattgg taaaggatgg ggatgcgtcc cattagcttg ttggcggggt    240

aacggcccac caaggcgacg atgggtaggg gttctgagag gaaggtcccc cacattggaa    300

ctgagacacg gtccaaactc ctacgggagg cagcagtgag gaatattggt caatgggcgc    360

gagcctgaac cagccaagta gcgtggagga cgacggccct acgggttgta aactcctttt    420

ataaggggat aaagttggcc atgtatggcc atttgcaggt accttatgaa taagcatcgg    480

ctaattccgt gccagcagcc gcggtaatac ggaagatgcg agcgttatcc ggatttattg    540

ggtttaaagg gagcgtaggc gggctgtcaa gtcagcggtc aaatggcgcg gctcaaccgc    600

gttccgccgt tgaaactggc agccttgagt atgcacaggg tacatggaat tcgtggtgta    660

gcggtgaaat gcttagatat cacgaggaac tccgatcgcg caggcattgt accggggcat    720

tactgacgct gaggctcgaa ggtgcgggta tcaaacagga ttagataccc tggtagtccg    780

cacagtaaac gatgaatgcc cgctgtcggc gacatagtgt cggcggccaa gcgaaagcgt    840

taagcattcc acctggggag tacgccggca acggtgaaac tcaaaggaat tgacgggggc    900

ccgcacaagc ggaggaacat gtggtttaat tcgatgatac gcgaggaacc ttacccgggc    960

ttgaatcgca ggtgcatggg ccggagacgg ccctttcctt cgggactcct gcgaaggtgc   1020

tgcatggttg tcgtcagctc gtgccgtgag gtgtcggctt aagtgccata acgagcgcaa   1080

ccccctccc cagttgccac cgggtaatgc cgggcacttt ggggacactg ccaccgcaag   1140

gtgcgaggaa ggtggggatg acgtcaaatc agcacggccc ttacgtccgg ggcgacacac   1200

gtgttacaat ggggggtaca gagggccgct gcccggtgac ggttggccaa tccctaaaac   1260

ccctctcagt tcggactgga gtctgcaacc cgactccacg aagctggatt cgctagtaat   1320

cgcgcatcag ccatggcgcg gtgaatacgt tcccgggcct tgtacacacc gcccgtcaag   1380

ccatgaaagc cgggggtgcc tgaagtccgt nnccgcga                           1418
```

<210> SEQ ID NO 7
<211> LENGTH: 1419
<212> TYPE: DNA
<213> ORGANISM: Parabacteroides johnsonii

<400> SEQUENCE: 7
gatgaacgct agcgacaggc ttaacacatg caagtcgagg ggcagcatgg taagtagcaa 60
tacttattga tggcgaccgg cgcacgggtg agtaacgcgt atgcaactta cctatcagag 120
ggggatagcc cggcgaaagt cggattaata ctccataaaa caggggttcc gcatgggact 180
atttgttaaa gattcatcgc tgatagatag gcatgcgttc cattaggcag ttggcggggt 240
aacggcccac caaaccgacg atggataggg gttctgagag gaaggtcccc cacattggta 300
ctgagacacg gaccaaactc ctacgggagg cagcagtgag gaatattggt caatggccga 360
gaggctgaac cagccaagtc gcgtgaagga tgaaggatct atggtttgta aacttctttt 420 atagggggaat aaagtgtggg acgtgttcca ttttgtatgt accctatgaa taagcatcgg 480
ctaactccgt gccagcagcc gcggtaatac ggaggatgcg agcgttatcc ggatttattg 540
ggtttaaagg gtgcgtaggt ggtaatttaa gtcagcggtg aaagtttgtg gctcaaccat 600
aaaattgccg ttgaaactgg gttacttgag tgtgtttgag gtaggcggaa tgcgtggtgt 660
agcggtgaaa tgcatagata tcacgcagaa ctccaattgc gaaggcagct tactaaacca 720
taactgacac tgaagcacga aagcgtgggt atcaaacagg attagatacc ctggtagtcc 780
acgcagtaaa cgatgattac taggagtttg cgatacacag taagctctac agcgaaagcg 840
ttaagtaatc cacctgggga gtacgccggc aacggtgaaa ctcaaaggaa ttgacggggg 900
cccgcacaag cggaggaaca tgtggtttaa ttcgatgata cgcgaggaac cttacccggg 960
tttgaacgta gtcagaccga ccttgaaaga ggttttctag caatagctga ttacgaggtg 1020
ctgcatggtt gtcgtcagct cgtgccgtga ggtgtcggct taagtgccat aacgagcgca 1080
acccttatca ctagttacta acaggttaag ctgaggactc tggtgagact gccagcgtaa 1140
gctgtgagga aggtggggat gacgtcaaat cagcacggcc cttacatccg ggcgacaca 1200 cgtgttacaa tggcatggac aaagggcagc tacctggcga caggatgcta atctctaaac 1260
catgtctcag ttcggatcgg agtctgcaac tcgactccgt gaagctggat tcgctagtaa 1320
tcgcgcatca gccatggcgc ggtgaatacg ttcccgggcc ttgtacacac cgcccgtcaa 1380
gccatgggag ccgggggtac ctgaagtccg taaccgcaa 1419

<210> SEQ ID NO 8
<211> LENGTH: 1414
<212> TYPE: DNA
<213> ORGANISM: Alistipes sp. JC136
<220> FEATURE:
<221> NAME/KEY: misc_feature
<222> LOCATION: (699)..(699)
<223> OTHER INFORMATION: n is a, c, g, or t
<220> FEATURE:
<221> NAME/KEY: misc_feature
<222> LOCATION: (731)..(731)
<223> OTHER INFORMATION: n is a, c, g, or t

<400> SEQUENCE: 8
gatgaacgct agcggcaggc ctaacacatg caagtcgagg ggcagcggga ttgaagcttg 60
cttcagttgc cggcgaccgg cgcacgggtg cgtaacgcgt atgcaaccta cccataacag 120
ggggataaca ctgagaaatc ggtactaata tcccataaca tcaagagggg catccctttt 180

```
ggttgaaaac tccggtggtt atggatgggc atgcgttgta ttagctagtt ggtgaggtaa    240

cggctcacca aggcgacgat acatagggg actgagaggt taacccccca cattggtact    300

gagacacgga ccaaactcct acgggaggca gcagtgagga atattggtca atggacgcaa    360

gtctgaacca gccatgccgc gtgcaggatg acggctctat gagttgtaaa ctgcttttgt    420

acgagggtaa acccggatac gtgtatccgg ctgaaagtat cgtacgaata aggatcggct    480

aactccgtgc cagcagccgc ggtaatacgg aggattcaag cgttatccgg atttattggg    540

tttaaagggt gcgtaggcgg tttgataagt tagaggtgaa ataccggtgc ttaacaccgg    600

aactgcctct aatactgttg agctagagag tagttgcggt aggcggaatg tatggtgtag    660

cggtgaaatg cttagagatc atacagaaca ccgattgcng aaggcagctt accaaactat    720

atctgacgtt ngaggcacga aagcgtgggg gagcaaacag gattagatac cctggtagtc    780

cacgcagtaa acgatgataa ctcgctgtcg gcgatacaca gtcggtggct aagcgaaagc    840

gataagttat ccacctgggg agtacgttcg caagaatgaa actcaaagga attgacgggg    900

gcccgcacaa gcggaggaac atgtggttta attcgatgat acgcgaggaa ccttacccgg    960

gcttgaaagt tactgacgat tctggaaaca ggatttccct tcggggcagg aaactaggtg   1020

ctgcatggtt gtcgtcagct cgtgccgtga ggtgtcgggt taagtcccat aacgagcgca   1080

acccctaccg ttagttgcca tcaggtcaag ctgggcactc tggcgggact gccggtgtaa   1140

gccgagagga aggtggggat gacgtcaaat cagcacggcc cttacgtccg ggctacaca   1200

cgtgttacaa tggtaggtac agagggcagc tacccagtga tgggatgcga atctcgaaag   1260

cctatctcag ttcggattgg aggctgaaac ccgcctccat gaagttggat tcgctagtaa   1320

tcgcgcatca gccatggcgc ggtgaatacg ttcccgggcc ttgtacacac cgcccgtcaa   1380

gccatggaag ctgggggtgc ctgaagttcg tgac                               1414
```

```
<210> SEQ ID NO 9
<211> LENGTH: 1416
<212> TYPE: DNA
<213> ORGANISM: Parabacteroides gordonii
<220> FEATURE:
<221> NAME/KEY: misc_feature
<222> LOCATION: (1408)..(1408)
<223> OTHER INFORMATION: n is a, c, g, or t

<400> SEQUENCE: 9
```

```
gatgaacgct agcgacaggc ttaacacatg caagtcgagg ggcagcagga agtagcaata     60

ctttgctggc gaccggcgca cgggtgagta acgcgtatgc aacctaccta tcagaggggg    120

ataacccggc gaaagtcgga ctaataccgc ataaaacagg ggtcccgcat gggaatattt    180

gttaaagatt tattgctgat agatgggcat gcgttccatt agatagttgg tgaggtaacg    240

gctcaccaag tcttcgatgg atagggggttc tgagaggaag gtcccccaca ctggtactga    300

gacacggacc agactcctac gggaggcagc agtgaggaat attggtcaat gggcgagagc    360

ctgaaccagc caagtcgcgt gaaggatgaa ggatctatgg ttcgtaaact tcttttatag    420

gggaataaag tgcaggacgt gtcctgtttt gtatgtaccc tatgaataag gatcggctaa    480

ctccgtgcca gcagccgcgg taatacggag gatccgagcg ttatccggat ttattgggtt    540

taaagggtgc gtaggtggct ttttaagtca gcggtgaaag tttgtggctc aaccataaaa    600

ttgccgttga aactggaggg cttgagtata tttgaggtag gcggaatgcg tggtgtagcg    660

gtgaaatgca tagatatcac gcagaactcc aattgcgaag gcagcttact aaactataac    720

tgacactgaa gcacgaaagc gtggggatca aacaggatta gataccctgg tagtccacgc    780
```

```
agtaaacgat gattactagg agtttgcgat acacagtaag ctctacagcg aaagcgttaa    840

gtaatccacc tggggagtac gccggcaacg gtgaaactca aaggaattga cgggggcccg    900

cacaagcgga ggaacatgtg gtttaattcg atgatacgcg aggaacctta cccgggtttg    960

aacgtaagtt gaccggagtg gaaacactct ttctagcaat agcaatttac gaggtgctgc   1020

atggttgtcg tcagctcgtg ccgtgaggtg tcggcttaag tgccataacg agcgcaaccc   1080

ttatctttag ttactaacag gtcgagctga ggactctaaa gagactgcca gcgtaagctg   1140

tgaggaaggt ggggatgacg tcaaatcagc acggccctta catccggggc gacacacgtg   1200

ttacaatggt ggggacaaag ggcagctacc tggcgacagg atgctaatct ccaaacccca   1260

tctcagttcg gatcgaagtc tgcaacccga cttcgtgaag ctggattcgc tagtaatcgc   1320

gcatcagcca tggcgcggtg aatacgttcc cgggccttgt acacaccgcc cgtcaagcca   1380

tgggagttgg gggtacctaa agtccgtnac cgcaag                             1416


<210> SEQ ID NO 10
<211> LENGTH: 1419
<212> TYPE: DNA
<213> ORGANISM: Eubacterium limosum

<400> SEQUENCE: 10

gacgaacgct ggcggtatgc ttaacacatg caagtcgaac gagaaggttt tgatggatcc     60

ttcgggtgac attagaactg gaaagtggcg aacgggtgag taacgcgtgg gtaacctgcc    120

ctatggaaag gaatagcctc gggaaactgg gagtaaagcc ttatattatg gttttgtcgc    180

atggcaagat catgaaaact ccggtgccat aggatggacc cgcgtcccat tagctagttg    240

gtgagataac agcccaccaa ggcgacgatg ggtaaccggt ctgagagggc gaacggtcac    300

actggaactg agacacggtc cagactccta cgggaggcag cagtggggaa tattgcgcaa    360

tgggggcaac cctgacgcag caataccgcg tgagtgaaga aggttttcgg atcgtaaagc    420

tctgttattg gggaagaaga atgacggtac ccaatgagga agtcccggct aactacgtgc    480

cagcagccgc ggtaatacgt aggggacaag cgttgtccgg aatgactggg cgtaaagggc    540

gcgtaggcgg tctattaagt ctgatgtgaa aggtaccggc tcaaccggtg aagtgcattg    600

gaaactggta gacttgagta ttggagaggc aagtggaatt cctagtgtag cggtgaaatg    660

cgtagatatt aggaggaaca ccagtggcga aggcggcttg ctggacaaat actgacgctg    720

aggtgcgaaa gcgtggggag cgaacaggat tagataccct ggtagtccac gccgtaaacg    780

atgaatgcta ggtgttgggg aaactcagtg ccgcagttaa cacaataagc attccgcctg    840

gggagtacga ccgcaaggtt gaaactcaaa ggaattgacg gggacccgca caagcagcgg    900

agcatgtggt ttaattcgaa gcaacgcgaa gaaccttacc aggtcttgac atcctctgac    960

gagcctagag ataggaagtt tccttcggga acagagagac aggtggtgca tggttgtcgt   1020

cagctcgtgt cgtgagatgt tgggttaagt cccgcaacga gcgcaacccc tgcctttagt   1080

tgccagcatt aagttgggca ctctagaggg actgccgtag acaatacgga ggaaggtggg   1140

gacgacgtca aatcatcatg ccccttatga cctgggctac acacgtgcta caatggtctg   1200

aacagagggc cgcgaagccg cgaggtgaag caaatccctt aaaacagatc ccagttcgga   1260

ttgcaggctg caactcgcct gcatgaagtt ggagttgcta gtaatcgcgg atcagaatgc   1320

cgcggtgaat gcgttcccgg gtcttgtaca caccgcccgt cacaccacga gagttggcaa   1380

cacccgaagc ctgtgagaga accgtaagga ctcagcagt                          1419
```

<210> SEQ ID NO 11
<211> LENGTH: 1413
<212> TYPE: DNA
<213> ORGANISM: Parabacteroides distasonis
<220> FEATURE:
<221> NAME/KEY: misc_feature
<222> LOCATION: (1387)..(1387)
<223> OTHER INFORMATION: n is a, c, g, or t

<400> SEQUENCE: 11
gatgaacgct agcgacaggc ttaacacatg caagtcgagg ggcagcacag gtagcaatac 60
cgggtggcga ccggcgcacg ggtgagtaac gcgtatgcaa cttgcctatc agagggggat 120
aacccggcga aagtcggact aataccgcat gaagcagggg ccccgcatgg ggatatttgc 180
taaagattca tcgctgatag ataggcatgc gttccattag gcagttggcg gggtaacggc 240
ccaccaaacc gacgatggat aggggttctg agaggaaggt cccccacatt ggtactgaga 300
cacggaccaa actcctacgg gaggcagcag tgaggaatat tggtcaatgg ccgagaggct 360
gaaccagcca agtcgcgtga gggatgaagg ttctatggat cgtaaacctc ttttataagg 420
gaataaagtg cgggacgtgt cccgttttgt atgtacctta tgaataagga tcggctaact 480
ccgtgccagc agccgcggta atacggagga tccgagcgtt atccggattt attgggttta 540
aagggtgcgt aggcggcctt ttaagtcagc ggtgaaagtc tgtggctcaa ccatagaatt 600
gccgttgaaa ctgggggggct tgagtatgtt tgaggcaggc ggaatgcgtg gtgtagcggt 660
gaaatgcata gatatcacgc agaaccccga ttgcgaaggc agcctgccaa gccattactg 720
acgctgatgc acgaaagcgt ggggatcaaa caggattaga taccctggta gtccacgcag 780
taaacgatga tcactagctg tttgcgatac actgtaagcg gcacagcgaa agcgttaagt 840
gatccacctg gggagtacgc cggcaacggt gaaactcaaa ggaattgacg gggggcccgca 900 caagcggagg aacatgtggt ttaattcgat gatacgcgag gaaccttacc cgggtttgaa 960
cgcattcgga ccgaggtgga aacacctttt ctagcaatag ccgtttgcga ggtgctgcat 1020
ggttgtcgtc agctcgtgcc gtgaggtgtc ggcttaagtg ccataacgag cgcaaccctt 1080
gccactagtt actaacaggt aaagctgagg actctggtgg gactgccagc gtaagctgcg 1140
aggaaggcgg ggatgacgtc aaatcagcac ggcccttaca tccggggcga cacacgtgtt 1200
acaatggcgt ggacaaaggg aagccacctg gcgacaggga gcgaatcccc aaaccacgtc 1260
tcagttcgga tcggagtctg caacccgact ccgtgaagct ggattcgcta gtaatcgcgc 1320
atcagccatg gcgcggtgaa tacgttcccg ggccttgtac acaccgcccg tcaagccatg 1380
ggagccnggg gtacctgaag tccgtaaccg cga 1413

<210> SEQ ID NO 12
<211> LENGTH: 1406
<212> TYPE: DNA
<213> ORGANISM: Bacteroides cellulosilyticus

<400> SEQUENCE: 12
gatgaacgct agctacaggc ttaacacatg caagtcgagg ggcagcatga cctagcaata 60
ggttgatggc gaccggcgca cgggtgagta acacgtatcc aacctaccgg ttattccggg 120
atagcctttc gaaagaaaga ttaataccgg atagtataac gagaaggcat ctttttgtta 180
ttaaagaatt tcgataaccg atggggatgc gttccattag tttgttggcg gggtaacggc 240
ccaccaagac atcgatggat aggggttctg agaggaaggt cccccacatt ggaactgaga 300
cacggtccaa actcctacgg gaggcagcag tgaggaatat tggtcaatgg acgagagtct 360
gaaccagcca agtagcgtga aggatgactg ccctatgggt tgtaaacttc ttttatatgg 420
gaataaagtg agccacgtgt ggctttttgt atgtaccata cgaataagga tcggctaact 480
ccgtgccagc agccgcggta atacggagga tccgagcgtt atccggattt attgggttta 540
aagggagcgt aggcggacta ttaagtcagc tgtgaaagtt tgcggctcaa ccgtaaaatt 600
gcagttgata ctggtcgtct tgagtgcagt agaggtaggc ggaattcgtg gtgtagcggt 660
gaaatgctta gatatcacga agaactccga ttgcgaaggc agcttactgg actgtaactg 720
acgctgatgc tcgaaagtgt gggtatcaaa caggattaga taccctggta gtccacacag 780
taaacgatga atactcgctg tttgcgatat acagcaagcg gccaagcgaa agcattaagt 840
attccacctg gggagtacgc cggcaacggt gaaactcaaa ggaattgacg gggcccgca 900 caagcggagg aacatgtggt ttaattcgat gatacgcgag gaaccttacc cgggcttaaa 960
ttgcatctga ataatttgga aacagattag ccgtaaggca gatgtgaagg tgctgcatgg 1020
ttgtcgtcag ctcgtgccgt gaggtgtcgg cttaagtgcc ataacgagcg caacccttat 1080
ctttagttac taacaggtca tgctgaggac tctagagaga ctgccgtcgt aagatgtgag 1140
gaaggtgggg atgacgtcaa atcagcacgg cccttacgtc cggggctaca cacgtgttac 1200 aatgggggt acagaaggca gctacacagc gatgtgatgc taatcccaaa agcctctctc 1260
agttcggatt ggagtctgca acccgactcc atgaagctgg attcgctagt aatcgcgcat 1320
cagccacggc gcggtgaata cgttcccggg ccttgtacac accgcccgtc aagccatgaa 1380
agccgggggt acctgaagtc cgtaac 1406

<210> SEQ ID NO 13
<211> LENGTH: 1415
<212> TYPE: DNA
<213> ORGANISM: Bacteroides clarus

<400> SEQUENCE: 13
gatgaacgct agctacaggc ttaacacatg caagtcgagg ggcagcgggg ttgaagcttg 60
cttcaaccgc cggcgaccgg cgcacgggtg agtaacacgt atccaacctg ccgataactc 120
cgggatagcc tttcgaaaga aagattaata ccggatggca tagttttccc gcatggaata 180
actattaaag aatttcggtt atcgatgggg atgcgttcca ttaggcagtt ggcggggtaa 240
cggcccacca aaccgacgat ggataggggt tctgagagga aggtccccca cattggaact 300
gagacacggt ccaaactcct acgggaggca gcagtgagga atattggtca atggacgaga 360
gtctgaacca gccaagtagc gtgaaggatg actgccctat gggttgtaaa cttcttttat 420
acgggaataa agttggccac gtgtggtttt ttgcatgtac cgtatgaata aggatcggct 480
aactccgtgc cagcagccgc ggtaatacgg aggatccgag cgttatccgg atttattggg 540
tttaaaggga gcgtaggcgg ggtattaagt cagttgtgaa agtttgcggc tcaaccgtaa 600
aattgcagtt gatactggta tccttgagtg cagcagaggt gggcggaatt cgtggtgtag 660
cggtgaaatg cttagatatc acgaagaact ccgattgcga aggcagctca ctggagtgta 720
actgacgctg atgctcgaaa gtgtgggtat caaacaggat tagataccct ggtagtccac 780
acagtaaacg atgaatactc gctgttggcg atacaatgtc agcggccaag cgaaagcatt 840
aagtattcca cctggggagt acgccggcaa cggtgaaact caaaggaatt gacgggggcc 900
cgcacaagcg gaggaacatg tggtttaatt cgatgatacg cgaggaacct tacccgggct 960
tgaattgcaa ctgactgagc tggaaacagt tctttcttcg gacagttgtg aaggtgctgc 1020
atggttgtcg tcagctcgtg ccgtgaggtg tcggcttaag tgccataacg agcgcaaccc 1080
ttatctatag ttaccatcag gtcatgctgg ggactctatg gagactgccg tcgtaagatg 1140
tgaggaaggt ggggatgacg tcaaatcagc acggccctta cgtccggggc tacacacgtg 1200
ttacaatggg gggtacagaa ggcagctaca cggcgacgtg atgctaatcc caaaaacctc 1260
tctcagttcg gattggagtc tgcaacccga ctccatgaag ctggattcgc tagtaatcgc 1320
gcatcagcca cggcgcggtg aatacgttcc cgggccttgt acacaccgcc cgtcaagcca 1380
tgaaagccgg gggtacctga agtacgtaac cgcaa 1415

<210> SEQ ID NO 14
<211> LENGTH: 938
<212> TYPE: DNA
<213> ORGANISM: Anaerostipes sp.
<220> FEATURE:
<221> NAME/KEY: misc_feature
<222> LOCATION: (884)..(884)
<223> OTHER INFORMATION: n is a, c, g, or t
<220> FEATURE:
<221> NAME/KEY: misc_feature
<222> LOCATION: (899)..(901)
<223> OTHER INFORMATION: n is a, c, g, or t

<400> SEQUENCE: 14
gatgaacgct ggcggcgtgc ttaacacatg caagtcgaac gaagcattta ggattgaagt 60
tttcggatgg atttcctata tgactgagtg gcggacgggt gagtaacgcg tggggaacct 120
gccctataca gggggataac agctggaaac ggctgctaat accgcataag cgcacagaat 180
cgcatgattc agtgtgaaaa gccctggcag tataggatgg tcccgcgtct gattagctgg 240
ttggtgaggt aacggctcac caaggcgacg atcagtagcc ggcttgagag agtgaacggc 300
cacattggga ctgagacacg gcccaaactc ctacgggagg cagcagtggg gaatattgca 360
caatggggga aaccctgatg cagcgacgcc gcgtgagtga agaagtattt cggtatgtaa 420
agctctatca gcagggaaga aaacagacgg tacctgacta agaagccccg gctaactacg 480
tgccagcagc cgcggtaata cgtagggggc aagcgttatc cggaattact gggtgtaaag 540
ggtgcgtagg tggcatggta agtcagaagt gaaagcccgg ggcttaaccc cgggactgct 600
tttgaaactg tcatgctgga gtgcaggaga ggtaagcgga attcctagtg tagcggtgaa 660
atgcgtagat attaggagga acaccagtgg cgaaggcggc ttactggact gtcactgaca 720
ctgatgcacg aaagcgtggg gagcaaacag gattagatac cctggtagtc cacgccgtaa 780
acgatgaata ctaggtgtcg ggccgtagaa ggcttcggtg ccgcagcaaa cgcagtaagt 840
attccacctg gggagtacgt tcgcaagaat gaaactcaaa gganttgacg gggaccgcnn 900
nagcggtgga gcatgtggtt aattcgaagc acgcgaag 938

<210> SEQ ID NO 15
<211> LENGTH: 1406
<212> TYPE: DNA
<213> ORGANISM: Bacteroides salyersiae

<400> SEQUENCE: 15
gatgaacgct agctacaggc ttaacacatg caagtcgagg ggcatcaggg tgtagcaata 60
caccgctggc gaccggcgca cgggtgagta acacgtatcc aacctgccct ttactcgggg 120
atagcctttc gaaagaaaga ttaatacccg atggtataac atgacctcct ggttttgtta 180
ttaaagaatt tcggtagagg atggggatgc gttccattag gcagttggcg gggtaacggc 240
ccaccaaacc ttcgatggat aggggttctg agaggaaggt cccccacatt ggaactgaga 300

```
cacggtccaa actcctacgg gaggcagcag tgaggaatat tggtcaatgg gcgagagcct     360

gaaccagcca agtagcgtga aggatgaccg ccctatgggt tgtaaacttc ttttatatgg     420

gaataaagtc tgccacgtgt ggcattttgt atgtaccata tgaataagga tcggctaact     480

ccgtgccagc agccgcggta atacggagga tccgagcgtt atccggattt attgggttta     540

aagggagcgt aggtggacat gtaagtcagt tgtgaaagtt tgcggctcaa ccgtaaaatt     600

gcagttgaaa ctgcgtgtct tgagtacagt agaggtgggc ggaattcgtg gtgtagcggt     660

gaaatgctta gatatcacga agaactccga ttgcgaaggc agctcactgg actgcaactg     720

acactgatgc tcgaaagtgt gggtatcaaa caggattaga taccctggta gtccacacag     780

taaacgatga atactcgctg tttgcgatat acagtaagcg gccaagcgaa agcattaagt     840

attccacctg ggagtacgcc ggcaacggt gaaactcaaa ggaattgacg ggggcccgca     900

caagcggagg aacatgtggt ttaattcgat gatacgcgag gaaccttacc cgggcttaaa     960

ttgcaaatga atatgccgga aacggcatag ccgcaaggca tttgtgaagg tgctgcatgg    1020

ttgtcgtcag ctcgtgccgt gaggtgtcgg cttaagtgcc ataacgagcg caacccttat    1080

cttcagttac taacaggtca tgctgaggac tctggagaga ctgccgtcgt aagatgtgag    1140

gaaggtgggg atgacgtcaa atcagcacgg cccttacgtc cggggctaca cacgtgttac    1200

aatggggggt acagaaggcc gctacacagc gatgtgatgc caatccctaa agcccctctc    1260

agttcggatc gaagtctgca acccgacttc gtgaagctgg attcgctagt aatcgcgcat    1320

cagccacggc gcggtgaata cgttcccggg ccttgtacac accgcccgtc aagccatggg    1380

agccgggggt acctgaagta cgtaac                                          1406
```

```
<210> SEQ ID NO 16
<211> LENGTH: 1417
<212> TYPE: DNA
<213> ORGANISM: Bacteroides fragilis

<400> SEQUENCE: 16

gatgaacgct agctacaggc ttaacacatg caagtcgagg ggcatcagga agaaagcttg      60

ctttctttgc tggcgaccgg cgcacgggtg agtaacacgt atccaacctg ccctttactc     120

ggggatagcc tttcgaaaga aagattaata cccgatagca taatgattcc gcatggtttc     180

attattaaag gattccggta aaggatgggg atgcgttcca ttaggttgtt ggtgaggtaa     240

cggctcacca agccttcgat ggataggggt tctgagagga aggtccccca cattggaact     300

gagacacggt ccaaactcct acgggaggca gcagtgagga atattggtca atgggcgcta     360

gcctgaacca gccaagtagc gtgaaggatg aaggctctat gggtcgtaaa cttcttttat     420

ataagaataa agtgcagtat gtatactgtt ttgtatgtat tatatgaata aggatcggct     480

aactccgtgc cagcagccgc ggtaatacgg aggatccgag cgttatccgg atttattggg     540

tttaaaggga gcgtaggtgg actggtaagt cagttgtgaa agtttgcggc tcaaccgtaa     600

aattgcagtt gatactgtca gtcttgagta cagtagaggt gggcggaatt cgtggtgtag     660

cggtgaaatg cttagatatc acgaagaact ccgattgcga aggcagctca ctggactgca     720

actgacactg atgctcgaaa gtgtgggtat caaacaggat tagataccct ggtagtccac     780

acagtaaacg atgaatactc gctgtttgcg atatacagta agcggccaag cgaaagcatt     840

aagtattcca cctggggagt acgccggcaa cggtgaaact caaaggaatt gacgggggcc     900

cgcacaagcg gaggaacatg tggtttaatt cgatgatacg cgaggaacct tacccgggct     960
```

taaattgcag tggaatgatg tggaaacatg tcagtgagca atcaccgctg tgaaggtgct 1020
gcatggttgt cgtcagctcg tgccgtgagg tgtcggctta agtgccataa cgagcgcaac 1080
ccttatcttt agttactaac aggttatgct gaggactcta gagagactgc cgtcgtaaga 1140
tgtgaggaag gtggggatga cgtcaaatca gcacggccct tacgtccggg gctacacacg 1200
tgttacaatg gggggtacag aaggcagcta acgggtgacc gtatgctaat cccaaaagcc 1260
tctctcagtt cggatcgaag tctgcaaccc gacttcgtga agctggattc gctagtaatc 1320
gcgcatcagc cacggcgcgg tgaatacgtt cccgggcctt gtacacaccg cccgtcaagc 1380
catgggagcc gggggtacct gaagtacgta accgcaa 1417

<210> SEQ ID NO 17
<211> LENGTH: 1407
<212> TYPE: DNA
<213> ORGANISM: Bacteroides uniformis

<400> SEQUENCE: 17
gatgaacgct agctacaggc ttaacacatg caagtcgagg ggcatcagga agaaagcttg 60
ctttctttgc tggcgaccgg cgcacgggtg agtaacacgt atccaacctg ccgatgactc 120
ggggatagcc tttcgaaaga aagattaata cccgatggta tatctgaaag gcatctttca 180
gctattaaag aatttcggtc attgatgggg atgcgttcca ttaggttgtt ggcggggtaa 240
cggcccacca agccatcgat ggataggggt tctgagagga aggtccccca cattggaact 300
gagacacggt ccaaactcct acgggaggca gcagtgagga atattggtca atggacgaga 360
gtctgaacca gccaagtagc gtgaaggatg actgccctat gggttgtaaa cttcttttat 420
acgggaataa agttaggcac gtgtgccttt ttgtatgtac cgtatgaata aggatcggct 480
aactccgtgc cagcagccgc ggtaatacgg aggatccgag cgttatccgg atttattggg 540
tttaaaggga gcgtaggcgg atgcttaagt cagttgtgaa agtttgcggc tcaaccgtaa 600
aattgcagtt gatactgggt gtcttgagta cagtagaggc aggcggaatt cgtggtgtag 660
cggtgaaatg cttagatatc acgaagaact ccgattgcga aggcagcttg ctggactgta 720
actgacgctg atgctcgaaa gtgtgggtat caaacaggat tagataccct ggtagtccac 780
acagtaaacg atgaatactc gctgtttgcg atatacagta agcggccaag cgaaagcgtt 840
aagtattcca cctggggagt acgccggcaa cggtgaaact caaaggaatt gacgggggcc 900
cgcacaagcg gaggaacatg tggtttaatt cgatgatacg cgaggaacct tacccgggct 960
taaattgcaa atgaatgttc tggaaacaga tcagccgcaa ggcatttgtg aaggtgctgc 1020
atggttgtcg tcagctcgtg ccgtgaggtg tcggcttaag tgccataacg agcgcaaccc 1080
ttatcgatag ttaccatcag gttatgctgg ggactctgtc gagactgccg tcgtaagatg 1140
tgaggaaggt ggggatgacg tcaaatcagc acggccctta cgtccggggc tacacacgtg 1200
ttacaatggg ggtacagaa ggcagctaca cggcgacgtg atgctaatcc ctaaaacctc 1260
tctcagttcg gattggagtc tgcaacccga ctccatgaag ctggattcgc tagtaatcgc 1320
gcatcagcca cggcgcggtg aatacgttcc cgggccttgt acacaccgcc cgtcaagcca 1380
tgaaagccgg gggtacctga agtgcgt 1407

<210> SEQ ID NO 18
<211> LENGTH: 1420
<212> TYPE: DNA
<213> ORGANISM: Bacteroides eggerthii
<220> FEATURE:
<221> NAME/KEY: misc_feature
<222> LOCATION: (220)..(220)
<223> OTHER INFORMATION: n is a, c, g, or t

<400> SEQUENCE: 18

```
gatgaacgct agctacaggc ttaacacatg caagtcgagg ggcagcatga ttgaagcttg      60

cttcaatcga tggcgaccgg cgcacgggtg agtaacacgt atccaacctg ccgataactc     120

ggggatagcc tttcgaaaga aagattaata cccgatagca tagtatttcc gcatggtttc     180

actattaaag aatttcggtt atcgatgggg atgcgttccn ttagatagtt ggcggggtaa     240

cggcccacca agtcaacgat ggataggggt tctgagagga aggtccccca cattggaact     300

gagacacggt ccaaactcct acgggaggca gcagtgagga atattggtca atggacgaga     360

gtctgaacca gccaagtagc gtgaaggatg actgccctat gggttgtaaa cttcttttat     420

acgggaataa agtggagtat gcatactcct ttgtatgtac cgtatgaata aggatcggct     480

aactccgtgc cagcagccgc ggtaatacgg aggatccgag cgttatccgg atttattggg     540

tttaaaggga gcgtaggcgg gtgcttaagt cagttgtgaa agtttgcggc tcaaccgtaa     600

aattgcagtt gatactgggc gccttgagtg cagcataggt aggcggaatt cgtggtgtag     660

cggtgaaatg cttagatatc acgaagaact ccgattgcga aggcagctta ctggactgta     720

actgacgctg atgctcgaaa gtgtgggtat caaacaggat tagataccct ggtagtccac     780

acagtaaacg atgaatactc gctgttggcg atacacagtc agcggccaag cgaaagcatt     840

aagtattcca cctggggagt acgccggcaa cggtgaaact caaaggaatt gacgggggcc     900

cgcacaagcg gaggaacatg tggtttaatt cgatgatacg cgaggaacct tacccgggct     960

taaattgcag cggaatgtag tggaaacatt acagccttcg ggccgctgtg aaggtgctgc    1020

atggttgtcg tcagctcgtg ccgtgaggtg tcggcttaag tgccataacg agcgcaaccc    1080

ttatctatag ttactatcag gtcatgctga ggactctatg gagactgccg tcgtaagatg    1140

tgaggaaggt ggggatgacg tcaaatcagc acggccctta cgtccggggc tacacacgtg    1200

ttacaatggg gggtacagaa ggcagctacc tggcgacagg atgctaatcc ctaaaacctc    1260

tctcagttcg gattggagtc tgcaacccga ctccatgaag ctggattcgc tagtaatcgc    1320

gcatcagcca cggcgcggtg aatacgttcc cgggccttgt acacaccgcc cgtcaagcca    1380

tgaaagccgg gggtacctga agtacgtaac cgcaaggagc                          1420
```

<210> SEQ ID NO 19
<211> LENGTH: 1408
<212> TYPE: DNA
<213> ORGANISM: Clostridium sp.

<400> SEQUENCE: 19

```
gatgaacgct ggcggcgtgc ctaatacatg caagtcggac gcaatgcttc ggcattgagt      60

ggcgaacggg tgagtaatac ataagcaacc tgcccctgtg agggggataa ctgctggaaa     120

cggcagctaa gaccgcatat gcatacatga cgcatgtcga gtatgttaaa tatcccacgg     180

gatagcacag ggatgggctt atgacgcatt agctagctgg tgaggtagag gctcaccagg     240

gcgacgatgc gtagccggcc tgagagggtg gacggccaca ctgggactga gacacggccc     300

agactcctac gggaggcagc agtagggaat tttcggcaat gggcgaaagc ctgaccgagc     360

aacgccgcgt gaaggaagaa gtcattcgtg atgtaaactt ctgttataaa ggaagaacgg     420

cgcctgtagg gaatgacagg cgagtgacgg tactttatga ggaagccacg gctaactacg     480

tgccagcagc cgcggtaata cgtaggtggc gagcgttatc cggaatcatt gggcgtaaag     540
```

agggagcagg cggcagtgca ggtctgcggt gaaagcccga agctaaactt cggtaagccg 600
tggaaaccgc acagctagag agcatcagag gatcgcggaa ttccatgtgt agcggtgaaa 660
tgcgtagata tatggaggaa caccagtggc gaaggcggcg gtctggggtg cagctgacgc 720
tcagtcccga aagcgtgggg agcaaatagg attagatacc ctagtagtcc acgccgtaaa 780
cgatgagtgc taagtgttgg gggtcagacc tcagtgctgc agttaacgca ataagcactc 840
cgcctgagta gtacgttcgc aagaatgaaa ctcaaaggaa ttgacggggg cccgcacaag 900
cggtggagca tgtggtttaa ttcgaagcaa cgcgaagaac cttaccaggt cttgacatgg 960
agataaaggc tctggagaca gagagatagg tatatctcac acaggtggtg catggttgtc 1020
gtcagctcgt gtcgtgagat gttgggttaa gtcccgcaac gagcgcaacc cctgttgcca 1080
gttgccagca ttaggttggg gactctggcg agactgcctc tgcaaggagg aggaaggcgg 1140
ggatgacgtc aaatcatcat gccccttatg acctgggcta cacacgtgct acaatggacg 1200
gatcagaggg aggcgaagcc gcgaggtgga gcgaaaccca gaaacccgtt cacagttcgg 1260
actgcagtct gcaactcgac tgcacgaagc tggaatcgct agtaatcgcg aatcagcatg 1320
tcgcggtgaa tacgttctcg ggccttgtac acaccgcccg tcacaccatg agagttggta 1380
acacccgaag ccggtggccc aaccgcaa 1408

<210> SEQ ID NO 20
<211> LENGTH: 1413
<212> TYPE: DNA
<213> ORGANISM: Parabacteroides goldsteinii

<400> SEQUENCE: 20
gatgaacgct agcgacaggc ttaacacatg caagtcgagg ggcagcacga tgtagcaata 60
cattggtggc gaccggcgca cgggtgagta acgcgtatgc aacctaccta tcagagggga 120
ataacccggc gaaagtcgga ctaataccgc ataaaacagg ggttccacat ggaaatattt 180
gttaaagaat tatcgctgat agatgggcat gcgttccatt agatagttgg tgaggtaacg 240
gctcaccaag tccacgatgg ataggggttc tgagaggaag gtcccccaca ctggtactga 300
gacacggacc agactcctac gggaggcagc agtgaggaat attggtcaat gggcgagagc 360
ctgaaccagc caagtcgcgt gaaggatgaa ggatctatgg tttgtaaact tcttttatat 420
gggaataaag tgaggaacgt gttccttttt gtatgtacca tatgaataag catcggctaa 480
ctccgtgcca gcagccgcgg taatacggag gatgcgagcg ttatccggat ttattgggtt 540
taaagggtgc gtaggtggtt aattaagtca gcggtgaaag tttgtggctc aaccataaaa 600
ttgccgttga aactggttga cttgagtata tttgaggtag gcggaatgcg tggtgtagcg 660
gtgaaatgca tagatatcac gcagaactcc gattgcgaag gcagcttact aaactataac 720
tgacactgaa gcacgaaagc gtggggatca aacaggatta gataccctgg tagtccacgc 780
agtaaacgat gattactagc tgtttgcgat acacagtaag cggcacagcg aaagcgttaa 840
gtaatccacc tggggagtac gccggcaacg gtgaaactca aaggaattga cgggggcccg 900
cacaagcgga ggaacatgtg gtttaattcg atgatacgcg aggaacctta cccgggtttg 960
aacgcatatt gacagctctg gaaacagagt ctctagtaat agcaatttgc gaggtgctgc 1020
atggttgtcg tcagctcgtg ccgtgaggtg tcggcttaag tgccataacg agcgcaaccc 1080
ttatcactag ttactaacag gtcatgctga ggactctagt gagactgcca gcgtaagctg 1140
tgaggaaggt ggggatgacg tcaaatcagc acggcccctta catccggggc gacacacgtg 1200
ttacaatggt ggggacaaag ggcagctacc gtgtgagcgg atgcaaatct ccaaacccca 1260
tctcagttcg gatcgaagtc tgcaacccga cttcgtgaag ctggattcgc tagtaatcgc 1320
gcatcagcca tggcgcggtg aatacgttcc cgggccttgt acacaccgcc cgtcaagcca 1380
tgggagttgg gggtacctaa agtccgtaac cgc 1413

<210> SEQ ID NO 21
<211> LENGTH: 1145
<212> TYPE: DNA
<213> ORGANISM: Bacteroides sp.
<220> FEATURE:
<221> NAME/KEY: misc_feature
<222> LOCATION: (167)..(167)
<223> OTHER INFORMATION: n is a, c, g, or t

<400> SEQUENCE: 21
gatgaacgct agctacaggc ttaacacatg caagtcgagg ggcagcattt cagtttgctt 60
gcaaactgga gatggcgacc ggcgcacggg tgagtaacac gtatccaacc tgccgataac 120
tcggggatag cctttcgaaa gaaagattaa tacccgatgg tataatnaga ccgcatggtc 180
ttgttattaa agaatttcgg ttatcgatgg ggatgcgttc cattaggcag ttggtgaggt 240
aacggctcac caaaccttcg atggataggg gttctgagag gaaggtcccc cacattggaa 300
ctgagacacg gtccaaactc ctacgggagg cagcagtgag gaatattggt caatgggcgc 360
aggcctgaac cagccaagta gcgtgaagga tgactgccct atgggttgta aacttctttt 420
atatgggaat aaagttttcc acgtgtggaa ttttgtatgt accatatgaa taaggatcgg 480
ctaactccgt gccagcagcc gcggtaatac ggaggatccg agcgttatcc ggatttattg 540
ggtttaaagg gagcgtaggt ggacagttaa gtcagttgtg aaagtttgcg gctcaaccgt 600
aaaattgcag ttgatactgg ctgtcttgag tacagtagag gtgggcggaa ttcgtggtgt 660
agcggtgaaa tgcttagata tcacgaagaa ctccgattgc gaaggcagct cactggactg 720
caactgacac tgatgctcga aagtgtgggt atcaaacagg attagatacc ctggtagtcc 780
acacagtaaa cgatgaatac tcgctgtttg cgatatacag taagcggcca agcgaaagca 840
ttaagtattc cacctgggga gtacgccggc aacggtgaaa ctcaaaggaa ttgacggggg 900
cccgcacaag cggaggaaca tgtggtttaa ttcgatgata cgcgaggaac cttacccggg 960
cttaaattgc atttgaatat attggaaaca gtatagccgt aaggcaaatg tgaaggtgct 1020
gcatggttgt cgtcagctcg tgccgtgagg tgtcggctta agtgccataa cgagcgcaac 1080
ccttatcttt agttactaac aggtcatgct gaggactcta gagagactgc cgtcgtaaga 1140
tgtga 1145

<210> SEQ ID NO 22
<211> LENGTH: 965
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(9)
<223> OTHER INFORMATION: n is a, c, g, or t
<220> FEATURE:
<221> NAME/KEY: misc_feature
<222> LOCATION: (57)..(57)
<223> OTHER INFORMATION: n is a, c, g, or t
<220> FEATURE:
<221> NAME/KEY: misc_feature
<222> LOCATION: (156)..(157)
<223> OTHER INFORMATION: n is a, c, g, or t
<220> FEATURE:

<221> NAME/KEY: misc_feature
<222> LOCATION: (861)..(861)
<223> OTHER INFORMATION: n is a, c, g, or t
<220> FEATURE:
<221> NAME/KEY: misc_feature
<222> LOCATION: (879)..(880)
<223> OTHER INFORMATION: n is a, c, g, or t
<220> FEATURE:
<221> NAME/KEY: misc_feature
<222> LOCATION: (913)..(913)
<223> OTHER INFORMATION: n is a, c, g, or t
<220> FEATURE:
<221> NAME/KEY: misc_feature
<222> LOCATION: (927)..(929)
<223> OTHER INFORMATION: n is a, c, g, or t
<220> FEATURE:
<221> NAME/KEY: misc_feature
<222> LOCATION: (937)..(937)
<223> OTHER INFORMATION: n is a, c, g, or t
<220> FEATURE:
<221> NAME/KEY: misc_feature
<222> LOCATION: (939)..(942)
<223> OTHER INFORMATION: n is a, c, g, or t
<220> FEATURE:
<221> NAME/KEY: misc_feature
<222> LOCATION: (953)..(953)
<223> OTHER INFORMATION: n is a, c, g, or t
<220> FEATURE:
<221> NAME/KEY: misc_feature
<222> LOCATION: (956)..(957)
<223> OTHER INFORMATION: n is a, c, g, or t
<220> FEATURE:
<221> NAME/KEY: misc_feature
<222> LOCATION: (959)..(962)
<223> OTHER INFORMATION: n is a, c, g, or t
<220> FEATURE:
<221> NAME/KEY: misc_feature
<222> LOCATION: (965)..(965)
<223> OTHER INFORMATION: n is a, c, g, or t

<400> SEQUENCE: 22

```
nnnnnnnnnt gcagtcgaac gaagcgattt gaatgaagtt ttcggatgga tttcaanttg      60

actgagtggc ggacgggtga gtaacgcgtg ggtaacctgc cccatacagg gggataacag     120

ttagaaatga ctgctaatac cgcataagac cacagnnccg catggtgcag ggtaaaaac     180

tccggtggta tgggatggac ccgcgtctga ttagcttgtt ggcggggtaa cggcccacca     240

aggcgacgat cagtagccga cctgagaggg tgaccggcca cattgggact gagacacggc     300

ccaaactcct acgggaggca gcagtgggga atattgcaca atgggggaaa ccctgatgca     360

gcgacgccgc gtgagtgatg aagtatttcg gtatgtaaag ctctatcagc agggaagaaa     420

atgacggtac ctgactaaga agccccggct aactacgtgc cagcagccgc ggtaatacgt     480

agggggcaag cgttatccgg atttactggg tgtaaaggga gcgtagacgg ctgtgcaagt     540

ctggagtgaa agcccggggc tcaaccccgg gactgctttg gaaactgtac ggctggagtg     600

ctggagaggc aagcggaatt cctagtgtag cggtgaaatg cgtagatatt aggaggaaca     660

ccagtggcga aggcggcttg ctggacagta actgacgttg aggctcgaaa gcgtggggag     720

caaacaggat tagataccct ggtagtccac gccgtaaacg atgaatgcta ggtgtcgggg     780

agcaaagctc ttcggtgccg ccgcaaacgc aataagcatt ccacctgggg agtacgttcg     840

caagaatgaa actcaaagga nttgacgggg accgcacann ggtggagcat gtggttattc     900

gagcacgcga aancttacca gtcttgnnnc ccctgangnn nngtatgtcg ctnctnngnn     960

nnggn                                                                 965
```

<210> SEQ ID NO 23
<211> LENGTH: 1457

<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1440)..(1440)
<223> OTHER INFORMATION: n is a, c, g, or t
<220> FEATURE:
<221> NAME/KEY: misc_feature
<222> LOCATION: (1451)..(1457)
<223> OTHER INFORMATION: n is a, c, g, or t

<400> SEQUENCE: 23

```
agtttgatta tggctcagga tgaacgctgg cggcgtgctt aacacatgca agtcgagcga     60

agcggtttca atgaagtttt cggatggatt tgaaattgac ttagcggcgg acgggtgagt    120

aacgcgtggg taacctgcct tacactgggg gataacagtt agaaatgact gctaataccg    180

cataagcgca cagggccgca tggtccggtg tgaaaaactc cggtggtgta agatggaccc    240

gcgtctgatt aggtagttgg cggggtaacg gcccaccaag ccgacgatca gtagccgacc    300

tgagagggtg accggccaca ttgggactga gacacggccc aaactcctac gggaggcagc    360

agtggggaat attggacaat gggcgaaagc ctgatccagc gacgccgcgt gagtgaagaa    420

gtatttcggt atgtaaagct ctatcagcag ggaagaaaat gacggtacct gactaagaag    480

ccccggctaa ctacgtgcca gcagccgcgg taatacgtag gggcaagcg ttatccggat    540

ttactgggtg taaagggagc gtagacggtt tagcaagtct gaagtgaaag cccggggctc    600

aaccccggta ctgctttgga aactgttaga cttgagtgca ggagaggtaa gtggaattcc    660

tagtgtagcg gtgaaatgcg tagatattag gaggaacacc agtggcgaag gcggcttact    720

ggactgtaac tgacgttgag gctcgaaagc gtggggagca aacaggatta gataccctgg    780

tagtccacgc cgtaaacgat gaatactagg tgtcgggggg caaagccctt cggtgccgcc    840

gcaaacgcaa taagtattcc acctggggag tacgttcgca agaatgaaac tcaaaggaat    900

tgacggggac ccgcacaagc ggtggagcat gtggtttaat tcgaagcaac gcgaagaacc    960

ttaccaagtc ttgacatccc actgaaaaca ctttaaccgg tgtccctctt cggagcagtg   1020

gagacaggtg gtgcatggtt gtcgtcagct cgtgtcgtga gatgttgggt taagtcccgc   1080

aacgagcgca acccttatcc ttagtagcca gcgagtagag tcgggcactc tggggagact   1140

gccagggata acctggagga aggtggggat gacgtcaaat catcatgccc cttatgattt   1200

gggctacaca cgtgctacaa tggcgtaaac aaagggaggc aaaggagcga tctggagcaa   1260

accccaaaaa taacgtctca gttcggattg caggctgcaa ctcgcctgca tgaagctgga   1320

atcgctagta atcgcgaatc agaatgtcgc ggtgaatacg ttcccgggtc ttgtacacac   1380

cgcccgtcac accatgggag ttggtaacgc ccgaagtcag tgacccaacc gcaaggaggn   1440

agctgccgaa nnnnnnn                                                  1457
```

<210> SEQ ID NO 24
<211> LENGTH: 1456
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (7)..(11)
<223> OTHER INFORMATION: n is a, c, g, or t
<220> FEATURE:
<221> NAME/KEY: misc_feature
<222> LOCATION: (1314)..(1315)

```
<223> OTHER INFORMATION: n is a, c, g, or t
<220> FEATURE:
<221> NAME/KEY: misc_feature
<222> LOCATION: (1358)..(1358)
<223> OTHER INFORMATION: n is a, c, g, or t
<220> FEATURE:
<221> NAME/KEY: misc_feature
<222> LOCATION: (1407)..(1407)
<223> OTHER INFORMATION: n is a, c, g, or t
<220> FEATURE:
<221> NAME/KEY: misc_feature
<222> LOCATION: (1440)..(1440)
<223> OTHER INFORMATION: n is a, c, g, or t
<220> FEATURE:
<221> NAME/KEY: misc_feature
<222> LOCATION: (1444)..(1444)
<223> OTHER INFORMATION: n is a, c, g, or t
<220> FEATURE:
<221> NAME/KEY: misc_feature
<222> LOCATION: (1449)..(1450)
<223> OTHER INFORMATION: n is a, c, g, or t
<220> FEATURE:
<221> NAME/KEY: misc_feature
<222> LOCATION: (1452)..(1456)
<223> OTHER INFORMATION: n is a, c, g, or t

<400> SEQUENCE: 24

agtttgnnnn ngctcaggat gaacgctggc ggcgtgccta acacatgcaa gtcgaacgaa     60

gcatttcaga tgaagttttc ggatggattc tgagatgact gagtggcgga cgggtgagta    120

acacgtggat aacctgcctc acactggggg acaacagtta gaaatgactg ctaataccgc    180

ataagcgcac agtaccgcat ggtacagtgt gaaaaactcc ggtggtgtga gatggatccg    240

cgtctgatta gccagttggc ggggtaacgg cccaccaaag cgacgatcag tagccgacct    300

gagagggtga ccggccacat tggactgag acacggccca aactcctacg ggaggcagca    360

gtggggaata ttgcacaatg ggcgaaagcc tgatgcagcg acgccgcgtg agtgaagaag    420

tatttcggta tgtaaagctc tatcagcagg gaagataatg acggtacctg actaagaagc    480

cccggctaac tacgtgccag cagccgcggt aatacgtagg gggcaagcgt tatccggatt    540

tactgggtgt aaagggagcg tagacggcat ggcaagtctg aagtgaaaac ccagggctca    600

accctgggac tgctttggaa actgtcaagc tagagtgcag gagaggtaag tggaattcct    660

agtgtagcgg tgaaatgcgt agatattagg aggaacacca gtggcgaagg cggcttactg    720

gactgtaact gacgttgagg ctcgaaagcg tggggagcaa acaggattag ataccctggt    780

agtccacgcc gtaaacgatg agtgctaggt gttgggggc aaagcccttc ggtgccgtcg     840

caaacgcaat aagcactcca cctggggagt acgttcgcaa gaatgaaact caaaggaatt    900

gacggggacc cgcacaagcg gtggagcatg tggtttaatt cgaagcaacg cgaagaacct    960

taccaagtct tgacatcctc ttgaccggcg tgtaacggcg cctttccttc gggacaagag   1020

agacaggtgg tgcatggttg tcgtcagctc gtgtcgtgag atgttgggtt aagtcccgca   1080

acgagcgcaa cccttatcct tagtagccag cattaagatg ggcactctag ggagactgcc   1140

agggacaacc tggaggaagg tggggatgac gtcaaatcat catgcccctt atgatttggg   1200

ctacacacgt gctacaatgg cgtaaacaaa gggaagcgac cctgcgaagg tgagcaaatc   1260

tcaaaaataa cgtcccagtt cggactgtag tctgcaaccc gactacacga agcnngaatc   1320

gctagtaatc gcgaatcaga atgtcgcggt gaatacgntc ccgggtcttg tacacaccgc   1380

ccgtcacacc atgggagtca gcaacgnccg aagtcagtga cccaaccgaa aggagggagn   1440

tgcngaagnn gnnnnn                                                   1456
```

<210> SEQ ID NO 25
<211> LENGTH: 1455
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (8)..(9)
<223> OTHER INFORMATION: n is a, c, g, or t
<220> FEATURE:
<221> NAME/KEY: misc_feature
<222> LOCATION: (1419)..(1419)
<223> OTHER INFORMATION: n is a, c, g, or t
<220> FEATURE:
<221> NAME/KEY: misc_feature
<222> LOCATION: (1443)..(1455)
<223> OTHER INFORMATION: n is a, c, g, or t

<400> SEQUENCE: 25
agtttgannt tggctcagga tgaacgctgg cggcgtgcct aacacatgca agtcgagcga 60
agcgctgttt tcagaatctt cggaggaaga ggacagtgac tgagcggcgg acgggtgagt 120
aacgcgtggg caacctgcct catacagggg gataacagtt agaaatgact gctaataccg 180
cataagcgca caggaccgca tggtgtagtg tgaaaaactc cggtggtatg agatggaccc 240
gcgtctgatt aggtagttgg tggggtaaag gcctaccaag ccgacgatca gtagccgacc 300
tgagagggtg accggccaca ttgggactga gacacggccc aaactcctac gggaggcagc 360
agtggggaat attgcacaat gggggaaacc ctgatgcagc gacgccgcgt gaaggaagaa 420
gtatttcggt atgtaaactt ctatcagcag ggaagaagat gacggtacct gagtaagaag 480
caccggctaa atacgtgcca gcagccgcgg taatacgtat ggtgcaagcg ttatccggat 540
ttactgggtg taaagggagc gtagacggat aggcaagtct ggagtgaaaa cccagggctc 600
aactctggga ctgctttgga aactgcagat ctggagtgcc ggagaggtaa gcggaattcc 660
tagtgtagcg gtgaaatgcg tagatattag gaggaacacc agtggcgaag gcggcttact 720
ggacggtgac tgacgttgag gctcgaaagc gtggggagca aacaggatta gataccctgg 780
tagtccacgc cgtaaacgat gactactagg tgtcggtgtg caaagcacat cggtgccgca 840
gcaaacgcaa taagtagtcc acctggggag tacgttcgca agaatgaaac tcaaaggaat 900
tgacggggac ccgcacaagc ggtggagcat gtggtttaat tcgaagcaac gcgaagaacc 960
ttacctggtc ttgacatccg gatgacgggc gagtaatgtc gccgtccctt cggggcatcc 1020
gagacaggtg gtgcatggtt gtcgtcagct cgtgtcgtga gatgttgggt taagtcccgc 1080
aacgagcgca acccttatct tcagtagcca gcatataagg tgggcactct ggagagactg 1140
ccagggagaa cctggaggaa ggtggggatg acgtcaaatc atcatgcccc ttatggccag 1200
ggctacacac gtgctacaat ggcgtaaaca aagggaagcg agagggtgac ctgaagcgaa 1260
tcccaaaaat aacgtctcag ttcggattgt agtctgcaac tcgactacat gaagctggaa 1320
tcgctagtaa tcgcggatca gcatgccgcg gtgaatacgt tcccgggtct tgtacacacc 1380
gcccgtcaca ccatgggagt cagtaacgcc cgaagccant gacccaacct tagaggaggg 1440
agnnnnnnnn nnnnn 1455

<210> SEQ ID NO 26
<211> LENGTH: 1458
<212> TYPE: DNA
<213> ORGANISM: Artificial Sequence
<220> FEATURE:
<223> OTHER INFORMATION: Synthetic polynucleotide
<220> FEATURE:

<221> NAME/KEY: misc_feature
<222> LOCATION: (1439)..(1439)
<223> OTHER INFORMATION: n is a, c, g, or t
<220> FEATURE:
<221> NAME/KEY: misc_feature
<222> LOCATION: (1445)..(1449)
<223> OTHER INFORMATION: n is a, c, g, or t
<220> FEATURE:
<221> NAME/KEY: misc_feature
<222> LOCATION: (1452)..(1457)
<223> OTHER INFORMATION: n is a, c, g, or t

<400> SEQUENCE: 26
agtttgatta tggctcagga tgaacgctgg cggcatgcct aatacatgca agtcgaacga 60
agtttcgagg aagcttgctt ccaaagagac ttagtggcga acgggtgagt aacacgtagg 120
taacctgccc atgtgtccgg gataactgct ggaaacggta gctaaaaccg gataggtata 180
cagagcgcat gctcagtata ttaaagcgcc catcaaggcg tgaacatgga tggacctgcg 240
gcgcattagc tagttggtga ggtaacggcc caccaaggcg atgatgcgta gccggcctga 300
gagggtaaac ggccacattg ggactgagac acggcccaaa ctcctacggg aggcagcagt 360
agggaatttt cgtcaatggg ggaaaccctg aacgagcaat gccgcgtgag tgaagaaggt 420
cttcggatcg taaagctctg ttgtaagtga agaacggctc atagaggaaa tgctatggga 480
gtgacggtag cttaccagaa agccacggct aactacgtgc cagcagccgc ggtaatacgt 540
aggtggcaag cgttatccgg aatcattggg cgtaaagggt gcgtaggtgg cgtactaagt 600
ctgtagtaaa aggcaatggc tcaaccattg taagctatgg aaactggtat gctggagtgc 660
agaagagggc gatggaattc catgtgtagc ggtaaaatgc gtagatatat ggaggaacac 720
cagtggcgaa ggcggtcgcc tggtctgtaa ctgacactga ggcacgaaag cgtggggagc 780
aaataggatt agataccta gtagtccacg ccgtaaacga tgagaactaa gtgttggagg 840
aattcagtgc tgcagttaac gcaataagtt ctccgcctgg ggagtatgca cgcaagtgtg 900
aaactcaaag gaattgacgg gggcccgcac aagcggtgga gtatgtggtt taattcgaag 960
caacgcgaag aaccttacca ggccttgaca tggaaacaaa taccctagag atagggggat 1020
aattatggat cacacaggtg gtgcatggtt gtcgtcagct cgtgtcgtga gatgttgggt 1080
taagtcccgc aacgagcgca acccttgtcg catgttacca gcatcaagtt ggggactcat 1140
gcgagactgc cggtgacaaa ccggaggaag gtggggatga cgtcaaatca tcatgcccct 1200
tatggcctgg gctacacacg tactacaatg gcgaccacaa agagcagcga cacagtgatg 1260
tgaagcgaat ctcataaagg tcgtctcagt tcggattgaa gtctgcaact cgacttcatg 1320
aagtcggaat cgctagtaat cgcagatcag catgctgcgg tgaatacgtt ctcgggcctt 1380
gtacacaccg cccgtcaaac catgggagtc agtaataccc gaagccggtg gcataaccnt 1440
aaggnnnnnc cnnnnnna 1458

<210> SEQ ID NO 27
<211> LENGTH: 1217
<212> TYPE: RNA
<213> ORGANISM: Phascolarctobacterium faecium

<400> SEQUENCE: 27
agaggaccgg ccaggacgaa cgcggcggcg gccaacacag caagcgaacg gagaaacgga 60
gaacagggcg aacggggaga acgcgaggca accgcccaga cggggacaac accgaaagga 120
ggcaaaccgg aggacacggc cgcaggcagg agaagaaaga ggcccacaag aagcacgcaa 180
aggagggccg cgcgaagcag ggaggaacgg acaccaaggc gagacagagc cggcgagagg 240

```
agaacggcca cagggacgag acacggccca aacccacggg aggcagcagg gggaacccgc    300
aaggacgaaa gcgacggagc aacgccgcgg aggagaagga cggcgaaagc cggagacgaa    360
cggcagggga acaagcagca agacggagaa acgaggaagc cacggcaaca cggccagcag    420
ccgcggaaac gaggggcgag cggccggaaa gggcgaaaga gcagaggcgg caaaagcgag    480
cggaaaagcg gggccaaccc cgaggcgcgg aaacgaggcg aggcaggaga ggaaagggga    540
acccaggagc gggaaagcga gaagggagga acaccagggc gaaggcgccc ggacggcgac    600
gcgagagcga aagccaggga gcgaacggga agaaccccgg agccggccga aacgagggac    660
agggaggagg acgacccccg gccggagaac gcaaaagacc ccgccgggga gacggccgca    720
agggaaacca aaggaagacg ggggcccgca caagcgggga gagggaacga cgcaacgcga    780
agaaccacca aggcgacaga gaacgccaga gaagagcccc cggggacaag aaaacagggg    840
gcaggcgcgc agccggcgga gaggggaagc ccgcaacgag cgcaacccca ccagaccagc    900
aagaaagggg gaccagggag acgccaggga caaccggagg aaggcgggga gacgcaagca    960
cagccccagc gggcacacac gacacaaggc ggaaacagag ggaagcgaag ccgcgaggca   1020
gagcaaaccc cagaaacccg accagcggac gcaggcgcaa cccgccgcgg aagcggaacg   1080
cagaacgcag gcagcaacgc gggaaacgcc cgggccgaca caccgcccgc acaccacgaa   1140
agggaacacc cgaagccggg aggaaccaag gagccagccg caagggggc cgagaggggg   1200
aagcgaacaa ggagccg                                                  1217
```

<210> SEQ ID NO 28
<211> LENGTH: 1104
<212> TYPE: RNA
<213> ORGANISM: Fusobacterium ulcerans

<400> SEQUENCE: 28

```
gccaggagaa cgcgacagaa gcaacacagc aagcacgacc cggggaaggg gcggacgggg     60
agaacgcgaa agaacgccac agacgggaca acaggaaacg aagcaaaccg gaaagagggc    120
gcagacgaag aaagcaagcg cggagagagc gcgcccaaga ggggaggaac ggccaccaag    180
acgagaggga gccggccgag aggggaacgg ccacaagggg acgagacacg gcccacccac    240
gggaggcagc agggggaaag gacaaggacc aaaagcgacc agcaacgggc acgagaagcg    300
gaagaaaggc caggggaaga agcaggacgg accaacagaa gaagcgacgg caaaacggcc    360
agcagccgcg gaaacgagcg caagcgaccg gaagggcgaa agcgcgcagg cggcagaagc    420
gaggaaaagc ggggccaacc ccgagcggga aacgcaaaca gagacggaga ggaggcggaa    480
cacaaggaga gggaaacgag aagaggaagc cgaggggaag ccagccacgg acagaacgac    540
gcaaagcgcg aaagcgggga gcaaacagga agaacccgga gccacgccga aacgagaaca    600
gggggggcg aacccagcgc ccaagcaacg cgaaagaacc gccggggaga cgacgcaaga    660
gaaaccaaag gaagacgggg acccgcacaa gcggggagca gggaacgacg caacgcgagg    720
aaccaccagc ggacacccaa gaagaacaga gagcggcccc ggaggaacgg gacagggggc    780
aggcgcgcag ccggcggaga ggggaagccc gcaacgagcg caaccccga gaccacaaag    840
ggggaccagc gagacgccgc gagagcagga ggaaggggg agacgcaagc acagccccaa    900
cgcgggcaca cacggcacaa gggagacaga gagcgcaaac cgcgagggaa gcaaccaaaa    960
acacagcgga gaccgcaacc gagacagaag ggaacgcaga acgcaaacag caggcgggaa   1020
acgccgggcg acacaccgcc cgcacaccac gagaggggca ccgaagaaca ggccaaccga   1080
```

aggagggagc cgagggggaa gcga 1104

<210> SEQ ID NO 29
<211> LENGTH: 1202
<212> TYPE: RNA
<213> ORGANISM: Bacteroides dorei

<400> SEQUENCE: 29
aacaagaaga ggaccggcca ggagaacgca gcacaggcaa cacagcaagc gaggggcagc 60
aggcagcgca aggcgaggcg accggcgcac ggggagaaca cgaccaaccg ccgcaccggc 120
cagcccgaaa ggaagaaacc aggagggaca gagcacagcc gcagaaaagg accggagacg 180
aggggagcgc caagaagagg cggggaacgg cccaccagca acgaggaagg ggcgagagga 240
aggcccccac aggaacgaga cacggccaaa cccacgggag gcagcaggag gaaaggcaag 300
ggcgaggccg aaccagccaa gagcggaagg agacgcccag gggaaaccaa aaggaaaaag 360
cgggagcaac ccggcagaca gaaaaggacg gcaacccggc cagcagccgc ggaaacggag 420
gaccgagcga ccggaaggga aagggagcga gaggagaagc agggaaaggc ggccaaccga 480
aaagcaggaa cggagcgagg caggaggcag gcggaacggg gagcgggaaa gcagaacacg 540
aagaacccga gcgaaggcag ccgcaagcgc aacgacagag gccgaaaggg ggacaaacag 600
gaagaacccg gagccacacg gaaacgagaa accgcggcga aacggcaagc ggccaagcga 660
aagcgaagac caccggggag acgccggcaa cgggaaacca aaggaagacg ggggcccgca 720
caagcggagg aacagggaac gagaacgcga ggaaccaccc gggcaaagca ccgaagaccg 780
gaaacggcag cagcaaagcg agggaagggc gcagggcgca gccggccgga gggcggcaag 840
gccaaacgag cgcaacccgg cagacaacag ggagcgagga ccgacaagac gccacgaaga 900
ggaggaaggg gggagacgca aacagcacgg cccacgccgg ggcacacacg gacaaggggg 960
gacagagggc cgcaccacgc gagggagcca acccaaaacc ccccagcgga cggagcgcaa 1020
cccgacccac gaagcggacg cagaacgcgc acagccacgg cgcgggaaac gcccgggccg 1080
acacaccgcc cgcaagccag ggagccgggg gaccgaaggc gaaccgcgag gacgcccagg 1140
gaaaacggga cggggcaagc gaacaaggag ccgaccggaa gggcggcgga acaccccccgg 1200 ag 1202

<210> SEQ ID NO 30
<211> LENGTH: 1148
<212> TYPE: RNA
<213> ORGANISM: Bacteroides uniformis

<400> SEQUENCE: 30
cggccaggag aacgcagcac aggcaacaca gcaagcgagg ggcagcagaa cagcgcaagg 60
aggcgaccgg cgcacgggga gaacacgacc aaccgccgag accggggaag cccgaaagaa 120
agaaaacccg aggcaagccc gcaggagaac aaaagaacgg cacgagggga gcgccaaggg 180
ggcggggaac ggcccaccaa gcccgaggaa ggggcgagag gaaggccccc acaggaacga 240
gacacggcca aacccacggg aggcagcagg aggaaaggca aggacgagag cgaaccagcc 300
aagagcggaa ggagacgccc aggggaaacc aacgggaaaa aggaggcacg ggccgagacc 360
gagaaaagga cggcaacccg gccagcagcc gcggaaacgg aggaccgagc gaccggaagg 420
gaaagggagc gaggcggacg caagcaggga aaggcggcca accgaaaagc aggaacgggg 480
cgagacagag aggcaggcgg aacggggagc gggaaagcag aacacgaaga acccgagcga 540
aggcagcgcg gacgaacgac gcgagccgaa agggggacaa acaggaagaa cccggagcca 600

```
cacagaaacg agaaaccgcg gcgaaacaga agcggccaag cgaaagcgaa gaccaccggg    660

gagacgccgg caacgggaaa ccaaaggaag acgggggccc gcacaagcgg aggaacaggg    720

aacgagaacg cgaggaacca cccgggcgaa gcaacgaaga gggagacagc agccgcaagg    780

cagggaaggg cgcagggcgc agccggccgg agggcggcaa ggccaaacga gcgcaaccca    840

cgaagaccac aggagcgggg accgcgagac gccgcgaaga ggaggaaggg gggagacgca    900

aacagcacgg cccacgccgg ggcacacacg gacaaggggg gacagaaggc agcacacggc    960

gacggagcaa cccaaagccc ccagcggagg agcgcaaccc gacccagaag cggacgcaga   1020

acgcgcacag ccacggcgcg ggaaacgccc gggccgacac accgcccgca agccagaaag   1080

ccgggggacc gaaggcgaac cgcaaggagc gcccagggaa aacgggaggg gcaagcgaac   1140

aaggaacc                                                            1148
```

<210> SEQ ID NO 31
<211> LENGTH: 1219
<212> TYPE: RNA
<213> ORGANISM: Subdoligranulum sp.

<400> SEQUENCE: 31

```
agaggaccgg ccaggacgaa cgcggcggcg cgccaacaca gcaagcgaac ggagcgccga     60

agcggaggaa gagagcagca gggcgaacgg ggagaacacg gagcaaccgc ccagggggga    120

caacaggaaa cgaagcaaac cgcaaagacc acaggcgcag gcacaggggc aaaggaaccg    180

cgaaagaggg ccgcgccgaa gcagagggag gaacggccca ccaggcgacg acggagccgg    240

acgagaggga acggccacag ggacgagaca cggcccagac ccacgggagg cagcaggggg    300

aaagcacaag gggaaaccc gagcagcgac gccgcgggag gaagaaggcc ggagaaaccc     360

gcccagggga cgaaagacgg acccgggagg aagcaccggc aacacggcca gcagccgcgg    420

aaaacgaggg gcaagcggcc ggaaacgggg aaagggagcg caggcggagg caaggggagg    480

aaacagggcc aacccaaaag ccaaaacgca gcgaggggag aggaggcgga acccgggagc    540

ggggaagcga gaacgggagg aacaccaggg cgaaggcggc cacgggcaca acgacgcgag    600

gccgaaagca gggagcaaac aggaagaacc cggagccagc cgaaacgaga acaggggga     660

ggagaccccc cggccgcaga acacaaaaga accaccgggg agacgaccgc aagggaaacc    720

aaaggaagac gggggcccgc acaagcaggg agagggaacg aagcaacgcg aagaaccacc    780

aggcgacacg gagcaaccaa gagaaggaa gcccgggaca ccagacaggg ggcagggcgc     840

agccggcgga gaggggaagc ccgcaacgag cgcaacccac gagacacgca agaggaccag    900

cgagacgccg gacaaaacgg aggaaggggg gagacgcaaa cacagcccag accgggcaca    960

cacgacacaa ggcaaacaga gagaagcgaa ccgcgagggg agcaaaccca caaaaaagcc   1020

agcggacgca ggcgcaaccc gccgcggaag ccggaagcag aacgcggaca gcagccgcgg   1080

gaaacgcccg ggccgacaca ccgcccgcac accagagagc cgggggggacc cgaagcggag  1140

caaccgaagg aggacgccgc cgaaggaaaa cgggaggggg aagcgaacaa ggagccgacg   1200

gaagggcggc ggacacccc                                                1219
```

<210> SEQ ID NO 32
<211> LENGTH: 1186
<212> TYPE: RNA
<213> ORGANISM: Paraprevotella xylaniphila

<400> SEQUENCE: 32
agaggaccgg ccaggagaac gcagcacagg caacacagca agcgaggggc agcagaacag 60
cgcaaggagg cgaccggcgc acggggagaa cgcgaccaac cgcccacgcg gggaagcccg 120
aaaggaagaa acccgagaac gagcgcaggc gagaaaaaga acagaaagga ggggagcgcc 180
caagcgggcg gggaacggcc caccaaggcg acgagggagg ggcgagagga aggcccccac 240
aggaacgaga cacggccaaa cccacgggag gcagcaggag gaaaggcaag ggcgcgagcc 300
gaaccagcca agagcgggag gacgacggcc cacggggaaa cccaaagggg aaaagggcca 360
gaggccagca ggaccagaaa agcacggcaa ccggccagca gccgcggaaa cggaagagcg 420
agcgaccgga agggaaaggg agcgaggcgg gcagcaagca gcggcaaagg cgcggccaac 480
cgcgccgccg gaaacggcag ccgagagcac agggacagga acggggagcg ggaaagcaga 540
acacgaggaa cccgacgcgc aggcagaccg gggcaacgac gcgaggccga agggcgggac 600
aaacaggaag aacccggagc cgcacagaaa cgagaagccc gcgcggcgac aaggcggcgg 660
ccaagcgaaa gcgaagcacc accggggaga cgccggcaac gggaaaccaa aggaagacgg 720
gggcccgcac aagcggagga acagggaacg agaacgcgag gaaccacccg ggcgaacgca 780
gggcagggcc ggagacggcc ccccgggacc cgcgaagggc gcagggcgca gccggccgga 840
gggcggcaag gccaaacgag cgcaaccccc cccccaggcc acgggaagcc gggcacgggg 900
acacgccacc gcaagggcga ggaagggggg agacgcaaac agcacggccc acgccggggc 960
gacacacgga caagggggga cagagggccg cgcccgggac ggggccaacc caaagccccc 1020
cagcggacgg agcgcaaccc gacccacgaa gcggacgcag aacgcgcaca gccaggcgcg 1080
ggaaacgccc gggccgacac accgcccgca agccagaaag ccgggggccc gaagccggac 1140
cgcgagggcg gccagggaaa accgggaggg gcaagcgaac aaggaa 1186

<210> SEQ ID NO 33
<211> LENGTH: 1165
<212> TYPE: RNA
<213> ORGANISM: Parabacteroides johnsonii

<400> SEQUENCE: 33
agaggaccgg ccaggagaac gcagcgacag gcaacacagc aagcgagggg cagcaggaag 60
agcaaacaga ggcgaccggc gcacggggag aacgcgagca acaccacaga gggggaagcc 120
cggcgaaagc ggaaaaccca aaaacagggg ccgcagggac agaaagacac gcgaagaagg 180
cagcgccaag gcagggcggg gaacggccca ccaaaccgac gaggaagggg cgagaggaag 240
gcccccacag gacgagacac ggaccaaacc cacgggaggc agcaggagga aaggcaaggc 300
cgagaggcga accagccaag cgcggaagga gaaggacagg gaaaccaagg ggaaaaaggg 360
ggacggccag agacccagaa aagcacggca acccggccag cagccgcgga aacggaggag 420
cgagcgaccg gaagggaaag gggcgagggg aaaagcagcg ggaaaggggc caaccaaaaa 480
gccggaaacg ggacgagggg aggaggcgga agcggggagc gggaaagcaa gaacacgcag 540
aacccaagcg aaggcagcac aaaccaaacg acacgaagca cgaaagcggg gacaaacagg 600
aagaacccgg agccacgcag aaacgagaac aggaggcgaa cacagaagcc acagcgaaag 660
cgaagaacca ccggggagac gccggcaacg ggaaaccaaa ggaagacggg ggcccgcaca 720
agcggaggaa cagggaacga gaacgcgagg aaccacccgg ggaacgagca gaccgaccga 780
aagaggccag caaagcgaac gagggcgcag ggcgcagccg gccggagggc ggcaaggcca 840
aacgagcgca acccacacag acaacaggca agcgaggacc gggagacgcc agcgaagcgg 900
aggaaggggg gagacgcaaa cagcacggcc cacaccgggg cgacacacgg acaaggcagg 960
acaaagggca gcaccggcga caggagcaac caaaccagcc agcggacgga gcgcaaccga 1020
cccggaagcg gacgcagaac gcgcacagcc aggcgcggga aacgcccggg ccgacacacc 1080
gcccgcaagc cagggagccg ggggaccgaa gccgaaccgc aaggacggcc agggaaaacg 1140
ggacggggca agcgaacaag gaacc 1165

<210> SEQ ID NO 34
<211> LENGTH: 1181
<212> TYPE: RNA
<213> ORGANISM: Alistipes sp

<400> SEQUENCE: 34
agaggaccgg ccaggagaac gcagcggcag gccaacacag caagcgaggg gcagcgggag 60
aagcgccaac gccggcgacc ggcgcacggg gcgaacgcga gcaaccaccc agaacagggg 120
gaaacacgag aaaggacaaa cccaaacaca aaggggcacc cgggaaaacc cggggcggag 180
ggcagcggaa gcgggggagg aacggccacc aaggcaacga acaaggggga cgagaggaac 240
cccccacagg acgagacacg gaccaaaccc acgggaggca gcaggaggaa aggcaaggac 300
gcaagcgaac cagccagccg cggcaggaag acggccagag gaaacgcgac agggaaacca 360
gaacgcgacg acgaaagaag acgaaaagga ccggcaaccc ggccagcagc cgcggaaacg 420
gagggccaag cgaccggaag ggaaaggggc gaggcggaga aagagaggga aaaccgggca 480
acaccggaac gcccaaacga gcagagaaag gcggaggsgg aagagggagc gggaaagcag 540
agacaacaga acaccgagcg aaggcagcac caagcacgac ggaggcacga aagcggggga 600
gcaaacagga agaacccgga gccacgcaga aacgagaaac cgcgcggcga acacagcggc 660
ggcaagcgaa agcgaaagac caccggggag acgcgcaaga agaaaccaaa ggaagacggg 720
ggcccgcaca agcggaggaa cagggaacga gaacgcgagg aaccacccgg gcgaaagacg 780
acgacggaaa caggaccccg gggcaggaaa cagggcgcag ggcgcagccg gccggagggc 840
gggaagccca aacgagcgca accccaccga ggccacaggc aagcgggcac cgacgggacg 900
ccgggaagcc gagaggaagg ggggagacgc aaacagcacg gcccacgccg gggcacacac 960
ggacaaggag gacagagggc agcacccgcg aagggagcga accgaaagcc accagcggac 1020
ggaggcgaaa cccgccccgg aagggacgca gaacgcgcac agccaggcgc gggaaacgcc 1080
cgggccgaca caccgcccgc aagccaggaa gcgggggccc gaagcggacc gcaaggagcg 1140
accagggcaa aaccgggacg gggcaagcga acaaggagcc g 1181

<210> SEQ ID NO 35
<211> LENGTH: 1157
<212> TYPE: RNA
<213> ORGANISM: Parabacteroides gordonii

<400> SEQUENCE: 35
agaggaccgg ccaggagaac gcagcgacag gcaacacagc aagcgagggg cagcaggaag 60
agcaaacgcg gcgaccggcg cacggggaga acgcgagcaa ccaccacaga gggggaaacc 120
cggcgaaagc ggacaaaccg caaaaacagg ggcccgcagg gaaagaaaga aagcgaagag 180
ggcagcgcca agaagggaag gaacggcacc aagcgcgagg aaggggcgag aggaaggccc 240
ccacacggac gagacacgga ccagacccac gggaggcagc aggaggaaag gcaagggcga 300
gagccgaacc agccaagcgc ggaaggagaa ggacaggcga aaccaaaggg aaaaaggcgg 360
acggccggag accagaaaag gacggcaacc cggccagcag ccgcggaaac ggaggaccga 420
gcgaccggaa gggaaagggg cgaggggaaa gcagcgggaa aggggccaac caaaaagccg 480
gaaacggaac gagaagagga ggcggaagcg gggagcggga aagcaagaac acgcagaacc 540
caagcgaagg cagcacaaac aaacgacacg aagcacgaaa gcgggggaca aacaggaaga 600
acccggagcc acgcagaaac gagaacagga ggcgaacaca gaagccacag cgaaagcgaa 660
gaaccaccgg ggagacgccg gcaacgggaa accaaaggaa gacgggggcc cgcacaagcg 720
gaggaacagg gaacgagaac gcgaggaacc acccggggaa cgcaggacag ccgaaagagg 780
accagcaaag ccagcgaggg cgcagggcgc agccggccgg agggcggcaa ggccaaacga 840
gcgcaaccca cagacaacag gcgcgaggac caaagagacg ccagcgaagc ggaggaaggg 900
gggagacgca aacagcacgg cccacaccgg ggcgacacac ggacaagggg ggacaaaggg 960
cagcacacag cgaggagcaa cccaaacccc accagcggac gaagcgcaac ccgaccggaa 1020
gcggacgcag aacgcgcaca gccaggcgcg ggaaacgccc gggccgacac accgcccgca 1080
agccagggag gggggaccaa agccgaaccg caaggacggc caggaaaacc gagacggggc 1140
aagcgaacca aggaacc 1157

<210> SEQ ID NO 36
<211> LENGTH: 1189
<212> TYPE: RNA
<213> ORGANISM: Eubacterium limosum

<400> SEQUENCE: 36
agaggaccgg ccaggacgaa cgcggcggag caacacagca agcgaacgag aagggaggac 60
ccggggacaa gaacggaaag ggcgaacggg gagaacgcgg ggaaccgccc aggaaaggaa 120
agcccgggaa acgggagaaa gccaaagggc gcaggcaaga cagaaaaccc gggccaagga 180
ggacccgcgc ccaagcaggg gagaaacagc ccaccaaggc gacgagggaa ccggcgagag 240
ggcgaacggc acacggaacg agacacggcc agacccacgg gaggcagcag ggggaaagcg 300
caagggggca acccgacgca gcaaaccgcg gaggaagaag gcggacgaaa gccgagggga 360
agaagaagac ggacccaaga ggaagcccgg caacacggcc agcagccgcg gaaacgaggg 420
gacaagcggc cggaagacgg gcgaaagggc gcgaggcggc aaagcgagga aaggaccggc 480
caaccgggaa ggcaggaaac ggagacgaga ggagaggcaa gggaaccagg agcgggaaag 540
cgagaaagga ggaacaccag ggcgaaggcg gcgcggacaa aacgacgcga gggcgaaagc 600
gggggagcga acaggaagaa cccggagcca cgccgaaacg agaagcaggg ggggaaacca 660
ggccgcagaa cacaaaagca ccgccgggga gacgaccgca agggaaacca aaggaagacg 720
gggacccgca caagcagcgg agcagggaac gaagcaacgc gaagaaccac caggcgacac 780
ccgacgagcc agagaaggaa gcccgggaac agagagacag ggggcagggc gcagccggcg 840
gagaggggaa gcccgcaacg agcgcaaccc cgccaggcca gcaaaggggc accagaggga 900
cgccgagaca aacggaggaa ggggggacga cgcaaacaca gccccagacc gggcacacac 960
ggcacaaggc gaacagaggg ccgcgaagcc gcgagggaag caaacccaaa acagacccag 1020
cggagcaggc gcaaccgccg cagaagggag gcagaacgcg gacagaagcc gcgggaagcg 1080
cccgggcgac acaccgcccg cacaccacga gagggcaaca cccgaagccg gagagaaccg 1140
caaggaccag cagcgaaggg gggcagaagg gggaagcgaa caaggaacc 1189

<210> SEQ ID NO 37
<211> LENGTH: 1190
<212> TYPE: RNA
<213> ORGANISM: Parabacteroides distasonis

<400> SEQUENCE: 37
agaggaccgg ccaggagaac gcagcgacag gcaacacagc aagcgagggg cagcggggga 60
gcaaacaccg ccggcgaccg gcgcacgggg agaacgcgag caacgccaca gagggggaaa 120
cccggcgaaa gcggacaaac cgcagaagca gggacccgca gggaaagcaa agacacgcga 180
agaaggcagc gccaaggcag ggcggggaac ggcccaccaa accgacgagg aaggggcgag 240
aggaaggccc ccacaggacg agacacggac caaacccacg ggaggcagca ggaggaaagg 300
caagggcgaa gccgaaccag ccaagcgcgg agggagaagg caggacgaaa cccaaaggga 360
aaaaggcggg acggcccgga gaccagaaaa ggacggcaac ccggccagca gccgcggaaa 420
cggaggaccg agcgaccgga agggaaaggg gcgaggcggc caagcagcgg gaaagcgggc 480
caaccaagaa gccggaaacg gggggcgaga ggaggcaggc ggaagcgggg agcgggaaag 540
caagaacacg cagaaccccg agcgaaggca gccgccaagc caacgacgcg agcacgaaag 600
cgggggacaa acaggaagaa cccggagcca cgcagaaacg agacacagcg gcgaacacga 660
agcggcacag cgaaagcgaa ggaccaccgg ggagacgccg gcaacgggaa accaaaggaa 720
gacgggggcc cgcacaagcg gaggaacagg gaacgagaac gcgaggaacc acccggggaa 780
cgcacggacc gaggggaaac acccagcaaa gccggcgagg gcgcagggcg cagccggccg 840
gagggcggca aggccaaacg agcgcaaccc gccacagaca acaggaggcg aggaccgggg 900
gacgccagcg aagcgcgagg aaggcgggga gacgcaaaca gcacggccca caccggggcg 960
acacacggac aaggcgggac aaagggaggc caccggcgac agggagcgaa ccccaaacca 1020
cgccagcgga cggagcgcaa cccgacccgg aagcggacgc agaacgcgca cagccaggcg 1080
cgggaaacgc ccgggccgac acaccgcccg caagccaggg agccgggggga ccgaagccga 1140
accgaaagga cggccaggga aaacgggacg gggcaagcga acaaggaacc 1190

<210> SEQ ID NO 38
<211> LENGTH: 1141
<212> TYPE: RNA
<213> ORGANISM: Bacteroides cellulosilyticus

<400> SEQUENCE: 38
agaggaccgg ccaggagaac gcagcacagg caacacagca agcgaggggc agcagaccag 60
caaagggagg cgaccggcgc acggggagaa cacgaccaac caccggaccg ggaagcccga 120
aagaaagaaa accggaagaa acgagaaggc acgaaaagaa cgaaaccgag gggagcgcca 180
aggggcgggg aacggcccac caagacacga ggaagggggcg agaggaaggc ccccacagga 240
acgagacacg gccaaaccca cgggaggcag caggaggaaa ggcaaggacg agagcgaacc 300
agccaagagc ggaaggagac gcccagggga aaccaaggga aaaaggagcc acggggcgag 360
accaacgaaa aggacggcaa cccggccagc agccgcggaa acggaggacc gagcgaccgg 420
aagggaaagg gagcgaggcg gacaaagcag cggaaaggcg gccaaccgaa aagcaggaac 480
ggcgcgaggc agagaggagg cggaacgggg agcgggaaag cagaacacga agaacccgag 540
cgaaggcagc acggacgaac gacgcgagcc gaaaggggga caaacaggaa gaacccggag 600
ccacacagaa acgagaaacc gcggcgaaac agcaagcggc caagcgaaag caaagaccac 660
cggggagacg ccggcaacgg gaaaccaaag gaagacgggg gcccgcacaa gcggaggaac 720
agggaacgag aacgcgagga accacccggg caaagcacga aaaggaaaca gaagccgcaa 780
ggcagaggaa gggcgcaggg cgcagccggc cggagggcgg caaggccaaa cgagcgcaac 840

-continued ccacagacaa caggcagcga ggaccagaga gacgccgcga agaggaggaa ggggggagac 900
gcaaacagca cggcccacgc cggggcacac acggacaagg ggggacagaa ggcagcacac 960
agcgaggagc aacccaaaag cccccagcgg aggagcgcaa cccgacccag aagcggacgc 1020
agaacgcgca cagccacggc gcgggaaacg cccgggccga cacaccgccc gcaagccaga 1080
aagccggggg accgaagccg aaccgcaagg agcggccagg gaaaacggaa ggggcaagcg 1140
a 1141

<210> SEQ ID NO 39
<211> LENGTH: 1155
<212> TYPE: RNA
<213> ORGANISM: Bacteroides clarus

<400> SEQUENCE: 39
gagaacgcag cacaggcaac acagcaagcg aggggcagcg ggggaagcgc caaccgccgg 60
cgaccggcgc acggggagaa cacgaccaac cgccgaaacc cgggaagccc gaaagaaaga 120
aaaccggagg caagcccgca ggaaaacaaa agaacggacg aggggagcgc caaggcaggg 180
cggggaacgg cccaccaaac cgacgaggaa ggggcgagag gaaggccccc acaggaacga 240
gacacggcca aacccacggg aggcagcagg aggaaaggca aggacgagag cgaaccagcc 300
aagagcggaa ggagacgccc aggggaaacc aacgggaaaa agagccacgg gggcagaccg 360
agaaaaggac ggcaacccgg ccagcagccg cggaaacgga ggaccgagcg accggaaggg 420
aaagggagcg aggcggggaa agcagggaaa ggcggccaac cgaaaagcag gaacggaccg 480
aggcagcaga gggggcggaa cggggagcgg gaaagcagaa cacgaagaac ccgagcgaag 540
gcagccacgg aggaacgacg cgagccgaaa gggggacaaa caggaagaac ccggagccac 600
acagaaacga gaaaccgcgg gcgaacaagc agcggccaag cgaaagcaaa gaccaccggg 660
gagacgccgg caacgggaaa ccaaaggaag acgggggccc gcacaagcgg aggaacaggg 720
aacgagaacg cgaggaacca cccgggcgaa gcaacgacgg aaggaaacag cccggacagg 780
gaagggcgca gggcgcagcc ggccggaggg cggcaaggcc aaacgagcgc aacccacgaa 840
gaccacaggc agcggggacc acgagacgcc gcgaagagga ggaagggggg agacgcaaac 900
agcacggccc acgccggggc acacacggac aagggggggac agaaggcagc acacggcgac 960
ggagcaaccc caaaaccccc agcggaggag cgcaaccccga cccagaagcg gacgcagaac 1020
gcgcacagcc acggcgcggg aaacgcccgg gccgacacac cgcccgcaag ccagaaagcc 1080
gggggaccga agacgaaccg caaggagcgc cagggaaaac gggaggggca agcgaacaag 1140
gagccgaccg gaagg 1155

<210> SEQ ID NO 40
<211> LENGTH: 408
<212> TYPE: RNA
<213> ORGANISM: Anaerostipes caccae

<400> SEQUENCE: 40
gaccaagacg agggcggacg gggagaacgc gggggaaccg cccaacaggg ggaaacagcg 60
gaaacggcgc aaaccgcaaa gcgcacagaa cgcagacagg gaaaagcccg gcagaaggag 120
gcccgcgcga agcgggggag gaacggccac caaggcgacg acagagccgg cgagagagga 180
acggccacag ggacgagaca cggcccaaac ccacgggagg cagcaggggg aaagcacaag 240
ggggaaaccc gagcagcgac gccgcggagg aagaagacgg agaaagccac agcagggaag 300
aaaacagacg gaccgacaag aagccccggc aacacggcca gcagccgcgg aaacgagggg 360
gcaagcgacc ggaaacgggg aaaggggcga ggggcaggaa gcagaagg 408

<210> SEQ ID NO 41
<211> LENGTH: 1111
<212> TYPE: RNA
<213> ORGANISM: Bacteroides salyersiae

<400> SEQUENCE: 41
aggagaacgc agcacaggca acacagcaag cgaggggcac aggggagcaa acaccgcggc 60
gaccggcgca cggggagaac acgaccaacc gcccaccggg gaagcccgaa agaaagaaaa 120
cccgaggcaa acagaccccg ggaaaagaac ggagaggagg ggagcgccaa ggcagggcgg 180
ggaacggccc accaaacccg aggaaggggc gagaggaagg cccccacagg aacgagacac 240
ggccaaaccc acgggaggca gcaggaggaa aggcaagggc gagagccgaa ccagccaaga 300
gcggaaggag accgcccagg ggaaaccaag ggaaaaaggg gccacggggc agagaccaag 360
aaaaggacgg caacccggcc agcagccgcg gaaacggagg accgagcgac cggaagggaa 420
agggagcgag gggacagaag cagggaaagg cggccaaccg aaaagcagga aacgcggcga 480
gacagagagg gggcggaacg gggagcggga aagcagaaca cgaagaaccc gagcgaaggc 540
agccacggac gcaacgacac gagccgaaag ggggacaaac aggaagaacc cggagccaca 600
cagaaacgag aaaccgcggc gaaacagaag cggccaagcg aaagcaaaga ccaccgggga 660
gacgccggca acgggaaacc aaaggaagac gggggcccgc acaagcggag gaacagggaa 720
cgagaacgcg aggaaccacc cgggcaaagc aaagaaagcc ggaaacggca agccgcaagg 780
caggaagggc gcagggcgca gccggccgga gggcggcaag gccaaacgag cgcaacccac 840
cagacaacag gcagcgagga ccggagagac gccgcgaaga ggaggaaggg gggagacgca 900
aacagcacgg cccacgccgg ggcacacacg gacaaggggg gacagaaggc cgcacacagc 960
gaggagccaa cccaaagccc cccagcggac gaagcgcaac ccgaccggaa gcggacgcag 1020
aacgcgcaca gccacggcgc gggaaacgcc cgggccgaca caccgcccgc aagccaggga 1080
gccgggggac cgaagacgaa ccgcaaggag c 1111

<210> SEQ ID NO 42
<211> LENGTH: 1146
<212> TYPE: RNA
<213> ORGANISM: Bacteroides fragilis
<220> FEATURE:
<221> NAME/KEY: misc_feature
<222> LOCATION: (205)..(205)
<223> OTHER INFORMATION: n is a, c, g, or u

<400> SEQUENCE: 42
agaggaccgg ccaggagaac gcagcacagg caacacagca agcgaggggc acaggaagaa 60
agcgccgcgg cgaccggcgc acggggagaa cacgaccaac cgcccaccgg ggaagcccga 120
aagaaagaaa acccgaagca aagaccgcag gcaaaaagga ccggaaagga ggggagcgcc 180 aagggggggag gaacggccac caagnccgag gaaggggcga gaggaaggcc cccacaggaa 240
cgagacacgg ccaaacccac gggaggcagc aggaggaaag gcaagggcgc agccgaacca 300
gccaagagcg gaaggagaag gccagggcga aaccaaaaga aaaaggcaga gaacggagaa 360
agaaaaggac ggcaacccgg ccagcagccg cggaaacgga ggaccgagcg accggaaggg 420
aaagggagcg aggggacgga agcagggaaa ggcggccaac cgaaaagcag gaacgcagcg 480
agacagagag gggcggaac ggggagcggg aaagcagaac acgaagaacc cgagcgaagg 540

-continued

```
cagccacgga cgcaacgaca cgagccgaaa gggggacaaa caggaagaac ccggagccac    600

acagaaacga gaaaccgcgg cgaaacagaa gcggccaagc gaaagcaaag accaccgggg    660

agacgccggc aacgggaaac caaaggaaga cgggggcccg cacaagcgga ggaacaggga    720

acgagaacgc gaggaaccac ccgggcaaag cagggaagag ggaaacagca ggagcaacac    780

cgcggaaggg cgcagggcgc agccggccgg agggcggcaa ggccaaacga gcgcaaccca    840

cagacaacag gagcgaggac cagagagacg ccgcgaagag gaggaagggg ggagacgcaa    900

acagcacggc ccacgccggg gcacacacgg acaagggggg acagaaggca gcagcgggga    960

ccgagcaacc caaaagcccc cagcggacga agcgcaaccc gaccggaagc ggacgcagaa   1020

cgcgcacagc cacggcgcgg gaaacgcccg ggccgacaca ccgcccgcaa gccagggagc   1080

cgggggaccg aagacgaacc gcaaggacgc cagggaaaac gggacggggc aagcgaacaa   1140

ggaacc                                                              1146


<210> SEQ ID NO 43
<211> LENGTH: 1150
<212> TYPE: RNA
<213> ORGANISM: Bacteroides uniformis

<400> SEQUENCE: 43

agaggaccgg ccaggagaac gcagcacagg caacacagca agcgaggggc acaggaagaa     60

agcgccgcgg cgaccggcgc acggggagaa cacgaccaac cgccgagacc ggggaagccc    120

gaaagaaaga aaacccgagg aacgaaaggc accagcaaaa gaacggcaga ggggagcgcc    180

aagggggcgg ggaacggccc accaagccac gaggaagggg cgagaggaag gcccccacag    240

gaacgagaca cggccaaacc cacgggaggc agcaggagga aaggcaagga cgagagcgaa    300

ccagccaaga gcggaaggag acgcccaggg gaaaccaacg ggaaaaagag gcacgggccg    360

agaccgagaa aaggacggca acccggccag cagccgcgga aacggaggac cgagcgaccg    420

gaagggaaag ggagcgaggc ggagcaagca gggaaaggcg gccaaccgaa aagcaggaac    480

ggggcgagac agagaggcag gcggaacggg gagcgggaaa gcagaacacg aagaacccga    540

gcgaaggcag cgcggacgaa cgacgcgagc cgaaaggggg acaaacagga agaacccgga    600

gccacacaga aacgagaaac cgcggcgaaa cagaagcggc caagcgaaag cgaagaccac    660

cggggagacg ccggcaacgg gaaaccaaag gaagacgggg gcccgcacaa gcggaggaac    720

agggaacgag aacgcgagga accacccggg caaagcaaag aagcggaaac agacagccgc    780

aaggcaggaa gggcgcaggg cgcagccggc cggagggcgg caaggccaaa cgagcgcaac    840

ccacgaagac cacaggagcg gggaccgcga gacgccgcga agaggaggaa ggggggagac    900

gcaaacagca cggcccacgc cggggcacac acggacaagg ggggacagaa ggcagcacac    960

gggacggagc aacccaaaac ccccagcgga ggagcgcaac ccgacccaga agcggacgca   1020

gaacgcgcac agccacggcg cgggaaacgc ccgggccgac acaccgcccg caagccagaa   1080

agccggggga ccgaaggcga accgcgagga gcgcccaggg aaaacgggag gggcaagcga   1140

acaaggaacc                                                          1150


<210> SEQ ID NO 44
<211> LENGTH: 1154
<212> TYPE: RNA
<213> ORGANISM: Bacteroides eggerthii

<400> SEQUENCE: 44

agaggaccgg ccaggagaac gcagcacagg caacacagca agcgaggggc agcagagaag     60
```

```
cgccaacgag gcgaccggcg cacggggaga acacgaccaa ccgccgaaac cggggaagcc    120

cgaaagaaag aaaacccgaa gaagccgcag gcacaaaaga acggacgagg ggagcgccaa    180

gaagggcggg gaacggccca ccaagcaacg aggaaggggc gagaggaagg cccccacagg    240

aacgagacac ggccaaaccc acgggaggca gcaggaggaa aggcaaggac gagagcgaac    300

cagccaagag cggaaggaga cgcccagggg aaaccaacgg gaaaaaggga gagcaacccg    360

agaccgagaa aaggacggca acccggccag cagccgcgga aacggaggac cgagcgaccg    420

gaagggaaag ggagcgaggc ggggcaagca gggaaaggcg gccaaccgaa aagcaggaac    480

gggcgccgag gcagcaagga ggcggaacgg ggagcgggaa agcagaacac gaagaacccg    540

agcgaaggca gcacggacga acgacgcgag ccgaaagggg gacaaacagg aagaacccgg    600

agccacacag aaacgagaaa ccgcgggcga acacagcagc ggccaagcga aagcaaagac    660

caccggggag acgccggcaa cgggaaacca aaggaagacg ggggcccgca caagcggagg    720

aacagggaac gagaacgcga ggaaccaccc gggcaaagca gcggaagagg gaaacaacag    780

cccgggccgc ggaagggcgc agggcgcagc cggccggagg gcggcaaggc caaacgagcg    840

caacccacaa gacacaggca gcgaggacca ggagacgccg cgaagaggag gaagggggga    900

gacgcaaaca gcacggccca cgccggggca cacacggaca agggggggaca gaaggcagca    960

ccggcgacag gagcaacccg aaaaccccca gcggaggagc gcaacccgac ccagaagcgg   1020

acgcagaacg cgcacagcca cggcgcggga aacgcccggg ccgacacacc gcccgcaagc   1080

cagaaagccg gggaccgaa  gacgaaccgc aaggagcgcc agggaaaacg ggaggggcaa   1140

gcgaacaagg aacc                                                     1154
```

<210> SEQ ID NO 45
<211> LENGTH: 1162
<212> TYPE: RNA
<213> ORGANISM: Clostridium sp.

<400> SEQUENCE: 45

```
acagcaagcg gacgcaagcc ggcagagggc gaacggggag aagacaaagc aaccgccccg     60

gagggggaaa cgcggaaacg gcagcaagac cgcaaggcaa gaggacgcag cgacagaaaa    120

cccacgggaa gcacagggag ggcagacgca agccagcggg aggaacggcc accagggcga    180

cgagcgagcc ggccgagagg gggacggcca cacgggacga gacacggccc agacccacgg    240

gaggcagcag agggaacggc aagggcgaaa gccgaccgag caacgccgcg gaaggaagaa    300

gcacggagaa accgagaagg aagaacggca gaggagggaa gccaggcgga cggaccagag    360

gaagccacgg caacacggcc agcagccgcg gaaacgaggg gcgagcgacc ggaacagggc    420

gaaagaggga gcaggcggca ggcaggcgcg ggaaagaccg gagcaaaccg gaagccggga    480

aaccgcacag cagagagcac agaggacgcg gaaccaggag cgggaaagcg agaaaggagg    540

aacaccaggg cgaaggcggc ggcgggggca gcgacgccag cccgaaagcg ggggagcaaa    600

aggaagaacc cagagccacg ccgaaacgag aggcaagggg gggcagaccc aggcggagaa    660

cgcaaaagca cccgccgaga gacgcgcaag aagaaaccaa aggaagacgg gggcccgcac    720

aagcggggag cagggaacga agcaacgcga agaaccacca ggcgacagga gaaaaggccc    780

ggagacaggg agaagaaacc acacaggggg cagggcgcag ccggcggaga ggggaagccc    840

gcaacgagcg caaccccggc caggccagca agggggggacc ggcgagacgc ccgcaaggag    900

gaggaaggcg gggagacgca aacacagccc cagaccgggc acacacggca caaggacgga    960
```

cagagggagg cgaagccgcg aggggagcga aacccagaaa cccgcacagc ggacgcagcg 1020
caaccgacgc acgaagcgga acgcagaacg cgaacagcag cgcgggaaac gccgggccga 1080
cacaccgccc gcacaccaga gagggaacac ccgaagccgg ggcccaaccg caaggaggga 1140
gcgcaagggg gacgagaggg gg 1162

<210> SEQ ID NO 46
<211> LENGTH: 1153
<212> TYPE: RNA
<213> ORGANISM: Parabacteroides goldsteinii

<400> SEQUENCE: 46
ggccaggaga acgcagcgac aggcaacaca gcaagcgagg ggcagcacga gagcaaacag 60
gggcgaccgg cgcacgggga gaacgcgagc aaccaccaca gaggggaaaa cccggcgaaa 120
gcggacaaac cgcaaaaaca ggggccacag gaaaagaaag aaacgcgaag agggcagcgc 180
caagaagggg aggaacggcc accaagccac gaggaagggg cgagaggaag gcccccacac 240
ggacgagaca cggaccagac ccacgggagg cagcaggagg aaaggcaagg gcgagagccg 300
aaccagccaa gcgcggaagg agaaggacag ggaaaccaag ggaaaaagga ggaacggccg 360
agaccaagaa aagcacggca acccggccag cagccgcgga aacggaggag cgagcgaccg 420
gaagggaaag gggcgagggg aaaagcagcg ggaaaggggc caaccaaaaa gccggaaacg 480
ggacgagaag aggaggcgga agcggggagc gggaaagcaa gaacacgcag aacccgagcg 540
aaggcagcac aaacaaacga cacgaagcac gaaagcgggg gacaaacagg aagaacccgg 600
agccacgcag aaacgagaac agcggcgaac acagaagcgg cacagcgaaa gcgaagaacc 660
accggggaga cgccggcaac gggaaaccaa aggaagacgg gggcccgcac aagcggagga 720
acagggaacg agaacgcgag gaaccacccg gggaacgcaa gacagccgga aacagagcca 780
gaaagcaagc gagggcgcag ggcgcagccg gccggagggc ggcaaggcca aacgagcgca 840
acccacacag acaacaggca gcgaggacca ggagacgcca gcgaagcgga ggaagggggg 900
agacgcaaac agcacggccc acaccggggc gacacacgga caagggggga caaagggcag 960
caccgggagc ggagcaaccc aaacccacca gcggacgaag cgcaacccga ccggaagcgg 1020
acgcagaacg cgcacagcca ggcgcgggaa acgcccgggc cgacacaccg cccgcaagcc 1080
agggaggggg gaccaaagcc gaaccgcaag gacggccagg gaaaaccgag acggggcaag 1140
cgaacaagga acc 1153

<210> SEQ ID NO 47
<211> LENGTH: 1125
<212> TYPE: RNA
<213> ORGANISM: Bacteroides thetaiotaomicron

<400> SEQUENCE: 47
caggagaacg cagcacaggc aacacagcaa gcgaggggca gcacaggcgc aaacggagag 60
gcgaccggcg cacggggaga acacgaccaa ccgccgaaac cggggaagcc cgaaagaaag 120
aaaacccgag gaaacagacc gcaggcgaaa agaacggacg aggggagcgc caaggcaggg 180
gaggaacggc caccaaaccc gaggaagggg cgagaggaag gcccccacag gaacgagaca 240
cggccaaacc cacgggaggc agcaggagga aaggcaaggg cgcaggccga accagccaag 300
agcggaagga gacgcccagg ggaaaccaag ggaaaaagcc acggggaaga gaccaagaaa 360
aggacggcaa cccggccagc agccgcggaa acggaggacc gagcgaccgg aagggaaagg 420
gagcgagggg acagaagcag ggaaaggcgg ccaaccgaaa agcaggaacg gcgcgagaca 480
gagagggggc ggaacgggga gcgggaaagc agaacacgaa gaacccgagc gaaggcagcc 540
acggacgcaa cgacacgagc cgaaaggggg acaaacagga agaacccgga gccacacaga 600
aacgagaaac cgcggcgaaa cagaagcggc caagcgaaag caaagaccac cggggagacg 660
ccggcaacgg gaaaccaaag gaagacgggg gcccgcacaa gcggaggaac agggaacgag 720
aacgcgagga accacccggg caaagcagaa aaggaaacag aagccgaagg caaaggaagg 780
gcgcagggcg cagccggccg gagggcggca aggccaaacg agcgcaaccc acagacaaca 840
ggcagcgagg accagagaga cgccgcgaag aggaggaagg ggggagacgc aaacagcacg 900
gcccacgccg gggcacacac ggacaagggg ggacagaagg cagcaccggg acaggagcaa 960
cccaaaagcc cccagcggac gaagcgcaac ccgaccggaa gcggacgcag aacgcgcaca 1020
gccaggcgcg ggaaacgccc gggccgacac accgcccgca agccagaaag ccgggggacc 1080
gaagacgaac cgcaaggagc gccagggaaa acggaagggg caagc 1125

<210> SEQ ID NO 48
<211> LENGTH: 420
<212> TYPE: RNA
<213> ORGANISM: Lachnospiraceae bacterium

<400> SEQUENCE: 48
gacgagcggc ggacggggag aacgcgggga accgcccaac agggggaaac agggaaacgg 60
cgcaaaccgc aaagcgcaca gaccgcagga ccgggaaaaa cccggggaga gaggacccgc 120
gcgaagcagg gggggaacgg ccaccaaggc gacgacagag ccgaccgaga ggggaccggc 180
cacagggacg agacacggcc caaacccacg ggaggcagca gggggaaagc acaaggggga 240
aacccgagca gcgacgccgc ggagcgagaa gacggagaaa gccacagcag ggaagaaaag 300
acggaccgac aagaagcccc ggcaacacgg ccagcagccg cggaaacgag ggggcaagcg 360
accggaacgg ggaaagggag cgagacggca ggcaagccag aggaaagccc ggggccaacc 420

<210> SEQ ID NO 49
<211> LENGTH: 1203
<212> TYPE: RNA
<213> ORGANISM: Clostridium hathewayi
<220> FEATURE:
<221> NAME/KEY: misc_feature
<222> LOCATION: (150)..(150)
<223> OTHER INFORMATION: n is a, c, g, or u
<220> FEATURE:
<221> NAME/KEY: misc_feature
<222> LOCATION: (166)..(166)
<223> OTHER INFORMATION: n is a, c, g, or u
<220> FEATURE:
<221> NAME/KEY: misc_feature
<222> LOCATION: (193)..(193)
<223> OTHER INFORMATION: n is a, c, g, or u
<220> FEATURE:
<221> NAME/KEY: misc_feature
<222> LOCATION: (791)..(791)
<223> OTHER INFORMATION: n is a, c, g, or u

<400> SEQUENCE: 49
ccaggagaac gcggcggcgg caacacagca agcgagcgaa gcggcaagaa gcggaggaga 60
aagacagcgg cggacgggga gaacgcgggg aaccgccaca cgggggaaac agagaaagac 120
gcaaaccgca aagcgcacag ggccgcaggn cggggaaaaa cccggnggga agaggacccg 180
cgcgaaggag ggnggggaac ggcccaccaa gccgacgaca gagccgaccg agaggggacc 240
ggccacaggg acgagacacg gcccaaaccc acgggaggca gcagggggaa aggacaaggg 300
cgaaagccga ccagcgacgc cgcggaggaa gaagacggag aaagccacag cagggaagaa 360
aagacggacc gacaagaagc cccggcaaca cggccagcag ccgcggaaac gagggggcaa 420
gcgaccggaa cggggaaagg gagcgagacg gagcaagcga aggaaagccc ggggccaacc 480
ccggacgcgg aaacgagacg aggcaggaga ggaagggaac caggagcggg aaagcgagaa 540
aggaggaaca ccagggcgaa ggcggcacgg acgaacgacg gaggccgaaa gcgggggagc 600
aaacaggaag aacccggagc cacgccgaaa cgagaaacag ggcgggggc aaagccccgg 660 gccgccgcaa acgcaaaaga ccaccgggga gacgcgcaag aagaaaccaa aggaagacgg 720
ggacccgcac aagcggggag cagggaacga agcaacgcga agaaccacca agcgacaccc 780
acgaaaacac naaccggacc cccggagcag ggagacaggg ggcagggcgc agccggcgga 840
gaggggaagc ccgcaacgag cgcaacccac cagagccagc gagagagcgg gcaccgggga 900
gacgccaggg aaaccggagg aagggggag acgcaaacac agccccagag ggcacacacg 960
gcacaaggcg aaacaaaggg aggcaaagga gcgacggagc aaaccccaaa aaaacgccag 1020
cggagcaggc gcaaccgccg cagaagcgga acgcagaacg cgaacagaag cgcgggaaac 1080
gcccgggcga cacaccgccc gcacaccagg gagggaacgc ccgaagcagg acccaaccga 1140
aaggagggag cgccgaaggc gggacgaaac gggggaagcg aacaaggagc cgacggaagg 1200
gcg 1203

<210> SEQ ID NO 50
<211> LENGTH: 1177
<212> TYPE: RNA
<213> ORGANISM: Clostridium lavalense
<220> FEATURE:
<221> NAME/KEY: misc_feature
<222> LOCATION: (887)..(887)
<223> OTHER INFORMATION: n is a, c, g, or u

<400> SEQUENCE: 50
gccaggagaa cgcggcggcg gccaacacag caagcgaacg aagcayagag aagcggagga 60
cgagagacga gggcggacgg ggagaacacg ggaaaccgcc cacacggggg acaacagaga 120
aagacgcaaa ccgcaaagcg cacagaccgc aggacaggga aaaacccggg gggagaggac 180
cgcgcgaagc cagggcgggg aacggcccac caaagcgacg acagagccga ccgagagggg 240
accggccaca gggacgagac acggcccaaa cccacgggag gcagcagggg gaaagcacaa 300
gggcgaaagc cgagcagcga cgccgcggag gaagaagacg gagaaagcca cagcagggaa 360
gaaagacgga ccgacaagaa gccccggcaa cacggccagc agccgcggaa acgagggggc 420
aagcgaccgg aacggggaaa gggagcgaga cggcaggcaa gcgaaggaaa acccagggcc 480
aacccgggac gcggaaacgc aagcagaggc aggagaggaa gggaaccagg agcgggaaag 540
cgagaaagga ggaacaccag ggcgaaggcg gcacggacga acgacggagg ccgaaagcgg 600
gggagcaaac aggaagaacc cggagccacg ccgaaacgag aggcaggggg ggggcaaagc 660
cccgggccgc gcaaacgcaa aagcacccac cggggagacg cgcaagaaga aaccaaagga 720
agacggggac ccgcacaagc ggggagcagg gaacgaagca acgcgaagaa ccaccaagcg 780
acacccgacc ggcggaacgg cgcccccggg acaagagaga cagggggcag ggcgcagccg 840
gcggagaggg gaagcccgca acgagcgcaa cccaccagag ccagcanrag agggcaccag 900
ggagacgcca gggacaaccg gaggaagggg ggagacgcaa acacagcccc agagggcaca 960
cacggcacaa ggcgaaacaa agggaagcga cccgcgaagg gagcaaacca aaaaaacgcc 1020
cagcggacga gcgcaacccg acacacgaag cggaacgcag aacgcgaaca gaagcgcggg 1080
aaacgcccgg gcgacacacc gcccgcacac cagggagcag caacgcccga agcaggaccc 1140
aaccgcaaga gagggagcgc cgaaggcggg gcaggaa 1177

<210> SEQ ID NO 51
<211> LENGTH: 1204
<212> TYPE: RNA
<213> ORGANISM: Ruminococcus sp

<400> SEQUENCE: 51
gaacgcggcg gcggccaaca cagcaagcga gcgaagcgcg cagaaccgga ggaagaggac 60
aggacgagcg gcggacgggg agaacgcggg gcaaccgccc aacaggggga aacagagaaa 120
gacgcaaacc gcaaagcgca caggaccgca gggagggaaa aacccgggga gagaggaccc 180
gcgcgaagga gggggggaaa ggccaccaag ccgacgacag agccgaccga gaggggaccg 240
gccacaggga cgagacacgg cccaaaccca cgggaggcag caggggggaaa gcacaagggg 300 gaaacccgag cagcgacgcc gcggaaggaa gaagacggag aaaccacagc agggaagaag 360
agacggaccg agaagaagca ccggcaaaac ggccagcagc cgcggaaacg agggcaagcg 420
accggaacgg ggaaagggag cgagacggaa ggcaagcgga ggaaaaccca gggccaaccc 480
gggacgcgga aacgcagacg gaggccggag aggaagcgga accaggagcg ggaaagcgag 540
aaaggaggaa caccagggcg aaggcggcac ggacgggacg acggaggccg aaagcggggg 600
agcaaacagg aagaacccgg agccacgccg aaacgagaca cagggcgggg caaagcacac 660
gggccgcagc aaacgcaaaa gagccaccgg ggagacgcgc aagaagaaac caaaggaaga 720
cggggacccg cacaagcggg gagcagggaa cgaagcaacg cgaagaacca ccggcgacac 780
cggagacggg cgagaagcgc cgccccgggg caccgagaca gggggcaggg cgcagccggc 840
ggagagggga agcccgcaac gagcgcaacc caccagagcc agcaaaaggg ggcaccggag 900
agacgccagg gagaaccgga ggaagggggg agacgcaaac acagccccag gccagggcac 960
acacggcaca aggcgaaaca aagggaagcg agaggggacc ggagcgaacc caaaaaaacg 1020
ccagcggaga gcgcaaccga cacagaagcg gaacgcagaa cgcggacagc agccgcggga 1080
aacgcccggg cgacacaccg cccgcacacc agggagcaga acgcccgaag ccaggaccca 1140
accagaggag ggagcgcgaa ggcgggacgg aaacggggga agcgaacaag gagccgacgg 1200
aagg 1204

<210> SEQ ID NO 52
<211> LENGTH: 1170
<212> TYPE: RNA
<213> ORGANISM: Clostridium innocuum

<400> SEQUENCE: 52
gaccggccag gagaacgcgg cggcagccaa acagcaagcg aacgaagcga ggaagcgccc 60
aaagagacag ggcgaacggg gagaacacga ggaaccgccc aggccgggaa acgcggaaac 120
ggagcaaaac cggaaggaac agagcgcagc cagaaaaagc gcccacaagg cggaacagga 180
ggaccgcggc gcaagcaggg gaggaacggc ccaccaaggc gagagcgagc cggccgagag 240
ggaaacggcc acagggacga gacacggccc aaacccacgg gaggcagcag agggaacgca 300
agggggaaac ccgaacgagc aagccgcgga ggaagaaggc cggacgaaag ccggaaggaa 360
gaacggccaa gaggaaagca gggaggacgg agcaccagaa agccacggca acacggccag 420
cagccgcgga aacgaggggc aagcgaccgg aacagggcga aaggggcgag gggcgacaag 480
cgagaaaagg caaggccaac cagaagcagg aaacggagcg gaggcagaag agggcgagga 540
accaggagcg gaaaagcgag aaaggaggaa caccagggcg aaggcggcgc cggcgaacga 600
cacgaggcac gaaagcgggg gagcaaaagg aagaacccag agccacgccg aaacgagaga 660
acaaggggag gaacaggcgc agaacgcaaa agcccgccgg ggagagcacg caagggaaac 720
caaaggaaga cgggggcccg cacaagcggg gagagggaac gaagcaacgc gaagaaccac 780
caggccgaca ggaaacaaaa cccagagaag ggggaaaagg acacacaggg ggcagggcgc 840
agccggcgga gaggggaagc ccgcaacgag cgcaacccgc gcagaccagc acaaggggga 900
ccagcgagac gccgggacaa accggaggaa ggggggagac gcaaacacag ccccaggccg 960
ggcacacacg acacaaggcg accacaaaga gcagcgacac aggaggaagc gaaccaaaag 1020
gcgccagcgg agaagcgcaa ccgaccagaa gcggaacgca gaacgcagac agcagcgcgg 1080
gaaacgccgg gccgacacac cgcccgcaaa ccagggagca gaaacccgaa gccggggcaa 1140
accgaaggag gagccgcgaa ggaggaccga 1170

<210> SEQ ID NO 53
<211> LENGTH: 8
<212> TYPE: PRT
<213> ORGANISM: Artificial Sequence
<220> FEATURE:
<223> OTHER INFORMATION: Synthetic polynucleotide

<400> SEQUENCE: 53

Lys Ser Pro Trp Phe Thr Thr Leu
1 5

<210> SEQ ID NO 54
<211> LENGTH: 1161
<212> TYPE: RNA
<213> ORGANISM: Artificial Sequence
<220> FEATURE:
<223> OTHER INFORMATION: Synthetic polynucleotide

<400> SEQUENCE: 54
cgaagaggac cggccaggag aacgcgacag aagcaacaca gcaagcacga cccggggaag 60
gggcggacgg ggagaacgcg aaagaacgcc acagacggga caacaggaaa cgaagcaaac 120
cggaaagagg gcgcagacga agaaagcaag cgcggagaga gcgcgcccaa gaggggagga 180
acggccacca agacgagagg gagccggccg agaggggaac ggccacaagg ggacgagaca 240
cggcccaccc acgggaggca gcagggggaa aggacaagga ccaaaagcga ccagcaacgg 300
gcacgaagaa gcggaagaaa ggccagggga agaagcagga cggaccaaca gaagaagcga 360
cggcaaaacg gccagcagcc gcggaaacga gcgcaagcga ccggaagggc gaaagcgcgc 420
aggcggcaga agcgaggaaa agcggggcca accccgagcg ggaaacgcaa acagagacgg 480
agaggaggcg gaacacaagg agagggaaac gagaagagga agccgagggg aagccagcca 540
cggacagaac gacgcaaagc gcgaaagcgg ggagcaaaca ggaagaaccc ggagccacgc 600
cgaaacgaga acaggggggg gcgaacccag cgcccaagca acgcgaaaga accgccgggg 660
agacgacgca agagaaacca aaggaagacg gggacccgca caagcgggga gcagggaacg 720
acgcaacgcg aggaaccacc agcggacacc caagaagaac agagagcggc cccggaggaa 780
cgggacaggg ggcaggcgcg cagccggcgg agaggggaag cccgcaacga gcgcaacccc 840
cgagaccaca aagggggacc agcgagacgc cgcgagagca ggaggaaggg gggagacgca 900
agcacagccc caacgcgggc acacacggca caagggagac agagagcgca aaccgcgagg 960
gaagcaacca aaaacacagc ggagaccgca accgagacag aagggaacgc agaacgcaaa 1020
cagcaggcgg gaaacgccgg gcgacacacc gcccgcacac cacgagaggg gcaccgaaga 1080
acaggccaac cgaaggaggg agccgagggg gaagcgaggg ggaagcgaac aaggaccgac 1140
gggaacggcg gaggacaccc c 1161

<210> SEQ ID NO 55
<211> LENGTH: 1190
<212> TYPE: RNA
<213> ORGANISM: Artificial Sequence
<220> FEATURE:
<223> OTHER INFORMATION: Synthetic polynucleotide

<400> SEQUENCE: 55
cgaagaggac cggccaggag aacgcagcga caggcaacac agcaagcgag gggcacagga 60
agagcaaaca gaggcgaccg gcgcacgggg agaacgcgag caacaccaca gagggggaag 120
cccggcgaaa gcggaaaacc caaaaacagg ggccgcaggg acagaaagac acgcgaagaa 180
ggcagcgcca aggcagggcg gggaacggcc caccaaaccg acgaggaagg ggcgagagga 240
aggcccccac aggacgagac acggaccaaa cccacgggag gcagcaggag gaaaggcaag 300
gccgagaggc gaaccagcca agcgcggaag gagaaggaca gggaaaccaa ggggaaaaag 360
ggggacggcc agagacccag aaaagcacgg caacccggcc agcagccgcg gaaacggagg 420
agcgagcgac cggaagggaa aggggcgagg ggaaaagcag cgggaaaggg gccaaccaaa 480
aagccggaaa cgggacgagg ggaggaggcg gaagcgggga gcgggaaagc aagaacacgc 540
agaacccaag cgaaggcagc acaaaccaaa cgacacgaag cacgaaagcg gggacaaaca 600
ggaagaaccc ggagccacgc agaaacgaga acaggaggcg aacacagaag ccacagcgaa 660
agcgaagaac caccggggag acgccggcaa cgggaaacca aaggaagacg ggggcccgca 720
caagcggagg aacagggaac gagaacgcga ggaaccaccc ggggaacgag cagaccgacc 780
gaaagaggca gcaaagcgaa cgagggcgca gggcgcagcc ggccggaggg cggcaaggcc 840
aaacgagcgc aacccacaca gacaacagga agcgaggacc gggagacgcc agcgaagcgg 900
aggaaggggg gagacgcaaa cagcacggcc cacaccgggg cgacacacgg acaaggcagg 960
acaaagggca gcaccggcga caggagcaac caaaccagcc agcggacgga gcgcaaccga 1020
cccggaagcg gacgcagaac gcgcacagcc aggcgcggga aacgcccggg ccgacacacc 1080
gcccgcaagc cagggagccg ggggaccgaa gccgaaccgc aaggacggcc agggaaaacg 1140
ggacggggca agcgaacaag gagccgaccg gaagggcggc ggaacacccc 1190

<210> SEQ ID NO 56
<211> LENGTH: 1061
<212> TYPE: RNA
<213> ORGANISM: Artificial Sequence
<220> FEATURE:
<223> OTHER INFORMATION: Synthetic polynucleotide

<400> SEQUENCE: 56
aaaaagaaag gaaaggaggg gagcgcccaa gcgggcgggg aacggcccac caaggcgacg 60
agggaggggc gagaggaagg cccccacagg aacgagacac ggccaaaccc acgggaggca 120
gcaggaggaa aggcaagggc gcgagccgaa ccagccaaga gcgggaggac gacggcccac 180
ggggaaaccc aaaggggaaa agggccagag gccagcagga ccagaaaagc acggcaaccg 240
gccagcagcc gcggaaacgg aagagcgagc gaccggaagg gaaagggagc gaggcgggca 300
gcaagcagcg gcaaaggcgc ggccaaccgc gccgccggaa acggcagccg agagcacagg 360
gacaggaacg gggagcggga aagcagaaca cgaggaaccc gacgcgcagg cagaccgggg 420
caacgacgcg aggccgaagg gcgggacaaa caggaagaac ccggagccgc acagaaacga 480
gaagcccgcg cggcgacaag gcggcggcca agcgaaagcg aagcaccacc ggggagacgc 540
cggcaacggg aaaccaaagg aagacggggg cccgcacaag cggaggaaca gggaacgaga 600
acgcgaggaa ccacccgggc gaacgcaggg cagggccgga gacggccccc cgggacccgc 660
gaagggcgca gggcgcagcc ggccggaggg cggcaaggcc aaacgagcgc aacccccccc 720
ccaggccacc gggaagccgg gcacggggac acgccaccgc aagggcgagg aagggggag 780 acgcaaacag cacggcccac gccggggcga cacacggaca agggggggaca gagggccgcg 840 cccgggacgg ggccaaccca aaaccccccca gcggacggag cgcaacccga cccacgaagc 900
ggacgcagaa cgcgcacagc caggcgcggg aaacgcccgg gccgacacac cgcccgcaag 960
ccagaaagcc gggggccgga agccggaccg cgagggcggc cagggaaaac cgggaggggc 1020
aagcgaacaa ggagccgacc ggaagggcgg cggaacaccc c 1061

<210> SEQ ID NO 57
<211> LENGTH: 1219
<212> TYPE: RNA
<213> ORGANISM: Artificial Sequence
<220> FEATURE:
<223> OTHER INFORMATION: Synthetic polynucleotide

<400> SEQUENCE: 57
cgaagaggac cggccaggag aacgcagcga caggcaacac agcaagcgag gggcagcaca 60
ggagcaaacc gggggcgacc ggcgcacggg gagaacgcga gcaacgccac agagggggaa 120
acccggcgaa agcggacaaa ccgcagaagc aggggccccg caggggaagc aaagacacgc 180
gaagaaggca gcgccaaggc agggcgggga acggcccacc aaaccgacga ggaaggggcg 240
agaggaaggc ccccacagga cgagacacgg accaaaccca cgggaggcag caggaggaaa 300
ggcaaggccg agaggcgaac cagccaagcg cggagggaga aggcaggacg aaacccaaag 360
ggaaaaaggc gggacggccc ggagaccaga aaaggacggc aacccggcca gcagccgcgg 420
aaacggagga ccgagcgacc ggaagggaaa ggggcgaggc ggccaagcag cgggaaagcg 480
ggccaaccaa gaagccggaa acgggggggcg agaggaggca ggcggaagcg gggagcggga 540
aagcaagaac acgcagaacc ccgagcgaag gcagccgcca agccaacgac gcgagcacga 600
aagcggggga caaacaggaa gaacccggag ccacgcagaa acgagacaca gcggcgaaca 660
cgaagcggca cagcgaaagc gaaggaccac cggggagacg ccggcaacgg gaaaccaaag 720
gaagacgggg gcccgcacaa gcggaggaac agggaacgag aacgcgagga accacccggg 780
gaacgcacgg accgagggga aacacccagc aaagccggcg agggcgcagg gcgcagccgg 840
ccggagggcg gcaaggccaa acgagcgcaa cccgccacag acaacaggaa agcgaggacc 900
gggggacgcc agcgaagcgc gaggaaggcg gggagacgca aacagcacgg cccacaccgg 960
ggcgacacac ggacaaggcg ggacaaaggg aagccaccgg cgacagggag cgaaccccaa 1020
accacgccag cggacggagc gcaacccgac ccggaagcgg acgcagaacg cgcacagcca 1080
ggcgcgggaa acgcccgggc cgacacaccg cccgcaagcc agggagccgg gggaccgaag 1140
ccgaaccgcg aggacggcca gggaaaacgg gacggggcaa gcgaacaagg agccgaccgg 1200
aagggcggcg gaacacccc 1219

<210> SEQ ID NO 58

<211> LENGTH: 1205
<212> TYPE: RNA
<213> ORGANISM: Artificial Sequence
<220> FEATURE:
<223> OTHER INFORMATION: Synthetic polynucleotide

<400> SEQUENCE: 58
aggagaggac cggccaggag aacgcagcgg caggccaaca cagcaagcga ggggcagcgg 60
gagaagcgcc aggccggcga ccggcgcacg gggcgaacgc gagcaaccac ccaaacaggg 120
ggaaacacga gaaacggaca aacccaaaca caagaggggc acccgggaaa acccggggag 180
gagggcagcg gaagcagggg aggaacggcc accaaggcga cgaacaaggg ggacgagagg 240
aaccccccac aggacgagac acggaccaaa cccacgggag gcagcaggag gaaaggcaag 300
gacgcaagcg aaccagccag ccgcggcagg agacggccag aggaaacgcg acgagggaaa 360
cccggaacgg accggcgaaa gacgacgaaa aggacggcaa cccggccagc agccgcggaa 420
acggaggaca agcgaccgga agggaaaggg gcgaggcggg aaagagaggg aaaaccgggc 480
aacaccggaa cgcccaaacg gagcagagag aggcggaggc ggaagaggga gcgggaaagc 540
agagacaaca gaacaccgag cgaaggcagc accaaacaac gacggaggca cgaaagcggg 600
ggagcaaaca ggaagaaccc ggagccacgc agaaacgaga aaccgcgcgg cgaacacagc 660
ggggcaagcg aaagcgaaag accaccgggg agacgcgcaa gaagaaacca aaggaagacg 720
ggggcccgca caagcggagg aacagggaac gagaacgcga ggaaccaccc gggcgaaaga 780
cgacgacgga aacaggaccc cggggcagga aacagggcgc agggcgcagc cggccggagg 840
gcgggaagcc caaacgagcg caaccccacc gaggccacag gcaagcgggc accggcggga 900
cgccgggaag ccgagaggaa gggggagac gcaaacagca cggcccacgc cggggcacac 960
acggacaagg aggacagagg gcagcaccca ggagggagcg aaccgaaagc caccagcgga 1020
ggaggcgaaa cccgccccag aagggacgca gaacgcgcac agccaggcgc gggaaacgcc 1080
cgggccgaca caccgcccgc aagccaggaa gcggggggcc gaagcggacc gcaaggagcg 1140
accagggcaa aaccgggacg gggcaagcga acaaggagcc gaccggaagg gcggcggaac 1200
acccc 1205

<210> SEQ ID NO 59
<211> LENGTH: 1213
<212> TYPE: RNA
<213> ORGANISM: Artificial Sequence
<220> FEATURE:
<223> OTHER INFORMATION: Synthetic polynucleotide

<400> SEQUENCE: 59
agagaggacc ggccaggacg aacgcggcgg agcaacacag caagcgaacg agaagggagg 60
acccggggaa cagaacggaa agggcgaacg gggagaacgc ggggaaccgc ccaggaaagg 120
aaagcccggg aaacgggaga aagccaaagg gcgcaggcaa gacagaaaac ccgggccaag 180
gaggacccgc gcccaagcag gggagaaaca gcccaccaag gcgacgaggg aaccggcgag 240
agggcgaacg gcacacggaa cgagacacgg ccagacccac gggaggcagc agggggaaag 300
cgcaaggggg caacccgacg cagcaaaccg cggaggaaga aggcggacga aagccgaggg 360
gaagaagaag acggacccaa gaggaagccc ggcaacacgg ccagcagccg cggaaacgag 420
gggacaagcg gccggaagac gggcgaaagg gcgcgaggcg gcaaagcgag gaaaggaccg 480
gccaaccggg aaggcaggaa acggagacga gaggagaggc aagggaacca ggagcgggaa 540
agcgagaaag gaggaacacc agggcgaagg cggcgcggac aaaacgacgc gagggcgaaa 600
gcgggggagc gaacaggaag aacccggagc cacgccgaaa cgagaagcag gggggaaac 660 caggccgcag aacacaaaag caccgccggg gagacgaccg caagggaaac caaaggaaga 720
cggggacccg cacaagcagc ggagcaggga acgaagcaac gcgaagaacc accaggcgac 780
acccgacgag ccagagaagg aagcccggga acagagagac agggggcagg gcgcagccgg 840
cggagagggg aagcccgcaa cgagcgcaac cccgccaggc cagcaaaggg gcaccagagg 900
gacgccgaga caaacggagg aagggggac gacgcaaaca cagccccaga ccgggcacac 960
acggcacaag gcgaacagag ggccgcgaag ccgcgaggga agcaaaccca aaacagaccc 1020
agcggagcag gcgcaaccgc cgcagaaggg aggcagaacg cggacagaag ccgcgggaag 1080
cgcccgggcg acacaccgcc cgcacaccac gagagggcaa cacccgaagc cggagagaac 1140
cgaaggacca gcagcgaagg ggggcagaag ggggaagcga acaaggagcc gacggaaggg 1200
cggcggacac ccc 1213

<210> SEQ ID NO 60
<211> LENGTH: 1193
<212> TYPE: RNA
<213> ORGANISM: Artificial Sequence
<220> FEATURE:
<223> OTHER INFORMATION: Synthetic polynucleotide

<400> SEQUENCE: 60
agaagaggac cggccaggag aacgcagcac aggcaacaca gcaagcgagg ggcagcaggc 60
agcgcaaggc gaggcgaccg gcgcacgggg agaacacgac caaccgccgc accggccagc 120
ccgaaaggaa gaaaccagga gggacagagc acagccgcag aaaaggaccg gagacgaggg 180
gagcgccaag aagaggcggg gaacggccca ccagcaacga ggaaggggcg agaggaaggc 240
ccccacagga acgagacacg gccaaaccca cgggaggcag caggaggaaa ggcaagggcg 300
aggccgaacc agccaagagc ggaaggagac gcccagggga aaccaaaagg aaaaagcggg 360
agcaacccgg cagacagaaa aggacggcaa cccggccagc agccgcggaa acggaggacc 420
gagcgaccgg aagggaaagg gagcgagagg agaagcaggg aaaggcggcc aaccgaaaag 480
caggaacgga gcgaggcagg aggcaggcgg aacggggagc gggaaagcag aacacgaaga 540
acccgagcga aggcagccgc aagcgcaacg acagaggccg aaagggggac aaacaggaag 600
aacccggagc cacacggaaa cgagaaaccg cggcgaaacg gcaagcggcc aagcgaaagc 660
gaagaccacc ggggagacgc cggcaacggg aaaccaaagg aagacggggg cccgcacaag 720
cggaggaaca gggaacgaga acgcgaggaa ccacccgggc aaagcaccga agaccggaaa 780
cggcagcagc aaagcgaggg aagggcgcag ggcgcagccg gccggagggc ggcaaggcca 840
aacgagcgca acccggcaga caacagggag cgaggaccga caagacgcca cgaagaggag 900
gaagggggga gacgcaaaca gcacggccca cgccggggca cacacggaca aggggggaca 960
gagggccgca ccacgcgagg gagccaaccc aaaacccccc agcggacgga gcgcaacccg 1020
acccacgaag cggacgcaga acgcgcacag ccacggcgcg ggaaacgccc gggccgacac 1080
accgcccgca agccagggag ccgggggacc gaaggcgaac cgcgaggacg cccagggaaa 1140
acgggacggg gcaagcgaac aaggagccga ccggaagggc ggcggaacac ccc 1193

<210> SEQ ID NO 61
<211> LENGTH: 1191
<212> TYPE: RNA
<213> ORGANISM: Artificial Sequence
<220> FEATURE:

<223> OTHER INFORMATION: Synthetic polynucleotide

<400> SEQUENCE: 61
cgaagaggac cggccaggag aacgcagcga caggcaacac agcaagcgag gggcagcagg 60
aagagcaaac gcggcgaccg gcgcacgggg agaacgcgag caaccaccac agagggggaa 120
acccggcgaa agcggacaaa ccgcaaaaac aggggcccgc agggaaagaa agaagcgaag 180
agggcagcgc caagaagggg aggaacggcc accaagccga ggaaggggcg agaggaaggc 240
ccccacacgg acgagacacg gaccagaccc acgggaggca gcaggaggaa aggcaagggc 300
gagagccgaa ccagccaagc gcggaaggag aaggacaggc gaaaccaagg ggaaaaaggc 360
aggacggccg gagacccaga aaaggacggc aacccggcca gcagccgcgg aaacggagga 420
ccgagcgacc ggaagggaaa ggggcgaggg gcaagcagcg ggaaaggggc caaccaaaaa 480
gccggaaacg gagggcgaga agaggaggcg gaagcgggga gcgggaaagc aagaacacgc 540
agaacccaag cgaaggcagc acaaacaaac gacacgaagc acgaaagcgg gggacaaaca 600
ggaagaaccc ggagccacgc agaaacgaga acaggaggcg aacacagaag ccacagcgaa 660
agcgaagaac caccggggag acgccggcaa cgggaaacca aaggaagacg gggggcccgca 720 caagcggagg aacagggaac gagaacgcga ggaaccaccc ggggaacgaa ggaccggagg 780
gaaacaccca gcaaagcaaa cgagggcgca gggcgcagcc ggccggaggg cggcaaggcc 840
aaacgagcgc aacccacaga caacaggcga gcgaggacca aagagacgcc agcgaagcgg 900
aggaaggggg gagacgcaaa cagcacggcc cacaccgggg cgacacacgg acaagggggg 960
acaaagggca gcaccggcga caggagcaac ccaaacccca ccagcggacg aagcgcaacc 1020
cgaccggaag cggacgcaga acgcgcacag ccaggcgcgg gaaacgcccg ggccgacaca 1080
ccgcccgcaa gccagggagg ggggaccaaa gccgaaccgc aaggacggcc agggaaaacc 1140
gagacggggc aagcgaacaa ggagccgacc ggaagggcgg cggaacaccc c 1191

<210> SEQ ID NO 62
<211> LENGTH: 1224
<212> TYPE: RNA
<213> ORGANISM: Artificial Sequence
<220> FEATURE:
<223> OTHER INFORMATION: Synthetic polynucleotide

<400> SEQUENCE: 62
aagaagagga ccggccagga cgaacgcggc ggcgcgccaa cacagcaagc gaacggagcg 60
ccgaagcgga ggaagagagc agcagggcga acggggagaa cacggagcaa ccgcccaggg 120
gggacaacag gaaacgaagc aaaccgcaaa gaccacaggc gcaggcacag gggcaaagga 180
accgcgaaag agggccgcgc cgaagcagag ggaggaacgg cccaccaggc gacgacggag 240
ccggacgaga gggaacggcc acagggacga gacacggccc agacccacgg gaggcagcag 300
ggggaaagca caagggggaa acccgagcag cgacgccgcg ggaggaagaa ggccggagaa 360
acccgcccag gggacgaaag acggacccgg gaggaagcac cggcaacacg gccagcagcc 420
gcggaaaacg aggggcaagc ggccggaaac ggggaaaggg agcgcaggcg gaggcaaggg 480
gaggaaacag ggccaaccca aaagccaaaa cgcagcgagg ggagaggagg cggaacccgg 540
gagcggggaa gcgagaacgg gaggaacacc agggcgaagg cggccacggg cacaacgacg 600
cgaggccgaa agcagggagc aaacaggaag aacccggagc cagccgaaac gagaacaggg 660
gggaggagac cccccggccg cagaacacaa aagaaccacc ggggagacga ccgcaaggga 720
aaccaaagga agacgggggc ccgcacaagc agggagaggg aacgaagcaa cgcgaagaac 780
caccaggcga cacggagcaa ccaagagaag ggaagcccgg gacaccagac agggggcagg 840
gcgcagccgg cggagagggg aagcccgcaa cgagcgcaac ccacgagaca cgcaagagga 900
ccagcgagac gccggacaaa acggaggaag gggggagacg caaacacagc ccagaccggg 960
cacacacgac acaaggcaaa cagagagaag cgaaccgcga ggggagcaaa cccacaaaaa 1020
agccagcgga cgcaggcgca acccgccgcg gaagccggaa gcagaacgcg gacagcagcc 1080
gcgggaaacg cccgggccga cacaccgccc gcacaccaga gagccggggg gacccgaagc 1140
ggagcaaccg caaggaggac gccgccgaag gaaaacggga gggggaagcg aacaaggagc 1200
cgacggaagg gcggcggaca cccc 1224

<210> SEQ ID NO 63
<211> LENGTH: 1186
<212> TYPE: RNA
<213> ORGANISM: Artificial Sequence
<220> FEATURE:
<223> OTHER INFORMATION: Synthetic polynucleotide

<400> SEQUENCE: 63
agaagaggac cggccaggag aacgcagcac aggcaacaca gcaagcgagg ggcagcagaa 60
cagcgcaagg aggcgaccgg cgcacgggga gaacacgacc aaccgccgag accggggaag 120
cccgaaagaa agaaaacccg aggcaagccc gcaggggaac aaaagaacgg cacgagggga 180
gcgccaaggg ggcggggaac ggcccaccaa gcccgaggaa ggggcgagag gaaggccccc 240
acaggaacga gacacggcca aacccacggg aggcagcagg aggaaaggca aggacgagag 300
cgaaccagcc aagagcggaa ggagacgccc aggggaaacc aacgggaaaa aggaggcacg 360
ggccgagacc gagaaaagga cggcaacccg gccagcagcc gcggaaacgg aggaccgagc 420
gaccggaagg gaaagggagc gaggcggacg caagcaggga aaggcggcca accgaaaagc 480
aggaacgggg cgagacagag aggcaggcgg aacggggagc gggaaagcag aacacgaaga 540
acccgagcga aggcagccgc ggacgaacga cgcgagccga aagggggaca aacaggaaga 600
acccggagcc acacagaaac gagaaaccgc ggcgaaacag aagcggccaa gcgaaagcga 660
agaccaccgg ggagacgccg gcaacgggaa accaaaggaa gacgggggcc cgcacaagcg 720
gaggaacagg gaacgagaac gcgaggaacc acccgggcga agcaacgaag agggagacag 780
cagccgcaag gcagggaagg gcgcagggcg cagccggccg gagggcggca aggccaaacg 840
agcgcaaccc acgaagacca cagggagcgg ggaccgcgag acgccgcgaa gaggaggaag 900
gggggagacg caaacagcac ggcccacgcc ggggcacaca cggacaaggg gggacagaag 960
gcagcacacg gcgacggagc aacccgaaag cccccagcgg aggagcgcaa cccgacccag 1020
aagcggacgc agaacgcgca cagccacggc gcgggaaacg cccgggccga cacaccgccc 1080
gcaagccaga aagccggggg accgaaggcg aaccgcaagg agcgcccagg gaaaacggga 1140
ggggcaagcg aacaaggagc cgaccggaag ggcggcggaa cacccc 1186

<210> SEQ ID NO 64
<211> LENGTH: 1241
<212> TYPE: RNA
<213> ORGANISM: Artificial Sequence
<220> FEATURE:
<223> OTHER INFORMATION: Synthetic polynucleotide

<400> SEQUENCE: 64
aggagaggac cggccaggac gaacgcggcg gcggccaaca cagcaagcga acggagaaac 60

-continued

| | |
|---|---|
| ggagaacagg gcgaacgggg agaacgcgag gcaaccaccc agacggggac aacaccgaaa | 120 |
| ggaggcaaac cggaggacac gccgcaggca ggagaagaaa gaggcccaca agaagcacgc | 180 |
| aaaggagggc cgcgcgaagc agggaggaac ggacaccaag gcgagacaga gccggcgaga | 240 |
| ggagaacggc cacagggacg agacacggcc caaacccacg ggaggcagca gggggaaccc | 300 |
| gcaaggacga aagcgacgga gcaacgccgc ggaggagaag gacggcgaaa gccggagacg | 360 |
| aacggcaggg gaacaagcag caagacggag aaacgaggaa gccacggcaa cacggccagc | 420 |
| agccgcggaa acgaggggcg agcggccgga aagggcgaaa gagcagaggc ggcaaaagcg | 480 |
| agcggaaaag cggggccaac cccgaggcgc ggaaacgagg cgaggcagga gaggaaaggg | 540 |
| gaacccagga gcgggaaagc gagaagggag gaacaccagg gcgaaggcgc ccggacggcg | 600 |
| acgcgagagc gaaagccagg gagcgaacgg gaagaacccc ggagccggcc gaaacgaggg | 660 |
| acagggagga ggacgacccc cggccggaga acgcaaaaga ccccgccggg gagacggccg | 720 |
| caagggaaac caaaggaaga cgggggcccg cacaagcggg gagagggaac gacgcaacgc | 780 |
| gaagaaccac caaggcgaca gagaacgcca gagaagagac cccggggaca agaaaacagg | 840 |
| gggcaggcgc gcagccggcg gagaggggaa gcccgcaacg agcgcaaccc caccagacca | 900 |
| gcaagaaagg gggaccaggg agacgccagg gacaaccgga ggaaggcggg gagacgcaag | 960 |
| cacagcccca gcgggcacac acgacacaag gcggaaacag agggaagcga agccgcgagg | 1020 |
| cagagcaaac cccagaaacc cgaccagcgg acgcaggcgc aacccgccgc ggaagcggaa | 1080 |
| cgcagaacgc aggcagcaac gcgggaaacg cccgggccga cacaccgccc gcacaccacg | 1140 |
| aaagggaaca cccgaagccg ggaggaacca aggagccagc cgcaaggggg gccgagaggg | 1200 |
| ggaagcgaac aaggagccga cggaagggcg gcggacaccc c | 1241 |